US011401516B2

(12) United States Patent
Green et al.

(10) Patent No.: US 11,401,516 B2
(45) Date of Patent: Aug. 2, 2022

(54) CHANNEL MODULATORS

(71) Applicants: AUCKLAND UNISERVICES LIMITED, Auckland (NZ); OCUNEXUS THERAPEUTICS, INC., San Diego, CA (US)

(72) Inventors: Colin Richard Green, Auckland (NZ); Yeri Kim, Auckland (NZ); Anthony Phillips, Auckland (NZ); Bradford James Duft, Solana Beach, CA (US)

(73) Assignees: AUCKLAND UNISERVICES LIMITED, Auckland (NZ); OCUNEXUS THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 16/673,729

(22) Filed: Nov. 4, 2019

(65) Prior Publication Data

US 2020/0239889 A1 Jul. 30, 2020

Related U.S. Application Data

(63) Continuation of application No. 14/833,041, filed on Aug. 21, 2015, now Pat. No. 10,465,188.

(60) Provisional application No. 62/147,488, filed on Apr. 14, 2015, provisional application No. 62/080,217, filed on Nov. 14, 2014, provisional application No. 62/085,226, filed on Nov. 26, 2014, provisional application No. 62/146,128, filed on Apr. 10, 2015.

(30) Foreign Application Priority Data

Aug. 22, 2014 (NZ) ........................................ 628630
Jul. 2, 2015 (NZ) ........................................ 709673

(51) Int. Cl.

| | |
|---|---|
| ***C07H 21/04*** | (2006.01) |
| ***C12N 15/113*** | (2010.01) |
| ***A61K 38/08*** | (2019.01) |
| ***A61K 38/39*** | (2006.01) |
| ***A61K 9/00*** | (2006.01) |
| ***A61K 31/167*** | (2006.01) |
| ***A61K 31/557*** | (2006.01) |
| ***A61K 31/498*** | (2006.01) |
| ***A61K 31/5575*** | (2006.01) |
| ***A61K 31/195*** | (2006.01) |
| ***A61K 31/382*** | (2006.01) |
| ***A61K 31/575*** | (2006.01) |
| ***A61K 31/5377*** | (2006.01) |
| ***A61P 27/02*** | (2006.01) |
| ***A61K 31/352*** | (2006.01) |
| ***A61K 31/713*** | (2006.01) |
| ***A61K 38/10*** | (2006.01) |
| ***A61K 45/06*** | (2006.01) |

(52) U.S. Cl.

CPC .......... *C12N 15/113* (2013.01); *A61K 9/0048* (2013.01); *A61K 31/167* (2013.01); *A61K 31/195* (2013.01); *A61K 31/352* (2013.01); *A61K 31/382* (2013.01); *A61K 31/498* (2013.01); *A61K 31/5377* (2013.01); *A61K 31/557* (2013.01); *A61K 31/5575* (2013.01); *A61K 31/575* (2013.01); *A61K 31/713* (2013.01); *A61K 38/08* (2013.01); *A61K 38/10* (2013.01); *A61K 38/39* (2013.01); *A61K 45/06* (2013.01); *A61P 27/02* (2018.01); *C12N 15/1138* (2013.01); *C12N 2310/11* (2013.01); *C12N 2310/3231* (2013.01)

(58) Field of Classification Search

CPC .................................................... C12N 15/113
See application file for complete search history.

(56) References Cited

U.S. PATENT DOCUMENTS

| | | | |
|---|---|---|---|
| 3,687,808 | A | 8/1972 | Merigan et al. |
| 3,773,919 | A | 11/1973 | Boswell et al. |
| 4,485,045 | A | 11/1984 | Regen |
| 4,544,545 | A | 10/1985 | Ryan et al. |
| 4,861,757 | A | 8/1989 | Antoniades et al. |
| 5,034,506 | A | 7/1991 | Summerton et al. |
| 5,044,810 | A | 9/1991 | Matsuoka et al. |
| 5,166,195 | A | 11/1992 | Ecker |
| 5,234,809 | A | 8/1993 | Boom et al. |
| 5,948,811 | A | 9/1999 | Chan et al. |
| 5,998,148 | A | 12/1999 | Bennett et al. |

(Continued)

FOREIGN PATENT DOCUMENTS

| | | |
|---|---|---|
| DE | 3218121 | 11/1983 |
| EP | 0036676 | 9/1981 |

(Continued)

OTHER PUBLICATIONS

A. Akopian et al: "Gap Junction—Mediated Death of Retinal Neurons Is Connexin and Insult Specific: A Potential Target for Neuroprotection", The Journal of Neuroscience : The Official Journal of the Society for Neuroscience, vol. 34, No. 32, Aug. 6, 2014 (Aug. 6, 2014), pp. 10582-10591.

(Continued)

*Primary Examiner* — Kimberly Chong
(74) *Attorney, Agent, or Firm* — Duane Morris LLP

(57) ABSTRACT

The inventions relate to compositions and articles of manufacture comprising connexin modulators, pannexin modulators, gap junction modulators, hemichannel modulators, and pannexin channel modulators and their use, alone or in combination, in treating ocular and other disorders.

25 Claims, 47 Drawing Sheets
(35 of 47 Drawing Sheet(s) Filed in Color)
Specification includes a Sequence Listing.

(56) References Cited

U.S. PATENT DOCUMENTS

| | | | |
|---|---|---|---|
| 6,319,907 | B1 | 11/2001 | Ferguson |
| 6,331,298 | B1 | 12/2001 | Ferguson |
| 6,334,856 | B1 | 1/2002 | Allen et al. |
| 6,387,364 | B1 | 5/2002 | Ferguson |
| 6,455,569 | B1 | 9/2002 | Ferguson |
| 6,458,590 | B1 | 10/2002 | Mukherjee et al. |
| 6,506,559 | B1 | 1/2003 | Driver et al. |
| 6,566,339 | B1 | 5/2003 | Ferguson et al. |
| 6,611,707 | B1 | 8/2003 | Prausnitz et al. |
| 6,685,971 | B2 | 2/2004 | Xu et al. |
| 6,696,433 | B2 | 2/2004 | Ferguson et al. |
| 6,743,211 | B1 | 6/2004 | Prausnitz et al. |
| 6,752,987 | B1 | 6/2004 | Post et al. |
| 6,855,505 | B2 | 2/2005 | Ferguson et al. |
| 6,900,181 | B2 | 5/2005 | Ferguson et al. |
| 6,903,078 | B1 | 6/2005 | Williams |
| 6,991,813 | B2 | 1/2006 | Xu et al. |
| 7,052,684 | B2 | 5/2006 | Ferguson |
| 7,097,776 | B2 | 8/2006 | Raju |
| 7,098,190 | B1 | 8/2006 | Becker et al. |
| 7,153,822 | B2 | 12/2006 | Jensen et al. |
| 7,250,397 | B2 | 7/2007 | Larsen et al. |
| 7,470,787 | B2 | 12/2008 | Delong et al. |
| 7,521,191 | B2 | 4/2009 | Khvorova et al. |
| 7,627,938 | B2 | 12/2009 | Kim et al. |
| 7,671,205 | B2 | 3/2010 | Delong et al. |
| 7,786,074 | B2 | 8/2010 | Gourdie et al. |
| 7,888,319 | B2 | 2/2011 | Gourdie et al. |
| 7,918,814 | B2 | 4/2011 | Prausnitz et al. |
| 8,034,943 | B2 | 10/2011 | Delong et al. |
| 8,063,023 | B2 | 11/2011 | Becker et al. |
| 8,197,435 | B2 | 6/2012 | Prausnitz et al. |
| 8,247,384 | B2 | 8/2012 | Green et al. |
| 8,357,699 | B2 | 1/2013 | Delong et al. |
| 8,450,344 | B2 | 5/2013 | Delong et al. |
| 8,455,513 | B2 | 6/2013 | Delong et al. |
| 8,455,514 | B2 | 6/2013 | Delong et al. |
| 8,455,647 | B2 | 6/2013 | Delong et al. |
| 8,636,713 | B2 | 1/2014 | Prausnitz et al. |
| 8,716,310 | B2 | 5/2014 | Delong et al. |
| 8,808,225 | B2 | 8/2014 | Prausnitz et al. |
| 8,809,326 | B2 | 8/2014 | Bosanac et al. |
| 8,815,819 | B2 | 8/2014 | Laux |
| 8,921,392 | B2 | 12/2014 | Delong et al. |
| 8,975,237 | B2 | 3/2015 | Becker |
| 9,096,569 | B2 | 8/2015 | Delong et al. |
| 9,248,141 | B2 | 2/2016 | Becker |
| 9,302,903 | B2 | 4/2016 | Park et al. |
| 9,415,043 | B2 | 8/2016 | Kopczynski et al. |
| 9,457,044 | B2 | 10/2016 | Green |
| 9,738,892 | B2 | 8/2017 | Becker |
| 2003/0105165 | A1 | 6/2003 | Griffiih |
| 2003/0108886 | A1 | 6/2003 | Finn et al. |
| 2003/0148968 | A1 | 8/2003 | Hammond |
| 2003/0215424 | A1 | 11/2003 | Seul et al. |
| 2004/0092429 | A1 | 5/2004 | Jensen et al. |
| 2004/0259768 | A1 | 12/2004 | Lauermann |
| 2005/0026836 | A1 | 2/2005 | Dack et al. |
| 2005/0053918 | A1 | 3/2005 | Barnea et al. |
| 2005/0075280 | A1 | 4/2005 | Larsen et al. |
| 2005/0119211 | A1 | 6/2005 | Chowrira et al. |
| 2005/0137525 | A1 | 6/2005 | Wang et al. |
| 2006/0105013 | A1 | 5/2006 | Ashkar et al. |
| 2006/0122117 | A1 | 6/2006 | Smith |
| 2007/0021704 | A1 | 1/2007 | Hariri et al. |
| 2007/0232526 | A1 | 10/2007 | Kvistgaard et al. |
| 2007/0244062 | A1* | 10/2007 | Laux .................... C12N 15/113 514/44 A |
| 2007/0254828 | A1 | 11/2007 | Dubreucq et al. |
| 2008/0095819 | A1 | 4/2008 | Gourdie et al. |
| 2008/0159979 | A1 | 7/2008 | Moore et al. |
| 2008/0261867 | A1 | 10/2008 | Klagsbrun et al. |
| 2009/0142295 | A1 | 6/2009 | Becker |
| 2009/0209627 | A1 | 8/2009 | Chatterton et al. |
| 2009/0215665 | A1 | 8/2009 | Gourdie et al. |
| 2010/0150877 | A1 | 6/2010 | O'Brien et al. |
| 2010/0279921 | A1 | 11/2010 | Duft |
| 2011/0038920 | A1 | 2/2011 | Mori et al. |
| 2011/0092449 | A1 | 4/2011 | Duft |
| 2011/0130345 | A1 | 6/2011 | Rohrer et al. |
| 2011/0130710 | A1 | 6/2011 | Becker et al. |
| 2011/0217313 | A1 | 9/2011 | Becker et al. |
| 2011/0243964 | A1 | 10/2011 | Duft |
| 2011/0245184 | A1 | 10/2011 | Duft |
| 2011/0300130 | A1 | 12/2011 | Becker et al. |
| 2011/0319482 | A1 | 12/2011 | Blower et al. |
| 2012/0093768 | A1 | 4/2012 | Laux et al. |
| 2012/0289579 | A1 | 11/2012 | Becker |
| 2012/0309822 | A1* | 12/2012 | Blower ................ A61K 31/353 514/456 |
| 2013/0143952 | A1 | 6/2013 | Becker |
| 2013/0281524 | A1 | 10/2013 | Blower et al. |
| 2014/0018305 | A1 | 1/2014 | Rohrer |
| 2014/0371297 | A1 | 12/2014 | Laux |
| 2016/0331805 | A1 | 11/2016 | Green |
| 2017/0296571 | A1 | 10/2017 | Green |

FOREIGN PATENT DOCUMENTS

| | | | |
|---|---|---|---|
| EP | 0052322 | | 5/1982 |
| EP | 0058481 | | 8/1982 |
| EP | 0088046 | | 9/1983 |
| EP | 0102324 | | 3/1984 |
| EP | 0142641 | | 5/1985 |
| EP | 0143949 | | 6/1985 |
| EP | 1 514 929 | A1 | 3/2005 |
| EP | 1100529 | B1 | 6/2005 |
| EP | 2238250 | | 10/2010 |
| EP | 2242844 | A2 | 10/2010 |
| EP | 2252690 | | 11/2010 |
| EP | 2510939 | | 10/2012 |
| JP | H11-502853 | | 3/1999 |
| JP | 2002-529421 | | 9/2002 |
| JP | 2002-535377 | A | 10/2002 |
| JP | 2003-238441 | A | 8/2003 |
| JP | 2003-529567 | | 10/2003 |
| JP | 2005-509621 | | 4/2005 |
| JP | 2009-537229 | A | 10/2009 |
| WO | WO 1994/012633 | | 6/1994 |
| WO | WO 1996/19194 | A1 | 6/1996 |
| WO | WO 1998/024797 | | 6/1998 |
| WO | WO 2000/044409 | A1 | 8/2000 |
| WO | WO 2000/069896 | | 11/2000 |
| WO | WO 2002/094981 | | 11/2000 |
| WO | WO 2002/042422 | | 5/2002 |
| WO | WO 2002/056910 | | 7/2002 |
| WO | WO 2003/014303 | | 2/2003 |
| WO | WO 2003/032964 | A2 | 4/2003 |
| WO | WO 2003032964 | | 4/2003 |
| WO | WO 2003/063891 | A1 | 8/2003 |
| WO | WO 2005/053600 | A2 | 6/2005 |
| WO | WO 2005/119211 | | 12/2005 |
| WO | WO 2006/032847 | A1 | 3/2006 |
| WO | WO 2006/069181 | A2 | 6/2006 |
| WO | WO 2006069181 | | 6/2006 |
| WO | WO 2006/134494 | | 12/2006 |
| WO | WO 2006134494 | A2 | 12/2006 |
| WO | WO-2007136769 | A2 | 11/2007 |
| WO | WO 2008/060622 | A2 | 5/2008 |
| WO | WO 2008/073479 | | 6/2008 |
| WO | WO 2008/151022 | A2 | 12/2008 |
| WO | WO 2008/157840 | A2 | 12/2008 |
| WO | WO 2009/075881 | A2 | 6/2009 |
| WO | WO 2009/075881 | A3 | 6/2009 |
| WO | WO 2009/075882 | A2 | 6/2009 |
| WO | WO 2009/075882 | A3 | 6/2009 |
| WO | WO 2009/082039 | A1 | 7/2009 |
| WO | WO 2009/085268 | A2 | 7/2009 |
| WO | WO 2009/085269 | A2 | 7/2009 |
| WO | WO 2009/085270 | A2 | 7/2009 |
| WO | WO 2009/085271 | A2 | 7/2009 |
| WO | WO 2009/085272 | A2 | 7/2009 |
| WO | WO 2009/085273 | A2 | 7/2009 |
| WO | WO 2009/085274 | A2 | 7/2009 |

(56) References Cited

FOREIGN PATENT DOCUMENTS

| | | |
|---|---|---|
| WO | WO 2009/085275 A2 | 7/2009 |
| WO | WO 2009/085277 A2 | 7/2009 |
| WO | WO 2009/085268 A3 | 8/2009 |
| WO | WO 2009/085269 A3 | 8/2009 |
| WO | WO 2009/085270 A3 | 8/2009 |
| WO | WO 2009/085271 A3 | 8/2009 |
| WO | WO 2009/085273 A3 | 8/2009 |
| WO | WO 2009/085274 A3 | 8/2009 |
| WO | WO 2009/085275 A3 | 8/2009 |
| WO | WO 2009/097077 A2 | 8/2009 |
| WO | WO 2009/085277 A3 | 10/2009 |
| WO | WO 2009/147442 A1 | 12/2009 |
| WO | WO 2009/148613 A1 | 12/2009 |
| WO | WO 2009155209 | 12/2009 |
| WO | WO 2009/085272 A3 | 6/2010 |
| WO | WO 2011/067608 A1 | 6/2011 |
| WO | WO 2011072091 A1 | 6/2011 |
| WO | WO 2013012758 | 1/2013 |
| WO | WO 2013148736 | 10/2013 |
| WO | WO 2013163423 A1 | 10/2013 |
| WO | WO 2014006407 | 1/2014 |

OTHER PUBLICATIONS

"A Chinese procedure involving stem cell transplants is providing some very interesting results." Oct. 24, 2003. Canadian Paraplegic Association. Sep. 27, 2006 http://www.canparapleQic.oro/national/level12.to1?var1=storv&var2=20031024154627.

Abdullah et al. "Cell-to-Cell Communication and Expression of Gap Junctional Proteins in Human Diabetic and Nondiabetic Skin Fibroblasts." Endocrine, 1999, 10(1):35-41, Humana Press Inc.

Abstracts, Society for Neuroscience, vol. 25, Part 1, 29th Annual Meeting, Miami Beach, FL, Oct. 23-28, 1999.

Addicks, et al., "Histologic characteristics of filtering blebs in glaucomatous eyes", Arch. Opthalmol., 1983, 101:795-798.

Adwan, et al. "Downregulation of osteopontin and bone sialoprotein II is related to reduced colony formation and metastasis formation of MDA-MB-231 human breast cancer cells." Cancer Gene Therapy (2004) 11: p. 109-120: Nature Publishing Group.

Agrawal, ed., "Antisense Oligonucleotides, towards clinical trials." Protocols for Oligonucleotides and Analogs, Synthesis and Properties Human Press Inc., "Antisense Oligonucleotides, towards clinical trials." New Jersey, 1996.

Aguayo, A.J., et al. J. Exp. Biol. 95:231-240 (1981).

Ahmadi, et al. Int. Ophthalmol. Clinics, 42(3):13-22 (2002).

Aitken, et al. "Adenoviral Down-Regulation of Osteopontin Inhibits Human Osteoclast Differentiation In Vitro." Journal of Cellular Biochemistry (2004) 93: p. 896-903. Wiley-Liss, Inc.

Akopian, A., et al., "Gap Junction-Mediated Death of Retinal Neurons is Connexin and Insult Specific: A Potential Target for Neuroprotection," The Journal of Neuroscience, Aug. 6, 2014, 34(32):10582-10591.

Altschul, "A Protein Alignment Scoring System Sensitive at All Evolutionary Distances", J. Mol. Evol., 1993, 36:290-300.

Altschul, S.F. et al., "Basic Local Alignment Search Tool", J. Mol. Biol., 1990, 215:403-410.

Altschul, S.F., "A Protein Alignment Scoring System Sensitive at All Evolutionary Distances," J Mol Evol (1993) 36:290-300.

Altschul, S.F., "Basic Alignment Search Tool," J. Mol. Biol (1990) 215, 403-410.

Anonymous: "EP13153125 Align SEQ ID No. 6, 7, 31, 45, 50, 55, 60", Dec. 1, 2015, XP55232734, Retrieved from the Internet: URL:http://ibis.internal.epo.org/exam/jobResult?id=359213 [retrieved on Dec. 1, 2015].

Antisense Research and Applications (1993), CRC Press, Chps. 2, 19, 28, 32.

Arnold, et al., Seminars in Ophthalmology 17:39-46 (2002).

Ashcroft, et al. Nat Cell Biol. 1:260-6 (1999).

Baker, D.W. et al., "ACC/AHA Guidelines for the Evaluation and Management of Chronic Heart Failure in the Adult." 2001 American Colleae of Cardioloav and the American Heart Association.

Baldwin, Heather C., et al., "Growth factors in corneal wound healing following refractive surgery: A Review" ACTA Ophthalmologica Scandinavica 80(3):238-247.

Barany and Merrifield, "The Peptides," eds. E. Gross and F. Meienhofer, vol. 2 (Academic Press, 1980) DD, 3-285.

Barker, and Gourdie, R.G. (Jan. 10, 2002). Connexin Interacting Proteins. In: Heart Cell Coupling and Impulse Propagation in Health and Disease. Eds., De Mello W.C. and Janse M.J., Kluwer, Boston, pp. 25-50.

Bashyam, Hema. "Scar-Free Healing." (Jan. 7, 2008) JEM 205(1): p. 2-3.

BBC News "Gels heal wounds more quickly"; http://news.bbc.co.uk/1/hi/health/3243633.stm. (2003).

Beaucage et al., eds., Current Protocols in Nucleic Acid Chemistry John Wiley & Sons, Inc., New York, 2000.

Becker DL, Green CR (2001) Gap junction—mediated interactions between cells. Chapter 3 in Cell-Cell Interactions—A Practical Approach TP Fleming, ed., Oxford University Press, pp. 47-70.

Becker et al., Seminars in Cell and Developmental Biology, 50:49-58, 2016.

Becker, D., "Wound-healing technology shortlisted for award," University College London News, Oct. 2003, www.ucl.ac.uk/news-archive/2003/october2003/latest/newsitem.shtml?0309 . . . , captured Sep. 29, 2006.

Becker, D.L. and Davies, C.S. (1995) The role of gap junctions in the development of the preimplantation mouse embryo. In Microscopy of Intercellular Communicating Junctions. Ed. R. Gourdie. Microsc. Res. Tech. 31, 364-374.

Becker, D.L. and Mobbs, P. (1999) Connexin alpha1 and cell proliferation in the developing chick retina. Experimental. Neurol. 156(2): 326-332.

Becker, D.L., Bonness, V., and Mobbs, P. (1998) Cell coupling in the retina: Patterns and purpose. Cell Biol. Int. 22 781-792.

Becker, D.L., Bonness, V., Catsicas, M. and Mobbs, P. (2002) Changing patterns of ganglion cell coupling and connexin expression during chick retinal development. J. Neurobiol. 52, 280-293.

Becker, D.L., Ciantar, D., Catsicas, M., Pearson, R. and Mobbs, P. (2001) Use of pIRES vectors to express EGFP and connexin constructs in studies of the role of gap junctional communication in the early development of the chick retina and brain. Cell Commun. Adhes. 8. 355-359.

Becker, D.L., Cook, J.E., Davies, C.S., Evans, W.H. and Gourdie, R. (1998) Expression of major gap junction connexin types in the working myocardium of eight chordates. Cell Biol. Int. 22, 527-543.

Becker, D.L., David-Leclerc, C. and Warner A.E. (1992) The relationship of gap junctions and compaction in the preimplantation mouse embryo. Development Suppl., 113-118.

Becker, D.L., et al. "Abnormal Connexin Expression is Associated with Delayed Would Healing in Diabetic Skin", Diabetes, vol. 56, Nov. 2007.

Becker, D.L., Evans, W.H., Green C.R. and Warner, A.E. (1995) Functional analysis of amino acid sequences in connexin 43 involved in intercellular communication through gap junctions. J. Cell Sci. 108, 1455-1467.

Becker, D.L., Evans, W.H., Green C.R. and Warner, A.E. (1995) Functional block of gap junctional communication using antipeptide antibodies: Molecular localization of the putative binding sites. Intercellular communication through gap junctions: Ed. Y. Kanno. Progress in Cell Research, 4; 427-430.

Becker, D.L., Lin, J.S. and Green G.R. (1999) Pluronic gel as a means of antisense delivery. In Antisense techniques in the CNS. A practical approach. Eds. R. Leslie, A.J. Hunter and H.A. Robertson, pp. 149-157.

Becker, D.L., McGonnell, I., Makarenkova, H., Patel, K., Tickle, C., Lorimer, J., and Green, C.R. (1999) Roles for alpha1 connexin in morphogenesis of chick embryos using a novel antisense approach. Dev. Genetics. 24, 33-42.

Beeley N., Trends Biotechnol. Jun.;12(6): 213-6 (1994).

(56) References Cited

OTHER PUBLICATIONS

Behrend, et. al. "Reduced Malignancy of ras-transformed NIH 3T3 Cells Expressing Antisense Osteopontin RNA." Cancer Research (Feb. 1, 1994) 54: p. 832-837.
Bennett, Zukin RS. Electrical coupling and neuronal synchronization in the Mammalian brain. Neuron. Feb. 19, 2004; 41(4):495-511.
Berge, et al., J. of Pharma Sci. 66, 1-19 (1977).
Berkovitz, B.K.B. and Becker, D.L. (2003) The detailed morphology and distribution of gap junction protein associated with cells from the intra-articular disc of the rat temporomandibular joint. Conn. Tiss. Res. 44, 12-18.
Bernstein, et al. Invest Ophthalmol Vis Sci 44:4153-4162 (2003).
Berthoud, et al, "Peptide inhibitors of intercellular communication", Am. J. Physiol. Lung Cell Mol. Physiol., 2000, 279:L619-L622.
Berthoud, V.M. and Seul, K.H., Am J. Physiol. Jung Cell Mol. Physiol. 279:L619-L622 (2000).
Bindlish et al., "Efficacy and safety of mitomycin-C in primary trabeculectomy: five-year follow-up", Ophthalmology, 2002, 109:1336-1341 & discussion 1341-1332.
Bioconjugate Techniques (Greg T. Hermanson, ed., Academic Press, 1996), Chapter 2 and 17.
Bittman, K., et al. (2002) Connexin expression in homotypic and heterotypic cell coupling in the developing cerebral cortex. J. Compo Neural 443, 201-212.
Blackburn JP, Connat JL, Severs NJ, Green CR. "Connexin43 gap junction levels during development of the thoracic aorta are temporally correlated with elastic laminae deposition and increased blood pressure." Cell Biol Int. Feb. 1997;21(2):87-97. PMID: 9080656 [PubMed—indexed for MEDLINE.
Blackburn JP, Peters NS, Yeh HI, Rothery S, Green CR, Severs NJ. "Upregulation of connexin43 gap junctions during early stages of human coronary atherosclerosis." Arterioscler Thromb Vase Biol. Aug. 1995;15(8):1219-28. PMID: 7627716 [PubMed—indexed for MEDLINE].
Bobbie et al., "Reduced connexin 43 expression and its effect on the development of vascular lesions in retinas of diabetic mice", Invest. Ophthalmol. Vis. Sci., 2010, 51(7):3758-63.
Boitano S. and Evans W., Am J Physiol Lung Cell Mol Physiol 279:L623-L630 (2000).
Boitano, et al., "Connexin mimetic peptides reversibly inhibit Ca2+ signaling through gap junctions in airway cells", Am. J. Physiol Lung Cell Mol. Physiol., 2000, 279:L623-L630.
Bork et al. Go hunting in sequence databases but watch out for the traps. Trends in Genetics. 12(10): 425-427, 1996.
Bork, A. "Powers and pitfalls in sequence analysis: the 70% hurdle." Genome Res 1O: 398-400, 2000.
Braasch, D.A. and Corey, D.R., Biochemistry 41, 4503-451 O (2002).
Braet, K., et al., "Pharmacological senstivity of aTP release triggered by photoliberation of inositol-1,4,5- triphosphate and zero extracellular calcium in brain endothelial cells," Journal of Cellular Physiology, 197(2):205-213 (2003).
Branch, A.D. Hepatology 24, 1517-1529 (1996).
Branch, et. al. "A good antisense molecule is hard to find." TIBS (Feb. 1998) 23: p. 45-50. Elsevier Science Ltd.
Brandner, et. al., "Connexins 26, 30, and 43: Differences Among Spontaneous, Chronic, and Accelerated Human Wound Healing." J. Invest Dermatol. 122:1310-20 (2004).
Bregman, B.S., Experimental Neurology 149, 13-27 (1998).
Brenner, S.E. Errors in genome function. Trends in Genetics 15(4): 132-133, 1999.
Brummelkamp T., et al., Science 296:550-553 (2002).
Brysch, W. "Antisense Technology in the Ventral Nervous System", ed. H.A. Robertson; Oxford University Press, pp. 21-41 (1999).
Buono, et al. Survey of Ophthalmology 50:15-26 (2005).
Buur, et al. J. Control Rel. 14:43-51 (1990).
Cairns, et al. Nat. Biotech 17:480-486 (1999).
Calabrese, A., "Connesin 36 Controls Snychronization of Ca2+ Oscillations and Insulin Secretion in MIN6 Cells," Diabetes, vol. 52, Feb. 2003.
Camelliti P, Devlin GP, Matthews KG, Kohl P, Green CR. Spatially and temporally distinct expression of fibroblast connexins after sheep ventricular infarction. Cardiovasc Res. May 1, 2004 ;62(2):415-25. PMID: 15094361 [PubMed—indexed for MEDLINE].
Camelliti P, Green CR, Kohl P. Structural and functional coupling of cardiac myocytes and fibroblasts. Adv Cardiol. 2006;42:132-49. Review. PMID: 16646588 [PubMed—indexed for MEDLINE].
Caplen N. et al., Proc Natl Acad Sci 98:9742-9747 (2001).
Cech, Biotechnology 13:323 (1995) Group I Introns: New Molecular Mechanisms for MRNA repair.
Celetti, et. al. "Overexpression of the Cytokine Osteopontin Identifies Aggressive Laryngeal Squamous Cell Carcinomas and Enhances Carcinoma Cell Proliferation and Invasiveness." (2005) Clinical Cancer Res 11(22): p. 8019-8027. AACR Journals.
Chakraborti, S. and Banerjee, A.C., Mol. Thar. 7, 817-826 (2003).
Chang CY, et al. "Comparison of stem cell properties in cell populations isolated from human central and limbal corneal epithelium." Cornea. Oct. 2011;30(10):1155-1162.
Chen et al. Cytotoxicity and vitreous stability of chemically modified connexin43 mimetic peptides for the treatment of optic neuropathy. Journal of Pharmaceutical Science. 2013;102:2322-2331.
Chen et al. Intravitreal injection of lipoamino acid modified Connexin43 mimetic peptide enhances neuroprotection after retinal ischemia. Drug Deliv Transl Res. 2015; 5:480-488.
Chen et al. Sustained intravitreal delivery of connexin43 mimetic peptide by poly(D,L-lactide-co-glycolide) acid micro- and nanoparticles—Closing the gap in retinal ischaemia. European Journal of Pharmaceutics and Biopharmaceutics. 2015. 95(Pt B):378-386.
Chen Ying-Shan et al: "Neuroprotection in the treatment of glaucoma—A focus on connexin43 gap junction channel blockers", European Journal of Pharmaceutics and Biopharmaceutics, Elsevier Science Publishers B.V., Amsterdam, NL, vol. 95, Feb. 9, 2015 (Feb. 9, 2015), pp. 182-193.
Chen YS, et al "Neuroprotection in the treatment of glaucoma—A focus on connexin43 gap junction channel blockers" Eur J Pharm Biopharm. Sep. 2015;95(Pt B):182-193.
Chen, et al, "In vitro release characteristics and cellular uptake of poly(D, L-lactic-co-glycolic acid) nanoparticles for topical delivery of antisense oligonucelotides", Drug Delivery, 2011, 18:493-50.
Chen, et al., "Cytotoxicity and vitreous stability of chemically modified connexin-43 mimetic peptides for the treatment of optic neuropathy", J. Pharm. Sci., 2013, 102:2322-2331.
Cheng et al. "Spinal Cord Repair in Adult Paraplegic Rats: Partial Restoration of Hind Limb Function" Science, Jul. 26, 1996, 273:510-513.
Cheng et al., J. Biol. Chem. 263:15110-15117 No. 29, (Oct. 15, 1998).
Cheng, et al., TrkB Gene Transfer Protects Retinal Ganglion Cells from Axotomy-Induced Death in Vivo., J. Neurosci., 2002, 22:3977-3896.
Chew SS, et al "Response of retinal Connexin43 to optic nerve injury." Invest Ophthalmol Vis Sci. Jun. 1, 2011;52(6):3620-3629.
Chew, et al., "Response of Retinal Connexin43 to Optic Nerve Injury", Invest. Ophthalmol. Vis. Sci., 2011, 52:3620-3629.
Chonn, et al., Current Op. Biotech. 6, 698-708 (1995).
Chou et al. "Quantitative Analysis of Dose-Effect Relationships: The Combined Effects of Multiple Drugs or Enzyme Inhibitors", Ad. Enzyme Reg., 1984, 22:27-55.
Chou, C., Current Protocols in Nucleic Acid Chemistry (2000) 10.1.1-10.1.25.
Coffey KL, Krushinsky A, Green CR, Donaldson PJ. "Molecular profiling and cellular localization of connexin isoforms in the rat ciliary epithelium." Exp Eye Res. Jul. 2002;75(1):9-21. PMID: 12123633 [PubMed • indexed for MEDLINE].
Collaborative Neuroscience the Spinal Cord Injury Project. Care Cure Community Postings for "Gel is helping wounds heal in half the time'/nexagon." Sep. 29, 2006 http://sci.rutqers.edu/forum/showthread.php?t=6653.

(56) References Cited

OTHER PUBLICATIONS

Collaborative Normal-Tension Glaucoma Study Group, Comparison of glaucomatous progression between untreated patients with normal-tension glaucoma and patients with therapeutically reduced intraocular pressures, Am. J. Ophthalmol., 1998, 126:487-497.
Collignon et al., Ophthalmology 111 : 1663-1672 (2004).
Common, J.E.A, Becker, D.L., Di, W.L., Leigh, I.M., O'Toole, E.A. and Kelsell, D.P. (2002) "Functional studies of human skin disease- and deafness-associated Connexin 30 mutations." Biochem. Biophys. Res. Commun. 298, 651-656.
Concise Encyclopedia of Polymer Science and Engineering, pp. 858-859 (1990).
Contreras, et al., "Functioning of Cx43 Hemichannels Demonstrated by Single Channel Properties, Cell Communication and Adhesion", 2003, 10(4-6):245-249.
Cook, J.E. and Becker, D.L. (1995) Gap Junctions in the vertebrate retina. In Microscopy of Intercellular Communicatina Junctions. Ed. R. Gourdie. Microsc. Res. Tech. 31, 408-419.
Cooper, et.al. "Wound healing and inflammation genes revealed by array analysis of macrophageless PU.I null mice." Genome Biology (2004) 6(I): Article 5.
Corredor and Goldberg, "Retinal Ganglion Cell Life and Death—Mechanisms and Implications for Ophthamology," European Ophthalmology Review Touch Briefings, p. 109-112 (2009).
Cotrina, et al. "Astrocytic gap junctions remain open during eschemic conditions." J. Neurosci., 18:2520-2537.
Cotter et al. Curr Opin Cardiol 16: 159-163, 2001.
Courtman, et al. J Biomed Mater Res 28:655-666 (1994).
Coutinho, et al. "Dynamic Changes in connexin expression correlate with key events in the wound healing process." Cell Biology International 27 (2003) 525-541.
Coutinho, P., Frank, S., Qiu, C., Wang, C.M., Brown, T., Green, C.R. and Becker D.L. (2005) Limiting wound extension by transient inhibition of connexin43 expression at the site of injury. Brit. J. Plast. Surg. 58, 658-667.
Crooke et al., J. Pharmacol. Exp. Ther., 1996, vol. 277, 923-937.
Crowe, M. et al., "Delayed Wound Healing in Immunodeficient TGF-βi Knockout Mice", *J. Invest. Dermatol.*, 2000, 115:3-11.
Cupps, et al., "Corticosteroid-mediated immunoregulation in man", Immunol. Rev., 1982, 65:133-155.
Current Protocols in Immunology (J.E. Coligan et al., eds., 1991) vol. I, Ch. 1.
Current Protocols in Molecular Biology (F.M. Ausubel et al., 1987, including supplements through 2001).
Cutroneo, K., "How Is Type I Procollagen Synthesis Regulated at the Gene Level During Tissue Fibrosis", *J. Cell. Biochem.*, 2003, 90:1-5.
Dagle et al., Nucleic Acids Research 19:1805 (1991).
Dahl G., et al., Biophys J 67:1816-1822 (1994).
Dahl, et al., "Attempts to Define Functional Domains of Gap Junction Proteins with Synthetic Peptides", Biophys. J., 1994, 67:1816-1822.
Danesh-Meyer et al. Connexin43 in retinal injury and disease. Prog Retinal Eye Res 51: 41-68, 2016.
Danesh-Meyer et al. Connexin43 mimetic peptide reduces vascular leak and retinal ganglion cell death following retinal ischaemia. Brain 135: 506-520, 2012.
Danesh-Meyer, et al., "Connexin43 mimetic peptide reduces vascular leak and retinal ganglion cell death following retinal ischaemiam", Brain, 2012, 135, p. 506.
Dang, et al. "The carboxy-tail of connexin-43 localizes to the nucleus and inhibits cell growth." Molecular and Cellular Biochemistry (2003) 242: p. 35-38. Kluwer Academic Publishers. Netherlands.
Dao-Yi et al. Pathogenesis and intervention stratedies in diabetic retinopathy. Clin Exp Ophthalmol 29: 164-166, 2001.
Darrow, B.J., "Expression of Multiple Connexins in Cultured Neonatal Rat Ventricular Myocytes," Circulation Research, 1995; 76:381-387.
Das, et al., "Protection of retinal cells from ischemia by a novel gap junction inhibitor", Biochem. Biophys. Res. Commun., 2008, 373:504-508.
Database EMBL, Jul. 9, 2006, "Rattus norvegicus piRNA piR-152346, complete sequence." Retrieved from EBI accession No. EMBL: DQ737024.
Database Geneseq, Dec. 28, 2007, "Viral regulatory miRNA SEQ ID No. 263327" Retrieved from EBI accession No. GSN: AJK11008.
Database Geneseq, Dec. 28, 2007, "Viral regulatory miRNA SEQ ID No. 286128" Retrieved from EBI accession No. GSN AJK33809.
Davidson JO, et al "Battle of the hemichannels—Connexins and Pannexins in ischemic brain injury." Int J Dev Neurosci. Oct. 2015;45:66-74.
Davidson JO, et al "Connexin hemichannel blockade is neuroprotective after asphyxia in preterm fetal sheep" PLoS One. May 27, 2014;9(5):e96558.
Davidson JO, et al "Deleterious effects of high dose connexin 43 mimetic peptide infusion after cerebral ischaemia in near-term fetal sheep." Int J Mol Sci. 2012;13(5):6303-6319.
Davidson JO, et al "Non-additive effects of delayed connexin hemi channel blockade and hypothermia after cerebral ischemia in near-term fetal sheep." J Cereb Blood Flow Metab. Dec. 2015;35(12):2052-2061.
Davidson JO, et al. "A key role for connexin hemichannels in spreading ischemic brain injury." Curr Drug Targets. Jan. 1, 2013;14(1):36-46.
Davidson JO, et al. "Connexin hemichannel blockade improves outcomes in a model of fetal ischemia" Ann Neurol. Jan. 2012;71(1):121-132.
Davidson, J.O. et al., Connexin Hemichannel Blockade is Neuroprotective After, But Not During, Global Cerebral Ischemia in Near-Term Fetal Sheep, Experimental Neurology, 2013, 248:301-308.
Davidson. "Animal Models for Wound Repair." Arch Dermatol. Res., 1998, 290:S1-S11, Springer-Verlag.
Davis, et al. "Modulation of Connexin43 Expression: Effects on Cellular Coupling" Journal of Cardiovascular Electroohvsioloav, Futura Publishina Co., 6(2):103-114 (1995).
De Carvalho, A.C.C., "Conduction Defects and Arrhythmias in Chagas' Disease: Possible Role of Gap Junctions and Humoral Mechanisms," J Cardiovasc Electrophysiol, vol. 5, pp. 686-698, Aug. 1994.
De Jong, "Age-related macular degeneration", N. Engl. J. Med., 2006, 355:1474-1485.
De Vries and Schwartz, "Hemi-gap-junction channels in solitary horizontal cells of the catfish retina " Journal of Physiology, 445:201-230 (1992).
De Vriese, A.S., Kidney International, vol. 61 (2002), pp. 177-185.
Decrock E, et al "Connexin and pannexin signaling pathways, an architectural blueprint for CNS physiology and pathology?" Cell Mol Life Sci. Aug. 2015;72(15):2823-2851.
Deitz, et al. Ophthalmology 93:1284 (1986).
Deva, N.C., et al., "Connexin43 Modulation Inhibits Scarring in a Rabbit Eye Glaucoma Trabeculectomy Model," Inflammation, vol. 35, No. 4, Aug. 2012.
Devereux, et al. Nucleic Acids Research 12:387-395 (1984).
Devereux, J. et al., "A comprehensive set of sequence analysis programs for the VAX", Nucleic Acids Research, 1984, 12(1):387-395.
Devlin, G., et al. J. "An ovine model of chronic stable heart failure" J. Card. Fail. 6:140-143 (2000).
Devriese, A.S., et al., "Effectsof connexin-mimetic peptides on nitric oxide syntase- and cyclooxygenase-independent renal vasodilation", Kidney Int., 2002, 61:177-185.
Dhein, et al., "A new synthetic antiarrhythmic peptide reduces dispersion of epicardial activation recovery interval and diminishes alterations of epicardial activation patterns induced by regional ischemia. A mapping study", Naunyn-Schmiedeberg's Arch. Pharm., 1994, 350:174-184.
Dhein, et al.,"Effects of the New Antiarrhythmic Peptide ZP123 on Epicardial Activation and Repolarization Pattern," Cell Commun. Adhes., 2003, 10:371-378.
Di, W.-L., Lachelin, G.C.L., McGarrigle, H.H.G., Thomas, N.S.B. and Becker, D.L. (2001) Oestriol and oestradiol increase cell to cell

(56) References Cited

OTHER PUBLICATIONS communication and connexin 43 protein expression in cultured human mvometrial cells. Mol. Human Reorod. 7, 671-679.
Dias, N. and Stein, C.A. Mol. Cancer Thor. 1347-355 (2002).
Diegelmann, et al. "Wound Healing: An Overview of Acute, Fibrotic and Delayed Healing." (Jan. 1, 2004) Frontiers in Bioscience 9: p. 283-289. Irvine, CA.
Dixon et al., VEGF Trap-Eye for the treatment of Neovascular age-related macular degeneration, Expert Opinion on Investigational Drugs, 18:1573-1580 (2009).
Doerks et al. Protein annotation: detective work for function prediction. Trends in Genetics 14(6): 248-250, 1998.
Dovi, J.V., et al. J Leukoc Biol 73:448-55 (2003).
Dublin, et al. "Satellite glial cells in sensory ganglia: Their possible contribution to inflammatory pain." (2007) Brain, Behaviior, and Immunity 21: p. 592-598. Elsevier Inc.
Duffy, H.S., Ashton, AW., O'Donnell, P., Coombs, W., Taffet, S.M., Delmar, M., and Spray, D.C. (Feb. 6, 2004). Regulation of connexin43 protein complexes by intracellular acidification. Circ. Res. 94, 215-222.
Eckstein, F., ed. Oligonucleotides and Analogues, A Practical Approach, IRL Press at Oxford University Press (1991).
Edgington, Biotechnology 10:256 (1992).
Einarson, M.B. et al., "Identification of Protein—Protein Interactions with Glutathione S—Transferase Fusion Proteins," In Protein-Protein Interactions: A Molecular Cloning Manual, Cold Springs Harbor Laboratory Press DD., Chapt. 4, pp. 37-57 (2002).
Elbashir S., et al., "Duplexes of 21-nucleotide RNAs mediate RNA interference in cultured mammalian cells." Nature 411 :494-498 (2001).
El-Fouly, et al., "Scrape-Loading and dye transfer: A rapid and simple technique to study gap junctional intercellular communication", Experimental Cell Research, 1987, 168(2):422-430.
El-Hariri, et al. J. Pharm. Pharmacol. 44:651-654 (1992).
Englisch et al., Angewandte Chemie, International Edition, 30, 613-722 (1991).
Evans and Boitano, "Connexin mimetic peptides: specific inhibitors of gap-junctional intercelluar communication", Biochem. Soc. Trans., 2001, 29(Pt. 4):606-612.
Evans et al., J. Med. Chem. 30:1229 (1987).
Evans, W.H., et al. "Connexin mimetic peptides: specific inhibitors of gap-junctional intercellular communication." Biochem. Soc. Trans., 2001, 29:606-612.
Fairless, R. et al., "N-cadherin differentially determines Schwann cell and olfactory ensheathing cell adhesion and migration responses upon contact with astrocytes", Mol. Cell. Neurosci., 2005, 28(2):253-263.
Fauchere, J. Adv. Drug Res. 15:29 (1986).
Fearon, K.L., Current Protocols in Nucleic Acid Chemistry (2000) 4.7.1-4.7-40.
Ferrin, Lance J. and Camerini-Otero, R. Daniel. "Selective Cleavage of Human DNA: RecA-Assisted Restriction Endonuclease (RARE) Cleavage." Science, Dec. 6, 1991, 254:1494-1497.
Finger, et al., "Opthalmic plaque radiotherapy for age-related macular degeneration associated with subretinal neovascularization", Am. J. Opthalmol., 1999, 127:170-177.
Fingl, et al., In: The Pharmacological Basis of Therapeutics, Ch.1, p. 1, 1975.
Flower NE, and Green CR. A new type of gap junction in the phylum Brachiopoda. Cell Tissue Res. 1982;227(1 ):231-4.
Fonseca CG, Green CR, Nicholson LF. Upregulation in astrocytic connexin 43 gap junction levels may exacerbate generalized seizures in mesial temporal lobe epilepsy. Brain Res. Mar. 1, 2002; 929(1): 105-16. PMID: 11852037 [PubMed—indexed for MEDLINE].
Foote et al. "The Pattern of Disulfide Linkages in the Extracellular Leep Regions of Connexin 32 Suggests a Model for the Docking Interface of Gap Junctions." Journal of Cell Biology, 1998, 140(5):1187-1197.
Ford et al., "Expression and role of VEGF-A in the ciliary body", Invest. Ophthalmol. Vis. Sci., 2012, 53:7520-7527.
Forge, "The inner ear contains heteromeric channels composed of cx26 and cx30 and deafness-related mutations in cx26 have a dominant negative effect on cx30", Cell Commun. Adhes., 2003, 10(4-6):341-346.
Forge, A, Becker, D.L., Casalotti, S., Edwards, J., Evans, W.H., Lench, N. and Souter, M. (1999) Gap junctions and connexin expression in the inner ear. In gap junction-mediated intercellular signalling in health and disease. Novartis foundation symposium 219. 134-156. Wiley.
Forge, A., Becker, D.L., Casalotti, S., Edwards, J., Marziano, N. and Nevill, G. (2003) Gap Junctions in the Inner Ear: Comparison of Distribution Patterns in Different Vertebrates and Assessment of Connexin Composition in Mammals, J. Comp. Neurol. 467, 207-231.
Forge, A., Becker, D.L., Casalotti, S., Edwards, J., Marziano, N. and Nickel, R. (2002) Connexins and gap junctions in the inner ear. Audiol. Neuro. Otol. 7 141-145.
Forge, A., Marziano, N., Casalotti, S.O., Becker, D.L. and Jagger, D. (2003). The inner ear contains heteromeric channels composed of Cx26 and Cx30 and deafness-related mutations in Cx26 have a dominant negative effect on Cx30. Cell Commun. Adhes. 10, 341-346.
Fortes, P. et al., Proc. Natl. Acad. Sci. USA 100, 8264-8269 (2003).
Foulkes MR, et al., Stroke 19:547-54 (1988).
Frantseva, M., et al. "Ischemia-Induced Brain Damage Depends on Specific Gap-Junctional Coupling." Journal of Cerebral Blood Flow and Metabolism, 22:453-462 (2002).
Fraser SE, Green CR, Bode HR, Gilula NB. Selective disruption of gap junctional communication interferes with a patterning process in hydra. Science. Jul. 3, 1987;237(4810):49-55. PMID: 3037697 [PubMed—indexed for MEDLINE].
Friedman et al., "Prevalence of age-related macular degneration in the United States", Arch. Ophthalomol., 2004, 122:564-572.
Galasso, et al. Seminars in Ophthalmology 19:75-77 (2004).
Garcia-Dorada et al. "Gap Junction Uncoupler Heptanol Prevents Cell-to- Cell Progression of Hypercontracture and Limits Necrosis During Myocardial Reperfusion", Circulation, Nov. 18, 1997, 96(10):3579-3586.
Gee et al., in Huber and Carr, 1994, "Molecular and Immunologic Approaches," Futura Publishing co, Mt. Kisco NY.
Gerrits, et al., Pediatr Res 57(3):342-6 (2005).
Ghatnekar et al. Regrn Med. 4(2):205-223, 2009.
Giaume, C., et al. "Control of gap-junctional communication in astrocytic networks." TINS, 19:319-325.
Giepmans BN. Gap junctions and Connexin-interacting proteins. Cardiovasc Res. May 1 ;62(2):233-45 (May 1, 2004).
Giepmans et al. "Interaction of c-Src with gap junction protein connexin-43. Role in the regulation of cell-cell communication." J Biol. Chem., 2001, 276(11):8544-8549.
Gil, J., Esteban M., "Induction of apoptosis by the dsRNA-dependent protein kinase (PKR): Mechanisms of action." Apoptosis 2000, 5:107-114.
Gil-Parrado, S., et al. (Mar. 2003). Calpastatin exon 1 B-derived peptide, a selective inhibitor of calpain:enhancing cell permeability by conjugation with penetratin. Biol Chem 3 84, 395-402.
Goadsby, Peter J. "Bench to bedside advances in the 21st century for primary headache disorders: migraine treatments for migraine patients." (2016): Brain, 139(10), 2571-2577.
Goliger et al. "Wounding Alters Epidermal Connexin Expression and Gap Junction-mediated Intercellular Communication." Molecular Biology of the Cell, 1995, 6:1491-1501.
Gonzalez-Mariscal, L. et al. (Jan. 2003). Tight junction proteins, Prog Biophys Mol Biol 81, 1-44.
Goodenough et al. "Topological Distribution of Two Connexin32 Antigenic Sites in Intact and Split Rodent Hepatocyte Gap Junctions." J Cell Biol., 1988, 107:1817-1824.
Goodenough et al. (Apr. 2003). Beyond the gap: functions of unpaired connexon channels. Nat Rev Mol Cell Biol 4, 285-294.
Goodenough, "Topological distribution of two connexin32 antigenic sites in intact and split rodent hepatocyte gap junctions", J. Cell Biol., 1988, 107:1817-1824.
Görbe, A., Becker, D.L, Dux, L. and Krenacs, T. (2005) In differentiating prefusion myoblasts connexin43 gap junction coupling is

(56) References Cited

OTHER PUBLICATIONS upregulated before myoblast alignment then reduced in postmitotic cells. Histochem Cell Biol 123:573-583 [Epub May 14, 2005].
Görbe, A., Becker, DL., Dux, L., Stelkovics, E., Krenacs, L., Bagdi, E., and Krenacs, T. (2005) Transient upregulation of connexin 43 gap junction coupling in myoblasts may synchronize cell cycle control preceding syncytial fusion during skeletal muscle differentiation Histochem. Cell Biol. 123; 573-583.
Gourdie RG, Green CR, Severs NJ, Anderson RH, Thompson RP. Evidence for a distinct gap-junctional phenotype in ventricular conduction tissues of the developing and mature avian heart. Circ Res. Feb. 1993;72(2):278-89. PMID: 8380357 [PubMed—indexed for MEDLINE].
Gourdie RG, Green CR, Severs NJ. Gap junction distribution in adult mammalian myocardium revealed by an anti-peptide antibody and laser scanning confocal microscopy. J Cell Sci. May 1991;99 (Pt 1):41-55. PMID: 1661743 [PubMed—indexed for MEDLINE].
Gourdie RG, Harfst E, Severs NJ, Green CR. Cardiac gap junctions in rat ventricle: localization using site-directed antibodies and laser scanning confocal microscopy. Cardioscience. Mar. 1990;1(1 ):75-82 PMID: 1966373 [PubMed—indexed for MEDLINE].
Gourdie, et al. "Immunolabeling patterns of gap junction connexins in the developing and mature rat heart." Anat Embrvol 185:363-378 (1992).
Gourdie, et al. "The spatial distribution and relative abundance of gap-junctional connexin40 and connexin43 correlate to functional properties of components of the cardiac atrioventricular conduction system." Journal of Cell Science 105, 985-991 (1993).
Gourdie, et al. "The Unstoppable Connexin43 Carboxyl-Terminus" (2006) Ann. N.Y. Acad. Sci. 1080: p. 49-62. New York Academy of Sciences.
Grazul-Bilska, et al. Abstract, Biology Reproduction, 58(1):78 (1998).
Green and Severs. "Distribution and role of gap junctions in normal myocardium and human ischaemic heart disease." Histochemistry, 1993, 99: 105-120.
Green C.R, Law, L.Y., Lin, U.S. and Becker, D.L. (2001) "Spatiotemporal depletion of connexins using antisense oligonucleotides. Techniques in the study of gap junctions." Connexin methods and protocols 154 175-185. Eds R. Bruzzone and C. Giuame.
Green CR, Bowles L, Crawley A, Tickle C. Expression of the connexin43 gap junctional protein in tissues at the tip of the chick limb bud is related to the epithelial-mesenchymal interactions that mediate morohoaenesis. Dev Biol. Jan. 1994;161(1):12-21. PMID: 8293868 [PubMed—indexed for MEDLINE].
Green CR, Harfst E, Gourdie RG, Severs NJ. Analysis of the rat liver gap junction protein: clarification of anomalies in its molecular size. Proc R Soc Lond B Biol Sci. Mar. 22, 1988;233(1271): 165-74. PMID: 2898146 (PubMed—Indexed for MEDLINE).
Green CR, Peters NS, Gourdie RG, Rothery S, Severs NJ. "Validation of immunohistochemical quantification in confocal scanning laser microscopy: a comparative assessment of gap junction size with confocal and ultrastructural techniques." J Histochem Cytochem. Sep. 1993;41 (9):1339-49. PMID: 8354875 [PubMed—indexed for MEDLINE].
Green CR, Severs NJ. Connexon rearrangement in cardiac gap junctions: evidence for cytoskeletal control? Cell Tissue Res. 1984;237(1):185-6. PMID: 6090023 [PubMed—indexed for MEDLINE].
Green CR, Severs NJ. Gap junction connexon configuration in rapidly frozen myocardium and isolated intercalated disks. J Cell Biol. Aug. 1984•99(2):453-63.
Green CR. Evidence mounts for the role of gap junctions during development. Bioessays. Jan. 1988;8(1):7-10. Review. No abstract available. PMID: 2835035 [PubMed—indexed for MEDLINE].
Greene CA, "Cells from the adult corneal stroma can be reprogrammed to a neuron-like cell using exogenous growth factors." Exp Cell Res. Mar. 10, 2014;322(1):122-132.
Greenfield et al., "Late-onset bleb leaks after glaucoma filtering surgery", Arch.Opthalmol., 1998, 116:443-447.
Grose, R. et al.., "Wound-Healing Studies in Transgenic and Knockout Mice", *Molecular Biotechnology*, 2004, 28:147-166.
Grupcheva CN, et al "Improved corneal wound healing through modulation of gap junction communication using connexin43-specific antisense oligodeoxynucleotides." Invest Ophthalmol Vis Sci. Mar. 2, 2012,53(3):1130-1138.
Guadana, et al., "Ocular Drug Delivery", The AAPS Journal, 2010, 12(3):348-360.
Guan, et al., Neuroscience, vol. 95, No. 3, pp. 831-839 (2000).
Gunn, et al., J Clin Invest 99(2):248-256 (1997).
Gunn, et al., Pediatr Res 46(3):274-280 (1999).
Guo CX, et al.. "Gap junction proteins in the light-damaged albino rat." Mol Vis. May 27, 2014;20:670-682.
Guo et al. Connexin43 mimetic peptide improves retinal function and reduces inflammation in a light damaged albino rat model. *Investigative Ophthalmology and Visual Science*, 2016; 57: 3961-3973.
Hall, Celia. "Gel is helping wounds heal in half the time." Telegraph UK. Oct. 20, 2003. http://www.telegraph.co.u k/news/main.i htm il?xml=/news/2003/10/20/nQe 120.xml&sSheet==.
Han Chunmao, et al. "Optimal time for the administration of rhGH in severely burned patients-analysis of the dynamic changes in IGF axis and blood sugar," Aug. 31, 2003, Chin J. Burns, vol. 19, No. 4 pp. 213-215.
Haopeng, L., Abstract: "Experimental study on spinal cord injury treated with the combination of fetal spinal cord transplantation and methylprednisolone," j Xi'an Med Uni (2001) vol. 13, No. 2, pp. 138-141.
Hardman, et al. McGraw-Hill, New York, N.Y., 934-935 (1996).
Hardy, K., Spanos, S. and Becker, D.L. (2003) Cell death (Apoptosis) in human blastocysts. Chpt. 9 p. 185-202 an Atlas of Human Blastocvsts. Eds. L.L. Veeck and N. Zaninovic. CRC Press.
Hardy, K., Warner, A.E., Winston, R.M.L. and Becker, D.L. (1996) Expression of intercellular junctions durino the preimolantation develooment of the human embrvo. Molec. Human Reprod. 2, 621-632.
Harfst E, Severs NJ, Green CR. Cardiac myocyte gap junctions: evidence for a major connexon protein with an apparent relative molecular mass of 70,000. J Cell Sci. 1990 Aua;S6 (Pt 4):591-604.
Harlow and Lane ( 1988) Antibodies, A Laboratory Manual, Cold Spring Harbor Publications, New York.
Harlow and Lane (1988) Antibodies, A Laboratory Manual, Cold Spring Harbor Publications, New York, 5 Pages.
Harlow and Lane (1999) Using Antibodies: A Laboratory Manual Cold Spring Harbor Laboratory Press, Cold Spring Harbor, NY, pp. 189-242, 511-531.
Haseloff and Gerlach, Nature Aug. 18;334(6183):585-91 (1988).
Hauge et al., Effects of tonabersat on migraine with aura: a randomised, double-blind, placebo-controlled crossover study, The Lancet Neurology, 2009, 8:718.
Hawat et al., "Connexin 43 mimetic peptide Gap26 confers protection to intact heart against myocardial ischemia injury," Pflugers Arch.—Eur. J. Physiol. 460(3):583-592 (Jun. 1, 2010).
Heasman, J., Dev. Biol., 243, 209-214 (2002).
Heijl et al., Reductionb of intraocular pressure and glaucoma progression: results from the Early Manifest Glaucoma Trial, Arch. Opthalmol., 2002, 120:1268-1279.
Henikoff and Henikoff. "Amino acid substitution matrices from protein blocks." Proc. Natl. Acad. Sci. USA, 1992, 89:10915-10919.
Hennemann et al. "Molecular cloning. of mouse connexins26 and -32: similar genomic organization but distinct promoter sequences of two gap junction genes" European Journal of Cell Biology, 1992, 58(1):81 -89.
Herbertt, et. al. "Protein Kinase C a Expression is required for heparin inhibition of rat smotth muscle cell proliferation in vitro and in vivo." (Oct. 18, 1996) J Biol Chem. 271(42):259 p. 28-35. The American Society for Biochemistry and Molecular Biology, Inc. U.S.A.
Herve et al. Diversity in protein-protein interactions of connexins: emerging roles. Biochim Biophys Acta 1662: 22-41, 2004.
Higginbotham et al., "Bleb-related endophthalmitis after trabeculectomy with mitomycin C", Opthalmology, 1996, 103:650-656.

(56) References Cited

OTHER PUBLICATIONS

Ho et. al. "Ischemic Optic Neuropathy Following Spine Surgery." Journal of Neurosurgical Anesthesiology, Jan. 2005, 17(1):38-44.
Hodgins, M. "Connecting Wounds with Connexins" J. Invest. Dermatol. 122:(5):ix-x commentary (2004).
Honjo, Megumi, et al. "Effects of rho-associated protein kinase inhibitor Y-27632 on intraocular pressure and outflow facility." Investigative Ophthalmology & Visual Science 42.1 (2001): 137-144.
Huang, et al. J Cell Biol 143:1725-34 (1998).
Hunter, et al. "Zonula occludens-1 alters connexin43 gap junction size and organization by influencing channel accretion." (Dec. 2005) Molecular Biology of the Cell 16: p. 5686-5698. The American Society for Cell Biology.
Hutnik et al., "The Protective Effect of Functional Connexin43 Channels on a Human Epithelial Cell Line Exposed to Oxidative Stress", Investigative Opthalmology & Visual Science, 2008, 49:800.
Iivesaro et al. Connexin-mimetic peptide Gap 27 decreases osteoclastic activity. BMC Musculoskel Dis 2:10, 2001 (6 pages total).
Inoue et al., "Rho-Associated Kinase Inhibitors: A Novel Glaucoma Therapy," Prog. Retin Eye Res., 2013, 37:1-12.
International Search Report/Written Opinion dated Jan. 20, 2016 in counterpart PCT Application No. PCT/US2015/46425.
Jackowski et al. Brit J Neurosurg 9: 303-317, 1995.
Janes, Andrew. "Speed healing." Dec. 1, 2004. Issue 67. Unlimited. Sep. 29, 2006 http://unlimited.co.nz/unllmited.nsf/ulfuture/250EA628CE599A70CC256F6B00046325.
Jen et al. "Suppression of Gene Expression by Targeted Disruption of Messenger RNA: Available Options and Current Strategies." Stem Cells, 2000, 18:307-319.
Jester, et al., Cornea 11:191 (1992).
Jiang-Depeng et al. "The expression of secretory leukocyte protease inhibitor in dermal pluripotent stem cells," May 31, 2006, Chin J. Crit. Care Med. vol. 26, No. 5 pp. 345-348.
Jin, Y., et al., Abstract: "Combination of fetal tissue transplantation and gene therapy to promote spinal cord regeneration," 2003 Neuroscience Meeting Planner, New Orleans, LA; Society for Neuroscience, 2003, Online.
Johnson et al. Am J Opthalmol 147: 11-21, 2009.
Johnsson et al. Transplant Int 12: 235-243, 1999.
Jyung, et al., "Increased wound-breaking strength induced by insulin-like growth factor I in combination with insulin-like growth factor binding protein-1", *Surgery*, 1994,115:233-239.
Kaal et al. Curr Opin Oncol 16: 593-600, 2004.
Kabanov et al., FEBS Lett. 259,327 330 (1990).
Kajstura J, et al. Bone marrow cells differentiate in cardiac cell lineages after infarction independently of cell fusion. Circ Res. Jan. 7;96(1 ):127-37 (Jan. 2005; published online Nov. 29, 2004).
Kandel ER, Schwartz JH, Jessell TM. Principles of Neural Science, 4th ed., pp. 178-180. McGraw-Hill, New York (2000).
Kandyba, et al. "A murine living skin equivalent amenable to live cell imaging: analysis of the roles of connexins in the epidermis." (Apr. 2008) The Society for Investigative Dermatology.
Kanter, H. Lee, et al., Molecular Cloning of Two Human Cardiac Gap Junction Proteins, Connexin40 and Connexin45, Nov. 18, 1993, 861-864, vol. 26, J Mol Cell Cardiol, Academic Press Limited.
Karlin and Atschul, "Applications and statistics for multiple high-scoring segments in molecular sequences", Proc. Natl. Acad. Sci. ,1993, 90:5873-5787.
Karlin, S., et al., "Applications and statistics for multiple high-scoring segments in molecular sequences," Proc. Natl. Acad. Sci. USA, vol. 90, pp. 5873-5877, Jun. 1993.
Kaur, C., et al. "Cellular and Molecular Mechanisms of Retinal Ganglion Cell Death in Hypoxic-Ischemic Injuries." J Neurol Exp Neurosci 1.1 (2015): 10-19.
Keirstead, H.S., et al. Exp. Neural. 159:225-236 (1999).
Kerr NM, et al "Gap junction protein connexin43 (GJA1) in the human glaucomatous optic nerve head and retina." J Clin Neurosci. Jan. 2011;18(1):102-108.
Kerr NM, et al "High pressure-induced retinal ischaemia reperfusion causes upregulation of gap junction protein connexin43 prior to retinal ganglion cell loss" Exp Neurol. Mar. 2012;234(1):144-152.
Kerr NM, et al "Immunolocalization of gap junction protein connexin43 (GJA1) in the human retina and optic nerve." Invest Ophthalmol Vis Sci. Aug. 2010;51(8):4028-4034.
Khosla, et al., Journal of Postgraduate Medicine 50:219-221 (2004).
Kieber-Emmons T, et al., Curr Opin Biotechnol. Aug.;8(4):435-41 (1997).
Kim et al., "Intrastromal Delivery of Bevacizumab Using Microneedles to Treat Corneal Neovascularization", Invest. Ophthalmol. Vis. Sci., 2014, 55(11):7376-7386.
Kim Yeri et al: "Tonabersat Prevents Inflammatory Damage in the Central Nervous System by Blocking Connexin43 Hemichannels", Neurotherapeutics, Elsevier Inc, US, vol. 14, No. 4, May 30, 2017 (May 30, 2017), pp. 1148-1165.
Kim, et al. Characterizing the mode of action of extracellular Connexin43 channel blocking mimetic peptides in an in vitro ischemia injury model. Biochim Biophys Acta. 2017; 1861 :68-78.
Kurpakus-Wheater, et al. Biotech. Histochem. 74:146-59 (1999).
Landau et al. Am Heart J 129(5): 924-931, 1995.
Laux-Fenton, W.T., et al., "Connexin Expression Patterns in the Rat Cornea," Cornea 22(5): 457-464, 2003.
Law, et. al. "In vitro optimization of antisense ologodeoxynucleotide design: an example using the connexin gene family." Journal of Biomolecular techniques. (Sep. 2006) 17(4): p. 270-282.
Law, L.-Y., Lin, J.S, Becker, D.L. and Green, C.R. (2002) Knockdown of Connexin 43 mediated regulation of ZPA activity in the developing chick limb bud leads to digit truncation. Dev. Growth Differ. 44, 537-547.
Laxat, "Nice blurb on biologies on cbsnews.com," Sep. 9, 2006 http://www.laxat.com/Nice-blurb-on- biolooics-on-cbsnews-com-1219610.html.
Le Gurun, S., "Connexin-36 Contributes to Control Function of Insulin-producing Cells," J of Biological Chemistry, vol. 278, No. 82, Sep. 26, 2003, pp. 37690-37697.
Lee, V.H.L., Mucosal Penetration Enhancers for Facilitation of Peptide and Protein Drug Absorption, Critical Reviews in Therapeutic Drug Carrier Systems 8:91-192 (1991).
Lemanske et al. J Allergy Clin Immunol 111 :S502-19, 2003.
Lepisto, J. et al., "Platelet-Derived Growth Factor Isoforms PDGF-AA, -AB and -BB Exert Specific Effects on Collagen Gene Expression and Mitotic Activity of Cultured Human Wound Fibroblasts", *Biochem. Biophys. Res. Comm.*, 1995, 209(2):393-399.
Letsinger et al., Proc. Natl. Acad. Sci. USA 86, 6553-6556 (1989).
Leybeart et. al., Cell Commun Adhes 10:251-257 (2003).
Li, C.H., "Hormonal Proteins and Peptides," Academic Press, Inc., New York, NY, 1973, vol. II, pp. 46-267.
Li, H., et al., "Properties and regulation of gap junctional hemichannels in the plasma membranes of cultured cells," Journal of Cell Biology 134(4):1019-1030 (1996).
Li, W.E.I., et al. Dev. 129:2031-42 (2002).
Li, X., et al. Neuronal connexin36 association with zonula occludens-1 protein (Z0-1) in mouse brain and interaction with the first PDZ domain of Z0-1. (Apr. 2004). Eur J Neurosci. 19,2132-46.
Liaw, et. al. "Altered wound healing in mice lacking a functional osteopontin gene (spp1)" (Apr. 1998) The Journal of Clinical Investigation 101(7): p. 1468-1478.
Lighter et al., "Interim clinical outcomes in the Collaborative Initial Glaucoma Treatment Study comparing initial treatment randomized to medications or surgery," Ophthalmology, 2001, 180:1943-1953.
Lin, et. al. "v-Src phosphorylation of connexin 43 on Tyr247 and Tyr265 disrupts gap junctional communication." (Aug. 20, 2001) Journal of Cell Biology. 154: p. 815-827. The Rockefeller University Press.
Lin, J.H. et al.,"Gap-Junction-mediated propagation and amplification of cell injury." Nature Neurosci. 1:431-432(1998).
Liu KC, et al. "Synergistic effect of chemical penetration enhancer and iontophoresis on transappendageal transport of oligodeoxynucleotides." Int J Pharm. Jan. 30, 2013;441(1-2):687-692.

(56) References Cited

OTHER PUBLICATIONS

Liu, et. al. "The Inhibition of in vivo tumorigenesis of osteosarcoma (OS)-732 Cells by antisense human osteopontin RNA." (2008) 13: p. 11-19. University of Wroclaw, Poland.
Loirand et al., "Rho Kinases in Cardiovascular Physiology and Pathophysiology", Circ. Res., 2006, 98:322-334.
Lyttle, M.H., "3'-Modified Oligonucleotides and their Conjugates," Current Protocols in Nucleic Acid Chemistry (2000), 4.6.1-4.6.8.
Makarenkova, H., Becker, D.L., Tickle, C. and Warner, A.E. (1997) Fibroblast growth factor 4 directs gap iunction expression in the mesenchvme of the vertebrate limb bud. J. Cell Biol. 138 1-13.
Mallard C, "Astrocytes and microglia in acute cerebral injury underlying cerebral palsy associated with preterm birth" Pediatr Res. Jan. 2014;75(1-2):234-240.
Malone et al. "Detergent-extracted small-diameter vascular prostheses." J Vase Surg, 1984, 1:181-191.
Manoharan et al. Nucleosides & Nucleotides 14, (3-5) 969-973 (1995).
Manoharan et al., Bioorg (1992). Med. Chem. Let. 3(12), 2765-2770 (1993).
Manoharan et al., Bioorg. Med. Chem. Lett. 4, 1053-1060 (1994).
Manoharan et al., Tetrahedron Lett. 36(21). 3651-3654 (1995).
Marmarou, A. Neurosurg Focus 22(5): E1-10, 2007.
Martin et al. "Wound Healing-Aimi ng for Perfect Skin Regeneration." Science, 1997, 276:75-81, Downloaded from www.sciencemag.org on Mar. 12, 2010.
Martin et al., "Ranibizumab and Bevacizumab for Treatment of Neovascular Age-Related Macular Degeneration: 2-Year Results: Comparison of Age-related Macular Degeneratiob Treatments Trials (CATT) Research Group," Ophthalmology, 2012, 119(7):1388-98.
Martin et al., Helv. Chim. Acta 1995, 78, 486-504.
Martin, P. et al., "Inflammatory cells during wound repair: the good, the bad and the ugly", *Trends in Cell Biology*, Nov. 2005, 15(11):599-607.
Martin, P., et al. Curr Biol 13:1122-8 (2003).
Marx, Jean. "Interfering with Gene Expression." Science 288:1370-1372 (2000).
Marziano et al., "Mutations in the gene for connexin 26 (GJB2) that cause hearing loss have a dominant negative effect on connexin 30", Hum. Mol. Genet., 2003, 12:805-812.
Marziano, N., Casalotti, S.O., Portelli A.E., Becker, D.L. and Forge, A. (2003) Deafness-related mutations in gap junction protein connexin 26 have a dominant negative effect on connexin 30. Human Molecular Genetics 203, 805-812.
Masseyeff, R.F., "Methods of Immunological Analysis," VCH Publishers, New York, 1993, vol. 1., pp. 1-305.
Masseyeff, R.F., "Methods of Immunological Analysis-Cell Fractionation and Purification," VCH Publishers, New York, 1993, vol. 3., pp. 1-305.
Matsushita M, et al. Photo-acceleration of protein release from endosome in the protein transduction system. FEBS Lett. 13;572(1-3}:221-6.J2004} Jul. 26, 2004.
Mattu et al. Emerg Med Clin N Am 23: 1105-1125, 2005.
McDonald, et al. Scientific American. 55-63 (Sep. 1999).
McDonnell, P.J., "Early Changes in Refractive Error Following Radial Keratotomy," Arch Opthalmol—vol. 106, Feb. 1988.
McGonnell, I., Green, C.R., Tickle, C. and Becker, D.L. (2001) Communication through connexin 43 gap junction channels contributes to the normal development of the embryonic face. Dev. Dynam. 222, 420-438.
Medical Futures—Innovation Awards. May 26, 2006 http://www.medicalfutures.co.uk/runner.php?bct Win=1.
Meienhofer in "Hormonal Proteins and Peptides," ed.; C.H. Li, vol. 2 (Academic Press, 1973) pp. 48-267.
Melton, D.A. Antisense RNA and DNA, Ed., Cold Spring Harbor Laboratory, Cold Spring Harbor, NY (1988).
Merrifield, J. Am. Chem. Soc. 85 2149 (1963).
Messmer et al., "In vivo confocal microscopy of filtering blebs after trabeculectomy," Arch. Opthalmol., 2006, 124:1095-1103.
Methods of Immunological Analysis (R. Masseyeff, W.H. Albert, and NA Staines, eds., Weinheim: VCH Verlaos oesellschaft mbH 1993) vol. I Ch. 1. 2 3. 4 vol. Ill, Ch. 4.
Meyer et al. "Inhibition of Gap Junction and Adherens Junction Assembly by Connexin and A-CAM Antibodies." J Cell Biol., 1992, 119: 179-189.
Meyer et al., "Inhibition of Gap Junction and Adherens Junction Assembly by Connexin and A-CAM Antibodies", J. Cell Biol., 1992, 119(1):179-189.
Middleton, "Synthesis biodegradable polymers as orthopedic devices", Biomaterials, 2000, 21(23):2335-2346.
Miller et al., "Wound healing in an animal model of glaucoma fistulizing surgery in the rabbit", Ophthalmic Surg., 1989, 20:350-357.
Miller et al., "Trabeculectomy combined with beta irradiation for congenital glaucoma", Br. J. Ophthalmol., 1991, 75:584-590.
Miller et al., "Wound healing in an animal model of glaucoma fistulizing surgery in the rabbit", Ophthalmic Surg., 1987, 20:350-357.
Miller, J.H., et al., Gene Transfer Vectors for Mammalian Cells, Introduction: Development and Uses of Gene Transfer Vectors, 1987 Cold Spring Harbor Laboratory, pp. 1-3.
Mishra et al., Biochim. Biophys. Acta 1264, 229-237 (1995).
Miyazaki, et. al. "Corneal Wound Healing in an Osteopontin-Deficient Mouse." (Apr. 2008) Investigative Ophthalmology & Visual Science 49(4): p. 1367-1375. Association for Research in Vision and Ophthalmology.
Molecular cloning: A Laboratory Manual, 3rd Edition Chapter 10 (Sambrook and Russel, 2001).
Moore et al. "Selective block of gap junction channel expression with connexin-specific antisense oligodeoxynucleotides." American Journal of Physiology, Nov. 1994, 265(1):C1371-C1388.
Moore, Clinical Techniques in Small Animal Practice, 18(3):168-177, 2003.
Mora et al., "Trabeculectomy with intraoperative sponge 5-fluorouracil", Ophthalmology, 1996, 103:963-970.
Mori, et al. Supplemental Materials and Methods. Online Supplemental Material. (2008) http://www.jem.org/cgi/content/full/jem.20071412/DC1 JEM the Rockefeller University Press.
Mori, et al., "Acute downregulation of connexin43 at wound sites leads to a reduced inflammatory response, enhanced keratinocyte proliferation and wound fibroblast migration." Journal of Cell Science. 119(24): p. 5193-5203 (Dec. 2006). The Company of Biologists 2006.
Mori, et. al. "Molecular mechanisms linking wound inflammation and fibrosis: knock down of osteopontin leads to rapid repair and reduced scarring." Department of Physiology and Biochemistry, School of Medical Sciences, University of Bristol, Bristol BS8 1TD, United Kingdom. (Jan. 7, 2008); p. 43-55.
Mori, R., et al. "Impairment of skin wound healing in beta-1,4-galactosyltransferase-deficient mice with reduced leukocyte recruitment." Am J. Pathol., 2004, 164:1303-14.
Morrissey, et al. J. Neuroscience 11 :2433-2442 (1991).
Mugisho, et al. The inflammasome pathway is amplified and perpetuated in an autocrine manner through connexin43 hemichannel mediated ATP release. Biochim Biophys Acta. 2017.
Muramatsu, et. al. "Inhibition of osteopontin expression and function in oral cancer cell lines by antisense oligonucleotides." (2005) Cancer Letters 217:87-95. Elsevier.
Muranishi. Critical Reviews in Therapeutic Drug Carrier Systems. 7:1-33 (1990).
Mustoe, T.A., et al. Science 237, 1333-6 (1987).
Nadarajah, B., Makarenkova, H., Becker, D.L., Evans, W.H. and Pamavelas, J.G. (1998) Basic FGF increases communication between cells of the developing a neocortex. J. Neurosci. 18, 7881-7890.
Nakano, et al. "Connexin43 Knockdown Accelerates Wound Healing but Inhibits Mesenchymal Transition after Corneal Endothelial Injury In Vivo" Investigative Ophthalmology & Visual Science, Jan. 2008, vol. 49, No. 1.
Nakano, et. al. "Changes in the expression of the gap junction protein connexin43 during wound healing of the rat corneal endothelium." (Dec. 2004) Bioimages 12(2-4). Bioimaging Society.

(56) References Cited

OTHER PUBLICATIONS

Narmadai C Deva et al: "Connexin43 Modulation Inhibits Scarring in a Rabbit Eye Glaucoma Trabeculectomy Model 1", Inflammation, Kluwer Academic Publishers—Plenum Publishers, NE, vol. 35, No. 4, Mar. 17, 2012 (Mar. 17, 2012), pp. 1276-1286.
New bio-active gel cuts wound healing time in half. Oct. 20, 2003. UCL Media Relations. University Colleoe London. Sep. 29, 2006 http://www.ucl.ac.uk/media/library/nexaoon0.
Ngo et al. Computational complexity, protein structure prediction, and the Levinthal paradox. The Protein Folding Problem and Tertiary Structure Prediction, pp. 492-495, 1994.
Nickel, R., Becker, D.L. and Forge, A. Molecular and functional characterization of gap junctions in the avian inner ear. J. Neurosci. Jun. 7, 2006:26(23):6190-9.
Nielsen et al., Science 254:1497 (1991).
Niessen et al., "Selective permeability of different connexin channels to the second messenger inositol 1,4,5-trisphosphate", J. Cell, Sci., 2000, 113(8):1365-1372.
Nowak, "Age-related macular degeneration (AMD): pathogenesis and therapy," Pharmacol. Res., 2006, 58:353-363.
Nowak, J.Z. Age-related macular degeneration (AMO): pathogenesis and therapy. Pharmacol Reports 58: 353-363, 2006.
Oberhauser et al., Nucl. Acids Res. 20, 533-538 (1992).
O'Boyle et al., "Synthesis and Evaluation of Azetidinone Analogues of Combretastatin A-4 as Tubulin Targeting Agents", Journal of Medicinal Chemistry, 2010, 53(24):8569-8584.
O'Carroll et al., "Connexin 43 mimetic peptides reduce swelling, astrogliosis, and neuronal cell death afterspinal cord injury", Cell Communication & Adhesion, 2008, 15(1):27-42.
O'Carroll et al., "Connexin43 mimetic peptide is neuroprotective and improves function following spinal cord injury", Neurosci. Research, Mar. 2013, 75(3):256-26.
O'Carroll SJ, et al. "The use of connexin-based therapeutic approaches to target inflammatory diseases." Methods Mol Biol. 2013;1037:519-546.
Okada, et. al. "Osteopontin expressed by renal tubular epithelium mediates interstitial monocyte infiltration in rats." Am Physiol Renal Physiol. (2000) 278:F110-F121. The American Physiological Society.
Oligonucleotide Synthesis Chapter 1 (M.J. Gait, ed., 1984.
Ormonde et al., "Regulation of Connexin43 Gap Junction Protein Triggers Vascular Recovery and Healing in Human Ocular Persistent Epithelial Defect Wounds", J. Membr. Biol., 2012, 245(7):381-388.
Ormonde S, et al. "Regulation of connexin43 gap junction protein triggers vascular recovery and healing in human ocular persistent epithelial defect wounds." J Membr Biol. Jul. 2012;245(7):381-388.
Oviedo-Orta E., et al. "Gap Junctions and Connexin-Mediated Communication in the Immune System." Biochimica et Biophysica Acta. Biomembranes, Amsterdam, NL vol. 1662, No. 1-2, 23, Mar. 2004, pp. 102-112.
Oviedo-Orta et al. Gap junctions and connexins: potential contributors to the immunological synpase. J Leuk Biol 72: 636-642, 2002.
Oviedo-Orta, E. et al., "Intercellular communication in the immune system: differential expression of connexin40 and 43, and perturbation of gap junction channel functionsin peripheral blood and tonsil human lymphocyte subpopulations", *Immunology*, 2000, 99:578-590.
Oviedo-Orta, E., "Immunoglobulin and cytokine expression in mixed lymphocyte cultures is reduced by disruption of gap junction intercellular communication," The FASEB Journal vol. 15, No. 3, pp. 768-774, May 2017.
Paddison, P., Caudy A., Bernstein, E., Hannon, G., Conklin, D., "Short hairpin RNAs (shRNAs) induce sequence-specific silencinQ in mammalian cells." Genes & Dev 16:948-958 (2002).
Paddison, P., Caudy A., Hannon G., "Stable suppression of gene expression by RNAi in mammalian cells." Proc Natl Acad Sci USA 99:1443-1448 (2002).
Papangelou et al. Curr Treatment Options in Neurol 11 :64-73, 2009.
Parker, J.D., et al. Nucleic Acids Res 19:3055-60 (1991).
Parsons et al., "Tonabersat (SB-220453) a novel benzopyran with anticonvulsant properties attenuates trigeminal nerve-induced neurovascular reflexes", British Journal of Pharmacology, 2001, 132(7):1549-1557.
PCR: The Polymerase Chain Reaction Chapter 1-19 (Mullis et al., eds., 1994).
Pearson, R., Uineborg N., Becker D.L. and Mobbs P. (2005) Gap junctions modulate interkinetic nuclear miQration in retinal oroaenitor cells. J. Neurosci. 25, 10803-10814.
Penn, et. al., Autoimmunity Reviews 2:199-203 (2003).
Pepose, J.S., et al. "The cornea; Adler's Physiology of the eye: Clinical application," 9th Ed. St. Louis: Mosbv Year Book, 1992, 29-47.
Peters NS, Green CR, Poole-Wilson PA, Severs NJ. Cardiac arrhythmogenesis and the gap junction. J Mol Cell Cardiol. Jan. 1995;27(1):37-44. Review. No abstract available. PMID: 7760358 [PubMed—indexed for MEDLINE].
Peters NS, Green CR, Poole-Wilson PA, Severs NJ. Reduced content of connexin43 gap junctions in ventricular myocardium from hypertrophied and ischemic human hearts. Circulation. Sep. 1993;88(3):864-75. PMTD: 8394786 [PubMed—indexed for MEDLINE].
Peters NS, Rowland E, Bennett JG, Green CR, Anderson RH, Severs NJ. The Wolff-Parkinson-White syndrome: the cellular substrate for conduction in the accessory atrioventricular pathway. Eur Heart J. Jul. 1994;15(7):981-7. PMTD: 7925521 [PubMed—indexed for MEDLINE].
Peters NS, Severs NJ, Rothery SM, Lincoln C, Yacoub MH, Green CR. Spatiotemporal relation between gap junctions and fascia adherens junctions during postnatal development of human ventricular mvocardium. Circulation. 1994 Auo;90(2):713-25. PMID: 8044940 [PubMed—indexed for MEDLINE].
Peters, T., et al. EMBO J. 24:3400-10 (2005).
Pich, A, et al. Prognostic relevance of cell proliferation in head and neck tumors Annals of Oncology 200415(9): 1319-1329. Sep. 2004.
Polo, L.M., et al., "Analysis of Oligonucleotides by Electrospray Ionization Mass Spectrometry," Current Protocols in Nucleic Acid Chemistry (2000) 10.2.1-10.2.20.
Pon, R.T., "Solid-Phase Supports for Oligonucleotide Synthesis," Current Protocols in Nucleic Acid Chemistry (2000) 3.1.1-3.1.28.
Qin et al, "Lysosomal and Proteasomal Degradation Play Distinct Roles in the Life Cycle of Cx43 in Gap Junctional Intercellular Communication-deficient and-competent Breast Tumor Cells", The Journal of Biological Chemistry, 2003, 278:30005-30014.
Qiu, et al., "Targeting connexin43 expression accelerates the rate of wound repair." Current Biology 13:1967-1703 (2003).
Qiu, et al; "Supplemental Data: Targeting Connexin43 Expression Accelerates the Rate of Wound Repair"; (2003) S1.
Rabinstein, A. Neurologist 12: 59-73, 2006.
Ramdas et al., J. Biol. Chem. 264:17395 (1989).
Ramer, et al. Spinal Cord. 38:449-472 (2000).
Ramezani A., et al., Frontiers in Bioscience 7:a,29-36 (2002).
Ramkumar, Hema L., et al. "Reduced Ganglion Cell Volume on Optical Coherence Tomography in Patients with Geographic Atrophy." Retina 38.11 (2018): 2159-2167.
Rando, J., "CoDa Therapeutics Achieves Positive Phase 2 Efficacy of NEXAGON® in Chronic Venous Leg Ulcers," http://www.codatherapeutics.com/news-nexagon.html, San Diego, CA, May 25, 2010.
Rapoport, A. "Antimigraine drugs: new frontiers." Neurological Sciences 30.1 (2009): S49-S54.
Rapoport, Antimigraine Drugs: new Frontiers, Neurol sci 30(Suppl 1): S49-S54 (2009).
Ratkay-Traub, I., Hopp, B., Bor, Zs., Dux, L., Becker, D.L. and Krenacs, T. (2001) Regeneration of rabbit cornea following excimer laser photorefractive keratectomy: a study on gap junctions, epithelial junctions and epidermal growth factor receptor expression in correlation with cell proliferation. Exp. Eye Res. 73, 291-302.
Reddy, K., et al., Pediatric Research 43(5):674-682 (1998).
Rennick RE, Connat JL, Bumstock G, Rothery S, Severs NJ, Green CR. Expression of connexin43 gap junctions between cultured

(56) References Cited

OTHER PUBLICATIONS vascular smooth muscle cells is dependent upon phenotype. Cell Tissue Res. Feb. 1993;271'2):323-32. PMID: 8384084 [PubMed—indexed for MEDLINE].
Reynolds, et al. Nat. Med. 11 :167-74 (2005).
Rhett, et. al. "Novel therapies for scar reduction and regenerative healing of skin wounds." (Mar. 4, 2008). Trends in Biotechnology. 26(4): 173-180. Cell Press.
Rigas et al., Proc. Natl. Acad. Sci U.S.A. 83:9591 (1986).
Rininsland et al., Proc. Natl. Acad. Sci. USA 94:5854 (1997).
Robbins, S. and Cotran, R. 1979 Pathologic basis of disease. 2nd edition. Chapters 1-3 WB Saunders Co. Philadelphia.
Roberts et al. "Follicle-stimulating hormone affects metaphase I chromosome alignment and increases aneuploidy in mouse oocytes matured in vitro." Biology of Reproduction, 2005, 72: 107-118, Published online before print Sep. 15, 2004.
Roberts, A.B., et al., "Transforming growth factor type Beta: Rapid induction of fibrosis and angiogenesis in vivo an stimulation of collagen formation in vitro," Proc. Natl. Acad. Sci. USA, vol. 83, pp. 4167-4171, Jun. 1986.
Roelfsema, et .al., J Cereb Blood Flow Metab 24(8):877-886 (2004).
Rosendaal M, Green CR, Rahman A, Morgan D. Up-regulation of the connexin43+ gap junction network in haemopoietic tissue before the growth of stem cells. J Cell Sci. Jan. 1994; 107 (Pt 1 ):29-37.
Rossi, D., et al., "The Biology of Chemokines and Their Receptors," Annu. Rev. Immunol. 2000, 18:217-242.
Rozenthal, et al. "Stable Transfection With Connexin43 Inhibits Neuronal Differentiation of PC12 Cells" Society for Neuroscience Abstracts, Society for Neuroscience 23(1-3), Oct. 25, 1997, p. 22.
Ruch et al. "Inhibition of Gap Junctional Intercellular Communication and Enhancement of Growth in BALBk 3T3 Cells Treated With Connexin43 Antisense Oligonucleotides." Molecular Carcinogenesis, 1995, 14:269-274.
Rupenthal ID, et al "Ion-activated in situ gelling systems for antisense oligodeoxynucleotide delivery to the ocular surface." Mol Pharm. Dec. 5, 2011;8(6):2282-2290.
Rutherford, R.B., Vascular Surgery, 3rd Ed. (W.B. Saunders Co. 1989).
Sabiston, D., The Textbook of Surgery, 14th Ed. Chapter 56 (W .B. Saunders Co. 1991).
Saez et al. Physiol Rev 83:1359-1400, 2003.
Saison-Behmoaras et al. EMBO J. 10, 1111-11118 (1991).
Saitongdee, P., Becker, D.L., Milner, P., Knight, G.E., and Bumstock, G. (2004) Levels of gap junction proteins in coronary arterioles and aorta of hamsters exposed to cold and during hibernation and arousal. J. Histochem Cvtochem 52). 603-615.
Saitongdee, P., Milner, P., Becker, D.L., Knight, G.E., and Bumstock, G. (2000) Increased connexin43 gap unction protein in hamster cardiomyocytes during cold acclimatization and hibernation. Cardiovascular Res. 47, 108-115.
Salameh et al., Pharmacology of Gap Junctions. New pharmacological targets for treatment of arrhythmia, seizure and cancer?, Biochim. Biophys. Acta, 2005, 1719:36-58.
Sambrook et a., Molecular Cloning: A Laboratory Manual, 1989.
Sanghvi, Y.S., Antisense Research and Applications, Chapter 15, 1993 by CRC Press, Inc., pp. 273-288.
Santoro, S.W. and Joyce, G.F. "A General Purpose RNA-Cleaving DNA Enzyme." Proc. Natl. Acad. Sci. USA 94, 4262-4266 ( 1997).
Santoro, S.W. and Joyce, G.F. Biochem. 37:13330-13342 (1998).
Scatchard et al., "The Attractions of Proteins for Small Molecules and Ions", Ann. N.Y. Acad., Sci., 1994, 51(4):660-672.
Scatchard, G., "The Attractions of Proteins for Small Molecules and Ions," Anais of the New York Academy of Sciences, vol. 51, Art. 4, pp. 575-852, May 31, 1949.
Scherer, L. J. and Rossi, J.J. Nature Biotechnol. 21(12): 1457-1465 (2003).
Schmidt, C.E., et al. Ann. Rev. Biomed. Eng. 5:293-347 (2003).
Schubert, S. et al., Nucleic Acids Res. 31, 5982-5992 (2003).
Schuck, P., "Reliable determination of binding affinity and kinetics using surface plasmon resonance biosensor," Current Opinion in Biotechnology, 8(4):498-502 (1997).
Schulz et al. Connexin 43 is an emerging therapeutic target in ischemia/reperfusion injury, cardioprotection and neuroprotection. Pharmacol Therapeut 153: 90-106, 2015.
Schumacher et al. Circulation 97: 645-650, 1998.
Segretain, D., et al. (2004). Regulation of connexin biosynthesis, assembly, gap junction formation, and removal. Bioch. Bioph. Acta 1662, 3-21. (Mar. 23, 2004).
Serena et al., "Acceleration of Venous Ulcer Healing Using a Topical Eonnexin43 Antisense Compound; Phase 2 Results." Symposium on Advanced Wound Care, Apr. 14-17, 2011 (Abstract Supp. at BRG.23).
Severs NJ, Gourdie RG, Harfst E, Peters NS, Green CR. Intercellular junctions and the application of microscopical techniques: the cardiac gap junction as a case model. J Microsc. Mar. 1993;169 (Pt 3):299-328. Review. PMID: 8478912 [PubMed—indexed for MEDLINE].
Severs NJ, Shovel KS, Slade AM, Powell T, Twist VW, Green CR. Fate of gap junctions in isolated adult mammalian cardiomyocytes. Circ Res. Jul. 1989;65( 1 ):22-42. PMID: 2736737 [Pub Med—indexed for MEDLINE].
Severs NJ, Slade AM, Powell T, Twist VW, Green CR. Integrity of the dissociated adult cardiac myocyte gap junction tearing and the mechanism of plasma membrane resealing. J Muscle Res Cell Motil. Apr. 1990;11C2):154-66. PMID: 2351753 [PubMed—indexed for MEDLINE].
Severs, N.J., et al. Remodelling of gap junctions and connexin expression in hemt disease. Biochim Biophys Acta. 1662, 138-48 (Mar. 23, 2004).
Shah, M. et al., "Role of Elevated Plasma Transforming Growth Factor-β1 Levels in Wound Healing", *Am. J. Pathol.*, 1999, 154(4):1115-1124.
Shea et al., Nucl. Acids Res. 18, 3777-3783 (1990).
Sheehan et al. "Percentage Change in Wound Area of Diabetic Foot Ulcers Over a 4-Week Period Is a Robust Predictor of Complete Healing in a 12-week Prospective Trial." Diabetes Care, Jun. 2003, 26(6): 1879-1882.
Shelley et al., "Cone degeration in aging and age-related macular degenerations", Arch. Opththalmol., 2009, 127(4):483-492.
Sherwood et al., "Long-term morphologic effects of antiglaucoma drugs on the conjunctiva ad Tenon's capsule in glaucomatous patients", Ophthalmology., 1989, 96:327-335.
Shevde, et. al "Osteopontin knockdown suppresses tumorigenicity of human metastatic breast carcinoma, MDA-MB-435." Clin Exp Metastasis (2006) 23: p. 123-133. Springer Science + Business Media B.V.
Shibayama et al., "Effect of Change Substitutions at Residue His-142 on Voltage Gating of Connexin43 Channels", Biophys. J., 2006, 91(11):4054-4063.
Sibbald et al. "Venous leg ulcers, in Chronic Wound Care: A Clinical Source Book for Healthcare Professionals." HMP Communications, Krasner DL, Rodeheaver GT, Sibbald RG, Eds., 4th ed. 2007, 429-442.
Sica, D. Heart Failure Clin 4: 511-518, 2008.
Sidoti et al., "Trabeculectomy with intraoperative 5-fluorouracil", Opthalmic Surg. Lasers, 1998, 29:552-561.
Silverman et al., "The Pannexin I Channel Activagtes the Inflammasome in Neurons and Astrocytes", J. Biological Chern.,Jul. 3, 2009, 284(27):18143-1815.
Simo et al. Angiogenic and Antiangiogenic factors in proliferative diabetic retinopathy. Current Diabetes Rev 2: 71-98, 2006.
Simons, et. al. "Anti-sense c-myb oligonucleotides inhibit intimal arterial smooth muscle cell accumulation in vivo." (Sep. 3, 1992): Nature, 359: p. 67-70. Nature Publishing Group.
Singh et al., "Intravenous transferring, RGD peptide and dual-targeted nanoparticles enhance anti-VEGF intraceptor gene delivery to laser-induced CNV", Gene Therapy, 2009, 16:645-659.
Singh, et al. "Inhibition of connexin 43 synthesis by antisense RNA in rat glioma cells." (1997) Cytobios 91: p. 103-123. The Faculty Press. Great Britain.

(56) References Cited

OTHER PUBLICATIONS

Skolnick et al. From genes to protein structure and function: novel applications of computational approaches in the genomic era. Trends in Biotech 18(1 ): 34-39, 2000.
Smith et al. The challenges of genome sequence annotation or "The devil is in the details". Nature Biotech 15: 1222-1223, 1997.
Smith JH, Green CR, Peters NS, Rothery S, Severs NJ. Altered patterns of gap junction distribution in ischemic heart disease. An immunohistochemical study of human myocardium using laser scanning confocal microscopy. Am J Pathol. Oct. 1991;139(4):801-21. PMID: 1656760 [PubMed—indexed for MEDLINE].
Söhl et al., "Gap junctions and the connexin protein family", Cardiovasc. Res.,2004, 62(2):228-232.
Söhl, G., et al., "The murine gap junction gene connexin36 is highly expressed in mouse retina and regulated during brain development," FEB Setters 428 (1998) 27-31.
Sotozono, C. et al., "Keratinocyte Growth Factor Accelerates Corneal Epithelial Wound Healing In Vivo", *Investigative Opthalmology &Visual Science*, 1995, 36(8):1524-1529.
Spanos, S., Rice, S., Karagiannis, P., Taylor, 0., Becker, O.L., Winston, R.M.L. and Hardy, K. (2002) Caspase activity and expression of cell death genes during human preimplantation embryo development. J. Reprod. 124, 353-363.
Spencer, W.H., "The cornea: Ophthalmic Patholgy: an atlas and textbook" 4th Ed. Philadelphia: W.B. Saunders Co. 1996. 157-165.
Stein C.A. and Krieg A.M. (eds), Chapters 7, 10, 22. Applied Antisense Oligonucleotide Technology, 1998 (Wilev-Uss).
Stewart, et al., "Solid Phase Peptide Synthesis," Chapter 2 Part B, Chapter 3. W .H. Freeman Co., San Francisco (1969).
Stilinovic A., Green, C.R., Klette R., Franke S., Klette G and Becker D.L. (2004) Texture analysis of collagen fibers in scar tissue. In Proc. Image Vision Computing New Zealand Nov. 21, 00185-190.
Strobel et al., Science 254:1639 (1991).
Sui, et al., Proc Natl Acad Sci 99(8):5515-5520 (2002).
Sundstrom, Drug Discovery Today 10:993-1000 (2005).
Suzuki, et. al. Protective effects of recombinant osteopontin on early brain injury after subarachnoid hemorrhage in rats. (2010) Crit Care Med 38(2): p. 612-618.
Svinarchuk et al., Biochimie 75, 49-54 (1993).
Takahashi, et al. J. Pharm. Pharmacol. 40:252-257 (1998).
Tan, et al., Ann Neural 32(5):677-682 (1992).
Tanaka, T., et al. Jpn. J. Ophthalinol. 43:348-54 (1999).
Tarnow, et al. Scand J. Plast Reconstr Hand Surg. 28:255-259 (1994).
Thompson AM, et al "A Study Investigating a Possible Link Between Lens Protein in the Vitreous Fluid of Eyes After Uncomplicated Cataract Surgery and Chronic Cystoid Macular Edema." Asia Pac J Ophthalmol (Phila). May-Jun. 2014;3(3):194-197.
Tian et al., "Effects of Topical H-7 on Outflow Facility, Intraocular Pressure, and Corneal Thickness in Monkeys", Arch. Ophthalmol., 2004, 122(8):1171-1178.
Tokuriki et al. Stability effects of mutations and protein evolvability. Curr Opinion Structural Biol 19: 596-604, 2009.
Tonkin RS, et al. "Gap junction proteins and their role in spinal cord injury." Front Mol Neurosci. Jan. 6, 2015;7:102, 9 pages.
Topol, E.J. (ed.) The Textbook of Interventional Cardiology, 2nd Ed. (W.B. Saunders Co. 1994).
Uhlmann, et al., Chem. Reviews 90:543-584 (1990).
Unger et al., "Electron cryo-crystallography of recombinant cardiac gap junction channel", Novartis Found Symp. & Discussion, 1999, 219:22-30, 31-43.
Upton et al., "Profile of SB-204269, a mechanistically novel anticonvulsant drug, in rat models of focal and generalized epileptic seizures", British Journal of Pharmacology, 1997, 121:1679-1686.
Veber and Freidinger, TINS, 392 (1985).
Vikis, H.G. and Guan, K.L. Glutathione-S-Transferase-Fusion Based Assays for Studying Protein-Protein Interactions in Protein-Protein Interactions, Methods and Applications, Methods in Molecular Biology, 261, Fu. H.Ed. Humana Press Totowa N.J. pp. 175-186 (2004).
Vis JC, Nicholson LF, Fault RL, Evans WH, Severs NJ, Green CR. Connexin expression in Huntington's diseased human brain. Cell Biol Int. Nov. 1998;22(11-12):837-47. PMID: 10873295 [PubMed—indexed for MEDLINE].
Wadia JS, et al. Transducible TAT-HA fusogenic peptide enhances escape of TAT-fusion proteins after lipid raft macropinocytosis. Nat Med. 10(3):310-5. (Feb. 8, 2004).
Waggett A.O., et al. Connexin 32 and 43 gap junctions differentially modulate tenocyte esonse to cyclic mechanical load. Eur. J. Cell. Biol. 085:1145-1154 (2006).
Wagner, R.W., et al. "Gene inhibition using anti-sense oligodeoxynucleotides." Nature 372:333-335 (1994).
Wai, et. al. "Osteopontin silencing by small interfering RNA suppresses in vitro and in vivo CT26 murine colon adenocarcinoma metastasis." (2005) Carcinogenesis 26(4): p. 741-751. Oxford University Press.
Walker, et al. Dev biol .284:479-98 (2005).
Wan CK, et al "Comparison of bidirectional and bicistronic inducible systems for coexpression of connexin genes and fluorescent reporters." Anal Biochem. Dec. 15, 2012;431(2):90-95.
Wan CK, et al "Spatiotemporal changes in Cx30 and Cx43 expression during neuronal differentiation of P19 EC and NT2/D1 cells." Cell Biol Int Rep (2010). Dec. 2013;20(2):13-23.
Wang et al., "Abnormal Connexin Expression Underlies Delayed Wound Healing in Diabetic Skin," Diabetes, Nov. 2007, 56:2809-2817.
Wang Xianyuan, et al. "The studies on thymosin beta-4 and the prospect thereof," Dec. 31, 2002, Foreign Medical Sciences (Section of Biologies for Prophylaxis, Diagnosis and Therapy) vol. 25, No. 3 pp. 126-129.
Waring, et al., Amer. J. Ophthalmol. 111 : 133 (1991).
Wei, et al., "Connexins and Cell Signaling in Development and Disease," Annu. Rev. Cell Dev. Biol., 2004, 20:811-38.
Welcome to the lab of David Becker and Jeremy Cook. Becker/Cook Lab. May 26, 2006 http://www.anat.ucl.ac.uk/research/becker/oeoole.htm.
Wells. J. A. Additivity of mutational effects in proteins. Biochemistry 29 (37): 8509-8517, 1990.
Wheater, M.K., "Review Corneal Cell Proteins and Ocular Surface Pathology," Biotechnic & Histochemistry, 1999, vol. 74, No. 3, pp. 146-159.
Wild, The Immunoassay Handbook (D. Wild, ed., Stockton Press NY 1994).
Wilgus TA, et al. Reduction of scar formation in full-thickness wounds with topical celecoxib treatment. Wound Rep Reg Jan.-Feb. 2003; 11 :25-34.
Willebrords J, et al "Connexins and their channels in inflammation" Crit Rev Biochem Mol Biol. Nov./Dec. 2016;51(6):413-439.
Willecke et al., "Structural and functional diversity of connexin genes in the mouse and human genome", Biol. Chem., 2002, 383:725-737.
Willecke Klaus, et al., Structural and functional diversity of connexin genes in the mouse and human genome. Biological Chemistry 383(5) 2002-05 (May 2002).
Willecke, et. al. "Mouse connexin37: Cloning and functional expression of a gap function gene highly expressed in lung." (Sep. 1991) The Journal of Cell Biology 114(5): p. 1049-1057. The Rockefeller University Press.
Wilson, et al. "Accellular Matrix" Trans Am Soc Artif Intern 36:340-343 (1990).
Wound-healing technology shortlisted for award. UCL News. University College London. Sep. 27, 2006 http://www.ucl.ac.uk/news-archive/archive/2003/october-2003/latest/newsitem.shtml?0309 . . . .
Wright et al., "Cell motility in models of wounded human skin is improved by Gap27 despite raised glucose, insulin and IGFBP-5," Experimental Cell Research, 2013, 319:390-401.
Wright, C.S., Becker, D.L., Lin, S.J., Warner, A.E. and Hardy, K. (2001) Stage-specific and differential expression of gap junctions in the mouse ovary: connexin-specific roles in follicular regulation. J. Reprod. Fert. 121, 77-88.

(56) References Cited

OTHER PUBLICATIONS

Wright, et. al. "Connexin mimetic peptides improve cell migration rates of human epidermal keratinocytes and dermal fibroblasts in vitro." (2009) Wound Rep Reg 17: p. 240-249. The Wound Healing Society.
Wu A, et al "Role of gap junctions in chronic pain." J Neurosci Res. Feb. 2012;90(2):337-345.
Wyngaarden J.B., et al. (eds.), The Cecil Textbook of Medicine, 19th Ed. (W.B. Saunders, 1992).
Xu, X.M., et al. J. Comp. Neurol. 351:145-160 (1995).
Xu, X.M., et al. J. Neuroscience. 11 :1723-1740 (1999).
Yamashita, et al. J. Phann. Pharmacol. 39:621-626 (1987).
Yang et al. "Synthesis and biological activities of potent peptideomimetics selective for somatostatin receptor subtype 2." Proc. Natl. Acad. Ci. USA, 1998, 95(18): 10836-10841.
Yang et al., "Synthesis and biological activities of potent peptidomimetics selective for somatostatin receptor subtype 2", Proc. Natl. Acad. Sci. U.S.A., 1998, 95:10836-10841.
Yeager, "Structure of cardiac gap junction intercellular channels", J. Struct. Biol., 1998, 121:231-245.
Yick, L.W., et al. Exp. Neurol. 159:131-138 (1999).
Yoon JJ, et al "Dose-dependent protective effect of connexin43 mimetic peptide against neurodegeneration in an ex vivo model of epileptiform lesion." Epilepsy Res. Dec. 2010;92(2-3):153-162.
Yuan, Xiaoyong et al, "Ocular Drug Delivery Nanowafer with Enhanced Therapeutic Efficacy", ACS Nano, 2015, 9(2):1749-1758.
Zarbin, "Current Concepts in the Pathogenesis of Age-Related Macular Degeneration," Arch. Ophthalmol. 122(4):598-614 (Apr. 2004).
Zhang et al., "Anti-inflammatory therapy for diabetic retinopathy", Immunotherapy, 2011, 3(5):609-28.
Zhang et al., "The Gap Junction-independent Tumor-suppressing Effect of Connexin 43," J. Biol. Chem. 278(45):44852-44856 (Nov. 2003).
Zhang J, et al. "Connexin hemichannel induced vascular leak suggests a new paradigm for cancer therapy." FEBS Lett. Apr. 17, 2014;588(8):1365-1371.
Zhang, X., Oglesbee, M., "Use of surface plasmon resonance for the measurement of low affinity binding interactions between HSP72 and measles virus nucleocapsid protein." Biological Procedures Onlin 5(1):170-181 (2003).
Zhou, et. al. "Blockade of Osteopontin Inhibits Glomerular Fibrosis in a Model of Anti-Glomerular Basement Membrane Glomerulonephritis." (Aug. 19, 2010) Am J Nephrol 32: p. 324-331. Karger AG, Basel. (Published Online.).
Zimmer DB, Green CR, Evans WH, Gilula NB. Topological analysis of the major protein in isolated intact rat liver gap junctions and gap junction-derived single membrane structures. J Biol Chem. Jun. 5, 1987:262(16):7751-63. PMID: 3034905 [PubMed—indexed for MEDLINE].
Zlotnik, A., et al. Annu rev Immunol 18:217-42 (2000).
Zon, G., Ann. N.Y. Acad. Sci., 616, 161-172 (1990).
Brunton. Chapter 38. In: Goodman & Gilman's the Pharmacological Basis of Therapeutics, 9th Ed., (1996).
Chen, Qing, et al. "Carcinoma-astrocyte gap junctions promote brain metastasis by cGAMP transfer." Nature 533.7604 (2016): 493-498.
Cronin M, Anderson PN, Green CR, Becker DL. "Antisense delivery and protein knockdown within the intact central nervous system" Front Biosci 11 (2006): 2967-2975.
Lampugnani, M.G., "Cell Migration into a wounded area in vitro" Adhesion protein protocols (1999): 177-182.
Neckers, et al. "Anti-sense technology: biological utility and practical considerations." Am. J. Physiol., Lung Cell Mol Physiol., 265(1) 1993, L1-L12.
Neckers, L., et al., "Nonantisense Effects of Antisense Oligonucleotides," Applied Antisense Oligonulceotide Technology, Stein,C. and Krieg,A. (eds), (1998) Chapters 7, 10 & 22.
Postlethwaite, A.E., et al. "Stimulation of the chemotactic migration of human fibroblasts by transforming growth factor beta." The Journal of Experimental Medicine 165.1 (1987): 251-256.
Sambrook, J., et al., "Molecular Cloning a Laboratory Manual," $2^{th}$ Ed., 1989, Chapters 11 and 12.
Summary of Safety and Effectiveness Data for Apligraf, May 8, 2000; available at http://www.accessdata.fda.gov/cdrh docs/pdf/P950032S016b.pdf.
Weir, O.M. & C.C. Blackwell, eds. Handbook of Experimental Immunology, 1986.
Wood, W.G., "Luminescent Labels," Principles of Immunoassays, 1993, pp. 320-715.
Mugisho et al. Targeting connexin hemichannels to control the inflammasome: the correlation between connexin43 and NLRP3 expression in chronic eye disease Expert Opinion on Therapeutic Targets vol. 23, 2019, pp. 855-863.
Mugisho, OO et al., Connexin43 hemichannel block protects against the development of diabetic retinopathy signs in a mouse model of the disease J. Mol. Med. (Berl) Feb. 2019;97(2):215-229.
Mat Nor, MN et al., Connexin Hemichannel Block Using Orally Delivered Tonabersat Improves Outcomes in Animal Models of Retinal Disease Neurotherapeutics Jan. 2020; 17(1): 371-387.
Lyon, H. et al., Tonabersat Inhibits Connexin43 Hemichannel Opening and Inflammasome Activation in an In Vitro Retinal Epithelial Cell Model of Diabetic Retinopathy Int. J. Mol. Sci. Jan. 2021; 22(1): 298.
Louie et al. Connexin43 hemichannel block inhibits NLRP3 inflammasome activation in a human retinal explant model of diabetic retinopathy Experimental Eye Research 202:108384.
Kim, Y et al., Role of Hemichannels in CNS Inflammation and the Inflammasome Pathway Adv. Protein Chem. Struct. Biol. 2016; 1-4:1-37.

* cited by examiner

FIG. 1F
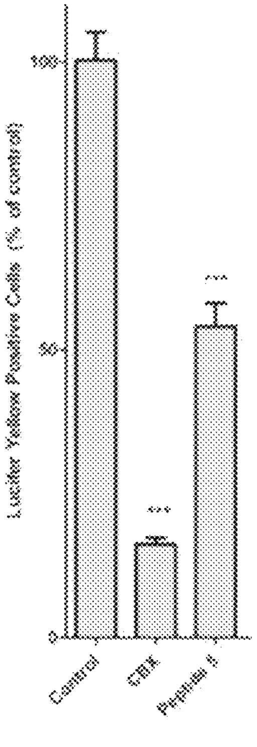
FIG. 1A
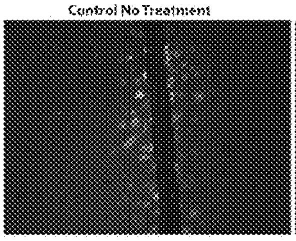
FIG. 1B
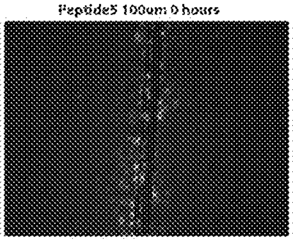
FIG. 1C
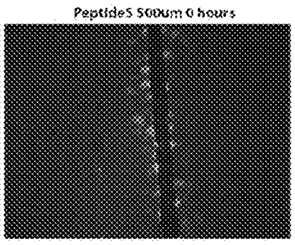
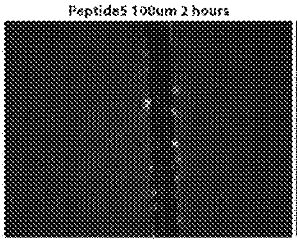
FIG. 1D
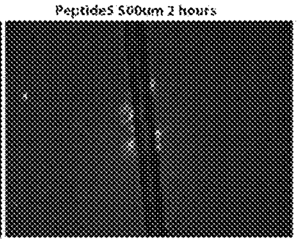
FIG.1E FIG. 4A
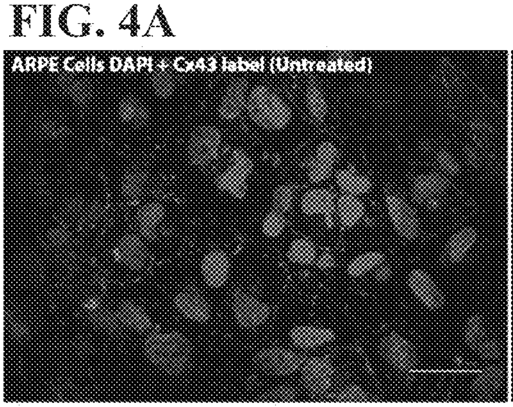
FIG. 4A1
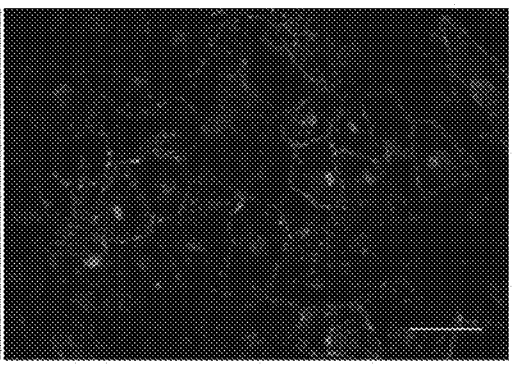
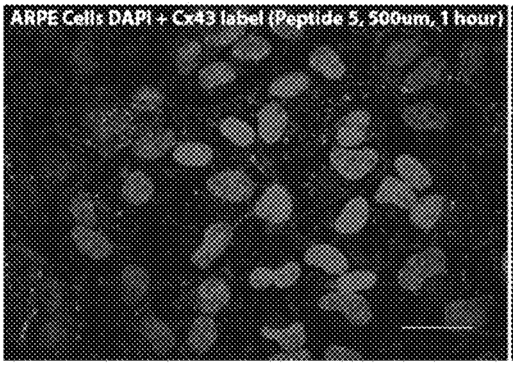
FIG. 4B
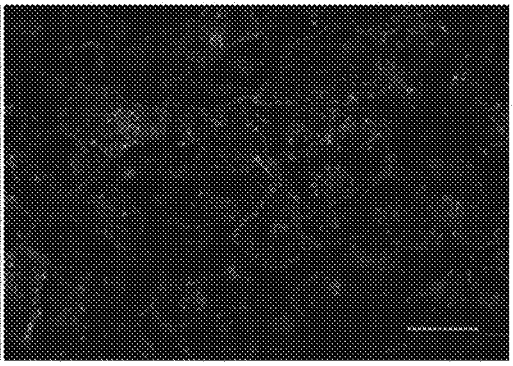
FIG. 4B1

FIG. 12A
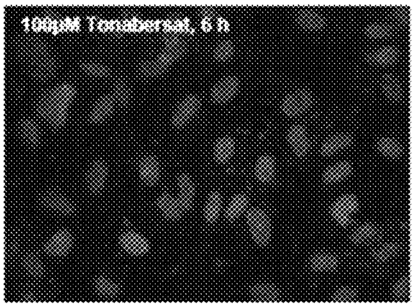
FIG. 12A1
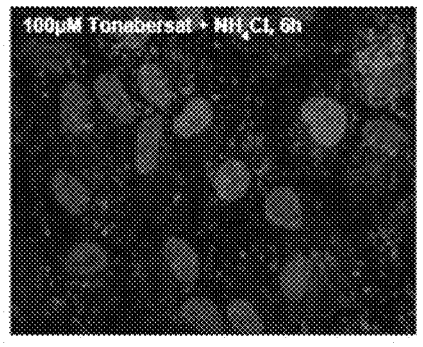
FIG. 12B
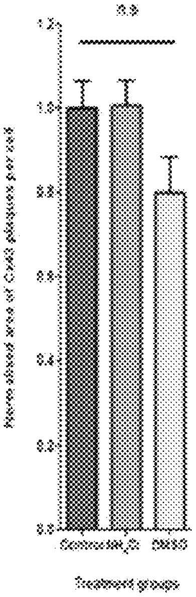
FIG. 12C
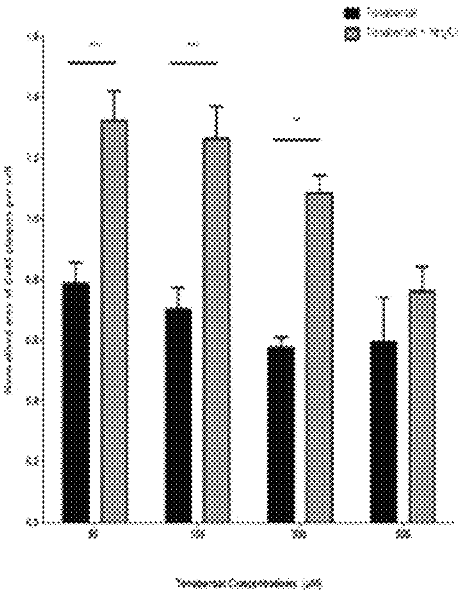

FIG. 16A1
FIG. 16A2
FIG. 16A3
FIG. 16A4
FIG. 16A5
FIG. 16A6
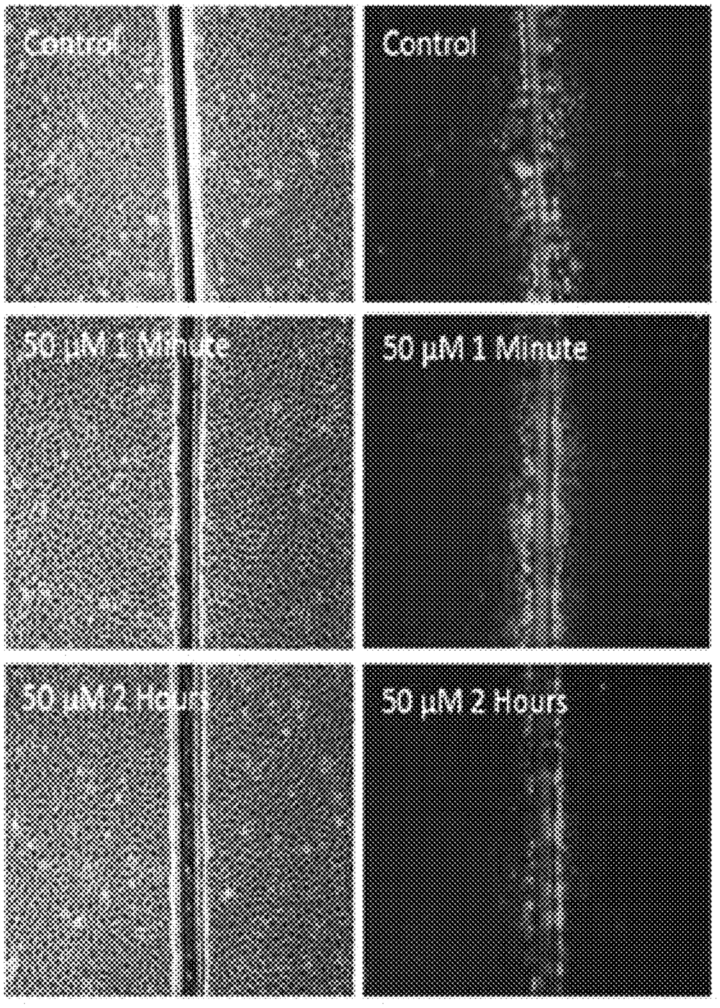

FIG. 23A
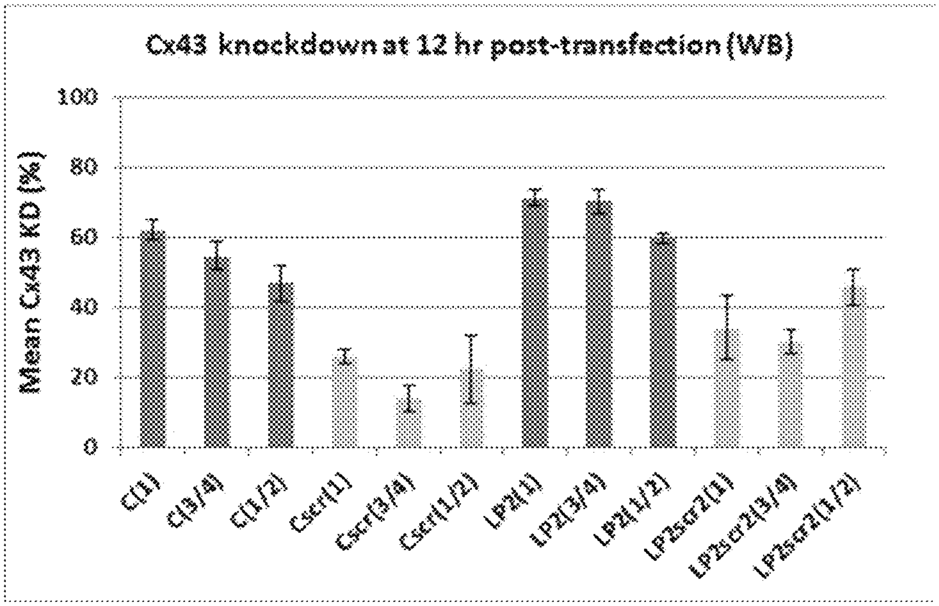
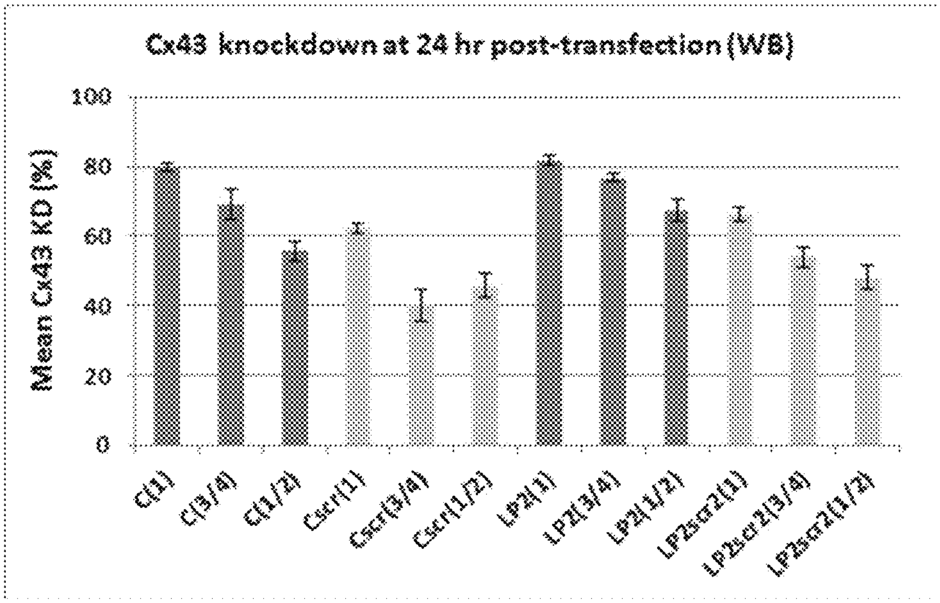
FIG. 23B

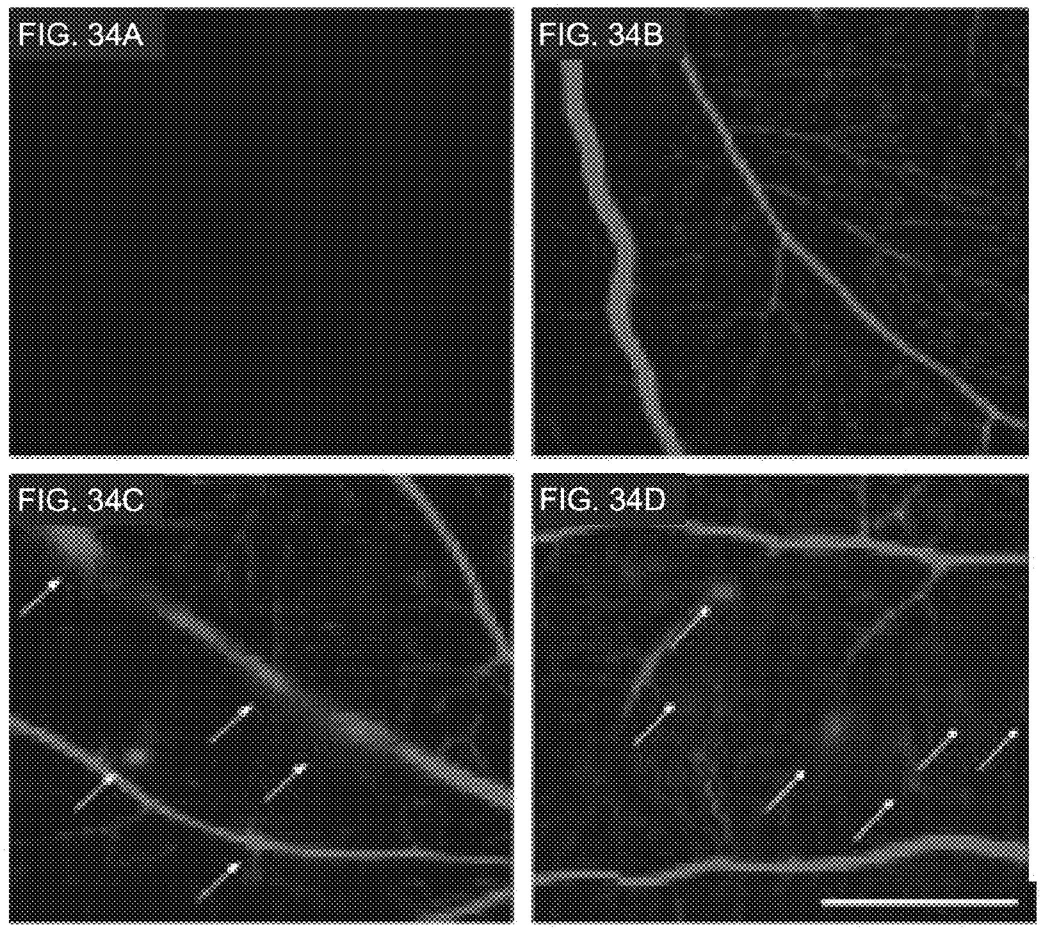
FIG. 34A – Control retina - No dye perfusion
FIG. 34B – Control retina - Evans Blue Dye Intraperitineal injection
FIG. 34C – Dye injection 4 hours Post-Ischemia
FIG. 34D – Dye injection 24 hours Post-Ischemia Peptide 5 VDCFLSRPTEKT
Mod 1 CFLSRPTEKT
Mod 2 LSRPTEKT
Mod 3 SRPTEKT
Mod 4 VDCFLSRPTE
Mod 5 VDCFLSRP
Mod 6 VDCFLS

| Formulation | Particle size | PDI | ZP (mV) | Yield (%) | EE (%) |
|---|---|---|---|---|---|
| Mps | 9.13±0.37 µm | 0.79±0.11 | -- | 90.32±2.75 | 97.41±2.59 |
| Nps | 113.38±0.74 nm | 0.31±0.01 | -31.3±0.94 | 91.26±4.28 | 70.04±1.63 |

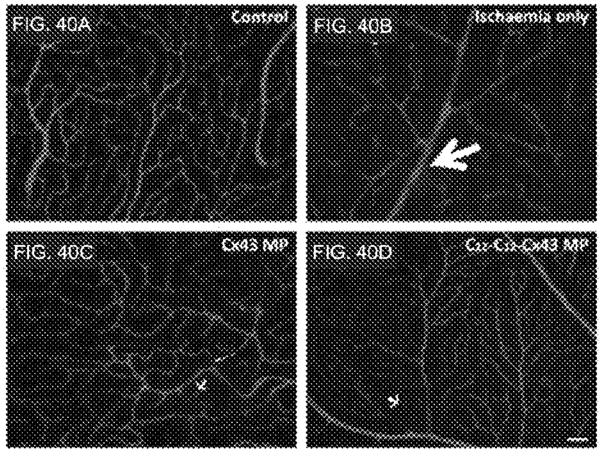
Vessel leak (4 hours post ischemia)
FIG. 40E
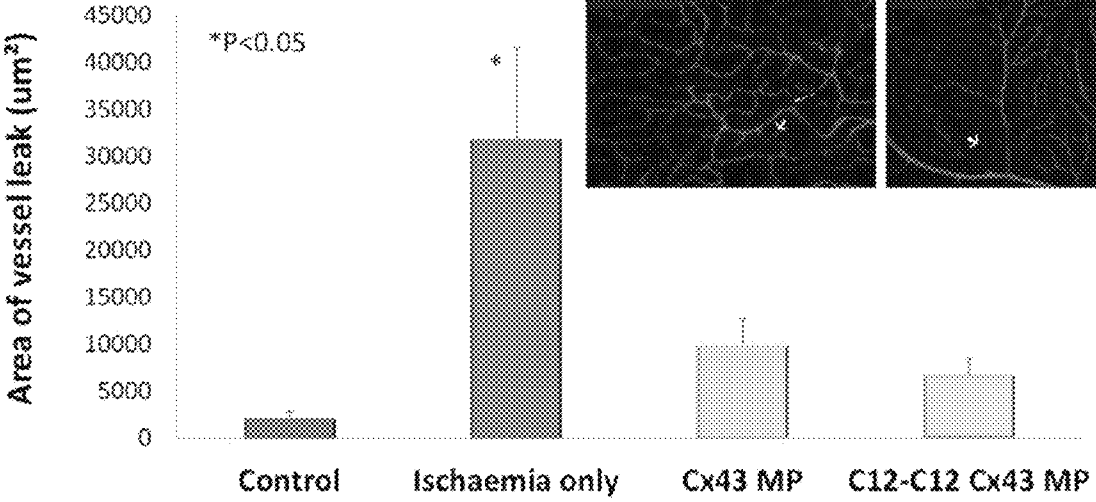

FIG. 41A FIG. 41B FIG. 41C
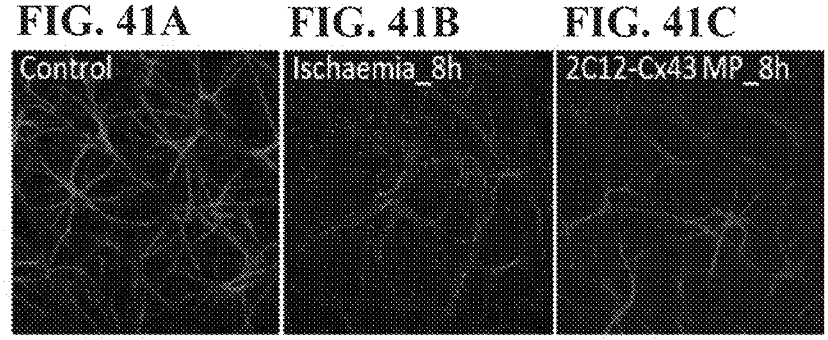
Cx43 spot counts
(wholemounts)
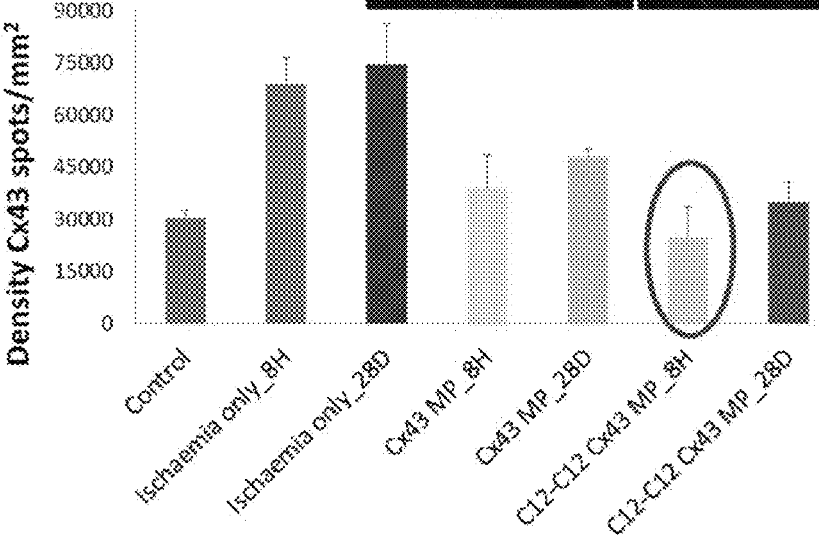
FIG. 41D FIG. 42A
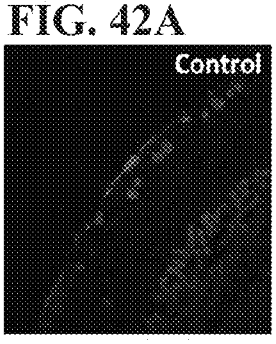
FIG. 42B
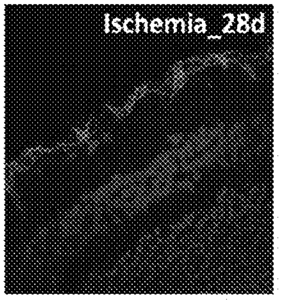
FIG. 42C
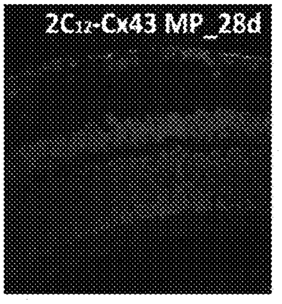
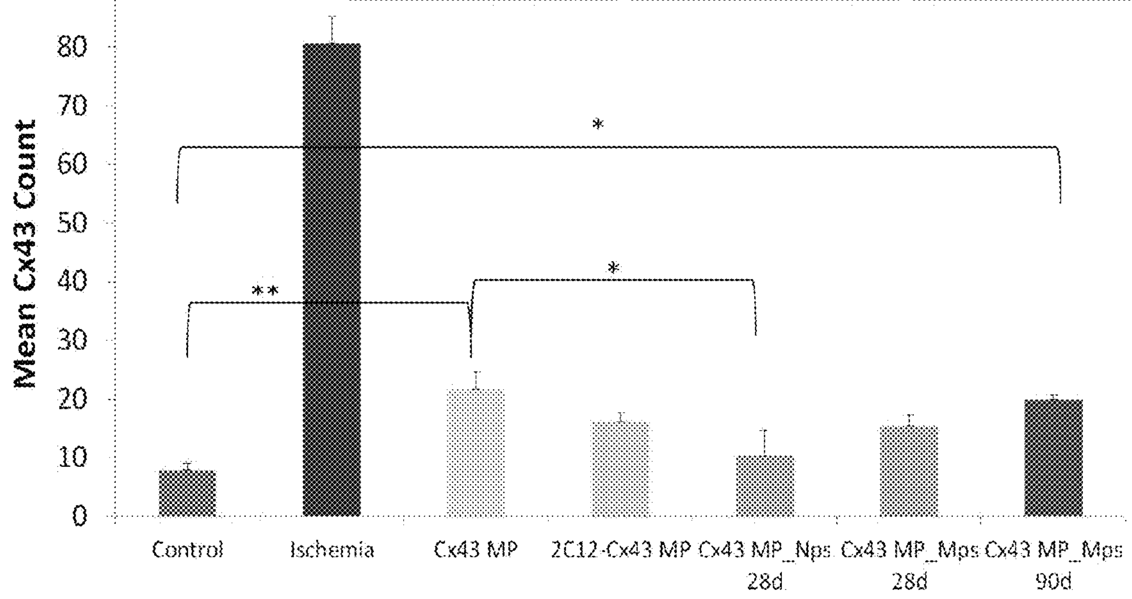
FIG. 42D FIG. 43A FIG. 43B FIG. 43C
Retinal ganglion cell count
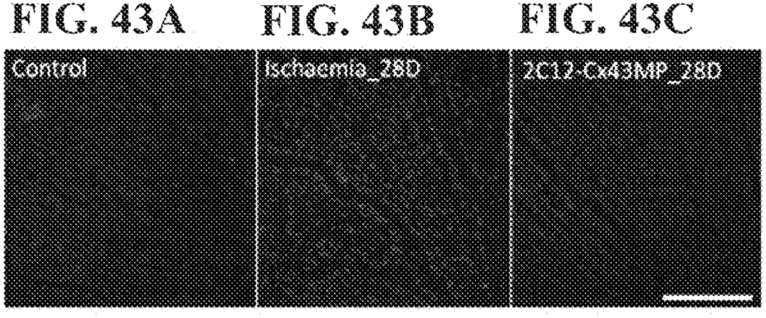
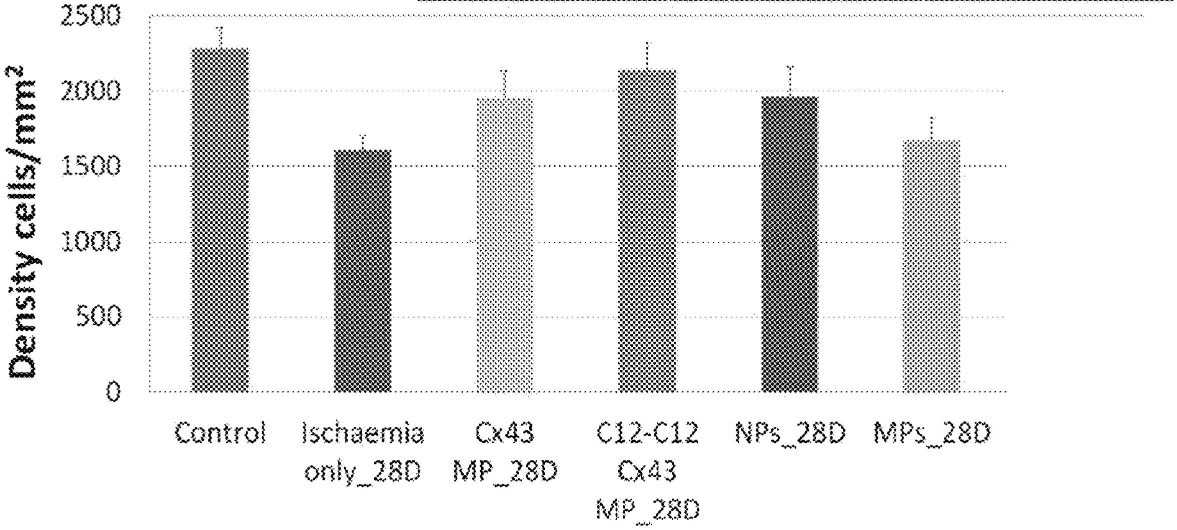
FIG. 43D FIG. 46
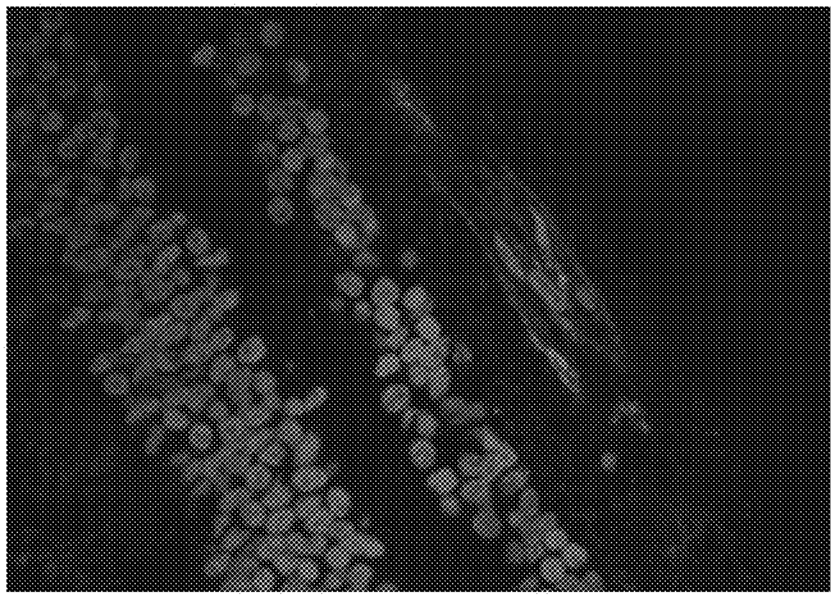
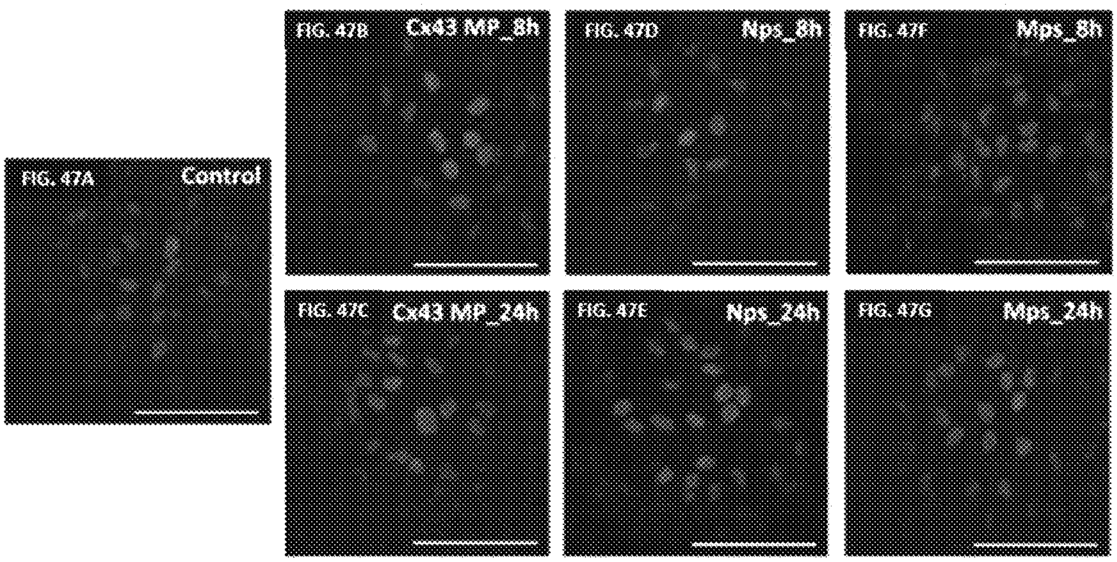

FIG. 48G
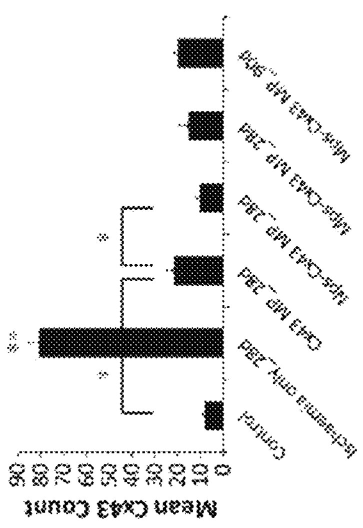
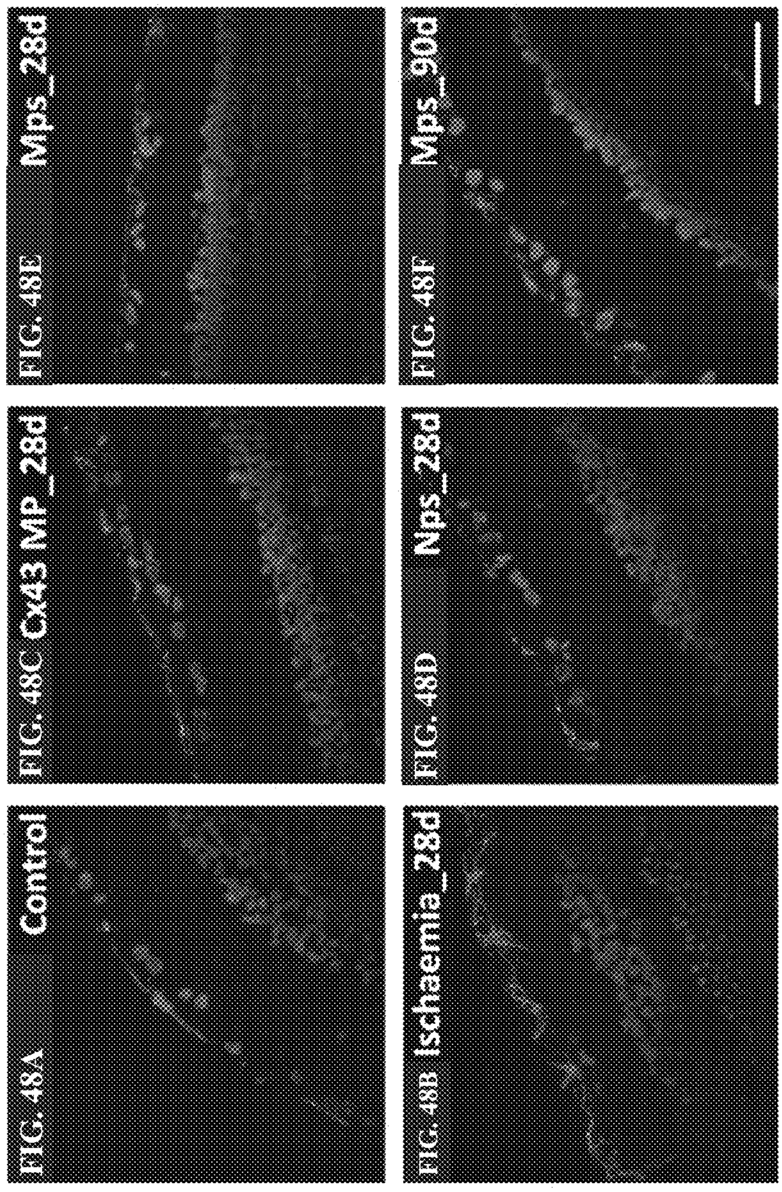

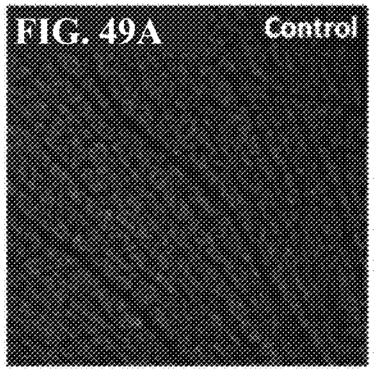
FIG. 49A Control
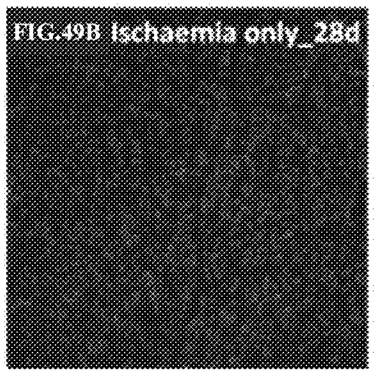
FIG. 49B Ischaemia only_28d
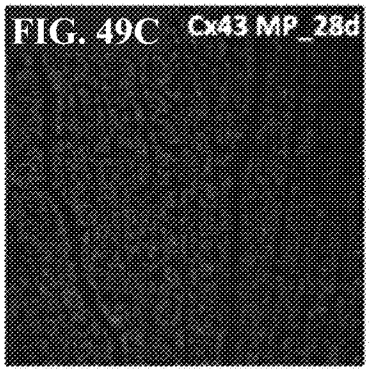
FIG. 49C Cx43 MP_28d
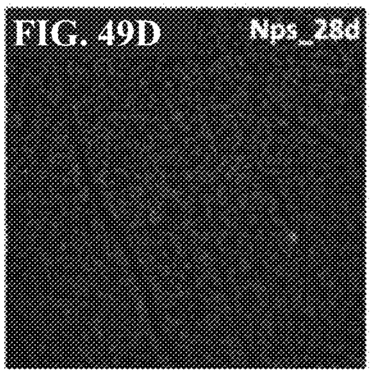
FIG. 49D Nps_28d
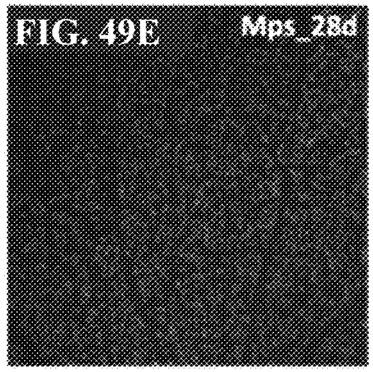
FIG. 49E Mps_28d
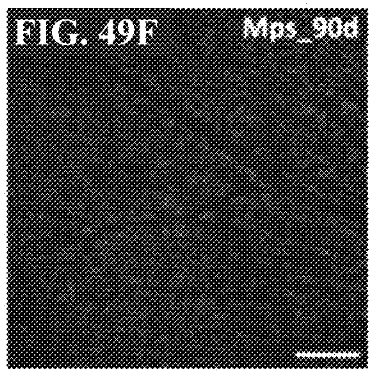
FIG. 49F Mps_90d
FIG. 49G
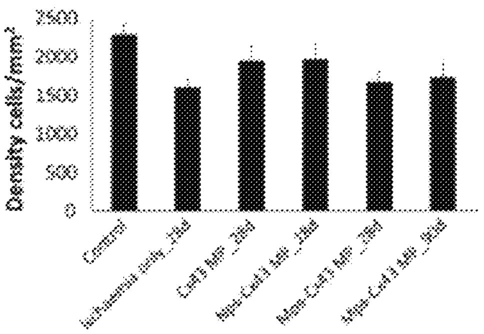
FIG. 49H
| | Control | Ischaemia _28d | Cx43 _28d | Nps _28d | Mps _28d | Mps _90d |
|---|---|---|---|---|---|---|
| Control | | ** | * | * | ** | ** |
| Ischaemia _28d | ** | | * | ** | | |
| Cx43_28d | * | * | | | | |
| Nps_28d | * | ** | | | * | |
| Mps_28d | ** | | | * | | |
| Mps_90d | ** | | | | | |

CHANNEL MODULATORS

RELATED APPLICATIONS

This is a Continuation of U.S. application Ser. No. 14/833,041 filed Aug. 21, 2015, which claimed priority to U.S. Provisional Application 62/146,128, filed Apr. 10, 2015; U.S. Provisional Application 62/147,488, filed Apr. 14, 2015; U.S. Provisional Application 62/080,217, filed Nov. 14, 2014; U.S. Provisional Application 62/085,226, filed Nov. 26, 2014; New Zealand Application 709673, filed Jul. 2, 2015; and New Zealand Application 628630, filed Aug. 22, 2014; the contents of each of which is herein incorporated by reference in its entirety.

SEQUENCE LISTING

The instant application contains a Sequence Listing which has been filed electronically in ASCII format and is hereby incorporated by reference in its entirety. Said ASCII copy, created on Jan. 31, 2020, is named E3697-00546_SL.txt and is 112,914 bytes in size.

FIELD

The inventions relate to connexin and pannexin channel modulators and modulation.

TECHNICAL BACKGROUND

The following includes information that may be useful in understanding the present invention. It is not an admission that any of the information, publications or documents specifically or implicitly referenced herein is prior art, or essential, to the presently described or claimed inventions. All publications, patents, related applications, and other written or electronic materials mentioned or identified herein are hereby incorporated herein by reference in their entirety. The information incorporated is as much a part of the application as filed as if all of the text and other content was repeated in the application, and should be treated as part of the text and content of the application as filed.

Gap junctions are specialized intercellular connections that are found between most animal cell-types. They are expressed in virtually all tissues of the body, with the exception of mature skeletal muscle and mobile cell types such as sperm and erythrocytes. Gap junctions directly connect the cytoplasm of two cells, which allows various molecules, ions and electrical impulses to directly pass through a regulated gate between cells.

In contrast to occluding (tight) junctions and anchoring (adherens and desmosome) junctions, gap junctions do not seal membranes together, nor is their function to restrict the passage of material between membranes. Rather, gap junction channels permit certain molecules to shuttle from one cell to another, thus providing physical communication channels by directly linking the interiors of adjacent cells.

One gap junction channel is composed of two connexons (or hemichannels), which connect across the intercellular space between adjacent cells and allow intracellular molecules to flow between those cells. Each connexon of a gap junction resides in the adjacent cell membrane and is formed by the covalent oligomerization of six individual connexin ("Cx", or "Cxn") proteins. Yeager (1998) Structure of cardiac gap junction intercellular channels, *J Struct Biol* 121: 231-245. Connexons can comprise one or more different connexin proteins, although they are usually in the form of homohexamers.

The human connexin family of genes and proteins now numbers 21. (Söhl G & Willecke K. (2004). Gap junctions and the connexin protein family. Cardiovasc Res. 62: 228-232). Structural and functional diversity of connexin genes in the mouse and human genome, *Biol Chem* 383: 725-737. There is much variation in the range of connexins expressed in various tissue types and often more than one connexin form is present within a cell type. See Sohl and Willecke (2004). It is possible for various combinations of connexins and connexons to interact with each other, although there are compatibility restrictions. Marziano, et al. *Hum Mol Genet.* 12:805-812 (2003) Connexin proteins and their associated gap junction channels come in a range of sizes and configurations that are thought to offer some specificity for the chemical species that can pass through. Niessen et al. (2000) Selective permeability of different connexin channels to the second messenger inositol 1,4,5-trisphosphate, *J Cell Sci* 113 (Pt 8): 1365-1372. All connexins share a common structure with four transmembrane domains, two extracellular loops, a cytoplasmic loop, a short cytoplasmic amino terminus and a carboxy terminus that can vary considerably in length. Unger, et al. (1999) Electron cryo-crystallography of a recombinant cardiac gap junction channel, *Novartis Found Symp* 219: 22-30 & discussion 31-43. The connexin proteins are commonly named according to their molecular weights, e.g. Cx26 is the connexin protein of 26 kDa. The principal structural difference between connexin proteins is the length of the C-terminal cytoplasmic tail, with connexin26 having almost no tail (16 μmino acids), while connexins 43 and 32 have long and intermediate ones (156 and 73 μmino acids, respectively). The differences in the size and amino acid sequence of the cytoplasmic tails for different connexins has been predicted to be involved in the channel open and closed conformations, amongst other things. The function and/or dysfunction of gap junctions has been implicated in a number of disorders. For example, connexin30 is mutated in Clouston syndrome (hidrotic ectodermal dysplasia), and mutations in the connexin26 gene are the most common cause of genetic deafness. Mutations in the human connexin32 gene cause X-linked Charcot-Marie-Tooth disease, a hereditary neuropathy, while oculodentodigital dysplasia is generally believed to be caused by a mutation in the gene that codes for connexin43.

Pannexins are a family of transmembrane channel glycoproteins that include Panx1, Panx2 and Panx3. Pannexins share similar structural features with connexins, consisting of 4 transmembrane domains, 2 extracellular and 1 intracellular loop, along with intracellular N- and C-terminal tails. Panx1 is expressed in many mammalian tissues, while Panx2 and Panx3 expression is more limited. Panx1 has been linked to propagation of calcium waves, regulation of tone, mucociliary lung clearance, and taste-bud function. Panx1 is expressed in the brain, bladder, testis, and ovary, whereas Panx2 is expressed primarily in the brain, and Panx3 is expressed in skin, cartilage, heart, kidney and cochlea. Panx1 hemichannels have been implicated in ATP release, calcium signalling, keratinocyte and osteoblast differentiation, taste reception, cell death, post-ischemic neurodegeneration, tumour suppression and seizure. Panx2 is involved in differentiation of neurons while Panx3 plays a role in the differentiation of chondrocytes, osteoblasts and the maturation and transport of sperm. Panx1 is localized to the plasma membrane whereas Panx2 is intracellularly located. One major difference between connexin and pannexin channels is that pannexin channels do not form cell-to-cell channels and it has been suggested that the highly glycosylated extracellular loops of pannexin proteins interferes with the docking process. As with connexin hemichannels, pannexin channels are said to be activated by a number of factors, but also show some differences. Both connexin hemichannels and pannexin channels contribute to glutamate and ATP release, although pannexin channels are insensitive to decreases in calcium ion concentration.

BRIEF SUMMARY

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this introduction, which is included for purposes of illustration only and not restriction.

It is an object of the invention to provide compounds, compositions, formulations, kits and methods for the modulation of a gap junction channel, hemichannel, and/or pannexin channel, and/or for the treatment of disorders that will benefit from modulation of a gap junction channel, hemichannel, and/or pannexin channel. Thus, in one aspect, the present invention relates to methods for the modulation of a gap junction channel, gap junction hemichannel, and/or a pannexin channel, and particularly, but not exclusively, to methods for the treatment of disorders for which modulation of a gap junction channel, gap junction hemichannel, and/or a pannexin channel, may be of benefit, the methods comprising administering a gap junction channel modulator, for example, compounds of formula I (for example tonabersat), a connexin peptidomimetic compound, and/or one or more analogue or prodrug of any of the foregoing compounds thereof, and/or administering a pannexin modulator, such as a compound of formula VI (for example probenecid) and/or one or more analogue or prodrug of any of the foregoing compounds thereof, and/or a pannexin peptidomimetic compound and/or one or more analogue or prodrug of any of the foregoing compounds thereof.

In one aspect, the invention provides methods for the modulation of a gap junction channel and/or a hemichannel using a gap junction channel modulator or hemichannel modulator. In some aspects, the gap junction channel modulator or hemichannel modulator may be a small molecule modulator. Small molecule gap junction channel modulators include, for example, compounds of formula I, for example tonabersat, and analogues and/or prodrugs thereof. In some aspects, the gap junction channel modulator or hemichannel modulator may be a peptidomimetic compound. Peptidomimetic gap junction channel modulators include, for example, peptide 5 (VDCFLSRPTEKT (SEQ ID NO: 168)) and analogues thereof. In other aspects, the gap junction channel modulator or hemichannel modulator may be an antisense oligonucleotide, which may be chemically modified or an unmodified oligonucleotide, e.g. an unmodified DNA oligonucleotide.

In some aspects this invention provides methods for the modulation of a pannexin channel using a pannexin modulator. In some aspects, the pannexin modulator may be a small molecule modulator. Small molecule pannexin channel modulators include, for example, compounds of formula VI, for example probenecid, and analogues and/or prodrugs of any of the foregoing compounds. In some aspects, the pannexin modulator may be a synthetic mimetic peptide blocker of pannexin 1. Peptidomimetic pannexin channel modulators include, for example, $^{10}$Panx1, or an analogue thereof. In some aspects, the pannexin modulator may be a synthetic mimetic peptide blocker of pannexin 2. In some aspects, the pannexin modulator may be a synthetic mimetic peptide blocker of pannexin 3.

In some aspects, the method comprises co-administering a gap junction channel modulator and a pannexin modulator. The co-administration of the gap junction channel modulator can be simultaneously with, subsequent to, or before the administration of the pannexin modulator. In some aspects, compounds of formula I, for example tonabersat, and/or peptide 5, or analogues of either or both, may be co-administered with a pannexin antagonist, e.g., compounds of formula VI, for example probenecid, and/or one or more analogues or prodrugs of any of the foregoing compounds, and/or a synthetic mimetic peptide blocker of pannexin 1, e.g., $^{10}$Panx1 or an analogue thereof.

In another aspect, the invention provides the use of a hemichannel modulator in the manufacture of a medicament for modulation of a gap junction channel and/or a hemichannel, or treatment of any of the diseases, disorders and/or conditions herein. Hemichannel modulators include, for example, compounds of formula I, for example tonabersat, and/or an analogue thereof, and/or peptide 5 or an analogue thereof, and/or an anti-sense oligonucleotide, as described herein.

In another aspect, the invention provides a gap junction channel modulator, a hemichannel modulator, a connexin modulator, and/or a pannexin modulator, such as compounds of formula I, for example tonabersat, and/or an analogue of any of the foregoing compounds or peptide 5 or an analogue thereof for use in the modulation of a gap junction channel and/or a hemichannel. In one aspect, the gap junction channel modulator, a hemichannel modulator, a connexin modulator, and/or a pannexin modulator, preferably modulates gap junction channels and/or hemichannels and pannexins, respectively, in humans or other animals. In some aspects the invention also features a pannexin modulator, e.g., compounds of formula VI, for example probenecid, and/or one or more analogue or prodrug of any of the foregoing compounds thereof and/or a synthetic mimetic peptide blocker of a pannexin such as pannexin 1, for example, $^{10}$Panx1 or an analogue thereof, for use in the modulation of a pannexin channel. Preferred pannexin channel modulators are pannexin 1 channel modulators. In some aspects, the gap junction channel modulator and/or hemichannel modulator can be used together with a pannexin modulator for modulation of a gap junction channel and/or a hemichannel together with modulation of a pannexin or pannexin channel. In some aspects, modulation of the pannexin and/or pannexin channel may be before, after or simultaneous with modulation of the connexin channel. In other aspects, modulation of the connexin channel may be before, or after, modulation of the pannexin channel.

In another aspect, the invention provides a method for the treatment of a disorder by modulation of a gap junction channel and/or a hemichannel where modulation of a gap junction channel and/or a hemichannel may be of benefit, the method comprising administering a connexin channel modulator and/or a hemichannel modulator to a subject. In some aspects the channel modulator may be, for example, compounds of formula I, for example tonabersat, and/or an analogue of any of the foregoing compounds to a subject, and/or a peptidomimetic compound, such as Peptide 5 or an analogue thereof. In some aspects where modulation of a pannexin channel may be of benefit, the method further comprises administering a pannexin antagonist or pannexin channel modulator. Pannexin modulators include, for example, compounds of formula VI, for example probenecid, and/or an analogue or prodrug of any of the foregoing compounds and/or a synthetic mimetic peptide blocker of pannexin 1, e.g., $^{10}$Panx1 or an analogue thereof. In some aspects, the method comprises administering compounds of formula I, for example tonabersat, and/or an analogue of any of the foregoing compounds, together with a pannexin antagonist, e.g., compounds of formula VI, for example probenecid, and/or one or more analogue or prodrug of any of the foregoing compounds and/or a synthetic mimetic peptide blocker of pannexin 1, e.g., $^{10}$Panx1 or an analogue thereof. The administration of compounds of formula I, for example tonabersat, and/or an analogue of any of the foregoing compounds can be simultaneously, subsequently, or before the administration of the pannexin antagonist. The administration of the pannexin antagonist can be subsequent to, or before, the administration of the connexin channel antagonist, e.g., compounds of formula I, for example tonabersat, and/or an analogue of any of the foregoing compounds. In some aspects, the method of treatment is applied to humans. In some aspects, the method of treatment is applied to mammals, e.g. humans.

In another aspect, the invention features the use of a pannexin modulator in the manufacture of a medicament for the modulation of a pannexin channel, or treatment of one or more of the diseases, disorders and/or conditions herein. Pannexin modulators include, for example, compounds of formula VI, for example probenecid, and/or analogues and prodruge of any of the foregoing compounds and/or a synthetic mimetic peptide blocker of pannexin 1, for example, $^{10}$Panx1 or an analogue thereof. In some aspects, a gap junction channel modulator or a hemichannel modulator and a pannexin modulator may be use for the manufacture of a single medicament, or a pair of medicaments, for the modulation of a gap junction channel and/or a hemichannel, and the modulation of a pannexin channel.

In another aspect, the invention provides the use of a connexin modulator such as compounds of formula I, for example tonabersat, and/or an analogue thereof or peptide 5 or an analogue thereof in the manufacture of a medicament for the treatment of a disorder where modulation of a gap junction channel and/or a hemichannel may be of benefit. In some aspects, where modulation of a pannexin channel may be of benefit, the invention features the use of a pannexin antagonist or pannexin channel modulator (e.g., compounds of formula VI, for example probenecid, and/or one or more analogue or prodrug of any of the foregoing compounds and/or a synthetic mimetic peptide blocker of pannexin 1, e.g., $^{10}$Panx1 or an analogue thereof) in the manufacture of a medicament for the treatment of a disorder where modulation of a pannexin channel may be of benefit, including for treatment of the diseases, disorders and/or conditions herein.

In some aspects, compounds of formula I, for example tonabersat, and/or an analogue of any of the foregoing compounds may be used together with a pannexin antagonist in the manufacture of a medicament for the treatment of a disorder where modulation of a gap junction channel and/or a hemichannel, and a pannexin channel is of benefit.

In another aspect, the invention provides a gap junction channel modulator, for example, compounds of formula I, for example tonabersat, and/or an analogue of any of the foregoing compounds or peptide 5 or an analogue thereof or another gap junction channel modulator, for use in the treatment of a disorder where modulation of a gap junction channel and/or a hemichannel may be of benefit. In some aspects where modulation of a pannexin channel may be of benefit, the invention also features a pannexin antagonist, for example, compounds of formula VI, for example probenecid, and/or one or more analogue or prodrug of any of the foregoing compounds thereof and/or a synthetic mimetic peptide blocker of a pannexin such as pannexin 1, for example, $^{10}$Panx1 or an analogue thereof, or another pannexin channel modulator, for use in the treatment of a disorder where modulation of a pannexin channel may be of benefit, including for treatment of the diseases, disorders and/or conditions described or referenced herein. In some aspects, compounds of formula I, for example tonabersat, and/or an analogue or prodrug of any of the foregoing compounds or peptide 5 or an analogue thereof can be used together with a pannexin antagonist for treatment of a disorder where modulation of a gap junction channel and/or a hemichannel and a pannexin channel may be of benefit. The administration of compounds of formula I, for example tonabersat, and/or an analogue of any of the foregoing compounds can be simultaneously, subsequently, or before the administration of the pannexin antagonist.

In any of the aspects of this invention, any of the following may be used as the gap junction channel modulator, for example: compounds of formula I, for example tonabersat, or analogs thereof, peptide 5 or an analogue thereof. Other compounds with some gap junction channel and/or hemichannel regulating activity include narcotics (including, for example, isoflurane, halothane, ethane) octanol, heptanol, 18α-glycyrrhetinic acid (including its metabolites), carbenoxolone, fenamates (including, for example, flufenamic or niflumic acid), cardiac glycosides (including for example, ouabain), platelet derived growth factor (PDGF), IGF-1, carbochol, phorbol esters and arachidonic, oleic or palmitoleic acids (See Salameh A, et al., (2005) *Biochim Biophys Acta* 1719:36-58, for further examples), and/or quinoline or mefloquine compounds (see for example Das S et al., *Biochem Biophys Res Commun* (2008) 373: 504-508).

In various embodiments, the gap junction channel and/or the hemichannel being modulated comprises one or more of connexin23, 25, 26, 30, 30.2, 30.3, 31, 31.1, 31.9, 32, 36, 37, 40, 40.1, 43, 45, 46, 47, 50, 59, and 62. In one embodiment, the gap junction channel and/or hemichannel being modulated comprises one or more of connexin 26, 30, 32, 36, 37, 40, 45 and 47. In one particular embodiment, the gap junction channel and/or hemichannel being modulated comprises connexin 30 and/or connexin 43.

In various embodiments, the pannexin and/or the pannexin channel being modulated is one or more of pannexin 1, pannexin 2 and pannexin 3.

In another aspect, the invention provides a method for the treatment of one or more diseases, disorders or conditions referred to herein, the method comprising administering a gap junction channel modulator to a subject. In some aspects, the gap junction channel modulator may be, for example, compounds of formula I, for example tonabersat, and/or an analogue of any of the foregoing compounds or peptide 5 or an analogue thereof. In some aspects this invention also provides a method for the treatment of one or more diseases, disorders or conditions referred to herein, the method comprising administering a pannexin modulator, alone or in combination with one or more gap junction channel or hemichannel modulators. In some aspects, the pannexin modulator may be, for example, compounds of formula VI, for example probenecid, and/or one or more analogue or prodrug of any of the foregoing compounds thereof and/or a synthetic mimetic peptide blocker of pannexin 1, e.g., $^{10}$Panx1 or an analogue thereof. In certain embodiments, the one or more diseases, disorders or conditions is chosen from the group comprising, for example: a chronic wound, a wound that does not heal at the/an expected rate, a dehiscent wound; fibrosis, a fibrotic disease, disorder or condition; abnormal or excessive scarring; a vascular disorder; tissue damage; an orthopedic disease or disorder; inflammation or an inflammatory disease; edema.

In another aspect, the invention provides the use of a gap junction channel modulator or hemichannel modulator, such as peptide 5, and/or an analogue thereof, compounds of formula I, for example tonabersat, and/or an analogue of any of the foregoing compounds, in the manufacture of a medicament for the treatment of one or more diseases, disorders and conditions referred to herein. In some aspects, the invention also provides the use of a pannexin modulator, e.g., compounds of formula VI, for example probenecid, and/or one or more analogue or prodrug of any of the foregoing compounds thereof and/or a synthetic mimetic peptide blocker of pannexin 1, e.g., $^{10}$Panx1, or an analogue of either thereof in the manufacture of a medicament for the treatment of one or more diseases, disorders and conditions referred to herein. In some aspects, a gap junction channel modulator may be used together with a pannexin modulator in the manufacture of separate medicaments or a combination medicament for the treatment of one or more diseases, disorders and conditions referred to herein. In certain embodiments, the one or more disorder is chosen from the group comprising, for example: a chronic wound, a wound that does not heal at the/an expected rate, a dehiscent wound; fibrosis, a fibrotic disease, disorder or condition; abnormal or excessive scarring; a vascular disorder; tissue damage; an orthopedic disease or disorder; inflammation or an inflammatory disease; and edema.

In another aspect, the invention provides a gap junction channel modulator or a hemichannel modulator, such as peptide 5, and/or an analogue thereof, compounds of formula I, for example tonabersat, and/or an analogue of any of the foregoing compounds, for the treatment of one or more diseases, disorders and conditions referred to herein. In some aspects, the invention also provides the use of a pannexin modulator, e.g., compounds of formula VI, for example probenecid, and/or one or more analogue or prodrug of any of the foregoing compounds thereof and/or a synthetic mimetic peptide blocker of pannexin 1, e.g., $^{10}$Panx1, or an analogue of either thereof, for example, for the treatment of one or more diseases, disorders and conditions referred to herein, either alone or in combination with a gap junction channel and/or hemichannel modulator of this disclosure. In certain embodiments, the one or more diseases, disorders or conditions is chosen from the group comprising, for example: a chronic wound, a wound that does not heal at the/an expected rate, a dehiscent wound; fibrosis, a fibrotic disease, disorder or condition; abnormal or excessive scarring; a vascular disorder; tissue damage; an orthopedic disease or disorder; inflammation or an inflammatory disease; and edema.

In another aspect, the invention provides a gap junction channel or hemichannel modulator, such as peptide 5, and/or an analogue thereof, compounds of formula I, for example tonabersat, and/or an analogue of any of the foregoing compounds, for example, for the treatment of one or more diseases, disorders and conditions referred to herein. In some aspects, the invention also provides the use of a pannexin modulator, e.g., compounds of formula VI, for example probenecid, and/or one or more analogues or prodrugs of any of the foregoing compounds and/or a synthetic mimetic peptide blocker of pannexin 1, e.g., $^{10}$Panx1, or an analogue of either thereof, for example, for the treatment of one or more disorder referred to herein, either alone or in combination with a gap junction channel modulator including those of this disclosure. In certain embodiments, the one or more diseases, disorders or conditions is chosen from the group comprising one or more of, for example, ischemia (including for example, perinatal ischemia, skin ischemia and cardiac ischemia), brain stroke, asphyxia, brain trauma, spinal cord injury, heart attack, inflammatory cardiac insult (including for example, pericarditis), reperfusion injury (including for example, cardiac reperfusion after surgery or transplant), liver reperfusion after surgery or transplant, retinal ganglion cell (RGC) loss and/or retinal ischemia or eye fibrosis.

In some aspects, the invention provides a method to improve the recovery from a surgery or procedure and/or to treat post-surgical contracture, the method comprising administering a gap junction channel modulator, such as peptide 5, and/or an analogue thereof, compounds of formula I, for example tonabersat, and/or an analogue of any of the foregoing compounds, to a subject. In a related embodiment, the invention provides the use of a gap junction channel modulator, such as peptide 5, and/or an analogue thereof, compounds of formula I, for example tonabersat, and/or an analogue of any of the foregoing compounds, in the manufacture of a medicament to improve the recovery from a surgery or procedure and/or to treat post-surgical contracture. In a related embodiment, the invention provides a gap junction channel modulator, such as peptide 5, and/or an analogue thereof, compounds of formula I, for example tonabersat, and/or an analogue of any of the foregoing compounds, for example, to improve the recovery from a surgery or procedure and/or to treat post-surgical contracture.

In some aspects, the invention provides a method to improve the recovery from a surgery or procedure and/or to treat post-surgical contracture, the method comprising administering a pannexin modulator, e.g., compounds of formula VI, for example probenecid, and/or one or more analogue or prodrug of any of the foregoing compounds thereof and/or a synthetic mimetic peptide blocker of pannexin 1, e.g., $^{10}$Panx1, or an analogue of either thereof, to a subject. In a related embodiment, the invention provides the use of a pannexin modulator, e.g., compounds of formula VI, for example probenecid, and/or one or more analogue or prodrug of any of the foregoing compounds thereof and/or a synthetic mimetic peptide blocker of pannexin 1, e.g., $^{10}$Panx1, or an analogue of either thereof, in the manufacture of a medicament to improve the recovery from a surgery or procedure and/or to treat post-surgical contracture. In a related embodiment, the invention provides a pannexin modulator, e.g., compounds of formula VI, for example probenecid, and/or one or more analogue or prodrug of any of the foregoing compounds thereof and/or a synthetic mimetic peptide blocker of pannexin 1, e.g., $^{10}$Panx1, or an analogue of either, for example, to improve the recovery from a surgery or procedure and/or to treat post-surgical contracture. In one embodiment, the surgery or procedure is an orthopedic surgery or procedure. In one embodiment, the post-surgical contracture is post-orthopedic surgical joint contracture.

In another aspect, the invention provides a method to treat or decrease adhesion formation in a subject, the method comprising administering a gap junction channel modulator, such as peptide 5, and/or an analogue thereof, compounds of formula I, for example tonabersat, and/or an analogue of any of the foregoing compounds, to a subject. In a related embodiment, the invention provides the use of a gap junction channel modulator, such as peptide 5, and/or an analogue thereof, compounds of formula I, for example tonabersat, and/or an analogue or prodrug of any of the foregoing compounds, in the manufacture of a medicament to treat or decrease adhesion formation in a subject. In a related embodiment, the invention provides a gap junction channel modulator, such as peptide 5, and/or an analogue thereof, compounds of formula I, for example tonabersat, and/or an analogue of any of the foregoing compounds, for example, to treat or decrease adhesion formation in a subject.

In another aspect, the invention provides a method to treat or decrease adhesion formation in a subject, the method comprising administering a pannexin modulator, e.g., compounds of formula VI, for example probenecid, and/or one or more analogues or prodrugs of any of the foregoing compounds thereof and/or a synthetic mimetic peptide blocker of pannexin 1, e.g., $^{10}$Panx1, or an analogue of either thereof, to a subject. In a related embodiment, the invention provides the use of a pannexin modulator, e.g., compounds of formula VI, for example probenecid, and/or one or more analogues or prodrugs of any of the foregoing compounds thereof and/or a synthetic mimetic peptide blocker of pannexin 1, e.g., $^{10}$Panx1, or an analogue of either thereof, in the manufacture of a medicament to treat or decrease adhesion formation in a subject. In a related embodiment, the invention provides a pannexin modulator, e.g., compounds of formula VI, for example probenecid, and/or one or more analogue or prodrug of any of the foregoing compounds thereof and/or a synthetic mimetic peptide blocker of pannexin 1, e.g., $^{10}$Panx1, or an analogue of either thereof, for example, to treat or decrease adhesion formation in a subject.

In another aspect, this invention relates to use of compounds of formula I, for example tonabersat, and/or an analogue of any of the foregoing compounds, for example, to directly and immediately block Cx43 hemichannels and to cause a concentration and time-dependent reduction in GJ coupling.

In still other aspects, various disorders can be treated by compositions and methods of the invention, including methods of treatment with a gap junction channel (e.g., hemichannel) modulator alone or together with a pannexin channel modulator. These disorders include but are not limited to neurodedenerative diseases (e.g. Alzheimer's disease, AIDS-related dementia, Parkinson's disease, amyotrophic lateral sclerosis, retinitis pigmentosa, spinal muscular atrophy and cerebellar degeneration); ischemic injury; fibrosis of the lung, kidney or liver; vascular disease (e.g. restenosis, artherosclerosis, atherosclerotic plaques coronary artery disease, or hypertension), respiratory disease (e.g. asthma, chronic bronchitis, bronchieactasis or cystic fibrosis), undesired or aberrant hypertrophy, arthritis, rheumatoid arthritis (RA), psoriasis, psoriatic plaques, sarcoidosis, CNS trauma, including spinal cord injury and optic nerve injury, diabetic and other proliferative retinopathies including retinopathy of prematurity, retrolental fibroplasia, glaucoma including open-angle glaucoma, angle-closure glaucoma, and normotensive glaucoma, as well as variants of open-angle and angle-closure glaucoma such as secondary glaucoma, pigmentary glaucoma, pseudoexfoliative glaucoma, traumatic glaucoma, neovascular glaucoma and irido corneal endothelial syndrome (ICE) and neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, uveitis, dry eye disease, ocular and corneal persistent epithelial defects, arteriovenous malformations (AVM), thyroid hyperplasias (including Grave's disease), corneal and other tissue transplantation, chronic inflammation, lung inflammation, ocular inflammation, acute lung injury/ARDS, sepsis, systemic capillary leak syndrome, multiple organ dysfunction syndrome (MODS), systemic inflammatory response syndrome (SIRS), acute respiratory distress syndrome, post burn vascular permeability syndromes, conditions marked by ascites, pleural effusions and pericardial effusions, permeability changes after cardiopulmonary bypass (particularly in infants and young children), reperfusion injury, snakebite, primary pulmonary hypertension, malignant pulmonary effusions, cerebral edema (e.g., associated with acute stroke/closed head injury/trauma), synovial inflammation, osteoarthritis (OA), 3rd spacing of fluid diseases (pancreatitis, compartment syndrome, burns, bowel disease), chronic inflammation such as inflammatory bowel disease (IBD) (including Crohn's disease and ulcerative colitis), renal allograft rejection, inflammatory bowel disease, nephrotic syndrome, hemophilic joints, hypertrophic scars, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), pleural effusion, post surgical tissue edema, acute orthopedic injuries, anaphylaxis, cystic fibrosis, and chronic dermal wounds, ulcers or ulcerous lesions, including diabetic foot ulcers, venous leg ulcers, and pressure ulcers, as well as infectious diseases including malaria, dengue fever, and pneumonia.

Certain preferred treaments for these diseases, disorders and conditions comprise administering a gap junction channel modulator, for example, compounds of formula I (for example tonabersat), a connexin peptidomimetic compound, and/or one or more analogue or prodrug of any of the foregoing compounds thereof, and/or administering a pannexin modulator, such as a compound of formula VI (for example probenecid) and/or one or more analogue or prodrug of any of the foregoing compounds thereof, and/or a pannexin peptidomimetic compound and/or one or more analogue or prodrug of any of the foregoing compounds thereof. Particulary preferred compounds are the compounds of formula I, for example tonabersat, and the compounds of formula VI, for example probenecid.

In some aspects the gap junction channel modulator or connexin modulator is a modulator of a gap junction and/or connexin present in blood vessels, for example, a connexin43 gap junction channel modulator or connexin43 modulator, a connexin40 gap junction channel modulator or connexin40 modulator or a connexin45 gap junction channel modulator or conneixn45modulator. Preferably, the connexin modulator is a connexin 43 modulator. Connexin modulators and connexin43 modulators include means for down-regulating the connexin transcription or translation of a connexin, such as antisense molecules, for example. They also include ZO-1 binding peptides in the case of connexin43. Preferably, the gap junction channel modulator is a connexin43 gap junction channel modulator. A preferred connexin43 gap junction channel modulator is tonabersat, or another compound of Formula I. The pharmaceutical compositions of this invention for any of the uses featured herein may also comprise a gap junction channel modulator, for example, a polynucleotide, which may inhibit or block, for example, connexin26 (Cx26), connexin30 (Cx30), connexin31.1 (Cx31.1), connexin36 (Cx36), connexin37

(Cx37), connexin40 (Cx40), connexin 45 (Cx45), connexin 50 (Cx50), or connexin 57 (Cx57), or any other connexin, or connexin gap junction or connexin hemichannel, in the eye or blood vessels. In another embodiment, pharmaceutical compositions of this invention for any of the uses featured herein may also be at least one pannexin modulator, and may further comprise any of the gap junction channel modulators or connexin modulators described or referenced herein.

In one aspect this invention relates to pharmaceutical compositions, articles of manufacture, and methods for treating ocular and other disorders, including for example glaucoma, diabetic retinopathy (DR), diabetic macular edema (DME), age related macular degneration (AMD), eye fibrosis, and/or neuropathic ocular disorders, by administering a therapeutically effective amount of at least one pannexin modulator to the eye of said subject. In some aspects the neuropathic ocular disorder may be, for example, glaucoma, loss of RGC and/or glaucomatous ocular neuropathy. In some aspects the glaucoma may result from ocular hypertension. In some aspects, the glaucoma may result from low-tension or normal-pressure glaucoma. In some aspects, administering a therapeutically effective amount of at least one connexin modulator is effective for treating (e.g., treating, preventing, slowing, reducing, stopping, or ameliorating) glaucoma, loss of retinal ganglion cells, and/or decreasing vitreal glutamate concentrations. The pharmaceutical compositions of this invention for any of the uses featured herein may also comprise a pannexin modulator, which may inhibit or block, for example, pannexin channels. In some aspects the pannexin modulator can include or exclude a Panx1, Panx2, or Panx3 modulator. In some aspects the pannexin modulator can include or exclude a Panx1 modulator.

In another aspect this invention relates to pharmaceutical compositions, articles of manufacture, and methods for treating ocular and other disorders, including for example DR, glaucoma, DME, AMD, eye fibrosis, and/or neuropathic ocular disorders, by administering a therapeutically effective amount of at least one pannexin modulator to the eye of said subject. In some aspects the neuropathic ocular disorder may be, for example, loss of retinal ganglion cells (RGC) and/or glaucomatous ocular neuropathy. In some aspects, administering a therapeutically effective amount of at least one pannexin modulator is effective for treating (e.g., treating, preventing, slowing, reducing, stopping, or ameliorating) loss of retinal ganglion cells are further useful for decreasing vitreal glutamate concentrations.

In one aspect this invention relates to pharmaceutical compositions, articles of manufacture, and methods for treating ocular hypertension. In some aspects, treating ocular hypertension treats or prevents intraocular pressure-associated neuropathy. In some aspects the method for treating ocular hypertension comprises, for example, administering a therapeutically effective amount of at least one hemichannel or connexin modulator and/or at least one pannexin channel or pannexin modulator to the eye of said subject. In one aspect, this invention relates, for example to pharmaceutical compositions and methods for treating glaucoma. The methods herein provide for treatment of intraocular pressure-associated optic neuropathy such as glaucoma, in an amount sufficient to reduce intraocular pressure. In some aspects, the connexin modulators and/or the pannexin modulators are useful in treating trauma associated with elevated intraocular pressure. In some aspects, the connexin modulator is a connexin43 modulator. In some aspects, the compositions and methods of this invention are useful in treating ocular hypertension and reducing the intraocular pressure to normal levels, e.g., below 21 mm Hg, for example, to a level between 8 and 21 mm Hg. In some aspects, the compositions and methods of this invention are useful in reducing the intraocular pressure to below about 22 mm, 21 mm, 20 mm Hg, or lower.

The compositions, articles of manufacture and methods described herein are useful, in one aspect, to treat glaucoma without toxic side effects. In some aspects, the glaucoma may be open-angle glaucoma or angle-closure glaucoma. In some aspects, administering a therapeutically effective amount of at least one connexin or hemichannel modulator, for example, a connexin43 modulator or a connexin43 hemichannel modulator, and/or at least one pannexin modulator to the eye tissue in a subject in need thereof increases flow through the trabecular meshwork.

In one aspect this invention relates to pharmaceutical compositions, articles of manufacture, and methods for treating normal tension or normatensive glaucoma. In some aspects this method comprises, for example, administering a therapeutically effective amount of at least one connexin or hemichannel modulator and/or at least one pannexin modulator to the eye of said subject. In one aspect, this invention relates, for example to pharmaceutical compositions and methods for treating glaucoma. In some aspects, the connexin modulator is a connexin43 or connexin43 hemichannel modulator. In some aspects the connexin modulator is a modulator of, and can include or exclude, for example, Cx26, Cx30, Cx31.1, Cx36, Cx37, Cx40, Cx45, Cx50, Cx57 or any other connexin or hemichannel comprising said connexin in the eye or blood vessels, and/or at least one pannexin or pannexin channel modulator. In some aspects, the compositions and methods of this invention are useful in treating glaucoma even when intraocular pressure is at normal levels, e.g., below 21 mm Hg. In some embodiments the modulator can include or exclude any of the foregoing.

In some aspects, this invention relates to pharmaceutical compositions, articles of manufacture, and methods for treating ocular disorders that can include or exclude glaucoma including hypertensive glaucoma and normatensive glaucoma, clinical geographic atrophy; AMD including dry AMD and exudative AMD, abnormalities or impairment, chronic macular ischemia, fibrosis of the eye, idiopathic polypoidal choroidopathy (IPC); diabetic maculopathy, diabetic retinopathy; hypertensive retinopathy, inflammatory choroidal neovascularization; central serous chorioretinopathy (CSR); macular telangiectasia; pattern dystrophy; subretinal/subPRD neovascularization; serous detachment of the neurosensory retina; RPE detachment; hemorrhages (subretinal pigment epithelial, subretinal, intraretinal or preretinal, including breakthrough bleeding into the vitreous); piretinal, intraretinal, subretinal or sub-pigment epithelial scar/glial tissue or fibrin-like deposits; retinal fibrosis, retinal angiomatous proliferations and retinochoroidal anatastamosis; choroidal neovascularization (CNV); cystic maculopathy; retinal thickening; non-exudative AMD; and retinal scarring, uveitis, including posterior uveitis, scleritis, episcleritis viral retinitis, including cytomegalovirus (CMV) retinitis, retinopathy of prematurity, retinal hypoxia, diffuse choroidal sclerosis, sclerosis of the choriocapillaris, dry eye, diabetic macular edema (DME), neuropathic ocular disorders, trauma induced lowering of intraocular pressure, epithelial basement membrane dystrophy, and/or other ocular disorders. The compositions and articles of manufacture useful in any of the methods of treating described herein comprise a therapeutically effective amount of at least one connexin or hemichannel modulator, for example, a connexin modulator, or at least one pannexin or pannexin channel modulator. In some aspects the connexin modulator is a modulator of, for example, a hemichannel comprising connexin 43 (Cx43), Cx26, Cx30, Cx31.1, Cx36, Cx37, Cx40, Cx45, Cx50, Cx57 or, such connexin, or any other connexin or connexin hemichannel in the eye or blood vessels. In an embodiment for treating diabetic retinopathy, the composition may comprise, for example, a pannexin or pannexin channel modulator, and/or a small molecule connexin or hemichannel modulator, for example, a small molecule inhibitor of connexin43 hemichannels or connexin43 itself. In some aspects, the connexin modulator for treating diabetic retinopathy, or other diseases, disorders or conditions herein, may be any connexin43 modulator of this disclosure, including or excluding polynucleotides having SEQ ID NOS.1-3 and/or modified versions thereof. In some embodiments the modulator can include or exclude any of the foregoing.

The inventions described and claimed herein may also be used in the treatment of cataracts. The central retinal artery provides blood to the eye, with branches to the choroid perfusing the back of the eye and superficial and deep vascular plexuses feeding the anterior retina. In addition, long branches perfuse the iris and ciliary body to provide nutrition and oxygen to the front of the eye, including (via the ciliary body) the lens. The inventors have surprisingly determined that diseases affecting the vascular bed, including diabetic retinopathy and age related macular degeneration, will also impact on flow to the anterior segment and therefore contribute to cataract formation, and note that cataracts are one of the most common causes of visual impairment in people with diabetes mellitus and that severe cataracts in the eye can also be associated with a higher prevalence of late AMD.

In some aspects, this invention relates to pharmaceutical compositions, articles of manufacture, and methods for treating ocular disorders that can include or exclude macular holes, macular degeneration, retinal tears, DME, diabetic retinopathy (DR), vitreoretinopathy, refractive disorders, dry eye, viral conjunctivitis, ulcerative conjunctivitis and scar formation in wound healing, corneal epithelial wounds, Sjogren's syndrome, cataracts, sequelae of radial keratotomy, increased thickness of cornea tissue. In this embodiment, the composition may comprise, for example, a pannexin modulator, or a connexin modulator, for example, a small molecule inhibitor of connexin 43 or a peptide inhibitor. In some aspects the connexin modulator is a modulator of, for example Cx43, a modulator of Cx26, Cx30, Cx31.1, Cx36, Cx37, Cx40, Cx 45, Cx50, and Cx57 or any other connexin in the eye or blood vessels. In some aspects of this embodiment, the compositions may comprise, for example, any connexin 43 modulator of this disclosure, including or excluding polynucleotides having SEQ ID NOS.1-3. In some embodiments the modulator can include or exclude any of the foregoing.

In some aspects, this invention relates to pharmaceutical compositions, articles of manufacture, and methods for treating cataracts. In this embodiment, the composition may comprise, for example, a pannexin or pannexin channel modulator, a gap junction modulator, a gap junction or hemichannel phosphorylation agent, or a connexin antagonist, for example, polynucleotides, peptides or peptidomimetics or small molecule antagonists of connexins. In some aspects the connexin modulator is a modulator of Cx43, Cx26, Cx30, Cx31.1, Cx36, Cx37, Cx40, Cx45, Cx50, Cx57 or any other connexin in the eye or blood vessels. In some aspects of this embodiment, the compositions may comprise, for example, any Cx43 modulator of this disclosure, excluding tonabersat. In some embodiments the modulator can include or exclude any of the foregoing.

In some aspects, this invention relates to pharmaceutical compositions, articles of manufacture, and methods for treating ocular disorders that can include or exclude retinal vein or artery occlusion, glaucoma, retinal stroke, trauma resulting in raised intraocular pressure, diabetic retinopathy, cystoid macular edema. In this embodiment, the composition may comprise, for example, a pannexin or pannexin channel modulator, a gap junction modulator, a gap junction or hemichannel phosphorylation agent, a ZO-1 binding site peptidomimetic in the case of Cx43, or another connexin antagonist, for example, polynucleotides, peptides or peptidomimetics or small molecule antagonists of connexins. In some aspects the connexin modulator is a modulator of Cx43, Cx26, Cx30, Cx31.1, Cx36, Cx37, Cx40, Cx45, Cx50, Cx57 or any other connexin in the eye or blood vessels. In some aspects of this embodiment, the compositions may comprise, for example, any Cx43 modulator of this disclosure, excluding tonabersat. In some embodiments the modulator can include or exclude any of the foregoing.

In some aspects, this invention relates to pharmaceutical compositions, articles of manufacture, and methods for treating Alzheimer's Disease, Parkinson's Disease, Huntington's Disease and Amyotrophic Lateral Sclerosis, migraine, or aura with or without migraine, sciatica/radiculopathy. In this embodiment, the composition may comprise, for example, alone or in combination, a pannexin modulator, a gap junction or hemichannel phosphorylation agent, or a connexin antagonist, for example. In some aspects the connexin modulator is a modulator of, for example, Cx43, Cx26, Cx30, Cx31.1, Cx36, Cx37, Cx40, Cx45, Cx50, Cx57 or any other connexin in the eye or blood vessels. In some aspects of this embodiment, the compositions may comprise, for example, any connexin 43 modulator of this disclosure, including compounds of formula I, for example tonabersat, and analogs of any of the foregoing compounds, as well as, for example, the tonabersat pro-drugs and pro-drugs of the compounds of formula I of this disclosure that target the eye. In some embodiments the modulator can include or exclude any of the foregoing.

In one aspect this invention relates to pharmaceutical compositions, articles of manufacture, and methods for treating ocular hypoxia, ocular vessel damage and/or blood vessel leakage. In some aspects treating or preventing ocular hypoxia comprises treating or preventing vessel leakage, vessel breakdown and/or any other condition that results in lower than normal oxygenated blood flow to the choroid or other blood vessels in the eye. In some aspects treating or preventing ocular hypoxia comprises treating conditions that result in compression of blood vessels or otherwise impinges on blood flow to the eye. In some aspects the method for treating ocular disorders such as ocular hypoxia, glaucoma, AMD, DME, fibrosis of the eye, and/or retinal perfusion disorders comprises, for example, administering a therapeutically effective amount of at least one gap junction modulator or connexin modulator or at least one pannexin or pannexin channel modulator to the eye of said subject. In one aspect, this invention relates, for example to pharmaceutical compositions and methods for treating glaucoma or for treating AMD.

In some aspects, the compositions of this invention are useful as adjuvants to improve trabeculectomy success rates.

The front of the eye is filled with aqueous humor, a clear fluid that provides nourishment to the structures in the anterior portion of the eye. This fluid is produced constantly by the ciliary body, which surrounds the lens of the eye.

Aqueous humor flows through the pupil and out of the eye through the trabecular meshwork channels located at the junction where the cornea attaches to the iris, which is referred to as the drainage angle of the eye. In some aspects of this invention, one or more gap junction or connexin modulators or pannexin or pannexin channel modulators is administered to the trabecular meshwork or ciliary body.

Also featured in one aspect of this invention are compositions, articles of manufacture, and methods for treating other ocular conditions, for example, retinal ischemic diseases or ocular ischemic diseases in a subject, comprising administering a therapeutically effective amount of a gap junction modulator, a connexin modulator, or a a pannexin or pannexin channel modulator, including, for example, amounts effective to reduce inflammation in the inner retina. In some aspects, the retinal ischemic disease is retinal artery occlusion, or central retinal vein occlusion. In some aspects, the optic ischemic disease is, for example, anterior ischemic optic neuropathy. In some aspects, the connexin modulator is a connexin 43 modulator.

This invention also features compositions, articles of manufacture, and methods for reducing impairment of choridal perfusion and/or choroidal inflammation, or choroidal overperfusion in a subject, comprising administering an amount of a gap junction modulator, a connexin modulator or a pannexin or pannexin channel modulator to the choroid of the subject, effective to reduce impairment of choridal perfusion and/or choroidal inflammation, or choroidal overperfusion in the inner retina. In some aspects of this invention, administering a therapeutically effective amount of a gap junction modulator, a connexin modulator or a pannexin or pannexin channel modulator to the choroid of the subject effective to reduce impairment of choridal perfusion and/or choroidal inflammation, or choroidal overperfusion, also reduces choriocapillaris endothelial cell loss and/or choriocapillaris dropout, thereby treating or preventing ocular disorders. In some aspects, reducing impairment of choridal perfusion and/or choroidal inflammation, or choroidal overperfusion also reduces retinal pigmental epithelium degeneration and/or Drusen development, or otherwise ameliorates, stops, slows, and/or reverses the progression of macular degeneration or macular dystrophy, which can be dry macular degeneration or wet macular degeneration. In some aspects, the gap junction modulator, a connexin modulator or a pannexin or pannexin channel modulator for reducing impairment of choridal perfusion and/or choroidal inflammation, or choroidal overperfusion is a Cx43 modulator. The gap junction modulator, a connexin modulator or a pannexin or pannexin channel modulator for reducing impairment of choridal perfusion and/or choroidal inflammation, or choroidal overperfusion may also be administered with an ocular treatment agent.

Impairment of choridal perfusion and/or choroidal inflammation, or choroidal overperfusion may induce vascular leak in the choroid and result in endothelial cell loss in the retinal pigment epithelium. As described herein, it has been surprisingly discovered that impairment of choridal perfusion and/or choroidal inflammation, and choriocapillaris dropout result from Cx43 upregulation, and that Cx43 upregulation is a contributing cause of AMD. Abnormal vasculature was observed in the choroid of AMD organ donor retinae associated with changes in Cx43 expression, supporting the role of Cx43 upregulation in AMD. In some embodiments treating or preventing vascular leak and impairment of choridal perfusion and/or choroidal inflammation, or choroidal overperfusion will be useful in treating or preventing retinal pigment epithelium degeneration or retinal neovascularisation associated with conditions such as non-exudative AMD, or dry AMD, neovascularization AMD or wet AMD, and Drusen development. As surprisingly discovered and described herein, upstream events such as vascular leak and impairment of choridal perfusion and/or choroidal inflammation are associated with AMD choroidal changes are then subsequently associated with symptoms such retinal pigment epithelium degeneration or retinal neovascularisation.

Thus, in one aspect, this invention features methods of administering a gap junction modulator, a connexin modulator and/or pannexin or pannexin channel modulator of this invention alone, or together with one or more ocular treatment agents for use in treating AMD, including ocular agents for use in treating neovascularization AMD, wet AMD, Drusen development, dry AMD, retinal pigment epithelium degeneration, or geographic atrophy. The gap junction modulator, connexin modulator or a pannexin or pannexin channel modulator of this invention may be administered separately, simultaneously, or in a combined composition with the ocular treatment agents.

In some aspects, the connexin or pannexin oligonucleotides and polynucleotides of this invention are made chemically, synthetically, or otherwise manufactured. In some embodiments the connexin modulator is a connexin oligonucleotide or polynucleotide. In one embodiment the connexin modulator is a connexin antisense oligodeoxynucleotide, whether chemically modified or unmodified, for example, a Cx43 antisense oligodeoxynucleotide or an antisense oligodeoxynucleotide to Cx26, Cx30, Cx31.1, Cx36, Cx37, Cx40, Cx45, Cx50, Cx57 or any other connexin in the eye or blood vessels. In some aspects modified connexin antisense polynucleotides or oligonucleotides may comprise mixtures of modified and unmodified nucleotides. In some aspects, the connexin antisense compound used in the methods herein is an antisense oligonucleotide comprising naturally occurring nucleotides and unmodified internucleoside linkages. In some embodiments the connexin oligonucleotide or polynucleotide and/or connexin antisense oligodeoxynucleotide may be, for example, a Cx43 antisense oligonucleotide, polynucleotide, and/or Cx43 antisense oligodeoxynucleotide. In some embodiments the modulator can include or exclude any of the foregoing.

Featured in this invention are connexin antisense oligonucleotides or polynucleotides comprising at least one unmodified nucleotide. In one aspect, the connexin antisense oligonucleotides or polynucleotides may comprise at least one modified nucleotide, and/or have at least one modified internucleoside linkage, and/or at least one modified sugar moiety. The modified internucleoside linkage may be, for example, a phosphorothioate linkage. In some aspects, for example, the connexin polynucleotide may comprise at least one nucleotide comprising a conformationally strained nucleotide, for example, a locked nucleic acid (LNA) or a bridged nucleic acid (BNA). The locked nucleotide may be selected, from one of the following types, for example: 2'-O—$CH_2$-4' (oxy-LNA), 2'-$CH_2$—$CH_2$-4' (methylene-LNA), 2'-NH—$CH_2$-4' (amino-LNA), 2'-N($CH_3$)— $CH_2$-4' (methylamino-LNA), 2'-S—$CH_2$-4' (thio-LNA), and 2'-Se—$CH_2$-4' (seleno-LNA). In some aspects the modified nucleotide may be a locked nucleic acid or an unlocked nucleic acid. In some aspects the modified and unmodified connexin antisense oligonucleotides or polynucleotides are modified and unmodified Cx43 antisense oligonucleotides or polynucleotides. In some aspects the modified and unmodified connexin antisense oligonucleotides or polynucleotides are modified and unmodified Cx26 antisense oligonucleotides or polynucleotides, Cx31.1 antisense oligonucleotides or polynucleotides, Cx30 antisense oligonucleotides or polynucleotides, Cx45 antisense oligonucleotides or polynucleotides, Cx36 antisense oligonucleotides or polynucleotides, Cx37 antisense oligonucleotides or polynucleotides, Cx40 antisense oligonucleotides or polynucleotides, Cx50 antisense oligonucleotides or polynucleotides, or Cx57 antisense oligonucleotides or polynucleotides. In some aspects, the connexin antisense oligonucleotides or polynucleotides comprise chiral phosphorous moieties such as those described in WO2013012758.

Also featured herein are exemplary modified or unmodified connexin 43 antisense compounds comprising a nucleotide sequence or modified from a nucleotide sequence selected from SEQ ID NO:1-16. The polynucleotides of this invention include polynucleotides having a length of less than 80 nucleotides, e.g., from 12-18 to about 50-80 nucleotides, preferably about 30 nucleotides or less, e.g., from 12 to about 30 nucleotides, and more preferably from about 15 to about 30 nucleotides. In one example, the polynucleotide has 30 nucleotides. The methods of this invention features, in some aspects, the use of connexin 43 antisense compounds up to 40 nucleotides in length, for example, 15 to 40 nucleotides in length, comprising a nucleotide sequence selected from SEQ ID NOs:1-17, from SEQ ID NOs:4-17, or comprising from about 8 to 40 nucleotides of SEQ ID NO: 17. In some embodiments the Cx43 antisense compounds may be modified by substituting one or more uridine nucleotides residues for one or more thymine nucleotides in SEQ ID NOs:4-17, or in SEQ ID Nos 1-3.

Also featured herein are modified or unmodified Cx45 antisense polynucleotides comprising from 8 to about 80 nucleotides of SEQ. ID. NO: 217 and modified and unmodified pannexin antisense polynucleotides comprising from 8 to about 80 nucleotides of SEQ. ID. NO: 279. The polynucleotides of this invention include synthesized polynucleotides having a length of less than 80 nucleotides, e.g., from 12-18 to about 50-80 nucleotides, preferably about 30 nucleotides or less, e.g., from 12 to about 30 nucleotides, and more preferably from about 15 to about 30 nucleotides. In one example, the polynucleotide has 30 nucleotides. The methods of this invention features, in some aspects, the use of connexin 45 antisense compounds up to 40 nucleotides in length, for example, 15 to 40 nucleotides in length, for example, comprising from about 8 to about 40 or from about 15 to about 40 nucleotides of SEQ ID NO:217. The methods of this invention features, in some aspects, the use of pannexin antisense compounds up to 40 nucleotides in length, for example, 15 to 40 nucleotides in length, for example, comprising from about 8 to about 40 or from about 15 to about 40 nucleotides of SEQ ID NO:117-121. In some embodiments the connexin 45 or pannexin antisense compounds may be modified by substituting one or more uridine nucleotides residues for one or more thymine nucleotides in SEQ ID NO:217, or SEQ ID NO:117-121.

Also featured for use in any of the methods featured herein are modified or unmodified Cx26 polynucleotides, Cx31.1 polynucleotides, Cx36 polynucleotides, Cx37 polynucleotides, Cx40 polynucleotides, Cx50 polynucleotides, or Cx57 polynucleotides or modified or unmodified antisense polynucleotides to any other connexin in the eye or blood vessels. The pharmaceutical compositions of this invention for any of the uses featured herein may also comprise a pannexin antisense polynucleotide modulator, which may inhibit pannexin channels, for example, Panx1 or Panx2, or Panx3. In some embodiments the modulator can include or exclude any of the foregoing.

In some aspects of this invention, the connexin 43 antisense oligonucleotide or polynucleotide has at least about 80%, 85%, 90%, 95%, 97%, 98%, or 99% homology to a polynucleotide having a sequence selected from SEQ ID NOs: 1 to 17. Connexin or pannexin modulators that are oligonucleotides or polynucleotides may have at least about 80%, 85%, 90%, 95%, 97%, 98%, or 99% homology to an 8 to 80 nucleotide portion of their respective sequences. For example, connexin 45 modulators that are oligonucleotides or polynucleotides may have at least about 80%, 85%, 90%, 95%, 97%, 98%, or 99% homology to an 8 to 80 nucleotide portion of SEQ ID NO:217, while pannexin modulators that are oligonucleotides or polynucleotides may have at least about 80%, 85%, 90%, 95%, 97%, 98%, or 99% homology to an 8 to 80 nucleotide portion of SEQ ID NO: 117 (Panx1 polynucleotide), (Panx1 polynucleotide RefSeq ID NM_015368.3), SEQ ID NO:118 (Panx2 polynucleotide), (Panx2 polynucleotide RefSeq ID NM_052839.3 for variant 1), SEQ IDNO:119 (RefSeq ID NM_001160300.1 for Panx2 polynucleotide variant 2), SEQ ID NO: 120 (RefSeq ID NR_027691.1 for Panx2 polynucleotide variant 3), or SEQ ID NO: 121 (Panx3 polynucleotide) (Panx3 polynucleotide RefSeq ID NM_052959.2), or variants thereof. In some aspects, the pannexin modulators can include or exclude pannexin peptide sequences. The pannexin peptide sequences can comprise 8-40 consecutive amino acids, an extracellular domain, an intracellular domain, a carboxy terminus part, or an amino terminus part, of the polypeptides SEQ ID NO: 122 (Panx1 peptide), SEQ ID NO: 123 (Panx2 peptide), or SEQ ID NO: 124 (Panx3 peptide), or variants thereof. In some embodiments the modulator can include or exclude any of the foregoing.

In other embodiments, the gap junction modulators or connexin modulators are connexin peptides or peptidomimetics, sometimes referred to anti-connexin peptides or peptdomimetics, e.g., anti-connexin hemichannel blocking peptides or peptidomimetics, for example, modified or unmodified peptides or peptidomimetics comprising connexin extracellular domains, transmembrane regions, and connexin carboxy-terminal peptides). The gap junction modulators or anti-connexin hemichannel blocking peptides or peptidomimetics may be modified or unmodified. The gap junction modulators and anti-connexin hemichannel blocking peptides or peptidomimetics are made chemically, synthetically, or otherwise manufactured. In some embodiments, the gap junction modulators or connexin modulators are Cx43 peptides or peptidomimetics. In some aspects, the therapeutically effective modified or unmodified peptide or peptidomimetic comprises a portion of an extracellular or transmembrane domain of a connexin, such as Cx43 or Cx45. In other embodiments, the pannexin or pannexin channel modulators are pannexin peptides or peptidomimetics, sometimes referred to anti-pannexin peptides or peptidomimetics, for example, modified or unmodified peptides or peptidomimetics.

In some embodiments the modulators of this invention include anti-Cx43 peptides or peptidomimetics, for example, any of the peptides described herein, including peptides comprising a portion of an extracellular domain of a connexin, and peptides comprising a portion of a carboxy-terminal portion of a connexin useful in the methods of this invention, which is therapeutically effective, for example, effective for healing any of the neuropathic ocular disorders described herein. In some aspects, the therapeutically effective modified or unmodified peptide or peptidomimetic comprises a portion of an extracellular or transmembrane domain of a connexin, such as Cx43.

In some embodiments the modulator may be gap junction closing compounds and hemichannel closing compounds. In some embodiments, the gap junction closing compounds and hemichannel closing compounds are connexin 43 gap junction closing compounds and connexin 43 hemichannel closing compounds. Preferred connexin carboxy-terminal polypeptides are connexin 43 carboxy-terminal polypeptides.

In other embodiments, the gap junction modulators are gap junction peptides or peptidomimetics, sometimes referred to anti-gap junction peptides or peptdomimetics, e.g., anti-gap junction or hemichannel blocking peptides or peptidomimetics, for example, modified or unmodified peptides or peptidomimentics comprising extracellular domains, transmembrane regions, or connexin carboxy-terminal peptides of proteins comprising gap junctions in the eye, including Cx43, Cx26, Cx30, Cx31.1, Cx36, Cx37, Cx40, Cx45, Cx50, and Cx57. The anti-gajp junction or hemichannel blocking peptides or peptidomimetics may be modified or unmodified. The anti-gap junction or hemichannel blocking peptides or peptidomimetics are made chemically, synthetically, or otherwise manufactured. In some embodiments, the gap junction modulators are Cx43, Cx26, Cx30, Cx31.1, Cx36, Cx37, Cx40, Cx45, Cx50, and Cx57 peptides or peptidomimetics.

Treatment of a subject for any of the ocular conditions described herein, e.g., for glaucoma, DME, eye fibrosis, AMD, or other ocular disorders as referenced herein with one or more pharmaceutical compositions of the invention, e.g., an anti-connexin ODN and a gap junction modulator such as a connexin hemichannel blocking agent, e.g., a peptide or peptidomimetic, or a first anti-connexin agent and a second anti-connexin agent, may comprise their simultaneous, separate, sequential or sustained administration.

In some aspects of this invention, the modulator is a gap junction closing or blocking compound or hemichannel closing or blocking compound, such as tonabersat. In some embodiments, the gap junction modulator can be a small molecule, which may also be referred to herein as an anti-connexin or connexin modulator. In some aspects, the anti-connexin modulator drug can have the structure in Formula I:

(I)

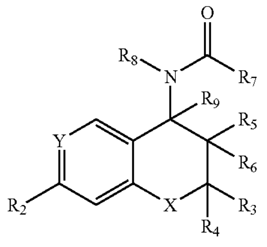

wherein Y is C—$R_1$;

$R_1$ is acetyl;

$R_2$ is hydrogen, $C_{3-8}$ cycloalkyl, $C_{1-6}$ alkyl optionally interrupted by oxygen or substituted by hydroxy, $C_{1-6}$ alkoxy or substituted aminocarbonyl, $C_{1-6}$ alkylcarbonyl, $C_{1-6}$ alkoxycarbonyl, $C_{1-6}$ alkylcarbonyloxy, $C_{1-6}$ alkoxy, nitro, cyano, halo, trifluoromethyl, or CF3S; or a group $CF_3$-A-, where A is —$CF_2$—, —CO—, —$CH_2$—, CH(OH), $SO_2$, SO, $CH_2$—O, or CONH; or a group $CF_2$H-A'- where A' is oxygen, sulphur, SO, $SO_2$, $CF_2$ or CFH; trifluoromethoxy, $C_{1-6}$ alkylsulphinyl, perfluoro $C_{2-6}$ alkylsulphonyl, $C_{1-6}$ alkylsulphonyl, $C_{1-6}$ alkoxysulphinyl, $C_{1-6}$ alkoxysulphonyl, aryl, heteroaryl, arylcarbonyl, heteroarylcarbonyl, phosphono, arylcarbonyloxy, heteroarylcarbonyloxy, arylsulphinyl, heteroarylsulphinyl, arylsulphonyl, or heteroarylsulphonyl in which any aromatic moiety is optionally substituted, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkylthiocarbonyloxy, 1-mercapto $C_{2-7}$ alkyl, formyl, or aminosulphinyl, aminosulphonyl or aminocarbonyl, in which any amino moiety is optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or —C($C_{1-6}$ alkyl)NOH or —C($C_{1-6}$ alkyl)$NNH_2$; or amino optionally substituted by one or two $C_{1-6}$ alkyl or by $C_{2-7}$ alkanoyl; one of $R_3$ and $R_4$ is hydrogen or $C_{1-4}$ alkyl and the other is $C_{1-4}$ alkyl, $CF_3$ or $CH_2X^a$ is fluoro, chloro, bromo, iodo, $C_{1-4}$ alkoxy, hydroxy, $C_{1-4}$ alkylcarbonyloxy, —S—$C_{1-4}$ alkyl, nitro, amino optionally substituted by one or two $C_{1-4}$ alkyl groups, cyano or $C_{1-4}$ alkoxycarbonyl; or $R_3$ and $R_4$ together are $C_{2-5}$ polymethylene optionally substituted by $C_{1-4}$ alkyl;

$R_5$ is $C_{1-6}$ alkylcarbonyloxy, benzoyloxy, $ONO_2$, benzyloxy, phenyloxy or $C_{1-6}$ alkoxy and $R_6$ and $R_9$ are hydrogen or $R_5$ is hydroxy and $R_6$ is hydrogen or $C_{1-2}$ alkyl and $R_9$ is hydrogen;

$R_7$ is heteroaryl or phenyl, both of which are optionally substituted one or more times independently with a group or atom selected from chloro, fluoro, bromo, iodo, nitro, amino optionally substituted once or twice by $C_{1-4}$ alkyl, cyano, azido, $C_{1-4}$ alkoxy, trifluoromethoxy and trifluoromethyl;

$R_8$ is hydrogen, $C_{1-6}$ alkyl, $OR_{11}$ or $NHCOR_{10}$ wherein $R_{11}$ is hydrogen, $C_{1-6}$ alkyl, formyl, $C_{1-6}$ alkanoyl, aroyl or aryl-$C_{1-6}$ alkyl and $R_{10}$ is hydrogen, $C_{1-6}$ alkyl, $C_{1-6}$ alkoxy, mono or di C.sub.1-6 alkyl amino, amino, amino-C.sub.1-6 alkyl, hydroxy-$C_{1-6}$ alkyl, halo-$C_{1-6}$ alkyl, $C_{1-6}$ acyloxy-$C_{1-6}$ alkyl, $C_{1-6}$ alkoxycarbonyl-$C_{1-6}$-alkyl, aryl or heteroaryl; the $R_8$—N—CO—$R_7$ group being cis to the $R_5$ group; and X is oxygen or $NR_{12}$ where $R_{12}$ is hydrogen or $C_{1-6}$ alkyl.

For any of the Markush groups set forth above, in some embodiments, each group can include or exclude any of the species listed for that group.

In some embodiments, the small molecule connexin modulator can be Tonabersat, carabersat, or SB-204269. SB-204269 is also known as (trans-(+)-6-acetyl-4S-(4-fluorobenzoylamino)-3,4-dihydro-2,2-dimethyl-2H-benzo[b]pyran-3R-ol). Carabersat is also known as N-[(3R,4S)-6-Acetyl-3-hydroxy-2,2-dimethyl-3,4-dihydro-2H-chromen-4-yl]-4-fluorobenzamide. Tonabersat is also known as N-(6-Acetyl-3-hydroxy-2,2-dimethyl-3,4-dihydro-2H-chromen-4-yl)-3-chloro-4-fluorobenzamide.

For any of the Markush groups set forth above, that group can include or exclude any of the species listed for that group.

In some embodiments, the connexin modulator may be a pro-drug of any the compounds for use in this invention. In one aspect the connexin modulator pro-drug of this invention may be a compound of Formula II:

(II)

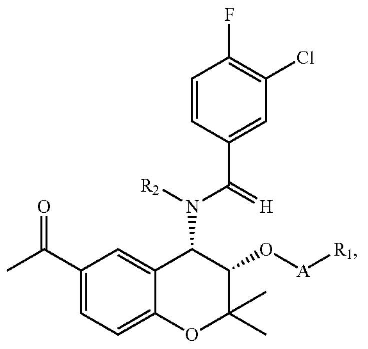

wherein

Q is O or an oxime, $R_2$ is H,

A is a direct bond, —C(O)O*—, —$C(R_3)(R_4)O$*—, —C(O)O—$C(R_3)(R_4)O$*—, or —$C(R_3)(R_4)OC(O)O$*— wherein the atom marked * is directly connected to $R_1$, $R_3$ and $R_4$ are selected independently from H, fluoro, $C_{1-4}$ alkyl, or $C_{1-4}$ fluoroalkyl, or $R_3$ and $R_4$ together with the atom to which they are attached form a cyclopropyl group, $R_1$ is selected from groups [1], [2], [2A], [3], [4], [5] or [6] wherein the atom marked ** is directly connected to A:

[1]

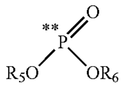

[2]

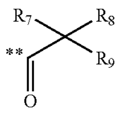

[2a]

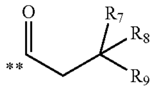

[3]

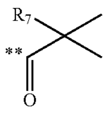

[4]

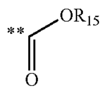

[5]

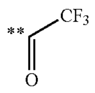

[6]

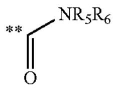

$R_5$ and $R_6$ are each independently selected from H, $C_{1-4}$ alkyl, $C_{1-4}$ fluoroalkyl, or benzyl;

$R_7$ is independently selected from H, $C_{1-4}$ alkyl, or $C_{1-4}$ fluoroalkyl;

$R_8$ is selected from:

(i) H, $C_{1-4}$ alkyl, or $C_{1-4}$ fluoroalkyl, or (ii) the side chain of a natural or unnatural alpha-amino acid, or a peptide as described herein, or (iii) biotin or chemically linked to biotin;

$R_9$ is selected from H, —$N(R_{11})(R_{12})$, or —$N^+(R_{11})(R_{12})(R_{13})X^-$, or —$N(R_{11})C(O)R_{14}$ wherein $R_{11}$, $R_{12}$, and $R_{13}$ are independently selected from H, $C_{1-4}$ alkyl, or $C_{1-4}$ fluoroalkyl, $R_{14}$ is H, $C_{1-4}$ alkyl, or $C_{1-4}$ fluoroalkyl, $R_{15}$ is selected from $C_{1-4}$ alkyl or $C_{1-4}$ fluoroalkyl, and $X^-$ is a pharmaceutically acceptable anion.

In some aspects, $R_2$ is B—$R_{21}$ wherein,

B is a direct bond, —C(O)O*—, —$C(R_{23})(R_{24})O$*, C(O)O $C(R_{23})(R_{24})$*, or $C(R_{23})(R_{24})OC(O)O$* wherein the atom marked * is directly connected to $R_{21}$, $R_{23}$ and $R_{24}$ are selected independently from H, fluoro, $C_{1-4}$ alkyl, or $C_{1-4}$ fluoroalkyl, $R_{21}$ is selected from groups [21], [22], [22A], [23], [24], [25] and [26] wherein the atom marked ** is directly connected to B:

[21]

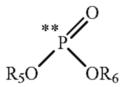

[22]

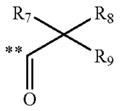

[22a]

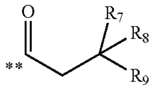

[23]

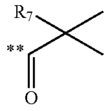

[24]

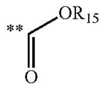

[25]

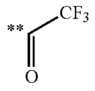

[26]

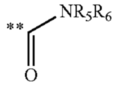

wherein $R_5$, $R_6$, $R_7$, $R_8$, $R_9$, and $R_{15}$ are as defined herein.

For any of the Markush groups set forth above, that group can include or exclude any of the species listed for that group.

In some aspects, the peptide as described herein can be a connexin modulator, calmodulin modulator, or pannexin modulator.

In some aspects,

Q is an oxime of formula=$NHOR_{43}$, wherein $R_{43}$ is (i) selected from H, $C_{1-4}$ fluoroalkyl or optionally substituted $C_{1-4}$ alkyl, or (ii) $-A_{300}-R_{300}$ wherein $A_{300}$ is a direct bond, —C(O)O*—, —$C(R_3)(R_4)O$*—, —C(O)O—$C(R_3)(R_4)O$*—, or —$C(R_3)(R_4)OC(O)O$*— wherein the atom marked * is directly connected to $R_{30}$, $R_3$ and $R_4$ are selected independently from H, fluoro, $C_{1-4}$ alkyl, or $C_{1-4}$ fluoroalkyl, or $R_3$ and $R_4$ together with the atom to which they are attached form a cyclopropyl group, $R_{300}$ is selected from groups [1], [2], [2A], [3], [4], [5] or [6] wherein the atom marked ** is directly connected to $A_{300}$:

[1]

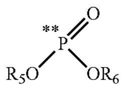

[2]

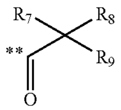

[2a]

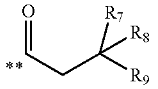

[3]

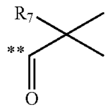

[4]

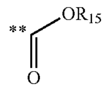

[5]

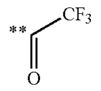

[6]

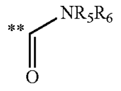

$R_5$ and $R_6$ are each independently selected from H, $C_{1-4}$ alkyl, $C_{1-4}$ fluoroalkyl, or benzyl;

$R_7$ is independently selected from H, $C_{1-4}$ alkyl, or $C_{1-4}$ fluoroalkyl;

$R_8$ is selected from:

(iii) H, $C_{1-4}$ alkyl, or $C_{1-4}$ fluoroalkyl, or (iv) the side chain of a natural or unnatural alpha-amino acid or a peptide as described herein, or (v) biotin or chemically linked to biotin;

$R_9$ is selected from H, —$N(R_{11})(R_{12})$, or —$N^+(R_{11})(R_{12})(R_{13})X^-$, or —$N(R_{11})C(O)R_{14}$ wherein $R_{11}$, $R_{12}$, and $R_{13}$ are independently selected from H, $C_{1-4}$ alkyl, or $C_{1-4}$ fluoroalkyl, $R_{14}$ is H, $C_{1-4}$ alkyl, or $C_{1-4}$ fluoroalkyl $R_{15}$ is selected from $C_{1-4}$ alkyl or $C_{1-4}$ fluoroalkyl, and $X^-$ is a pharmaceutically acceptable anion.

In an embodiment $R_{43}$, is $C_{1-4}$ alkyl optionally substituted with a phosphate group ($P(O)OR_{61}R_{62}$). In an example of such an embodiment $OR_{43}$ is —$OCH_2P(O)OR_{61}OR_{62}$, wherein $R_{61}$ and $R_{62}$ are independently H or $C_{1-4}$ alkyl.

In another embodiment $R_{43}$ is an amino acid derivative having the structure $C(O)CH(R_{100})NH_2$ wherein the group $R_{100}$ is the side chain of a natural or unnatural amino acid or a peptide as described herein.

In an embodiment $OR_{43}$ is —$OC(O)CH(CH(CH_3)_2)NH_2$.

For any of the Markush groups set forth above, in some embodiments, each group can include or exclude any of the species listed for that group.

In some aspects, the peptide as described herein can be any of the peptide or peptidomimetic modulators disclosed herein, for example, a peptide or peptidomimetic connexin modulator or pannexin modulator. In some aspects the peptide connexin modulator can be any of SEQ ID NOs: 140-200, 72-139, 216-224, 244-256 and 132.

The compositions described herein can be used to an ocular condition including or excluding those described herein.

In some aspects, the pro-drug can be those described in WO 2014/006407, and herein incorporated by reference. In some aspects the promoiety of the connexin modulator may comprise a chaperone moeity that targets one or more regions or structures of the eye. The promoiety may be any peptidomimetic or peptide antagonist of this disclosure. In some embodiments, the promoeity can be a single amino acid which is optionally protected on its functional groups. In some embodiments, the promoeity can be a targeting species. In some aspects, the promoeity can be a substrate for an influx or efflux transporters on the cell membrane. The promoeity can be, for example, chemically-linked biotin. The promoeity can be, for example, chemically-linked D-serine.

In one aspect of the methods of this invention, one or more gap junction modulators, one or more pannexin channel modulators, one or more hemichannel modulators, one or more connexin modulators, or one or more pannexin modulators as described herein may be administered in combination with one or a plurality of ocular treatment agents useful for treating ocular disorders, including, for example, glaucoma, ocular fibrosis, ocular hypoxia, AMD, DME, ocular hypoxia, and/or neuropathic disorders of the eye. In some aspects of this invention, the one or more connexin modulators or pannexin modulators, administered for the treatment of ocular disorders, for example, wet or dry AMD, neuropathic ocular disorders such as intraocular loss of retinal ganglion cells glaucomatous ocular neuropathy and/or intraocular pressure-associated neuropathy, may be administered with an ocular treatment agent. In some embodiments the one or more gap junction modulators, one or more pannexin channel modulators, one or more hemichannel modulators, one or more connexin modulators or or or more pannexin modulators may be co-administered in a formulation comprising the one or more gap junction modulators, one or more pannexin channel modulators, one or more hemichannel modulators, one or more connexin modulators or or or more pannexin modulators and the ocular treatment agent.

Ocular treatment agents for use in combination with one or more gap junction modulators, one or more pannexin channel modulators, one or more hemichannel modulators, one or more connexin modulators or one or more pannexin modulators of this invention include, for example, anti-VEGF modulating agents such as VEGF antagonists, mTOR inhibitors, PDGF modulators such as PDGF antagonists, inhibitors of S1P production, squalamine, PEDF producers, tubulin binding agents, integrin inhibitors, or other therapeutic agents useful, in treating, for example, neovascularation AMD or wet AMD. Preferably, the ocular treatment agent for use in combination with one or more of the modulators of this invention is a PDGF modulator. In some aspects, the modulator can include or exclude any of the foregoing.

In some aspects, VEGF modulators can be antagonists that inhibit and/or block VEGF or that inhibit and/or block upstream agonists of VEGF. In some aspects the VEGF antagonists include, for example, antagonists that bind to and inhibit VEGF, compounds that inhibit expression of VEGF, and/or viral vectors comprising VEGF inhibitors or encoding proteins or antisense polynucleotides that block or inhibit VEGF. In some aspects, species that inhibit VEGF and/or upstream agonists of VEGF can be antibodies or antibody fragments, nanobodies, peptide or peptidomimetics, receptor fragments, recombinant fusion proteins, aptamers, small molecules, or single chain variable fragments (scFv). In some aspects, VEGF antagonist antibodies can be, for example, Lucentis™ (ranibizumab), and/or Avastin™ (bevacizumab).

Increased mTOR activity in cells can lead to secretion of VEGF and PDGF, which promotes angiogenesis by increasing mTOR activity in vascular cells. In some aspects of this invention, the VEGF modulators decrease the activity of VEGF-R or mTOR, thereby reducing angiogenesis. In some aspects, VEGF antagonists that inhibit and/or block upstream agonists of VEGF binding partners and inhibit VEGF can be a RTP801 inhibitor or REDD1 blocker. In addition, increased mTOR activity in cells can lead to secretion of VEGF and PDGF, which promotes angiogenesis by increasing mTOR activity in vascular cells. Accordingly, in some aspects, the VEGF modulators can be mTOR inhibitors, for example, macrolides or small molecules.

Ocular treatment agents for use in combination with one or more of the gap junction modulators, one or more pannexin channel modulators, one or more hemichannel modulators, one or more connexin modulators or one or more pannexin modulators of this invention also include, for example, complement modulators, and other therapeutic agents useful, for example, in treating geographic atrophy, dry AMD, non-exudative AMD, and/or Drusen development. The complement modulators can be, for example, compstatin, TP10, Eculizumab, ARC1905, JPE-1375, PMX53, Lampalizumab, or rhCFHp.

In some aspects, ocular treatment agents for use in combination with one or more of the gap junction modulators, one or more pannexin channel modulators, one or more hemichannel modulators, one or more connexin modulators or one or more pannexin modulators of this invention can include TNF-alpha inhibitors, C-raf kinase inhibitors, NSAIDs, or nAChR inhibitors.

The anti-connexin modulator used in any of the admistration, co-administrations, compositions, kits or methods of treatment of this invention may be a Cx43 modulator, a Cx45 modulator, a modulator of Cx26, Cx30, Cx31.1, Cx36, Cx37, Cx40, Cx50, and Cx57 or a modulator of any connexin present in ocular (or other) blood vessels.

The ocular treatment agent useful in treating an ocular disorder, such as glaucoma and/or retinal perfusion impairment, wet and/or dry AMD, or any other ocular disorder referenced herein, may be, for example, an alpha 2 agonist, such as brimonidine, a carbonic anyhydrase inhibitor, a beta blocker, F2α prostaglandin analogs, anti-apoptosis agents, N-methyl-D-aspartate (NMDA) receptor antagonists, a Rho kinase inhibitor, or glutamate release inhibitors. The ocular treatment agent may also be a combination therapy comprising administering two or more ocular treatment agents, for example can include or exclude, a beta blocker and a carbonic anhydrase inhibitor, such as timolol & travoprost or timolol & dorzolamide, a combination of an alpha 2 agonist and a beta-blocker such as brimonidine and timolol, or a combination of an alpha 2 agonist and a carbonic anyhydrase inhibitor such as brinzolamide and brimonidine. In some aspects, the ocular treatment agents may include or exclude rho kinase inhibitors. In other aspects the ocular treatment agents may be adenosine mimetics. Other ocular treatment agents may include neurotrophins such as ciliary neurotropic factor or nerve growth factor. In some aspects the ocular treatment agent can include or exclude one or more of alibercept, lampalizumab, sonepcizumab, fenretinide, ranibizumab (e.g., Lucentis™), bevacizumab (e.g., Avastin™), protein ciliary neutrophic factor, a vascular endothelial growth factor-modulating compound, and a hypoxia-inducible factor 1-alpha-modulating compound, and any mixture thereof. In one aspect, the gap junction modulator, pannexin channel modulator, hemichannel modulator, connexin modulator or pannexin modulator administered alone or in combination with one or more ocular treatment agents may be modified or unmodified. In some aspects of this invention, a modified connexin or pannexin modulator may comprise modified and unmodified moieties, such as modified and unmodified nucleotides or modified and unmodified amino acids. In some aspects, the connexin or other modulator, may be, for example, a modified oligonucleotide, a modified polynucleotide, or a modified peptide or peptidomimetic, as described herein. In some aspects, the connexin modulator may be co-administered before, with or after, or on the same or parallel administration schedules as, or in the same formulation as the one or more ocular treatment agents. In some aspects, the pannexin or other modulator, may be, for example, a modified oligonucleotide, a modified polynucleotide, or a modified peptide or peptidomimetic, as described herein. In some aspects, the pannexin or other modulator may be administered before, with or after, or on the same or parallel administration schedules as, the one or more ocular neuropathic treatments. In some aspects, the pannexin or other modulator, may be, for example, a modified oligonucleotide, a modified polynucleotide, or a modified peptide or peptidomimetic, as described herein. In some aspects, the pannexin or other modulator may be administered before, with or after, or on the same or parallel administration schedules as, the one or more ocular neuropathic treatments.

In some aspects of the methods of this invention, two or more gap junction modulators, hemichannel modulators, or such as two or more connexin modulators as described herein may be administered, which can be the same or a different type of modulator, for example, two or more polynucleotides, two or more peptides or peptidomimetic compounds, or two or more compounds. For example, in some aspects of the methods of this invention, two or more Cx43 modulators as described herein may be administered, which can be the same or a different type of modulator, for example, two or more polynucleotides, two or more peptides or peptidomimetic compounds, or two or more compounds. In some embodiments, for example, one or more Cx43 polynucleotides may be co-administered with one or more Cx43 peptides or peptidomimetics and/or one or more anti-connexin compounds, or any subcombination thereof. In some aspects, the methods of this invention may comprise administering an connexin anti-sense polynucleotide to transiently modulate gap junction channels: by modulating protein expression, and further comprise administering a connexin peptide or peptidomimetic to directly and more immediately modulate gap junction channel function. For example, the methods of this invention may comprise administering an Cx43 anti-sense polynucleotide to transiently modulate gap junction channels: by modulating protein expression, and further comprise administering a Cx43 peptide or peptidomimetic to directly modulate gap junction channel function. The modulators may also be targeted to the same or different proteins, such as Cx43, Cx45 and/or a pannexin. The connexin modulators and/or blockers, pannexin modulators and/or blockers, gap junction modulators, hemichannel modulators and/or blockers may be modified or unmodified.

In some aspects of the methods of this invention, one or more gap junction and/or connexin modulators as described herein may be administered with a pannexin modulator, which can be the same or a different type of modulator, for example, two or more polynucleotides, two or more peptides or peptidomimetic compounds, or two or more compounds. In some aspects the connexin modulator is a Cx43 modulator.

In some aspects of the methods of this invention, two or more pannexin or pannexin channel modulators as described herein may be administered, which can be the same or a different type of modulator, for example, two or more polynucleotides, two or more peptides or peptidomimetic compounds, or two or more compounds.

As described further herein, the modified oligonucleotide further comprises one or more of the following selected components: a modified internucleoside linkage, for example, a phosphorothioate linkage, and a modified sugar moiety, for example, a conformationally-strained sugar, for example, an LNA or BNA.

In some aspects of this invention the connexin modulators (for example, Cx26, Cx30, Cx31.1, Cx36, Cx37, Cx40, Cx43, Cx45, Cx50, or Cx57 modulators) or pannexin modulators of the invention are combined with a pharmaceutically acceptable carrier or diluent to produce a pharmaceutical composition. In some aspects, suitable carriers and diluents include buffered, aqueous solutions, isotonic saline solutions, for example phosphate-buffered saline, isotonic water, and the like.

In another aspect, a P2X7 receptor antagonist is administered alone or together with a gap junction modulator, a pannexin channel modulator, a hemichannel modulator, a connexin modulator and/or a pannexin modulator to treat the diseases, disorders and conditions referenced herein. P2X7 antagonists include NF279 suramin analog), calmidazolium (a calmodulin antagonist), KN-62 (a CaM kinanse II antagonist), zinc, calcium, magnesium and copper.

Various preferred embodiments include use of a small molecule that blocks or ameliorates or otherwise antagonizes or inhibits hemichannel opening, alone or together with a small molecule that blocks or ameliorates or otherwise antagonizes or inhibits pannexin channel opening, to treat the diseases, diorders and conditions referenced herein. In various preferred embodiments, the small molecule that blocks or ameliorates or inihibits hemichannel opening is tonabersat or an analogue thereof, or a prodrug of either. In various embodiments, the small molecule that blocks or ameliorates or inhibits pannexin channel opening is probenecid or an analogue thereof, or a prodrug of either. In various preferred embodiments, the disease, disorder or condition is an ocular neovascular disease, an ocular edema, an ocular microvascular disorder, and a diabetic ocular disease. In certain embodiments, the disease, disorder or condition is diabetic retinopathy, ischemic retinopathy, choroidal neovascularization, iris neovascularization, corneal neovascularization, retinal neovascularization, intraocular neovascularization, wet age-related macular degeneration, dry age-related macular degeneration, ocular geographic atrophy, diabetic macular edema, diabetic retinopathy, diabetic retinal ischemia, proliferative diabetic retinopathy, Coates disease, central retinal vein occlusion (CRVO), branched central retinal vein occlusion (BRVO), retinopathy of prematurity (ROP), subconjunctival hemorrhage, and hypertensive retinopathy, uveitis or cataracts.

In other preferred embodiments, the disease, disorder or condition is glaucoma, including open-angle glaucoma, angle-closure glaucoma, and normotensive glaucoma, as well as variants of open-angle and angle-closure glaucoma such as secondary glaucoma, pigmentary glaucoma, pseudoexfoliative glaucoma, traumatic glaucoma, neovascular glaucoma and irido corneal endothelial syndrome (ICE) and neovascular glaucoma. In another preferred embodiments, the disease, disorder or condition is dry eye disease. In another embodiment, the disease, disorder or condition is ocular and corneal persistent epithelial defect. In still other preferred embodiments, the disease, disorder or condition is a chronic dermal wound, ulcer or ulcerous lesion, including diabetic foot ulcers, venous leg ulcers, and pressure ulcers. In another preferred embodiment, the disease, disorder or condition is a CNS trauma, including spinal cord injury and optic nerve injury. The invention also features a method for treating a patient diagnosed with or at risk for developing a neovascular disorder wherein, in addition to administration of a small molecule that blocks or ameliorates or otherwise antagonizes or inhibits hemichannel opening alone or together with a small molecule that blocks or ameliorates or otherwise antagonizes or inhibits pannexin channel opening, the method also includes administering to the patient an anti-VEGF agent and/or an anti-PDGF agent as a therapeutic treatment. In one aspect, a PDGF antagonist and/or a VEGF antagonist is/are administered to a patient simultaneously with, or within about 1 to 5, 10 or 90 days of, administration of, a hemichannel antagonist and/or pannexin channel antagonist, in amounts sufficient to suppress the neovascular disorder in the patient. In a particular embodiment of the method of the invention, the PDGF antagonist and/or the VEGF antagonist are administered simultaneously with the hemichannel antagonist or inhibitor and/or the pannexin channel antagonist or inhibitor. In one embodiment, the PDGF antagonist is a PDGF-B antagonist. In another embodiment, the VEGF antagonist is a VEGF-A antagonist. In certain embodiments, the PDGF antagonist is a nucleic acid molecule, an aptamer, an antisense RNA molecule, a ribozyme, an RNAi molecule, a protein, a peptide, a cyclic peptide, an antibody, a binding fragment of an antibody fragment, a sugar, a polymer, or a small molecule. In another embodiment, the VEGF antagonist is a nucleic acid molecule, an aptamer, an antisense RNA molecule, a ribozyme, an RNAi molecule, a protein, a peptide, a cyclic peptide, an antibody, a binding fragment of an antibody fragment, a sugar, a polymer, or a small molecule. In a particular embodiment, this method of the invention involves administration of a VEGF antagonist that is an aptamer, such as an EYE001 aptamer. In another embodiment, this method of the invention involves administration of a VEGF antagonist that is an antibody or binding fragment thereof, such as Avastin® (bevacizumab) or Lucentis® (ranibizumab). In a particular embodiment, this method of the invention involves administration of a PDGF antagonist that is an aptamer, an antibody or a binding fragment thereof. In another particular embodiment, this method of the invention involves administration of a PDGF antagonist that is an antisense oligonucleotide. In yet another embodiment of this aspect of the invention, the PDGF antagonist and/or the VEGF antagonist are pro-drugs. In another embodiment, this method of the invention provides a means for suppressing or treating an ocular neovascular disorder. In some embodiments, ocular neovascular disorders amenable to treatment or suppression by the method of the invention include ischemic retinopathy, iris neovascularization, intraocular neovascularization, age-related macular degeneration, corneal neovascularization, retinal neovascularization, choroidal neovascularization, diabetic retinal ischemia, or proliferative diabetic retinopathy. In still another embodiment, the method of the invention provides a means for suppressing or treating psoriasis or rheumatoid arthritis in a patient in need thereof or a patient diagnosed with or at risk for developing such a disorder. The invention also provides a pharmaceutical composition that includes a PDGF antagonist and/or a VEGF antagonist, as well a pharmaceutically acceptable carrier, along with one or more of a small molecule that blocks or ameliorates or otherwise antagonizes or inhibits hemichannel opening alone or together with a small molecule that blocks or ameliorates or otherwise antagonizes or inhibits pannexin channel opening. In this aspect, the PDGF and/or VEGF antagonists are present in amount(s) sufficient to suppress the neovascular disorder in the patient. This pharmaceutical composition of the invention may include a pharmaceutically acceptable carrier that includes a microsphere, nanoparticle, or a hydrogel formulation. Another embodiment of this aspect of the invention provides a pharmaceutical pack that includes a PDGF antagonist and/or a VEGF antagonist together with a small molecule that blocks or ameliorates or otherwise antagonizes or inhibits hemichannel opening alone or together with a small molecule that blocks or ameliorates or otherwise antagonizes or inhibits pannexin channel opening. In one embodiment of this aspect, the pharmaceutical pack includes a PDGF antagonist that is a PDGF-B antagonist. In another embodiment of this aspect, the pharmaceutical pack includes a VEGF antagonist that is a VEGF-A antagonist. In another embodiment, the PDGF antagonist and VEGF antagonist of the pharmaceutical pack are formulated separately and in individual dosage amounts. In still another embodiment, the PDGF antagonist and VEGF antagonist of the pharmaceutical pack are formulated together. It will be seen that the combination of an anti-VEGF agent and/or an anti-PDGF agent can also afford surprisingly synergistic therapeutic benefits for treating an ocular neovascular disease.

BRIEF DESCRIPTION OF THE FIGURES

The patent of application file contains at least one drawing executed in color. Copies of this patent or patent application publication with color drawing(s) will be provided by the Office upon request and payment of the necessary fees. FIG. 1A-FIG. 1F. Scrape loading studies using Lucifer yellow spread to neighbouring hCMVEC cells as an indication of gap junction coupling levels. In the no treatment arm dye spreads readily to neighbouring cells (FIG. 1A). Peptide5 at the lower dose of 100 μM has little effect on coupling (FIG. 1B) but at the higher 500 μM dose there is an immediate reduction in spread (FIG. 1C). Over time, both peptide concentrations show gap junction uncoupling by two hours (FIG. 1D and FIG. 1E). The graph to the right shows quantification of a similar experiment comparing peptide5 blocking efficacy (immediate block, 500 μM) with the non-specific gap junction channel blocker carbenoxolone (FIG. 1F).

FIG. 4A-FIG. 4B1. DAPI (nuclear staining) and labelling of the gap junction protein Connexin43 (left panels, FIG. 4A and FIG. 4B) and matching Connexin43 only labelling (right hand panels, FIG. 4A1 and FIG. 4B 1) in ARPE-19 cells. In untreated cells gap junction labelling is primarily at cell-cell interfaces (top panels, FIG. 4A and FIG. 4A1). In cells treated for one hour with peptide5 (500 μM) the cell-cell interfaces are still apparent but the bulk of the gap junctions have been internalized (lower panels (FIG. 4B and FIG. 4B 1).

(FIG. 8A) ATP released from hCMVEC cells following 2-hour exposure to injury in vitro. Quantification of total extracellular ATP release is presented as a percentage of the injury control for each treatment group. A significant reduction in ATP was present across all treatment groups compared to injury control: 100 μM CBX, 100 μM Peptide5 and 1 mM Probenecid, and 100 μM Peptide5 in combination with 1 mM Probenecid; the latter combination reduced total ATP release to the same level as CBX. (FIG. 8B) Quantification of total extracellular ATP release is presented as a percentage of the injury control for each treatment group. A significant reduction in ATP was present across all treatment groups compared to injury control: 100 μM CBX, 0.1 μM to 100 μM Tonabersat in combination with 1 mM Probenecid. (FIG. 8C) In this experiment, Tonabersat did not reduce ATP release from hCMVEC cells in the absence of 1 mM Probenecid ($p>0.09$) One-way ANOVA, Tukey's multiple comparison test. Values represent mean±standard error. *** $P<0.001$ μgainst injury control.

(FIG. 10A and FIG. 10B) Immunolabeling of Cx43 in 100 μM Tonabersat (above, FIG. 10A), and 100 μM Tonabersat+NH4Cl for 1 h in serum-supplemented media (n=3 wells, 2 independent experiments) (FIG. 10B) Tonabersat controls (FIG. 10C) Quantification of the total area of Cx43 plaques per cell following treatment with Tonabersat (5-500 μM) for 1 h. (FIG. 10D) Quantification of the total area of Cx43 plaques per cell following treatment with Tonabersat (50-500 μM) with NH4Cl for 6 h (D). (FIG. 10C) and (FIG. 10D) are normalized to untreated control. Significant differences are represented as *** $p<0.0001$. Bars represent mean±S.E.M and the differences between. Scale bars=30 μm.

(FIG. 11A) Immunolabeling of Cx43 in untreated control (above), 100 μM Tonabersat (below), for 1 h in serum-supplemented media (n=3 wells, 2 independent experiments) (FIG. 11B) Quantification of the total area of Cx43 plaques per cell following treatment with Tonabersat (5-500 μM) for 1 h. (FIG. 11C) Quantification of the total area of Cx43 plaques per cell following treatment with Tonabersat (5-500 μM) for 6 h. B and C are normalized to untreated control. Bars represent mean±S.E.M and the significant difference represent *** $p<0.0001$. Statistical test One-way ANOVA, Scale bars=30 μm.

FIG. 12A-FIG. 12C. 6 h treatment with Tonabersat down-regulates Cx43 GJ plaques via the lysosomal degradation pathway in ARPE-19 cells. Immunolabeling of Cx43 in 100 μM Tonabersat (above, FIG. 12A), and 100 μM Tonabersat+NH4Cl for 6 h (FIG. 12A1) in serum-supplemented media (n=3 wells, 2 independent experiments) (FIG. 12B) Quantification of the total area of Cx43 plaques per cell following treatment with Tonabersat (5-500 μM) for 1 h. (FIG. 12C) Quantification of the total area of Cx43 plaques per cell following treatment with Tonabersat (50-500 μM) with NH4Cl for 6 h. (FIG. 12B) and (FIG. 12C) are normalized to untreated control. Significant difference *** $p<0.0001$. Bars represent mean±S.E.M and the differences between. Scale bars=30 μm.

FIG. 16A1-FIG. 16D. Functional effect of Tonabersat on intercellular communication in hCMVEC cells in vitro. (FIG. 16A1, FIG. 16A2) In vehicle control, LY dye spreads readily to neighbouring cells via coupled GJs. Immediate (FIG. 16A3, FIG. 16A4) or 2-hour (FIG. 16A5, FIG. 16A6) Tonabersat treatment (50 μM) causes a reduction in LY dye transfer, as GJs are uncoupled.

(FIG. 17A) NT, (FIG. 17B) SEQ4-O, (FIG. 17C.) SEQ4-PTO.

FIG. 23A-FIG. 23B. (FIG. 23A) and (FIG. 23B) Knockdown efficiency as measured by Western blot. The data show standard deviation for 3 replicates. Knockdown efficiency as measured by Western blot (n=3). Oligo concentration: (1)=200 nM; (¾)=150 nM; (½)=100 nM; C: SEQ1; SEQ4: 37501; Cscr: SEQ1 scrambled; LP2scr: SEQ4 scrambled; Orange bars: negative controls FIG. 24. Different sequences analyzed by qPCR for their knockdown efficiency of connexin 43. Cscr: SEQ1 scrambled, Csen: SEQ1 sense strand, LP2scr2: SEQ4 scrambled, LP2sen: SEQ4 sense strand, 47001scr2: SEQ5 scrambled, 47001sen: SEQ5 sense strand, NC1: universal negative 1, NC2: universal negative 2

FIG. 34A-FIG. 34D. Dye perfusion of Evans Blue Dye post-ischemia to map the connexin 43 following ischemia-reperfusion. (FIG. 34A) Control retina-no dye perfusion. (FIG. 34B) Control retina-Evans Blue Dye intraperitineal injection. (FIG. 34C) Dye injection 4 hours post-ischemia. (FIG. 34D) Dye injection 24 hours post-ischemia.

FIG. 38A-FIG. 38E. SEM images of nanoparticles (Nps, FIG. 38A and FIG. 38C) and Microparticles (Mps, FIG. 38B and FIG. 38D), before (FIG. 38A and FIG. 38B) and after (FIG. 38C and FIG. 38D) three days in release media. FIG. 38E shows formulation, particle size, PDI, ZP (mV), Yield (%), and EE (%) of Mps and Nps.

FIG. 40A-FIG. 40E. Measurement of Vessel leak, post-ischemia, of unmodified (Cxn43 MP) and chemically modified (C12-C12 Cxn43 MP) connexin 43 modulator peptides. Vessel leak (4 hours post ischemia): (FIG. 40A) Control, (FIG. 40B) Ischaemia only, (FIG. 40C) Cx43 MP, (FIG. 40D) $C_{12}$-$C_{12}$—Cx43 MP. (FIG. 40E) Area of vessel leak.

FIG. 41A-FIG. 41D. Representative images of stained tissues and quantitation of spot counts which were reduced moreso with the chemically modified (C12-C12 Cxn43 MP) connexin 43 modulator peptide than the unmodified peptide. Cx43 spot counts (wholemounts): (FIG. 41A) Control, (FIG. 41B) Ischaemia 8 h, (FIG. 41C) 2C12-Cx43 MP 8 h. (FIG. 41D) Density Cx43 spots/$mm^2$.

FIG. 42A-FIG. 42D. Representative images of stained tissues and quantitation that formulations involving nanoparticles for the delivery resulted in lower Cxn43 expression than formulations without the nanoparticles. Cx43 spot counts 28 days: (FIG. 42A) Control, (FIG. 42B) Ischaemia 28 d, (FIG. 42C) $2C_{12}$-Cx43 MP 28 d. (FIG. 42D) Mean Cx43 count.

FIG. 43A-FIG. 43D. Representative images of stained tissues and quantitation that the chemically modified peptide treatment resulted in over 93% RGC survival after 28 days compare to less than 70% for untreated eyes (ischemia only). Retinal ganglion cell count: (FIG. 43A) Control, (FIG. 43B) Ischaemia 28 D, (FIG. 43C) 2C12-Cx43MP 28 D. (FIG. 43D) Density cells/$mm^2$.

FIG. 46. Representative images of stained tissues indicating Cxn43 expression profile in retina images taken near a haemorrhage of a retina sample of a deceased human. The figure shows merged images of nuclei stained with DAPI (blue) and Cxn43 gap junction plaques (red).

FIG. 47A-FIG. 47G. Representative confocal microscope images of retinas indicating the Cxn43 expression profile in ARPE-19 cells. Control (FIG. 47A). After 8 h of exposure to the native peptide (FIG. 47B), Cxn43 levels in ARPE-19 cells were slightly reduced while after 24 h (FIG. 47C), Cxn43 was back to normal (FIG. 47A). There were no significant differences in Cxn43 labelling after 8 h of incubation with Nps (FIG. 47D) and Mps (FIG. 47F), while after 24 h of exposure, both Nps (FIG. 47E) and Mps (FIG. 47G) groups exhibited a considerable reduction in Cxn43 levels indicating sustained peptide release and thus the potential of longer term treatment with these particles possibly reducing new gap junction channel formation. The figure shows merged images of nuclei stained with DAPI (blue) and Cxn43 gap junction plaques (red) (Scale bar represents 50 μm).

FIG. 48A-FIG. 48G. Representative confocal microscope images of retinas labelled for GFAP (red), Cxn43 (green) and DAPI (blue). Control (FIG. 48A). Twenty-eight days after ischemia-reperfusion, Cx43 and GFAP were significantly upregulated in the untreated group (FIG. 48B). Intravitreal injection of native Cxn43 MP in solution displayed limited Cxn43 upregulation after 28 d (FIG. 48C). The Nps-Cxn43 MP treatment group resulted in a significant reduction of Cxn43 upregulation at 28 d post-injury (FIG. 48D), while Mps-Cxn43 MP exhibited similar Cxn43 and GFAP levels at 28 d (FIG. 48E) and 90 d (FIG. 48F) following ischemia-reperfusion (scale bar represents 50 μm). (FIG. 48G) Average Cxn43 spot counts in uninjured control retinas and following ischemia-reperfusion without and with treatment. Stars denote statistical significance between each group (n=3, mean±SD, *p<0.05, **p<0.01).

FIG. 49A-FIG. 49H. Representative confocal microscope images of flat mounted retinas with Brn3a labelled RGC (red) post ischemia-reperfusion. Control (FIG. 49A). RGC distribution is significantly reduced with almost complete loss of blood vessel delineation in untreated retinas (FIG. 49B). Eyes treated with Cxn43 MP in solution and Nps-Cxn43 MP exhibted fewer patches of RGC loss (FIG. 49C and FIG. 49D). Eyes treated with Mps still exhibited some RGC loss at 28 d (FIG. 49E) and 90 d (FIG. 49E). Scale bar=300 lm. (FIG. 49G) Average density of RGC. (FIG. 49H) Stars denote statistical significance between each group (n=6, mean±SD, **p<0.01, *p<0.05).

DETAILED DISCLOSURE

Figure 2:
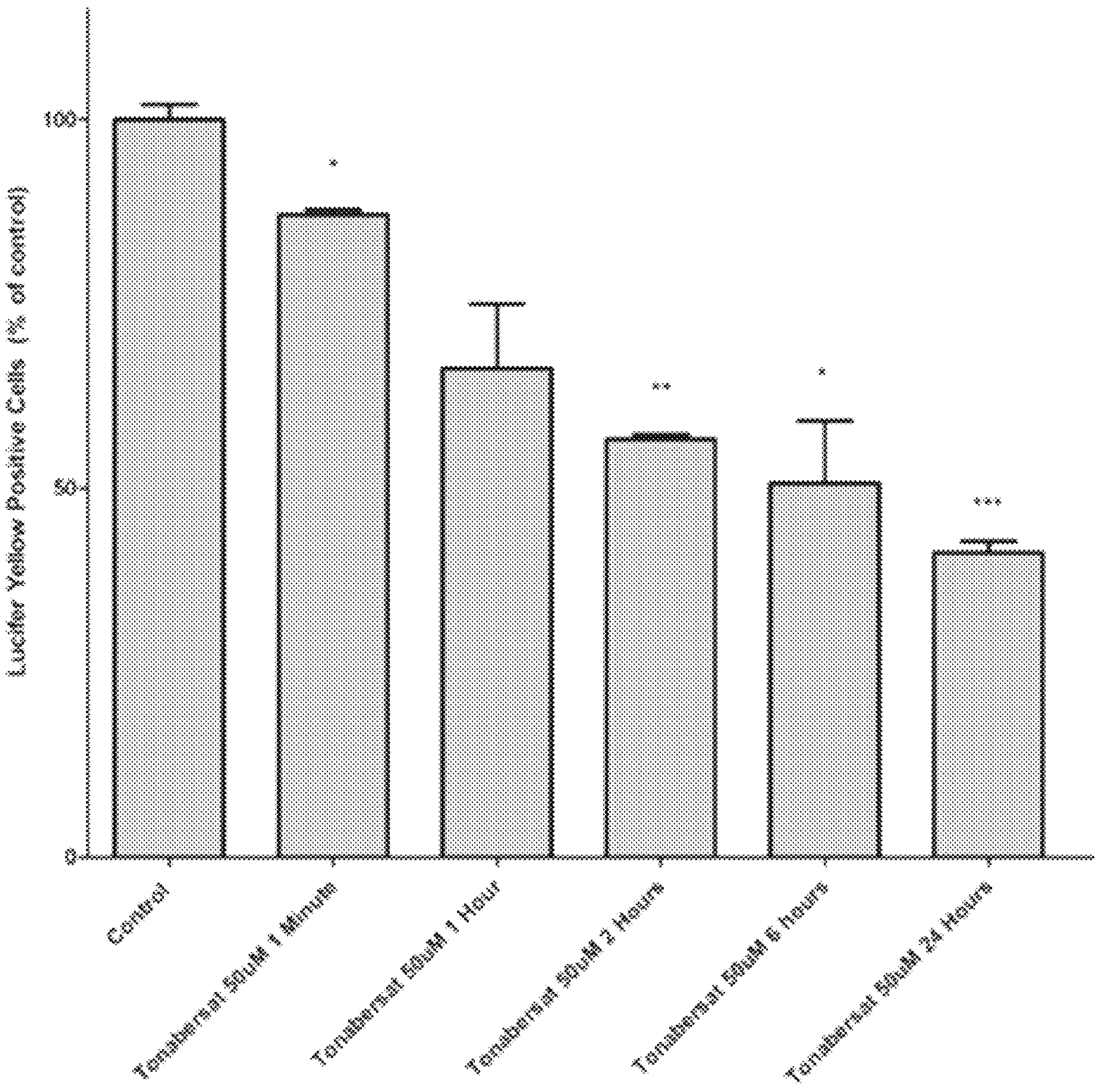
FIG. 2. Quantification of scrape loaded dye spread in hCMVEC cells treated with 50 μM Tonabersat for various periods of time. Tonabersat has some immediate channel blocking effect, and its efficacy increases with time. *=$p<0.05$, =$p<0.001$, *=$p<0.001$.

The inventions relate to modulators of gap junction channels, modulators of hemichannels, modulators of pannexin channels, modulators of pannexin transcription, translation, function and/or activity, and modulators of connexin transcription, translation, function and/or activity, including small molecule modulators. Modulators may be used alone or in combination to treat a disease, disorder or condition as described herein, including ocular diseases, disorders or conditions in the anterior segment, the posterior segment, and in ocular blood vessels including in the retina, the choroid and the choriocapillaris.

Tonabersat, a benzoylamino benzopyran, has been reported to be central nervous system-specific and to act at the level of downregulating connexin 26 and/or p38 expression. The inventors have surprisingly identified that gap junction channel modulators such as Tonabersat can modulate the activity of gap junction channels and hemichannels in a number of different cell types which are not limited to the central nervous system and in a manner which is not specific to a particular connexin (such as connexin 26). In particular, the inventors have shown that Tonabersat can modulate the activity of hemichannels comprising connexin 43. While not wishing to be bound by any particular theory, the inventors have surprisingly discovered that tonabersat acts directly on gap junction channels and/or hemichannels, rather than indirectly through a cellular receptor or by affecting the expression of a connexin (for example, connexin 26) and/or p38.

It has been shown that a gap junction channel modulator such as peptide 5 inhibits Cx43 hemichannel activity and/or ATP release during and following injury, for example, during ischemia and in hypoxia reperfusion, as described in detail herein. It has also been shown that a pannexin modulator such as Probenecid inhibits injury induced ATP release, for example, ATP release during ischemia.

The instant inventions provides, inter alia, (1) methods for modulation of a gap junction channel and/or hemichannel; (2) the use of a gap junction channel modulator, such as peptide 5, and/or an analogue thereof, compounds of formula I, for example tonabersat, and/or an analogue or pro-drug of any of the foregoing compounds, and/or a pannexin modulator, e.g., probenecid and/or a synthetic mimetic peptide blocker of pannexin 1, e.g., $^{10}$Panx1, or an analogue of either thereof, in the manufacture of a medicament for modulation of a gap junction and/or hemichannel; (3) a gap junction channel modulator, such as peptide 5, and/or an analogue thereof, compounds of formula I, for example tonabersat, and/or an analogue or pro-drug of any of the foregoing compounds, and/or, a pannexin modulator, e.g., probenecid and/or a synthetic mimetic peptide blocker of pannexin 1, e.g., $^{10}$Panx1, or an analogue of either thereof, for modulating a gap junction channel and/or hemichannel; (4) methods for the treatment of a disorder where modulation of a gap junction channel, hemichannel, and/or pannexin channel may be of benefit by administering a gap junction channel modulator, such as peptide 5, and/or an analogue thereof, compounds of formula I, for example tonabersat, and/or an analogue or pro-drug of any of the foregoing compounds, and/or, a pannexin modulator, e.g., probenecid and/or a synthetic mimetic peptide blocker of pannexin 1, e.g., $^{10}$Panx1, or an analogue of either thereof; (5) the use of a gap junction channel modulator, such as peptide 5, peptide 5, and/or an analogue thereof, compounds of formula I, for example tonabersat, and/or an analogue or pro-drug of any of the foregoing compounds, and/or, a pannexin modulator, e.g., probenecid and/or a synthetic mimetic peptide blocker of pannexin 1, e.g., $^{10}$Panx1, or an analogue of either thereof, in the manufacture of a medicament for the treatment of a disorder where modulation of a gap junction channel, hemichannel, and/or pannexin channel may be of benefit; and (6) a gap junction channel modulator, such as peptide 5, and/or an analogue thereof, compounds of formula I, for example tonabersat, and/or an analogue or pro-drug of any of the foregoing compounds, and/or, a pannexin modulator, e.g., probenecid and/or a synthetic mimetic peptide blocker of pannexin 1, e.g., $^{10}$Panx1, or an analogue of either thereof, for use in the treatment of a disorder where modulation of a gap junction channel and/or hemichannel may be of benefit.

In some embodiments, this invention relates to the use of a pannexin modulator, e.g., probenecid and/or a synthetic mimetic peptide blocker of pannexin 1, e.g., $^{10}$Panx1, or an analogue of either thereof, for one of more of these purposes, either alone or in combination with a gap junction channel modulator of this disclosure.

In certain embodiments, the inventors contemplate the invention providing one or more of the following methods which comprising administering a gap junction channel modulator such as peptide 5, and/or an analogue thereof, compounds of formula I, for example tonabersat, and/or an analogue or pro-drug of any of the foregoing compounds, and/or administering a pannexin modulator, e.g., probenecid and/or a synthetic mimetic peptide blocker of pannexin 1, e.g., $^{10}$Panx1, or an analogue of either thereof, to a subject, either alone or in combination with a gap junction channel modulator: a method for preventing or decreasing abnormal or excessive scar formation in a subject undergoing a surgical procedure; a method for treating a subject having abnormal scarring by excising the scar and then administering a gap junction channel modulator such as peptide 5, and/or an analogue thereof, compounds of formula I, for example tonabersat, and/or an analogue or pro-drug of any of the foregoing compounds, and/or administering a pannexin modulator, e.g., probenecid and/or a synthetic mimetic peptide blocker of pannexin 1, e.g., $^{10}$Panx1, or an analogue of either thereof, to the subject at the site of excision, either alone or in combination with a gap junction channel modulator; the use of a gap junction channel modulator such as peptide 5, and/or an analogue thereof, compounds of formula I, for example tonabersat, and/or an analogue or pro-drug of any of the foregoing compounds, and/or administering a pannexin modulator, e.g., probenecid and/or a synthetic mimetic peptide blocker of pannexin 1, e.g., $^{10}$Panx1, or an analogue of either thereof, either alone or in combination with a gap junction channel modulator in any of the following methods: a method of preventing or decreasing contracture in a tissue of a subject and thereby decreasing fibrosis; a method for tissue engineering in association with an ophthalmic procedure; a method of promoting the accumulation of epithelial cells in the eye or in a tissue associated with the eye; a method of inhibiting hypercellularity in the eye or in a tissue associated with the eye; a method for preventing, decreasing or lessening lesion spread; a method for the treatment of vascular leak or any disorder in which vascular leak is implicated; a method for the treatment of one or more of ischemia (including for example, perinatal ischemia, skin ischemia and cardiac ischemia), brain stroke, asphyxia, brain trauma, spinal cord injury, heart attack, inflammatory cardiac insult (including for example, pericarditis), reperfusion injury (including for example, cardiac reperfusion after surgery or transplant, liver reperfusion after surgery or transplant); a method for treating injury, tissue damage or inflammation associated with a surgical procedure or medical treatment (including for example, chemotherapy, radiotherapy, plastic surgery, and for example including stomatitis or rash associated with such treatments); a method for the treatment of surface wounds or lesions (including for example, persistent epithelial defects in the cornea, ulcers, burns, psoriasis); a method for the treatment of a hearing disorder; a method for the treatment of an ocular disorder (including for example, retinal vein or artery occlusion, glaucoma, retinal stroke, trauma resulting in raised intraocular pressure, diabetic retinopathy, cystoid macular edema, age related macular degeneration, infection, burns (including chemical and thermal, for example)); a method for the treatment of epilepsy, Parkinson's disease; and, a method for the treatment of trauma (including trauma which is associated with blood vessel haemorrhage, edema, lesions, lesion spread, and/or inflammation, for example). In addition, the inventors contemplate the invention providing: a dressing for preventing and/or treating fibrosis or other disorder comprising a gap junction channel modulator such as peptide 5, and/or an analogue thereof, compounds of formula I, for example tonabersat, and/or an analogue or pro-drug of any of the foregoing compounds, and/or a pannexin modulator, e.g., probenecid and/or a synthetic mimetic peptide blocker of pannexin 1, e.g., $^{10}$Panx1, or an analogue of either thereof; and/or, the use of a gap junction channel modulator such as peptide 5, and/or an analogue thereof, compounds of formula I, for example tonabersat, and/or an analogue or pro-drug of any of the foregoing compounds, and/or administering a pannexin modulator, e.g., probenecid and/or a synthetic mimetic peptide blocker of pannexin 1, e.g., $^{10}$Panx1, or an analogue of either thereof, in the manufacture of a medicament for the treatment of a disorder as herein described.

In some embodiments, this invention features the use of compounds of formula I, for example tonabersat, and/or an analogue or pro-drug of any of the foregoing compounds to directly and immediately block Cx43 hemichannels and to cause a concentration and time-dependent reduction in GJ coupling. In some aspects a low concentration of compounds of formula I, for example tonabersat, and/or an analogue or pro-drug of any of the foregoing compounds can be used in any of the methods of treatment or uses of this invention. In some embodiments, a low dose of compounds of formula I, for example tonabersat, and/or an analogue or pro-drug of any of the foregoing compounds may be combined with a pannexin channel modulator in any of the methods of treatment or uses of this invention. In some embodiments, a low dose of compounds of formula I, for example tonabersat, and/or an analogue or pro-drug of any of the foregoing compounds may be combined with a pannexin channel modulator may be used, for example, as an effective treatment during ischeamic injury, to protect RGCs from damage following retinal ischemia, or to treat retinal ischemia or eye fibrosis, or in any of the other methods of treatmet or uses of this invention.

Channel Modulators

By way of example, tonabersat may be known by the IUPAC name N-[(3S,4S)-6-acetyl-3-hydroxy-2,2-dimethyl-3,4-dihydrochromen-4-yl]-3-chloro-4-fluorobenzamide or (3S-cis)-N-(6-acetyl-3,4-dihydro-3-hydroxy-2,2-(dimethyl-d6)-2H-1-benzopyran-4-yl)-3-chloro-4-fluorobenzamide.

In one embodiment, tonabersat and/or an analogue or prodrug thereof is chosen from the group of compounds having the formula I:

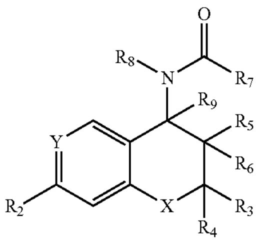

Y is C—$R_1$;

$R_1$ is acetyl;

$R_2$ is hydrogen, $C_{3-8}$ cycloalkyl, $C_{1-6}$ alkyl optionally interrupted by oxygen or substituted by hydroxy, $C_{1-6}$ alkoxy or substituted aminocarbonyl, $C_{1-6}$ alkylcarbonyl, $C_{1-6}$ alkoxycarbonyl, $C_{1-6}$ alkylcarbonyloxy, $C_{1-6}$ alkoxy, nitro, cyano, halo, trifluoromethyl, or $CF_3S$; or a group $CF_3$-A-, where A is —$CF_2$—, —CO—, —$CH_2$—, CH(OH), $SO_2$, SO, $CH_2$—O—, or CONH; or a group $CF_2$H-A'- where A' is oxygen, sulphur, SO, $SO_2$, $CF_2$ or CFH; trifluoromethoxy, $C_{1-6}$ alkylsulphinyl, perfluoro $C_{2-6}$ alkylsulphonyl, $C_{1-6}$ alkylsulphonyl, $C_{1-6}$ alkoxysulphinyl, $C_{1-6}$ alkoxysulphonyl, aryl, heteroaryl, arylcarbonyl, heteroarylcarbonyl, phosphono, arylcarbonyloxy, heteroarylcarbonyloxy, arylsulphinyl, heteroarylsulphinyl, arylsulphonyl, or heteroarylsulphonyl in which any aromatic moiety is optionally substituted, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkylthiocarbonyloxy, 1-mercapto $C_{2-7}$ alkyl, formyl, or aminosulphinyl, aminosulphonyl or aminocarbonyl, in which any amino moiety is optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or —C($C_{1-6}$ alkyl)NOH or —C($C_{1-6}$ alkyl)$NNH_2$; or amino optionally substituted by one or two $C_{1-6}$ alkyl or by $C_{2-7}$ alkanoyl; one of $R_3$ and $R_4$ is hydrogen or $C_{1-4}$ alkyl and the other is $C_{1-4}$ alkyl, $CF_3$ or $CH_2X^a$ is fluoro, chloro, bromo, iodo, $C_{1-4}$ alkoxy, hydroxy, $C_{1-4}$ alkylcarbonyloxy, —S—$C_{1-4}$ alkyl, nitro, amino optionally substituted by one or two $C_{1-4}$ alkyl groups, cyano or $C_{1-4}$ alkoxycarbonyl; or $R_3$ and $R_4$ together are $C_{2-5}$ polymethylene optionally substituted by $C_{1-4}$ alkyl;

$R_5$ is $C_{1-6}$ alkylcarbonyloxy, benzoyloxy, $ONO_2$, benzyloxy, phenyloxy or $C_{1-6}$ alkoxy and $R_6$ and $R_9$ are hydrogen or $R_5$ is hydroxy and $R_6$ is hydrogen or $C_{1-2}$ alkyl and $R_9$ is hydrogen;

$R_7$ is heteroaryl or phenyl, both of which are optionally substituted one or more times independently with a group or atom selected from chloro, fluoro, bromo, iodo, nitro, amino optionally substituted once or twice by $C_{1-4}$ alkyl, cyano, azido, $C_{1-4}$ alkoxy, trifluoromethoxy and trifluoromethyl;

$R_8$ is hydrogen, $C_{1-6}$ alkyl, $OR_{11}$ or $NHCOR_{10}$ wherein $R_{11}$ is hydrogen, $C_{1-6}$ alkyl, formyl, $C_{1-6}$ alkanoyl, aroyl or aryl-$C_{1-6}$ alkyl and $R_{10}$ is hydrogen, $C_{1-6}$ alkyl, $C_{1-6}$ alkoxy, mono or di $C_{1-6}$ alkyl amino, amino, amino-C.sub.1-6 alkyl, hydroxy-$C_{1-6}$ alkyl, halo-$C_{1-6}$ alkyl, $C_{1-6}$ acyloxy-$C_{1-6}$ alkyl, $C_{1-6}$ alkoxycarbonyl-$C_{1-6}$-alkyl, aryl or heteroaryl; the $R_8$—N—CO—$R_7$ group being cis to the $R_5$ group; and X is oxygen or $NR_{12}$ where $R_{12}$ is hydrogen or $C_{1-6}$ alkyl.

For any of the Markush groups set forth above, that group can include or exclude any of the species listed for that group.

Tonabersat may be known by the IUPAC name N-[(3S,4S)-6-acetyl-3-hydroxy-2,2-dimethyl-3,4-dihydrochromen-4-yl]-3-chloro-4-fluorobenzamide or (3S-cis)-N-(6-acetyl-3,4-dihydro-3-hydroxy-2,2-(dimethyl-d6)-2H-1-benzopyran-4-yl)-3-chloro-4-fluorobenzamide.

In embodiment the analogue of formula 1 is the compound carabersat (N-[(3R,4S)-6-acetyl-3-hydroxy-2,2-dimethyl-3,4-dihydrochromen-4-yl]-4-fluorobenzamide) or trans-(+)-6-acetyl-4-(S)-(4-fluorobenzoylamino)-3,4-dihydro-2,2-dimethyl-2H-1-benzo[b]pyran-3R-ol, hemihydrate.

In certain embodiments, tonabersat and/or an analogue thereof are in the form of a free base or a pharmaceutically acceptable salt. By way of example, a pharmaceutically acceptable salt includes a hydrochloride salt and salts derived from acid including, but not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid (besylate), benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid (mesylate), naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), and undecylenic acid. In one embodiment, the salt is a hydrochloride salt.

In other embodiments, one or more polymorph, one or more isomer, and/or one or more solvate of tonabersat and/or an analogue thereof may be used.

Peptide 5

Various small organic molecules have been reported to have activity in inhibition of gap junction or hemichannel currents. They include triarylmethanes (TRAMs), quinine, mefloquine, fenamates, 2-aminophenoxyborate and derivatives, glycyrrhetinic acid and derivatives, volatile anesthetics such as halothane and ethane, lipophilic compounds such as long-chain alcohols (e.g., heptanol and octanol), fatty acid amides including oleamide, cyclodextrins, cisplatin, polyamines and tetraalylammonium ions. An increasing number of studies have also reported on the inhibition of gap junction channels and hemichannels using peptides corresponding to specific sequences within extracellular loops E1 and E2 involving the conserved QPG and SHVR (SEQ ID NO: 18) motifs of E1 (Gap26 peptide) and the SRPTEK (SEQ ID NO: 20) motif in E2 (Gap27 peptide) as well as the cytoplasmic loop (Gap19 peptide). The most potent such peptidomimetic is Peptide5 (VDCFLSRPTEKT) (SEQ.ID NO: 168).

In some embodiments, the gap junction channel modulators are connexin peptides or peptidomimetics, sometimes referred to anti-connexin peptides or peptdomimetics, e.g., anti-connexin hemichannel blocking peptides or peptidomimetics, for example, modified or unmodified peptides or peptidomimentics comprising connexin extracellular domains, transmembrane regions, and connexin carboxy-terminal peptides). The anti-connexin hemichannel blocking peptides or peptidomimetics may be modified or unmodified. The anti-connexin hemichannel blocking peptides or peptidomimetics are made chemically, synthetically, or otherwise manufactured. In some embodiments, the gap junction channel modulators are connexin 43 peptides or peptidomimetics. In some aspects, the therapeutically effective modified or unmodified peptide or peptidomimetic comprises a portion of an extracellular or transmembrane domain of a connexin, such as connexin 43 or connexin 45. In some aspects peptide or peptidomimetic comprises a portion of an extracellular or transmembrane domain of connexin Cx26, Cx30, Cx31.1, Cx36, Cx37, Cx40, Cx50, Cx57 or any other connexin in the eye or blood vessels.

In some embodiments the gap junction channel modulators of this invention include anti-connexin 43 peptides or peptidomimetics, for example, any of the peptides described herein, including peptides comprising a portion of an extracellular domain of a connexin, and peptides comprising a portion of a carboxy-terminal portion of a connexin useful in the methods of this invention, which is therapeutically effective, for example, effective for healing any of the neuropathic ocular disorders described herein. In some aspects, the therapeutically effective modified or unmodified peptide or peptidomimetic comprises a portion of an extracellular domain of a connexin, such as connexin 43 or connexin 45, preferably connexin 43.

Peptide5 is an established gap junction channel blocker that can operate in a dose dependent manner, with lower doses blocking gap junction hemichannel opening and higher doses uncoupling gap junctions between cells. See, e.g., O'Carroll et al, 2008. With sustained low dose application of Peptide5 there is also gradual loss of gap junction coupling, considered to be peptide interference with hemichannel docking (in parallel with gradual removal of existing gap junctions during normal turnover). Peptide5 has proven to be effective in a number of in vitro, ex vivo and in vivo (animal) studies, especially when used at doses that block hemichannels without uncoupling gap junctions (see for example Davidson et al, 2012; Danesh-Meyer et al, 2012; O'Carroll et al, 2013). The results in O'Carroll et al, 2008 indicate that Peptide5 at low or high concentration blocks hemichannels, but will uncouple gap junctions directly at high concentrations. Peptide5 data is shown here for comparison with tonabersat.

Compounds for pannexin modulation can be the compounds of formula VI:

(VI)

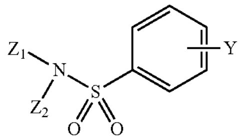

wherein $Z_1$ and $Z_2$ are independently selected from: $(C_1\text{-}C_4)$alkyl, halo$(C_1\text{-}C_4)$alkyl, $(C_1\text{-}C_4)$alkoxy, halo$(C_1\text{-}C_4)$, $(C_1\text{-}C_4)$cycloalkyl, $(C_1\text{-}C_4)$alkyl-S—, $(C_1\text{-}C_4)$alkylamino, $(C_1\text{-}C_4)$cycloalkylamino, di$(C_1\text{-}C_4)$alkylamino, and amino$(C_1\text{-}C_4)$alkyl;

Y is selected from: hydrogen, halo, cyano, hydroxy, $(C_1\text{-}C_4)$alkyl, halo$(C_1\text{-}C_4)$alkyl, $(C_1\text{-}C_4)$alkoxy, halo$(C_1\text{-}C_4)$ alkoxy, cyano$(C_1\text{-}C_4)$alkyl, amino, $(C_1\text{-}C_4)$alkylamino, di$(C_1\text{-}C_4)$alkylamino, amino$(C_1\text{-}C_4)$alkyl, $(C_1\text{-}C_4)$alkylamino$(C_1\text{-}C_4)$alkyl, di$[(C_1\text{-}C_4)$alkyl$]$amino$(C_1\text{-}C_4)$alkyl, trifluoromethylthio, hydroxy$(C_1\text{-}C_4)$alkyl, $(C_1\text{-}C_4)$alkoxy $(C_1\text{-}C_4)$alkyl, —C(O)R, —C(O)OR$_1$, —OC(O)R$_1$, —C(O)—N(R$_1$)$_2$, —CH$_2$—C(O)R$_1$, —CH$_2$—C(O)OR$_1$, —CH$_2$—OC(O)R$_1$, —CH$_2$—C(O)—N(R$_1$)$_2$, S(O)$_2$R$_1$, (O)$_2$N(R$_1$)$_2$, $(C_3\text{-}C_5)$cycloalkyl, $(C_3\text{-}C_5)$cycloalkyl$(C_1\text{-}C_4)$ alkyl, $SO_3H$, and $SO_4H$;

$R_1$ is selected from: hydrogen, $NH_2$, $NR_2R_3$, OH, —$CH_2OH$, and —$CH_2CH_2OH$;

R2 and R3 are independently selected from: hydrogen, $(C_1\text{-}C_4)$alkyl, $(C_1\text{-}C_4)$alkoxy, and $(C_1\text{-}C_4)$cycloalkyl; and halo is chlorine, bromine, iodine, or fluorine.

For example, compounds of formula VI can be probenecid, as shown below:

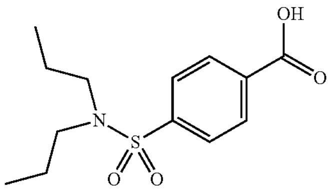 [SMILES: CCCN(CCC)S(=O)(=O)c1ccc(C(=O)O)cc1]

Probenecid may be known by the IUPAC name p-[Dipropylsulfamoyl]benzoic acid and has the structure shown above.

In certain embodiments, probenecid and/or an analogue thereof are nonionic, are in the form of a free base, a free acid, or a pharmaceutically acceptable salt. By way of example, a pharmaceutically acceptable salt includes a hydrochloride salt and salts derived from acid including, but not limited to, hydrobromic acid, phosphoric acid, acetic acid, fumaric acid, maleic acid, salicylic acid, citric acid, oxalic acid, lactic acid, malic acid, methanesulphonic acid and p-toluene sulphonic acid, a salt of itself. In one embodiment, the salt is a hydrochloride salt. In other embodiments, one or more polymorph, one or more isomer, and/or one or more solvate of probenecid and/or an analogue thereof may be used.

Panx1

In some aspects, the pannexin modulators can include or exclude pannexin peptide sequences. The pannexin peptide sequences can comprise 8-40 consecutive amino acids, an extracellular domain, an intracellular domain, a carboxy terminus part, or an amino terminus part, of the polypeptides Panx1, Panx2 or Panx3. Pannexin modulators may comprise, in some embodiments, a portion of an extracellular loop of Panx1, 2 or 3. In some embodiments, for example, the pannexin modulator may comprise, for example, the Panx1 mimetic blocking peptide [10]Panx1 (WRQAAFVDSY (SEQ ID NO: 21)). In some embodiments the pannexin modulators that are oligonucleotides or polynucleotides may have at least about 80%, 85%, 90%, 95%, 97%, 98%, or 99% homology to an 8 to 80 nucleotide portion of SEQ ID NO: 117 (Panx1 polynucleotide), (Panx1 polynucleotide RefSeq ID NM_015368.3), SEQ ID NO:118 (Panx2 polynucleotide), (Panx2 polynucleotide RefSeq ID NM_052839.3 for variant 1), SEQ ID NO: 119 (RefSeq ID NM_001160300.1 for Panx2 polynucleotide variant 2), SEQ ID NO: 120 (RefSeq ID NR_027691.1 for Panx2 polynucleotide variant 3), or SEQ ID NO: 121 (Panx3 polynucleotide) (Panx3 polynucleotide RefSeq ID NM_052959.2). In some aspects, the pannexin modulators can include or exclude pannexin peptide sequences. The pannexin peptide sequences can comprise 8-40 consecutive amino acids, an extracellular domain, an intracellular domain, a carboxy terminus part, or an amino terminus part, of the polypeptides SEQ ID NO: 122 (Panx1 peptide), SEQ ID NO: 123 (Panx2 peptide), or SEQ ID NO: 124 (Panx3 peptide), or variants thereof. The sequences of Panx1, 2, and 3 polypeptides are shown below.

```
(Panx1)
                                                SEQ ID NO: 122
MAIAQLATEYVFSDFLLKEPTEPKFKGLRLELAVDKMVTCIAVGLPLLLISLAFAQEISIG

TQISCFSPSSFSWRQAAFVDSYCWAAVQQKNSLQSESGNLPLWLHKFFPYILLLFAILLY

LPPLFWRFAAAPHICSDLKFIMEELDKVYNRAIKAAKSARDLDMRDGACSVPGVTENLQ

SLWEVSESHFKYPIVEQYLKTKKNSNNLIIKYISCRLLTLIIILLACIYLGYYFSLSSLSDEF

VCSIKSGILRNDSTVPDQFQCKLIAVGIFQLLSVINLVVYVLLAPVVVYTLFVPFRQKTDV
```

-continued

LKVYEILPTFDVLHFKSEGYNDLSLYNLFLEENISEVKSYKCLKVLENIKSSGQGIDPMLL

LTNLGMIKMDVVDGKTPMSAEMREEQGNQTAELQGMNIDSETKANNGEKNARQRLLD

SSC (Panx2)

SEQ ID NO: 123

MHHLLEQSADMATALLAGEKLRELILPGAQDDKAGALAALLLQLKLELPFDRVVTIGT

VLVPILLVTLVFTKNFAEEPIYCYTPHNFTRDQALYARGYCWTELRDALPGVDASLWPS

LFEHKFLPYALLAFAAIMYVPALGWEFLASTRLTSELNFLLQEIDNCYHRAAEGRAPKIE

KQIQSKGPGITEREKREIIENAEKEKSPEQNLFEKYLERRGRSNFLAKLYLARHVLILLLS

AVPISYLCTYYATQKQNEFTCALGASPDGAAGAGPAVRVSCKLPSVQLQRIIAGVDIVLL

CVMNLIILVNLIHLFIFRKSNFIFDKLHKVGIKTRRQWRRSQFCDINILAMFCNENRDHIKS

LNRLDFITNESDLMYDNVVRQLLAALAQSNHDATPTVRDSGVQTVDPSANPAEPDGAA

EPPVVKRPRKKMKWIPTSNPLPQPFKEPLAIMRVENSKAEKPKPARRKTATDTLIAPLLD

RSAHHYKGGGGDPGPGPAPAPAPPPAPDKKHARHFSLDVHPYILGTKKAKAEAVPAAL

PASRSQEGGFLSQAEDCGLGLAPAPIKDAPLPEKEIPYPTEPARAGLPSGGPFHVRSPPAA

PAVAPLTPASLGKAEPLTILSRNATHPLLHINTLYEAREEEDGGPRLPQDVGDLIAIPAPQ

QILIATFDEPRTVVSTVEF (Panx3)

SEQ ID NO: 124

MSLAHTAAEYMLSDALLPDRRGPRLKGLRLELPLDRIVKFVAVGSPLLLMSLAFAQEFS

SGSPISCFSPSNFSIRQAAYVDSSCWDSLLHHKQDGPGQDKMKSLWPHKALPYSLLALA

LLMYLPVLLWQYAAVPALSSDLLFIISELDKSYNRSIRLVQHMLKIRQKSSDPYVFWNEL

EKARKERYFEFPLLERYLACKQRSHSLVATYLLRNSLLLIFTSATYLYLGHFHLDVFFQE

EFSCSIKTGLLSDETHVPNLITCRLTSLSIFQIVSLSSVAIYTILVPVIIYNLTRLCRWDKRLL

SVYEMLPAFDLLSRKMLGCPINDLNVILLFLRANISELISFSWLSVLCVLKDTTTQKHNID

TVVDFMTLLAGLEPSKPKHLTNSACDEHP

The sequences of the mRNA encoding the pannexins are shown below.

(Panx1 mRNA)

SEQ ID NO: 117

```
  1 gggcggcgcg gaggggcagg gccagaggga agcgctttgt tccgcgcgtg gttcccgcgc
 61 ctgggggtgc gcgggagagg cgcgaatccg agtgccgcgc gcggcccggg gacttgcacg
121 ggcgtgcggg gtggaaccgc aggaagcgga gctctcgggt tcccgccccg ccccgccccg
181 ccggcggcgg aggcagcgag cgcgagagcc cagcggagtc gctgggagcc tgaggcaccg
241 agacacaaag gcaggcggga tgcgggagca ggcaaaggga aagcgaaagc cgcgcgcccg
301 gccggtgact gggtgaaggc gccgcgcagc tttcccgacg ccggctgtac ccggacctcc
361 tggtcgagcc tggcgcgccg cagccatggc catcgctcaa ctggccacgg agtacgtgtt
421 ctcggatttc ttgctgaagg agcccacgga gcccaagttc aaggggctgc gactggagct
481 ggctgtggac aagatggtca cgtgcattgc ggtggggctg cccctgctgc tcatctcgct
541 ggccttcgcg caggagatct cgattggtac acagataagc tgtttctctc caagttcttt
601 ctcctggcgt caggctgcct ttgtggattc atattgctgg gcggctgttc agcagaagaa
661 ctcactgcag agcgagtctg gaaacctccc actgtggctg cataagtttt tcccctacat
721 cctgctgctc tttgcgatcc tcctgtacct gcccccgctg ttctggcgtt tcgcagctgc
781 tcctcatatt tgctcagact tgaagtttat catggaagaa cttgacaaag tttacaaccg
841 tgcaattaag gctgcaaaga gtgcgcgtga ccttgacatg agagatggag cctgctcagt
```

-continued 901 tccaggtgtt accgagaact tagggcaaag tttgtgggag gtatctgaaa gccacttcaa 961 gtacccaatt gtggagcagt acttgaagac aaagaaaaat tctaataatt taatcatcaa 1021 gtacattagc tgccgcctgc tgacactcat cattatactg ttagcgtgta tctacctggg 1081 ctattacttc agcctctcct cactctcaga cgagtttgtg tgcagcatca aatcagggat 1141 cctgagaaac gacagcaccg tgcccgatca gtttcagtgc aaactcattg ccgtgggcat 1201 cttccagttg ctcagtgtca ttaaccttgt ggtttatgtc ctgctggctc ccgtggttgt 1261 ctacacgctg tttgttccat tccgacagaa gacagatgtt ctcaaagtgt acgaaatcct 1321 ccccactttt gatgttctgc atttcaaatc tgaagggtac aacgatttga gcctctacaa 1381 tctcttcttg gaggaaaata taagtgaggt caagtcatac aagtgtctta aggtactgga 1441 gaatattaag agcagtggtc aggggatcga cccaatgcta ctcctgacaa accttggcat 1501 gatcaagatg gatgttgttg atggcaaaac tcccatgtct gcagagatga gagaggagca 1561 ggggaaccag acggcagagc tccaaggtat gaacatagac agtgaaacta aagcaaataa 1621 tggagagaag aatgcccgac agagacttct ggattcttct tgctgatgat ttttttcctt 1681 gagctgtaaa tctgtgactt ctgcgacatg ggatttaatt tggctaaagc acccctgttg 1741 gtttcacagc tggtttgcaa taaatggttc ttggtggaga tactgagcat gtcttattga 1801 gtccctaatg gaaatggtga tcaacaaaag gttatggaag aatggtttat gaacttccca 1861 taggaagcac ctgagagata gtaaactgca gcaagtaact atgtgtaagt cctcatcaaa 1921 tgaaaagcag aaagacaaga acaattagtc aagagcagta gccctgtcag agcctcggag 1981 caatacccttt ctgtacccgt ggtgagacaa gacccagagc tactggaaaa caagcacttt 2041 ggaagatttg ttttgttttc atggaataat aatatgtcag ggtataattt aacgtgagtt 2101 tcttatgtgc ccttaaagac tgttagacaa gaaaagcatt cactggctaa taatccatag 2161 gtcgacctat gtcctaagtt aggtgtaagg tccgatgcct tggcccacac tcgagctctc 2221 tttacattgt tagttgtcaa ccttggctga tggaaatccc gtaaccacta tttgttgcac 2281 tgtgccttga agggcagcag gcccaagtgc tgctctgact gaaaactgag ttaacaagat 2341 gaaatctaaa ggatattcac agtgacttca attcaggaag aatgcttcca aaagagccca 2401 gtggggaaat ctgacatcac agaagacatt aattcagtca ctttcaaaga gtttgtctac 2461 aggcggtttc tctgttatca aaggcatttg aaataggatt ttacttaaac aataatggaa 2521 cacaggagta tttaaagtga agaacacttt gcctgaatgt gatcagggca cataagtgac 2581 attggcatgc ttcatatggc gtgcttggag ccagaaaaac ttagcggttt attttgttta 2641 tatttaagca cagctttaaa aaattcatta tcgtttattc agtgtccgaa ttgaggccat 2701 ttgggaagaa aattctagca ctggtggaga attatagaat aaagattata aatggttgga 2761 taagacaaaa aaaaaaaaaa aa (Panx2 mRNA, transcript variant 1)

SEQ ID NO: 118

1 atgcaccacc tcctggagca gtcggcggac atggcgaccg cgctgctggc gggagagaag 61 ctgcgggagc tgatcctgcc gggcgcgcag gacgacaagg cgggcgcgct ggccgcgctg 121 cttctgcagc tgaagctgga gctgccgttc gaccgggtgg tcaccatcgg caccgtgctg 181 gtgcccatcc tgctggtcac cctggtcttc accaagaact tcgcagagga acccatttac 241 tgttacaccc cgcacaactt cacgcgcgac caggcgctgt acgcccgcgg ctactgctgg 301 acggagctgc gggacgcgct gcccggcgtg gacgccagcc tgtggccgtc gctgtttgag 361 cacaagttcc tgccctacgc gctgctggcc ttcgccgcca tcatgtacgt gcccgcgctg 421 ggctgggagt tcctggcctc cacgcgcctc acctccgagc tcaacttcct gctgcaggag -continued

```
481   atcgacaact gttaccaccg ggcggccgag ggccgcgcgc ccaagatcga gaagcagatc
541   cagtccaagg gcccgggcat cacggagcgc gagaagcgcg agatcatcga gaacgcggag
601   aaggagaaga gcccggagca gaacctgttc gagaagtacc tggagcgccg cggccgcagc
661   aacttcctgg ccaagctgta cctggcgcgg cacgtgctga tcctgctgct gagcgccgtg
721   cccatctcct acctgtgcac ctactacgcc acgcagaagc agaacgagtt cacctgcgcg
781   ctgggcgcgt ccccggacgg ggcggcaggt gcggggcccg cggtgcgcgt gagctgcaag
841   ctcccgtccg tgcaactgca gcgcatcatc gcgggcgtgg acatcgtgct gctgtgcgtc
901   atgaacctca tcatcctcgt caacctcatc cacctcttca tcttccgcaa gagcaacttc
961   atcttcgaca agctgcacaa ggtgggcatc aagacgcgcc ggcagtggcg ccgctcgcag
1021  ttctgcgaca tcaacatcct ggccatgttc tgcaacgaga accgcgacca catcaagtcg
1081  ctcaaccggc tggacttcat caccaacgag agcgacctca tgtacgacaa cgtggtccgg
1141  cagctgctgg cggcgctggc gcagtccaac cacgacgcca cccccacggt gcgcgactcg
1201  ggggtgcaga ccgtggaccc cagcgccaac cccgccgagc ccgacggcgc cgccgagccg
1261  cccgtggtca agcggccgcg caagaagatg aagtggatcc ccaccagcaa cccgcttccg
1321  cagcccttca aggagccgct ggccatcatg cgcgtggaga acagcaaggc ggagaagccg
1381  aagcccgcgc gcaggaagac ggccacggac acgctgatcg cgccgctgct ggaccgctcc
1441  gcccaccact acaagggcgg agggggcgac ccgggccccg gccccgcccc tgcccccgcc
1501  ccgccgcccg cccctgacaa gaagcacgcg cgccacttct ccctggacgt gcacccctac
1561  atcctcggca ccaagaaggc caaggccgag gcggtgcccg ccgccctgcc cgcctcccgg
1621  agccaggagg ggggcttcct gtcccaggcg gaggactgtg ggctaggcct ggccccggcg
1681  cccatcaaag atgctccgct ccccgagaag gaaatcccgt accccacaga gccagcccgg
1741  gcagggcttc cctcgggggg cccgttccac gtccgctcac ctcccgccgc ccctgctgtg
1801  gcccctctga caccagccag cctgggcaag gcggagcccc tcaccatcct gagccgaaac
1861  gccacacacc cgctgctgca catcaacacg ctgtacgagg cccgggagga ggaggacggg
1921  ggcccccgcc tgccgcagga cgtgggggac ctcatcgcca tccctgcccc acagcagatc
1981  ctcatcgcca ccttcgacga gccgagaacg gtcgtgagta ctgtggagtt ttgagggatg
2041  gcaccgtcca ggccgccgag agcccctctg cctgtgtcgt gtggcctggc cagcctcccg
2101  gtggacacca gccctgcgtg gacgtggcct gtgcttcgcc cgcactgcgc gcatccccaa
2161  cctctgtccg catgcctggg gccttcgccc ccacgtgctc gacaggggaa cccgcccgga
2221  cggcatcgcc aggcactggc tggggtgggg aaaggtggcc cagtggagcc ggtggccagg
2281  aaggctgaag cccgcttccc atgctcctgc atcaggtgcc cagccgtggg tgggggccct
2341  gaggtgaaga gtttattttt ttagtccgtt tcgtcctggc cccgggctgt ggcgagacag
2401  cccaactccc ccagcccagc tcccccagcc cagagccagg gaagaggaag gtggggccag
2461  tcccaccagt ggggtggcca cgcccatggg gtcacatgct caggggtcac cccctgcagg
2521  gacctgatgc cctcgggtgg gagggaccga ggtccaccct cgggtcaaag gtcaacgtgc
2581  actttctcct tgtcgcctga cagacatttt attttactaa gactgctgta ccgaacaagc
2641  atatttatca tcaggagaca ggatgggttt aaagcaggat ggtgtgtgtg tgaacgggca
2701  tgagcagagg tgagcgtgag cgagcgggtg tgtatgtacg agtgtgcacg tgtgtgcgtg
2761  tgcacagagg gtgtggtgcc agcttgagtg ggagtgtgtg agtgtgagca ggcgggcgag
2821  tgcgtgagtg cacgccagcg cgtggcccat gtatgaggag tgaaggggcc caacgcaata
```

-continued

```
2881   accacgtccc ccacccgggc cccccgccgc ggctgaggcc acatggcttc ctgtgggagc

2941   cccggccggc acccggctgg tcccacccca aatacctcag ccatggagac catgtcatgc

3001   agaattaaca aggtagcacc gagcatatca ataaatatta ttctgataat caaaaaaaaa

3061   aaaaaaaaa
```

(Panx2 mRNA, transcript variant 2)

SEQ ID NO: 119

```
   1   atgcaccacc tcctggagca gtcggcggac atggcgaccg cgctgctggc gggagagaag

  61   ctgcgggagc tgatcctgcc gggcgcgcag gacgacaagg cgggcgcgct ggccgcgctg

 121   cttctgcagc tgaagctgga gctgccgttc gaccgggtgg tcaccatcgg caccgtgctg

 181   gtgcccatcc tgctggtcac cctggtcttc accaagaact tcgcagagga acccatttac

 241   tgttacaccc cgcacaactt cacgcgcgac caggcgctgt acgcccgcgg ctactgctgg

 301   acggagctgc gggacgcgct gcccggcgtg gacgccagcc tgtggccgtc gctgtttgag

 361   cacaagttcc tgccctacgc gctgctggcc ttcgccgcca tcatgtacgt gcccgcgctg

 421   ggctgggagt tcctggcctc cacgcgcctc acctccgagc tcaacttcct gctgcaggag

 481   atcgacaact gttaccaccg ggcggccgag ggccgcgcgc ccaagatcga gaagcagatc

 541   cagtccaagg gcccgggcat cacggagcgc gagaagcgcg agatcatcga gaacgcggag

 601   aaggagaaga gcccggagca gaacctgttc gagaagtacc tggagcgccg cggccgcagc

 661   aacttcctgg ccaagctgta cctggcgcgg cacgtgctga tcctgctgct gagcgccgtg

 721   cccatctcct acctgtgcac ctactacgcc acgcagaagc agaacgagtt cacctgcgcg

 781   ctgggcgcgt ccccggacgg ggcggcaggt gcggggcccg cggtgcgcgt gagctgcaag

 841   ctcccgtccg tgcaactgca gcgcatcatc gcgggcgtgg acatcgtgct gctgtgcgtc

 901   atgaacctca tcatcctcgt caacctcatc cacctcttca tcttccgcaa gagcaacttc

 961   atcttcgaca agctgcacaa ggtgggcatc aagacgcgcc ggcagtggcg ccgctcgcag

1021   ttctgcgaca tcaacatcct ggccatgttc tgcaacgaga accgcgacca catcaagtcg

1081   ctcaaccggc tggacttcat caccaacgag agcgacctca tgtacgacaa cgtggtccgg

1141   cagctgctgg cggcgctggc gcagtccaac cacgacgcca cccccacggt gcgcgactcg

1201   ggggtgcaga ccgtggaccc cagcgccaac cccgccgagc ccgacggcgc cgccgagccg

1261   cccgtggtca agcggccgcg caagaagatg aagtggatcc ccaccagcaa cccgcttccg

1321   cagcccttca aggagccgct ggccatcatg cgcgtggaga acagcaaggc ggagaagccg

1381   aagcccgcgc gcaggaagac ggccacggac acgctgatcg cgccgctgct ggaccgctcc

1441   gcccaccact acaagggcgg agggggcgac ccgggccccg gccccgcccc tgcccccgcc

1501   ccgccgcccg cccctgacaa gaagcacgcg cgccacttct ccctggacgt gcacccctac

1561   atcctcggca ccaagaaggc caaggccgag gcggtgcccg ccgccctgcc cgcctcccgg

1621   agccaggagg ggggcttcct gtcccaggcg gaggactgtg ggctaggcct ggccccggcg

1681   cccatcaaag atgctccgct ccccgagaag gaaatcccgt accccacaga gccagcccgg

1741   gcagggcttc cctcgggggg cccgttccac gtccgctcac ctcccgccgc ccctgctgtg

1801   gcccctctga caccagccag cctgggcaag gcggagcccc tcaccatcct gagccgaaac

1861   gccacacacc cgctgctgca catcaacacg ctatcctcat cgccaccttc gacgagccga

1921   gaacggtcgt gagtactgtg gagttttgag ggatggcacc gtccaggccg ccgagagccc

1981   ctctgcctgt gtcgtgtggc ctggccagcc tcccggtgga caccagccct gcgtggacgt

2041   ggcctgtgct tcgcccgcac tgcgcgcatc cccaacctct gtccgcatgc ctggggcctt

2101   cgcccccacg tgctcgacag gggaacccgc ccggacggca tcgccaggca ctggctgggg
```

-continued

```
2161 tggggaaagg tggcccagtg gagccggtgg ccaggaaggc tgaagcccgc ttcccatgct
2221 cctgcatcag gtgcccagcc gtgggtgggg gccctgaggt gaagagttta tttttttagt
2281 ccgtttcgtc ctggccccgg gctgtggcga gacagcccaa ctcccccagc ccagctcccc
2341 cagcccagag ccagggaaga ggaaggtggg gccagtccca ccagtggggt ggccacgccc
2401 atggggtcac atgctcaggg gtcacccccct gcagggacct gatgccctcg ggtgggaggg
2461 accgaggtcc accctcgggt caaaggtcaa cgtgcacttt ctccttgtcg cctgacagac
2521 attttatttt actaagactg ctgtaccgaa caagcatatt tatcatcagg agacaggatg
2581 ggtttaaagc aggatggtgt gtgtgtgaac gggcatgagc agaggtgagc gtgagcgagc
2641 gggtgtgtat gtacgagtgt gcacgtgtgt gcgtgtgcac agagggtgtg gtgccagctt
2701 gagtgggagt gtgtgagtgt gagcaggcgg gcgagtgcgt gagtgcacgc cagcgcgtgg
2761 cccatgtatg aggagtgaag gggcccaacg caataaccac gtcccccacc cgggcccccc
2821 gccgcggctg aggccacatg gcttcctgtg ggagccccgg ccggcacccg gctggtccca
2881 ccccaaatac ctcagccatg gagaccatgt catgcagaat taacaaggta gcaccgagca
2941 tatcaataaa tattattctg ataatcaaaa aaaaaaaaaa aaaa
```

(Panx2 mRNA, transcript variant 3)

SEQ ID NO: 120

```
   1 atgcaccacc tcctggagca gtcggcggac atggcgaccg cgctgctggc gggagagaag
  61 ctgcgggagc tgatcctgcc gggcgcgcag gacgacaagg cgggcgcgct ggccgcgctg
 121 cttctgcagc tgaagctgga gctgccgttc gaccgggtgg tcaccatcgg caccgtgctg
 181 gtgcccatcc tgctggtcac cctggtcttc accaagaact tcgcagggtg gacgctcttc
 241 tctggctcct gggattggct gtgaggacaa aacataaagg aacccattta ctgttacacc
 301 ccgcacaact tcacgcgcga ccaggcgctg tacgcccgcg gctactgctg gacggagctg
 361 cgggacgcgc tgcccggcgt ggacgccagc ctgtggccgt cgctgtttga gcacaagttc
 421 ctgccctacg cgctgctggc cttcgccgcc atcatgtacg tgcccgcgct gggctgggag
 481 ttcctggcct ccacgcgcct cacctccgag ctcaacttcc tgctgcagga gatcgacaac
 541 tgttaccacc gggcggccga gggccgcgcg cccaagatcg agaagcagat ccagtccaag
 601 ggcccgggca tcacggagcg cgagaagcgc gagatcatcg agaacgcgga gaaggagaag
 661 agcccggagc agaacctgtt cgagaagtac ctggagcgcc gcggccgcag caacttcctg
 721 gccaagctgt acctggcgcg gcacgtgctg atcctgctgc tgagcgccgt gcccatctcc
 781 tacctgtgca cctactacgc cacgcagaag cagaacgagt tcacctgcgc gctgggcgcg
 841 tccccggacg gggcggcagg tgcggggccc gcggtgcgcg tgagctgcaa gctcccgtcc
 901 gtgcaactgc agcgcatcat cgcgggcgtg gacatcgtgc tgctgtgcgt catgaacctc
 961 atcatcctcg tcaacctcat ccacctcttc atcttccgca agagcaactt catcttcgac
1021 aagctgcaca aggtgggcat caagacgcgc cggcagtggc gccgctcgca gttctgcgac
1081 atcaacatcc tggccatgtt ctgcaacgag aaccgcgacc acatcaagtc gctcaaccgg
1141 ctggacttca tcaccaacga gagcgacctc atgtacgaca acgtggtccg gcagctgctg
1201 gcggcgctgg cgcagtccaa ccacgacgcc acccccacgg tgcgcgactc gggggtgcag
1261 accgtggacc ccagcgccaa ccccgccgag cccgacggcg ccgccgagcc gcccgtggtc
1321 aagcggccgc gcaagaagat gaagtggatc cccaccagca acccgcttcc gcagcccttc
1381 aaggagccgc tggccatcat gcgcgtggag aacagcaagg cggagaagcc gaagcccgcg
1441 cgcaggaaga cggccacgga cacgctgatc gcgccgctgc tggaccgctc cgcccaccac
```

-continued

```
1501 tacaagggcg gagggggcga cccgggcccc ggccccgccc ctgcccccgc cccgccgccc
1561 gcccctgaca agaagcacgc gcgccacttc tccctggacg tgcaccccta catcctcggc
1621 accaagaagg ccaaggccga ggcggtgccc gccgccctgc ccgcctcccg gagccaggag
1681 gggggcttcc tgtcccaggc ggaggactgt gggctaggcc tggccccggc gcccatcaaa
1741 gatgctccgc tccccgagaa ggaaatcccg taccccacag agccagcccg ggcagggctt
1801 ccctcggggg gcccgttcca cgtccgctca cctcccgccg cccctgctgt ggcccctctg
1861 acaccagcca gcctgggcaa ggcggagccc ctcaccatcc tgagccgaaa cgccacacac
1921 ccgctgctgc acatcaacac gctatcctca tcgccacctt cgacgagccg agaacggtcg
1981 tgagtactgt ggagttttga gggatggcac cgtccaggcc gccgagagcc cctctgcctg
2041 tgtcgtgtgg cctggccagc ctcccggtgg acaccagccc tgcgtggacg tggcctgtgc
2101 ttcgcccgca ctgcgcgcat ccccaacctc tgtccgcatg cctggggcct tcgcccccac
2161 gtgctcgaca ggggaacccg cccggacggc atcgccaggc actggctggg gtggggaaag
2221 gtggcccagt ggagccggtg gccaggaagg ctgaagcccg cttcccatgc tcctgcatca
2281 ggtgcccagc cgtgggtggg ggccctgagg tgaagagttt attttttttag tccgtttcgt
2341 cctggccccg ggctgtggcg agacagccca actcccccag cccagctccc ccagcccaga
2401 gccagggaag aggaaggtgg ggccagtccc accagtgggg tggccacgcc catggggtca
2461 catgctcagg ggtcaccccc tgcagggacc tgatgccctc gggtgggagg gaccgaggtc
2521 caccctcggg tcaaaggtca acgtgcactt tctccttgtc gcctgacaga cattttattt
2581 tactaagact gctgtaccga acaagcatat ttatcatcag gagacaggat gggtttaaag
2641 caggatggtg tgtgtgtgaa cgggcatgag cagaggtgag cgtgagcgag cgggtgtgta
2701 tgtacgagtg tgcacgtgtg tgcgtgtgca cagagggtgt ggtgccagct tgagtgggag
2761 tgtgtgagtg tgagcaggcg ggcgagtgcg tgagtgcacg ccagcgcgtg gcccatgtat
2821 gaggagtgaa ggggcccaac gcaataacca cgtcccccac ccgggccccc cgccgcggct
2881 gaggccacat ggcttcctgt gggagccccg gccggcaccc ggctggtccc accccaaata
2941 cctcagccat ggagaccatg tcatgcagaa ttaacaaggt agcaccgagc atatcaataa
3001 atattattct gataatcaaa aaaaaaaaaa aaaaa
```

(Panx3 mRNA)

SEQ ID NO: 121

```
  1 atgtcacttg cacacacagc tgcagagtac atgctctcag atgccctgct gcctgaccgc
 61 aggggacccc gcctcaaagg actgcgtctg gaactgcccc tggaccggat agtcaagttc
121 gtagctgtgg gctccccctt gttgctgatg tccctggcat tcgcccagga gttctcctct
181 gggtctccga tcagctgctt ctctcccagt aacttcagca tccggcaggc agcctacgtg
241 gacagctcct gctgggactc actgcttcac cataagcagg acgggcctgg ccaggacaaa
301 atgaaatctc tctggcccca caaggccctc ccctactccc tgctggccct ggccttgctc
361 atgtacctgc cggtgctgct gtggcagtat gcagctgtgc cagccctcag ctccgatctg
421 ctgttcatca tcagcgaact ggacaaatct tataatcgct ccatccgcct cgtgcagcac
481 atgctgaaga tccggcagaa gagttccgac ccctatgtgt tctggaatga gctggagaag
541 gctcggaaag aacgatactt tgaattccct ttgctagagc ggtacctggc atgtaagcag
601 cgttcacatt cgctagtggc tacctacctc ctgaggaact ccctcttgct catcttcacc
661 tccgccactt acctatacct tggtcatttc catctggatg tcttcttcca ggaagaattc
721 agctgctcca tcaagacagg gctgctaagt gatgagaccc atgtccccaa tctgatcaca
781 tgcaggctga catcactgtc cattttccag attgttagcc tctccagtgt agcaatatac
```

-continued

```
841    accatattgg ttccagtgat aatatacaac ctcacacggc tatgtcggtg ggacaaacga
901    cttttatctg tctatgagat gctcccagct tttgatctcc tcagcagaaa gatgctagga
961    tgtcccatca atgacctcaa tgtgatcctt cttttcctcc gagctaacat ctctgagctc
1021   atctctttta gctggctgag tgtcttatgt gtgttgaagg atacaaccac ccagaagcac
1081   aatattgaca cagtagttga ttttatgact ttattggctg gcttagaacc ctcaaaaccc
1141   aaacacctca ccaactcggc atgtgatgaa cacccatagt taagaaacca tggagcaaga
1201   aagcttgtgg aaagtctctc tccttcctca taagacatgc acactaatac acatacacac
1261   caaaaaatta cacattttaa aactgctaag cttggattta actgaatcat atatctttta
1321   tcatgttatc ctaaaagtga gaagacataa ccaagacatg gaaataaatg tgaaagctgg
1381   agccgaagag tcaaagagct aaaaaattaa gtctagaaca ttctatgagg atagtataaa
1441   taaaaagaaa tacagtctag acatgctgca aggaaagaag attctaaagt ccgtttatgg
1501   aggcaattcc atatcctttc ttgaacgcac attcagctta ccccagagag caagtgaggc
1561   aatctggcaa aagattaata aagatgtaaa cccctggaaa aaaaaaaaa
```

Connexins and pannexins are the hemichannel-forming proteins in vertebrates. In one aspect this invention relates to pharmaceutical compositions, articles of manufacture, and methods for treating ocular and other disorders, for example, glaucoma, DME, AMD, DR, ocular fibrosis, ocular hypoxia, retinal perfusion impairment, and/or neuropathic ocular disorders by administering a therapeutically effective amount of at least one connexin modulator to the eye of said subject. In some aspects the neuropathic ocular disorder may be, for example, loss of retinal ganglion cells and/or glaucomatous optic neuropathy. In some aspects, administering a therapeutically effective amount of at least one connexin modulator is effective for stopping, preventing, or treating loss of retinal ganglion cells are further useful for increasing the levels of neurotrophins in the glaucomatous optic nerve and decreasing vitreal glutamate concentrations.

The major risk factor for most glaucomas is increased intraocular pressure, i.e. ocular hypertension. Intraocular pressure is a function of production of liquid aqueous humor by the ciliary processes of the eye, and its drainage through the trabecular meshwork. Aqueous humor flows from the ciliary processes into the posterior chamber, bounded posteriorly by the lens and the zonules of Zinn, and anteriorly by the iris. It then flows through the pupil of the iris into the anterior chamber, bounded posteriorly by the iris and anteriorly by the cornea. From here, the trabecular meshwork drains aqueous humor via Schlemm's canal into scleral plexuses and general blood circulation. However, in other glaucoma patients, normal tension glaucoma may be present.

In open/wide-angle glaucoma, flow is reduced through the trabecular meshwork, due to the degeneration and obstruction of the trabecular meshwork, whose original function is to absorb the aqueous humor. Loss of aqueous humor absorption leads to increased resistance and thus a chronic, painless buildup of pressure in the eye. In close/narrow-angle, the iridocorneal angle is completely closed because of forward displacement of the final roll and root of the iris against the cornea, resulting in the inability of the aqueous fluid to flow from the posterior to the anterior chamber and then out of the trabecular network. This accumulation of aqueous humor causes an acute increase of pressure and pain.

The inconsistent relationship of glaucoma with ocular hypertension has provoked studies on anatomic structure, eye development, nerve compression trauma, optic nerve blood flow, excitatory neurotransmitter, trophic factor, retinal ganglion cell/axon degeneration, glial support cell, immune system, aging mechanisms of neuron loss, and severing of the nerve fibers at the scleral edge. As featured herein, in some embodiments, the gap junction, connexin and/or pannexin modulators featured herein are useful in treating or preventing ocular disorders as disclosed herein, including, for example, conditions such as hypertensive and normatensive glaucoma and for other uses featured herein, treating or preventing DME or ocular fibrosis, or for treating AMD from its earliest stages through its later stages.

Age-related macular degeneration (ARMD or AMD) is another leading cause of irreversible visual impairment, and the leading cause of visual impairment in people over the age of 60 years in developed nations. AMD most commonly affects the macula, an area of the retina that subserves fine and detailed vision (but may not be confined to the macular). In the United States one in seven of the population over 50 show neovascular AMD and/or geographic atrophy with 1.8 million citizens having AMD (and expected to rise to 3 million by 2020). Friedman, et al. (2004) Prevalence of age-related macular degeneration in the United States, Arch Ophthalmol 122: 564-572. The incidence of AMD increases dramatically with age, however, and more than 15% of white women older than 80 years having neovascular AMD and/or geographic atrophy. Worldwide AMD costs are estimated at $345B per annum with $255B of that in direct health care costs. AMD was included in the 2010 eye disease priority list by the World Health Organization as a disease without satisfactory treatment options.

The etiology of AMD is most likely to be multifactorial, involving a complex interaction of metabolic, genetic and environmental factors. A conventional understanding of AMD is that it affects four functionally interrelated layers in the eye: the photoreceptors, the RPE, Bruch's membrane, and the choriocapillaris. Shelley, et al. (2009) Cone degeneration in aging and age-related macular degeneration, Arch Ophthalmol 127: 483-492. Research has primarily focused on the degeneration of the RPE which leads to irreversible damage to the photoreceptors. Nowak (2006) Age-related macular degeneration (AMD): pathogenesis and therapy, Pharmacol Rep 58: 353-363. Along with this degeneration, deposits (Drusen) can accumulate within the RPE and Bruch's membrane. These deposits can be associated with abnormal blood vessel ingrowth, which in turn can lead to leakage, bleeding and ultimately scar formation at the macula. See de Jong P T (2006) Age-related macular degeneration, *N Engl J Med* 355: 1474-1485; Finger, et al. (1999) Ophthalmic plaque radiotherapy for age-related macular degeneration associated with subretinal neovascularization, *Am J Ophthalmol* 127: 170-177.

In one aspect this invention relates to pharmaceutical compositions, articles of manufacture, and methods for treating ocular disorders, for example, glaucoma, DME, AMD, DR ocular fibrosis, and/or ocular hypoxia and/or retinal perfusion impairment, and/or neuropathic ocular disorders intraocular pressure-associated neuropathies, for example, by administering a therapeutically effective amount of at least one connexin modulator and/or at least one pannexin modulator to the eye of said subject. In one aspect, this invention relates, for example to pharmaceutical compositions and methods for treating glaucoma. The methods herein provide for treatment of intraocular pressure-associated optic neuropathy such as glaucoma, in an amount sufficient to reduce intraocular pressure. In some aspects, the connexin modulators are useful in treating trauma associated with elevated intraocular pressure. In some aspects, the connexin modulator is a connexin 43 modulator. In some aspects, the compositions and methods of this invention are useful in reducing the intraocular pressure to normal levels, e.g., below 21 mm Hg, for example to below 21, 20 or 19 mm Hg, for example to levels between about 8 and about 21 mm Hg.

The compositions, articles of manufacture and methods described herein are useful, in one aspect, to treat glaucoma without toxic side effects. In some aspects, the glaucoma may be open-angle glaucoma or angle-closure glaucoma. In some aspects, administering a therapeutically effective amount of at least one pannexin modulator and/or at least one connexin modulator, for example, a connexin 43 channel modulator, to the eye tissue in need thereof increases flow through the trabecular meshwork. Also useful are gap junction modulators, pannexin channel modulators, and hemichannel modulators. In some aspects, the compositions of this invention are useful as adjuvants to improve trabeculectomy success rates.

The front of the eye is filled with aqueous humor, a clear fluid that provides nourishment to the structures in the anterior portion of the eye. This fluid is produced constantly by the ciliary body, which surrounds the lens of the eye. The aqueous humor flows through the pupil and out of the eye through the trabecular meshwork channels located at the junction where the cornea attaches to the iris, which is referred to as the drainage angle of the eye. In some aspects of this invention, one or more gap junction or connexin modulators, or panenxin modulators, for example, a connexin 43 modulator, is administered at or near the trabecular meshwork or the ciliary body. Also useful are gap junction modulators, pannexin channel modulators, and hemichannel modulators.

Also featured in one aspect of this invention are compositions, articles of manufacture, and methods for treating retinal perfusion impairment, retinal ischemic diseases or optic ischemic diseases in a subject, comprising administering a therapeutically effective amount of a gap junction and/or connexin modulator, and/or a pannexin or pannexin channel modulator, effective to reduce inflammation in the inner retina. In some aspects, the retinal ischemic disease is retinal artery occlusion, or central retinal vein occlusion. In some aspects, the optic ischemic disease is, for example, anterior ischemic optic neuropathy. In some aspects the connexin modulator is a modulator of Cx43, Cx26, Cx30, Cx31.1, Cx36, Cx37, Cx40, Cx45, Cx50, Cx57 or any other connexin in the eye or blood vessels. In some aspects, the connexin modulator is a Cx43 modulator, for example a Cx43 hemichannel modulator. In some aspects, the modulator can include or exclude any of the foregoing.

This invention also features compositions, articles of manufacture, and methods for treating ocular disorders, for example, glaucoma, AMD, ocular fibrosis, and/or ocular hypoxia and/or retinal perfusion impairment, and/or neuropathic ocular disorders intraocular pressure-associated neuropathies, by, for example, reducing impairment of choridal perfusion and/or choroidal inflammation, or choroidal overperfusion in a subject, comprising administering an amount of a gap junction and/or connexin modulator and/or a pannexin or pannexin channel modulator to the choroid of the subject, effective to reduce impairment of choridal perfusion and/or choroidal inflammation, or choroidal overperfusion and/or inflammation in the inner retina. In some aspects of this invention, administering a therapeutically effective amount of a gap junction and/or connexin modulator to the choroid of the subject effective to reduce impairment of choridal perfusion and/or choroidal inflammation, or choroidal overperfusion, also reduces choriocapillaris endothelial cell loss and/or choriocapillaris dropout. In some aspects, reducing impairment of choridal perfusion and/or choroidal inflammation, or choroidal overperfusion also reduces retinal pigmental epithelium degeneration and/or Drusen development, or otherwise ameliorates, stops, slows, and/or reverses the progression of macular degeneration or macular dystrophy, which can be dry macular degeneration or wet macular degeneration. The connexin modulator or pannexin modulator for reducing impairment of choridal perfusion and/or choroidal inflammation, or choroidal overperfusion may also be administered with an ocular treatment agent. In some embodiments, the modulator for reducing impairment of choridal perfusion and/or choroidal inflammation, or choroidal overperfusion is a Cx43 modulator, hemichannel modulator, pannexin modulator or pannexin channel modulator.

In some aspects of the methods of this invention, the gap junction modulator and/or connexin modulator, or pannexin or pannexin channel modulator may be administered to the eye by intraocular injection, or intravitreal injection. The gap junction modulator and/or connexin modulator, pannexin or pannexin channel modulator may be administered once, or more than once. Other methods of administering modulators are featured herein.

In some embodiments the connexin modulators of this invention include connexin oligonucleotides or polynucleotides, such as connexin anti-sense oligonucleotides or polynucleotides, or connexin peptides or peptidomimetics, such as connexin peptides or peptidomimetics. Connexin peptides or peptidomimetics comprise, for example, any of the peptides described herein, including peptides comprising a portion of an extracellular domain of a connexin, and peptides comprising a portion of a carboxy-terminal portion of a connexin or gap junction closing compounds, and hemichannel closing compounds useful in the methods of this invention, such as healing any of the ocular disorders described herein.

In some embodiments the connexin protein modulating agents of this invention include connexin 43 oligonucleotides or polynucleotides, such as connexin 43 anti-sense oligonucleotides or polynucleotides, or anti-connexin 43 peptides or peptidomimetics, for example, any of the peptides described herein, including peptides comprising a portion of an extracellular domain of a connexin, and peptides comprising a portion of a carboxy-terminal portion of a connexin or gap junction closing compounds, and hemichannel closing compounds useful in the methods of this invention, such as healing any of the neuropathic ocular disorders described herein.

In some embodiments the pannexin modulators of this invention include pannexin oligonucleotides or polynucleotides, such as pannexin anti-sense oligonucletoides or polynucleotides, or anti-pannexin peptides or peptidomimetics useful in the methods of this invention, such as healing any of the ocular disorders, such as glaucoma, AMD, ocular fibrosis, DME, ocular hypoxia and/or neuropathic ocular disorders described herein.

In some embodiments "promoiety" refers to a species acting as a protecting group which masks a functional group within an active agent, thereby converting the active agent into a pro-drug. The active agent may be any of the modulators or ocular therapeutics disclosed herein. Typically, the promoiety will be attached to the drug via bond(s) that are cleaved by enzymatic or non-enzymatic means in vivo, thereby converting the pro-drug into its active form. In some embodiments the promoiety may also be an active agent. In some embodiments the promoiety may be bound to a gap junction modulator, a connexin modulator, or a pannexin modulator. In some embodiments the promoiety may be bound to any of the polynucleotides, peptides or peptidomimetics, small molecule antagonists and/or ocular treatments disclosed herein. In some embodiments the promoeity may be bound to a compound of Formula I. In some embodiments the pro-drug may be a compound of Formula II.

In some embodiments the promoiety may be any peptidomimetic or peptide antagonist of this disclosure. In some embodiments, the promoeity is a single amino acid which is optionally protected on its functional groups. In some embodiments, the promoeity is a targeting species. In some aspects, the promoeity is a substrate for an influx or efflux transporters on the cell membrane, for example those described in Gaudana, R. et al. *The AAPS Journal,* 12:3, 348-360 (2012). The promoeity can be, for example, chemically-linked biotin. The promoeity can be, for example, chemically-linked D-serine.

In some embodiments the pannexin modulators of this invention include pannexin oligonucleotides or polynucleotides, such as pannexin anti-sense oligonucletoides or polynucleotides, or anti-pannexin peptides or peptidomimetics useful in the methods of this invention, such as healing any of the ocular hypoxia or neuropathic ocular disorders described herein.

Definitions

A "small molecule" is defined herein to have a molecular weight below about 600 daltons, and is generally an organic compound. A small molecule can be an active agent of a prodrug.

As used herein, "treatment" (and grammatical variations thereof such as "treat" or "treating") refers to clinical intervention in an attempt to alter the natural course of the individual, tissue or cell being treated, and can be performed either for prophylaxis or during the course of clinical pathology. Desirable effects of treatment include, but are not limited to, preventing occurrence or recurrence of a disease, disorder or condition, alleviation of signs or symptoms, diminishment of any direct or indirect pathological consequences of the disease, decreasing the rate of disease progression, amelioration or palliation of the disease state, and remission or improved prognosis. In some embodiments, compounds, methods and compositions of the invention can be used to delay development of a disease, disorder or condition, or to slow the progression of a disease, disorder or condition. The term does not necessarily imply that a subject is treated until total recovery. Accordingly, "treatment" includes reducing, alleviating or ameliorating the symptoms or severity of a particular disease, disorder or condition or preventing or otherwise reducing the risk of developing a particular disease, disorder or condition. It may also include maintaining or promoting a complete or partial state of remission of a condition.

The term "treating ocular disorders" or the like, including diseases and conditions, may refer to preventing, slowing, reducing, decreasing, stopping and/or reversing the ocular disorder, disease or condition, such as, for example, neuronal loss and/or neuropathy, vessel leak and/or hemorrhage, neovascularization, inflammation and/or edema in the eye.

The term "preventing" means preventing in whole or in part, or ameliorating or controlling.

As used herein, "effective amount" refers to an amount effective, at dosages and for periods of time necessary, to achieve the desired therapeutic or prophylactic result. For example, and not by way of limitation, an "effective amount" can refer to an amount of a compound or composition, disclosed herein, that is able to treat the signs and/or symptoms of a disease, disorder or condition.

As used herein, "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is preferably also one in which any toxic or detrimental effects of the substance/molecule, agonist or antagonist may be outweighed by the therapeutically beneficial effects.

As used herein, "prophylactically effective amount" refers to an amount effective, at dosages and for periods of time necessary, to achieve a desired prophylactic result. Typically but not necessarily, since a prophylactic dose is used in subjects prior to or at an earlier stage of a disease, disorder or condition, the prophylactically effective amount will be less than the therapeutically effective amount.

The term "pharmaceutical formulation" refers to a preparation which is in such form as to permit the biological activity of an active ingredient contained therein to be effective, and which does not contain additional components that are unacceptably toxic to a subject to which the formulation would be administered.

A "pharmaceutically acceptable carrier," as used herein, refers to an ingredient in a pharmaceutical formulation, other than an active ingredient, which can be safely administered to a subject. A pharmaceutically acceptable carrier includes, but is not limited to, a buffer, excipient, stabilizer, or preservative.

As used herein, the term "subject" or the like, including "individual," and "patient", all of which may be used interchangeably herein, refers to any mammal, including humans, domestic and farm animals, and zoo, wild animal park, sports, or pet animals, such as dogs, horses, cats, sheep, pigs, cows, etc. The preferred mammal herein is a human, including adults, children, and the elderly. Preferred sports animals are horses and dogs. Preferred pet animals are dogs and cats. The subject may be, for example, an aquatic park animal, such as a dolphin, whale, seal or walrus. In certain embodiments, the subject, individual or patient is a human.

The invention is described herein with reference to the use of a gap junction channel modulator, including modulators such as peptide 5 and/or an analogue thereof, compounds of formula I, for example tonabersat, and/or an analogue or pro-drug of any of the foregoing compounds, and/or the use of a pannexin modulator, e.g., probenecid and/or a synthetic mimetic peptide blocker of pannexin 1, e.g., $^{10}$Panx1, or an analogue of either thereof. It should be appreciated that one or more salt, polymorph, solvate and/or isomer of a gap junction channel modulator such as peptide 5 and/or an analogue thereof, compounds of formula I, for example tonabersat, and/or an analogue or pro-drug of any of the foregoing compounds, and/or a pannexin modulator, e.g., probenecid and/or a synthetic mimetic peptide blocker of pannexin 1, e.g., $^{10}$Panx1, or an analogue of either, may also be used in the invention. Accordingly, references to "tonabersat and/or an analogue thereof," "peptide 5 and/or an analogue thereof," "probenecid and/or an analogue thereof," or "$^{10}$Panx1, or an analogue of either thereof," should be taken to include reference to any one or more salts, solvates, polymorphs, and/or isomers of an of the foregoing compounds.

Methods, uses and compositions of the invention may comprise the use of a combination of compounds of formula I, for example tonabersat, and/or an analogue of any of the foregoing compounds and one or more analogues thereof, peptide 5 and one or more analogues thereof, probenecid and one or more analogues thereof, or $^{10}$Panx1 and one or more analogues thereof, or a combination of one or more of these analogues. Accordingly, reference herein to "compounds of formula I, for example tonabersat, and/or an analogue," "peptide 5 and/or an analogue thereof," "compounds of formula VI, for example probenecid, and/or an analogue thereof," or "$^{10}$Panx1, or an analogue of either thereof," should be taken to include reference to such combinations.

As used herein, the term "hemichannel" is a part of a gap junction (two hemichannels or connexons connect across an intercellular space between adjacent cells to form a gap junction) and is comprised of a number of connexin proteins, typically homo- or hetero-meric hexamers of connexin proteins that form the pore for a gap junction between the cytoplasm of two adjacent cells. The hemichannel is supplied by a cell on one side of the junction, with two hemichannels from opposing cells normally coming together to form the complete intercellular gap junction channel. However, in some cells, and in cells under some circumstances, the hemichannel itself is active as a conduit between the cytoplasm and the extracellular space allowing the transference of ions and small molecules.

Compounds of formula I, for example tonabersat, and/or an analogue or pro-drug of any of the foregoing compounds, can modulate the function and/or activity of hemichannels, preferably those comprising any type of connexin protein. Accordingly, reference to "hemichannel" should be taken broadly to include a hemichannel comprising any one or more of a number of different connexin proteins, unless the context requires otherwise. However, by way of example, a hemichannel may comprise one or more of connexin23, 25, 26, 30, 30.2, 30.3, 31, 31.1, 31.9, 32, 36, 37, 40, 40.1, 43, 45, 46, 47, 50, 59, and 62. In one embodiment, a hemichannel consists of one of the aforementioned connexins. In one embodiment, a hemichannel comprises one or more of connexin26, 30, 32, 36, 37, 40, 45 and 47. In one embodiment, a hemichannel consists of one of connexin26, 30, 32, 36, 37, 40, 45 or 47. In one particular embodiment, a hemichannel comprises one or more of connexin30 and connexin43. In one particular embodiment, a hemichannel consists of one of connexin30 or connexin43. In one particular embodiment, a hemichannel consists of one of connexin45 or connexin46 or connexin50 In one embodiment, the hemichannel comprises one or more connexin excluding connexin26.

As used herein, the term "gap junction channel" comprises two hemichannels which connect across an intercellular space between adjacent cells and allow certain molecules to flow between those cells.

Hemichannels and gap junction channels may be present in cells of any type. Accordingly, reference to a "hemichannel" or a "gap junction channel" should be taken to include reference to a hemichannel or gap junction channel present in any cell type, unless the context requires otherwise. In one embodiment of the invention, the hemichannel or gap junction channel is present in a cell outside of the central nervous system. In one embodiment, the hemichannel or gap junction channel comprises one or more connexin excluding connexin 26 and is present in a cell outside the central nervous system. In one embodiment of the invention, the hemichannel or gap junction channel is present in a cell in the eye. In one embodiment of the invention, the hemichannel or gap junction channel is present in a cell in the front of the eye, i.e., the anterior segment. In one embodiment of the invention, the hemichannel or gap junction channel is present in a cell in the back of the eye, i.e., the posterior segment. In one embodiment of the invention, the hemichannel or gap junction channel is present in a cell in the uvea. In one embodiment of the invention, the hemichannel or gap junction channel is present in a cell in the optic nerve. In one embodiment of the invention, the hemichannel or gap junction channel is present in a cell in the microvasculature of the eye. In one embodiment of the invention, the hemichannel or gap junction channel is present in a cell in the choroid. In one embodiment of the invention, the hemichannel or gap junction channel is present in a cell in the choriocapillaris.

As used herein, "modulation of a hemichannel and/or a gap junction channel" is the modulation of one or more functions and/or activities of a hemichannel and/or gap junction channel. Such functions and activities may include, for example, docking of hemichannels on adjacent cells and opening to form a gap junction channel. They may also include intercellular communication between cells, and the flow of molecules between cells through a gap junction channel. Such functions and activities may include, for example, the flow of molecules from the extracellular space or environment through a hemichannel into a cell, and/or the flow of molecules through a hemichannel from the intracellular space or environment of a cell into the extracellular space or environment.

Modulation of the function of a hemichannel and/or a gap junction channel may occur by any means. However, by way of example only, modulation may occur by one or more of: preventing, blocking, inhibiting or decreasing the formation of a gap junction through hemichannel docking; inducing or promoting closure of a hemichannel; preventing, blocking, inhibiting or decreasing hemichannel opening; inducing or promoting loss of coupling between hemichannels; triggering, inducing or promoting cellular internalization of a hemichannel and/or gap junction. Use of the words such as "blocking", "inibiting", "preventing", "decreasing" and "antagonizing", and the like, should not be taken to imply complete blocking, inhibition, prevention, or antagonism, although this may be preferred, and should be taken to include partial blocking, inhibition, prevention or antagonism to at least reduce the function or activity of a hemichannel and/or gap junction channel. Similarly, "inducing" or "promoting" should not be taken to imply complete loss of coupling or complete internalization of a hemichannel and/or gap junction (or group of hemichannels and/or gap junctions), and should be taken to include partial loss of coupling or partial internalization to at least reduce the function or activity of a hemichannel and/or gap junction channel.

As used herein, the term "gap junction channel modulator" is a compound that prevents, inhibits, and/or reduces the function or activity of a gap junction channel or the function or activity of a gap junction hemichannel, together or separately, including, for example, prevention, inhibition and/or reduction in expression, activity and/or the formation of hemichannels and/or gap junctions, including the expression of a connexin protein, its trafficking and/or assembly. Prevention, inhibition and/or reduction of function or activity may be direct or indirect (for example, but not limited to, directly blocking a channel, inducing a conformational change, or modifying a connexin phosphorylation state). The gap junction channel blocker may be of any chemical nature. However, by way of example, the agent may be a nucleic acid (including antisense molecules, RNAi molecules, morpholinos, and other nucleic acids as described herein), a peptide, a small molecule, a chemical element, hormone, antibody, antibody fragment or a metabolite. In certain embodiments, it is a compound that targets one or more component of a gap junction, including connexins, hemichannels (also known as connexons), to inhibit or block its activity, expression, trafficking and/or assembly. "Inhibits" or "blocks" should not be taken to imply that the activity, expression, trafficking and/or assembly of a connexin, hemichannel or gap junction is completely inhibited or blocked, although this may be preferred, but should be taken to include any reduction in the activity, expression, trafficking and/or assembly of a connexin, hemichannel or gap junction.

As used herein, the term "disorder where modulation of a gap junction hemichannel and/or gap junction channel may be of benefit" includes any disease, disorder or condition in which gap junction channel and/or hemichannel function or activity may be implicated in the onset, progression, or persistence of the disease, disorder or condition. In one embodiment, the disease, disorder or condition is one in which the function or activity of a gap junction channel and/or hemichannel comprising one or more of connexins23, 25, 26, 30, 30.2, 30.3, 31, 31.1, 31.9, 32, 36, 37, 40, 40.1, 43, 45, 46, 47, 50, 59, and 62 is implicated. In one embodiment, the disease, disorder or condition is one in which the function or activity of a gap junction channel and/or hemichannel consisting of one of the aforementioned connexins is implicated. In one embodiment, the disease, disorder or condition is one in which the function or activity of a gap junction channel and/or hemichannel comprising one or more of connexin26, 30, 32, 36, 37, 40, 45 and 47 is implicated. In one embodiment, the disease, disorder or condition is one in which the function or activity of a gap junction channel and/or hemichannel consisting of one of connexin26, 30, 32, 36, 37, 40, 45 or 47 is implicated. In one particular embodiment, the disease, disorder or condition is one in which the function or activity of a gap junction channel and/or hemichannel comprising one or more of connexin 30 and connexin 43 is implicated. In one particular embodiment, the disease, disorder or condition is one in which the function or activity of a gap junction channel and/or hemichannel consisting of one of connexin30 or connexin43 or connexin45 or connexin46 or connexin50 is implicated. In one embodiment, the disease, disorder or condition is one in which the function or activity of a gap junction channel and/or hemichannel comprising one or more connexin excluding connexin26 is implicated. In one embodiment, the disease, disorder or condition is one in which the function or activity of a gap junction channel and/or hemichannel present in a cell outside of the central nervous system is implicated. In one embodiment, the disease, disorder or condition is one in which the function or activity of a gap junction channel and/or hemichannel comprising one or more connexins excluding connexin26 and is present in a cell outside the central nervous system is implicated. In one embodiment of the invention, the disease, disorder or condition is one in which the function or activity of the hemichannel or gap junction channel to be modulated is present in a cell in the eye. In one embodiment of the invention, the disease, disorder or condition is one in which the function or activity of the hemichannel or gap junction channel to be modulated is present in a cell in the front of the eye, i.e., the anterior segment. In one embodiment of the invention, the disease, disorder or condition is one in which the function or activity of the hemichannel or gap junction channel to be modulated is present in a cell in the back of the eye, i.e., the posterior segment. In one embodiment of the invention, the disease, disorder or condition is one in which the function or activity of the hemichannel or gap junction channel to be modulated is present in a cell in the uvea. In one embodiment of the invention, the disease, disorder or condition is one in which the function or activity of the hemichannel or gap junction channel to be modulated is present in a cell in the optic nerve. In one embodiment of the invention, the disease, disorder or condition is one in which the function or activity of the hemichannel or gap junction channel to be modulated is present in a cell in the choroid. In one embodiment of the invention, the disease, disorder or condition is one in which the function or activity of the hemichannel or gap junction channel to be modulated is present in a cell in the choriocapillaris. In one embodiment of the invention, the disease, disorder or condition is one in which the function or activity of the hemichannel or gap junction channel to be modulated is present in a cell in the microvasculature of the eye. In one embodiment, the composition can include or exclude any gap junction channel and/or hemichannel modulator of the foregoing.

As used herein, the term "disorder where modulation of a pannexin channel may be of benefit" should be taken to include any disorder in which pannexin or pannexin channel function or activity may be implicated in the onset, progression, or persistence of a disease, disorder or condition. In one embodiment, the disease, disorder or condition is one in which the function or activity of a pannexin channel comprises one or more of the three isoforms of pannexins. In one embodiment, the disease, disorder or condition is one in which the function or activity of a pannexin channel to be modulated comprises pannexin 1. In one embodiment, the disease, disorder or condition is one in which the function or activity of a pannexin channel to be modulated is in or on the eye, including the surface of the eye, the retina, and vessels associated with or comprising the eye.

"Chronic wounds", "wounds that do not heal at the/an expected rate", and "dehiscent wounds" and like terms and phrases, as used herein, have the meaning as provided in US2011/0300130, which is herein incorporated by reference and includes a number of examples of the types of wounds to which the present invention may be applied. However, by way of example, such wounds may include diabetic ulcers (including for example, diabetic foot ulcers), venous ulcers, venous stasis ulcers, pressure ulcers, decubitus ulcers, vasculitic ulcers, arterial ulcers, infectious ulcers, pressure ulcers, burn ulcers, traumatic or trauma-induced ulcers, inflammatory ulcers, ulcerations associated with pyoderma gangrenosum, ocular ulcers, including persistent epithelial defects, mixed ulcers.

"Fibrosis" and "fibrotic diseases, disorders or conditions" or like terms and phrases, as used herein, have the meaning as provided in US2011/0092449, which is herein incorporated by reference and includes a number of examples of fibrosis, diseases, disorders or conditions to which the present invention may be applied. However, by way of example, such fibrosis, fibrotic diseases, disorders or conditions may include liver fibrosis, cardiac fibrosis, lung fibrosis (including for example, silicosis, asbestosis, idiopathic pulmonary fibrosis), oral fibrosis (including for example, oral submucous fibrosis), retroperitoneal fibrosis, deltoid fibrosis, endomyocardial fibrosis, kidney fibrosis (including for example, diabetic nephropathy), glomerulosclerosis, acute fibrosis. In one embodiment, the liver fibrosis has arisen from chronic liver injury or is associated with haemochromatosis, Wilson's disease, alcoholism, schistosomiasis, viral hepatitis, bile duct obstruction, exposure to toxins, and/or metabolic disorders. In one embodiment, the cardiac fibrosis is endocardial fibrosis or endomyocardial fibrosis. In one embodiment, the acute fibrosis is associated an accidental injuriy, an infection, and/or radiation and/or chemotherapy treatments. In one embodiment, the fibrosis may occur in a subject that has a disease, disorder or condition selected from the group comprising scleroderma, pancreatitis, inflammatory bowel disease, Crohn's disease, nodular facilitis and/or eosinophilic facititis. In one embodiment, the scleroderma may be morphea, generalized morphea, or linear scleroderma.

"Abnormal or excessive scarring" and the like, as used herein, have the meaning as provided in US2011/0130710, which is herein incorporated by reference and includes a number of examples of abnormal or excessive scarring to which the present invention may be applied. However, by way of example, abnormal or excessive scarring may include scars present in or on the skin, scars in or on the eye, a keloid scar, a hypertrophic scar, an atrophic scar, a widespread scar.

"Vascular disorders" and like terms or phrases, as used herein, have the meaning as provided in EP2510939, which is herein incorporated by reference and includes a number of examples of vascular disorders to which the present invention may be applied. However, by way of example, vascular disorders may include atherosclerosis, microvascular disorders, macrovascular disorders, thrombosis, vascular injuries resulting from trauma, vascular damage, diabetic retinopathy, organ ischemia, endothelial cell disruption, vascular diseases of the extremities.

An "orthopedic disease or disorder" and like phrases, as used herein, have the meaning as provided in EP2238250, which is herein incorporated by reference and includes a number of examples orthopedic diseases or disorder to which the present invention may be applied. However, by way of example, the orthopedic disease or disorder includes one which is characterized in whole or in part by abnormal tissue formation inside and/or around a joint, one which is associated with altered or abnormal joint mobility or joint architecture which may be associated with or caused by a variety of injuries and conditions such as, for example, metabolic disorders, ischemia, trauma, injury to joint, capsule, bone, cartilage, tendon, ligament or muscle, fractures, subluxation, dislocation, crush injuries, prolonged immobilization (e.g., immobilization of a joint in a cast or splint), and/or paralysis.

The phrase an "orthopedic surgery or procedure" and like phrases, as used herein, will be readily understood by persons skilled in the art. However, by way of example, it should be taken to include any surgery or procedure outlined in EP2242844. "Improving" the recovery from such a procedure should also be taken broadly and may include, for example, reducing pain, and improving mobility and/or recovery time.

"Post-orthopedic surgical joint contracture" and like phrases, as used herein, have the meaning as provided in EP2242844, which is herein incorporated by reference.

"Adhesions" and like phrases, as used herein, have the meaning as provided in EP2252690, which is herein incorporated by reference. However, by way of example, it may include surgical adhesions and adhesions which form in any tissue including epithelia, connective tissue, muscle, and tissue.

"Tissue damage", "tissue damage associated with an ophthalmic procedure" and like phrases and terms, as used herein, have the meaning as provided in US2012/0093768, which is herein incorporated by reference and includes a number of examples of tissue damage to which the present invention may be applied. However, by way of example, tissue damage may include enhancing tissue repair processes and/or ameliorating tissue damage.

An "inflammatory disorder", "inflammatory disease" and like phrases, as used herein, have the meaning as provided in provided in WO2013/148736, which is herein incorporated by reference and includes a number of examples of disorders to which the present invention may be applied. In one embodiment, hemichannel and pannexin modulators are used, alone or together, to inhibit activation of one or more inflammasomes. In one embodiment, modulators including hemichannel and pannexin or pannexin channel modulators are used, alone or together, to inhibit activation of an inflammatory cascade by an inflammasome. In one embodiment, modulators including gap junction, hemichannel and pannexin and/or pannexin channel modulators are used, alone or together, to treat a subject for a disease, disorder or condition characterized, at least in part, by the activation of one or more inflammasomes and/or by the activation of an inflammatory cascade by an inflammasome. In one embodiment, gap junction, hemichannel, pannexin channel, connexin and pannexin modulators are used, alone or together, to modulate activity of the NLRP3 inflammasome The inflammasome is a multiprotein complex comprising caspase 1, PYCARD, NALP, and optionally caspase 5 (also known as caspase 11 or ICH-3). The exact composition of an inflammasome depends on the activator that initiates inflammasome assembly. For example, dsRNA will trigger one inflammasome composition whereas asbestos will assemble a different variant. Inflammasomes promote the maturation of the inflammatory cytokines Interleukin 1β (IL-1β) and Interleukin 18 (IL-18). Inflammasomes are responsible for activation of inflammatory processes, and has been shown to induce cell pyroptosis, a process of programmed cell death distinct from apoptosis. The NLRP3 inflammasome blockade inhibits VEGF-A-induced age-related macular degeneration.

The terms "modulating agent," "modulator" and "modulation" of a gap junction channel, a hemichannel, a pannexin or pannexin channel, or connexin function or activity, as used herein in its various forms, refers to inhibition in whole or in part of the expression, action or activity of a connexin or a connexin hemichannel or connexin gap junction or a pannexin or pannexin channel, in whole or in part, and may function as anti-connexin agents, including as gap junction modulation agents, and as anti-pannexin agents, including as pannexin channel modulation agents. In some aspects the gap junction and/or connexin modulator may be a modulator of a connexin present in blood vessels, for example, a connexin 43 modulator and/or a connexin 45 modulator. Thus, as used herein, the term "connexin modulator" refers generally to connexin modulators, but also specifically to connexin 43 modulators and connexin 45 modulators (and Cx43 and Cx45 hemichannel modulators), and modulators of other blood vessel connexins and hemichannels, unless otherwise provided. In some aspects, the connexin modulator is a connexin43 modulator, e.g., a connexin43 hemichannel modulator that blocks hemichannel opening. In some aspects the gap junction modulator also includes modulators of other connexins found in the eye, such as Cx26, Cx30, Cx31.1, Cx36, Cx37, Cx40, Cx50 and Cx57, and their hemichannels and gap junctions. In some aspects the pannexin and/or pannexin channel modulator may be a modulator of pannexin 1, particularly a modulator of pannexin 1 channel opening. In some aspects, the modulating agent can include or exclude any of the foregoing.

In some embodiments, "ocular disorders" include or exclude glaucoma including hypertensive glaucoma and normatensive glaucoma, clinical geographic atrophy; AMD including dry AMD and exudative AMD, abnormalities or impairment, chronic macular ischemia, fibrosis of the eye, idiopathic polypoidal choroidopathy (IPC); diabetic maculopathy, diabetic retinopathy; hypertensive retinopathy, inflammatory CNV; central serous chorioretinopathy (CSR); macular telangiectasia; pattern dystrophy; subretinal/sub-PRD neovascularization; serous detachment of the neurosensory retina; RPE detachment; hemorrhages (subretinal pigment epithelial, subretinal, intraretinal or pre-retinal, including breakthrough bleeding into the vitreous); piretinal, intraretinal, subretinal or sub-pigment epithelial scar/glial tissue or fibrin-like deposits; retinal fibrosis, retinal angiomatous proliferations and retinochoroidal anatastamosis; choroidal neovascularization (CNV); cystic maculopathy; retinal thickening; non-exudative AMD; and retinal scarring, uveitis, including posterior uveitis, scleritis, episcleritis viral retinitis, including cytomegalovirus (CMV) retinitis, retinopathy of prematurity, retinal hypoxia, diffuse choroidal sclerosis, sclerosis of the choriocapillaris, dry eye, ocular and corneal persistent epithelial defects, diabetic macular edema (DME), neuropathic ocular disorders, trauma induced lowering of intraocular pressure, epithelial basement membrane dystrophy, and/or other ocular disorders, including those noted elsewhere herein.

As used herein, "ocular neuropathy" or "neuropathic ocular disorder" is any ocular disorder, disease, or condition that would benefit from an agent that treats ocular neuronal loss, such as stopping or reducing loss of RGCs or damage or loss of other ocular neurons or structures, or restoring lost RGCs or other ocular structures or neurons. Also included are disorders in connection with neuropathic, ischemic, perfusion impairment, inflammatory or microvascular pathology in the eye, which may result from choroidal or retinal perfusion impairment, ocular hypertension, inflammation of the choroid or inner retina, or other internal tissues of the eye, or retinal vein or artery occlusion. In some embodiments, chroroidal or retinal perfusion impairment may result in ocular hypoxia. Also included are any ocular diseases, disorders and conditions characterized by elevated expression of a connexin present in eye blood vessels or neurons. Also included are ocular diseases, disorders and conditions characterized by unwanted pannexin activity. Also included are diseases, disorders and conditions characterized by unwanted ZO-1 protein or ZO-1 protein activity or that would benefit from reduced ZO-1 protein or ZO-1 protein activity. Also included are diseases, disorders and conditions characterized by unwanted lower Rac 1 or Rac 1 activity or that would benefit from increased Rac 1 or Rac 1 activity. Also included are diseases, disorders and conditions characterized by unwanted reduced RhoA GTPase or RhoA GTPase activity or that would benefit from reduced RhoA GTPase or RhoA GTPase activity.

"Glaucomatous ocular neuropathy" refers to any "ocular neuropathy" associated with glaucoma, for example, neuropathic damage to retinal ganglion cells (RPGs) and glaucomatous optic neuropathy associated with glaucoma. In some embodiments, glaucomatous optic neuropathy may or may not be associated with elevated intraocular pressure or choroidal or retinal perfusion impairment. In some embodiments, methods of treating neovascular glaucoma include treatment by administering to a subject in need, a modulator, including a gap junction modulator, a pannexin modulator, a pannexin channel modulator and/or a connexin modulator.

The term "intraocular pressure-associated neuropathy" refers to glautomatous optic neuropathy associated with ocular hypertension, i.e., elevated intraocular pressure.

The term "ocular hypoxia" refers to any eye condition or disorder resulting from hypoxia, including from choroidal or retinal perfusion impairment, hypertension, or interruption of blood flow and/or oxygen flow to the eye, including, for example, ischemia and/or blood vessel leakage and/or blood vessel breakdown in the eye. Conditions that result from ocular hypoxia include, for example, glaucoma, glaucomatous ocular neuropathy intraocular pressure associated neuropathy, ocular neuropathy, clinical geographic atrophy, DME, choriocapillaris dropout and/or breakdown of capillaries in the choroid or other conditions described herein and below.

Clinical Geographic Atrophy (GA)

The presentation of GA is usually insidious and often detected during routine fundus examination. When GA is bilateral and involves the fovea of both eyes, patients may complain of deterioration of central vision. A common mode of presentation is difficulty with reading initially with the smallest sizes of print and then later with larger print and or words. The confirmation of the diagnosis of GA is by clinical examination using a high definition fundus lens for stereo biomicroscopy. This will reveal the characteristic area or areas of pallor with sharply defined and scalloped edges. When the area of GA is larger than 500 microns, large choroidal vessels are clearly visible within the area of pallor.

Usually areas of drusen and focal hyperpigmentation are visible in the retina adjacent to the patch of GA. Several imaging modalities may be useful, in particular fundus autofluorescence, in the evaluation of GA. Fundus autofluorescence along with spectral domain OCT has made it easier to diagnose GA, as these imaging modalities can reveal areas of GA that may not be clinically visible on biomicroscopy.

Geographic atrophy is the advanced (late) form of dry AMD. Here, atrophy refers to the degeneration of the deepest cells of the retina. Usually defined as any sharply delineated round or oval area of hypopigmentation, or apparent absence of the retinal pigment epithelium (RPE), in which choroidal vessels are more visible than in surrounding areas. The most common sequence of events leading to GA is the progression of a large drusen to hyperpigmentation, followed by regression of the drusen, hypopigmentation and ultimately RPE cell death, with development of an atrophic area of retina and underlying choriocapillaris, sometimes preceded by the appearance of refractile deposits.

In some embodiments, the modulator, e.g. a gap junction and/or connexin modulator, or pannexin or pannexin channel modulator prevents inflammation of the choroid vessels, maintains the retinal pigment epithelium cell layer, and/or prevents atrophy in the area of the retina and underlying choriocapillaris.

Exudative Age-Related Macular Degeneration (AMD)

The commonest symptoms typical of onset of exudative AMD are central visual blurring and distortion. Most patients will complain that straight lines appear crooked or wavy. Sometimes patients do not notice visual symptoms when the first eye is affected. When exudative AMD occurs in the second eye, patients suddenly become unable to read, drive, and see fine detail such as facial expressions and features. This symptom described by many with AMD of a central dark patch in the visual field noticed at night, which clears within a few minutes as they adapt. This symptom can also be present in patients with AMD who do not necessarily develop exudative AMD.

Examination of the macula usually reveals an exudative macular lesion along with other features of early AMD such as drusen and pigmentary irregularities. Sometimes these latter features are not visible once exudative AMD has supervened. However the fellow eye, if free of advanced disease, will often exhibit some or all of these early clinical signs and their presence is helpful in supporting the diagnosis that the neovascular lesion is due to AMD. Following slit lamp biomicroscopy the presence or absence of the following signs should be noted: (1) subretinal or sub-RPE neovascularisation which may be visible as grey green lesions (occasionally the lesion will have a dark pigmented edge which is thought to be due to proliferation of the RPE at the edge of the membrane); serous detachment of the neurosensory retina; (3) RPE detachment; (4) hemorrhages—subretinal pigment epithelial, subretinal, intraretinal or pre-retinal (breakthrough bleeding into the vitreous may also occur); (5) hard exudates (lipids) within the macular area related to any of the above, and not related to other retinal vascular disease; (6) piretinal, intraretinal, subretinal or sub-pigment epithelial scar/glial tissue or fibrin-like deposits; (7) retinal angiomatous proliferations and retinochoroidal anatastamosis. This disorder may be treated with a modulator, e.g. a gap junction and/or connexin modulator, or pannexin or pannexin channel modulator, as described herein.

Idiopathic Polypoidal Choroidopathy (IPC)

This is an atypical form of neovascular AMD in which highly exudative lesions with steep walled hemorrhagic pigment epithelial detachments are seen most typically adjacent to the optic disc, but can occur anywhere within the macula and even outside the macula. High speed fluorescein or indocyanine green angiography typically reveals hyperfluorescent dilated complexes of choroidal vessels (branching vascular networks) that leak in the later phases of the angiograms. These dilated complexes look like polyps or grapes and hence the name. It was originally described in middle aged black populations and was more commonly seen in females. IPC is considered part of the spectrum of AMD and a strong association with hypertension and ischemic heart disease has been described. The use of confocal high speed imaging devices allows IPC to be diagnosed more frequently and IPC accounts for more than a third of serosanguinous maculopathy in older adults in Asian populations and for 8-13% of that seen in Caucasians. This disorder may also be treated with a modulator, e.g. a gap junction and/or connexin modulator, or pannexin or pannexin channel modulator, as described herein.

Ocular Fibrosis

Disruption of the highly ordered tissue architecture in the eye caused by vascular leakage, hemorrhage, and concomitant fibrosis can lead to mechanical disruption of the visual axis and/or biological malfunctioning. Ocular fibrosis can also include, for example, fibrosis of the lens, macula or retina, and may include, for example, progressive subretinal fibrosis and premacular fibrosis (PMF). Macular fibrosis occurs when a thin sheet of fibrotic scar tissue forms on top of the macula, in response to damage or injury. Damage to the macula may occur due to eye trauma, retinal tears or detachments, the shrinking of the vitreous, or systemic disease, such as diabetes or hypertension. Macular fibrosis may also be referred to as a macular pucker, epiretinal membrane, or cellophane maculopathy. Subretinal fibrosis may be associated with chronic vitreous inflammation resulting in fibrotic subretinal leasions which pregressively enlarge and coalesce, and may be associated with cystoid macular edema. PMF which affects the macula, on the front side of the retina, whereas macular degeneration affects the underside of the retina. The primary symptom of PMF is the gradual development of distortion in vision in one eye, which may develop over weeks to months. This disorder can be treated with a modulator, e.g. a gap junction and/or connexin modulator, or pannexin or pannexin channel modulator, as described herein.

Uveitis

Uveitis is inflammation of the uvea, the middle layer of the eye. The uvea consists of the middle, pigmented vascular structures of the eye, and includes the iris, choroid and ciliary body. The choroid is sandwiched between the retina and the white of the eye (sclera), and provides blood flow to the deep layers of the retina. Uveitis may include inflammation of the iris called iritis (anterior uveitis). This disorder can also be treated with a modulator, e.g. a gap junction and/or connexin modulator, or pannexin or pannexin channel modulator, as described herein.

Diabetic Maculopathy

This is the most common exudative central macular disorder in older adults. Patients with diabetes frequently exhibit retinal microaneurysms, hemorrhages and exudates often in the context of macular edema. The presence of more extensive vascular signs outside the macular arcade along with venous engorgement or beading should alert the clinician to a diagnosis of diabetic maculopathy. The visual function is less markedly reduced in eyes with diabetic maculopathy when compared to eyes with CNV involving the fovea. Blood vessels near to the macula leak fluid or protein onto the macula. Fluorescein angiography is needed to confirm the absence of choroidal neovascularisation and sub RPE pathology. Sometimes exudative AMD and diabetic maculopathy can coexist as both are common conditions. This disorder can be treated with a modulator, e.g. a gap junction and/or connexin modulator, or pannexin or pannexin channel modulator, as described herein, as can high myopia associated with choroidal neovascularization.

High myopia can be associated with choroidal neovascularisation. These neovascular complexes are believed to occur as a consequence of the development of minute cracks in thinned Bruch's membrane allowing choroidal vessels to access the subretinal space.

Diabetic Macular Edema

Diabetic macular edema is swelling of the retina in subjects with diabetes due to leaking of fluid from blood vessels within the macula. The macula is the central portion of the retina, a small area rich in cones, the specialized nerve endings that detect color and upon which daytime vision depends. As macular edema develops, blurring occurs in the middle or just to the side of the central visual field. Visual loss from diabetic macular edema can progress over a period of months and make it impossible to focus clearly. Macular edema in common in diabetes. The lifetime risk for diabetics to develop macular edema is about 10%. The condition is closely associated with the degree of diabetic retinopathy (retinal disease). Hypertension (high blood pressure) and fluid retention also increase the hydrostatic pressure within capillaries which drives fluid from within the vessels into the retina. A common cause of fluid retention in diabetes is kidney disease with loss of protein in the urine (proteinuria). Diabetic macular edema is classified into focal and diffuse types. This is an important difference because the two types differ in treatment. Focal macular edema is caused by foci of vascular abnormalities, primarily microaneurysms, which tend to leakage fluid whereas diffuse macular edema is caused by dilated retinal capillaries in the retina. This disorder can also be treated with a modulator, e.g. a gap junction and/or connexin modulator, or pannexin or pannexin channel modulator, as described herein.

Diabetic Retinopathy

Diabetic retinopathy can eventually lead to blindness. It is the ocular manifestation of a systemic disease and afflicts up to 80% of all patients who have had diabetes for at least 10 years. In diabetic retinopathy hyperglycemia induces pericyte death and basement membrane thickening leading to compromise of vascular walls. This damage alters the blood-retinal barrier to make retinal blood vessels permeable. Small blood vessels such as in the eye are especially vulnerable to poor blood sugar control. Abnormal connexin expression in diabetes is associated with complications in several tissues including the skin, kidneys, bladder, perineurium, lens and heart 76. In the retina, hyperglycemia is known to induce apoptosis leading to vascular drop out and pericyte loss, hallmarks of background diabetic retinopathy. Recent evidence shows that reduced Cxn43 expression initiates the apoptosis and the breakdown of vascular homeostasis (Bobbie M W, Roy S, Trudeau K, Munger S J, Simon A M, Roy S, *Invest Ophthalmol Vis Sci.;* 51(7): 3758-63, 2010). The above description, however, refers in the main to the underlying background of the disease during the initial stage of non-proliferative diabetic retinopathy and most patients will not notice any change in their vision, although some will develop macular edema when damaged blood vessels leak fluid and lipids onto the macula. As the disease progresses, diabetic retinopathy enters a blood vessel proliferation stage. Owing to low oxygen levels in the retina the new vessels are fragile and grow along the retina and into the vitreous humour. These vessels can bleed, cloud vision, and destroy the retina. Fibrovascular proliferation can cause retinal detachment and vessels can also grow into the angle of the anterior chamber of the eye, causing neovascular glaucoma. Diabetic retinopathy has prominent features of chronic, subclinical inflammation (Zhang W, Liu H, Rojas M, Caldwell R W, Caldwell R B, *Immunotherapy,* 3(5): 609-28, 2011. This disorder can be treated with a modulator, e.g. a gap junction and/or connexin modulator, or pannexin or pannexin channel modulator, as described herein. In some embodiments, the modulator can also treat this inflammatory phase of diabetic retinopathy.

Inflammatory CNV

A number of the choroidal inflammatory white dot syndromes (e.g. presumed ocular histoplasmosis, punctate inner choroidopathy, multifocal inner choroidopathy) can be associated with inflammatory choroidal neovascularisation. In some embodiments, modulator as described herein prevents inflammation of the choroid, thereby preventing inflammatory CNV.

Central Serous Chorioretinopathy (CSR)

This is characterized by a collection of serous fluid in the sub-neurosensory retina without any evidence of neovascularisation. Chronic CSR can sometimes be confused with AMD, again the history, symptoms and a combination of retinal imaging usually helps distinguish between the two. CNV and IPCV can occur as a complication of chronic CSR. It is characterized by leakage of fluid under the retina that has a propensity to accumulate under the central macula. This allows choroidal fluid to leak into the subretinal space. The build-up of fluid occurs because of small breaks in the retinal pigment epithelium. In some embodiments, the modulators described herein prevent or otherwise ammeliorate inflammation of the choroid, and/or prevents or ameliorates choiroidal capillarisis dropout. Retention of the choroid can prevent leakage of choroidal fluid into the subretinal space.

Macular Telangiectasia

Idiopathic macular telangiectasia (MACTEL) also sometimes termed perifoveal or juxtafoveal telangiectasia may be difficult to distinguish from nAMD, particularly with the RAP form of n AMD. Two types of telangiecgtasia have been described: Type 1 MACTEL occurs in middle age persons; the condition is usually unilateral and exhibits exudative features as the vessels are leaky and intraretinal fluid accumulation occurs with a cystic maculopathy and surrounding exudates. Type 2 MACTEL occurs in older people and is usually bilateral with evidence of crystalline deposits, pigmentary charges, and right angled venules evident temporal to the fovea and extending to the entire perifoveal region. While leakage is detectable on fluorescein angiography, there is no evidence of increased retinal thickening. Cystic spaces are evident within the retina using OCT and these spaces are thought to reflect the loss of retinal tissue. Occasionally, sub-retinal neovascularization develops and arises from the retinal circulation. Macular telangiectasia develops when there are problems with the tiny blood vessels around the fovea, the center of the macula. There are two types of macular telangiectasia, and each affects the blood vessels differently. Type 2 macular telangiectasia: The most common form of macular telangiectasia is Type 2 macular telangiectasia, in which the tiny blood vessels around the fovea leak, become dilated (widen), or both. In some cases, new blood vessels form under the retina and they can also break or leak. Fluid from leaking blood vessels causes the macula to swell or thicken, a condition called macular edema, which affects your central vision. Also, scar tissue can sometimes form over the macula and the fovea, causing loss of detail vision. Type 2 affects both eyes but not necessarily with the same severity. Type 1 macular telangiectasia: In Type 1 macular telangiectasia, the blood vessels become dilated forming tiny aneurysms, causing swelling and damaging macular cells. The disease almost always occurs in one eye, which differentiates it from Type 2. These disorders can also be treated with a modulator, e.g. a gap junction and/or connexin modulator, or pannexin or pannexin channel modulator, as described herein.

Pattern Dystrophy (PD)

PD affects the macula and can be mistaken for nonexudative AMD. The most common types of PD seen are adult vitelliform macular dystrophy (AVMD) and less commonly butterfly shaped pattern dystrophy. PD is a condition that has a genetic basis; although a family history is often not present. PD is usually associated with a better visual outcome than AMD, unless complicated by choroidal neovascularisation or atrophic changes. Differentiating AVMD in particular from AMD can be difficult. Symptoms may be similar particularly if CNV or atrophy complicates PD, but often AVMD is identified in an asymptomatic individual at a routine fundoscopic review. Fundus autofluorecence imaging especially when combined with optical coherence tomography is helpful in distinguishing PD from AMD. Fluorescein angiography can show a typical 'corona sign' in AVMD, and the branching lines seen in butterfly shaped PD are associated with a hyperfluorescence distributed in the area of the deposits, which does not show leakage throughout the phases of the angiogram. Occasionally, fluorescein angiographic staining of the vitelliform lesion can be mistaken for active leakage from CNV. This disorder can be treated with a modulator, e.g. a gap junction and/or connexin modulator, or pannexin or pannexin channel modulator, as described herein.

Subretinal/subPRD Neovascularization

Subretinal neovascularization is a pathological process consisting of the formation of new blood vessels in the choroid. In the wet form of AMD, abnormal blood vessels grow under the macula and leak fluid and blood. The abnormal vessels, called subretinal neovascularization, may also lift up the retina. This disorder can be treated with a modulator, e.g. a gap junction and/or connexin modulator, or pannexin or pannexin channel modulator, as described herein.

Serous Detachment of the Neurosensory Retina

Retinal detachment occurs when subretinal fluid accumulates between the neurosensory retina and the retinal pigment epithelium. This process can occur in three ways. One mechanism involves a break in the retina allowing vitreous to directly enter the subretinal space. This is known as a rhegmatogenous retinal detachment. A second mechanism involves proliferative membranes on the surface of the retina or vitreous. These membranes can pull on the neurosensory retina causing a physical separation between the neurosensory retina and retinal pigment epithelium. This is called a traction retinal detachment. The third mechanism for retinal detachment is due to accumulation of subretinal fluid due to inflammatory mediators or exudation of fluid from a mass lesion. This mechanism is known as a serous or exudative retinal detachment. Serous detachments are caused by a number of inflammatory, or exudative retinal disease processes such as Sarcoidosis or choroidal neoplasms. In some aspects, a modulator described herein is used to control inflammation in the underlying choriocapillaris, controls buildup of subretinal fluid, and/or prevents an accumulation of subretinal fluid, which can lead, for example, to serous detachment of the neurosensory retina.

RPE Detachment

RPE detachment is a non-specific anatomical alteration that may result from any number of choroidal disorders that disrupt the normal junction between the basement membrane of the RPE and the inner collagenous layer of Bruch's membrane. This disruption permits serous fluid from the underlying choriocapillaris to gain access into the sub-RPE space. Age-related macular degeneration, choroidal neovascular membranes, high myopia, angioid streaks, hereditary choroidal degeneration, POHS, and tumors of the choroid have all been identified as precipitating conditions in the development of RPE detachment. This disorder can be treated with a modulator, e.g. a gap junction and/or connexin modulator, or pannexin or pannexin channel modulator, as described herein.

Hemorrhages—Subretinal Pigment Epithelial, Subretinal, Intraretinal or Pre-Retinal, Including Breakthrough Bleeding into the Vitreous Retinal hemorrhage is a disorder of the eye in which bleeding occurs into the retensitive tissue on the back wall of the eye. A retinal hemorrhage can be caused by hypertension, retinal vein occlusion (a blockage of a retinal vein), or diabetes mellitus (which causes small fragile blood vessels to form, which are easily damaged). Retinal hemorrhages, especially mild ones not associated with chronic disease, will normally resorb without treatment. Laser surgery is a treatment option which uses a laser beam to seal off damaged blood vessels in the retina. This disorder can be treated with a modulator, e.g. a gap junction and/or connexin modulator, or pannexin or pannexin channel modulator, as described herein.

Piretinal, Intraretinal, Subretinal or Sub-Pigment Epithelial Scar/Glial Tissue or Fibrin-Like Deposits In some aspects, the connexin modulator can prevent scarring, inflammation, and the creation of fibrin formation. Thus, the connexin modulator can prevent piretinal, intraretinal, subretinal or sub-pigment epithelial scar/glial tissue or fibrin-like deposits. This disorder can be treated with a modulator, e.g. a gap junction and/or connexin modulator, or pannexin or pannexin channel modulator, as described herein.

Retinal Angiomatous Proliferations and Retinochoroidal Anatastamosis

The retinochoroidal anastomosis represents a communication between the retinal and choroidal circulation and is described in a subset of patients with neovascular age-related macular degeneration (AMD). Retinal Angiomatous Proliferations are evidenced by the presence of anastomoses between the retinal and choroidal circulations in eyes with disciform scars. This disorder can be treated with a modulator, e.g. a gap junction and/or connexin modulator, or pannexin or pannexin channel modulator, as described herein.

Choroidal Neovascularization (CNV)

Choroidal neovascularization (CNV) is the creation of new blood vessels in the choroid layer of the eye. This is a common sign of the degenerative maculopathy wet AMD (age-related macular degeneration). CNV can occur rapidly in individuals with defects in Bruch's membrane, the innermost layer of the choroid. It is also associated with excessive amounts of vascular endothelial growth factor (VEGF). As in wet AMD, CNV can also occur frequently with the rare genetic disease pseudoxanthoma elasticum and rarely with the more common optic disc drusen. CNV has also been associated with extreme myopia or malignant myopic degeneration, where in choroidal neovascularization occurs primarily in the presence of cracks within the retinal (specifically) macular tissue known as lacquer cracks. This disorder can be treated with a modulator, e.g. a gap junction and/or connexin modulator, or pannexin or pannexin channel modulator, as described herein.

Cystic Maculopathy

Cystic maculopathy is a cyst in or around the macula, and can be treated with a modulator, e.g. a gap junction and/or connexin modulator, or pannexin or pannexin channel modulator, as described herein.

Retinal Thickening

Macular thickening (edema) is swelling or thickening of the part of the retina that is responsible for central vision. In some aspects, a modulator described herein can control the chorioicapillaris breakdown, thereby preventing the thickening of the retina. Thus, the modulator can treat retinal thickening. Retinal thickening can be treated with a modulator, e.g. a gap junction and/or connexin modulator, or pannexin or pannexin channel modulator, as described herein.

Nonexudative AMD

Nonexudative AMD ("dry AMD") results from a gradual breakdown of the retinal pigment epithelium (RPE), the accumulation of drusen deposits, and loss of function of the overlying photoreceptors. In some aspects, as described above, the modulator, e.g., a gap junction or connexin modulator, alone or together with a pannexin or pannexin channel modulator, as described herein can treat nonexudative AMD.

Retinal Scarring

Retinal scarring is the development of scar tissue on, in, or under the retina, an important structure in the back of the eye. Mild scarring may not be a serious medical issue, but large scars can cause vision distortion and eventual vision loss. A care provider can evaluate a patient with retinal scarring to determine the extent and provide advice on treatment options. Treatments for this condition can be invasive, and a doctor does not want to recommend a procedure that may cause more harm than good. Patients can develop retinal scarring for a number of reasons, including very severe myopia, ocular histoplasmosis syndrome, and wet age-related macular degeneration. It starts with irritation to the retina that causes inflammation and leads to changes in the tissue. If this occurs repeatedly, it can start to cause significant problems for the patient. It may wrinkle the surface of the retina or could cause the retina to swell. Sometimes, retinal scarring causes a retinal detachment. In some aspects, the modulator, for example, a gap junction and/or connexin modulator and/or pannexin or pannexin channel modulator can control or inhibit retinal scarring and retinal inflammation, which controls the tissue changes, thereby preventing or ameliorating retinal scarring.

Ocular Hypoxia

Ocular hypoxia, including retinal hypoxia, is the potentially blinding mechanism underlying a number of sight-threatening disorders including some types of glaucoma, central retinal artery occlusion, ischemic central retinal vein thrombosis, complications of diabetic eye disease (e.g., DME), AMD, and fibrosis of the eye. Hypoxia is implicated in loss of retinal ganglion cells (RGCs) occurring in such conditions. RGC death occurs by apoptosis or necrosis. Hypoxia-ischemia induces the expression of hypoxia inducible factor-1$\alpha$ and its target genes such as vascular endothelial growth factor (VEGF) and nitric oxide synthase (NOS). Increased production of VEGF results in disruption of the blood retinal barrier leading to retinal edema. Enhanced expression of NOS results in increased production of nitric oxide which may be toxic to the cells resulting in their death. Excess glutamate release in hypoxic-ischemic conditions causes excitotoxic damage to the RGCs through activation of ionotropic and metabotropic glutamate receptors. Activation of glutamate receptors is thought to initiate damage in the retina by a cascade of biochemical effects such as neuronal NOS activation and increase in intracellular $Ca^{2+}$ is a major contributing factor to RGC loss. In the posterior segment of the eye, diabetes-associated retinal hypoxia can lead to fibrosis and traction retinal detachment, a complication of advanced diabetic retinopathy (DR). Under the retina, similar fibrosis can occur subsequent to subretinal hemorrhage associated with neovascular age-related macular degeneration (AMD). A therapeutically effective amount of the modulator, e.g., connexin modulator, such as a connexin 43 modulator, is any amount effective to slow, stop or reverse ocular neuropathy, or to treat any of the ocular disorders described herein.

A gap junction and/or connexin polynucleotide or oligonucleotide may be selected, for example, from modified or unmodified connexin polynucleotides or oligonucleotides, such as modified or unmodified connexin 43 antisense polynucleotides or oligonucleotides. In some embodiments, the modified modified connexin antisense polynucleotides, or oligonucleotides or polynucleotides comprise mixtures of modified and unmodified nucleotides. In some aspects, the connexin 43 antisense compound used in the methods herein is an antisense oligonucleotide comprising naturally occurring nucleobases and an unmodified internucleoside linkage.

In some aspects, gap junction, connexin and/or pannexin modulators are antagonists that inhibit and/or block gap junction, connexin and/or pannexin or that inhibit and/or block upstream agonists of gap junction, connexin and/or pannexin. In some aspects the gap junction, connexin and/or pannexin antagonists include, for example, antagonists that bind to and inhibit gap junction, connexin and/or pannexin, compounds that inhibit expression of gap junction, connexin and/or pannexin, and/or viral vectors comprising gap junction, connexin and/or pannexin inhibitors or encoding proteins or antisense polynucleotides that block or inhibit gap junctions, connexin and/or pannexin. In some aspects, species that inhibit gap junctions, connexin and/or pannexin and/or upstream agonists of gap junction, connexin and/or pannexin can be antibodies or antibody fragments, nanobodies, peptide or peptidomimetics, receptor fragments, recombinant fusion proteins, aptamers, small molecules, or single chain variable fragments (scFv).

The methods herein provide for treatment of intraocular pressure-associated optic neuropathy such as glaucoma, in an amount sufficient to reduce intraocular pressure. In some aspects, the pannexin modulators and connexin modulators are useful in treating trauma associated with elevated intraocular pressure. In some aspects, the compositions, articles of manufacture and methods of this invention are useful in reducing the intraocular pressure to normal levels, e.g., below 21 mm Hg, for example, below 21, 20, or 19 mm Hg. In some aspects, for example, the connexin modulators and pannexin modulators and methods of this invention are useful in reducing the intraocular pressure to between, for example, about 8 to about 21 mm Hg, to between about 10 and about 22 mm Hg, between about 10 and 21 mm Hg, or between about 12 to about 21 mm Hg. In some aspects the compositions and methods of this invention are also useful in treating glaucomatous optic neuropathy even in the absence of high intraocular pressure. In some embodiments, the connexin modulator is, for example, a connexin 43 modulator or a connexin 45 modulator, preferably a connexin 43 modulator. In some aspects the connexin modulator is a modulator of Cx26, Cx30, Cx31.1, Cx36, Cx37, Cx40, Cx50, Cx57 or any other connexin in the eye or blood vessels. In some aspects, the connexin modulator can include or exclude any of the foregoing.

Featured in this invention are connexin or pannexin antisense oligonucleotides or polynucleotides comprising at least one unmodified nucleotide. In one aspect, the connexin antisense oligonucleotides or polynucleotides may comprise at least one modified nucleotide, and/or have at least one modified internucleoside linkage, and/or at least one modified sugar moiety. The modified internucleoside linkage may be, for example, a phosphorothioate linkage. In some aspects, for example, the connexin 43 polynucleotide may comprise at least one nucleotide comprising a conformationally strained nucleotide, for example, a locked nucleic acid (LNA) or a bridged nucleic acid (BNA). The locked nucleotide may be selected, from one of the following types, for example: 2'-O—CH2-4' (oxy-LNA), 2'-CH2-CH2-4' (methylene-LNA), 2'-NH—CH2-4' (amino-LNA), 2'-N (CH3)-CH2-4' (methylamino-LNA), 2'-S—CH2-4' (thio-LNA), and 2'-Se—CH2-4' (seleno-LNA). In some aspects the modified nucleotide may be a locked nucleic acid or an unlocked nucleic acid. In some embodiments, the connexin antisense oligonucleotides or polynucleotides, are, for example, connexin 43 antisense oligonucleotides or polynucleotides or connexin 45 antisense oligonucleotides or polynucleotides, preferably a connexin 43 antisense oligonucleotides or polynucleotides. In some embodiments the connexin antisense oligonucleotides or polynucleotides, are, for example, modulators of Cx26, Cx31.1, Cx36, Cx37, Cx40, Cx50, Cx57 or any other connexin in the eye or blood vessels.

Also featured herein are exemplary modified or unmodified connexin 43 antisense compounds comprising a nucleotide sequence or modified from a nucleotide sequence selected from SEQ ID NO:1-16 and or which can be included or excluded from the methods, compositions, kits and articles of manufacture of this disclosure. The polynucleotides of this invention include synthesized polynucleotides having a length of less than 80 nucleotides, e.g., from 12-18 to about 50-80 nucleotides, preferably about 30 nucleotides or less, e.g., from 12 to about 30 nucleotides, and more preferably from about 15 to about 30 nucleotides. In one example, the polynucleotide has 30 nucleotides. The methods of this invention features, in some aspects, the use of connexin 43 antisense compounds up to 40 nucleotides in length, for example, 15 to 40 nucleotides in length, comprising a nucleotide sequence selected from SEQ ID NO:1-17, or comprising from about 8 to 40 nucleotides of SEQ ID NO: 17.

TABLE 1

List of exemplary connexin 43 antisense oligonucleotides

| ASN code name | SEQ ID NO. for ASN sequence | ASN sequence | ASN target site from 5' end |
|---|---|---|---|
| | SEQ ID NO: 1 | GTAATTGCGGCAAGA AGAATTGTTTCTGTC | |
| | SEQ ID NO: 2 | GTAATTGCGGCAGGA GGAATTGTTTCTGTC | |
| | SEQ ID NO: 3 | GGCAAGAGACACCAA AGACACTACCAGCAT | |
| 24501 | SEQ ID NO: 5 | ACCCATGTTGCCTGG GCACC | 237-256 |
| 30004 | SEQ ID NO: 6 | GTAGGCTTGAACCTT GTCAA | 281-300 |
| 37503 | SEQ ID NO: 7 | TCTCCCCAGGCTGAC TCAAC | 372-389 |

TABLE 1-continued

List of exemplary connexin 43 antisense oligonucleotides

| ASN code name | SEQ ID NO. for ASN sequence | ASN sequence | ASN target site from 5' end |
|---|---|---|---|
| LP2/ 37501 | SEQ ID NO: 4 | CCAGGCTGACTCAAC CGCTG | 368-385 |
| 47001 | SEQ ID NO: 8 | CAGAAGCGCACATGA GAGAT | 464-483 |
| 47002 | SEQ ID NO: 9 | GAAGCGCACATGAGA GATTG | 462-481 |
| 50501 | SEQ ID NO: 10 | AGTGTGGGTACAGAC ACAAA | 500-519 |
| LP3 | SEQ ID NO: 11 | CAGACACAAATATGA TTCGC | 490-509 |
| 50506 | SEQ ID NO: 12 | ATATGATCTGCAGGA CCCAG | 481-500 |
| 112304 | SEQ ID NO: 13 | GTAATTGCGGCAAGA AAGAT | 1134-1153 |
| 1233 | SEQ ID NO: 14 | AGGCTGTGCATGGGA GTTAG | 1233-1252 |
| 133704 | SEQ ID NO: 15 | CGCTGGTCCACAATG GCTAG | 1316-1335 |
| 133705 | SEQ ID NO: 16 | GCTGGCTCTGCTTGA AGGTC | 1335-1354 |

Table 1 lists the polynucleotide sequences of exemplary connexin 43 polynucleotide modulators. When sequences such as SEQ ID NO:1-16 are provided, they represent both modified and unmodified oligonucleotides or polynucleotides. In some embodiments, the linkages between the nucleotides, and the structure of the sugar moiety of the nucleotides may be modified. In some embodiments, the internucleoside linkage between any two nucleotides can be a standard phosphodiester linkage. In some embodiments, the internucleoside linkage between any two nucleotides can be a phosphorothioate linkage. For example, SEQ ID NO:1 can be one of the following selected structures: $G_sT_sA_sA_s$-TTGCGGCAAGAAGAATTGTTTC$_s$T$_s$G$_s$T$_s$C, wherein "$_s$" denotes a phosphorothioate linkage between the two nucleotides. As another non-limiting example, SEQ ID NO:1 can be (G)(T)(A)(A)TTGCGGCAAGAAGAATTGTTTC(T)(G)(T)(C), wherein the parenthetical nucleotides have modified sugar moieties, as described below.

Exemplary sequences are show in Table 2, which are useful in the treatment of ocular diseases, disorders and conditions characterized by unwanted ZO-1 protein or ZO-1 protein activity or that would benefit from reduced ZO-1 protein or ZO-1 protein activity.

TABLE 2

List of exemplary ZO-1 AS ODNs.

| ASN Name | Sequence | SEQ ID NO: |
|---|---|---|
| siRNA p53 | 5'-AAAACUCAUGUUCA AGACAGAAGGGU-3' | SEQ ID NO: 228 |
| siRNA p53_revcompl | 3'-UUUUGAGUACAAGU UCUGUCUUCCCA-5' | SEQ ID NO: 229 |

TABLE 2-continued

List of exemplary ZO-1 AS ODNs.

| ASN Name | Sequence | SEQ ID NO: |
|---|---|---|
| siRNA ZO-1 1681 | 5'-CCAUCUGAUGGUGU CCUACCUAAUU-3' | SEQ ID NO: 230 |
| siRNA ZO-1 1681_ revcompl | 3'-GGUAGACUACCACA GGAUGGAUUAA-5' | SEQ ID NO: 231 |
| siRNA ZO-1 2137 | 5'-GGGCUCUUGGCUUG CUAUUCGAAUU-3' | SEQ ID NO: 232 |
| siRNA ZO-1 2137_ revcompl | 3'-CCCGAGAACCGAAC GAUAAGCUUAA-5' | SEQ ID NO: 238 |
| siRNA ZO-1 5518 | 5'-CCUUCCACCUUUAG AUAAAGAGAAA-3' | SEQ ID NO: 239 |
| siRNA ZO-1 5518_ revcompl | 3'-GGAAGGUGGAAAUC UAUUUCUCUUU-5' | SEQ ID NO: 240 |

Table 2 lists the polynucleotide sequences of ZO-1 AS ODNs (antisense oligodeoxtribonucleotides), shRNAs (small hairpin RNA molecules), and siRNAs (small interfering RNA molecules).

ZO-1 was originally been identified at tight junctions, which form a network inside cells. This structure is only present at the intersection between two cells at the cell-cell contact zone. ZO-1 is a 220-kDa membrane protein, which co-localizes with the transmembrane proteins claudins and occludin. Later, ZO-1 was demonstrated and identified at adherens junctions that zip cells together and thereby maintain cell and tissue polarity. These junctions also anchor the cytoskeleton, allowing the formation of large complexes at the plasma membrane.

One sequence selected for synthesis of antisense polynucleotides that target ZO-1, 5'-CTGCTTTCTGTT-GAGAGGCT-3' (SEQ ID NO:236), corresponds to the segment from base pair 3154-3169 in MUSZO1 accession number D14340I.

In some aspects, the connexin 43 antisense compound is targeted to at least about 8 nucleobases of a nucleic acid molecule encoding a connexin having a nucleobase sequence selected from SEQ ID NO: 17. The polynucleotides and oligonucleotides, for example, connexin 43 antisense compounds, may have from about 8 to about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, or about 80 nucleotides of SEQ ID NO:17, or a sequence complementary thereto, and/or the antisense polynucleotide or oligonucleotide may contain any range of lengths between any two of the recited lengths. The polynucleotides of this invention include synthesized polynucleotides having a length of less than 80 nucleotides, e.g., from 12-18 to about 50-80 nucleotides, preferably about 30 nucleotides or less, e.g., from 12 to about 30 nucleotides, and more preferably from about 15 to about 30 nucleotides. In one example, the polynucleotide has 30 nucleotides. The methods of this invention features, in some aspects, the use of connexin 43 antisense compounds up to 40 nucleotides in length, for example, 15 to 40 nucleotides in length, comprising a nucleotide sequence selected from SEQ ID NO:1-17. The methods of this invention features, in some aspects, the use of connexin 43 antisense compounds up to 40 nucleotides in length, for example, 15 to 40 nucleotides in length, comprising a nucleotide sequence selected from SEQ ID NO:4-17.

```
Human Cx 43, □ 1
LOCUS NM_000165 3088 bp mRNA linear PRI 26 Oct. 2004
DEFINITION Homo sapiens gap junction protein, alpha 1, 43kDa (connexin
43) (GJA1), mRNA.
                                                        (SEQ ID NO: 17)
   1  acaaaaaagc ttttacgagg tatcagcact tttctttcat tagggggaag gcgtgaggaa

  61  agtaccaaac agcagcggag ttttaaactt taaatagaca ggtctgagtg cctgaacttg

 121  ccttttcatt ttacttcatc ctccaaggag ttcaatcact tggcgtgact tcactacttt

 181  taagcaaaag agtggtgccc aggcaacatg ggtgactgga gcgccttagg caaactcctt

 241  gacaaggttc aagcctactc aactgctgga gggaaggtgt ggctgtcagt acttttcatt

 301  ttccgaatcc tgctgctggg gacagcggtt gagtcagcct ggggagatga gcagtctgcc

 361  tttcgttgta acactcagca acctggttgt gaaaatgtct gctatgacaa gtctttccca

 421  atctctcatg tgcgcttctg ggtcctgcag atcatatttg tgtctgtacc cacactcttg

 481  tacctggctc atgtgttcta tgtgatgcga aaggaagaga aactgaacaa gaaagaggaa

 541  gaactcaagg ttgcccaaac tgatggtgtc aatgtggaca tgcacttgaa gcagattgag

 601  ataaagaagt tcaagtacgg tattgaagag catggtaagg tgaaaatgcg aggggggttg

 661  ctgcgaacct acatcatcag tatcctcttc aagtctatct ttgaggtggc cttcttgctg

 721  atccagtggt acatctatgg attcagcttg agtgctgttt acacttgcaa aagagatccc

 781  tgcccacatc aggtggactg tttcctctct cgccccacgg agaaaaccat cttcatcatc

 841  ttcatgctgg tggtgtcctt ggtgtccctg gccttgaata tcattgaact cttctatgtt

 901  ttcttcaagg gcgttaagga tcgggttaag ggaaagagcg acccttacca tgcgaccagt

 961  ggtgcgctga gccctgccaa agactgtggg tctcaaaaat atgcttattt caatggctgc
```

-continued

```
1021  tcctcaccaa ccgctcccct ctcgcctatg tctcctcctg ggtacaagct ggttactggc
1081  gacagaaaca attcttcttg ccgcaattac aacaagcaag caagtgagca aaactgggct
1141  aattacagtg cagaacaaaa tcgaatgggg caggcgggaa gcaccatctc taactcccat
1201  gcacagcctt ttgatttccc cgatgataac cagaattcta aaaaactagc tgctggacat
1261  gaattacagc cactagccat tgtggaccag cgaccttcaa gcagagccag cagtcgtgcc
1321  agcagcagac ctcggcctga tgacctggag atctagatac aggcttgaaa gcatcaagat
1381  tccactcaat tgtggagaag aaaaaaggtg ctgtagaaag tgcaccaggt gttaattttg
1441  atccggtgga ggtggtactc aacagcctta ttcatgaggc ttagaaaaca caaagacatt
1501  agaataccta ggttcactgg gggtgtatgg ggtagatggg tggagaggga ggggataaga
1561  gaggtgcatg ttggtattta aagtagtgga ttcaaagaac ttagattata aataagagtt
1621  ccattaggtg atacatagat aagggctttt tctccccgca aacaccccta agaatggttc
1681  tgtgtatgtg aatgagcggg tggtaattgt ggctaaatat ttttgtttta ccaagaaact
1741  gaaataattc tggccaggaa taaatacttc ctgaacatct taggtctttt caacaagaaa
1801  aagacagagg attgtcctta agtccctgct aaaacattcc attgttaaaa tttgcacttt
1861  gaaggtaagc tttctaggcc tgaccctcca ggtgtcaatg gacttgtgct actatatttt
1921  tttattcttg gtatcagttt aaaattcaga caaggcccac agaataagat tttccatgca
1981  tttgcaaata cgtatattct ttttccatcc acttgcacaa tatcattacc atcacttttt
2041  catcattcct cagctactac tcacattcat ttaatggttt ctgtaaacat ttttaagaca
2101  gttgggatgt cacttaacat tttttttttt tgagctaaag tcagggaatc aagccatgct
2161  taatatttaa caatcactta tatgtgtgtc gaagagtttg ttttgtttgt catgtattgg
2221  tacaagcaga tacagtataa actcacaaac acagatttga aaataatgca catatggtgt
2281  tcaaatttga acctttctca tggattttttg tggtgtgggc caatatggtg tttacattat
2341  ataattcctg ctgtggcaag taaagcacac tttttttttc tcctaaaatg tttttccctg
2401  tgtatcctat tatggatact ggttttgtta attatgattc tttattttct ctcctttttt
2461  taggatatag cagtaatgct attactgaaa tgaatttcct ttttctgaaa tgtaatcatt
2521  gatgcttgaa tgatagaatt ttagtactgt aaacaggctt tagtcattaa tgtgagagac
2581  ttagaaaaaa tgcttagagt ggactattaa atgtgcctaa atgaattttg cagtaactgg
2641  tattcttggg ttttcctact taatacacag taattcagaa cttgtattct attatgagtt
2701  tagcagtctt ttggagtgac cagcaacttt gatgtttgca ctaagatttt atttggaatg
2761  caagagaggt tgaaagagga ttcagtagta cacatacaac taatttattt gaactatatg
2821  ttgaagacat ctaccagttt ctccaaatgc ctttttttaaa actcatcaca gaagattggt
2881  gaaaatgctg agtatgacac ttttcttctt gcatgcatgt cagctacata aacagttttg
2941  tacaatgaaa attactaatt tgtttgacat tccatgttaa actacggtca tgttcagctt
3001  cattgcatgt aatgtagacc tagtccatca gatcatgtgt tctggagagt gttctttatt
3061  caataaagtt ttaatttagt ataaacat
//
```

In some embodiments, the sugar moiety can be a modified sugar moiety. In some embodiments, the modified sugar moiety can be a sugar moiety which is a conformationally-strained sugar. In some embodiments, the conformationally-strained sugar can be a locked nucleotide (locked nucleic acid, or LNA). In some embodiments, the locked nucleotide can be selected from one of the following types: 2'-O—$CH_2$-4' (oxy-LNA), 2'-$CH_2$—$CH_2$-4' (methylene-LNA), 2'-NH—$CH_2$-4' (amino-LNA), 2'-N($CH_3$)— $CH_2$-4' (methylamino-LNA), 2'-S—$CH_2$-4' (thio-LNA), and 2'-Se—$CH_2$-4' (seleno-LNA). In some embodiments, the conformationally-strained sugar can be a bridged nucleic acid. (BNA).

As shown in Formula III, the conformationally-strained sugar can be a locked nucleic acid. In some aspects, the sugar moiety of the nucleoside compounds can be a ribofuranose. Accordingly, a particularly suitable substituent X is oxygen. However, other various alternative sugar moieties are also appropriate, and it is generally contemplated that modified sugars and carbocyclic moieties are also considered suitable for use herein. Accordingly, X may also include an atom or group other than oxygen, and especially contemplated alternative groups X include S where the sugar is a sulfur sugar, $CH_2$, C═O, C═$CH_2$ or a covalent bond where the sugar is a carbocyclic compound, and NR (with R selected from the group consisting of hydrogen, alkyl, alkenyl, alkynyl, aryl, and acyl) where the sugar is an amino sugar. The groups Y and Z may also vary. In some aspects, substituents Y and Z can be selected from the group consisting of: O, S, $CH_2$, NR, C═O, C═$CH_2$ or a covalent bond, wherein R is selected from the group consisting of hydrogen, alkyl, alkenyl, alkynyl, aryl, and acyl. In some embodiments, Q may be selected from none, O, S, NHR, or $CH_2$, wherein R is selected from the group consisting of hydrogen, alkyl, alkenyl, alkynyl, aryl, and acyl.

Formula III

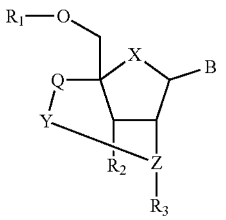

In some embodiments, B can be a base selected from one of the following types of bases: substituted and unsubstituted deazapurines, azapurines, deazapyrimidines, purines, pyrimidines, and azapyrimidines. The term "substituted" as used herein refers to addition of one or more functional groups, wherein particularly contemplated functional groups include nucleophilic (eg.: —$NH_2$, —OH, —SH, and —NC) and electrophilic groups (eg.: C(O)OR, and C(X)OH), polar groups, non-polar groups (eg.: aryl, alkyl, alkenyl, or alkynyl), ionic groups (eg.: —$NH_3^+$), and halogens (—F, —Cl, —I, —Br), and all chemically reasonable combinations thereof. In some aspects, B is selected from one of the following: Adenosine, Thymine, Uracil, Guanine, and Cytosine.

The groups $R_1$, $R_2$, and $R_3$ may be selected from the group consisting of none, —H, —OH, —$OCH_3$, alkyl, and especially methyl, —O-acyl, —$N_3$, —CN, and halogen. Furthermore, where contemplated nucleoside analogs include a phosphate, phosphonate group, or phosphorothioate group, it is contemplated that especially suitable $R_1$ and/or $R_2$ groups include a monophosphate, diphosphate, triphosphate, monophosphonate, diphosphonate, triphosphonate, phosphorothioate, an amino acid ester with a sugar OH group, or a pro-drug of the monophosphate, diphosphate, triphosphate, monophosphonate, diphosphonate, triphosphonate, or phosphorothioate.

As shown in Formula IV, the structure of the locked nucleic acid can further comprise Z as Oxygen ("O"), Y is $CH_2$, Q is none, and $R_3$ is none. The groups B, $R_1$, and $R_2$ can be selected from the groups as described above.

For any of the Markush groups set forth above, in some embodiments, each group can include or exclude any of the species listed for that group.

Formula IV

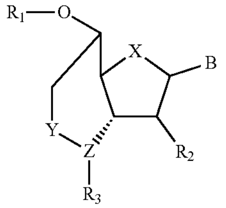

As shown in Formula V, the structure of the conformationally-strained nucleotide can be a bridged nucleic acid (BNA). The groups X, Y, Z, $R_1$, $R_2$, $R_3$, and B can be selected from the groups as described above.

Formula V

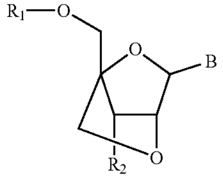

In some embodiments, the connexin 43 modulators can comprise peptides. The peptide sequence can comprise, for example, one or more of the following sequences: SRPTEKT "Mod 3", (SEQ ID NO:173), "Peptide 1" ADCFLSRPTEKT (SEQ ID NO: 125), "Peptide 2" VACFLSRPTEKT (SEQ ID NO: 126), "Peptide 11" VDCFLSRPTAKT (SEQ ID NO: 127), "Peptide 12" VDCFLSRPTEAT (SEQ ID NO: 128), "Peptide 5" VDCFLSRPTEKT (SEQ ID NO: 168), "Mod 1" CFLSRPTEKT (SEQ ID NO: 171), "Mod 2" LSRPTEKT (SEQ ID NO: 172). In some embodiments, the Carboxy-terminus can be modified. In some aspects, the carboxy-terminus modification can comprise n-alkyl chains which can optionally be further linked to hydrogen or other moieties. In some embodiments, the connexin 43 peptides can include or exclude any of the peptides listed above or disclosed herein.

In some aspects of this invention, the connexin 43 antisense oligonucleotide or polynucleotide has at least about 80%, 85%, 90%, 95%, 97%, 98%, or 99% homology to a polynucleotide having a sequence selected from SEQ ID NOs: 1 to 17 and 19.

Also featured herein are modified or unmodified connexin 45 antisense polynucleotides comprising from 8 to about 80 nucleotides of SEQ. ID. NO:217 and modified and unmodified pannexin antisense polynucleotides comprising from 8 to about 80 nucleotides of SEQ. ID. NO: 113. The polynucleotides of this invention include synthesized polynucleotides having a length of less than 80 nucleotides, e.g., from 12-18 to about 50-80 nucleotides, preferably about 30 nucleotides or less, e.g., from 12 to about 30 nucleotides, and more preferably from about 15 to about 30 nucleotides. In one example, the polynucleotide has 30 nucleotides. The methods of this invention features, in some aspects, the use of connexin 45 antisense compounds up to 40 nucleotides in length, for example, 15 to 40 nucleotides in length, for example, comprising from about 8 to about 40 or from about 15 to about 40 nucleotides of SEQ ID NO:217. The methods of this invention features, in some aspects, the use of pannexin antisense compounds up to 40 nucleotides in length, for example, 15 to 40 nucleotides in length, for example, comprising from about 8 to about 40 or from about 15 to about 40 nucleotides of SEQ ID NO: 117-121. In some embodiments the connexin 45 or pannexin antisense compounds may be modified by substituting one or more uridine nucleotides residues for one or more thymine nucleotides in SEQ ID NO:217, or SEQ ID NO: 117-121.

In some aspects, the pannexin modulators can include or exclude pannexin peptide sequences. The pannexin peptide sequences can comprise 8-40 consecutive amino acids, an extracellular domain, an intracellular domain, a carboxy terminus part, or an amino terminus part, of the polypeptides

```
Human Cx45, α7
LOCUS NM_005497 1191 bp mRNA linear PRI 23 Dec. 2003
DEFINITION Homo sapiens gap junction protein, alpha 7, 45kDa (connexin
45) (GJA7), mRNA.
                                                        (SEQ ID NO: 217)
   1  atgagttgga gctttctgac tcgcctgcta gaggagattc acaaccattc cacatttgtg

  61  gggaagatct ggctcactgt tctgattgtc ttccggatcg tccttacagc tgtaggagga

 121  gaatccatct attacgatga gcaaagcaaa tttgtgtgca acacagaaca gccgggctgt

 181  gagaatgtct gttatgatgc gtttgcacct ctctcccatg tacgcttctg ggtgttccag

 241  atcatcctgg tggcaactcc ctctgtgatg tacctgggct atgctatcca caagattgcc

 301  aaaatggagc acggtgaagc agacaagaag gcagctcgga gcaagcccta tgcaatgcgc

 361  tggaaacaac accgggctct ggaagaaacg gaggaggaca acgaagagga tcctatgatg

 421  tatccagaga tggagttaga aagtgataag gaaaataaag agcagagcca acccaaacct

 481  aagcatgatg gccgacgacg gattcgggaa gatgggctca tgaaaatcta tgtgctgcag

 541  ttgctggcaa ggaccgtgtt tgaggtgggt tttctgatag ggcagtattt tctgtatggc

 601  ttccaagtcc acccgtttta tgtgtgcagc agacttcctt gtcctcataa gatagactgc

 661  tttatttcta gacccactga aaagaccatc ttccttctga taatgtatgg tgttacaggc

 721  ctttgcctct tgcttaacat ttgggagatg cttcatttag ggtttgggac cattcgagac

 781  tcactaaaca gtaaaaggag ggaacttgag gatccgggtg cttataatta tcctttcact

 841  tggaatacac catctgctcc ccctggctat aacattgctg tcaaaccaga tcaaatccag

 901  tacaccgaac tgtccaatgc taagatcgcc tacaagcaaa acaaggccaa cacagcccag

 961  gaacagcagt atggcagcca tgaggagaac ctcccagctg acctggaggc tctgcagcgg

1021  gagatcagga tggctcagga acgcttggat ctggcagttc aggcctacag tcaccaaaac

1081  aaccctcatg gtccccggga gaagaaggcc aaagtggggt ccaaagctgg gtccaacaaa

1141  agcactgcca gtagcaaatc aggggatggg aagaactctg tctggattta a
//
```

In some aspects of this invention, the connexin 43 antisense oligonucleotide or polynucleotide has at least about 80%, 85%, 90%, 95%, 97%, 98%, or 99% homology to a polynucleotide having a sequence selected from SEQ ID NOs: 1 to 17. Connexin or pannexin modulators that are oligonucleotides or polynucleotides may have at least about 80%, 85%, 90%, 95%, 97%, 98%, or 99% homology to an 8 to 80 nucleotoide portion of their respective sequences. For example, connexin 45 modulators that are oligonucleotides or polynucleotides may have at least about 80%, 85%, 90%, 95%, 97%, 98%, or 99% homology to an 8 to 80 nucleotide portion of SEQ ID NO:217, while pannexin modulators that are oligonucleotides or polynucleotides may have at least about 80%, 85%, 90%, 95%, 97%, 98%, or 99% homology to an 8 to 80 nucleotide portion of SEQ ID NO: 117 (Panx1 polynucleotide), (Panx1 polynucleotide RefSeq ID NM_015368.3), SEQ ID NO:118 (Panx2 polynucleotide), (Panx2 polynucleotide RefSeq ID NM_052839.3 for variant 1), SEQ IDNO:119 (RefSeq ID NM_001160300.1 for Panx2 polynucleotide variant 2), SEQ ID NO: 120 (RefSeq ID NR_027691.1 for Panx2 polynucleotide variant 3), or SEQ ID NO: 121 (Panx3 polynucleotide) (Panx3 polynucleotide RefSeq ID NM_052959.2).

SEQ ID NO: 122, Panx1 peptide), SEQ ID NO: 123, Panx2 peptide), or SEQ ID NO: 124, Panx3 peptide).

In other embodiments, the connexin modulators are connexin peptides or peptidomimetics, sometimes referred to anti-connexin peptides or peptdomimetics, e.g., anti-connexin hemichannel blocking peptides or peptidomimetics, for example, modified or unmodified peptides or peptidomimentics comprising connexin extracellular domains, transmembrane regions, and connexin carboxy-terminal peptides). The anti-connexin hemichannel blocking peptides or peptidomimetics may be modified or unmodified. The anti-connexin hemichannel blocking peptides or peptidomimetics are made chemically, synthetically, or otherwise manufactured. In some embodiments, the connexin modulators are connexin 43 peptides or peptidomimetics. In some aspects, the therapeutically effective modified or unmodified peptide or peptidomimetic comprises a portion of an extracellular or transmembrane domain of a connexin, such as connexin 43 or connexin 45. In some aspects peptide or peptidomimetic comprises a portion of an extracellular or transmembrane domain of connexin Cx26, Cx30, Cx31.1, Cx36, Cx37, Cx40, Cx50, Cx57 or any other connexin in the eye or blood vessels. In other embodiments, the modulators are pannexin peptides or peptidomimetics, sometimes referred to anti-pannexin peptides or peptdomimetics, for example, modified or unmodified peptides or peptidomimentics. In other embodiments, the modulators are pannexin peptides or peptidomimetics, sometimes referred to anti-pannexin pannexin or peptdomimetics, for example, modified or unmodified peptides or peptidomimetics. In some aspects, the connexin modulators can include or exclude any of the foregoing.

In some embodiments the connexin modulators of this invention include anti-connexin 43 peptides or peptidomimetics, for example, any of the peptides described herein, including peptides comprising a portion of an extracellular domain of a connexin, and peptides comprising a portion of a carboxy-terminal portion of a connexin useful in the methods of this invention, which is therapeutically effective, for example, effective for healing any of the neuropathic ocular disorders described herein. In some aspects, the therapeutically effective modified or unmodified peptide or peptidomimetic comprises a portion of an extracellular domain of a connexin, such as connexin 43 or connexin 45, preferably connexin 43. The protein sequence of connexin 43 is shown below.

```
Connexin 43
                                         (SEQ ID NO.: 19)
Met Gly Asp Trp Ser Ala Leu Gly Lys Leu Leu Asp Lys
1           5              10           15

Val Gln Ala Tyr Ser Thr Ala Gly Gly Lys Val Trp Leu
                    20           25            30

Ser Val Leu Phe Ile Phe Arg Ile Leu Leu Leu Gly Thr
                            35            40

Ala Val Glu Ser Ala Trp Gly Asp Glu Gln Ser Ala Phe
  45                                    50

Arg Cys Asn Thr Gln Gln Pro Gly Cys Glu Asn Val Cys
55            60                                 65

Tyr Asp Lys Ser Phe Pro Ile Ser His Val Arg Phe Trp
        70            75                80

Val Leu Gln Ile Ile Phe Val Ser Val Pro Thr Leu Leu
                    85           90            95

Tyr Leu Ala His Val Phe Tyr Val Met Arg Lys Glu Glu
                           100           105

Lys Leu Asn Lys Lys Glu Glu Glu Leu Lys Val Ala Gln
 110                                   115         120

Thr Asp Gly Val Asn Val Asp Met His Leu Lys Gln Ile
            125                                130

Glu Ile Lys Lys Phe Lys Tyr Gly Ile Glu Glu His Gly
        135            140

Lys Val Lys Met Arg Gly Gly Leu Leu Arg Thr Tyr Ile
    145           150            155          160

Ile Ser Ile Leu Phe Lys Ser Ile Phe Glu Val Ala Phe
                        165           170

Leu Leu Ile Gln Trp Tyr Ile Tyr Gly Phe Ser Leu Ser
 175                                180           185

Ala Val Tyr Thr Cys Lys Arg Asp Pro Cys Pro His Gln
          190                                  195

Val Asp Cys Phe Leu Ser Arg Pro Thr Glu Lys Thr Ile
      200          205
```

-continued

```
Phe Ile Ile Phe Met Leu Val Val Ser Leu Val Ser Leu
  210            215            220

Ala Leu Asn Ile Ile Glu Leu Phe Tyr Val Phe Phe Lys
            225           230           235

Gly Val Lys Asp Arg Val Lys Gly Lys Ser Asp Pro Tyr
 240                               245          250

His Ala Thr Ser Gly Ala Leu Ser Pro Ala Lys Asp Cys
        255                                  260

Gly Ser Gln Lys Tyr Ala Tyr Phe Asn Gly Cys Ser Ser
    265           270

Pro Thr Ala Pro Leu Ser Pro Met Ser Pro Pro Gly Tyr
 275           280           285

Lys Leu Val Thr Gly Asp Arg Asn Asn Ser Ser Cys Arg
           290          295           300

Asn Tyr Asn Lys Gln Ala Ser Glu Gln Asn Trp Ala Asn
                    305           310           315

Tyr Ser Ala Glu Gln Asn Arg Met Gly Gln Ala Gly Ser
        320                                325

Thr Ile Ser Asn Ser His Ala Gln Pro Phe Asp Phe Pro
 330            335

Asp Asp Asn Gln Asn Ser Lys Lys Leu Ala Ala Gly His
340           345           350

Glu Leu Gln Pro Leu Ala Ile Val Asp Gln Arg Pro Ser
        355            360           365

Ser Arg Ala Ser Ser Arg Ala Ser Ser Arg Pro Arg Pro
                  370           375            380

Asp Asp Leu Glu Ile
```

Table 3 shows extracellular loops for connexin 43 and connexin 45. In some embodiments, the therapeutically effective modified or unmodified peptide or peptidomimetic comprises a portion of the E2 extracellular domain of a connexin, such as connexin 43 or connexin 45, preferably connexin 43. In some embodiments, the therapeutically effective modified or unmodified peptide or peptidomimetic comprises a portion of the C-terminal domain of a connexin, such as connexin 43 or connexin 45, preferably connexin 43. If a peptide or peptidomimetic modulator comprises a portion of an intracellular domain of a connexin, the peptide may, in some embodiments, be conjugated to a cell internalization transporter and may, in some instances, block zona occludens (ZO-1) binding to connexin 43.

TABLE 3

Extracellular loops for connexin 43 and connexin 45

| | |
|---|---|
| **E1** | |
| huCxn43 | ESAWGDEQSAFRCNTQQPGCENVCYDKSFPISHVR (SEQ ID NO: 129) |
| huCx45 | GESIYYDEQSKFVCNTEQPGCENVCYDAFAPLSHVR (SEQ ID NO: 130) |
| **E2** | |
| huCxn43 | LLIQWYIYGFSLSAVYTCKRDPCPHQVDCFLSRPTEKT (SEQ ID NO: 131) |
| huCx45 | LIGQYFLYGFQVHPFYVCSRLPCHPKIDCFISRPTEKT (SEQ ID NO: 132) |

Sequences of the E2 domain of different connexin isotypes are shown with amino acids homologous to peptide shown in bold in Table 4. Note that last 4 μmino acids of peptide are part of the fourth membrane domain.

Table 4 provides the extracellular domain for connexin family members which are used to develop peptide inhibitors described herein. The peptides and provided in Table 4, and fragments thereof, are used as peptide inhibitors in certain non-limiting embodiments. In other non-limiting embodiments, peptides comprising from about 8 to about 15, of from about 11 to about 13 μmino contiguous amino acids acids of the petides in this Table are peptide inhibitors of the invention. In other embodiments, conservative amino acid changes are made to the peptides or fragments thereof.

TABLE 4

| Extracellular domains | |
|---|---|
| peptide | VDCFLSRPTEKT (SEQ ID NO: 168) |
| peptide | SRPTEKTIFII (SEQ ID NO: 169) |
| huCxn43 | LLIQWYIYGFSLSAVYTCKRDPCPHQ**VDCFLSRPTEKTIFII** (SEQ ID NO: 115) |
| huCx45 | LIGQYFLYGFQVHPFYVCSRLPCHPKI**DCFISRPTEKTIF**LL (SEQ ID NO: 116) |

Other peptide sequences known to inhibit the interconnexin binding that can regulate connexin activity are the cytoplasmic loop of connexin 43 (amino acids 119-144) L2 peptide and subparts of the L2 peptide of connexin 43. In some embodiments, these peptides may include or exclude, for example, the nine amino acid sequence of Gap 19, KQIEIKKFK (SEQ ID NO: 133); the native Gap19 sequence, DGVNVEMHLKQIEIKKFKYGIEEHGK (SEQ ID NO: 134); the His144→Glu L2 derivative of Gap19, as reported by Shibayama (Shibayama, J. et al., *Biophys. J.* 91, 405404063, 2006), GVNVEMHLKQIEIKKFKYGIE-EQGK (SEQ ID NO: 135); the TAT-Gap19 sequence, YGRKKRRQRRRKQIEIKKFK (SEQ ID NO: 136); the SH3 binding domain, CSSPTAPLSPMSPPGYK (SEQ ID NO: 137), or subpart thereof PTAPLSPMSPP (SEQ ID NO: 138); the C-terminal sequence of the CT9 or CT10 peptide, with or without a TAT leader sequence to increase cell penetration, RPRDDEI (SEQ ID NO: 139), SRPRDDLEI (SEQ ID NO: 218), YGRKKRRQRRRSRPRDDEI (SEQ ID NO: 216), or YGRKKRRQRRRRPRDDEI (SEQ ID NO: 219). Other peptidomimetic sequences that can be included or excluded in the compositions, methods, kits or articles of manufacture disclosed herein are those reported by Dhein (Dhein, S., *Naunyn-Schmiedeberg 's Arch. Pharm.,* 350: 174-184, 1994); the AAP10 peptide, $H_2N$-Gly-Ala-Gly-4Hyp-Pro Tyr-CONH2 (SEQ ID NO: 220), and the ZP123 peptide (rotigapeptide), Ac-D-Tyr-Pro-D-4Hyp-Gly-D-Ala-Gly-NH2 (SEQ ID NO: 221), (Dhein, S., et al. *Cell Commun. Adhes.* 10, 371-378, 2013). Rotigapeptide is comprised of the D-form of the peptides for enhanced efficacy over the native L-form of the peptide.

Examples of anti-pannexin agents are anti-pannexin polynucleotides, including the anti-pannexin antisense oligodeoxynucleotides ("ODN") described below. Examples of anti-pannexin polynucleotides include anti-pannexin oligodeoxynucleotides, including antisense (including modified and unmodified backbone antisense), RNAi, and miRNA and siRNA. Suitable anti-pannexin peptides include peptides that bind pannexin extracellular domains, for example, or pannexin intracellular domains. Suitable anti-pannexin agents include, for example, antisense ODNs, peptides, and peptidomimetics against Panx1. Included peptides or peptidomimetics are anti-pannexin peptides or peptidomimetics, e.g., pannexin complex blocking peptides (for example, anti-pannexin antibodies and antibody binding fragments) or peptidomimetics (for example, peptidometics directed against one or more extracellular or intracellular regions of pannexin). Peptidomimetics may be complexed to one or more other agents, for example, antennapedia in order to facilitate membrane transport for binding to intracellular pannexin regions and domains.

The terms "peptide," "peptidomimetic" and "mimetic" include synthetic or genetically engineered chemical compounds that may have substantially the same structural and functional characteristics of protein regions which they mimic. In the case of connexins, these may mimic, for example, the extracellular loops of opposing connexins involved in connexon-connexon docking and cell-cell channel formation, and/or the extracellular loops of hemichannel connexins.

As used herein, the term "peptide analogs" refer to the compounds with properties analogous to those of the template peptide and can be non-peptide drugs. "Peptidomimetics" (also known as peptide mimetics) which include peptide and peptide-based compounds, also include such non-peptide based compounds such as peptide analogs. Peptidomimetics that are structurally similar to therapeutically useful peptides can be used to produce an equivalent or enhanced therapeutic or prophylactic effect. Peptides and peptidomimetics may, in some aspects, be modified or unmodified. Generally, peptidomimetics are structural or functional mimics (e.g., identical or similar) to a paradigm polypeptide (i.e., a polypeptide that has a biological or pharmacological function or activity), but can also have one or more peptide linkages optionally replaced by a linkage selected from the group consisting of, for example, $-CH_2NH-$, $-CH_2S-$, $-CH_2-CH_2-$, $-CH=CH-$ (cis and trans), $-COCH_2-$, $-CH(OH)CH_2-$, and $-CH_2SO-$. The mimetic can be either entirely composed of natural amino acids, synthetic chemical compounds, non-natural analogues of amino acids, or, is a chimeric molecule of partly natural peptide amino acids and partly non-natural analogs of amino acids. The mimetic can also comprise any amount of natural amino acid conservative substitutions as long as such substitutions also do not substantially alter mimetic activity. In the case of connexins, these can mimic, for example, the extracellular loops of opposing connexins involved in connexon-connexon docking and cell-cell channel formation. For example, a mimetic composition can be useful as a gap junction modulating agent if it is capable of down-regulating biological actions or activities of connexons, such as, for example, preventing the docking of connexons to form gap-junction-mediated cell-cell communications, or preventing the opening of connexons to expose the cell cytoplasm to the extracellular millieu. Peptidomimetics encompass those described herein, as well as those as may be known in the art, whether now known or later developed. Peptides and peptimimetic connexin modulators may also be modified to increase stability, improve bioavailability and/or to increase cell membrane permeability.

In some aspects of this invention, the connexin modulator is a peptide or peptidomimetic. Exemplary connexin 43 (Cx43) or Cx26, Cx30, Cx30.3, Cx31, Cx31.1, Cx32, Cx36, Cx37, Cx40.1, Cx43, Cx46, Cx46.6, or Cx40 peptide modulators that may be included or excluded in certain embodiments of this disclosure are provided in Table 64 below (E2 and T2 refer to the location of a peptide in, for example, the second extracellular domain or the second transmembrane domain).

TABLE 64

| SEQ ID NO: | Identifier | Sequence |
|---|---|---|
| SEQ ID NO: 140 | CXT 2 | PSSRASSRASSRPRPDDLEI |
| SEQ ID NO: 141 | CXT 1 | RPRPDDLEI |
| SEQ ID NO: 142 | CXT 3 | RPRPDDLEV |
| SEQ ID NO: 143 | CXT 4 | RPRPDDVPV |
| SEQ ID NO: 144 | CXT 5 | KARSDDLSV |
| SEQ ID NO: 145 | hCx40 | QKPEVPNGVSPGHRLPHGYHSDKRRLSKASSKARSDDLSV |
| SEQ ID NO: 146 | Antp/ CXT 2 | RQPKIWFPNRRKPWKKPSSRASSRASSRPRPDDLEI |
| SEQ ID NO: 147 | Antp/ CXT 2 | RQPKIWFPNRRKPWKKPSSRASSRASSRPRPDDLEI |
| SEQ ID NO: 148 | Antp/ CXT 1 | RQPKIWFPNRRKPWKKRPRPDDLEI |
| SEQ ID NO: 149 | Antp/ CXT 3 | RQPKIWFPNRRKPWKKRPRPDDLEV |
| SEQ ID NO: 150 | Antp/ CXT 4 | RQPKIWFPNRRKPWKKRPRPDDVPV |
| SEQ ID NO: 151 | Antp/ CXT 5 | RQPKIWFPNRRKPWKKKARSDDLSV |
| SEQ ID NO: 152 | conservative Cxn43 variant | RPKPDDLDI |
| SEQ ID NO: 153 | HIV-Tat/ CXT 1 | GRKKRRQRPPQRPRPDDLEI |
| SEQ ID NO: 154 | Penetratin/ CXT 1 | RQIKIWFQNRRMKWKKRPRPDDLEI |
| SEQ ID NO: 155 | Antp-3A/ CXT 1 | RQIAIWFQNRRMKWAARPRPDDLEI |
| SEQ ID NO: 156 | Tat/ CXT 1 | RKKRRQRRRRPRPDDLEI |
| SEQ ID NO: 157 | Buforin II/ Vnrs 1 | TRSSRAGLQFPVGRVHRLLRKRPRPDDLEI |
| SEQ ID NO: 158 | Transportan/ CXT 1 | GWTLNSAGYLLGKINKALAALAKKILRPRPDDLEI |
| SEQ ID NO: 159 | MAP/ CXT 1 | KLALKLALKALKAALKLARPRPDDLEI |
| SEQ ID NO: 160 | K-FGF/ CXT 1 | AAVALLPAVLLALLAPRPRPDDLEI |
| SEQ ID NO: 161 | Ku70/ CXT 1 | VPMLKPMLKERPRPDDLEI |
| SEQ ID NO: 162 | Prion/ CXT 1 | MANLGYWLLALFVTMWTDVGLCKKRPKPRPRPDDLEI |
| SEQ ID NO: 163 | pVEC/ CXT 1 | LLIILRRRIRKQAHAHSKRPRPDDLEI |
| SEQ ID NO: 164 | Pep-1/ CXT 1 | KETWWETWWTEWSQPKKKRKVRPRPDDLEI |
| SEQ ID NO: 165 | SynB1/ CXT 1 | RGGRLSYSRRRFSTSTGRRPRPDDLEI |

TABLE 64-continued

| SEQ ID NO: | Identifier | Sequence |
|---|---|---|
| SEQ ID NO: 166 | Pep-7/ CXT 1 | SDLWEMMMVSLACQYRPRPDDLEI |
| SEQ ID NO: 167 | HN-1/ CXT 1 | TSPLNIHNGQKLRPRPDDLEI |
| SEQ ID NO: 168 | SEQ-pept5, or Peptide 5 | VDCFLSRPTEKT |
| SEQ ID NO: 169 | SEQ-Gap27 | SRPTEKTIFII |
| SEQ ID NO: 170 | SEQ-Gap26 | VCYDKSFPISHVR |
| SEQ ID NO: 171 | SEQ-Mod1 | CFLSRPTEKT |
| SEQ ID NO: 172 | SEQ-Mod2 | LSRPTEKT |
| SEQ ID NO: 173 | SEQ-Mod3 | SRPTEKT |
| SEQ ID NO: 174 | SEQ-Mod4 | VDCFLSRPTE |
| SEQ ID NO: 175 | SEQ-Mod5 | VDCFLSRP |
| SEQ ID NO: 176 | SEQ-Mod6 | VDCFLS |
| SEQ ID NO: 177 | HIV-Tat/SEQ-pept5 | GRKKRRQRPPQVDCFLSRPTEKT |
| SEQ ID NO: 178 | Penetratin/ SEQ-pept5 | RQIKIWFQNRRMKWKKVDCFLSRPTEKT |
| SEQ ID NO: 179 | Antp-3A/ SEQ-pept5 | RQIAIWFQNRRMKWAAVDCFLSRPTEKT |
| SEQ ID NO: 180 | Tat/ SEQ-pept5 | RKKRRQRRRVDCFLSRPTEKT |
| SEQ ID NO: 181 | Buforin II/ SEQ-pept5 | TRSSRAGLQFPVGRVHRLLRKVDCFLSRPTEKT |
| SEQ ID NO: 182 | Transportan/ SEQ-pept5 | GWTLNSAGYLLGKINKALAALAKKILVDCFLSRPTEKT |
| SEQ ID NO: 183 | MAP/ SEQ-pept5 | KLALKLALKALKAALKLAVDCFLSRPTEKT |
| SEQ ID NO: 184 | K-FGF/ SEQpept5 | AAVALLPAVLLALLAPVDCFLSRPTEKT |
| SEQ ID NO: 185 | Ku70/ SEQpept5 | VPMLKPMLKEVDCFLSRPTEKT |
| SEQ ID NO: 186 | Prion/ SEQpept5 | MANLGYWLLALFVTMWTDVGLCKKRPKPVDCFLSRPTEKT |
| SEQ ID NO: 187 | pVEC/ SEQ-pept5 | LLIILRRRIRKQAHAHSKVDCFLSRPTEKT |
| SEQ ID NO: 188 | Pep-1/ SEQpept5 | KETWWETWWTEWSQPKKKRKVVDCFLSRPTEKT |
| SEQ ID NO: 189 | SynB1/ SEQpept5 | RGGRLSYSRRRFSTSTGRVDCFLSRPTEKT |
| SEQ ID NO: 190 | Pep-7/ SEQpept5 | SDLWEMMMVSLACQYVDCFLSRPTEKT |
| SEQ ID NO: 191 | HN-1/ SEQpept5 | TSPLNIHNGQKLVDCFLSRPTEKT |

TABLE 64-continued

| SEQ ID NO: | Identifier | Sequence |
|---|---|---|
| SEQ ID NO: 192 | SEQ M3E2 | FEVAFLLIQWI |
| SEQ ID NO: 193 | SEQ E2a | LLIQWYIGFSL |
| SEQ ID NO: 194 | SEQ E2b | SLSAVYTCKRDPCPHQ |
| SEQ ID NO: 195 | SEQ E2c | SRPTEKTIFII |
| SEQ ID NO: 196 | SEQ M1E1 | LGTAVESAWGDEQ |
| SEQ ID NO: 197 | SEQ E1a | QSAFRCNTQQPG |
| SEQ ID NO: 198 | SEQ E1b | QQPGCENVCYDK |
| SEQ ID NO: 199 | SEQ E1c | VCYDKSFPISHVR |
| SEQ ID NO: 200 | SEQ E2d | KRDPCHQVDCFLSRPTEK |
| SEQ ID NO: 125 | Peptide 1 | ADCFLSRPTEKT |
| SEQ ID NO: 126 | Peptide 2 | VACFLSRPTEKT |
| SEQ ID NO: 127 | Peptide 11 | VDCFLSRPTAKT |
| SEQ ID NO: 128 | Peptide 12 | VDCFLSRPTEAT |
| SEQ ID NO: 133 | Gap 19subpart | KQIEIKKFK |
| SEQ ID NO: 134 | Gap 19-full | DGVNVEMHLKQIEIKKFKYGIEEHGK |
| SEQ ID NO: 135 | Gap 19-deriv | DGVNVEMHLKQIEIKKFKYGIEEQGK |
| SEQ ID NO: 136 | TAT-Gap19 | YGRKKRRQRRRKQIEIKKFK |
| SEQ ID NO: 137 | SH3-full | CSSPTAPLSPMSPPGYK |
| SEQ ID NO: 138 | 5H3-subpart | PTAPLSPMSPP |
| SEQ ID NO: 139 | C-terminus CT9 | RPRDDEI |
| SEQ ID NO: 216 | C-terminus CT9-TAT | YGRKKRRQRRRSRPRDDEI |
| SEQ ID NO: 218 | C-terminus CT10 | SRPRDDLEI |
| SEQ ID NO: 219 | C-terminus CT10-TAT | YGRKKRRQRRRRPRDDEI |
| SEQ ID NO: 220 | AAP10 | $H_2N$-Gly-Ala-Gly-4Hyp-Pro Tyr-$CONH_2$ |
| SEQ ID NO: 221 | ZP123 | Ac-D-Tyr-Pro-D-4Hyp-Gly-D-Ala-Gly-$NH_2$ |

TABLE 64-continued

| SEQ ID NO: | Identifier | Sequence |
|---|---|---|
| SEQ ID NO: 222 | plsl/ SEQpept5 | RVIRVWFQNKRCKDKKVDCFLSRPTEKT |
| SEQ ID NO: 223 | MGB Peptide P-beta/ SEQpept5 | GALFLGFLGAAGSTMGAWSQPKKKRKVVDCFLSRPTEKT |
| SEQ ID NO: 224 | MGB Peptide P-alpha/ SEQpept5 | GALFLAFLAAALSLMGLWSQPKKKRRVVDCFLSRPTEKT |
| SEQ ID NO: 244 | huCx26 | MYVFYVMYDGFSMQRLVKCNAWPCPNTVDCFVSRPTEKT |
| SEQ ID NO: 245 | huCx30 | MYVFYFLYNGYHLPWVLKCGIDPCPNLVDCFISRPTEKT |
| SEQ ID NO: 246 | huCx30.3 | LYIFHRLYKDYDMPRVVACSVEPCPHTVDCYISRPTEKK |
| SEQ ID NO: 247 | huCx31 | LYLLHTLWHGFNMPRLVQCANVAPCPNIVDCYIARPTEKK |
| SEQ ID NO: 248 | huCx31.1 | LYVFHSFYPKYILPPVVKCHADPCPNIVDCFISKPSEKN |
| SEQ ID NO: 249 | huCx32 | MYVFYLLYPGYAMVRLVKCDVYPCPNTVDCFVSRPTEKT |
| SEQ ID NO: 250 | huCx36 | LYGWTMEPVFVCQRAPCPYLVDCFVSRPTEKT |
| SEQ ID NO: 251 | huCx37 | LYGWTMEPVFVCQRAPCPYLVDCFVSRPTEKT |
| SEQ ID NO: 252 | huCx40.1 | GALHYFLFGFLAPKKFPCTRPPCTGVVDCYVSRPTEKS |
| SEQ ID NO: 253 | huCx43 | LLIQWYIYGFSLSAVYTCKRDPCPHQVDCFLSRPTEKT |
| SEQ ID NO: 254 | huCx46 | IAGQYFLYGFELKPLYRCDRWPCPNTVDCFISRPTEKT |
| SEQ ID NO: 255 | huCx46.6 | LVGQYLLYGFEVRPFFPCSRQPCPHVVDCFVSRPTEKT |
| SEQ ID NO: 256 | huCx40 | IVGQYFIYGIFLTTLHVCRRSPCPHPVNCYVSRPTEKN |

In some embodiments the connexin 43 modulator may comprise, for example, a peptide or peptidomimetic comprising, for example SEQ ID NO: 173 (SRPTEKT). The peptide or peptidomimetic may also comprise, for example SEQ ID NO: 168 (VDCFLSRPTEKT). The peptide may contain one or more modified amino acids, amino acid analogs, or may be otherwise modified to improve bioavailability or to increase penetration across the cell membrane. For example, SEQ ID NO: 168 may be modified to obtain SEQ ID NOS:134-139 and 216. In some aspects the peptide or peptidomimetic comprising, for example SEQ ID NO: 173 (SRPTEKT) or SEQ ID NO: 168 (VDCFLSRPTEKT) comprises from 7 to 40 μmino acids or amino acid analogues and does not comprise a C-terminal peptide. In some embodiments the peptides may also be used as promoieties.

In some aspects, the Connexin 45 modulators can be peptide or peptidomimetics comprising portions of the Connexin 45 protein that antagonize or inhibit or block connexin-connexin interactions. Exemplary peptide sequences for Connexin 45 peptides and peptidomimetic modulators are provided in Table 63.

TABLE 63

Sequences of Connexin 45 modulator peptides or peptidomimetics

| SEQ ID NO. | Sequence |
|---|---|
| SEQ ID NO: 72 | LTAVGGESIYYDEQSKFVCNTEQPGCENVCYDA FAPLSHVRFWVFQ |
| SEQ ID NO: 73 | LTAVGGESIYYDEQS |
| SEQ ID NO: 74 | DEQSKFVCNTEQP |
| SEQ ID NO: 75 | TEQPGCENVCYDA |
| SEQ ID NO: 76 | VCYDAFAPLSHVR |
| SEQ ID NO: 77 | APLSHVRFWVFQ |
| SEQ ID NO: 78 | FEVGFLIGQYFLYGFQVHPFYVCSRLPCHPKID CFISRPTEKTIFLL |
| SEQ ID NO: 79 | FEVGFLIGQYF |

TABLE 63-continued

Sequences of Connexin 45 modulator peptides or peptidomimetics

| SEQ ID NO. | Sequence |
|---|---|
| SEQ ID NO: 80 | LIGQYFLYGFQV |
| SEQ ID NO: 81 | GFQVHPFYVCSRLP |
| SEQ ID NO: 82 | SRLPCHPKIDCF |
| SEQ ID NO: 83 | IDCFISRPTEKT |
| SEQ ID NO: 84 | SRPTEKTIFLL |
| SEQ ID NO: 85 | SRPTEKTIFII |
| SEQ ID NO: 86 | YVCSRLPCHP |
| SEQ ID NO: 87 | QVHPFYVCSRL |
| SEQ ID NO: 88 | FEVGFLIGQYFLY |
| SEQ ID NO: 89 | GQYFLYGFQVHP |
| SEQ ID NO: 90 | GFQVHPFYVCSR |
| SEQ ID NO: 91 | AVGGESIYYDEQ |
| SEQ ID NO: 92 | YDEQSKFVCNTE |
| SEQ ID NO: 93 | NTEQPGCENVCY |
| SEQ ID NO: 94 | CYDAFAPLSHVR |
| SEQ ID NO: 95 | FAPLSHVRFWVF |
| SEQ ID NO: 96 | LIGQY |
| SEQ ID NO: 97 | QVHPF |
| SEQ ID NO: 98 | YVCSR |
| SEQ ID NO: 99 | SRLPC |
| SEQ ID NO: 100 | LPCHP |
| SEQ ID NO: 101 | GESIY |
| SEQ ID NO: 102 | YDEQSK |
| SEQ ID NO: 103 | SKFVCN |
| SEQ ID NO: 104 | TEQPGCEN |
| SEQ ID NO: 105 | VCYDAFAP |
| SEQ ID NO: 106 | LSHVRFWVFQ |
| SEQ ID NO: 107 | LIQYFLYGFQVHPF |
| SEQ ID NO: 108 | VHPFYCSRLPCHP |
| SEQ ID NO: 109 | VGGESIYYDEQSKFVCNTEQPG |
| SEQ ID NO: 110 | TEQPGCENVCYDAFAPLSHVRF |
| SEQ ID NO: 111 | AFAPLSHVRFWVFQ |
| SEQ ID NO: 112 | IDCFISRPTEKTIFLL |
| SEQ ID NO: 113 | DCFISRPTEKT |
| SEQ ID NO: 114 | SRPTEKT |
| SEQ ID NO: 132 | LIGQYFLYGFQVHPFYVCSRLPCHPK1DCFISR PTEKT |

In some embodiments the connexin 45 modulator may comprise, for example, a peptide or peptidomimetic comprising, a portion of the E2 or C terminal domain of connexin 45, for example, comprising SEQ ID NO: 114 (SRPTEKT). The peptide or peptidomimetic may also comprise, for example SEQ ID NO: 113 (DCFISRPTEKT). In some embodiments the peptides may only be 3 μmino acids in length, including SRL, PCH, LCP, CHP, IYY, SKF, QPC, VCY, APL, HVR, or longer.

In some aspects, the Connexin 40 modulators can be peptide or peptidomimetics comprising portions of the Connexin 40 protein which antagonize or inhibit connexin-connexin interactions.

Peptide Chemistry Modifications

In certain embodiments, the connexin 43 modulator peptides of the present invention can be linked at the amino or carboxy terminus to a cellular internalization transporter. The cellular internalization transporter linked to the connexin 43 modulator peptides of the present invention may be any internalization sequence known or newly discovered in the art, or conservative variants thereof. Non-limiting examples of cellular internalization transporters and sequences include Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (BisGuanidinium-Tren-Cholesterol).

The sequences of exemplary cellular internalization peptides are provided in Table 65 below.

TABLE 65

| SEQ ID NO. | Identifier | Sequence |
|---|---|---|
| SEQ ID NO: 201 | ANTP | RQPKIWFPNRRKPWKK |
| SEQ ID NO: 202 | HIV-TAT | GRKKRRQRPPQ |
| SEQ ID NO: 203 | Trans-portan | GWTLNSAGYLLGKINKALAAL AKKIL |
| SEQ ID NO: 204 | Buforin II | TRSSRAGLQFPVGRVHRLLRK |
| SEQ ID NO: 205 | Tat | RKKRRQRRR |
| SEQ ID NO: 206 | Penetratin | RQIKIWFQNRRMKWKK |
| SEQ ID NO: 207 | MAP | KLALKLALKALKAALKLA |
| SEQ ID NO: 208 | K-FGF | AAVALLPAVLLALLAP |
| SEQ ID NO: 209 | Ku70 | VPMLKPMLKE |
| SEQ ID NO: 210 | Prion | MANLGYWLLALFVTMWTDVGL CKKRPKP |
| SEQ ID NO: 211 | pVEC | LLIILRRRIRKQAHAHSK |
| SEQ ID NO: 212 | Pep-1 | KETWWETWWTEWSQPKKKRRV |
| SEQ ID NO: 213 | SynB1 | RGGRLSYSRRRFSTSTGR |
| SEQ ID NO: 214 | Pep-7 | SDLWEMMMVSLACQY |
| SEQ ID NO: 215 | HN-1 | TSPLNIHNGQKL |
| SEQ ID NO: 225 | plsl | RVIRVWFQNKRCKDKK |
| SEQ ID NO: 226 | MGB Peptide Pbeta | GALFLGFLGAAGSTMGAWSQP KKKRKV |

TABLE 65-continued

| SEQ ID NO. | Identifier | Sequence |
|---|---|---|
| SEQ ID NO: 227 | MGB Peptide Palpha | GALFLAFLAAALSLMGLWSQP KKKRRV |

Table 65 lists sequences of exemplary cellular internalization transporters.

In some embodiments, the connexin, pannexin and/or pannexin modulator peptide is fused to a transport peptide to increase the penetration into the target cell. In some embodiments, the transport peptide can be part of a viral coating for cell penetration. In some embodiments, the transport peptide can be fused to the connexin and/or pannexin modulator peptide at the carboxy or amino terminus. The transport peptide can be selected from one of the following peptides: ANTP, HIV-TAT, Transportan, Buforin II, Tat, Penetratin, MAP, K-FGF, Ku70, Prion, pVEC, Pep-1, SynB1, Pep-7, RGD, or HN-1. In some embodiments, the connexin, pannexin and/or pannexin modulator peptide can include or exclude any of the foregoing.

In one embodiment of the present invention, the amino acid sequence of the connexin 43 modulator peptides can be selected from the group consisting of any peptide SEQ ID listed herein, or a conservative variant thereof. In a further embodiment of the present invention, the connexin 43 modulator peptides can comprise the amino acid sequence of SEQ ID NO: 140-200. In another embodiment of the present invention, the connexin 43 modulator peptide further comprises a cellular internalization transporter. In a further embodiment, the connexin 43 modulator peptide can be linked at the amino terminus to the cellular internalization transporter.

different residue inserted in its place. Such substitutions are referred to as conservative substitutions. The replacement of one amino acid residue with another that is biologically and/or chemically similar is known to those skilled in the art as a conservative substitution. A conservative substitution could replace one hydrophobic residue for another, or one polar residue for another. Conservatively substituted variations of each explicitly disclosed sequence are included within the peptides provided herein. Conservative substitutions typically have little to no impact on the biological activity of a resulting polypeptide. A conservative substitution can be an amino acid substitution in a peptide that does not substantially affect the biological function of the peptide. A peptide can include one or more amino acid substitutions, from 2-10 conservative substitutions, 2-5 conservative substitutions, or 4-9 conservative substitutions.

Chemical Structure Modification

In certain embodiments, the chemical structure of the peptides or peptidomimetics can be synthetically modified so as to increase transfection uptake of the peptide. For example, the peptide or peptidomimetic may be modified by conjugating the peptide to a hydrophobic compound, in some embodiments, through a linker moiety. The hydrophobic compound may be, for example, one or more n-alkyl groups, which may be, for example, C6-C14 alkyl groups. In some embodiments, the peptides may be conjugated at the N terminus to one or two dodecyl (C12) groups as described in Chen, Y S et al., *J. Pharm. Sci.,* 102: 2322-2331 (2013), herein incorporated by reference. In one embodiment, the peptide sequence CFLSRPTEKT (SEQ ID NO: 171) or VDCFLSRPTEKT (SEQ ID NO: 168) can be conjugated to two dodecyl groups to create a modified peptide which can modulate connexin 43, "C12-C12-Cxn43 MP." (SEQ ID NO: 237) The resulting structure is shown in FIG. 80.

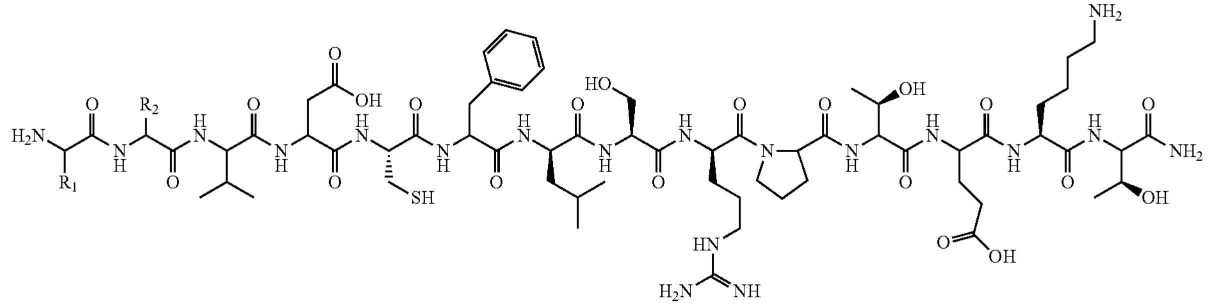

When specific proteins are referred to herein, derivatives, variants, and fragments are contemplated. Protein derivatives and variants are well understood to those of skill in the art and can involve amino acid sequence modifications. For example, amino acid sequence modifications can fall into one or more of three classes: insertional, substitutional or deletional variants. Insertions include amino and/or carboxyl terminal fusions as well as intrasequence insertions of single or multiple amino acid residues. Insertions can be smaller insertions than those of amino or carboxyl terminal fusions, for example, on the order of one to four residues. Deletions are characterized by the removal of one or more amino acid residues from the protein sequence(s). Substitutions, deletions, insertions or any combination thereof may be combined to arrive at a final construct. Substitutional variants are those in which at least one residue has been removed and a FIG. 80. The structure of C12-C12-Cxn43 MP (SEQ ID NO:237). $R_1$ and $R_2$ can be hydrogen or alkyl groups. In some aspects, $R_1$=$R_2$=n-dodecyl chains.

Anti-Connexin Modulator Drugs

In some embodiments, the gap junction modulator can be a small molecule, that is, an anti-connexin modulator drug. In some aspects, the anti-connexin modulator drug can have the structure in Formula I, as described herein.

Pannexin, Pannexin Channel Modulators and Other Gap Junction Modulators

Also useful in the methods of this invention are modulators including pannexin and pannexin channel modulators and gap junction modulator or connexin modulator drugs that may be used in any of the compositions, kits and methods described herein, in place of or in addition to the connexin modulator or pannexin modulator.

The modulators of this invention for any of the uses featured herein may also comprise a gap junction modulator, which may inhibit or block Cx26, Cx31.1, Cx36, Cx37, Cx40, Cx50, Cx57 or any other connexin in the eye or blood vessels. The pharmaceutical compositions of this invention for any of the uses featured herein may also comprise a pannexin modulator, which may inhibit or block, for example, pannexin channels.

Gap junction modulators include connexin modulators and gap junction drugs. Accordingly, connexin modulators are not necessarily gap junction drug modulators and not all gap junction drug modulators are connexin modulators. Tonabersat, carabersat and the compounds of Formula I are connexin modulators.

The gap junction drugs can be, for example, mycotoxins, glycyrrhetinic acid and glycyrrhetinic acid derivatives, phorbol esters, DDTs, triphenylmethanes, triphenylethanes, longchain alcohols, anesthetics, fatty acids amides, fenamates, quinine and quinine derivatives, 2-APB and 2-APB derivatives, polyamines, cyclodextrins, and peptides which have not been discussed above.

In some embodiments, the gap junction drugs can be selected from one of the following: carbamazepine, octanol, bisphenol-A, heptanol, 4-(2-Butyl-6,7-dichloro-2-cyclopentyl-indan-1-on-5-yl) oxobutyric acid (DCPIB), carabersat, genistein, trans-resveratrol, carbenoxolone, HMG-CoA reductase inhibitor lovastatin, rotigaptide, metoprolol, forskolin, apigenin, tangeritin, halothane, ochratoxin A mycotoxin, patulin mycotoxin, okadaic acid, 18-alpha- and 18-beta-glycyrrhetinic acid, 17-beta-estradiol methyl ester, testosterone methyl ester, 12-O-tetradecanoylphorbol-13-acetate (TPA), phorbol esters, 1,1,1-trichloro-2,2-bis(p-chlorophenyl) ethane, triphenylmethane, tris(4-chlorophenyl) methanol, (2-chlorophenyl)(diphenyl)methane, triphenylmethylchloride, sodium tetraphenylborate, tamoxifen, clomiphene, enflurane, oleamide, anandamide, arylaminobenzoates such as meclofenamic acid and flufenamic acid, niflumic acid, 5-nitro-2-(3-phenylpropylmino) benzoic acid (NPPB), quinine, quinidine, Mefloquine, PQ1 (the primaquine derivative of Mefloquine), 2-aminophenoxyborate (2-APB), spermidine, spermine, cyclodextrins containing six, seven or eight glycopyranose units, Gap26 peptide (Val-Cys-Tyr-Asp-Lys-Ser-Phe-Pro-Ile-Ser-His-Val-Arg (SEQ ID NO: 170)), and Gap27 peptide (Ser-Arg-Pro-Thr-Glu-Lys-Thr-Ile-Phe-Ile-Ile (SEQ ID NO: 169)).

Any antisense molecule or shRNA that targets a region suitable to disrupt pannexin expression will be useful in the practicing the invention. In some aspects this invention features RNA interference (RNAi) to pannexin. As is the case with the expression of many other genes, pannexin expression can be knocked down in vivo or vitro through the use RNAi. A representative class of molecules that can be used for RNAi are short hairpin RNAs (shRNAs). One such anti-pannexin shRNA molecule can be constructed as follows using the vector termed pSuper-Ncad.

Antisense and short hairpin RNAs targeted against human pannexin also include those that target specific sequences. Any antisense molecule or shRNA that targets a region suitable to disrupt pannexin expression, for example, expression of Panx1 or Panx2 or Panx3, will be useful in the practicing the invention. In some aspects this invention features RNA interference (RNAi) to Panx1 or Panx2 or Panx3. As is the case with the expression of many other genes, Panx1 or Panx2 or Panx3 expression can be knocked down in vivo or vitro through the use RNAi. A representative class of molecules that can be used for RNAi are short hairpin RNAs (shRNAs). Inhibitors of Panx1 may include probenecid, mefloquine and carbenoxolone, or an anti-peptide.

Chemical Delivery Modification

The modulators, inclusing gap junction, connexin and/or pannexin and pannexin channel modulators, of the present invention can also be formulated into microparticle (microspheres, Mps) or nanoparticle (nanospheres, Nps) formulations, or both. Particulate ocular drug delivery systems include nanoparticles (1 to 1,000 nm) and microparticles (1 to 1,000 m), which are further categorized as nanospheres and microspheres and nanocapsules and microcaps. In nanocapsules and microcapsules, the drug particles or droplets are entrapped in a polymeric membrane. Particulate systems have the advantage of intraocular delivery by injection, and their size and polymer composition influence markedly their biological behavior in vivo. Microspheres can remain in the vitreous for much longer periods of time than nanospheres, therefore, microparticles act like a reservoir after intravitreal injection. Nanoparticles diffuse rapidly and are internalized in ocular tissues and cells of the anterior and posterior segment.

Pharmaceutical compositions are also provided for co-administration in the form of a combined preparation, for example, as an admixture of two or more modulators, e.g. gap junction, connexin and/or pannexin or pannexin channel modulators which may be modified or unmodified, for example one or more gap junction, connexin and/or pannexin or pannexin channel modulator polynucleotides and one or more gap junction, connexin and/or pannexin or pannexin channel modulator peptides or peptidomimetics.

The term "a combined preparation" includes a "kit of parts" or "article of manufacture" in the sense that the combination partners as defined above can be dosed independently or by use of different fixed combinations with distinguished amounts of the combination partners (a) and (b), i.e. simultaneously, separately or sequentially, whether in pharmaceutical form or dressing/matrix form or both. The parts of the kit can then, for example, be administered simultaneously or chronologically staggered, that is at different time points and with equal or different time intervals for any part of the kit of parts.

In one embodiment a combined preparation is administered, wherein two or more separate modulator compositions are administered to a subject, wherein the first composition comprises a therapeutically effective amount of modulator, such as a gap junction, connexin and/or pannexin modulator, e.g., an anti-connexin 43 polynucleotide, peptide, or peptidomimetic, or a hemichannel closing compound, and the second composition comprises a therapeutically effective amount of a second modulator, such as a gap junction, connexin and/or pannexin modulator or ocular treatment agent, e.g., an anti-connexin 43 polynucleotide, peptide, or peptidomimetic, a hemichannel closing compound and/or an ocular treatment agent. In another embodiment a third composition is administered comprising one or more anti-connexin polynucleotides, peptides, or peptidomimetics, a hemichannel closing compound and/or an ocular treatment agent.

Pharmaceutical compositions are provided for single, combined, simultaneous, separate, sequential, or sustained administration. In one embodiment, a composition comprising one or more gap junction, connexin and/or pannexin modulator polynucleotides is administered at in or more desired doses at one or more times. In another embodiment, a composition comprising one or more gap junction, connexin and/or pannexin modulator is administered about the same time as one or more peptide or peptidomimetic gap junction, connexin and/or pannexin modulators. When the two compositions are administered at different times, they may be administered within, for example, 30 minutes, 1 hour, 1 day, 1 week, or 1 month part, or any time interval between any two of the recited time periods. In one embodiment, for example, a composition comprising one or more anti-connexin polynucleotides is administered about the same time as one or more anti-connexin peptides or peptidomimetics. In one embodiment, a composition comprising one or more gap junction, connexin and/or pannexin modulator polynucleotides is administered within at least about thirty minutes of one or more gap junction, connexin and/or pannexin modulator peptides. In one embodiment, a composition comprising one or more gap junction, connexin and/or pannexin modulator polynucleotides is administered within at least about one hours of one or more gap junction, connexin and/or pannexin modulator peptides or peptidomimetics. In one embodiment, a composition comprising one or more gap junction, connexin and/or pannexin modulator polynucleotides is administered within at least about twelve hours of one or more gap junction, connexin and/or pannexin modulator peptides or peptidomimetics. In one embodiment, a composition comprising one or more gap junction, connexin and/or pannexin modulator polynucleotides is administered within at least about twenty-four hours of one or more gap junction, connexin and/or pannexin modulator peptides or peptidomimetics. In another embodiment the anti-connexin polypnucleotide and gap junction, connexin and/or pannexin modulator peptide or peptidomimetic are administered within about one hour of each other, within about one day of each other, or within about one week of each other. Other embodiments include administration of one or more gap junction, connexin and/or pannexin modulator polynucleotides and/or one or more anti-connexin peptides or peptidomimetics (for example, anti-connexin peptides or peptidomimentics comprising connexin extracellular and/or connexin carboxy-terminal peptides useful for wound healing), and one or more gap junction closing compounds useful for wound healing, one or more hemichannel closing compounds useful for wound healing, and/or one or more connexin carboxy-terminal polypeptides useful for wound healing. Modulator doses may be administered QD, BID, TID, QID, or in weekly doses, e.g., QIW, BIW QW. They may also be administered PRN, and hora somni.

Dosage Forms and Formulations and Administration

All descriptions with respect to dosing, unless otherwise expressly stated, apply to the modulators of the invention, including gap junction modulators, pannexin channel modulators, connexin modulators and pannexin modulators.

The modulators, including hemichannel, gap junction, and/or pannexin modulators, of the invention can be dosed, administered or formulated as described herein.

The modulators, including hemichannel, gap junction, and/or pannexin modulators, of the invention can be administered to a subject in need of treatment, having an ocular neuropathy. Thus, in accordance with the invention, there are provided formulations by which pannexin and/or a connexin, for example, connexin 43 or connexin 45 can be modulated and/or cell-cell communication can be downregulated in a transient and site-specific manner.

The modulators, including gap junction, connexin and/or pannexin and pannexin channel modulators may be present in the formulation in a substantially isolated form. It will be understood that the product may be mixed with carriers or diluents that will not interfere with the intended purpose of the product and still be regarded as substantially isolated. A product of the invention may also be in a substantially purified form, in which case it will generally comprise about 80%, 85%, or 90%, e.g. at least about 88%, at least about 90, 95 or 98%, or at least about 99% of a polynucleotide, for example (or other connexin modulator such as a connexin 43 modulator) or dry mass of the preparation.

In one embodiment, the gap junction, connexin and/or modulator is a modified or unmodified connexin 43 or 45 antisense polynucleotide or oligonucleotide, a modified or unmodified connexin peptide or anti-connexin 43 or 45 peptidomimetic. In some embodiments, the connexin modulator can block or reduce hemichannel opening. In some embodiments, a modified or unmodified connexin peptide or peptidomimetic, is administered to block hemichannel or gap junction function and/or to exert regulatory effects that reduce connexin expression or the formation of hemichannels or gap junctions, e.g., by downregulation of connexin protein expression. In some embodiments, the modified or unmodified connexin peptide or peptidomimetic, is administered prior to the administration of a modified or unmodified anti-connexin polynucleotide or oligonucleotide, to block hemichannel or gap junction function prior to downregulation of connexin protein expression by the polynucleotide or oligonucleotide. In some embodiments the connexin modulator is a connexin 43 modulator.

The pharmaceutical formulations of this invention may further comprise one or more pharmaceutically acceptable excipients suitable for delivering the modulators, including gap junction, connexin and/or pannexin and pannexin channel modulators to the eye. In some aspects, administering a pannexin modulator, or a connexin modulator (for example, a connexin 43 modulator or connexin 45 modulator, preferably a connexin 43 modulator), to the eye of a subject provides therapeutically effective amounts of the connexin modulator or pannexin modulator to the eye or specific compartment of the eye. In some instances the gap junction, connexin and/or, pannexin modulator may be administered by topical, corneal, intravitreal, subconjunctival, or periocular administration. In some aspects, administration may also be intraperitoneal administration or parenteral administration, provided that a therapeutically effective dose contacts the eye. In some aspects of the methods of this invention, the gap junction, connexin and/or pannexin modulator may be administered to the eye by injection, for example, by intraocular injection, intravitreal injection or by periocular routes including subconjunctival, retrobulbar, peribulbar, and posterior sub-Tenon injections. In some aspects, the gap junction, connexin and/or pannexin modulator may be provided to or injected directly into or near the trabecular meshwork. In some aspects, sub-conjunctival administration may provide for sustained delivery, while minimizing the dose frequency. In some embodiments, subconjunctival administration may increase the bioavailabiltiy of hydrophilic drugs because they do not have to penetrate the conjunctival epithelium. In some embodiments, a microneedle, needle, iontophoresis device or implant may be used for administration of the connexin modulator or pannexin modulator. The implant can be, for example, a dissolvable disk material such as that described in S. Pflugfelder et al., ACS Nano, 9 (2), pp 1749-1758 (2015). The modulator, e.g. gap junction, connexin and/or pannexin or pannexin channel modulator of this invention may also be administered at or near the trabecular meshwork or ciliary body, so that the gap junction, connexin and/or pannexin or pannexin channel modulator contacts the trabeular meshwork and/or the ciliary body, respectively. The modulator, e.g. gap junction, connexin and/or pannexin and/or pannexin channelmodulator may be administered once, or more than once. The connexin modulator may be, for example, a connexin 43 modulator or a connexin 45 modulator, preferably be a connexin 43 modulator. In some embodiments a microneedle may be used to deliver any of the compositions of this invention to the choroid.

For example, in some embodiments, a modulator, such as a connexin 43 modulator, is administered to the subject, e.g. the eye of the subject, providing therapeutically effective amounts of the modulator to the eye or specific compartment of the eye. In some instances the modulator, e.g. connexin 43 or pannexin 1 or pannexin 1 channel modulator, may be administered by topical, corneal, intravitreal, subconjunctival, or periocular administration. In some aspects, administration may also be intraperitoneal administration. In some embodiments, a microneedle, needle, iontophoresis device, or implant may be used for administration of the modulator, e.g. connexin 43 modulator. The modulators, e.g. connexin 43 modulators, of this invention may also be administered to the trabecular meshwork or ciliary body. In some aspects, the modulators, e.g. connexin 43 modulators of this invention may be administered via intraventricular, and/or intrathecal, and/or extradural, and/or subdural, and/or epidural routes.

A modulator, e.g. a gap junction channel modulator, such as peptide 5, and/or an analogue or prodrug thereof, compounds of formula I, for example tonabersat, and analogs or prodrugs of any of the foregoing compounds, and/or a pannexin or pannexin channel modulator, e.g., compounds of formula VI, for example probenecid and an analogues or prodrugs thereof, and/or a synthetic mimetic peptide blocker of pannexin 1, e.g., $^{10}$Panx1, or an analogue or prodrug thereof may be administered alone or in combination with one or more additional ingredients and may be formulated into pharmaceutical compositions including one or more pharmaceutically acceptable excipients, diluents and/or carriers.

"Pharmaceutically acceptable diluents, carriers and/or excipients" is intended to include substances that are useful in preparing a pharmaceutical composition, may be co-administered with compounds of formula I, for example tonabersat, and analogs of any of the foregoing compounds, while allowing it to perform its intended function, and are generally safe, non-toxic and neither biologically nor otherwise undesirable. Pharmaceutically acceptable diluents, carriers and/or excipients include those suitable for veterinary use as well as human pharmaceutical use. Suitable carriers and/or excipients will be readily appreciated by persons of ordinary skill in the art, having regard to the nature of compounds of formula I, for example tonabersat, and analogs of any of the foregoing compounds. However, by way of example, diluents, carriers and/or excipients include solutions, solvents, dispersion media, delay agents, polymeric and lipidic agents, emulsions and the like. By way of further example, suitable liquid carriers, especially for injectable solutions, include water, aqueous saline solution, aqueous dextrose solution, and the like, with isotonic solutions being preferred for intravenous, intraspinal, and intracisternal administration and vehicles such as liposomes being also especially suitable for administration of agents.

Compositions may take the form of any standard known dosage form including tablets, pills, capsules, semisolids, powders, sustained release formulation, solutions, suspensions, elixirs, aerosols, liquids for injection, gels, creams, transdermal delivery devices (for example, a transdermal patch), inserts such as ocular inserts, or any other appropriate compositions. Persons of ordinary skill in the art to which the invention relates will readily appreciate the most appropriate dosage form having regard to the nature of the condition to be treated and the active agent to be used without any undue experimentation. It should be appreciated that one or more of gap junction channel modulator, such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof may be formulated into a single composition. In certain embodiments, preferred dosage forms include an injectable solution and an oral formulation.

Compositions of the invention may contain any appropriate level of modulator, e.g. gap junction channel modulator, such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof, having regard to the dosage form and mode of administration. However, by way of example, compositions of use in the invention may contain from approximately 0.1% to approximately 99% by weight, preferably from approximately 1% to approximately 60% by weight, of compounds of formula I, for example tonabersat, and analogs of any of the foregoing compounds, depending on the method of administration.

In addition to standard diluents, carriers and/or excipients, a composition in accordance with the invention may be formulated with one or more additional constituents, or in such a manner, so as to enhance the activity or bioavailability of gap junction channel modulator, such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof, help protect the integrity or increase the half-life or shelf life thereof, enable slow release upon administration to a subject, or provide other desirable benefits, for example. For example, slow release vehicles include macromers, poly(ethylene glycol), hyaluronic acid, poly(vinylpyrrolidone), or a hydrogel. By way of further example, the compositions may also include preserving agents, solubilising agents, stabilising agents, wetting agents, emulsifying agents, sweetening agents, colouring agents, flavouring agents, coating agents, buffers and the like. Those of skill in the art to which the invention relates will readily identify further additives that may be desirable for a particular purpose.

Compounds of Formula I, for example tonabersat, and analogs of any of the foregoing compounds, may be administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773,919; EP 58,481), copolymers of L-glutamic acid and gamma-ethyl-L-glutamate, poly(2-hydroxyethyl methacrylate), ethylene vinyl acetate, or poly-D-(−)-3-hydroxybutyric acid (EP 133,988). Sustained-release compositions also include a liposomally entrapped compound. Liposomes containing compounds of formula I, for example tonabersat, and analogs of any of the foregoing compounds, may be prepared by known methods, including, for example, those described in: DE 3,218,121; EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mole percent cholesterol, the selected proportion being adjusted for the most efficacious therapy. Slow release delivery using PGLA nano- or microparticles, or in situ ion activated gelling systems may also be used, for example.

Additionally, it is contemplated that a pharmaceutical composition in accordance with the invention may be formulated with additional active ingredients or agents which may be of therapeutic or other benefit to a subject in particular instances. Persons of ordinary skill in the art to which the invention relates will readily appreciate suitable additional active ingredients having regard to the description of the invention herein and nature of the disorder to be treated.

The compositions may be formulated in accordance with standard techniques as may be found in such standard references as Gennaro AR: Remington: The Science and Practice of Pharmacy, $20^{th}$ ed., Lippincott, Williams & Wilkins, 2000, for example. However, by way of further example, the information provided in US2013/0281524 or U.S. Pat. No. 5,948,811 may be used.

In certain embodiments, the invention provides a combination product comprising (a) compounds of formula I, for example tonabersat, and analogs of any of the foregoing compounds and (b) one or more additional active agent wherein the components (a) and (b) are adapted for administration simultaneously or sequentially.

In a particular embodiment of the invention, a combination product in accordance with the invention is used in a manner such that at least one of the components is administered while the other component is still having an effect on the subject being treated.

The gap junction channel modulator, such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof and one or more additional active agent may be formulated in suitable form for direct administration to a subject (for example, as an agent or pharmaceutical composition). Alternatively, the combination product may comprise one or more pharmaceutical carrier compositions in one or more separate containers; the agent(s) being mixed with a one or more pharmaceutical carrier composition prior to administration.

The compounds of formula I, for example tonabersat, and analogs of any of the foregoing compounds and one or more additional active agent may be contained in the same or one or more different containers and administered separately, or mixed together, in any combination, and administered concurrently.

The combination product may also comprise additional agents and compositions in further separate containers as may be necessary for a particular application.

Any container suitable for storing and/or administering a pharmaceutical composition may be used in a combination product of the invention. Suitable containers will be appreciated by persons skilled in the art. By way of example, such containers include vials and syringes. The containers may be suitably sterilised and hermetically sealed.

Such combination products may be manufactured in accordance with the methods and principles provided herein and those known in the art.

Also provided is combination product used in a method as herein described.

The pharmaceutical compositions of this invention include, for example, ocular delivery forms and formulations. Such delivery forms and formulations include those for the treatment of a subject as disclosed herein. The pharmaceutical formulations of this invention may further comprise one or more pharmaceutically acceptable excipients. The pharmaceutically acceptable excipients for ocular administration may be ophthalmologically acceptable excipients. In some aspects, the formulations may provide for sustained delivery of the connexin modulator and/or ocular treatment agent to a selected segment or compartment of the eye. The formulations may, in some aspects, provide high ocular drug bioavailability, be safe and non-toxic, and/or have little systemic side effects or complications at the site of administration. Exemplary polynucleotide formulations for use in the methods of this invention have the ease of localized delivery, ease of administration and a "no side effect" profile.

In some embodiments the pharmaceutical formulations of this invention may comprise any of the modulators, e.g. gap junction and/or connexin modulators or pannexin modulators described herein, for example, a modified or unmodified connexin 43 antisense oligonucleotide or polynucleotide or a modified or unmodified connexin 43 peptide or peptidomimetic. Connexin 43 antisense oligonucleotide that are included in the formulation may be, in some embodiments, an unmodified connexin 43 antisense oligodeoxynucleotide or a modified connexin 43 antisense oligodeoxynucleotide. In some aspects, the pharmaceutical compositions can include or exclude any of the foregoing.

In some aspects, administering a modulator, for example, a connexin modulator, pannexin modulator, and/or a gap junction modulator (for example, a connexin 43 modulator or a Cx45, Cx26, Cx30, Cx31.1, Cx36, Cx37, Cx40, Cx45, Cx50, Cx57, or any other connexin in the eye), to the eye of a subject provides therapeutically effective amounts of the connexin modulator or pannexin modulator to the eye or specific compartment of the eye. The connexin modulator may preferably be a connexin 43 modulator. In some instances the pannexin modulator or connexin modulator may be administered by topical, intravitreal, subconjunctival, or periocular administration. In some aspects, administration may also be intraperitoneal administration or parenteral administration, provided that a therapeutically effective dose contacts the eye. In some aspects of the methods of this invention, the connexin modulator or pannexin modulator may be administered to the eye by injection, for example, by intraocular injection, intravitreal injection or by periocular routes including subconjunctival, retrobulbar, peribulbar, and posterior sub-Tenon injections. In some aspects, the connexin modulator may be injected directly into or near the trabecular meshwork. In some aspects, sub-conjunctival administration may provide for sustained delivery, while minimizing the dose frequency. In some embodiments, subconjunctival administration may increase the bioavailabiltiy of hydrophilic drugs because they do not have to penetrate the conjunctival epithelium. In some embodiments, a microneedle, needle, or implant may be used for administration of the connexin modulator. The connexin modulators of this invention may also be administered to the ciliary body. The connexin modulator may be administered once, or more than once. The connexin modulator may be, for example, any of the connexin modulators described herein. In some aspects, the connexin or pannexin modulator can include or exclude any of the foregoing.

The connexin and pannexin channel modulators of this invention may also be administered to the trabecular meshwork or ciliary body.

The connexin and pannexin channel modulators of this invention may also be administered to the trabecular meshwork or ciliary body.

The gap junction, connexin, hemichannel, and/or pannexin modulators, for example, connexin 43 modulators and pannexin 1 modulators may, in some aspects, be formulated to provide controlled and/or compartmentalized release to the site of administration in the eye. In some aspects of this invention, the formulations may be immediate, or extended or sustained release dosage forms. In some aspects, the dosage forms may comprise both an immediate release dosage form, in combination with an extended and/or sustained release dosage form. In some aspects both immediate and sustained and/or extended release of connexin or pannexin modulators can be obtained by combining a modified or unmodified connexin or pannexin antisense oligonucleotide or polynucleotide, together with a modified or unmodified peptide or peptidomimetic in an immediate release form. In some aspects of this invention the connexin modulators are, for example, connexin 43 modulators or other connexin modulators of this disclosure. In some aspects of this invention, the dosage forms may be ocular implants, for example, biodegradable or nonbiodegradable implants.

In some aspects of this invention, the caderin modulator or gap junction and/or connexin modulator, e.g., a connexin 43 modulator, may be formulated for compartmentalized release of the modulator, for example, by adjusting the size or coating of the particles. For example, in some aspects, particle formulations of the caderin modulator or connexin modulator, e.g., a connexin 43 modulator, can be administered for use in the methods of this invention. Ocular drug delivery systems comprising particles may comprise, in some aspects, nanoparticles having a mean diameter of less than 1,000 nm, for example, 1-1000 nm, and/or microparticles having a mean diameter between 1 to 1,000 μm. The nanoparticles or microparticles may be, for example, nanospheres or microspheres, or encapsulated nanocapsules and microcapsules, in which the connexin modulator is encapsulated in a polymeric coating. The particle formulations may also comprise liposomes. In some aspects the connexin modulator is can include or exclude a modulator of connexin 45, Cx26, Cx30, Cx31.1, Cx36, Cx37, Cx40, Cx50, or Cx57 or any other connexin in the eye or blood vessels.

In some aspects, the gap junction and/or connexin modulator or pannexin modulator can be formulated for targeted delivery to the choroid and/or retina following peripheral administration, for example, intravenous or intraperitoneal administration. In some aspects, the connexin modulator may be, for example, a connexin 43 modulator or other connexin modulators of this disclosure.

In some aspects, the formulation for targeted delivery to the choroid and/or retina can comprise the administering of gap junction and/or connexin modulator or pannexin modulator infused particles that present an ocular targeting moiety on the surface of the particles.

The invention comprises methods for modulating the function of a gap junction channel and/or a hemichannel and for the treatment of various disorders. It should be appreciated that such methods may be performed in vivo, ex vivo and/or in vitro, as is appropriate. In certain embodiments, the methods may be performed for experimental and/or non-therapeutic purposes. In certain embodiments, such methods may comprise the step of administering gap junction channel modulator, such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof to one or more cell or a sample comprising one or more cell in vitro or ex vivo. In other embodiments, such methods may comprise the step of administering a gap junction channel modulator, such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof to a subject.

Methods of the invention comprise administering modulator, e.g. a gap junction channel modulator, such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof alone or in a combination with one or more other agents (including for example active agents) or therapies as may be desired.

Administration of a modulator, e.g. a gap junction channel modulator, such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof to a subject may occur by any means capable of delivering the agents to a target site within the body of a subject. By way of example, gap junction channel modulator, such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof may be administered by one of the following routes: oral, topical, systemic (eg. Intravenous, intra-arterial, intra-peritoneal, transdermal, intranasal, or by suppository), parenteral (eg. intramuscular, subcutaneous, or intravenous or intra-arterial injection), by implantation, and by infusion through such devices as osmotic pumps, transdermal patches, and the like. Skilled persons may identify other appropriate administration routes. Exemplary administration routes are also outlined in: Binghe, W. and B. Wang (2005). Drug delivery: principles and applications, Binghe Wang, Teruna Siahaan, Richard Soltero, Hoboken, N.J. Wiley-Interscience, c2005. In one embodiment, gap junction channel modulator, such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof is administered systemically. In another embodiment, gap junction channel modulator, such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof is administered orally. In another embodiment, gap junction channel modulator, such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof is administered topically.

In another embodiment, compounds of formula I, for example tonabersat, and analogs of any of the foregoing compounds is administered systemically, such as by intravenous, intra-arterial or intraperitoneal administration, such that the final circulating concentration is from approximately 0.001 to approximately 150 micromolar, or higher up to 200, 300, 400, 500, 600, 700, 800, 900 or 1000 micromolar. The final circulating concentration can be 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2., 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 100, 110, 120, 130, 140, or 150 micromolar, or any concentration between any of the two recited numbers, or higher as described above and any concentration within the ranges noted. As mentioned herein, the invention also comprises combination therapies in which one or more additional active agent is also administered to a subject. Skilled persons will appreciate desirable dosages for the one or more active agent having regard to the nature of that agent and the principles discussed herein before.

A modulator, e.g. a gap junction channel modulator, such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof may be used in the invention alone or in combination with one or more additional agent or composition of use in the treatment of a particular disorder. Co-administration may allow for improved alleviation or amelioration of one or more symptoms, reduction of the length or extent of a disease, delay or slowing of the progression of disease, amelioration, palliation or stabilization of the disease state, partial or complete remission, prolonged survival and/or other beneficial therapeutic results. Such treatments may be administered simultaneously or sequentially in any order with a period of time between administrations. One of skill in the art will readily appreciate methods of administering agents or therapies simultaneously or sequentially and possible time periods between administrations. The therapies may be administered by the same or different routes.

In certain embodiments, treatment according to the invention may involve the administration of one or more other agents to a subject. For example, one or more agents of use in promoting the general health of a subject, or reducing one or more side-effects of therapy could be administered. Skilled persons will readily appreciate various agents which may be beneficial to administer having regard to the disease to be treated, for example. In some embodiments where a pannexin modulator is initially co-administered with a gap junction channel modulator, the administration of the pannexin modulator may be stopped or tapered, while administration of the gap junction channel modulator continues. In some embodiments a pannexin modulator may be administered immediately after or shortly after an ischemic injury, while a gap junction channel modulator may be administered post-ischemia.

Administration of a modulator, e.g. a gap junction channel modulator, such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof, and optionally one or more other active agent, may occur at any time during the progression of a disorder, or prior to or after the development of a disorder or one or more symptom of a disorder. In one embodiment, gap junction channel modulator, such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof is administered on a daily basis for an extended period to assist with ongoing management of symptoms. In another embodiment, gap junction channel modulator, such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof is administered on a daily basis for an extended period or life-long to prevent or delay the development of a disorder.

Preferably the modulator, e.g. gap junction, connexin, and/or pannexin or pannexin channel modulators of the invention are combined with a pharmaceutically acceptable carrier or diluent to produce a pharmaceutical composition. The term "pharmaceutically acceptable carrier" refers to any pharmaceutical carrier that does not itself induce the production of antibodies harmful to the individual receiving the composition, and which can be administered without undue toxicity.

"Pharmaceutically acceptable carrier" for ocular administration will be opthalmologically acceptable carriers.

Pharmaceutically acceptable salts can also be present, e.g., mineral acid salts such as hydrochlorides, hydrobromides, phosphates, sulfates, and the like; and the salts of organic acids such as citrates, acetates, propionates, malonates, benzoates, and the like.

Suitable carriers and diluents include buffered, aqueous solutions, saline, dextrose, glycerol, isotonic saline solutions, for example phosphate-buffered saline, isotonic water, and the like and combinations thereof. In some embodiments, carriers may include propylene glycol, dimethyl isosorbide, and water, and even more particularly, phosphate buffered saline, isotonic water, deionized water, monofunctional alcohols and symmetrical alcohols. In some embodiments pharmaceutically acceptable carrier or diluent may be or contain a thermosetting poloxamer (which may be a liquid or gel, depending on the temperature), a carboxycellulose (e.g. carboxymethylcellulose), a collagen (e.g., a Type I collagen), a collagenous material comprising tropocollagen, a hyaluronan or derived-hyaluronic acid, and/or an oil (e.g., Emu oil). Suitable carriers can be large, slowly metabolized macromolecules such as proteins, polysaccharides, polylactic acids, polyglycolic acids, polymeric amino acids, and amino acid copolymers. The pharmaceutical compositions of this invention do not comprise a connexin modulator in sterile water as the only vehicle. In some embodiments, the formulations will comprise pannexin or connexin modulators, for example, connexin 43 modulators, for example, 43 antisense oligonucleotide that are included in the formulation may be, in some embodiments, an unmodified or modified connexin 43 antisense oligodeoxynucleotide.

In one aspect the reverse-thermosetting gel may be a liquid at low temperatures, for example at 2-8° C., and which undergoes a reversible liquid to gel transition at temperatures greater than approximately 15° C. Thus, in some embodiments the carrier may be a liquid at temperatures below approximately 15° C., but may form a gel at temperatures above approximately 15° C., such as room temperature or at body temperature. In some instances, the gel is a nonionic polyoxyethylene-polyoxypropylene copolymer gel. In some embodiments the gel is a pluronic gel. The pluronic gel may be, for example, poloxamer 407, also sometimes referred to as Pluronic F-127 (BASF). In some embodiments, the formulations of this invention may comprise from about 15 to about 30% (w/v) gel. In some embodiments, the formulations of this invention may comprise from about 20 to about 25% (w/v) gel. In some embodiments, the formulations of this invention may comprise about 22.6% (w/v) poloxamer 407 gel. Other suitable formulations include pluronic gel-based formulations, hydroxymethylcellulose formulations, hydroxyethylcellulose formulations, carboxymethylcellulose(CMC)-based formulations, and hydroxypropylmethylcellulose(HPMC)-based formulations. The composition may be formulated for any desired form of delivery, including topical, instillation, parenteral, intramuscular, subcutaneous, or transdermal administration. Other useful formulations include slow or delayed release preparations.

In addition, if desired substances such as wetting or emulsifying agents, stabilizing or pH buffering agents, or preservatives may also be present. In some embodiments, the pharmaceutical compositions of this invention will comprise suitable ophthalmically acceptable buffers, such as acetate buffers, citrate buffers, phosphate buffers, borate buffers and mixtures thereof. In some embodiments, the buffers useful in the present invention include boric acid, sodium borate, sodium phosphates, including mono, di- and tri-basic phosphates, such as sodium phosphate monobasic monohydrate and sodium phosphate dibasic heptahydrate, and mixtures thereof. In some emboidments, the preservative may be stabilized chlorine dioxide, cationic polymers or quaternary ammonium compounds. In some embodiments the pharmaceutical compositions may also comprise wetting agents, nutrients, viscosity builders, antioxidants, and the like, for example, disodium ethylene diamine tetraacetate, alkali metal hexametaphosphate, citric acid, sodium citrate, sodium metabisulfite, sodium thiosulfate, N-acetylcysteine, butylated hydroxyanisole, butylated hydroxytoluene, polyvinyl alcohol, polyoxamers, polyvinyl pyrrollidone, hydroxypropyl methyl cellulose, hydroxyethylmethyl cellulose, and mixtures thereof and mixtures thereof. In some embodiments, the pharmaceutical formulations of this invention will not include a preservative.

Where the modulator, e.g. gap junction, connexin, and/or pannexin or pannexin channel modulator is a nucleic acid, such as a polynucleotide, uptake of nucleic acids by mammalian cells is enhanced by several known transfection techniques for example those including the use of transfection agents. Such techniques may be used with certain anti-connexin agents, including polynucleotides. The formulation that is administered may contain such transfection agents. Examples of these agents include cationic agents (for example calcium phosphate and DEAE-dextran) and lipofectants (for example Lipofectam™ and Transfectam™), and surfactants.

Where the gap junction, connexin, and/or pannexin modulator comprises a polynucleotide, conveniently, the formulation further includes an agent to assist with cell penetration or the formulation may contain any suitable loading agent, such as a surfactant, a signalling molecule such as an antenna peptide, or any other agent suitable for administration to the eye.

In one embodiment of the invention, the modulator, e.g. gap junction, connexin, and/or pannexin or pannexin channel modulators of the present invention are topically administered. Topical formulations of the gap junction, connexin, and/or pannexin modulators can comprise ointments, gels, which may be, for example, thermosetting gels, drops, sprays, liquids and powders, or a sustained or non-sustained release dosage form.

In some embodiments, the modulator, e.g. the gap junction, connexin, and/or pannexin or pannexin channel modulators, for example, a connexin 43 modulator, can be administered as a pharmaceutical composition comprising one or a plurality of particles. In some aspects the pharmaceutical composition may be, for example, an immediate release formulation or a controlled release formulation, for example, a delayed release particle.

In some aspects, a modulator, e.g. pannexin or connexin modulators, for example, connexin 43 and pannexin 1 modulators, gap junction modulators, etc., can be formulated in a particulate formulation one or a plurality of particles for selective delivery to the physiological region to be treated. In some embodiments, the particle can be, for example, a nanoparticle, a nanosphere, a nanocapsule, a liposme, a polymeric micelle, or a dendrimer. In some embodiments, the particle can be a microparticle. The nanoparticle or microparticle can comprise a biodegradable polymer.

In some aspects, a modulator, e.g. pannexin or connexin modulators, for example, connexin 43 and pannexin 1 modulators, gap junction modulators, etc., are formulated to provide compartmentalized release to the site of administration. In some aspects of this invention, the modulator may be formulated for compartmentalized release of the modulator, for example, by adjusting the size or coating of the particles. For example, in some aspects, particle formulations of a connexin 43 modulator or a pannexin 1 modulator or a hemichannel modulator or a gap junction modulator can be administered for use in the methods of this invention. Ocular drug delivery systems comprising particles may comprise, in some aspects, nanoparticles a mean diameter of less than 1,000 nm or microparticles between 1 to 1,000 m, as determined, for example, by scanning electron microscopy. The nanoparticles or microparticles may be, for example, nanospheres or microspheres, or encapsulated nanocapsules and microcapsules, in which the connexin modulator is encapsulated in a polymeric or lipid coating. Other methods may be employed to measure the particle size, including but not limited to light scattering, zeta potential analysis, coulter counting (electrical sensing zone method), and optical microscopy.

The nanoparticle or microparticle can comprise poly (lactic-co-glycolic acid) ("PLGA") loaded with the gap junction, connexin, and/or pannexin modulators, for example, connexin 43 modulators. The modulators can be loaded into the particle volume, onto the particle exterior surface, or both.

In some embodiments, the biodegradable particle can be a particle selected from one of the following particle types: polylactide (PLA) nanoparticles, poly-DL-lactic acid (PDLLA) microspheres or nanospheres, poly (lactic acid) nanoparticles or microparticles, chitosan-modified poly (D,L-lactide-co-glycolide) nanospheres and microspheres (CS-PLGA NSs), chitosan-alginate coated nanoparticles or microparticles, solid lipid nanoparticles or microparticles (SLNs), silicon nanoparticles or microparticles, polylactic-co-glycolic acid (PLGA) nanoparticles or microparticles, polylactic-co-glycolic acid (PLGA) nanoparticles or microparticles, pH-sensitive Eudragit P-4135F nanoparticles or microparticles, thioketal nanoparticles or microparticles (TKNs) made from the polymer poly-PPADT (1,4-phenyleneacetone dimethylene thioketal), lipopolysaccharides (LPS), alginate nanoparticles or microparticles, phospholipid nanoparticles or microparticles, and type B gelatin enclosed in poly(e-caprolactone) (PCL) microspheres and nanospheres. In some embodiments, the particle is a polylactic-co-glycolic acid (PLGA) nanoparticles or microparticles. The connexin 43 modulator may also be entrapped in microcapsules or nanocapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, polymeric micelles, liposomes and pegylated liposomes, albumin microspheres, microemulsions, nano-particles, and nanocapsules), or in macroemulsions. Such techniques are disclosed in Remington's Pharmaceutical Sciences (1980) 16th edition, Osol, A. Ed., and herein incorporated by reference.

In some aspects, the formulation for targeted delivery to the choroid and/or retina can comprise the administering of a modulator, e.g. a gap junction and/or connexin modulator, or pannexin modulator infused particles that present a targeting moiety on the surface of the particles. In some aspects, the targeting moiety on the surface can be covalently-linked by EDAC coupling (N-(3-dimethylaminopropyl)-N'-ethylcarbodiimide hydrochloride) transferrin protein. In some aspects, the targeting moiety on the surface can be covalently-linked RGD peptide (with the peptide sequence GRGDSPK, SEQ ID NO: 233). The particles can be nanoparticles or microparticles. In some aspects, the nanoparticles can be from about 200 nm to 450 nm in diameter. In some aspects, the particles can comprise a polymer as described above. In some aspects, the particles can comprise poly-(lactide-co-glycolide). In some embodiments, the gap-junction and/or connexin modulator can be infused into the particle as the particle is being synthesized via emulsion preparation. In some embodiments, the gap-junction and/or connexin or pannexin modulator can be infused into the particles as described in Singh, S. R. et al., *Gene Therapy,* 16:645-659 (2009) and herein incorporated by reference) after the particles have been synthesized by diffusion into the particles.

In some embodiments, the particles can comprise both a peptide for targeted delivery to the choroid and/or retina for targeted delivery and a peptide for use as a cellular internalization transporter. The particle can be a microparticle or nanoparticle, as described herein. The peptide for targeted delivery to the choroid and/or retina can be the RGD peptide covalently liked to the particle, as described herein. The peptide for use as a cellular internalization transporter can be presented at the exterior surface of the particle or within the particle as fused to the gap junction and/or connexin modulator. The fusion can be via a covalent bond, hydrogen bond or bonds, electrostatic interaction, or van der Walls interaction. The peptide for use as a cellular internalization transporter can be any peptide listed in Table 65 of this disclosure.

In some embodiments, the modulator, e.g. gap junction and/or connexin modulator, pannexin modulator or pannexin channel modulator formulated for targeted delivery to the choroid and/or retina following peripheral administration, can be administered by intravenous or intraperitoneal injection. In some aspects, the connexin modulator may be, for example, a connexin 43 modulator. In some aspects, the gap junction and/or connexin modulator or pannexin modulator formulated for targeted delivery to the choroid and/or retina following peripheral administration, can be administered by periocular delivery to the eye. In some aspects, the formulation for periocular delivery can be in the form of eye drops or a gel or a contact lens infused with the gap junction and/or connexin modulator or pannexin modulator formulation.

In some embodiments, the modulator, e.g. gap junction and/or connexin modulator, pannexin modulator or pannexin modulator can be formulated for targeted delivery by forming a complex with a choroid or retina-targeting agent. The complex can be formed by a covalent bond, hydrogen bond or bonds, electrostatic interaction, or van der Walls interaction.

In some aspects, the modulator, e.g. gap junction, connexin, or pannexin orpannexin channel modulators of this invention can be directly bound to compounds that target the choroid and or retina, or which function as an cell interanalization transporter.

Administering a modulator, e.g. a connexin modulator, for example, a connexin 43 modulator to the eye of a subject means administering the modulator to the subject, to provide therapeutically effective amounts of the connexin 43 modulator to the eye or specific compartment of the eye. In some instances the connexin modulator, for example, a connexin 43 modulator, may be administered by topical, corneal, intravitreal, subconjunctival, or periocular administration. In some aspects, administration may also be intraperitoneal administration. In some embodiments, a microneedle, needle, or implant may be used for administration of the connexin 43 modulator. The connexin 43 modulators of this invention may also be administered to the ciliary body. In some aspects, the connexin 43 modulators of this invention may be administered via intraventricular, and/or intrathecal, and/or extradural, and/or subdural, and/or epidural routes.

In some aspects, the modulator, e.g. gap junction, connexin 43, pannexin 1 and pannexin channel modulators of this invention are formulated for ocular administration. The modulators, e.g. connexin 43 and other modulators may, in some aspects, be formulated to provide controlled and/or compartmentalized release following administration. In some aspects, the formulations may be immediate, or extended or sustained release dosage forms. In some aspects, the dosage forms may comprise both an immediate release dosage form, in combination with an extended and/or sustained release dosage form. In some aspects both immediate and sustained and/or extended release of modulators, e.g. connexin 43 modulators, can be obtained by combining a modified or unmodified connexin 43 antisense oligonucleotide or polynucleotide, together with a modified or unmodified peptide or peptidomimetic in an immediate release form. In some aspects, the dosage forms may be implantable.

In some embodiments, the compositions are isotonic with the fluids of the eye, and may have an osmolality of at least about 200 mOsmol/kg, preferably in the range of about 200 to about 350, or about 400 mOsmol/kg. The compositions may comprise, for example, sodium chloride, potassium chloride, calcium chloride and/or magnesium chloride.

In some embodiments, any of the modulators, e.g. gap junction channe, pannexin channe, pannexin or connexin modulators of this disclosure, such as connexin 43 and pannexin 1 channel modulators, is formulated to provide compartmentalized release to the site of administration. In some aspects of this invention, the pannexin or connexin modulator may be formulated for compartmentalized release of the modulator, for example, by adjusting the size or coating of the particles. For example, in some aspects, particle formulations of the modulator, e.g. pannexin modulator or the connexin modulator, for example, a connexin 43 modulator, can be administered for use in the methods of this invention. Ocular drug delivery systems comprising particles may comprise, in some aspects, nanoparticles having a mean diameter of less than 1,000 nm, for example, 1-1000 nm, and/or microparticles having a mean diameter between 1 to 1,000 μm. The nanoparticles or microparticles may be, for example, nanospheres or microspheres, or encapsulated nanocapsules and microcapsules, in which the modulator, e.g. connexin modulator is encapsulated in a polymeric and/or lipid coating.

In some embodiments the formulated modulator is a connexin 43 or connexin 45 modulator, preferably a connexin 43 modulator.

In other embodiments of any formulation, dose or delivery method described herein, the modulator is a pannexin channel modulator, preferably a pannexin 1 channel modulator. In still other embodiments of any formulation, dose or delivery method described herein, the modulator is a gap junction or hemichannel channel modulator, and preferably in some embodiments, a connexin43 or connexin43 gap junction channel or hemichannel modulator Particle formulations may be administered, for example, intraocularly by injection, or intravitreally, subconjunctivally, or periocularly. The size and polymer composition of the particles can be selected to control the release of the modulator, e.g. connexin 43 modulator from the particles, for example, the timing and location of release of the modulator. For example, in some aspects of this invention, modulator, e.g. connexin 43 hemichannel or pannexin 1 channel modulators formulated as poly-lactic acid (PLA) microspheres may be remain in the compartment of the eye to which they were administered for more than 1, 2, 3, 4, 5, 6, or 7 days, or more than one week, more than 10 days, more than 2, 3, 4, 5, or 6 weeks, or longer. In some aspects, modulator microparticles delivered intravitreally by injection or a microneedle may provide sustained release of the modulator. In other aspects, smaller particles such as nanoparticles comprising modulators, may diffuse rapidly from one compartment of the eye to another, any may be readily internalized in ocular tissues and cells of the anterior and posterior segments of the eye. Intravitreal delivery of polylactide nanoparticles comprising connexin 43 or other modulators may, in some aspects of this invention, provide delivery across the retina with preferential localization in retinal pigment epithelium cells for 1, 2, 3, 4, 5, 6, or 7 days, or more than one week, more than 10 days, more than 2, 3, 4, 5, 6, 7, 8, 9, 10, 11, 12, 13, 14, 15, or more than 16 weeks. Nanosphere and microsphere ocular drug delivery formulations of connexin 43 or other modulators can, in some aspects, enhance cellular penetration, improve bioavailability, for example, by protecting against degradation, and/or provide sustained delivery. In some embodiments, formulations comprising larger nanoparticles (greater than 150, 200, 300, 400, 500, 600, 700, 800, 900 nm) or microparticles, for example, particles having a mean diameter between 150 nm and 9 micrometers, or between 1 and 9 micrometers, for example, 1, 2, 3, 4, 5, 6, 7, 8 micrometers, or any range between any two of the recited mean diameters may be suitable for compartmentalized ocular administration as a result of slower release and/or diffusion from the particles of this size.

The particle formulations of any of the pannexin, or connexin modulators of this disclosure, such as connexin 43 modulators may also comprise liposomes. In some aspects, the liposomes may have a diameter ranging between 50 nm to a few micrometers. In some aspects the liposomes can be injected, or applied topically or subconjunctivally to a segment or compartment of the eye, and may, in some embodiments, provide slow drug release from a relatively inert dosage form. The liposome formulations may also have fewer side effects, because only a limited amount of connexin 43 μgents or other ocular treatment compounds come in direct contact with ocular tissues.

Increased corneal penetration into the anterior segments can be achieved with the addition of permeability enhancers to the drug formulation. Cell penetration agents may also be used to enhance deliver of the connexin 43 modulator to RGC neurons or other cells in the eye. Formulations may also contain, for example, surfactants, bile acids, chelating agents, and/or preservatives. In some embodiments, formulations for intravitreal administration may be free of preservatives.

As used herein, "matrix" includes for example, matrices such as polymeric matrices, biodegradable or non-biodegradable matrices, and other carriers useful for making implants or applied structures for delivering the connexin modulators and/or ocular neuropathic treatment agents.

Ocular Implants

In some embodiments, the dosage forms of this invention may be ocular implants. In some embodiments, the implants may be implanted, for example intravitreally, suprachoroidally, intrasclerally, or subconjunctivally. Ocular implants deliver sustained levels of modulator, e.g. connexin and/or pannexin modulators, to the desired ocular site, and bypassing the blood-brain barrier. Implants may be implanted, for example, subconjunctivally, into the episcleral or intrascleral space, in contact with the sclera, into the vitrous cavity. Intrascleral administration for use with the connexin modulators of this invention may, in some embodiments, be useful for delivery to the posterior segment of the eye, with lower systemic absorption of the modulator than subconjunctival or peribulbar administration. Implants may also be placed intravitreally, which permits delivery to the posterior segment of the eye. In some embodiments, the implant can be inserted intravitreally through a sclerotomy site, for example, over the pars plana.

Subconjunctival implants may be inserted through a small incision in the conjunctiva and placed in contact with the sclera. Intrascleral devices, implanted in a small scleral pocket at one-half the total scleral thickness, may also be used, and are useful for delivery to the posterior of the eye with less systemic absorption of the drug than subconjunctival or peribulbar injections.

Intravitreal placement of ocular implants also permits delivering a drug directly to target tissues of the posterior segment. The implant may be inserted into the vitreous, for example, through a sclerotomy site, or injected with an applicator. The site of implantation is commonly over the pars plana, which is anterior to the insertion of the retina and posterior to the lens, to minimize damage to those structures.

In some embodiments where the dosage form is an implant, the implant, may, in some embodiments, comprise at least one copolymer coating comprising a connexin 43 modulator and a biodegradable and biocompatible copolymer and at least one coating comprising a biodegradable polyester and a connexin 43 modulator. In some embodiments, the dosage form may have an inner coating comprising a biodegradable polyester and a connexin 43 modulator and an outer coating comprising a connexin 43 modulator and a biodegradable and biocompatible copolymer.

The dosage form core or implant may comprise a connective tissue blended with a biodegradable polymer. In some embodiments, the connective tissue may comprise one or more of the following connective tissues: collagen, elastin, and chondroitin-4-sulfate. In some embodiments, the connective tissue may be present at an amount about 50-99% collagen (w/w). In some embodiments, the biodegradable polymer may comprise a biodegradable polyester polymer. In some embodiments, the polyester polymer may comprise one or more of the following selected biodegradable polyester polymers: poly(L-lactide), poly(glycolide), poly(DL-lactide), poly(dioxanone), poly(DL-lactide-co-L-lactide), poly(DL-lactide-co-glycolide), poly(glycolide-co-trimethylene carbonate), and poly(caprolactone) ("polycaprolactone"). In some embodiments, the polyester polymer may comprise polycaprolactone (PCL). In some embodiments, the amount of polycaprolactone may be present at an amount about 1-50% polycaprolactone (w/w). In some embodiments, the molecular weight of the polycaprolactone may range from 10,000 Da to 3,000,000 Da.

In some embodiments, the collagen and the polymer comprising the implant may be electrospun into fibers to create the implant or core, or a scaffold sheet, from which the desired implant form may be obtained. Alternatively, by controlling fiber orientation during deposition, a three-dimensional implant may be fabricated having a desired shape. Three-dimensional printing may also be used to obtain a core for implantable dosage forms of this invention. Alternatively the scaffold substrate maybe extracted from a natural source and reonstitute itself upon processing into a suitable matrix such as collagenous materials extracted from marine organisms, including but not limited to jellyfish or from mammalian sources including but limited to bovine, equine, ovine sources.

In some embodiments, the implant may be coated with a mixture comprising a modulator, e.g. a connexin or pannexin channel modulator, for example, a connexin 43 or hemichannel modulator. The mixture may also comprise a polymer that temporarily binds the modulator, e.g. pannexin or connexin channel modulator, to the implant ("binding polymer", or "eluting polymer"). Such polymers may include, but are not limited to, one or more of the following homopolymers or copolymers of the following selected polymers: poly(lactic-co-glycolic acid (PLGA), poly(L-lactide), poly(glycolide), poly(DL-lactide), poly(dioxanone), poly(DL-lactide-co-L-lactide), poly(DL-lactide-co-glycolide), poly(glycolide-co-trimethylene carbonate), and polycaprolactone (PCL), Multiple coatings may be applied to the implant to achieve a desired elution profile of the connexin 43 modulator. In some embodiments, each coating layer may be applied by immersing the core or implantable form in a solution of the dissolved binding polymer and the modulator, e.g. connexin or pannexin channel modulator, for example, a connexin 43 hemichannel or gap junction modulator. The core or implantable form may then be removed and freeze-dried (lyophilized) to remove the solvent. Alternatively, the core or implantable form may be removed and subject to quick evaporation by placing the core or implantable form in a vacuum chamber. The core or implantable form comprising the first binding polymer layer may be subsequently immersed into another solution comprising the same or another connexin or pannexin modulator, for example, a modulator, e.g. connexin 43 and/or pannexin 1 channel modulator, than that used in a prior immersion, and further comprising the same binding polymer as used in the prior immersion, or a different binding polymer. The steps of immersion and lyophilization may be repeated up to twenty times to create one or more layers of coating and/or one or more coatings on the core or implantable form.

Practitioners in the art will appreciate that the polymer which temporarily binds the anti-connexin agent to the core or implantable form may comprise any polymer suitable for drug-elution in implants. Such polymers exhibit the following properties: are non-toxic (proportional to their beneficial effect), are metabolized directly or whose hydrolysis products are metabolized, and may easily be sterilized. A review of such applicable materials is found in J. C. Middleton, A. J. Tipton, *Biomaterials,* 21 (2000), 2335-2346, herein incorporated by reference.

Nonbiodegradable or biodegradable polymeric devices for controlled or sustained release may also be used in the methods of this invention. Nonbiodegradable implants can provide steady, controlled release of a desired modulator(s). Biodegradable implants can be manufactured into a desired shape, can be injected in an office or outpatient procedure, and do not require removal.

Nonbiodegradable (Reservoir) Implants

Reservoir implants are typically made with a pelleted drug core surrounded by nonreactive substances such as silicon, ethylene vinyl acetate (EVA), or polyvinyl alcohol (PVA); these implants are nonbiodegradable and can deliver continuous amounts of a drug for months to years.

In some embodiments, the modulators of this invention may be formulated as implantable nonbiodegradable reservoir dosage forms suitable for delivering the connexin modulators, alone, or in combination with other ocular neuropathic treatment agents, for a sustained period of time, for example, over 1 month, or over 2, 3, 4, 5, 6, 7, 8, 9, 10, 11, 12, 13, 14, 15, 16, 17, 18, 19, 20, 21, 22, 23, 24, 30, or over 36 months. In some embodiments, the reservoir dosage forms may comprise a core comprising one or more modulators as described herein, alone, or in combination with other ocular neuropathic treatment agents as described herein, surrounded by a nonreactive coating comprising silicon, such as polydimethylsiloxane (PDMS), ethylene vinyl acetate (EVA), or polyvinayl alcohol (PVA).

Biodegradable Matrix Implants

The dosage forms of this invention may also comprise copolymer implants useful in delivering a loading dose of the modulator, e.g. connexin and/or pannexin channel modulator, as well as tapering doses of the modulator over a sustained period of time lasting up to 6-months or more. Copolymer implants may be made from the copolymers poly-lactic-acid (PLA) and/or poly-lactic-glycolic acid (PLGA), which are biodegraded to water and carbon dioxide. The rate and extent of release of the modulator from the implant can be decreased by altering the relative concentrations of lactide (slower release) and glycolide (faster release), altering the polymer weight ratios, adding additional coats of polymer. Unlike Nonbiodegradable implants, biodegradable implants do not require removal, and provide flexibility in dose and treatment from a short duration of weeks to more sustained release of months to a year or more, depending on the polymer PLA/PLGA ratio. In some aspects, biodegradable dosage forms can be personalized in accordance with the subject's disease progression. In some aspects, the biodegradable matrix implant can be, for example, a dissolvable disk material such as that described in S. Pflugfelder et al., *ACS Nano,* 9 (2), pp 1749-1758 (2015).

Microneedles

In some embodiments, the modulator compounds and formulations of this invention can be administered via microneedles. Microneedles are individual needles or arrays of micrometer-sized needles, as described in Kim, Y. et al., *Invest. Ophthalmol. Vis. Sci.* Nov. 13, 2014 vol. 55 no. 11 7376-7386. In some embodiments, microneedles can be from 500 to 750 micrometers in length, and can be coated with the formulations described herein. An array of microneedles can be used for the administration of formulations of this invention. The shafts of solid microneedles can be coated with formulations of this invention which then dissolve into the regions of the eye after insertion.

In some embodiments, a modulator, e.g. a connexin 43 and/or a pannexin 1 channel modulator, for example, is administered to the subject, providing therapeutically effective amounts of the connexin 43 modulator to the eye or specific compartment of the eye. In some instances the modulator(s), may be administered by topical, intravitreal, subconjunctival, or periocular sub-tenon administration. In some aspects, administration may also be intraperitoneal or other form of systemic administration. In some embodiments, a microneedle, microneedle array, needle, or implant may be used for administration of the modulator(s). In some embodiments a microneedle may be used to administer a modulator as described herein, for example, a connexin 43 modulator, a pannexin channel modulator, a gap junction modulator, and/or a pannexin modulator to the eye, or a specific compartment or structure of the eye, for example, the choroid, suprachoroidal space, or retina, or sclera. For example, a hollow microneedle may be inserted into the sclera, suprachoridal space and the modulator may be administered and/or infused into that location or compartment of the eye. Administration to the choroid may, in some embodiments, be performed by administering the modulator to the suprachoroidal space, from which the infused drug flows circumferentially within the suprachoroid space toward the choroid, retina, macula, optic nerve and other structures and compartments in the back of the eye. In some embodiments, the microneedle may be inserted through the sclera into the suprachoroidal space without penetrating the choroid. In some embodiments, the microneedle may be retracted following infusion. In some embodiments the penetration of the microneedle may be controlled to a desired depth within a tissue, stroma, and/or compartment of the eye. In some embodiments the microneedle may also be coated with the modulators of this invention or other ocular drug agents. In some aspects the volume of modulator and/or ocular drug agent administered by microneedle may be from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 295, or 300 al, or any range of volume between any two of the recited numbers or any volume between any two recited numbers. Any suitable formulation of this invention may be administered by microneedle injection, including, for example, nanoparticle or microparticle formulations, or other formulations injectable by microneedle.

In some aspects, the microneedle comprises a base from which one or more microneedles extend, typically in a direction perpendicular to the base. The microneedle may be solid or hollow. A hollow microneedle may comprise, for example, a single, straight bore through the center of the microneedle, or multiple bores. In some embodiments the hollow microneedles may comprise bores that follow complex paths through the microneedle, multiple entry and exit points from the bore(s), and intersecting or networks of bores that form one or more continuous pathways from the base of the microneedle to an exit point in the shaft and/or tip of the microneedle. See, e.g., U.S. Pat. Nos. 7,918,814, 8,197,435, 8,636,713 and 8,808,225. In some embodiments, microneedles can be from 50 to 2000 micrometers in length, from 50 to 500 micrometers in width (diameter), and can be coated with the formulations described herein. The microneedle can comprise a shaft and a tip. The shaft and tip can be in contact. The tip of the microneedles can be straight or tapered. The tapered microneedle tip can be a point, or a blunt end. In some embodiments, drilling microneedles may also be used. See, for example, U.S. Publication 20050137525. Other microneedles are described in, for example, U.S. Patent Publication Nos. 2006/0086689, 2006/0084942, 2005/0209565, 2002/0082543, U.S. Pat. Nos. 6,334,856, 6,611,707, and 6,743,211.

The microneedle and/or ocular implants can comprise one or more suitable biocompatible materials, including metals, glasses, semi-conductor materials, ceramics, or polymers, for example, pharmaceutical grade stainless steel, gold, titanium, nickel, iron, gold, tin, chromium, copper, and alloys thereof. Polymers for use in microneedles and/or ocular implants can be biodegradable or non-biodegradable. Examples of suitable biocompatible, biodegradable polymers include poly(lactic-co-glycolic acid (PLGA), poly(L-lactide), poly(glycolide), poly(DL-lactide), poly(dioxanone), poly(DL-lactide-co-L-lactide), poly(DL-lactide-co-glycolide), poly(glycolide-co-trimethylene carbonate), and polycaprolactone (PCL), polyanhydrides, polyorthoesters, polyetheresters, polyesteramides, poly(butyric acid), poly(valeric acid), polyacrylamides, polyacrylates, polyurethanes and copolymers and blends and crosslinked variants thereof. The microneedles can comprise one or more shafts for the administration of formulations of this invention. The shafts can be porous or non-porous. The shafts can be hollow or solid. The microneedles can further comprise a tip that is composed of a material which is different from the shaft. The tip of the microneedles can be of a different hardness (as measured by durometry) than the shaft of the microneedles. The tip or shaft or both of the microneedles can be biodegradable or non-biodegradable. The non-biodegradable microneedle tip or shaft can be composed of metals, glasses, semi-conductor materials, ceramics, or polymers. Examples of suitable metals include pharmaceutical grade stainless steel, titanium, gold, silver, nickel, iron, gold, tin, chromium, copper, and alloys thereof. Representative non-biodegradable polymers include various thermoplastics or other polymeric structural materials known in the fabrication of FDA-approved medical devices. Examples include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers and crosslinked variants thereof. The biodegradable microneedle tip or shaft can be formulated to dissolve after administration of the formulations described herein, such that any residual microneedle material which may be present at the administration site can be dissolved in the body of the subject. For example, the microneedle can be composed of a material which is formulated to be a solid material (optionally, as a function of temperature) during injection, and which after injection (and optionally, exposure to the subject's temperature) partially or fully degrades. Such microneedles can optionally be composed of water-soluble polymers, water-soluble inorganic materials, or ice. Biodegradable microneedles can provide an increased level of safety compared to non-biodegradable ones, such that they are essentially harmless even if inadvertently broken off into the ocular tissue.

Microneedles can be inserted into any compartment or structure of the eye to administer the moculator compounds and formulations described herein. Microneedles can be inserted into one or more of the choroid, the retina, the sclera, the suprachoroidal space, the Bruch's membrane, the retinal pigment epithelium, the subretinal space, the macula, the optic disk, the optic nerve, the ciliary body, the trabecular meshwork, the aqueous humor, or the vitreous humor for the administration of the formulations described herein. For example, a microneedle can be inserted perpendicularly into the sclera, reaching the suprachoroidal space in a short penetration distance. The delivery of the formulations described herein into the suprachoroidal region allows for the delivery of the formulation over a large tissue area and affords targeting difficult to target tissues in a single administration as compared single canula needle administration. In one embodiment, the administration can be confined to one specific structure or compartment of the eye. The specific structure or compartment of the eye to which the microneedle administration is localized can be one of the following: the choroid, the retina, the sclera, the suprachoroidal space, the Bruch's membrane, the retinal pigment epithelium, the subretinal space, the macula, the optic disk, the optic nerve, the ciliary body, the trabecular meshwork, the aqueous humor, or the vitreous humor. Not wishing to be bound by any theory, it is believed that upon entering the suprachoroidal space the administered formulation flows circumferentially from the insertion site toward the retinochoroidal tissue and optic nerve in the posterior segment of the eye as well as anteriorly toward the uvea and ciliary body. Furthermore, a portion of the administered formulation may remain in the sclera near the microneedle insertion site, serving as additional reservoir of the administered formulation that subsequently can diffuse into the suprachoroidal space and other adjacent tissues. As defined herein, "suprachoroidal space," also known as suprachoroid or suprachoroidia, describes the potential space in the region of the eye disposed between the sclera and choroid.

The administration of the formulations described herein using microneedles can afford an extended duration of the modulator, e.g. connexin or pannexin channel modulating agent within the targeted region or structure of the eye. The microneedle delivery method affords a longer duration of the administered formulation than if the formulation were administered via topical application of the formulation to the ocular tissue.

Administering a modulator and/or ocular drug agent of this invention to tissue or a compartment of the eye the eye with a microneedle may comprise inserting a microneedle into the ocular tissue and depositing a drug formulation into the ocular tissue. In some embodiments, at least one microneedle is inserted into the tissue of the eye without penetrating across the tissue stroma. In one embodiment, the method of administration may further include partially retracting the hollow microneedle after the insertion step and before and/or during the depositing of the drug formulation, which, in some embodiments, may form a space for the infusion of the modulator and/or ocular drug agent. In some embodiments the modulator is, for example, a connexin modulator, a gap junction modulator, or a pannexin or pannexin channel modulator.

The administration via a microneedle can be controlled by controlling the infusion pressure. The infusion pressure will concomitantly determine the amount of drug being delivered. In some embodiments, the infusion pressure may be at least 125 kPa, at least 150 kPa, at least 175 kPa, at least 200 kPa, at least 250 kPa, or at least 300 kPa. The infusion pressure through the microneedle can be generated by diffusion, capillary action, a mechanical pump, electroosmosis, electrophoretic, convection or other driving forces. The infusion pressure can optionally be monitored by measuring the backpressure so as to regulate the continuous pressure. The infusion pressure can optionally be controlled by microcontrollers, sensors, mechanical force-feedback circuits, actuators, valves, or pumps.

Combinations of Connexin or Pannexin Modulators with Rho Kinase Inhibitors or Other Agents Open-angle glaucoma is characterized by abnormally high resistance to fluid (aqueous humor) drainage from the eye. Normal resistance is required to provide an intraocular pressure sufficient to maintain the shape of the eye for optical integrity. The resistance is provided by the trabecular meshwork, a complex, multilaminar tissue consisting of specific cells with a dense actomyosin cytoskeleton network, collagenous beams and extracellular matrix. In the glaucomatous eye, the rate of aqueous humor production remains constant, while the increased resistance to outflow is responsible for the elevated intraocular pressure. Rho-kinase functions as a key downstream mediator of Rho and is ubiquitously expressed. Rho-kinase enzymes are serine/threonine kinases that regulate the function of a number of substrates including cytoskeletal proteins such as adducing, moesin, sodium ion-proton ion exchanger 1 (NHE1), LIM-kinase and vimentin, contractile proteins such as the myosin light chain phosphatase binding subunit (MYPT-I), CPI-17, myosin light chain and calponin, microtubule associated proteins such as Tau and MAP-2, neuronal growth cone associate proteins such as CRMP-2, and transcription factors such as serum response factor (Loirand et al., Circ. Res. 98:322-334 (2006)). Rho-kinase is also required for cellular transformation induced by RhoA. Rho-kinase is an intermediary of multiple signaling pathways, regulating a variety of cellular phenomena including cytoskeletal rearrangement, actin stress fiber formation, proliferation, chemotaxis, cytokinesis, cytokine and chemokine secretion, endothelial or epithelial cell junction integrity, apoptosis, transcriptional activation and smooth muscle contraction. As a result of these cellular actions, rho-kinase enzymes regulate physiologic processes such as vasoconstriction, bronchoconstriction, tissue remodeling, inflammation, edema, platelet aggregation and proliferative disorders. Rho kinase acts on the trabecular meshwork to maintain the IOP. Accordingly, inhibiting rho kinase will increase fluid outflow through the trabecular meshwork thus decreasing the IOP via a mechanism which is different from connexin and/or pannexin or hemichannel and/or pannexin channel modulation to reduce IOP.

In some embodiments, Rho kinase inhibitors are used to treat normal pressure glaucoma.

Inhibitors of rho kinase have been shown to reduce IOP in mammals by increasing aqueous humor drainage through the trabecular meshwork (Tian and Kaufman, Arch Ophthalmol. 122: 1171-1178, 2004). The inventors appreciate that the coadministration of a rho kinase inhibitor with a modulator, e.g. connexin or pannexin channel modulator will work on two independent mechanisms for reducing IOP in a subject, thereby resulting in a more efficacious treatment than any single treatment.

Additional agents for coadministration with the modulator, e.g. connexin or pannexin channel modulators can include other treatments which otherwise reduce IOP, including but not limited to lantanoprost, anti-VEGF compounds, Timolol, Brimonidine, Brimonidine tartarate, Rescula (unoprostone isopropyl ophthalmic solution, 0.15%), Dorzolamide, Roclatan, and AR-13533 (Aerie Pharmaceuticals, Bedminster, N.J.). By acting on mechanisms other than connexin or pannexin channel modulation, the coadministration of multiple treatments for treating ocular disorders can result in synergistic effects such as (1) reduced overall dosages, (2) reduced overall side effects, (3) reduced overall treatment frequency, and (4) increased patient compliance and thus efficacy of treatment.

In some aspects, the VEGF modulators for use in this invention are antagonists that inhibit and/or block VEGF or that inhibit and/or block upstream agonists of VEGF. In some aspects the VEGF antagonists include, for example, antagonists that bind to and inhibit VEGF, compounds that inhibit expression of VEGF, and/or viral vectors comprising VEGF inhibitors or encoding proteins or antisense polynucleotides that block or inhibit VEGF. In some aspects, species that inhibit VEGF and/or upstream agonists of VEGF are, for example, antibodies or antibody fragments, nanobodies, peptide or peptidomimetics, receptor fragments, recombinant fusion proteins, aptamers, small molecules, or single chain variable fragments (scFv). In some aspects, VEGF antagonist antibodies are, for example, Lucentis™ (ranibizumab), and/or Avastin™ (bevacizumab).

In some aspects, the VEGF antagonist can be an antibody to VEGF, for example, Lucentis™ (ranibizumab), or Avastin™ (bevacizumab).

In some aspects, VEGF antagonists which are antisense to upstream agonists of VEGF species that bind to and therefore inhibit VEGF can be a RTP801 inhibitor or REDD1 blocker. In some aspects, the RTP801 inhibitor or REDD1 blocker can be PF-655 (by Quark Pharmaceuticals and Pfizer), also known as REDD14NP or RTP801i). In some aspects the REDD1 blocker can have the mRNA sequence 5'-AGCUGCAUCAGGUUGGCAC-3' (SEQ ID NO: 234).

In some aspects of this invention, the VEGF antagonist is, for example, a peptide or peptidomimetic, for example, pegaptanib sodium (Macugen™), and AGN-150998.Macugen™ is a modified RNA sequence, ((2'-deoxy-2'-fluoro)C-Gm-Gm-A-A-(2'-deoxy-2'-fluoro)U-(2'-deoxy-2'-fluoro)C-Am-Gm-(2'-deoxy-2'-fluoro)U-Gm-Am-Am-(2'-deoxy-2'-fluoro)U-Gm-(2'-deoxy-2'-fluoro)C-(2'-deoxy-2'-fluoro)U-(2'-deoxy-2'-fluoro)U-Am-(2'-deoxy-2'-fluoro)U-Am-(2'-deoxy-2'-fluoro)C-Am-(2'-deoxy-2'-fluoro)U-(2'-deoxy-2'-fluoro)C-(2'-deoxy-2'-fluoro)C-Gm-(3'→3')-dT) (SEQ ID NO: 235), 5'-ester with α,α'-[4,12-dioxo-6-[[[5-(phosphoonoxy)pentyl]amino]carbonyl]-3,13-dioxa-5,11-diaza-1,15-pentadecanediyl]bis[ω-methoxypoly(oxy-1,2-ethanediyl)], sodium salt. AGN-150998/MP0112 is an anti-VEGF DARPin, a small protein that binds to VEGF.

In some aspects of this invention, the VEGF antagonist is, for example, a recombinant fusion protein such as, for example, aflibercept (Eyelea™) or conbercept. Aflibercept is a recombinant fusion protein consisting of portions of human VEGF receptors 1 and 2 extracellular domains fused to the Fc portion of human IgG. Conbercept is a recombinant fusion protein composed of the second Ig domain of VEGFR1 and the third and fourth Ig domains of VEGFR2 to the constant region (Fc) of human IgG1.

In some aspects, the scFv VEGF antagonist is, for example, ESBA1008. ESBA1008 is a humanized monoclonal single-chain FV (scFv) antibody fragment targeting VEGFA.

In some aspects, the viral vector VEGF antagonist can be AAV-sFLT01 (also known as "AVA-101"). AAV2-sFlt01 is an adeno-associated viral vector that carries the gene construct for a secreted chimeric protein—sFLT01—that binds to VEGF. sFLT01 is a VEGF-binding protein that consists of domain 2 of Flt-1 linked to a human immunoglobulin $G_1$ heavy chain Fc fragment (sFlt01), combined with an adeno-associated virus (AAV) to produce AAV2-sFlt01.

In some aspects of this invention, VEGF antagonists are small molecules, for example, Vatalanib, Cediranib, AL39324, Pazopanib, TG100572, or TG100801. Vatalanib (N-(4-chlorophenyl)-4-(pyridin-4-ylmethyl)phthalazin-1-amine) is also known as PTK787, PTK/ZK, or CGP 79787. Cediranib, also known as AZD 2171, Recentin™, ZD 2171, or CAS Number 288383-20-0, is also known as 4-[(4-fluoro-2-methyl-1H-indol-5-yl)oxy]-6-methoxy-7-[3-(1-pyrrolidinyl)propoxy]-quinazoline. AL39324, also known as Linifanib, CAS No. 796967-16-3, 1145655-58-8 (as the HCl salt), or 796967-17-4 (as the trifluoroacetate salt), is also known as 1-[4-(3-amino-1H-indazol-4-yl)phenyl]-3-(2-fluoro-5-methylphenyl)urea. Pazopanib, also known as Votrient™, Armala™, or Patorma™, is also known as 5-[[4-[(2,3-dimethyl-2H-indazol-6-yl)methylamino]-2-pyrimidinyl]amino]-2-methylbenzenesulfonamide monohydrochloride. TG100801 is a pro-drug version of TG100572, and is also known as 4-Chloro-3-(5-methyl-3-((4-(2-(pyrrolidin-1-yl)ethoxy)phenyl)-amino)benzo[e][1,2,4]triazin-7-yl) p; 4-Chloro-3-[5-methyl-3-[[4-[2-(1-pyrrolidinyl)ethoxy]phenyl]amino]-1,2,4-benzotriazin-7-yl] phenol 1-benzoate.

In some aspects, mTOR inhibitors for use in the methods of this invention are, for example, macrolides or small molecules. In some embodiments, the macrolide mTor inhibitors are, for example, temsirolimus, sirolimus, or everolimus. Temsirolimus, also known as Torisel™, or CCI-779, is also known as (1R,2R,4S)-4-{(2R)-2-[(3S,6R,7E,9R,10R,12R,14S,15E,17E,19E,21S,23S,26R,27R,34aS)-9,27-dihydroxy-10,21-dimethoxy-6,8,12,14,20,26-hexamethyl-1,5,11,28,29-pentaoxo-1,4,5,6,9,10,11,12,13,14,21,22,23,24,25,26,27,28,29,31,32,33,34,34a-tetracosahydro-3H-23,27-epoxypyrido[2,1-c][1,4]oxazacyclohentriacontin-3-yl]propyl}-2-methoxycyclohexyl 3-hydroxy-2-(hydroxymethyl)-2-methylpropanoate. Sirolimus is also known as rapamycin, Rapamune™, AY-22989, Perceiva™, WY-090217, or (3S,6R,7E,9R,10R,12R,14S,15E,17E,19E,21S,23S,26R,27R,34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]-oxaazacyclohentriacontine-1,5,11,28,29(4H,6H,31H)-pentone. Everolimus, also known as Afinitor™, Certican™ Votubia™, or Zortress™, is also known as dihydroxy-12-[(2R)-1-[(1S,3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo[30.3.1.0 hexatriaconta-16,24,26,28-tetraene-2,3,10,14,20-pentone.

This invention also features small molecule mTor inhibitors suc as, for example, Palomid 529, XL388, or Dactolisib. Palomid 529 is also known as 3-(4-methoxybenzyloxy)-8-(1-hydroxyethyl)-2-methoxy-6H-benzo[c]chromen-6-one. XL388 is also known as [7-(6-amino-3-pyridinyl)-2,3-dihydro-1,4-benzoxazepin-4(5H)-yl][3-fluoro-2-methyl-4-(methylsulfonyl)phenyl]-methanone. Dactolisib, also known as BEZ235, or NVP-BEZ235, is also known as 2-methyl-2-(4-(3-methyl-2-oxo-8-(quinolin-3-yl)-2,3-dihydroimidazo[4,5-c]quinolin-1-yl)phenyl)propanenitrile.

In some aspects, PDGF modulators for use in the methods of this invention include, for example, Fovista™ (also known as E-10030), a anti-platelet-derived growth factor (anti-PDGF-B) aptamer.

In some aspects, PEDF modulators for use in the methods of this invention include, for example, AdGVPEDF.11D (GenVec). AdGVPEDF.11D is a adenovirus vector containing the gene for PEDF. AdGVPEDF.11D uses an adenovector to deliver the PEDF gene to target cells, resulting in the local production of PEDF in the treated eye. Pigment epithelium-derived factor (PEDF) is a potent inhibitor of new vessel growth. PEDF is also known as serpin F1.

In some aspects, S1P production blockers for use in the methods of this invention include, for example, sonepcizumab, also known as LT1009, Asonep, Sphingomab™, or iSONEP™. iSONEP™ is a humanized monoclonal antibody that binds to sphingosine 1-phosphate (S1P).

In some aspects, the ocular treatment agent for use in combination with one or more of the modulator, e.g. gap junction, connexin and/or pannexin channel modulators, of this invention is, for example, squalamine. Squalamine is also known as Evizon™, or (1S,2S,5S,7R,9R,10R,11S,14R,15R)—N-{3-[(4-aminobutyl)amino]propyl}-9-hydroxy-2,15-dimethyl-14-[(2R,5R)-6-methyl-5-(sulfooxy)heptan-2-yl]tetracyclo[8.7.0.0^{2,7}.0^{11,15}]heptadecan-5-aminium.

In some aspects, tubulin binding agents for use in the methods of this invention include, for example, combretastatin, combretastatin A-4 phosphate, combrestastin derivatives, or OC-10X. Combretastatin is also known as 2-Methoxy-5-[(Z)-2-(3,4,5-trimethoxy-phenyl)-vinyl]-phenol. OC-10X (OcuCure, Roanoke, Va.) is a low-molecular-weight quinazolinone. The tubulin binding agents can also be beta-lactam based derivatives of combrestastin, as described in O'Boyle, N. et al. *Journal of Medicinal Chemistry* 53 (24): 8569-8584, 2010. doi:10.1021/jm101115u. PMID 21080725, and herein incorporated by reference.

In some aspects, integrin inhibitors for use in the methods of this invention include, for example, ALG-1001, Volociximab, or JNJ-26076713. ALG-1001 (Allegro Ophthalmics) is a small peptide. Volociximab, also known as M200, or Opthotec™, is a chimeric monoclonal antibody that binds to and inhibits the functional activity of $\alpha5\beta1$ integrin. JNJ-26076713 is a tetrahydroquinoline-containing $\alpha V\beta3/\alpha V\beta5$ integrin antagonist and is also known as 3-Quinolinepropanoic acid, 1,2,3,4-tetrahydro-beta-((1-(1-oxo-3-(1,5,6,7-tetrahydro-1,8-naphthyridin-2-yl)propyl)-4-piperidinyl)methyl)-, (betaS,3S)—.

Ocular treatment agents for use in combination with one or more of the modulator, e.g. gap junction, connexin, and/or pannexin or pannexin channel modulators, of this invention also include, for example, complement modulators, and other therapeutic agents useful, for example, in treating geographic atrophy, dry AMD, non-exudative AMD, and/or Drusen development.

Complement modulators for use as ocular treatment agents in combination with one or more modulators, e.g. gap junction, connexin, and/or pannexin or pannexin channel modulators, are, for example, compstatin, TP10, Eculizumab, ARC1905, JPE-1375, PMX53, Lampalizumab, or rhCFHp. Compstatin, also known as AL-78898A or POT-4, is a cyclic peptide with the sequence -[ICVVQDWGHHRCT]- (SEQ ID NO: 22). TP10 (Avant Immunotherapeutics) is a recombinant protein and is an inhibitor of soluble complement receptor one (sCR1). Eculizumab, also known as Soliris™, or Solaris™, is a humanized monoclonal antibody. ARC1905, also known as Zimura™ is a PEGylated, stabilized aptamer targeting complement factor C5. JPE-1375 is a small molecule peptidomimetic antagonist targeting C5aR, the receptor for complement factor C5a. PMX53 is a cyclic hexapeptide, with the sequence Ace-Phe-[Orn-Pro-dCha-Trp-Arg]. Lampalizumab, also known as anti-factor D, or FCFD4514S, is a monoclonal antibody that inhibits complement factor D. rhCFHp is a recombinant fusion protein form of full-length Factor H in its protective to correct abnormal Factor H activity.

In some aspects, ocular treatment agents for use in combination with one or more of modulator, e.g. gap junction, connexin, and/or pannexin or pannexin channel modulators, of this invention include TNF-alpha inhibitors, C-raf kinase inhibitors, NSAIDs, or nAChR inhibitors. In some embodiments, the TNF-alpha inhibitor can be Adalimumab or infliximab. In some embodiments, the C-raf kinase inhibitor can be iCo-007. In some embodiments, the NSAID can be Brofenac. In some embodiments, the nAChR inhibitor can be mecamylamine.

Ocular treatment agents for use in combination with one or more of the modulator, e.g. gap junction, connexin, and/or pannexin or pannexin channel modulators, of this invention can also include pharmaceutical agents such as verteporfin (e.g., Chlorin™, Visudyne, talaporfin sodium (e.g., Aptocine™, Laserphyrin™, Litx™), isopropyl unoprostone (e.g., Ocuseva™, Rescula™), interferon beta (e.g., Feron™), fluocinolone acetonide (e.g., Envision TD™, Retisert™), dexamethasone (e.g., Osurdex™, Ozurdex™, Posurdex™, Surodex™), canakinumab (e.g., Ilaris™), bromfenac (Bromday™), ophthalmic (e.g., Bronac™, Bronuck™, Xibrom™, Yellox™), brimonidine (e.g., Alphagan™, Bromoxidine™, Enidin™), anecortave acetate (e.g., Retaane™, Edex™, Prostavasin™, Rigidur™, Vasoprost™, Viridal™), VEGF-Trap-Eye™, ocriplasmin (e.g., Iluvien™, Medidur™, Medidur FA™), NT-501, KH-902, fosbretabulin tromethamine (e.g., Zybrestat™), AL-8309, aganirsen (e.g., Norvess™), volociximab (e.g., Opthotec™), triamcinolone (e.g., Icon Bioscience), TRC-105, Burixafor (e.g., TG-0054), TB-403 (e.g., R-7334), SB-623, S-646240, RTP-8011-14 (e.g., PF-4523655), RG-7417 (e.g., FCFD-4514S), PG-11047 (e.g., CGC-11047), padeliporfin (e.g., Stakel™), OT-551, ontecizumab, NOX-A12, hCNS-SC, Neu-2000, NAFBOO1, MA09-hRPE, LFG-316, iCo-007 (e.g., ISIS-13650), hl-conl, GSK-933776A, GS-6624 (e.g., AB-0024), epitalon, dalantercept, MP-0112, CNTO-2476, CERE-120, CCX-168, Brimonidine-DDS, bevasiranib sodium (e.g., Cand5), bertilimumab, ACU-4429, A6 (e.g., Paralit™), TT-30, sFLT-01 gene therapy, RetinoStat™, PRS-050 (e.g., Angiocal™), PF-4382923, MC-1101, GW-824575, Dzl3 (e.g., TRC-093), D93, ATL-1103, XV-615, pSivida, VEGF/rGel, VAR-10200, VAL-566-620-MULTI, TKI, TK-001, STP-601, dry AMD stem cell therapy (e.g., EyeCyte), OpRegen, SMT-D004, SAR-397769, RTU-007, RST-001, RGNX-004, RFE-007-CAI, MC-2002, lycium anti-angiogenic proteoglycan, IXSVEGF, integrin inhibitors, GW-771806, GBS-007, Eos-013, EC-400, dry-AMD therapy (e.g., Neuron Systems), CGEN-25017, CERE-140, AP-202, AC-301, 4-IPP, zinc-monocysteine complexes (e.g., Adeona), prinomastat, Neovastat, mecamylamine, CereCRIB, BA-285, ATX-S 10, AG-13958, verteporfin/alphavB3 conjugate, VEGF/rGel, VEGF-saporin, VEGF-R2 antagonist (e.g., Allostera), VEGF inhibitors (e.g., Santen), VEGF antagonists (e.g., Ark), Vangiolux™, Triphenylmethanes (e.g., Alimera), TG-100-801, TG-100-572, TA-106, T2-TrpRS, SU-0879, SHEF-1, rostaporfin (e.g., Photrex™, Purlytin™, SnET2), retino-NPY, PJ-34, PI3K conjugates (e.g., Semafore), PhotoPoint, PAN-90806, Opt-21, OPK-HVB-010, OPK-HVB-004, Ophthalmologicals (e.g., Cell NetwoRx), OcuXan, NTC-200, NT-502, NOVA-21012, Neurosolve™, neuroprotective (e.g., BDSI), MEDI-548, MCT-355, McEye™, LentiVue™, LYN-002, LX-213, lutetium texaphyrin (e.g., Antrin™), LG-339 inhibitors (e.g., Lexicon), KDR kinase inhibitors (e.g., Merck), ISV-616, INDUS-815C, ICAM-1 aptamer (e.g., Eyetech), GTx-822, GS-102, Granzyme B/VEGF™, gene therapy (e.g., EyeGate), GCS-1OO analogue programme, FOV-RD-27, fibroblast growth factor (e.g., Ramot), Panzem SR™, ETX-6991, ETX-6201, EG-3306, Dz-13, disulfiram (e.g., ORA-102), Diclofenac (e.g., Ophthalmopharma), ACU-02, CLT-010, CLT-009, CLT-008, CLT-007, CLT-006, CLT-005, CLT-004, CLT-003 (e.g., Chirovis™), CLT-001, Cethrin™ (e.g., BA-210), celecoxib, CD91 antagonist (e.g., Ophthalmophar), CB-42, BNC-4, bestrophin, batimastat, BA-1049, AVT-2, AVT-1, atu012, Apel programme (e.g., ApeX-2), anti-VEGF (e.g., Gryphon), AMD ZFPs (e.g., ToolGen), AM-1101, ALN-VEG01, AK-1003, AGN-211745, ACU-XSP-001 (e.g., Excellair™), ACU-HTR-028, ACU-HHY-011, ACT-MD (e.g., NewNeural), ABCA4 modulators (e.g., Active Pass), A36 (e.g., Angstrom), 267268 (e.g., SB-267268), 131-TTM-601, vandetanib (e.g., Caprelsa™, Zactima™, Zictifa™), sunitinib malate (e.g., Sutene™, Sutent™), sorafenib (e.g., Nexavar™), axitinib (e.g., Inlyta™), tivozanib, XL-647, RAF-265, pegdinetanib (e.g., Angiocept™), MGCD-265, icrucumab, foretinib, ENMD-2076, BMS-690514, regorafenib, ramucirumab, plitidepsin (e.g., Aplidin™), orantinib, nintedanib (e.g., Vargatef™), motesanib, midostaurin, linifanib, telatinib, lenvatinib, elpamotide, dovitinib, cediranib (e.g., Recentin™), JI-101, cabozantinib, brivanib, apatinib, Angiozyme™, X-82, SSR-106462, rebastinib, PF-337210, IMC-3C5, CYC116, AL-3818, VEGFR2 inhibitor (e.g., AB Science), VEGF/rGel (e.g., Clayton Biotechnologies), TLK-60596, TLK-60404, R84 antibody (e.g., Peregrine), MG-516, FLT4 kinase inhibitors (e.g., Sareum), flt-4 kinase inhibitors, Sareum, DCC-2618, CH-330331, XL-999, XL-820, vatalanib, SU-14813, semaxanib, KRN-633, CEP-7055, CEP-5214, ZK-CDK, ZK-261991, YM-359445, YM-231146, VEGFR2 kinase inhibitors (e.g., Takeda), VEGFR-2 kinase inhibitors (e.g., Hanmi), VEGFR-2 antagonist (e.g., Affymax), VEGF/rGel (e.g., Targa), VEGF-TK inhibitors (e.g., AstraZeneca), resveratrol, tyrosine kinase inhibitors (e.g., Abbott), tyrosine kinase inhibitors (e.g., Abbott), Tie-2 kinase inhibitors (e.g., GSK), SU-0879, SP-5.2, sorafenib bead (e.g., Nexavar™ bead), SAR-131675, Ro-4383596, R-1530, Pharmaprojects No. 6059, OSI-930, OSI-817, OSI-632, MED-A300, L-000021649, KM-2550, kinase inhibitors (e.g., MethylGene), kinase inhibitors (e.g., Amgen), Ki-8751, KDR kinase inhibitors (e.g., Celltech), KDR kinase inhibitors (e.g., Merck), KDR kinase inhibitors (e.g., Amgen), KDR inhibitors (e.g., Abbott), KDR inhibitor (e.g., LGLS), JNJ-17029259, and IMC-1C11.

In some embodiments, the modulator, e.g. connexin or pannexin channel modulator, and the ocular treatment agent can be co-formulated for co-administration. In some aspects, the formulation of the modulator, e.g. connexin or pannexin channel modulator, and the ocular treatment agent can be a pill, a solution, a gel, a pre-filled syringe, a tablet, eye drops, or as part of a particle-based formulation. In some aspects, the compound which acts by a different mechanism to reduce IOP can be Rhopressa. In some embodiments, the compound which acts by a different mechanism to reduce IOP can be Roclatan. In some aspects, the compound which acts by a different mechanism to reduce IOP can be an adenosine mimetic. In some embodiments, the adenosine mimetic can be Trabodenoson (N-Cyclopentyladenosine 5'-nitrate).

In some embodiments, provided are methods of modulating and/or inhibiting the action of a rho kinase and connexin or pannexin channel activity in a cell or medium. A cell may be in a body in vivo, or in a living body in vivo, or in vitro. A medium may include an assay medium. The methods may comprise applying to a medium or contacting a cell with an effective amount of a rho kinase inhibitor and a modulator, e.g. connexin or pannexin channel modulator.

In some embodiments, the rho kinase inhibitor may be amino isoquinolyl amides or amino benzamidyl amides of deLong et al. (U.S. Pat. No. 8,716,310, and herein incorporated by reference), 2H-isoquinolin-1-one and 3H-isoquinolin-4-one derivatives of Bosanac et al. (U.S. Pat. No. 8,809,326), 6-aminoisoquinoline derivaties of deLong (U.S. Patent Publ. 2013/0137721), beta and gamma-amino isoquinoline amide compounds and substituted benzamide compounds of deLong (U.S. Patent Publ. 2014/0249201), the isoquinoline compounds covalently linked to a prostaglandin or a prostaglandin analog of Kopczynski (U.S. Patent Publ. 2014/0275161 and U.S. Patent Publ. 2014/0275160), the isoquinoline compounds of deLong (U.S. Pat. No. 8,034,943), the isoquinoline compounds of deLong (U.S. Pat. Nos. 7,671,205, 7,470,787, 8,455,513, 8,450,344, 8,357,699, 8,455,647, and 8,455,514), Rhopressa, Roclatan, or the compounds and formulations of Richards (PCT App. No. PCT/US2009/047108).

In some embodiments, provided are methods of treating a disease, disorder, or condition. The methods may comprise administering to a subject a rho kinase and a modulator, e.g. connexin and/or pannexin channel modulator. The methods may comprise administering to a subject a composition comprising a rho kinase inhibitor compound and a modulator, e.g. connexin and/or pannexin channel modulator, and a pharmaceutically acceptable carrier. Diseases, disorders, or conditions may include ocular diseases or conditions associated with rho kinase activity or ocular diseases or conditions affected by rho kinases. For example, the disease may be selected from the group consisting of glaucoma, Wet AMD, Dry AMD (inflammation), and DME. The combination of a rho kinase inhibitor with a modulator, e.g. a connexin and/or pannexin channel modulator, of the present invention may also be useful in decreasing intraocular pressure. Thus, these formulations may be useful in the treatment of glaucoma, such as hypertensive glaucoma or normatensive glaucoma. The rho kinase inhibitor and modulator, e.g. connexin and/or pannexin channel modulator can be formulated as distinct species for separate administrations, or as a mixture for a common administration. For the separate administration of the rho kinase inhibitor, the route of administration for treating ocular diseases can be topically, interperitonally, intravitrealously, or systemically. For the common administration of the rho kinase inhibitor and modulator, the route of administration for treating ocular diseases can be topically, interperitonally, intravitrealously, or systemically. In some embodiments, for separate or common administration the formulation of the rho kinase inhibitor or its derivatives may be formulated for parenteral delivery by a route such as intravenous, subcutaneous, intramuscular, and intra-articular administration. These formulations are either liquids or lyophilizates. The liquid or lyophilized formulations can comprise of 1-50% of a rho kinase inhibitor or its derivatives, the range of dosages of the modulators as described herein, and remaining ingredients selected from solubilizers, stabilizers, buffers, tonicity modifiers, bulking agents, viscosity enhancers/reducers, surfactants, chelating agents, and adjuvants. These ingredients are well known to one of ordinary skill in the art. Lyophilized formulations need to be reconstituted prior to administration. Liquid formulations are optionally diluted with pharmaceutically acceptable diluents such as 5% Dextrose Injection, USP or 0.9% Sodium Chloride Injection, USP. These formulations are preferably administered by infusion although bolus administration is also possible.

For the separate administration (coadministration) of the rho kinase inhibitor and the modulator, e.g. connexin or pannexin channel modulator, the administrations can be sequential or simultaneous. For sequential administrations, the rho kinase inhibitor and the connexin or pannexin modulator can be administered within one hour of each other, within one day of each other, within one week of each other, or within one month of each other. For simultaneous administration (coadministration), the rho kinase inhibitor and the modulator can be administered together as a mixture, or as a formulation comprising both the rho kinase inhibitor and the modulator, e.g. connexin or pannexin channel modulator.

In some aspects, the invention provides methods of modulating rho kinase activity and connexin or pannexin channel activity, the methods comprising contacting a cell with a rho kinase inhibitor, in an amount effective to modulate rho kinase activity, and contacting a cell with a connexin and/or pannexin channel modulator, for example, in an amount effective to modulate connexin and/or pannexin channel activity.

In some aspects, the invention provides methods of reducing intraocular pressure, the methods comprising contacting a cell with a rho kinase inhibitor and a modulator, e.g. connexin or pannexin channel modulator, as described herein, in an amount effective to reduce intraocular pressure.

For separate or common administration, the dosage range of the rho kinase inhibitor for systemic administration is from about 0.001 to about 100 mg/kg body weight, preferably from about 0.01 to about 10 mg/kg per body weight, most preferably form about 0.05 to about 5 mg/kg body weight per day. The rho kinase inhibitor dose can be 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2., 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg body weight or any range between any two of the recited dosages or any dose between any two recited numbers. For separate or common administration, the dosage range of the modulator, e.g. connexin or pannexin channel modulator, is from about 1.0 ng/kg body weight to about 10 mg/kg body weight, or from about 1 ug/kg body weight to about 5 mg/kg body weight, or from about 50 ug/kg body weight to about 1 mg/kg body weight. The modulator, e.g. connexin and/or pannexin channel modulator dose can be 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 ng/kg body weight, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 ug/kg body weight, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg body weight, or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, or 25 g/kg body weight.

For separate or common administration, the formulation may be prepared to provide for rapid or slow release; immediate, delayed, timed, or sustained release; or a combination thereof. Formulations may be in the form of liquids, solutions, suspensions, emulsions, elixirs, syrups, electuaries, drops (including but not limited to eye drops), tablets, granules, powders, lozenges, pastilles, capsules, gels, ointments, creams, lotions, oils, foams, sprays, mists, or aerosols. As an additional embodiment, the pharmaceutical formulation can be contained within, delivered by, or attached to contact lenses that are placed on the eye.

Articles of Manufacture/kits of Combinations of Connexin or Pannexin Modulators with Rho Kinase Inhibitors or Other Agents In another embodiment of the invention, an article of manufacture, or "kit", containing materials useful for treating the diseases and disorders described above is provided. The kit comprises a container comprising a rho kinase inhibitor and a modulator, e.g. connexin and/or pannexin channel modulator. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, e.g., bottles, vials, syringes, blister pack, etc. The container may be formed from a variety of materials such as glass or plastic. The container may hold a rho kinase inhibitor and a modulator, e.g. connexin and/or pannexin channel modulator, or a formulation thereof which is effective for treating the condition and may have a sterile access port (e.g., the container may be an intravenous solution bag or a vial having a stopper pierceable by a hypodermic injection needle). At least one active agent in the composition is a modulator, e.g. a connexin and/or pannexin channel modulator. The label or package insert indicates that the composition is used for treating the condition of choice, such as hypertensive or normatensive glaucoma, DME, ocular fibrosis, wet AMD, or dry AMD, or any of the ocular disorders described above. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the modulator, e.g. connexin and/or pannexin channel modulator, and, if present, the rho kinase inhibitor or other agent which acts on a separate mechanism from connexin and/or pannexin channel modulation to reduce IOP as described herein. For example, if the kit comprises a first composition comprising a connexin or pannexin modulator, and a second pharmaceutical formulation, the kit may further comprise directions for the simultaneous, sequential or separate administration of the first and second pharmaceutical compositions to a patient in need thereof.

In certain other embodiments wherein the kit may comprise a modulator, e.g. connexin and/or pannexin channel modulator, and a rho kinase inhibitor or other agent which acts on a separate mechanism from connexin and/or pannexin channel modulation, e.g., to reduce IOP as described herein, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., ocular and parenteral), are administered at different dosage intervals, or when titration of the individual components of the combination is desired by the prescribing physician.

The invention includes an article of manufacture comprising packaging material containing one or more dosage forms containing modulator, e.g. connexin and/or pannexin channel modulators and a rho kinase inhibitor or other agent which acts on a separate mechanism from connexin and/or pannexin channel modulation to reduce IOP as described herein, wherein the packaging material has a label that indicates that the dosage form can be used for a subject having or suspected of having or predisposed to any of the diseases, disorders and/or conditions described or referenced herein. Such dosage forms include, for example, tablets, capsules, solutions and suspensions for parenteral and ocular delivery forms and formulations.

In some aspects, the kit can comprise the rho kinase inhibitor compartmentalized in a different compartment than the modulator, e.g. connexin and/or pannexin channel modulator, for separate administration. The compartments can be separate vials, separate syringes, separate contact lenses, separate solutions, or separate particles-infused with the agents as described above. In some aspects, the rho kinase inhibitor can be compartmentalized for delivery to the front of the eye while the connexin and/or pannexin channel modulator, e.g., can be compartmentalized for delivery to the posterior segments of the eye (retina, choroid, RPE, Bruch's membrane). In some aspects, the connexin and/or pannexin channel modulator, e.g., can be compartmentalized in the form of nanoparticle or microparticle form as described herein for sustained delivery to the back of the eye while the rho kinase inhibitor can be compartmentalized for immediate or sustained delivery to the front of the eye in the form of eye drops or contact lens infused with the rho kinase inhibitor.

In one aspect, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In some aspects, the first and second (and optionally, third) compositions of the kit can be administered in combination, can be administered simultaneously, can be administered separately, can be administered sequentially, or can be administered in a sustained manner. Iontophoresis The connexin modulator formulations of this invention may also be administered by iontophoresis, a non-invasive procedure in which drug penetration is enhanced by applying a a small electric current. The modulator, e.g. connexin and/or pannexin channel modulator is applied with an electrode carrying the same charge as the drug, and the ground electrode, which is of the opposite charge, is placed elsewhere on the body to complete the circuit. The modulator helps to conduct the current through the tissue. Transcleral iontophoresis can be used to deliver therapeutic levels of bioactive polynucletoides and peptides to the retina and the choroid.

Doses, Amounts and Concentrations

As will be appreciated, the dose of modulator, e.g. gap junction channel modulator, such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof administered, the period of administration, and the general administration regime may differ between subjects depending on such variables as the target site to which it is to be delivered, the severity of any symptoms of a subject to be treated, the type of disorder to be treated, size of unit dosage, the mode of administration chosen, and the age, sex and/or general health of a subject and other factors known to those of ordinary skill in the art.

Data obtained from cell culture assays and animal studies can be used in formulating a range of dosages for use in humans. The modulator dosage may vary within this range depending upon the dosage form employed and the route of administration utilized. For any agent used in the method of the invention, the therapeutically effective dose can be estimated initially from cell culture assays. A dose may be formulated in cell cultures or animal models to achieve a cellular concentration range that includes the IC50 (i.e., the concentration of the test compound that achieves a half-maximal inhibition of symptoms) as determined in cell culture. Such information can be used to more accurately determine useful doses in humans. The exact formulation, route of administration and dosage can be chosen by the individual physician in view of the patient's condition. (See, e.g., Fingl et al., 1975, In: The Pharmacological Basis of Therapeutics, Ch. 1, p. 1). The dosage can be determined from the concentration of the amount administered, expected mass of the animal model tested (200-300 g per rat for adult Wistar rats), to determine the dose in units of mg/kg from concentration (micromolar) administered or amount (mg) administered.

Examples of effective doses that may be used for the treatment of ocular disorders such as glaucoma ocular hypoxia, retinal perfusion impairment, AMD, DME, eye fibrosis and/or ocular neuropathy, or any other ocular disorder described herein are described and claimed herein. In some aspects, the therapeutically effective amount of the modulator, e.g. connexin modulator, and/or pannexin channel modulator, for example a connexin 43 or connexin 43 hemichannel modulator, which is effective to treat ocular disorders, for example, ocular hypertension, glaucoma, AMD, DME, ocular fibrosis, glaucomatous ocular neuropathy, RGC loss, impairment of choridal perfusion, choroidal inflammation, choroidal overperfusion, and/or choriocapillaris dropout is a concentration of about 0.001 to about 1.0 microgram/ml, or from about 0.001 to about 0.01 mg/ml, or from about 0.1 mg/mL to about 100 mg/mL, or more, or any range between any two of the recited dosages or any dose between any two recited numbers. The dose can be 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2., 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/ml or any range between any two of the recited dosages or any dose between any two recited numbers. In some embodiments, the therapeutically effective amount of the modulator, e.g. connexin and/or pannexin channel modulating agent protein modulating agent is present at a concentration ranging from about 0.5 to about 50 mg/mL. In some embodiments, the modulating agent is present at a concentration ranging from about 0.3 to about 30 mg/mL. In some embodiments, the modulating agent is present at a concentration ranging from about 0.1 or 1.0 to about 10 mg/mL. In some embodiments, the modulating agent is present at a concentration ranging from about 0.1 or 1.0 to about 0.3 or 3.0 mg/mL. In some embodiments, the modulating agent is present at a concentration of about 3.0 mg/mL. In any of these aspects the modulating agent may be a connexin protein antisense oligonucleotide. When the modulating agent is a modified antisense oligonucleotide, e.g., a backbone-modified oligonucleotide, or chemically modified oligonucleotide for increased half-life, the above-noted dose concentrations may be the same, or may be decreased or increased as appropriate based on potency and specificity, for example. In any of these aspects, the carrier (vehicle) may be a pharmaceutically acceptable carrier.

In some aspects the modulator, e.g. connexin modulator and/or pannexin channel modulator may be administered at a therapeutically effective dose between about 0.001 to about 100 mg/kg, between about 0.001 to about 0.01 mg/kg, between about 0.01 to about 0.1 mg/kg, between 0.1 to about 1 mg/kg, between about 1 to about 10 mg/kg, or between about 10 to about 100 mg/kg, or any range between any two recited dosages or any dose between any two recited dosages. In some aspects, the dose can be 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2., 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/ml or any range between any two of the recited dosages or any dose between any two recited numbers.

Although each of the therapeutically effective concentrations, amounts or doses for use with this invention as exemplified above may be useful for modified or unmodified nucleic acid modulators, modified or unmodified peptide or peptidomimetic modulators, or small molecule modulators, in some aspects of this invention, for each of the therapeutically effective concentrations, amounts or doses described above, the dose of a peptide or peptidomimetic connexin modulator or pannexin modulator may be between 1/10 to 1/100, or between 1/100, to 1/1000 of any of the recited concentrations, amounts or doses. In addition, the therapeutically effective concentrations, amounts or dose for a modified modulator, e.g. connexin modulator, pannexin modulator, or pannexin channel modulator may, in some aspects, be between 1/10 to 1/100, or between 1/100, to 1/1000 of the recited concentrations, amounts or doses, or any range between any two recited dosages or any dose between any two recited dosages.

It should be appreciated that administration may include a single daily dose, administration of a number of discrete divided doses, or continuous administration, as may be appropriate. By way of example, unit doses may be administered once or more than once per day, for example 1, 2, 3, 4, 5 or 6 times a day to achieve a desired total daily dose. By way of example, a unit dose of a gap junction channel modulator, e.g., such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof may be administered in a single daily dose or a number of discrete doses, or continuously to achieve a daily dose of approximately 0.1 to 10 mg, 10 to 100 mg, 100 to 1000 mg, 1000 to 2000 mg, or 2000 mg to 5000 mg, 0.1 to approximately 2000 mg, approximately 0.1 to approximately 1000 mg, approximately 1 to approximately 500 mg, approximately 1 to approximately 200 mg, approximately 1 to approximately 100 mg, approximately 1 to approximately 50 mg, or approximately 1 to approximately 25 mg, or any range between any two recited dosages or any dose between any two recited dosages.

By way of further example, a unit dose of a modulator, e.g. gap junction channel modulator, such as peptide 5, tonabersat and/or an analogue of either, and/or a pannexin modulator, e.g., probenecid and an analogue thereof, and/or a synthetic mimetic peptide blocker of pannexin 1, e.g., $^{10}$Panx1, or an analogue thereof may be administered once or more than once a day (for example 1, 2, 3, 4, 5 or 6, typically 1 to 4 times a day), such that the total daily dose is in the range (for a 70 kg adult) of approximately 1 to approximately 1000 mg, for example approximately 1 to approximately 500 mg, or 500 mg to 1000 mg, 1000 to 2000 mg, or 2000 mg to 5000 mg, or any range between any two recited dosages or any dose between any two recited dosages. For example, a gap junction channel modulator, such as peptide 5, and/or an analogue thereof, compounds of formula I, for example tonabersat, and analogs of any of the foregoing compounds, and/or a pannexin modulator, e.g., probenecid and an analogue thereof, and/or a synthetic mimetic peptide blocker of pannexin 1, e.g., $^{10}$Panx1, or an analogue thereof may be administered to a subject at a dose range of approximately 0.01 to approximately 15 mg/kg/day, for example approximately 0.1 to approximately 6 mg/kg/day, for example approximately 1 to approximately 6 mg/kg/day, for example, 6 mg/kg/day to 100 mg/kg/day or any range between any two recited dosages or any dose between any two recited dosages. In one embodiment, tonabersat may be administered orally once a day at a dose of approximately 2 mg to approximately 40 mg.

In one embodiment, the dose of compounds of formula I, for example tonabersat, and analogs of any of the foregoing compounds is approximately 0.001 micromolar to 0.1 micromolar, 0.1 micromolar and up to approximately 200 micromolar at the site of action, or higher, within the circulation to achieve those concentrations at the site of action. By way of example, the dose may be (but not limited to) a final circulating concentration of about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2., 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 micromolar, or any range between any two recited concentrations, or any concentration between any two recited numbers. Further examples of doses expected to block hemichannels but not to uncouple gap junctions are described in O'Carroll et al, 2008, herein incorporated by reference. In some embodiments, tonabersat may be used at a lower dose, for example, 0.001 to 20 micromolar. A low dose can be 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2., 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, or 20 micromolar. It was surprisingly determined, for example, that lower doses of tonabersat are useful to inhibit Cx43 hemichannel mediated ATP release during reperfusion. The use of such lower doses of tonabersat in the methods and uses of this invention, alone or in combination with a pannexin modulator, are also advantageous in reducing side effects of tonabersat.

In other aspects, the time-dependent action of tonabersat with respect to transiently counteracting a rise in Cx43 following injury, and hence de novo formation of GJ hemichannels could be utilised for controlled transient modulation of Connexin 43 channels, e.g., following injury while minimizing the complete removal of the 'spatial-buffering' effect to prevent the accumulation of toxic metabolites and to synchronise tissues following injury, particularly in the central nervous system.

In one embodiment, the dose of a modulator, e.g. a gap junction channel modulator, such as peptide 5 and/or an analogue thereof, and/or a pannexin channel modulator, e.g., probenecid and an analogue thereof, and/or a synthetic mimetic peptide blocker of pannexin 1, e.g., $^{10}$Panx1, or an analogue thereof is approximately 0.001 micromolar and up to approximately 200 micromolar, or 200 to 2000 or 5000 micromolar at the site of action, or higher within the circulation to achieve those concentrations at the site of action. By way of example, the dose may be (but not limited to) a final circulating concentration of about 1, 5, 10, 20, 50, 100, 200, 250, 500, 1000, 2000, 3000, 4000, or 5000 micromolar, or any range between any two recited dosages or any dose between any two recited dosages. Doses of peptide 5 effective to block hemichannels but not to uncouple gap junctions are discussed in O'Carroll et al, 2008. In some embodiments, tonabersat may be used at a lower dose, for example, 1 to 20 micromolar, 1 to 50 micromolar, 20 to 30, 30 to 40 or 40 to 50 micromolar. A low dose can be 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2., 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, or 20 micromolar. It was surprisingly determined, for example, that a lower dose of tonabersat inhibits Cx43 hemichannel mediated ATP release during ischemia-reperfusion. It was surprisingly determined that cetain doses of tonabersat inhibit hemichannels formating, thereby treating reperfusion following ischemia.

In some embodiments, a suitable therapeutically effective dose of a modulator, e.g. a connexin modulator or pannexin modulator or channel modulators thereof, may be at least about 1.0 mg/mL of the modulator, e.g. connexin modulator or pannexin or channel modulator. In some embodiments, the therapeutically effective dose of the modulator, e.g. connexin modulator and/or pannexin modulator, and channels thereof, may be from about 0.001 mg/mL to 0.01 mg/mL, from about 0.01 mg/mL to about 0.1 mg/mL, or from about 0.1 mg/mL to about 100 mg/mL. In some embodiments, the suitable therapeutically effective dose of connexin modulator or pannexin modulator may be about about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0, 25.0, 26.0, 27.0, 28.0, 29.0, 30.0, 31.0, 32.0, 33.0, 34.0, 35.0, 36.0, 37.0, 38.0, 39.0, 40.0, 41.0, 42.0, 43.0, 44.0, 45.0, 46.0, 47.0, 48.0, 49.0, 50.0, 52.5, 55.0, 57.5, 60.0, 62.5, 65.0, 67.5, 70.0, 72.5, 75.0, 77.5, 80.0, 82.5, 85.0, 87.5, 90.0, 92.5, 95.0, 97.5, or about 100.0 ug/mL, or any range or subrange between any two of the recited doses, or any dose falling within the range of about 0.1 to about 100 ug/mL. In some embodiments, the suitable therapeutically effective dose of an anti-connexin agent may be about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0, 25.0, 26.0, 27.0, 28.0, 29.0, 30.0, 31.0, 32.0, 33.0, 34.0, 35.0, 36.0, 37.0, 38.0, 39.0, 40.0, 41.0, 42.0, 43.0, 44.0, 45.0, 46.0, 47.0, 48.0, 49.0, 50.0, 52.5, 55.0, 57.5, 60.0, 62.5, 65.0, 67.5, 70.0, 72.5, 75.0, 77.5, 80.0, 82.5, 85.0, 87.5, 90.0, 92.5, 95.0, 97.5, or about 100.0 mg/mL, or any range or subrange between any two of the recited doses, or any dose falling within the range of about 0.1 to about 100 mg/mL. In some embodiments, the modulator, e.g. connexin modulator and/or pannexin channel modulator, is present at a concentration ranging from about 0.5 to about 50 mg/mL. In other embodiments, the modulator, e.g. connexin modulator and/or pannexin channel modulator, is present at a concentration ranging from about 0.3 to about 30 mg/mL. In other embodiments, the modulator is present at a concentration ranging from about 0.1 or 1.0 to about 10 mg/mL. In other embodiments, the modulator is present at a concentration ranging from about 0.1 or 1.0 to about 0.3 or 3.0 mg/mL. In other embodiments, a modulator, e.g., a connexin modulator or pannexin modulator, such as a connexin 43 modulating agent, and/or a connexin 45 modulating agent is present at a concentration of about 3.0 mg/mL. In any of these aspects the modulator, e.g. connexin modulating agent may be a connexin 43, or connexin 45 modulating agent, for example, a connexin 43 or connexin 45 antisense oligonucleotide, preferably a connexin 43 modulating agent, for example, a connexin 43 antisense oligonucleotide. When the modulator is a modified connexin or pannexin antisense oligonucleotide the above-noted dose concentrations may be increased by from about 2- to about 10-fold, for example. When the modulator is a modified or unmodified peptide or peptidomimetic, the dose may be decreased by 10, 100, or 1000 fold.

In certain embodiments, the connexin or pannexin modulators, for example, the connexin 43 modulator may be administered at about 0.001 micromolar (aM) or 0.05 μM to about 200 μM, or up to 300 μM or up to 1000 μM or up to 2000 μM or up to 3200 μM or more, for example up to about 10 mM, 20 mM, or 30 mM final concentration at the treatment site and/or adjacent to the treatment site, and any doses and dose ranges within these dose numbers. In one embodiment, the connexin modulator (anti-connexin agent) composition is applied at greater than about 1000 μM. Preferably, the antisense polynucleotide composition is applied at about 1000 μM to about 10 mM final concentration, more preferably, the anti-connexin agent composition is applied at about 3 mM to about 10 mM final concentration, and more preferably, the anti-connexin agent composition is applied at about 1-3 mM to about 5-10 mM final concentration. The connexin modulator concentration can be 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2., 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 micromolar; or 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2., 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 millimolar, or any range between any two of the recited dosages or any dose between any two recited numbers.

Additionally, modulator, e.g. connexin and pannexin channel modulators, for example, connexin 43 modulators may be present in the formulation at about 1 μM to about 20 μM final concentration, and alternatively the connexin 43 modulator is present at about 5 μM to about 20 μM final concentration, or at about 10 to about 15 μM final concentration. In certain other embodiments, the modulator is present at about 10 μM final concentration. In yet another embodiment, the modulator is present at about 1-15 μM final concentration. In other embodiments, the modulator is present at about 20 μM, 30 μM, 40 μM, 50 μM, 60 μM, 70 μM, 80 μM, 90 μM, 100 μM, 10-200 μM, 200-300 μM, 300-400 μM, 400-500 μM, 500-600 μM, 600-700 μM, 700-800 μM, 800-900 μM, 900-1000 or 1000-1500 μM, or 1500 μM-2000 μM, 2000 μM-3000 μM, 3000 μM-4000 μM, 4000 μM-5000 μM, 5000 μM-6000 μM, 6000 μM-7000 μM, 7000 μM-8000 μM, 8000 μM-9000 μM, 9000 μM-10,000 μM, 10,000 μM-11,000 μM, 11,000 μM-12,000 μM, 12,000 μM-13,000 μM, 13,000 μM-14,000 μM, 14,000 μM-15,000 μM, 15,000 μM-20,000 μM, 20,000 μM-30,000 μM, 30,000 μM-50,000 μM, or greater, or any range or subrange between any two of the recited doses, or any dose falling within the range of from about 20 μM to about 50,000 μM.

Still other dosage levels between about 1 nanogram (ng)/kg and about 1 mg/kg body weight per day of each of the modulators described herein. In certain embodiments, the dosage of each of the subject compounds will generally be in the range of about 1 ng to about 1 microgram per kg body weight, about 1 ng to about 0.1 microgram per kg body weight, about 1 ng to about 10 ng per kg body weight, about 10 ng to about 0.1 microgram per kg body weight, about 0.1 microgram to about 1 microgram per kg body weight, about 20 ng to about 100 ng per kg body weight, about 0.001 mg to about 0.01 mg per kg body weight, about 0.01 mg to about 0.1 mg per kg body weight, or about 0.1 mg to about 1 mg per kg body weight. In certain embodiments, the dosage of each of the subject compounds will generally be in the range of about 0.001 mg to about 0.01 mg per kg body weight, about 0.01 mg to about 0.1 mg per kg body weight, about 0.1 mg to about 1 mg per kg body weight. If more than one modulator, e.g. connexin and/or pannexin channel modulator, is used, the dosage of each modulator need not be in the same range as the other. For example, the dosage of one connexin or pannexin channel modulator may be between about 0.01 mg to about 10 mg per kg body weight, and the dosage of another connexin or pannexin channel modulator may be between about 0.1 mg to about 1 mg per kg body weight, 0.1 to about 10, 0.1 to about 20, 0.1 to about 30, 0.1 to about 40, or between about 0.1 to about 50 mg per kg body weight. The dosage may also be about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2., 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg body weight or any range or subrange between any two of the recited doses, or any dose falling within the range of from about 0.001 to about 100 mg per kg body weight.

In one embodiment, the combined use of one or more modulators, e.g. connexin, hemichannel, pannexin or pannexin channel modulator polynucleotides or one or more connexin or pannexin modulator peptides or peptidomimetics reduces the effective dose of any such agent compared to the effective dose when said agent administered alone. In certain embodiments, the effective dose of the agent when used in combination is about 1/15 to about 1/2, about 1/10 to about 1/3, about 1/8 to about 1/6, about 1/5, about 1/4, about 1/3 or about 1/2 the dose of the agent when used alone. In another preferred embodiment, the combined use of one or more anti-connexin polynucleotides and one or more anti-connexin peptides or peptidomimetics, or other anti-connexin agents in combination with either or both, reduces the frequency in which said agent is administered compared to the frequency when said agent is administered alone. Thus, these combinations allow the use of lower and/or fewer doses of each agent than previously required to achieve desired therapeutic goals.

In one embodiment, the dose of a connexin or pannexin modulator peptide or peptidomimetic may be 10, 100 or 1000 fold lower than any of the recited doses set forth herein.

Conveniently, the modulator is administered in a sufficient amount to downregulate expression of its respective protein. The connexin modulator, for example, a connexin 43 or 45 modulator is administered in a sufficient amount to downregulate expression of connexin 43 or modulate gap junction formation or connexon opening for at least about 0.5 to 1 hour, at least about 1-2 hours, at least about 2-4 hours, at least about 4-6 hours, at least about 6-8 hours, at least about 8-10 hours, at least about 12 hours, or at least about 24 hours post-administration.

The doses of the connexin or pannexin channel modulator, such as the connexin 43 or 45 modulator, may be administered in single or divided applications. The doses may be administered once, or application may be repeated. Typically, application will be repeated weekly, biweekly, or every 3 weeks, every month, or every 2, 3, 4, 5, 6, 7, 8, 9, 10, 11, 12, 13, 14, 15, 16, 17, 18, 19, 20, 21, 22, 23, or every 24 months or more as needed to prevent, slow, or treat ocular neuropathy, or any ocular condition described herein. The dose may be repeated, and/or increased or decreased in the event that neuronal loss increases or decreases. Doses may also be applied every 12 hours to 7 days apart, or more. For example, doses may be applied 12 hours, or 1, 2, 3, 4, 5, 6, or 7 days apart, or at any time interval falling between any two of these times, or between 12 hours and 7 days. The connexin 43 modulator may be administered for up to four, six, eight, ten, twelve, fourteen, sixteen, eighteen, twenty, twenty-two, twenty-four or twenty-six weeks. For some indications, such as certain ocular uses, more frequent dosing, up to hourly may employed.

Kits, Medicaments and Articles of Manufacture

Optionally, one or more modulators, e.g. connexin or pannexin modulator polynucleotides and/or one or more the connexin or pannexin modulator peptides or peptidomimetics and/or other anti-connexin agents such as a gap junction or hemichannel phosphorylation agent or connexin carboxy-terminal polypeptide, or small molecule modulators, alone or in combinations of any of the modulating agents, or other resistant wound healing agents, may also be used in the manufacture of the medicament, or in a kit. Suitable anti-connexin protein modulating agents, polynucleotides or peptides may be anti-connexin 43, 30 or 26 modulating agents, polynucleotides or peptides. In some aspects any of these connexin modulators is a modulator of Cx31.1, Cx36, Cx37, Cx40, Cx45, Cx50, Cx57 or any other connexin in the eye or blood vessels.

In one aspect, the invention provides an article of manufacture or kit comprising one or more compositions or formulations described. For example, the kit may include a pharmaceutical formulation comprising an effective amount of one or more the connexin or pannexin modulator polynucleotides and/or one or more connexin or pannexin modulator peptides or peptidomimetics and/or other anti-connexin agents, such as a gap junction or hemichannel phosphorylation agent or connexin carboxy-terminal polypeptide, alone or in combinations of any of the connexin or pannexin modulator, or other ocular treatment agents. In some emboidments, the kit may include a pharmaceutical formulation comprising an effective amount of one or more anti-connexin 43 polynucleotides and/or one or more anti-connexin 43 peptides or peptidomimetics and/or other anti-connexin agents, such as a gap junction or hemichannel phosphorylation agent or connexin carboxy-terminal polypeptide, alone or in combinations of any of the anti-connexin 43 modulating agents, or other ocular treatment agents. In some aspects any the kit may comprise is a modulator of Cx26, Cx30, Cx31.1, Cx36, Cx37, Cx40, Cx45, Cx50, Cx57 or any other connexin in the eye or blood vessels.

A kit may comprise one or more pharmaceutical compositions, in separate vessels, or a partitioned vessel, together with packaging and instructions for use. The kit may also comprise a pharmaceutically acceptable carrier. In some embodiments the kit may also include components for administering the pharmaceutical compositions, for example, a syringe, needle, microneedle, a loadable implant, or an iontophoresis device. The connexin or pannexin modulator and ocular treatment partners as described herein can be dosed independently or by use of different fixed combinations with distinguished amounts of the combination partners (a) and (b), i.e. simultaneously, separately or sequentially, whether in pharmaceutical form or dressing/matrix form or both. A parts of the kit can then, for example, be administered simultaneously or chronologically staggered, that is at different time points and with equal or different time intervals for any part of the kit of parts.

Articles of manufacturer are also provided, comprising a vessel containing a compound, composition or formulation of the invention as described herein and instructions for use for the treatment of a subject. For example, in another aspect, the invention includes an article of manufacture comprising a vessel containing a therapeutically effective amount of one or more connexin or pannexin modulator polynucleotides and/or one or more connexin or pannexin modulator peptides or peptidomimetics and/or other anti-connexin agents, such as a gap junction or hemichannel phosphorylation agent or connexin carboxy-terminal polypeptide, alone or in combinations of any of the anti-connexin protein modulating agents, or other resistant wound healing agents, together with instructions for use, including use for the treatment of a subject. Suitable anti-connexin protein modulating agents, polynucleotides or peptides may be connexin 43 or 45 modulating agents, polynucleotides or peptides.

In some aspects the article of manufacture may comprise a matrix that comprises one or more connexin or pannexin modulator peptides or peptidomimetics or other ocular treatment agents or anti-connexin agents, such as a gap junction or hemichannel phosphorylation agent or connexin carboxy-terminal polypeptide, alone or in combinations of any of the anti-connexin 43 modulating agents, or other resistant wound healing agents, Suitable connexin or pannexin modulator agents, polynucleotides or peptides may be anti-connexin 43 or 45 modulating agents, polynucleotides or peptides.

Connexin Modulators

Connexin modulators described herein, e.g., connexin 43 or connexin 45 modulators, modulate cellular communication (e.g. cell to cell), by, for example, blocking or inhibiting the transport of molecules into and out of cells. Connexin modulators affect transmission of molecules between the cell cytoplasm and the periplasmic or extracellular space. Such modulators are generally targeted to hemichannels (also called connexons), which may be independently involved in the exchange of small molecules between the cell cytoplasm and an extracellular space or tissue. Thus, a compound provided herein may directly or indirectly reduce coupling between cells (via gap junctions) or between a cell and an extracellular space or tissue (via hemichannels), and the modulation of transport of molecules from a cell into an extracellular space is within the scope of certain compounds and embodiments of the invention. In some aspects the connexin modulator is a modulator of Cx26, Cx30, Cx31.1, Cx36, Cx37, Cx40, Cx 43, Cx45, Cx50, Cx57 or any other connexin in the eye or blood vessels.

Any modulator that is capable of eliciting a desired inhibition of the passage (e.g., transport) of molecules through a gap junction or connexin hemichannel in ocular blood vessels may be used in embodiments of the invention. Any connexin agents that modulates the passage of molecules through a gap junction or connexin hemichannel are also provided in particular embodiments (e.g., those that modulate, block or lessen the passage of molecules from the cytoplasm of a cell into an extracellular space or adjoining cell cytoplasm). Such anti-connexin agents may modulate the passage of molecules through a gap junction or connexin hemichannel with or without gap junction uncoupling (blocking the transport of molecules through gap junctions). Such compounds include, for example, binding proteins, polypeptides, and other organic compounds that can, for example, block the function or activity of a gap junction or a hemichannel in whole or in part. In some embodiments, the anti-connexin modulator may be an anti-connexin 43 modulator or an anti-connexin 45 modulator. In some aspects the connexin modulator is a modulator of Cx26, Cx31.1, Cx36, Cx37, Cx40, Cx50, Cx57 or any other connexin in the eye or blood vessels.

Certain connexin modulators, such as connexin 43 or connexin 45 modulators, provide downregulation of connexin expression (for example, by downregulation of mRNA transcription or translation) or otherwise decrease or inhibit the activity of the connexin protein, connexin hemichannels or gap junctions. In the case of downregulation, this will have the effect of reducing direct cell-cell communication by gap junctions, or exposure of cell cytoplasm to the extracellular space by hemichannels, at the site at which connexin expression is downregulated.

In certain embodiments, an anti-connexin agent prevents, decreases or alters the activity or function of a hemichannel or a gap junction. As used herein, modulation of the gap junction activity or function by the anti-connexin agent may include the closing of gap junctions, closing of hemichannels, and/or passage of molecules or ions through gap junctions and/or hemichannels.

Pannexin or connexin modulators include anti-connexin, or anti-pannexin polynucleotides, such as antisense polynucleotides or oligonucleotides, for example, connexin 43 oligodeoxynucleotides and other polynucleotides (such as polynucleotides having siRNA or ribozyme functionalities), as well as antibodies and binding fragments thereof that bind connexin protein and a pannexin, and pannexin or connexin peptides and polypeptides, including peptidomimetics and peptide analogs of connexin that modulate hemichannel or gap junction activity or function, and other gap junction blocking agents and gap junction protein phosphorylating agents. Connexin protein peptides and polypeptides may, for example, bind to connexin protein to inhibit its function, or may inhibit connexin function by mimicking regions of connexin protein to inhibit or disrupt its binding to other gap junction proteins.

Pannexin peptides and polypeptides may, for example, inhibit or disrupt pannexin channels.

In other embodiments, the connexin modulators are anti-connexin 43 peptides or peptidomimetics, e.g., anti-connexin 43 hemichannel blocking peptides or peptidomimetics, for example, modified or unmodified peptides or peptidomimentics comprising connexin extracellular domains, transmembrane regions, and connexin carboxy-terminal peptides). The anti-connexin hemichannel blocking peptides or peptidomimetics may be modified or unmodified. The anti-connexin hemichannel blocking peptides or peptidomimetics are made chemically, synthetically, or otherwise manufactured.

In some embodiments the connexin modulators of this invention include anti-connexin peptides or peptidomimetics, e.g., connexin 43 peptides or peptidomimetics, for example, any of the peptides described herein, including peptides comprising a portion of an extracellular domain of a connexin, and peptides comprising a portion of a carboxy-terminal portion of a connexin useful in the methods of this invention, which is therapeutically effective, for example, effective for healing any of the neuropathic ocular disorders described herein. In some aspects, the therapeutically effective modified or unmodified peptide or peptidomimetic comprises a portion of an extracellular or transmembrane domain of a connexin, such as connexin 43.

Methods of synthesizing antibodies and binding fragments as well as peptides and polypeptides, including peptidomimetics and peptide analogs can also be performed using suitable methods. See e.g. Lihu Yang et al., Proc. Natl. Acad. Sci. U.S.A., 1; 95(18): 10836-10841 (Sep. 1, 1998); Harlow and Lane (1988) "Antibodies: A Laboratory Manuel" Cold Spring Harbor Publications, New York; Harlow and Lane (1999) "Using Antibodies" A Laboratory Manuel, Cold Spring Harbor Publications, New York.

Connexin Polynucleotides and Oligonucleotides

In some aspects of this invention, the connexin modulator is a peptide or peptidomimetic. The connexin modulator may comprise, for example, a connexin 43 or connexin 45 peptide or peptidomimetic, preferably a connexin 43 peptide or peptidomimetic. In some aspects the connexin peptide or peptidomimetic may be a Cx26, Cx30, Cx31.1, Cx36, Cx37, Cx40, Cx50, Cx57 peptide or peptidomimetic. In some aspects, the connexin modulator can include or exclude any of the foregoing.

In some embodiments, the connexin 43 modulator may comprise, for example, SEQ ID NO: 173 (SRPTEKT), SEQ ID NO: 168 (VDCFLSRPTEKT), or SEQ ID NO:168 conjugated to two dodecyl groups at the N-terminus, through a linker. The peptide may contain one or more modified amino acids, amino acid analogs, or may be otherwise modified, for example, conjugated or bound to cell internalization transporter.

In another non-limiting but preferred embodiment, an anti-connexin compound comprises a peptide comprising an amino acid sequence corresponding to a portion of a transmembrane region of a connexin, such as connexin 43 or connexin 45, or Cx26, Cx31.1, Cx36, Cx37, Cx40, Cx50, Cx57 or any other connexin in the eye or blood vessels. In particular non-limiting embodiments, the anti-connexin compound is a peptide having an amino acid sequence that comprises a peptide having an amino acid sequence that comprises about 3 to about 30 contiguous amino acids of the connexin, e.g., connexin 43 or 45 protein sequence, about 5 to about 20 contiguous amino acids of the connexin, e.g., connexin 43 or 45 protein sequence, a peptide having an amino acid sequence that comprises about 8 to about 15 contiguous amino acids of the connexin, e.g., connexin 43 or 45 protein sequence, or a peptide having an amino acid sequence that comprises about 11, 12, or 13 contiguous amino acids of connexin 43 or 45 protein sequence. Other non-limiting embodiments include an anti-connexin compound that is a peptide having an amino acid sequence that comprises at least about 5, 6, 7, 8, 9, 10, 11, 12, 13, 14, 15, 20, 25, or 30 contiguous amino acids of the connexin 43 or 45 protein sequence. In some aspects, the connexin modulator (anti-connexin compound) can include or exclude any of the foregoing.

In other anti-connexin compounds, mimetic peptides are based on the extracellular domains of connexin 43 corresponding to the amino acids at positions 37-76 and 178-208 of connexin 43 protein sequence. Thus, certain peptides described herein have an amino acid sequence corresponding to the regions at positions 37-76 and 178-208 of the connexin 43 protein sequence. The peptides need not have an amino acid sequence identical to those portions of the connexin 43 protein sequence, and conservative amino acid changes may be made such that the peptides retain binding activity or functional activity in the assays described herein and otherwise known in the art. In other embodiments, mimetic peptides are based on peptide target regions within the connexin protein other than the extracellular domains (e.g. the portions of the connexin 43 protein sequence not corresponding to positions 37-76 and 178-208).

In some embodiments, the connexin 45 modulator may comprise, for example, peptides. The peptide may contain one or more modified amino acids, amino acid analogs, or may be otherwise modified, for example, conjugated or bound to a cell internalization transporter or bioavailability agent.

In a non-limiting but preferred embodiment, a connexin modulator comprises a peptide comprising an amino acid sequence corresponding to a portion of a transmembrane region of connexin 45 or a C-terminal region of connexin 45. In particular non-limiting embodiments, for example, the anti-connexin compound is a peptide having an amino acid sequence that comprises about 3 to about 30 contiguous amino acids of the known connexin 45 sequence, a peptide having an amino acid sequence that comprises about 5 to about 20 contiguous amino acids of the known connexin 45 sequence, a peptide having an amino acid sequence that comprises about 8 to about 15 contiguous amino acids of the known connexin 45 sequence, or a peptide having an amino acid sequence that comprises about 11, 12, or 13 contiguous amino acids of the known connexin 45 sequence. Other non-limiting embodiments include an anti-connexin compound that is a peptide having an amino acid sequence that comprises at least about 3, 4, 5, 6, 7, 8, 9, 10, 11, 12, 13, 14, 15, 20, 25, or 30 contiguous amino acids of the known connexin 45 sequence. In certain anti-connexin compounds provided herein, mimetic peptides are based on the extracellular domains of connexin 45 corresponding to the amino acids at positions 46-75 and 199-228 of the known connexin 45 sequence. Thus, certain peptide described herein have an amino acid sequence corresponding to the regions at positions 46-75 and 199-228 of the known connexin 45 sequence. The peptides need not have an amino acid sequence identical to those portions of the known connexin 45 sequence. and conservative amino acid changes may be made such that the peptides retain binding activity or functional activity in the assays described herein and otherwise known in the art. In other embodiments, mimetic peptides are based on peptide target regions within the connexin protein other than the extracellular domains (e.g. portions of the known connexin 45 sequence not corresponding to positions 46-75 and 199-228). WO2006/134494, disclosing various connexin sequences is incorporated by reference. In some aspects, the connexin modulator can include or exclude any of the foregoing.

In some aspects the anti-connexin modulator used in any of the methods of treatment of this invention is a connexin modulator, for example, a connexin 45 or connexin 43 modulator. In some embodiments the connexin modulator is a connexin 43 oligonucleotide or polynucleotide, which may be, for example, a connexin 43 antisense oligonucleotide or polynucleotide. The oligonucleotides and polynucleotides of this invention are made chemically, synthetically, or otherwise manufactured. In one embodiment the connexin modulator is a connexin protein antisense oligodeoxynucleotide, whether chemically modified or unmodified. This invention features connexin 43 modulators selected, for example, from modified or unmodified connexin 43 polynucleotides or oligonucleotides. In some aspects this invention relates to a connexin anti-sense compound such as modified or unmodified connexin 43 antisense oligonucleotides and modified or unmodified connexin 43 antisense polynucleotides, or oligonucleotides or polynucleotides comprising mixtures of modified and unmodified nucleotides. In some aspects, the connexin 43 antisense compound used in the methods herein is an antisense oligonucleotide comprising naturally occurring nucleobases and an unmodified internucleoside linkage. Typically the polynucleotides are single stranded, but may be double stranded.

Also featured herein are modified or unmodified connexin 43 antisense compounds comprising a nucleobase sequence selected from SEQ ID NO:1-16. The polynucleotides of this invention include synthesized polynucleotides having a length of less than 80 nucleotides, e.g., from 12-18 to about 50-80 nucleotides, preferably about 30 nucleotides or less, e.g., from 12 to about 30 nucleotides, and more preferably from about 15 to about 30 nucleotides. In one example, the polynucleotide has 30 nucleotides. The methods of this invention features, in some aspects, the use of connexin 43 antisense compounds up to 40 nucleotides in length, for example, 15 to 40 nucleotides in length, comprising a nucleotide sequence selected from SEQ ID NO:1-16, or comprising from about 8 to 40 nucleotides of SEQ ID NO: 17.

In some aspects of this invention, the connexin 43 antisense oligonucleotide or polynucleotide has at least about 80%, 85%, 90%, 95%, 97%, 98%, or 99% homology to a polynucleotide having a sequence selected from SEQ ID NOs: 1 to 16 or a portion of SEQ ID NO:17.

The connexin modulators, including those provided and used in certain embodiments, may comprise one or polynucleotides, selected, for example, from the group consisting of antisense oligonucleotides, antisense polynucleotides, deoxyribozymes, morpholino oligonucleotides, RNAi molecules, siRNA molecules, PNA molecules, DNAzymes, and 5'-end-mutated U1 small nuclear RNAs, and analogs of the preceding. These and other compounds may be used alone or in combination with one more mimetic or other binding peptides.

Featured in this invention are connexin antisense oligonucleotides or polynucleotides comprising at least one unmodified nucleotide. In one aspect, the connexin antisense oligonucleotides or polynucleotides may comprise at least one modified nucleotide, and/or have at least one modified internucleoside linkage, and/or at least one modified sugar moiety. The modified internucleoside linkage may be, for example, a phosphorothioate linkage. In some aspects, for example, the connexin polynucleotide may comprise at least one nucleotide comprising a conformationally strained nucleotide, for example, a locked nucleic acid (LNA) or a bridged nucleic acid (BNA). The locked nucleotide may be selected, from one of the following types, for example: 2'-O—$CH_2$-4' (oxy-LNA), 2'-$CH_2$—$CH_2$-4' (methylene-LNA), 2'-NH—$CH_2$-4' (amino-LNA), 2'-N($CH_3$)— $CH_2$-4' (methylamino-LNA), 2'-S—$CH_2$-4' (thio-LNA), and 2'-Se—$CH_2$-4' (seleno-LNA). In some aspects the modified nucleotide may be a locked nucleic acid or an unlocked nucleic acid. In some aspects the connexin antisense oligonucleotides or polynucleotides are connexin 43 antisense oligonucleotides or polynucleotides.

Synthesis of antisense polynucleotides and other anti-connexin polynucleotides such as RNAi, siRNA, and ribozyme polynucleotides as well as polynucleotides having modified and mixed backbones can be performed. See e.g. Stein C. A. and Krieg A. M. (eds), Applied Antisense Oligonucleotide Technology, 1998 (Wiley-Liss).

The antisense polynucleotide may inhibit transcription and/or translation of a connexin protein, such as connexin 43 or connexin 45. The antisense polynucleotide is generally antisense to connexin protein mRNA, for example, connexin 43. Such a polynucleotide may be capable of hybridizing to connexin protein mRNA and may thus inhibit the expression of connexin by interfering with one or more aspects of connexin protein mRNA metabolism including transcription, mRNA processing, mRNA transport from the nucleus, translation or mRNA degradation. The antisense polynucleotide typically hybridizes to the connexin mRNA to form a duplex which can cause direct inhibition of translation and/or destabilization of the mRNA. Such a duplex may be susceptible to degradation by nucleases. Preferably the polynucleotide is a specific inhibitor of transcription and/or translation from the connexin 43 gene or mRNA, and does not inhibit transcription and/or translation from other genes or mRNAs. Screening of the polynucleotide sequence in a human genome sequence database for specificity may also be performed. The product may bind to the connexin 43 gene or mRNA either (i) 5' to the coding sequence, and/or (ii) to the coding sequence, and/or (iii) 3' to the coding sequence.

The antisense polynucleotide may hybridize to part of the connexin protein mRNA, such as connexin 43 mRNA. Typically the antisense polynucleotide hybridizes to the ribosome binding region or the coding region of the connexin protein mRNA. The polynucleotide may be complementary to a region of the connexin mRNA. For example, the polynucleotide may be the exact complement of a part of connexin mRNA. However, absolute complementarity is not required and polynucleotides which have sufficient complementarity to form a duplex having a melting temperature of greater than about 20° C., 30° C. or 40° C. under physiological conditions are particularly suitable for use in the present invention.

Thus the polynucleotide is typically a homologue of a sequence complementary to the mRNA. The polynucleotide may be a polynucleotide which hybridizes to the connexin protein mRNA under conditions of medium to high stringency such as 0.03M sodium chloride and 0.03M sodium citrate at from about 50° C. to about 60° C.

For certain embodiments of this invention, the polynucleotides of this invention include synthesized polynucleotides having a length of less than 80 nucleotides, e.g., from 12-18, or 15-18 to about 50-80 nucleotides, preferably about 30 nucleotides or less, e.g., from 12 to about 30 nucleotides, and more preferably from about 15 to about 20, or from about 15 to about 30 nucleotides. In one example, the polynucleotide has 30 nucleotides. The methods of this invention features, in some aspects, the use of connexin 43 antisense compounds up to 40 nucleotides in length, for example, 15 to 40 nucleotides in length, comprising a nucleotide sequence selected from SEQ ID NO:1-16, or comprising from about 8 to 40 nucleotides of SEQ ID NO:17.

Alternatively, the antisense polynucleotides may be part of compositions which may comprise polynucleotides to more than one connexin protein. Preferably, the connexin protein to which polynucleotides are directed is connexin 43. Suitable exemplary polynucleotides (and ODNs) directed to various connexins are set forth in Table 1.

The polynucleotides for use in the invention may suitably be unmodified phosphodiester oligomers, or may be modified. Such oligodeoxynucleotides may vary in length. A 30 mer polynucleotide has been found to be suitable, although polynucleotides having 15-30 nucleotides or less are also suitable.

Many aspects of the invention are described with reference to oligodeoxynucleotides. However it is understood that other suitable polynucleotides (such as RNA polynucleotides) may be used in these aspects.

The antisense polynucleotides may be chemically modified. This may enhance their resistance to nucleases and may enhance their ability to enter cells. For example, phosphorothioate oligonucleotides may be used. Other deoxynucleotide analogs include methylphosphonates, phosphoramidates, phosphorodithioates, N3'P5'-phosphoramidates and oligoribonucleotide phosphorothioates and their 2'-O-alkyl analogs and 2'-O-methylribonucleotide methylphosphonates. Alternatively mixed backbone oligonucleotides ("MBOs") may be used. MBOs contain segments of phosphothioate oligodeoxynucleotides and appropriately placed segments of modified oligodeoxy- or oligoribonucleotides. MBOs have segments of phosphorothioate linkages and other segments of other modified oligonucleotides, such as methylphosphonate, which is non-ionic, and very resistant to nucleases or 2'-O-alkyloligoribonucleotides. Methods of preparing modified backbone and mixed backbone oligonucleotides are known in the art.

Featured in this invention are connexin 43 antisense oligonucleotides or polynucleotides comprising at least one unmodified nucleotide. In one aspect, the connexin 43 antisense oligonucleotides or polynucleotides may comprise at least one modified nucleotide, and/or have at least one modified internucleoside linkage, and/or at least one modified sugar moiety. The modified internucleoside linkage may be, for example, a phosphorothioate linkage. In some aspects, for example, the connexin 43 polynucleotide may comprise at least one nucleotide comprising a conformationally strained nucleotide, for example, a locked nucleic acid (LNA) or a bridged nucleic acid (BNA). The locked nucleotide may be selected, from one of the following types, for example: 2'-O—$CH_2$-4' (oxy-LNA), 2'-$CH_2$—$CH_2$-4' (methylene-LNA), 2'-NH—$CH_2$-4' (amino-LNA), 2'-N($CH_3$)— $CH_2$-4' (methylamino-LNA), 2'-S—$CH_2$-4' (thio-LNA), and 2'-Se—$CH_2$-4' (seleno-LNA). In some aspects the modified nucleotide may be a locked nucleic acid or an unlocked nucleic acid.

In some aspects of this invention, the connexin 43 antisense oligonucleotide or polynucleotide has at least about 80%, 85%, 90%, 95%, 97%, 98%, or 99% homology to a polynucleotide having a sequence selected from SEQ ID NOs: 1 to 17 and 19.

Other Connexin 43 Modulators

Connexin modulators, for example, connexin 43 or 45 modulators, including peptides, peptidomimetics, antibodies, antibody fragments, and the like, are also suitable modulators of gap junctions and hemichannels. Exemplary gap junction modulators may include, without limitation, polypeptides (e.g. antibodies, binding fragments thereof, and synthetic constructs), and other gap junction blocking agents, and gap junction protein phosphorylating agents. In some aspects the connexin modulator is a modulator of Cx26, Cx30, Cx31.1, Cx36, Cx37, Cx40, Cx43, Cx50, Cx57 or any other connexin in the eye or blood vessels.

Connexin modulators, for example, connexin 43 or 45 modulators include, for example, monoclonal antibodies, polyclonal antibodies, antibody fragments (including, for example, Fab, F(ab')2 and Fv fragments; single chain antibodies; single chain Fvs; and single chain binding molecules such as those comprising, for example, a binding domain, hinge, CH2 and CH3 domains, recombinant antibodies and antibody fragments which are capable of binding an antigenic determinant (i.e., that portion of a molecule, generally referred to as an epitope) that makes contact with a particular antibody or other binding molecule. These binding proteins, including antibodies, antibody fragments, and so on, may be chimeric or humanized or otherwise made to be less immunogenic in the subject to whom they are to be administered, and may be synthesized, produced recombinantly, or produced in expression libraries. Any binding molecule known in the art or later discovered is envisioned, such as those referenced herein and/or described in greater detail in the art. For example, binding proteins include not only antibodies, and the like, but also ligands, receptors, peptidomimetics, or other binding fragments or molecules (for example, produced by phage display) that bind to a target (e.g. connexin, hemichannel, or associated molecules).

Binding molecules will generally have a desired specificity, including but not limited to binding specificity, and desired affinity. Affinity, for example, may be a Ka of greater than or equal to about $10^4$ M−1, greater than or equal to about $10^6$ M−1, greater than or equal to about $10^7$ M−1, greater than or equal to about $10^8$ M−1. Affinities of even greater than about $10^8$ M−1 are suitable, such as affinities equal to or greater than about $10^9$ M−1, about $101^0$ M−1, about $10^{11}$ M−1, and about $10^{12}$ M−1. Affinities of binding proteins according to the present invention can be readily determined using conventional techniques, for example those described by Scatchard et al., (1949) Ann. N.Y. Acad. Sci. 51: 660.

Exemplary compounds used for closing gap junctions (e.g. phosphorylating connexin 43 tyrosine and/or serine residue) have been reported in U.S. Pat. Nos. 7,153,822 and 7,250,397. Exemplary peptides and peptidomimetics are reported in Green et al., WO2006134494. See also WO2006069181 and WO2003032964. Examples of other agents used for closing gap junctions include anti-connexin agents, for example anti-connexin polynucleotides (for example, connexin inhibitors such as alpha-1 connexin oligodeoxynucleotides), anti-connexin peptides (for example, antibodies and antibody binding fragments) and peptidomimetics (for example, alpha-1 anti-connexin peptides or peptidomimetics), gap junction closing or blocking compounds, hemichannel closing or blocking compounds, and connexin carboxy-terminal polypeptides, e.g., polypeptides that bind to ZO-1 or a ZO-1 binding site, anti-ZO-1 polynucleotides.

By using data obtained from hydropathy plots, it has been proposed that a connexin contains four-transmembrane-spanning regions and two short extra-cellular loops. The positioning of the first and second extracellular regions of connexin was further characterized by the reported production of anti-peptide antibodies used for immunolocalization of the corresponding epitopes on split gap junctions. Goodenough D. A. J Cell Biol 107: 1817-1824 (1988); Meyer R. A., J Cell Biol 119: 179-189 (1992).

The extracellular domains of a hemichannel contributed by two adjacent cells "dock" with each other to form complete gap junction channels. Reagents that interfere with the interactions of these extracellular domains can impair cell-to-cell communication. Peptide inhibitors of gap junctions and hemichannels have been reported. See for example Berthoud, V. M. et al., Am J. Physiol. Lung Cell Mol. Physiol. 279: L619-L622 (2000); Evans, W. H. and Boitano, S. Biochem. Soc. Trans. 29: 606-612, and De Vriese A. S., et al. Kidney Int. 61: 177-185 (2001). Short peptides corresponding to sequences within the extracellular loops of connexins were said to inhibit intercellular communication. Boitano S. and Evans W. Am J Physiol Lung Cell Mol Physiol 279: L623-L630 (2000). The use of peptides as inhibitors of cell-cell channel formation produced by connexin (Cx) 32 expressed in paired Xenopus oocytes has also been reported. Dahl G, et al., Biophys J 67: 1816-1822 (1994). Berthoud, V. M. and Seul, K. H., summarized some of these results. Am J., Physiol. Lung Cell Mol. Physiol. 279: L619-L622 (2000).

Anti-connexin agents include peptides having an amino acid sequence that comprises about 5 to 20 contiguous amino acids of a connexin protein such as connexin 43 (SEQ.ID.NO: 19), peptides having an amino acid sequence that comprises about 8 to 15 contiguous amino acids of connexin 43, or peptides having an amino acid sequence that comprises about 11 to 13 contiguous amino acids of connexin 43. Other anti-connexin agents include a peptide having an amino acid sequence that comprises at least about 5, at least about 6, at least about 7, at least about 8, at least about 9, at least about 10, at least about 11, at least about 12, at least about 13, at least about 14, at least about 15, at least about 20, at least about 25, or at least about 30 contiguous amino acids of connexin 43. Other anti-connexin 43 modulators comprise the extracellular domains of connexin 43, for example, peptide or peptidomimetic comprising SRPTEKT (SEQ ID NO: 173) or VDCFLSRPTEKT (SEQ ID NO: 168). Other anti-connexin 43 modulators comprise the C-terminus region of connexin 43, see WO2006/069181, or modified versions thereof.

In one aspect this invention relates to pharmaceutical compositions, articles of manufacture, and methods for treating neuropathic ocular disorders by administering a therapeutically effective amount of at least one connexin or pannexin modulator to the eye of said subject. In some aspects the neuropathic ocular disorder may be, for example, loss of retinal ganglion cells and/or glaucomatous optic neuropathy. In some aspects, administering a therapeutically effective amount of at least one connexin modulator is effective for stopping, preventing, or treating loss of retinal ganglion cells are further useful for increasing the levels of neurotrophins in the glaucomatous optic nerve and decreasing vitreal glutamate concentrations.

In certain another aspect, gap junction modifying agent may include, for example, compounds of Formula I or Formula II. In certain another aspect, gap junction modifying agent may include, for example, aliphatic alcohols; octanol; heptanol; anesthetics (e.g. halothane), ethrane, fluothane, propofol and thiopental; anandamide; arylaminobenzoate (FFA: flufenamic acid and similar derivatives that are lipophilic); carbenoxolone; Chalcone: (2',5'-dihydroxychalcone); CHFs (Chlorohydroxyfuranones); CMCF (3-chloro-4-(chloromethyl)-5-hydroxy-2(5H)-furanone); dexamethasone; doxorubicin (and other anthraquinone derivatives); eicosanoid thromboxane A(2) (TXA(2)) mimetics; NO (nitric oxide); Fatty acids (e.g. arachidonic acid, oleic acid and lipoxygenase metabolites; Fenamates (flufenamic (FFA), niflumic (NFA) and meclofenamic acids (MFA)); Genistein; glycyrrhetinic acid (GA):18a-glycyrrhetinic acid and 18-beta-glycyrrhetinic acid, and derivatives thereof; lindane; lysophosphatidic acid; mefloquine; menadione; 2-Methyl-1,4-naphthoquinone, vitamin K(3); nafenopin; okadaic acid; oleamide; oleic acid; PH, gating by intracellular acidification; e.g., acidifying agents; polyunsaturated fatty acids; fatty acid GJIC inhibitors (e.g., oleic and arachidonic acids); quinidine; quinine; all trans-retinoic acid; and tamoxifen.

Polynucleotide Homologues

Homology and homologues are discussed herein (for example, the polynucleotide may be a homologue of a complement to a sequence in pannexin mRNA). Such a polynucleotide typically has at least about 70% homology, preferably at least about 80%, at least about 90%, at least about 95%, at least about 97% or at least about 99% homology with the relevant sequence, for example, over a region of at least about 15, at least about 20, at least about 25, at least about 30, at least about 40, at least about 50, or at least about 100 more contiguous nucleotides (of the homologous sequence).

Homology or sequence identity may be calculated based on any method in the art. For example, the UWGCG Package provides the BESTFIT program that can be used to calculate homology (Devereux, et al. (1984) Nucleic Acids Research 12, p387-395). The PILEUP and BLAST algorithms can also be used to calculate sequence identity or align sequences, for example, as described in Altschul, S. F. (1993), J Mol Evol 36: 290-300; Altschul, et al (1990), J Mol Biol 215: 403-10. Software for performing BLAST analyses is publicly available through the National Center for Biotechnology Information (http://www.ncbi.nlm.nih.gov/). The BLAST algorithm performs a statistical analysis of the similarity between two sequences; see e.g., Karlin and Altschul (1993) Proc. Natl. Acad. Sci. USA 90: 5873-5787. The homologous sequence typically differs from the relevant sequence by at least about (or by no more than about) 2, 5, 10, 15, 20, or more nucleotide differences (which may be substitutions, deletions, or insertions). These differences can be measured across any of the regions mentioned above in relation to calculating sequence identity or homology.

The homologous sequence typically hybridizes selectively to the original sequence at a level significantly above background. Selective hybridization is typically achieved using conditions of medium to high stringency (for example 0.03M sodium chloride and 0.03M sodium citrate at from about 50° C. to about 60° C.). However, such hybridization may be carried out under any suitable conditions known in the art (see Sambrook, et al. (1989), Molecular Cloning: A Laboratory Manual). For example, if high stringency is required, suitable conditions include 0.2×SSC at 60° C. If lower stringency is required, suitable conditions include 2×SSC at 60° C.

Peptide and Polypeptide Anti-Pannexin Agents

Pannexin binding proteins, including peptides, peptidomimetics, antibodies, antigen-binding antibody fragments, and the like, are also suitable modulators of adherens junctions.

Binding proteins include, for example, monoclonal antibodies, polyclonal antibodies, antibody fragments (including, for example, Fab, F(ab')2 and Fv fragments; single chain antibodies; single chain Fvs; and single chain binding molecules such as those comprising, for example, a binding domain, hinge, CH2 and CH3 domains, recombinant antibodies, and antibody fragments which are capable of binding an antigenic determinant (i.e., that portion of a molecule, generally referred to as an epitope) that makes contact with a particular antibody or other binding molecule. These binding proteins, including antibodies, anti-binding antibody fragments, and so on, may be chimeric or humanized or otherwise made to be less immunogenic in the subject to whom they are to be administered, and may be synthesized, produced recombinantly, or produced in expression libraries. Any binding molecule known in the art or later discovered is envisioned, such as those referenced herein and/or described in greater detail in the art. For example, binding proteins include not only antibodies, and the like, but also ligands, receptors, peptidomimetics, or other binding fragments or molecules (for example, produced by phage display) that bind to a target (e.g., a pannexin protein).

Binding molecules will generally have a desired specificity, including but not limited to binding specificity, and desired affinity. Affinity, for example, may be a $K_a$ of greater than or equal to about $10^4$ $M^{-1}$, greater than or equal to about $10^6$ $M^{-1}$, greater than or equal to about $10^7$ $M^{-1}$, greater than or equal to about $10^8$ $M^{-1}$. Affinities of even greater than about $10^8$ $M^{-1}$ are suitable, such as affinities equal to or greater than about $10^9$ $M^{-1}$, about $10^{10}$ $M^{-1}$, about $10^{11}$ $M^{-1}$, and about $10^{12}$ $M^{-1}$. Affinities of binding proteins according to the present invention can be readily determined using conventional techniques, for example those described by Scatchard, et al., 1949 *Ann. N.Y. Acad. Sci.* 51: 660.

Anti-pannexin agents include peptides comprising an amino acid sequence corresponding to a pannexin domain motif from a pannexin protein (e.g., pannexin1, pannexin2, pannexin3 etc.). Other embodiments are directed to an anti-connexin agent that is a peptide having an amino acid sequence that comprises at least about 5, at least about 6, at least about 7, at least about 8, at least about 9, at least about 10, at least about 11, at least about 12, at least about 13, at least about 14, at least about 15, at least about 20, at least about 25, or at least about 30 contiguous amino acids encoded by a pannexin gene, for example, an pannexin1 gene as set forth in Example 1, below. In certain anti-connexin agents provided herein, the extracellular domains of pannexin1 may be used to develop the particular peptide sequences. The peptides need not have an amino acid sequence identical to those portions of naturally occurring pannexin, and conservative amino acid changes may be made such that the peptides retain binding activity or functional activity. Alternatively, peptides may target other regions of the extracellular domain.

Anti-pannexin peptides may comprise sequences corresponding to a portion of a pannexin extracellular domain with conservative amino acid substitutions such that peptides are functionally active anti-pannexin agents. Exemplary conservative amino acid substitutions include for example the substitution of a nonpolar amino acid with another nonpolar amino acid, the substitution of an aromatic amino acid with another aromatic amino acid, the substitution of an aliphatic amino acid with another aliphatic amino acid, the substitution of a polar amino acid with another polar amino acid, the substitution of an acidic amino acid with another acidic amino acid, the substitution of a basic amino acid with another basic amino acid, and the substitution of an ionizable amino acid with another ionizable amino acid.

Manufacture and Stability

The polynucleotides of this invention can be manufactured using solid-phase chemistries for synthesizing oligonucleotides. In one aspect, the formulations of this invention will comprise a salt of the polynucleotides of this invention, such as the sodium salt of the polynucleotides of this invention. In one embodiment the formulation may comprise the sodium salt of a polynucleotide having any one of SEQ.ID.NO:1-16 or a portion of SEQ ID NO:17, for example. In some embodiments, the polynucleotide having any one of SEQ.ID.NO: 1-16 may be a modified oligodeoxynucleotide having any one of SEQ.ID.NO:1-16, or a portion of SEQ ID NO:17.

In some embodiments, the formulations of this invention are substantially pure. By substantially pure is meant that the formulations comprise less than about 10%, 5%, or 1%, and preferably less than about 0.1%, of any nucleotide or non-nucleotide impurity. In some embodiments the total impurities, including metabolities of the connexin 43 modulating agent, will be not more than 15%. In some embodiments the total impurities, including metabolities of the connexin 43 modulating agent, will be not more than 12%. In some embodiments the total impurities, including metabolities of the connexin 43 modulating agent, will be not more than 11%. In other embodiments the total impurities, including metabolities of the connexin 43 modulating agent, will be not more than 10%.

In some embodiments, the purity of the formulations of this invention may be measured using a method selected from anion exchange HPLC (AEX-HPLC) or mass spectrometry. Mass spectrometry may include LC/MS, or LC/MS/MS. The assay may in some embodiments comprise both AEX-HPLC and LC/MS.

Sterile compositions comprising the connexin 43 modulating agents of this invention prepared using aseptic processing by dissolving the anti-connexin modulating agent in the formulation vehicle. In one embodiment, the formulation may also be sterilized by filtration. Excipients used in the manufacture of of the formulations of this invention are widely used in pharmaceutical products and released to pharmacopeial standards.

EXAMPLES

Various small organic molecules have been reported to have activity in inhibition of gap junction or hemichannel currents. They include triarylmethanes (TRAMs), quinine, mefloquine, fenamates, 2-aminophenoxyborate and derivatives, glycyrrhetinic acid and derivatives, volatile anesthetics such as halothane and ethane, lipophilic compounds such as long-chain alcohols (e.g., heptanol and octanol), fatty acid amides including oleamide, cyclodextrins, cisplatin, polyamines and tetraalylammonium ions. An increasing number of studies have also reported on the inhibition of gap junction channels and hemichannels using peptides corresponding to specific sequences within extracellular loops E1 and E2 involving the conserved QPG and SHVR (SEQ ID NO: 18) motifs of E1 (Gap26 peptide) and the SRPTEK (SEQ ID NO: 20) motif in E2 (Gap27 peptide) as well as the cytoplasmic loop (Gap19 peptide). The most potent such peptidomimetic is Peptide5 (VDCFLSRPTEKT (SEQ ID NO: 168)).

Peptide5 is an established gap junction channel blocker that can operate in a dose dependent manner, with lower doses blocking gap junction hemichannel opening and higher doses uncoupling gap junctions between cells. See, e.g., O'Carroll et al, 2008. With sustained low dose application of Peptide5 there is also gradual loss of gap junction coupling, considered to be peptide interference with hemichannel docking (in parallel with gradual removal of existing gap junctions during normal turnover). Peptide5 has proven to be effective in a number of in vitro, ex vivo and in vivo (animal) studies, especially when used at doses that block hemichannels without uncoupling gap junctions (see for example Davidson et al, 2012; Danesh-Meyer et al, 2012; O'Carroll et al, 2013). The results in O'Carroll et al, 2008 indicate that Peptide5 at low or high concentration blocks hemichannels, but will uncouple gap junctions directly at high concentrations. Peptide5 data is shown here for comparison with tonabersat.

Example 1: Methods and Materials for hCMVEC and ARPE-19 Cell Studies

In the below Examples 2, 4, 5, 8 and 10 using human cerebral microvascular endothelial cells (hCMVEC), cells were prepared by growing them in collagen coated (30 μg/mL) T25 or T75 flasks maintained in Medium M199 supplemented with 10% FCS, 1 μg/mL hydrocortisone, 3 ng/mL hFGF, 1 ng/mL hEGF, 10 μg/mL heparin, 1× penicillin streptomycin neomycin (Life Technologies), and cAMP (100 μL 100% cAMP to 100 mL media). Cells were maintained at 37° C. with 95% $O_2$ and 5% $CO_2$.

In the below Examples 3, 6 and 7 using human retinal epithelial (ARPE-19) cells, the cells were grown in DMEM/F: 12 (Invitrogen), supplemented with 10% fetal calf serum (FCS), 100 units/mL of penicillin, 100 μg/mL of streptomycin, and 0.25 μg/mL of Fungizone® Antimycotic (Invitrogen).

With respect to the chemicals used in these studies, tonabersat (Medchemexpress, USA) was dissolved in dimethyl sulfoxide (DMSO) at a stock concentration of 100 mM. Ammonium chloride (NH4Cl, Sigma) was dissolved in dH20 at a stock concentration of 100 mM. Connexin43 mimetic peptide (Peptide5, sequence VDCFLSRPTEKT (SEQ.ID NO:168)) (Auspep, Australia), and Peptide 8 (CDEQSAFRCNTQQ (SEQ.ID NO:241)) were synthesized at purity>95% and dissolved in dH20 at a concentration of 10 mM. Probenecid (C13H19NO4S, Sigma) was solubilized in 1 M NaOH at a concentration of 50 mg/mL.

All animal model procedures were conducted in compliance with the ARVO Statement of Use of Animals in Ophthalmic and Vision Research and were approved by the Animal Ethics Committee of the University of Auckland. Seventeen adult male Wistar rats weighing between 240-260 g were obtained from the Vernon Jenson Unit of the University of Auckland and housed with a 12-hour light/dark cycle and received food and water ad libitum.

Example 2: Scrape Load Assay

In this Example, human cerebral microvascular endothelial cells (hCMVEC) were grown in collagen coated (1 μg/mL) T25 flasks maintained in Medium M199 supplemented with 10% FBS, 1 μg/mL hydrocortisone, 3 ng/mL hFGF, 1 ng/mL hEGF, 10 μg/mL heparin and cAMP (100 μL 100% cAMP to 100 mL media) in a humidified atmosphere at 37° C. with 5% CO2. One day prior to experimentation, these cells were trypsinized and plated at a density of 4×105 cells/well in a collagen-coated 12 well-plate in the same medium. For treatments, cells were cultured in the presence of peptide5, a control gap junction channel blocker (carbenoxolone), or tonabersat for the respective time intervals prior to scrape dye loading. The blockers were also present in the respective scrape loading solutions.

For scrape loading the hCMVEC cells were washed three times with phosphate buffered saline (PBS) (without divalent cations). A solution of PBS+0.05% lucifer yellow was added to cells. The cells then received a scrape to the monolayer using a size 10 carbon steel surgical blade and incubated in the dark at 37° C. with 5% CO2 for 5 minutes. The cells were washed with PBS four times and then 1 mL of PBS added for fluorescent microscopy.

The live cells were then imaged on a Nikon TE2000E fluorescent microscope whilst maintained in a chamber heated to 37° C. with 5% CO2. Three images pairs were obtained at 10× magnification for each of a phase contrast image to view total cells and a fluorescent image to visualize Lucifer yellow using 488 nm excitation and a GFP filter block. Gap junctional communication was determined by counting the number of Lucifer yellow positive cells and presented as a percentage to the positive cells of the control group. Data was graphed as mean+standard error of the mean using Prism v5.02 software. Significance was determined through students two-tailed, unpaired, T Tests. *=$p<0.05$, =$p<0.001$, *=$p<0.001$.

Results in FIG. 1 (using peptide5 as an example) show that dye taken up by cells adjacent to the scrape spreads to neighboring cells. Peptide5 at 100 μM concentration added immediately before scraping has little effect on cell-cell transfer of dye through gap junctions. The higher 500 μM concentration of peptide5 lead to a marked reduction in dye transfer. With longer, 2-hour incubations, dye transfer is reduced with peptide5 at both concentrations. This indicates that peptide5 can be used in a dose dependent manner given the finding that it can block gap junctions immediately at higher concentrations and that, with sustained treatment, low dose application leads to a reduction in gap junction coupling, the latter being considered to be peptide interference with hemichannel docking (in parallel with gradual removal of existing gap junctions during normal turnover). The graph to the right of FIG. 3 compares the efficacy of peptide5 block (high dose) with the non-specific gap junction channel blocker carbenoxolone.

Figure 3A:
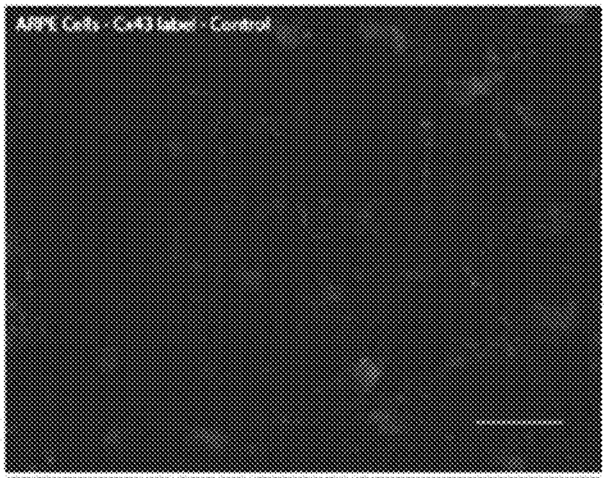
FIG. 3A-FIG. 3C. Tonabersat knockdown of Cx43 in APRE-19 cells in a dose dependent manner. ARPE-19 cells in control medium (FIG. 3A) and after 6 hours preincubation with Tonabersat at 50 (FIG. 3B) and 100 (FIG. 3C) micromolar concentrations. Cells have been labelled for Connexin43. In control cells the gap junctions are clearly localized at cell-cell interfaces but after 6 hours with 50 micromolar Tonabersat most junctions have been internalised or lost. In the higher 100 micromolar Tonabersat for 6 hours very little Connexin43 labelling remains.
Figure 3B:
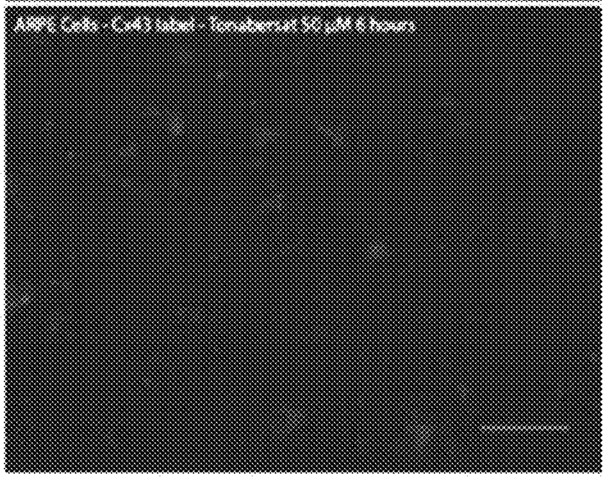
Figure 3C:
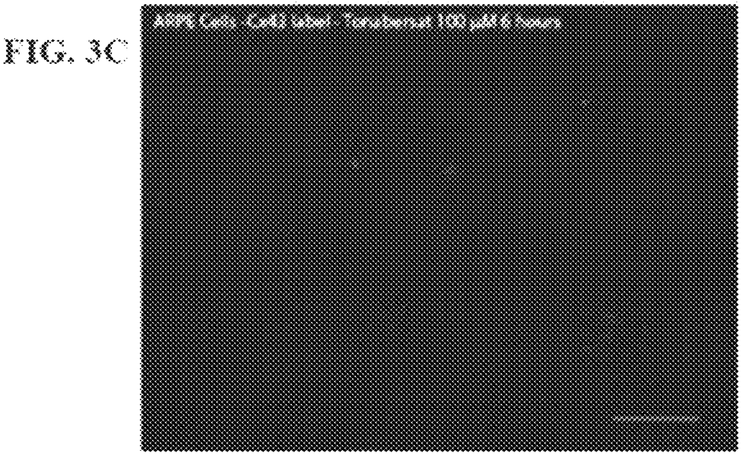

FIG. 3 shows comparable scrape loading dye transfer for tonabersat at 50 μM concentration. Added immediately tonabersat has a statistically significant gap junction uncoupling effect within 1 minute, but block increases in a time dependent manner indicating that tonabersat is also acting in a similar manner to peptide5. Without wishing to be bound by any particular theory, the inventors consider this may be the result of interference with hemichannel docking or triggering internalization of hemichannels in parallel with gradual removal of existing gap junctions during normal turnover, internalisation of gap junctions (see FIG. 4).

Example 3: Immunohistochemistry of ARPE-19 Retinal Epithelial Cells Treated with Peptide5 and Tonabersat Cells were seeded at 0.05×106 per well in 8-well sterile glass microscope chamber slides (Falcon, Corning Life Sciences), and the monolayer was labeled for connexin expression at ~90-100% confluency. The following steps were conducted at room temperature. Cells were fixed in 4% paraformaldehyde (P6148, Sigma-Aldrich) in PBS with 0.1 mM CaCl2 for 10 min, and washed three times in PBS with 0.1 mM CaCl2. After blocking in 10% normal goat serum in PBS with 0.1 mM CaCl2 for one hour, cells were incubated overnight in primary antibody solution (rabbit anti-Cx43, Sigma C6219) diluted in PBS with 0.1 mM CaCl2. The chamber slides were then washed three times with PBS containing 0.1 mM CaCl2 for 10 minutes, and incubated for a further 45 minutes in goat anti-rabbit Alexa 568 conjugated secondary antibody (Invitrogen #A11036). Cells were counter labeled with DAPI for 5 minutes and washed three times with PBS containing 0.1 mM CaCl2. Chamber wells were removed and cells were mounted anti-fade medium (Citiflour AF-1). Dilution ratios for specified primary and secondary antibodies were used according to manufacturer's recommendations.

FIG. 4 shows DAPI (nuclear staining) and labelling of the gap junction protein connexin43 (left panels) and matching connexin43 only labelling (right hand panels). In the untreated cells gap junction labelling is primarily at cell-cell interfaces (top panels). In the lower panels showing cells treated for one hour with peptide5 (500 μM) the cell-cell interfaces are still apparent but the bulk of the gap junctions have been internalized and label is cytoplasmic. This indicates that once the peptide uncouples gap junctions, it triggers internalization and junction degradation. FIG. 3 shows an equivalent experiment with untreated and tonabersat treated cells (50 μM, 6 hours). Tonabersat treatment over time results in total gap junction loss at cell-cell interfaces.

Thus, which the scrape-loading experiments in Example 2 showed the functional loss of gap junctions, this Example 3 explains how this can happen, i.e., by the loss of gap junctions between cells.

Example 4: Electrophysiology of Gap Junction Hemichannels

Whole-cell voltage clamp studies were conducted on connexin deficient HeLa cells, Connexin43 transfected HeLa cells and isolated human cerebral microvascular endothelial cells (hCMVEC).

HeLa cells were seeded at 0.045×106 cells/mL on 18 mm rat collagen I coated coverslips 16-24 hours before each experiment. Cx43IRESeGFP HeLa cells were cultured overnight in DMEM supplemented with 10% FCS and 1 μg/mL Puromycin at 37° C. at 95% O2 and 5% CO2. Control Cx-deficient cells were maintained in DMEM supplmented with 10% FCS. Coverslips were transferred to a chamber continuously perfused with modified Krebs-Ringer solution containing (in mM): 140 NaCl, 5.4 KCl, 1 MgCl2, 10 mM Hepes and pH adjusted to 7.4 at room temperature. The internal pipette solution contained (in mM): 130 KCl, 10 sodium aspartate, 0.26 CaCl2, 2 EGTA, 5 tetraethylammonium-Cl, 1 MgCl, 3 MgATP, and 5 Hepes at pH 7.2; and was kept on ice. The solutions are described in Contreras J E, et al., Cell Communication and Adhesion (2003), 10:245-249. To resolve single currents in whole-cell configuration, cells with low capacitance (<10 pF) and high resistance pipettes (6-10 mOhm) with a seal resistance of (>5 GOhm) were selected for recording and analysis.

HCMVEC Cells were placed into an extracellular artificial cerebral spinal fluid solution containing (in mM): 144 NaCl, 3.3 KCl, 1.8 CaCl2, 1.8 MgCl2, 10 mM glucose, pH: 7.385 at temperature 37° C. The intracellular pipette solution contained (in mM): 130 KCl, 10 sodium aspartate, 0.26 CaCl2, 2 EGTA, 5 tetraethylammonium-Cl, 1 MgCl2,3 MgATP, 5 Hepes at pH 7.2; and was kept on ice to prevent MgATP breakdown. Pipette resistance was 3.4MΩ with seal resistance=1.3 GΩ. Voltage and perfusion protocols are conducted simultaneously, with cells continuously perfused. Recordings for analysis were taken before Tonabersat perfusion, during and after washout. For channel block studies, 50 μM Tonabersat was washed in for three mins prior to recording, and subsequently washed out three mins before taking the washout recordings.

Figure 5A:
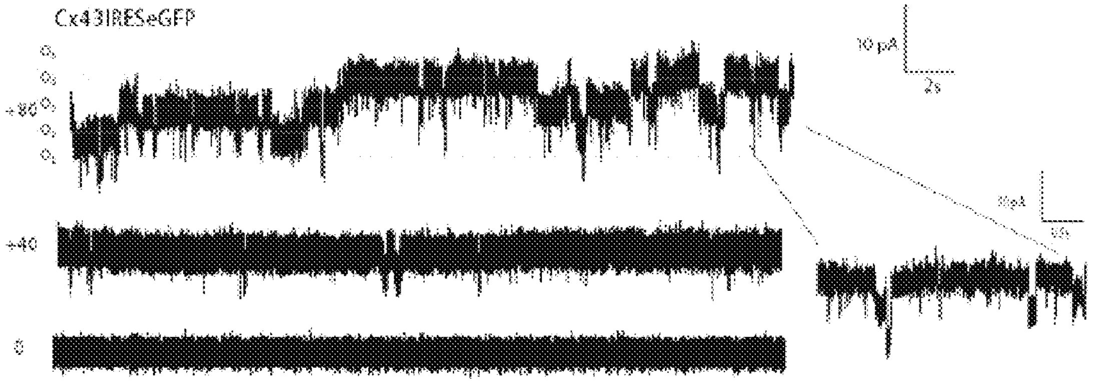
FIG. 5A-FIG. 5B. Electrophysiological recordings in Connexin43 transfected HeLa cells (top traces, FIG. 5A) and connexin null HeLa cells (bottom traces, FIG. 5B). As the voltage steps are raised, increased channel activity is observed in the transfected cells but not present in the connexin null cells. This channel activity in the transfected cells is therefore the result of Connexin43 hemichannel opening.
Figure 5B:
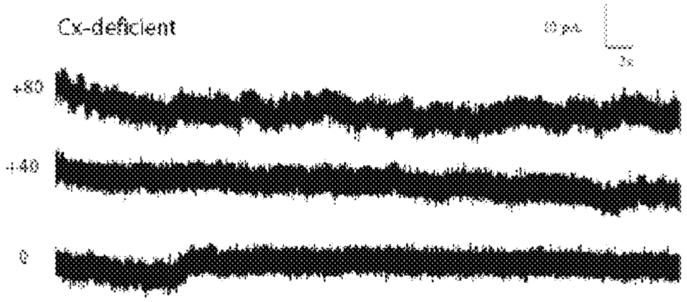
Figure 6A:
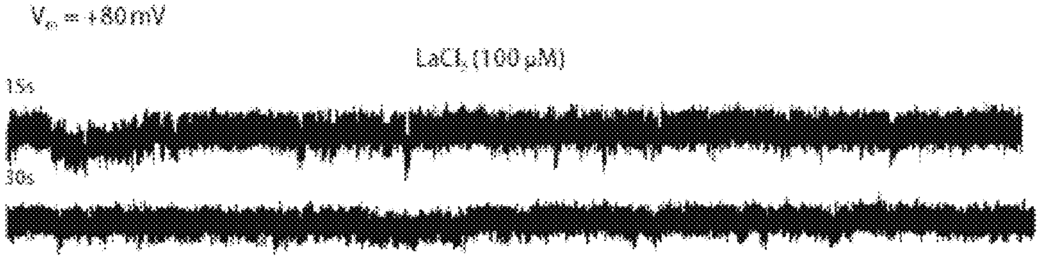
FIG. 6A-FIG. 6C. Electrophysiological traces from Connexin43 transfected HeLa cells that have been treated with the non-specific channel blockers carbenoxolone (FIG. 6B) and $LaCl3$ (FIG. 6A), and with peptide5 (100 μM) (FIG. 6C). The non-specific channel blockers show virtually complete hemichannel block (compared with untreated HeLa cells in FIG. 7A-7C) with little channel activity remaining. Peptide5 also shows significant hemichannel blockade.
Figure 6B:
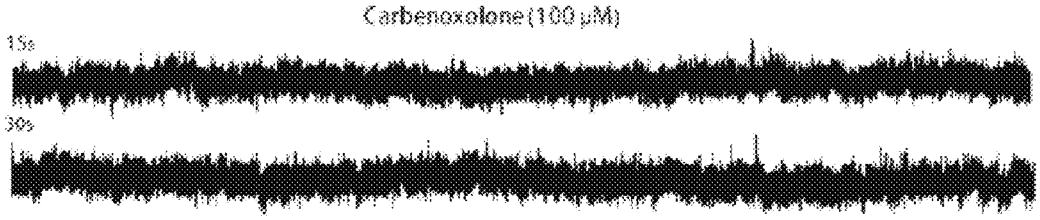
Figure 6C:
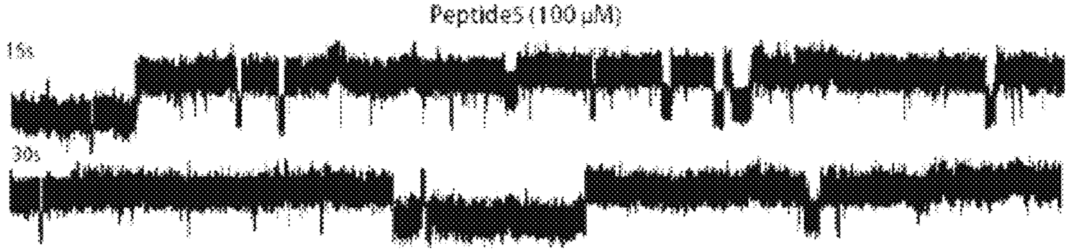

FIG. 5 shows recordings in connexin43 transfected HeLa cells (top traces) and connexin null HeLa cells (bottom traces). As the voltage steps are raised, increased channel activity is observed in the transfected cells which is not present in the connexin null cells. This channel activity in the transfected cells is therefore the result of connexin43 hemichannel opening. FIG. 6 shows traces from connexin43-transfected HeLa cells that have been treated with the non-specific channel blockers carbenoxolone and LaCl3, and with peptide5 (100 μM). The non-specific channel blockers show virtually complete hemichannel block with little channel activity remaining. Peptide5 also shows significant hemichannel blockade.

Figures 7A, 7B, 7C:
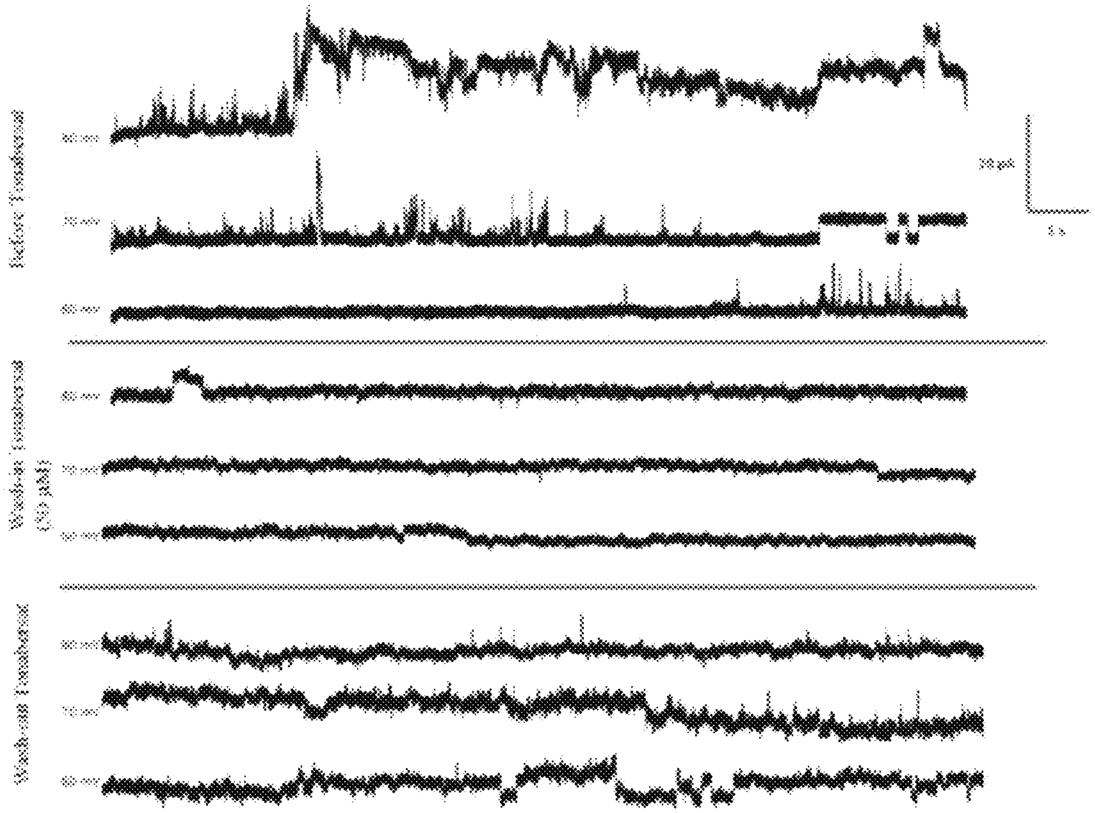
FIG. 7A-FIG. 7C. Electrophysiological traces form an equivalent experiment to those shown in FIGS. 5A-5B and FIGS. 6A-6C. In this case HCMVEC cells are shown prior to addition of Tonabersat (50 μM) (top panel, FIG. 7A), during incubation with Tonabersat (middle panel, FIG. 7B), and after three minutes of washout (bottom panel, FIG. 7C). The results demonstrate that Tonabersat almost completely abolishes hemichannel activity, with signs of activity returning after washout, indicating that Tonabersat is a very effective and direct hemichannel blocker.

FIG. 7 shows an equivalent experiment in HCMVEC cells prior to addition of tonabersat (50 μM), during incubation with tonabersat, and after three minutes of washout. Tonabersat almost completely abolishes hemichannel activity, with some activity returning after washout. These results indicate that tonabersat is a very effective hemichannel blocker, that may exceed the efficacy of peptide5 at the concentrations used, and that active hemichannels are recoverable.

Discussion

The inventors have suprisingly determined that the established connexin43 channel blocker peptide5 and tonabersat exhibit a similar mode of action. At high concentrations peptide5 can block connexin43 hemichannels and can uncouple connexin43 gap junctions. At lower doses peptide5 blocks connexin43 hemichannels but does not have an immediate effect on gap junction coupling. With sustained low dose application of peptide5 there is also gradual loss of gap junctions at the cell-cell interface, indicating peptide interference with hemichannel docking (in parallel with gradual removal of existing gap junctions during normal turnover). The results herein indicate that tonabersat is primarily a hemichannel blocker, and is also able to block gap junction channels and, like peptide5, can be used to decrease gap junction coupling, possibly by preventing hemichannel docking to form replacement gap junction channels during turnover or by triggering internalization from the plasma membrane. In these experiments, tonabersat was shown to block connexin hemichannels within one minute and provide a decrease in cell-cell coupling within one minute.

Tonabersat can reduce connexin26 expression in the central nervous system through a specific receptor and the p38 pathway. The inventors have surprisingly discovered that tonabersat can be used to block hemichannels in a number of cell types (hCMVEC, HeLa, ARPE), including endothelial cells. Thus, the inventors have surprisingly discovered that tonabersat is not central nervous system specific. The results also indicate that tonabersat has significant efficacy in blocking conenxin43 hemichannels, and that it can be used to uncouple connexin43 gap junctions. Thus, it is also not connexin isoform specific.

The results support the inventor's observation that tonabersat is primarily a connexin hemichannel blocker, but can be used at higher doses to uncouple gap junction. Its hemichannel block efficacy and speed of action, and the fact that it could be washed out within three minutes to restore channel activity, implies it has a direct effect on hemichannels, as opposed to a slower pathway whereby mRNA or protein expression is affected.

Example 5: Connexin43 Hemichannels and Pannexin Channels Release ATP During Ischaemia Injury-Reperfusion In Vitro Using an in vitro ischemia injury model, the Cx43 hemichannel and pannexin channel mediated ATP release was differentiated using the connexin hemichannel blocking mimetic peptide5 at 100 μM concentration (S. J. O'Carroll, et al., *Cell communication & adhesion* 15, 27 (May, 2008)) and 1 mM Probenecid (W. R. Silverman et al., *The Journal of biological chemistry* 284, 18143 (Jul. 3, 2009)).

In Vitro Ischaemia Injury-Reperfusion ATP Assay

Human cerebral microvascular endothelial cells (hCMVEC) were trypsinised (TrypLE Express, Life technologies) and plated at a density of 0.025×106 cells per well in a collagen-coated 12-well plate (1 μg/cm2) a day prior to the experiment. Cells were incubated in culture medium overnight. Hypoxic, acidic, ion-shifted Ringer injury solution that mimics ionic concentrations and acid-base shifts of the interstitial space in hypoxic-ischemic brains (A. Bondarenko, et al., Glia 34, 143 (Apr. 15, 2001)) was used to trigger hemichannel opening. The injury solution (in mM): 38 NaCl, 13 NaHCO3, 3 Na-gluconate, 65 K-gluconate, 38 NMDG-Cl, 1 NaH2PO4, 1.5 MgCl2, was bubbled in N2 gas (>99% purity, 20 L/min) for 5 minutes and pH adjusted to 6.6 using 5 M HCl. Control solution that mimics physiological conditions contained (in mM): 124 NaCl, 3 KCl, 26 $NaHCO_3$, 26 $NaHCO_3$, 1 NaH2PO4, 1.3 CaCl2, 1.5 MgCl2, and 10 Glucose, and pH 7.4 was adjusted using 5 M HCl (Bondarenko, 2001). In the injury model, hCMVEC cells were incubated in 500 μL control solution, or injury solution, or Tonabersat (0.1-50 μM)+/−Probenecid (1 mM) dissolved in injury solution for 2 hours in 37° C. in 95% O2 and 5% CO2. Following a 2-hour injury the solutions were immediately placed on ice. In the injury and reperfusion model, hCMVEC cells were incubated in 500 μL of normal solution or injury solution for 2 hours at 37° C. in 95% O2 and 5% CO2. Following 2 hour injury, the solutions were discarded and replaced with 500 μL of the normal solution, or Tonabersat (10 μM) dissolved in normal solution, and were incubated for 2 hours at 37° C. in 95% O2 and 5% CO2. These solutions were also then immediately placed on ice. Peptide5 (100 μM)+/−Probenecid (1 mM) were used as controls for both injury and injury-reperfusion models. ATP concentration in the samples was determined using a Luciferin/luciferase bioluminescence reaction (ATP Determination Kit, Molecular Probes) and detected using a luminescence plate reader (VICTOR X, Perkin Elmer #2030-0010). Standard curves were generated in each experiment from an ATP standard (500 nM) to quantify the concentration of ATP in the test samples. The data is presented as mean±standard error relative to the injury or injury-reperfusion control. Statistically significant differences between samples were identified using one-way analysis of variance and Tukey's multiple comparisons test.

Figure 8A:
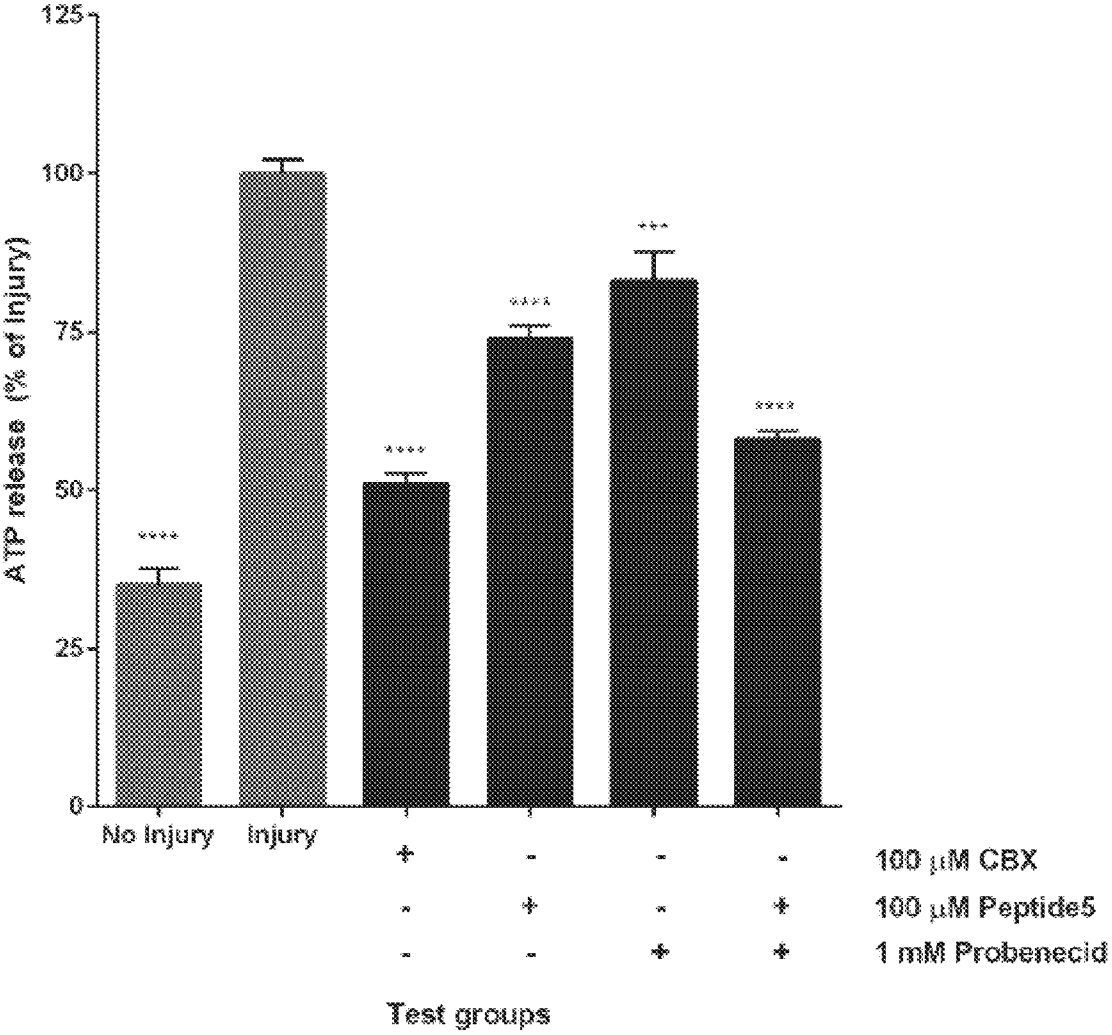
FIG. 8A-FIG. 8C. Tonabersat inhibits hemichannel-mediated ATP release from injured hCMVEC cells.
Figure 10A:
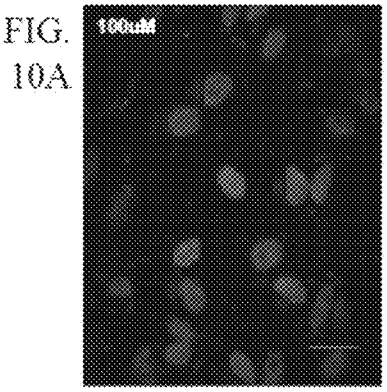
FIG. 10A-FIG. 10D. 1 hour treatment with Tonabersat down-regulates Cx43 GJ plaques via the lysosomal degradation pathway in ARPE-19 cells.

FIG. 8 summarizes the total ATP released from a sub-confluent culture of human cerebral microvascular endothelial cells (hCMVEC) following two hours in the in vitro injury model. When compared with injury group (100±2.2%), there was a basal level of 35±2.6% ATP released from no injury control that may reflect normal cellular activity and/or dead cells prior to injury. A significant difference in extracellular ATP was observed between no injury and injury control (p<0.0001) (FIG. 10A). Compared to injury (100±2.2%), Peptide5 significantly lowered ATP down to 73.9±2.1% (p<0.0001), and Probenecid also significantly reduced ATP down to 83.1±4.5% (p<0.001) (FIG. 10A). Interestingly, a combined treatment of Peptide5 and Probenecid reduced ATP to a level that was comparable to 100 μM carbenoxolone (CBX), a non-specific blocker that blocks both Cx43 hemichannels and pannexin channel, with no significant difference observed between these two groups (p=0.28). Data from these experiments demonstrate that both connexin hemichannels and pannexin channels open under ischemic conditions.

Figure 8B:
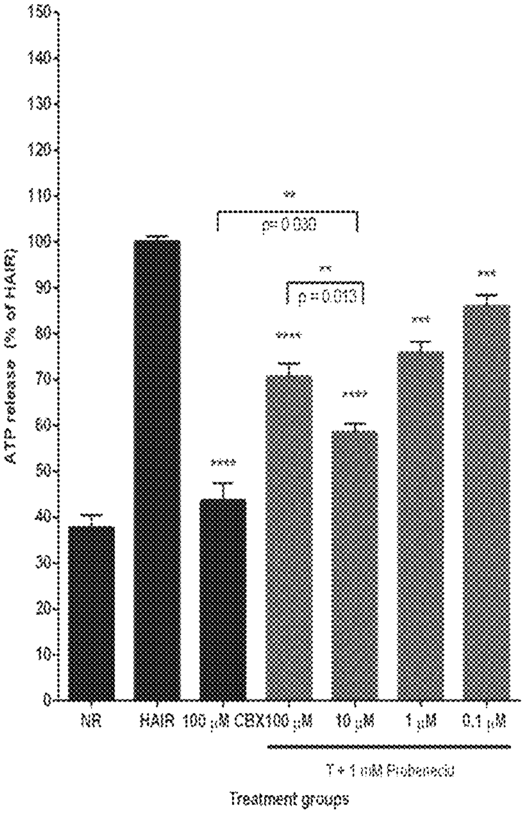
Figure 8C:
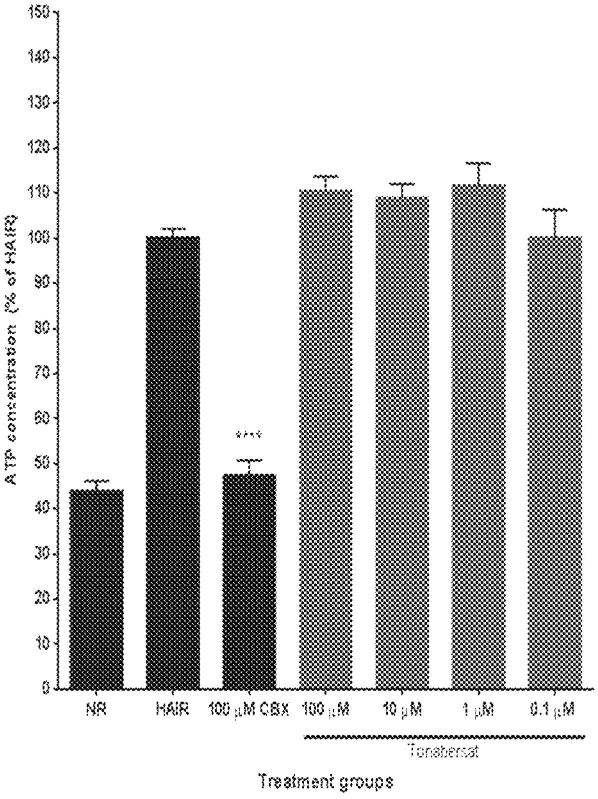
Figure 10B:

Inhibition of Cx43 Hemichannels by Tonabersat is Concentration Dependent, but Only in the Absence of Pannexin Channel Activity During Injury In Vitro The following experiment was performed to demonstrate that Cx43 HC-mediated ATP release from injured hCMVEC cells decreases as the concentration of tonabersat increases. Utilizing the injury model in FIG. 8A, the effect of Tonabersat on Cx43 HC mediated ATP release was isolated using Probenecid to inhibit Panx channels. Compared to injury (100±1.2%), ATP release was significantly reduced at Tonabersat concentrations of 0.1 μM (85.9±2.4%), 1 μM (75.9±2.3%), 10 μM (58.5±1.9%), and 100 μM (70.5±3.9%) in combination with 1 mM Probenecid (FIG. 10B). Increasing the concentration of Tonabersat (0.1 μM to 10 μM) significantly reduced Cx43 HC-mediated ATP release (FIG. 8B). Maximal inhibition was achieved at 10 μM tonabersat, and this was significantly greater by 12.1±3.2% than the highest concentration of 100 μM (p=0.005) (FIG. 8B). However, there remained a significant difference of 14.9±4% between CBX, and 10 μM Tonabersat in 1 mM Probenecid (p=0.0059) (FIG. 10B). Tonabersat (0.1 μM to 100 μM) significantly reduced Cx43 HC mediated ATP release compared to injury when in combination with Probenecid; however, Tonabersat did not reduce ATP release from hCMVEC cells in the absence of 1 mM Probenecid (p>0.09) (FIG. 8C).

Figure 9:
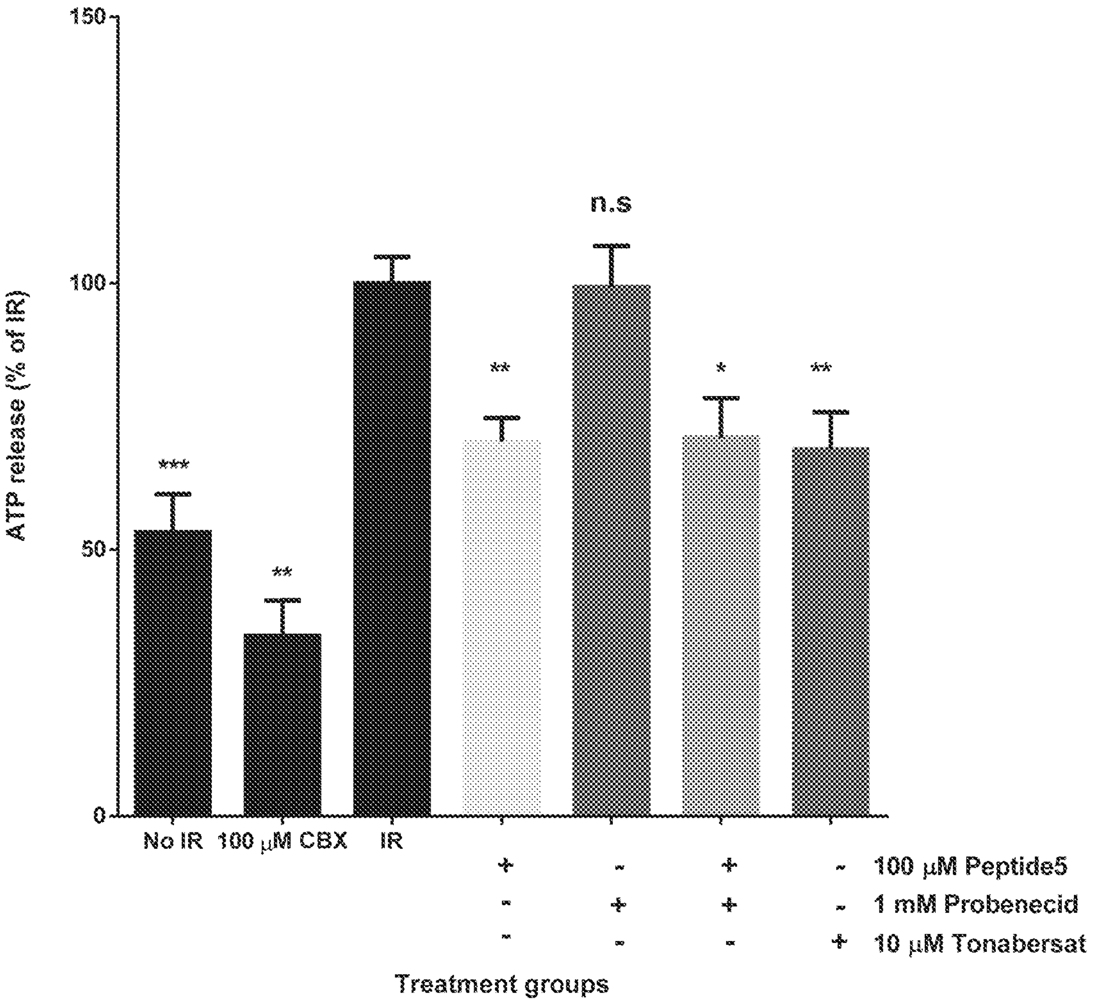
FIG. 9. Hypoxia Reperfusion: ATP released from sub-confluent hCMVEC cells following 2-hour exposure to injury then 2-hour exposure to reperfusion in vitro. ATP is quantified as a percentage of the injury-reperfusion (IR) control. A significant reduction in ATP was observed with 100 μM CBX, 100 μM Peptide5, and 100 μM Peptide5 and 1 mM Probenecid, but not with 1 mM Probenecid on its own. A significant reduction in ATP was also observed with 10 μM Tonabersat. Values represent mean±standard error. One-way ANOVA Tukey's multiple comparison test *$P<0.05$ μgainst IR control.
Figure 11A:
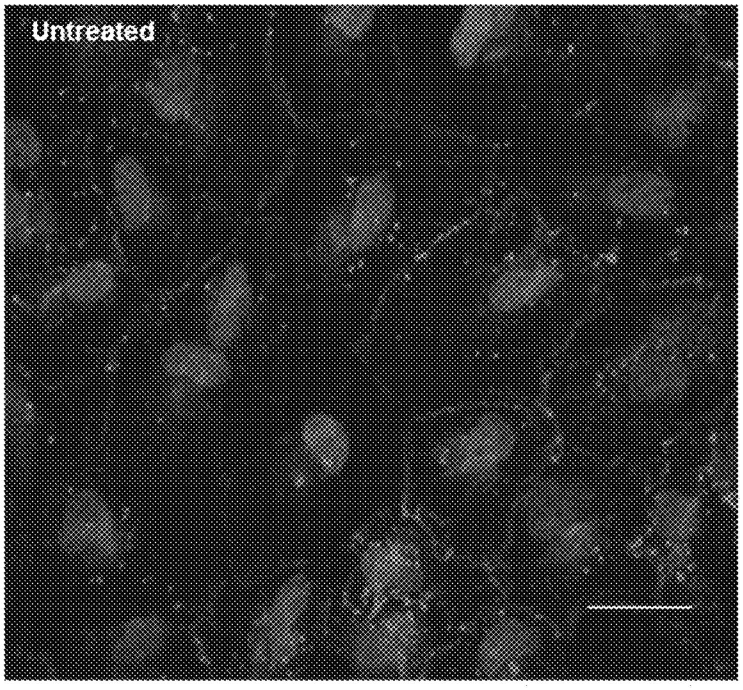
FIG. 11A-FIG. 11C. Tonabersat internalises and down regulates Cx43 GJ plaques in ARPE-19 cells.
Figure 11B:
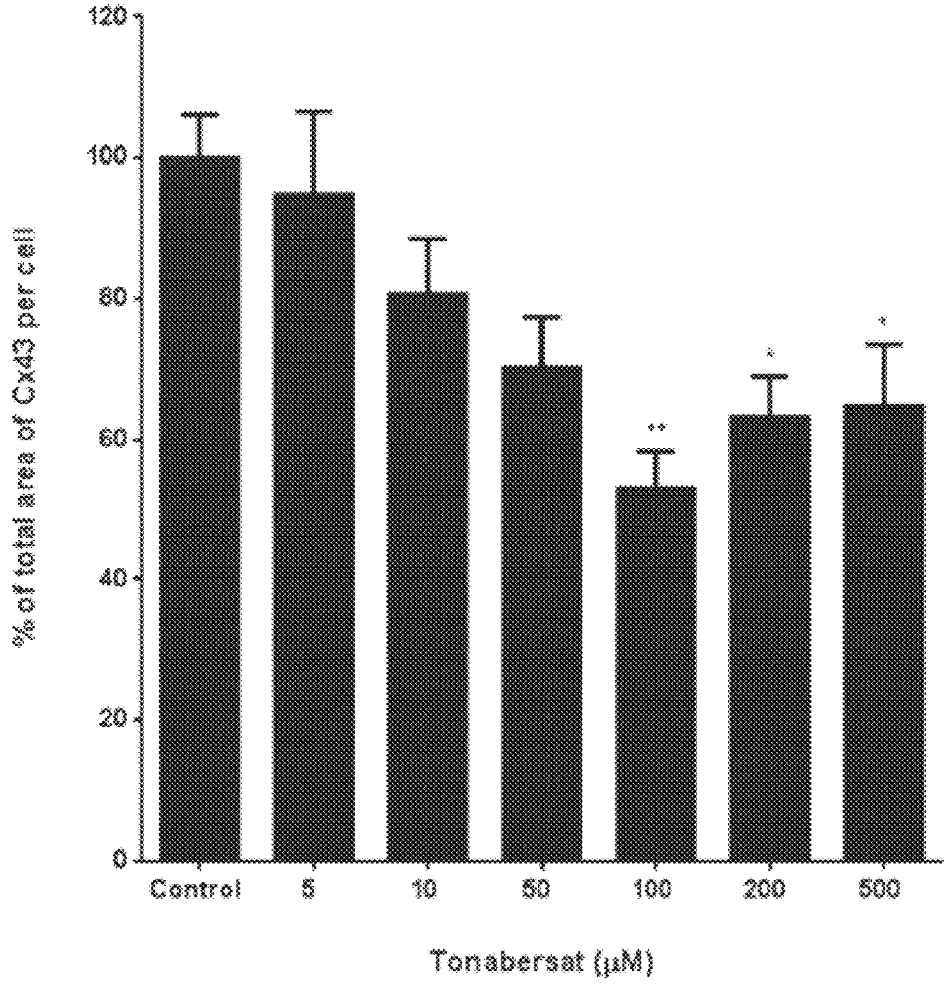
Figure 11C:
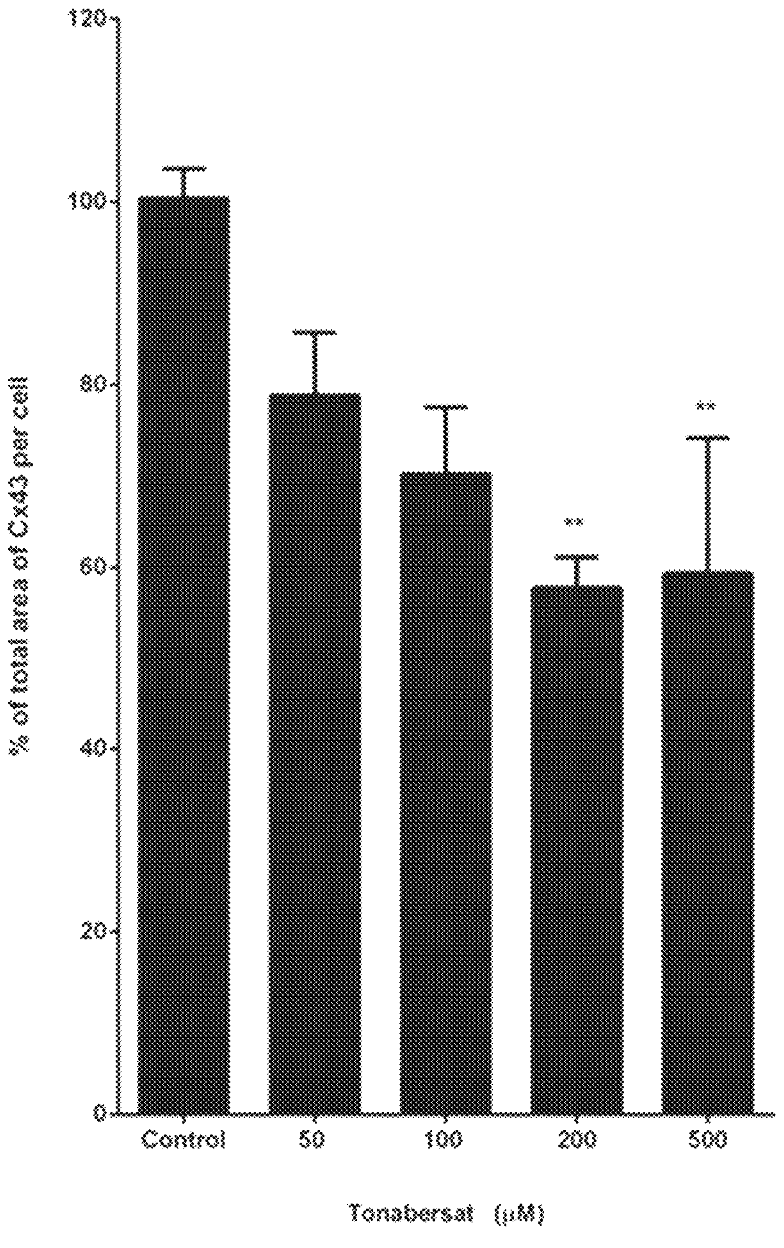

Connexin43 Hemichannels, but not Pannexin Channels, Release ATP During Reperfusion In Vitro The role of Cx43 hemichannel and pannexin channel during the reperfusion period post-ischemia (return to normal media post two hours in HAIR solution) was further characterized. A significant difference in ATP release between no injury-reperfusion (No IR) and injury-reperfusion control (IR) (p=0.0006) was observed (FIG. 11). While Peptide5 significantly lowered ATP release to 70.3±4.4% (p=0.0196), Probenecid did not significantly reduce ATP compared to reperfusion injury (99.3±4.4%, p>0.99) (FIG. 9). A combined treatment of peptide5 and probenecid also significantly reduced ATP compared to reperfusion injury (71.1±7.4%, p=0.025), but this was comparable to Peptide5 treatment alone (FIG. 11). In contrast to injury only (FIG. 10B), CBX significantly lowered ATP release further to 33.8±33.5% compared to Peptide5 only (p=0.0127) (FIG. 9).

A Low Concentration of Tonabersat Inhibits Cx43 Hemichannel Mediated ATP Release During Reperfusion In Vitro The ischaemia-reperfusion assay demonstrated that Probenecid had no significant effect on the release of ATP from hCMVEC cells during reperfusion (FIG. 9). The low dose at 10 μM Tonabersat alone will be sufficient to inhibit the ATP released from hCMVEC cells in vitro, and the level of inhibition will be comparable to Peptide5. A significant reduction in ATP in the presence of 10 μM Tonabersat was observed (68.9±6.9%, p=0.02) which was comparable to 100 μM Peptide5 during reperfusion injury in vitro (FIG. 9).

Example 6: High Concentrations of Tonabersat Causes Internalization of Cx43 Plaques in ARPE-19 Cells Immunocytochemistry and Quantification of Cx43 Plaques ARPE-19 cells were grown until confluent in 8-well glass chamber-slides (BD Falcon). Confluent monolayers of ARPE-19 cells were incubated at a final concentration of 5 to 500 μM) Tonabersat, and/or 10 mM NH4Cl (H. Qin, et al., The Journal of biological chemistry 278, 30005 (Aug. 8, 2003)) in culture medium for 1 or 6 hours. Cells were fixed in 4% PFA (ProSciTech) at pH 7.4 for 10 min at room temperature, permeabilized with 0.05% Triton-X100 in PBS, and incubated in 10% normal goat serum to block non-specific labelling. Cells were rinsed three times with PBS containing 0.1 mM CaCl2 between each fixation, permeabilization, and blocking steps. Cx43 polyclonal rabbit antibody (C6219, Sigma, 1:2000) was applied for 24 hours, followed by a goat anti-rabbit Alexa Fluor® 568 secondary antibody (Invitrogen, 1:200) for 45 minutes. Nuclei were counterstained with DAPI (Invitrogen) at 10,000-fold dilution for 5 mins, and mounted with Citifluor™ mounting medium. Images were visualised and captured using a 63× oil immersion lens on an Olympus FV1000 upright confocal laser scanning microscope and software. The transfluor feature in MetaXpress® Image acquisition and analysis software (Version 5.3.0.1, Molecular Devices) was used to automate and quantify the total area of Cx43 plaques per image. Results represent mean±standard error and statistical tests were conducted using one-way ANOVA and Tukey's multiple comparisons test.

Immunocytochemistry, as described above, was used to visualise the distribution and size of the Cx43 GJ plaques in a native human cell line, retinal pigmented epithelial cells (ARPE-19), which reportedly has an abundant expression of Cx43 (C. M. Hutnik, et al., Investigative ophthalmology & visual science 49, 800 (February, 2008)). Cx43 plaques between cell-to-cell contacts were observed that were labelled in a regular tile-like pattern under basal conditions (FIG. 13A). Cx43 labelling was also visible in the perinuclear region, which indicated an intracellular pool of Cx43 in the Golgi apparatus (J. Das Sarma et al., Journal of cell science 114, 4013 (November, 2001)). However, significant reductions in Cx43 plaques were observed following 1 hour exposure to Tonabersat at concentrations of 100 μM (52.8±5.6%, p=0.0012), 200 μM (63.2±5.6%, p=0.0286), and 500 μM (63.2±5.6%, p=0.0420) compared to normal control (FIG. 13B). The reductions in Cx43 plaques were visible between cell-to-cell contacts and the intracellular pool (FIG. 10A, top image). However, compared to control, there was no significant reduction in Cx43 plaques at lower concentrations of 5 μM (p=0.99), 10 μM (p=0.5777), or 50 μM (p=0.1146) (FIG. 11B).

The results show that tonabersat causes internalization of Cx43 GJs from the plasma membrane. The reductions in Cx43 plaques were demonstrated to be time-dependent by exposing ARPE-19 cells in Tonabersat (50 to 500 μM) for an extended period of 6 hours. Comparable to FIG. 10, 6 hour treatment in tonabersat also led to reductions in Cx43 labeling between cell-to-cell contacts and the intracellular pool (FIG. 12A). Furthermore, the total area of Cx43 plaques was also significantly reduced at 100 μM (66.5±5.4%, p<0.0001), 200 μM (62.5±2.3%, p<0.0001), and 500 μM (60.2±13.6%, p<0.0001).

Figure 10C:
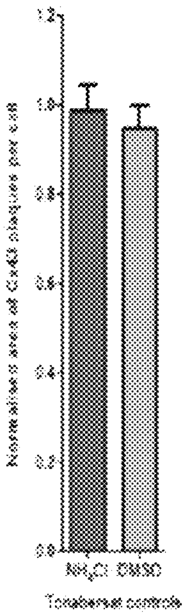
Figure 10D:
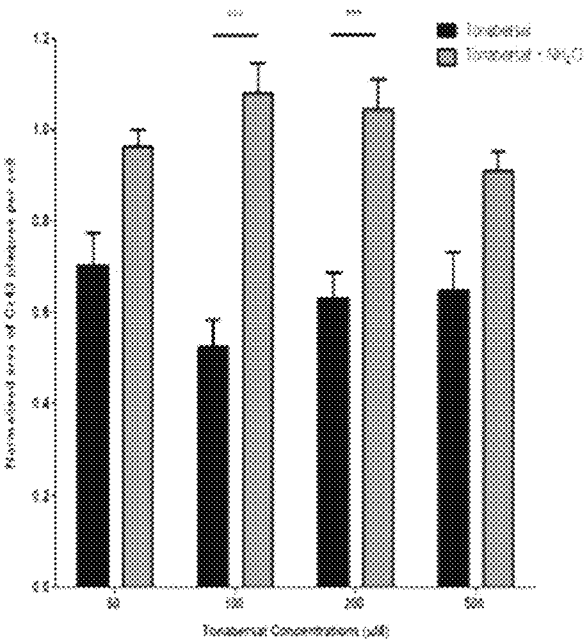
Figure 14A:
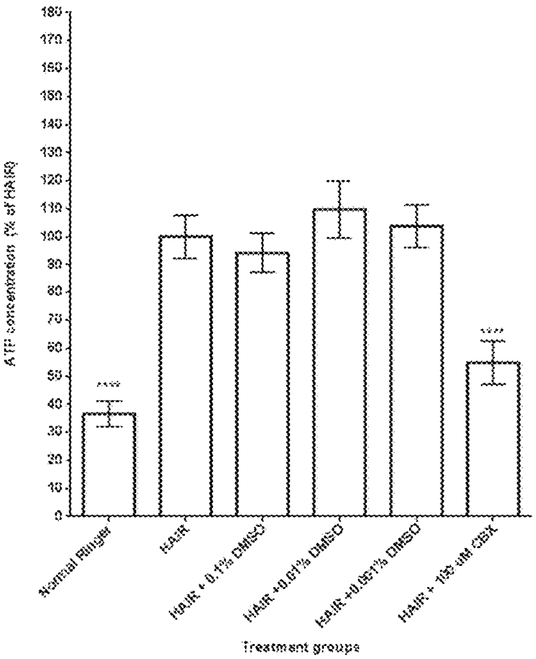
FIG. 14A-FIG. 14B. Comparison of (FIG. 14A) ATP concentration, or (FIG. 14B) % Cell Viability, relative to control, for the various treatment groups.

Tonabersat Targets Internalized Cx43 Plaques for Degradation Via the Lysosomal Pathway In contrast to peptide 5, which only internalized gap junctions, it was also demonstrated that tonabersat facilitates turnover of Cx43 plaques from the plasma membrane. See FIG. 11. The lysosomal degradation pathway in ARPE-19 cells was immobilized using ammonium chloride (NH4Cl), a weak-base lysosome inhibitor (H. Qin, et al., The Journal of biological chemistry 278, 30005 (Aug. 8, 2003)). Following 1 hour treatment in Tonabersat and 10 mM NH4Cl, Cx43 plaques were removed from cell-to-cell contacts, but remained in the cytoplasm with punctate labelling expressed along the intracellular region immediately below the plasma membrane. In addition there was now dense labelling visible around the perinucleus (in what appears to be the golgi body) (FIG. 14A, lower image). In tonabersat with NH4Cl, significantly more Cx43 labelling was present (up 104.8%) compared to 100 μM Tonabersat alone (p<0.001), and up 65.4% more when compared to 200 μM Tonabersat alone (p=0.0002) (FIG. 10C).

Following 6-hour treatment in tonabersat and 10 mM NH4Cl, punctate Cx43 labeling was distributed throughout the cell (FIG. 15A, lower image). In contrast to the 1-hour period, there were no visible Cx43 labeling between cell-to-cell contacts following treatment in Tonabersat and NH4Cl (FIG. 15A, lower image). However, NH4Cl significantly increased the amount of Cx43 labeling (total area), up 67.9% 5 in 50 μM (p=0.0015), up 80.3% in 100 μM (p=0.0001), and up 87.9% in 200 μM (p=0.0062) Tonabersat when compared to Tonabersat treatment alone (FIG. 12C). There were no significant differences in the total area of Cx43 plaques per cell between untreated, DMSO (vehicle control), or NH4Cl only control following 1-hour and 6-hour post incubation (FIGS. 10B and 12B).

Example 7: Tonabersat does not Affect Cx43 mRNA Transcription or Translation

Tonabersat does not affect Cx43 mRNA transcription or translation, as indicated in published literature. Rather, the observed tonabersat-mediated down-regulation of Cx43 is caused by activation of internalization and degradation pathways.

Real-Time Reverse Transcription PCR

Real time reverse transcription PCR was used to determine the relative level of Cx43 mRNA. A confluent monolayer of ARPE-19 cells was treated with Tonabersat for 1 hour. Cells were harvested with TRIzol® (Life Technologies), and total RNA was isolated using SuperScript III First Strand kit (Invitrogen) according to manufacturer's instructions. All RNA samples were quantified using a nanodrop 1000 micro volume spectrophotometer (Thermo Scientific). cDNA from samples were synthesised using SuperScript® III First-Strand Synthesis SuperMix (Invitrogen) according to manufacturer's instructions. Primer sequences for hCx43, GenBank Accession No. M65188.1, were obtained from the Harvard Primer bank. The sequences for human Cx43 were forward 5'-TGGTAAGGTGAAAATGCGAGG-3' (SEQ.ID NO:242) and reverse 5'-GCACTCAAGCTGAATCCATAGAT-3' (SEQ.ID NO:243). The appropriate reference gene to be used for relative fold-difference in Cx43 mRNA was determined by screening commonly used house-keeping genes, ß-actin [ACTB], Hypoxanthine phosphoribosyltransferase 1 [HPRT1], peptidylprolyl isomerase A [PPIA], and glyceraldehyde-3-phosphate dehydrogenase [GAPDH]. We chose beta-actin as the control gene as it showed no significant difference in expression between the treatment groups. All PCR reactions were performed on the Rotor gene600 (Qiagen) using a cycle program of 50° C. for 2 min then 95° C. for 2 min; 95° C. for 15 s and 60° C. repeated 40 times; 95° C. for 15 s, 60° C. for 15 s, 95° C. for 15 s, in order to generate threshold cycles for relative quantification (Ct). Relative changes in Cx43 mRNA expression were calculated as fold-differences against ß-actin using the 2-ΔΔCt method. Results represent mean±standard error and statistical tests were conducted using a one-way ANOVA followed by Tukey's multiple comparisons test.

Figure 13:
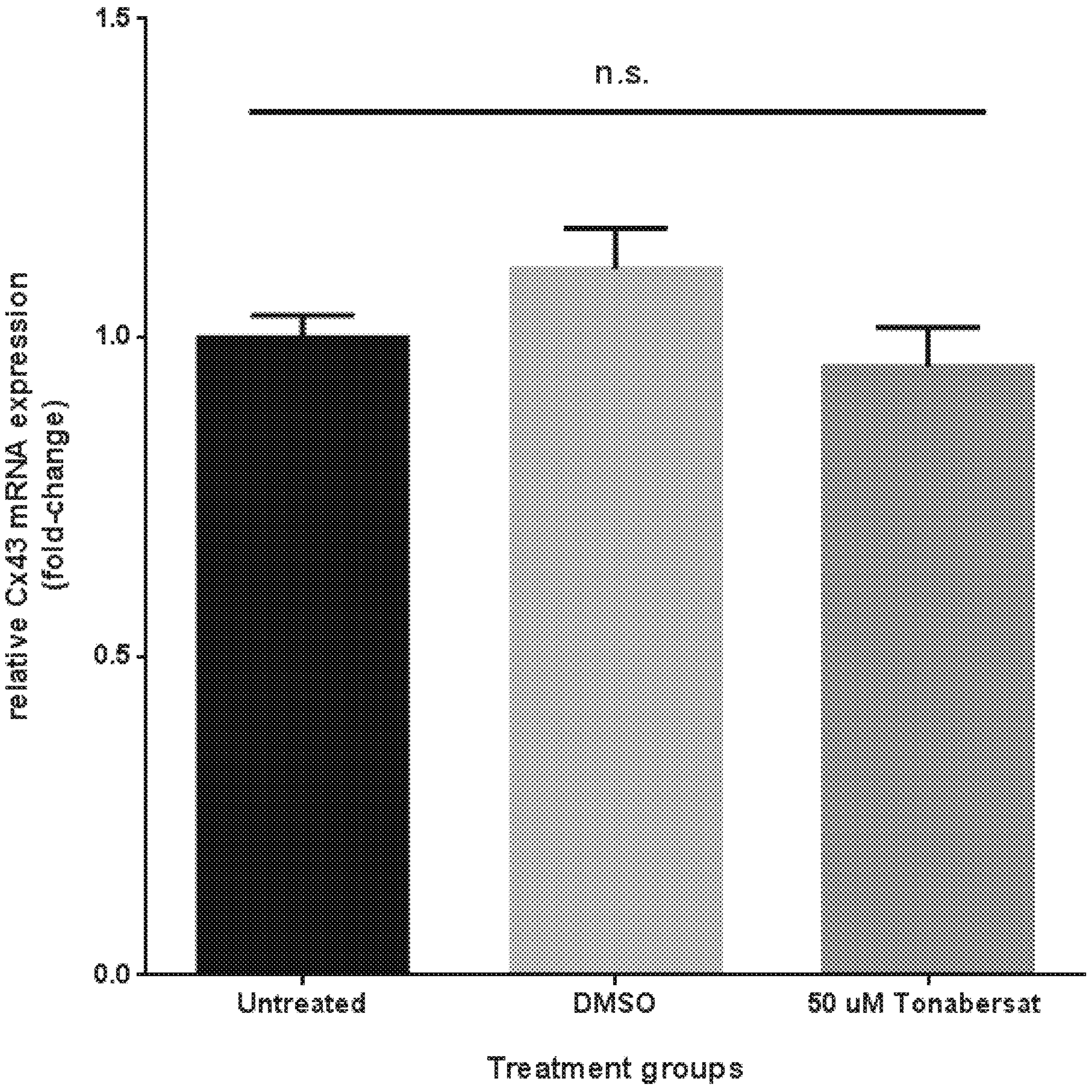
FIG. 13. Cx43 mRNA levels in confluent monolayers of ARPE-19 cells incubated with DMSO (vehicle control), or with 50 μM Tonabersat for 1 h. Bars represent means±S.E.M (n=3). There was no significant difference in Cx43 mRNA in ARPE-19 cells following treatment with 50 μM tonabersat compared to both untreated ($p=0.7572$) and vehicle controls ($p=0.10245$). One-way ANOVA Tukey's multiple-comparisons test.

To test the possibility that Tonabersat-mediated reduction in Cx43 plaques seen in FIGS. 10 and 12 was caused by down-regulation in Cx43 mRNA transcription, we used real time reverse transcriptase-PCR to compare the relative differences Cx43 mRNA following 1 hour treatment with tonabersat. There was no significant difference in Cx43 mRNA in ARPE-19 cells following treatment with 50 μM tonabersat compared to both untreated ($p=0.7572$) and vehicle controls ($p=0.10245$) (FIG. 13).

Example 8: Tonabersat does not Affect hCMVEC Cell Viability

MTT Assay for Cell Viability

Stock MTT was prepared by dissolving 5 mg in 1 mL PBS producing a concentration of 5 mg/mL. After the treatment incubation period of cells seeded in a 96 well-plate (at 1×104 cells/well) the media was removed and replaced with 100 μL of PBS. 10 μL of MTT stock solution was added to each well, except for those that were used as a blank, and left to incubate at 37° C. for 4 hours at which time the solutions was aspirated from each well. Then 50 μL DMSO (Sigma) was added to each well to dissolve the crystalline product. Viability was determined by measuring the absorbance of the purple crystal produced. This was measured by reading the absorbance at 595 nm in a plate reader; the data was standardized to each control as an internal standard. Statistically was investigated using One-way ANOVA and Tukey's post hoc test where $*p<0.05$.

Figure 14B:
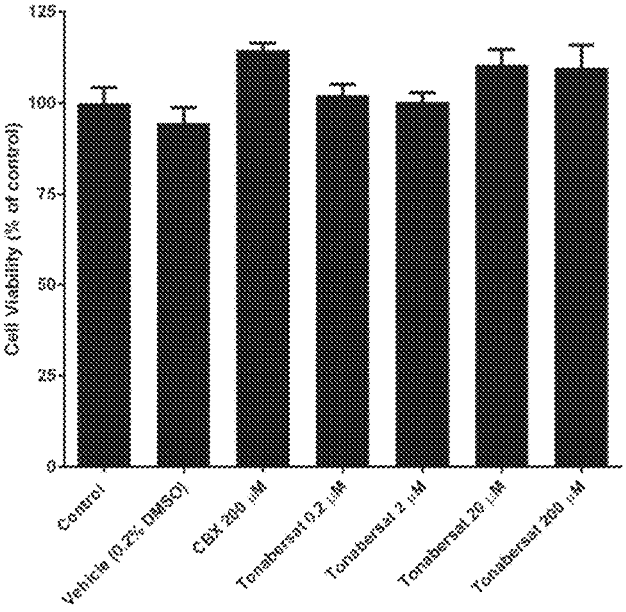

The effect of tonabersat (0.2 μM to 200 μM) on hCMVEC cell viability over 24 hours was examined. Tonabersat (200 μM) did not significantly reduce cell viability after 24-hour treatment ($p=0.378$), indicating a lack of toxicity. Furthermore, there was no significant reduction in cell viability in response to vehicle (0.2% DMSO) or carbenoxolone (200 μM) ($p=0.9029$, $p=0.4719$) (FIG. 14B).

Example 9: Tonabersat Prevents Retinal Ganglion Cell Loss in Retinal Ischemia-Reperfusion In Vivo Retinal Ischaemia-Reperfusion Model and Treatment Animals were anesthetized with an intraperitoneal injection of ketamine (60 mg/kg) and medetomidine hydrochloride (0.4 mg/kg) and the cornea anaesthetized with oxybuprocaine hydrochloride (0.4%). The technique of retinal ischaemia-reperfusion has previously been described (D. Sun, et al., The Journal of comparative neurology 505, 114 (Nov. 1, 2007)). Briefly, the left anterior chamber was cannulated with a 30-gauge infusion needle connected by silicone tubing to a reservoir of sterile 0.9% saline. Cannulation was performed using a stereotaxic manipulator arm to avoid injury to the corneal endothelium, iris, or lens. The intraocular pressure of the cannulated eye was raised to 120 mmHg for 60 minutes by elevating the saline reservoir. Retinal ischaemia-reperfusion was confirmed by pallor of the posterior segment. After 60 minutes, the cannula was removed and reperfusion of the retinal vessels was confirmed by ophthalmoscopy. Three experimental arms were applied at the end of 60 minutes of ischaemia. These included: no treatment ($n=6$), 10 mg/kg Tonabersat ($n=6$), or 1 mg/kg Tonabersat ($n=4$). Systemic delivery of 0.25 mL of a 10 mg/ml or 1 mg/ml Tonabersat solution diluted in 40% PEG, 60% cyclodextrin solution was achieved through intraperitoneal delivery at the start of reperfusion. A final blood Tonabersat concentration of 0.319 mM or 0.0319 mM was intended, assuming a blood volume of 20 mL and total systemic uptake of peptide. Animals were euthanized with CO2 at 7 days after reperfusion. One uninjured animal was euthanized to obtain uninjured retinas as normal controls.

After euthanasia eyes were enucleated, and the cornea, lens, and vitreous humour removed. The dorsal aspect of the retina was notched to retain orientation. The retina and sclera were fixed in 4% PFA in PBS for 60 minutes at room temperature (RT). The retina was then carefully removed from the sclera and permeabilized via incubation in 0.5% Triton-X100 in PBS solution for 15 minutes at −80° C. Following thorough washing with PBS, free floating retinas were incubated overnight at 4° C. in goat anti-Brn3a primary antibody (SC-31984, Santa-Cruz Biotechnology, 1:100) in 2% horse serum and 2% Triton-X100 in PBS solution. After further washing of the retinas with PBS a donkey anti-goat Cy3 secondary antibody (705-165-147, Jackson Immuno Research, 1:500) solution was applied for 2 hours at RT. Retinas were mounted onto SuperFrost Plus slides using citifluor mounting medium, and imaged.

Imaging and Quantification

Two fields in each quadrant of each retina were imaged giving a total of eight images per retina. This method insured similar locations were assessed between different eyes and avoided any possible area bias present in the retina. Retinal ganglion cell (RGC) labelling was imaged at 10× magnification. Voltage and offset settings were adjusted to best discriminate individual antibody labelling and to avoid oversaturation of the image. Quantification was performed using automated spot counts in NIH ImageJ software. For RGC quantification each image was first filtered with a sharpen filter to delineate cell edges before being converted to a binary image using a threshold of 33. Spots of one or two pixels that resulted from noise and artefacts that were clearly not RGC of origin were excluded during particle counts. RGC density was calculated as the number of RGCs per cm2.

Prevention of Retinal Ganglion Cell Loss in Retinal Ischemia-Reperfusion

Figure 15:
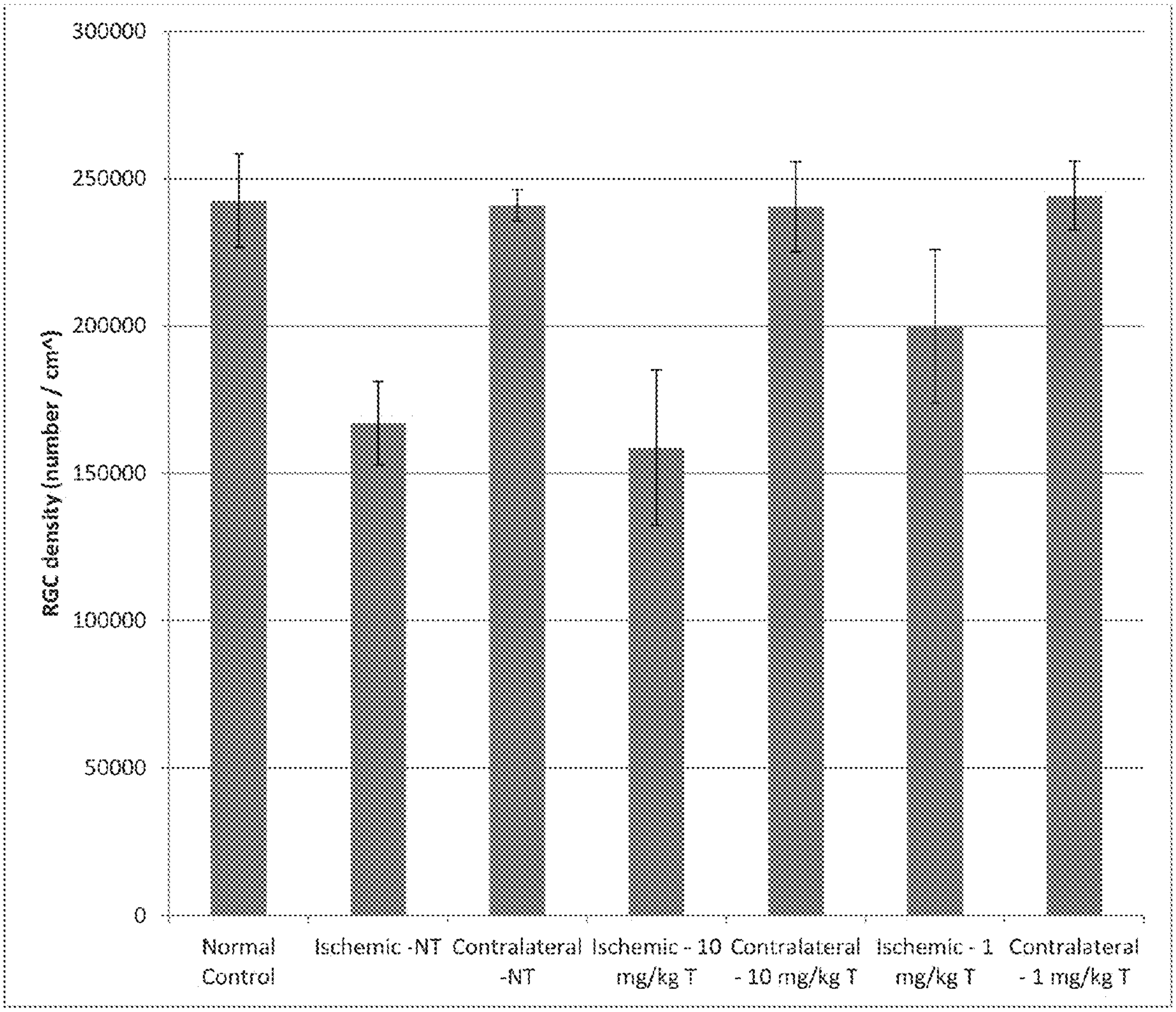
FIG. 15. Retinal ganglion cell density 7 days after retinal ischemia at 120 mmHg for 60 minutes. Results for both the ischaemic eyes and contralateral eyes are shown. Mean±standard error. N=2, 6, 6, 6, 5, 4, 4. NT, no treatment; T, Tonabersat. A statistically significant ($p<0.01$) 31% loss of RGCs was found in ischaemic eyes with no treatment (167111±14188 cells/cm2, mean±standard error) compared to normal controls (242558±15840 cells/cm2). A statistically significant ($p=0.03$) 35% RGC loss was found in ischaemic eyes treated with 10 mg/kg Tonabersat (158739±26370 cells/cm2). However, ischaemic eyes treated with 1 mg/kg tonabersat sustained fewer cell loss (18%, 199927±26058 cells/cm2) than the other groups. The difference between this group and the normal controls was a trend ($p=0.17$). No loss of RGCs was found in all contralateral eyes.

A low concentration of tonabersat is protective against retinal cell death as shown by an established in vivo model of retinal ischemia-reperfusion (H. V. Danesh-Meyer et al., Brain 135, 506 (February, 2012). A statistically significant ($p<0.01$) 31% loss of RGCs was found in ischemic eyes with no treatment (167111±14188 cells/cm2, mean±standard error) compared to normal controls (242558±15840 cells/cm2) (FIG. 15). A statistically significant ($p=0.03$) 35% RGC loss was found in ischemic eyes treated with 10 mg/kg Tonabersat (158739±26370 cells/cm2). However, ischemic eyes treated with 1 mg/kg Tonabersat had reduced neuronal loss (18%, 199927±26058 cells/cm2) compared with the other groups. Although not reaching statistical difference for improvement over injured but untreated eyes, the difference between this group and the normal controls was no longer statistically significant ($p=0.17$). No loss of RGCs was found in all contralateral eyes.

Figure 16B:
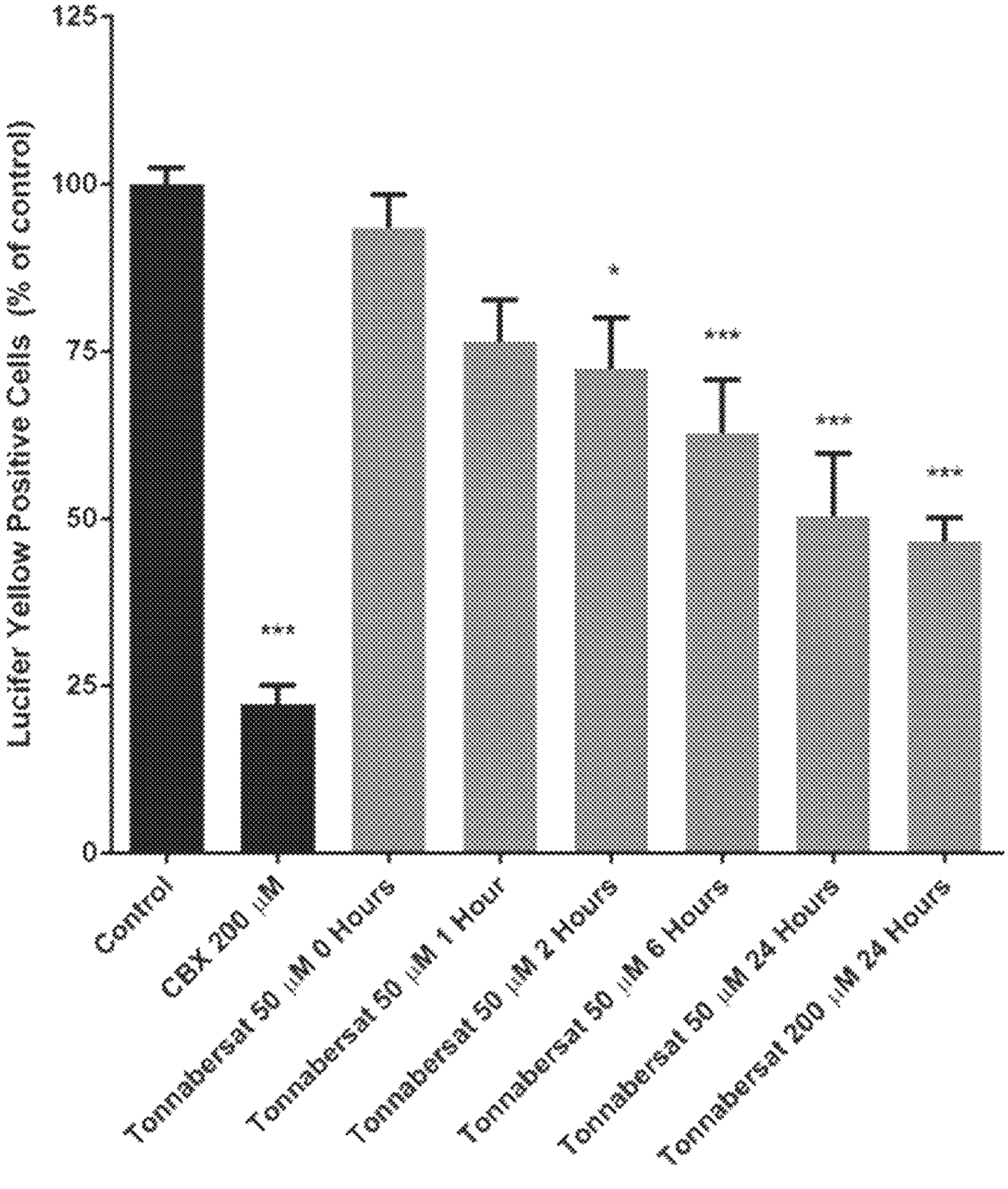
(FIG. 16B) Quantification of LY positive hCMVEC cells treated with 50 μM Tonabersat at immediate to 24 h time-intervals. Tonabersat-mediated uncoupling of GJs increases with time.
Figure 16C:
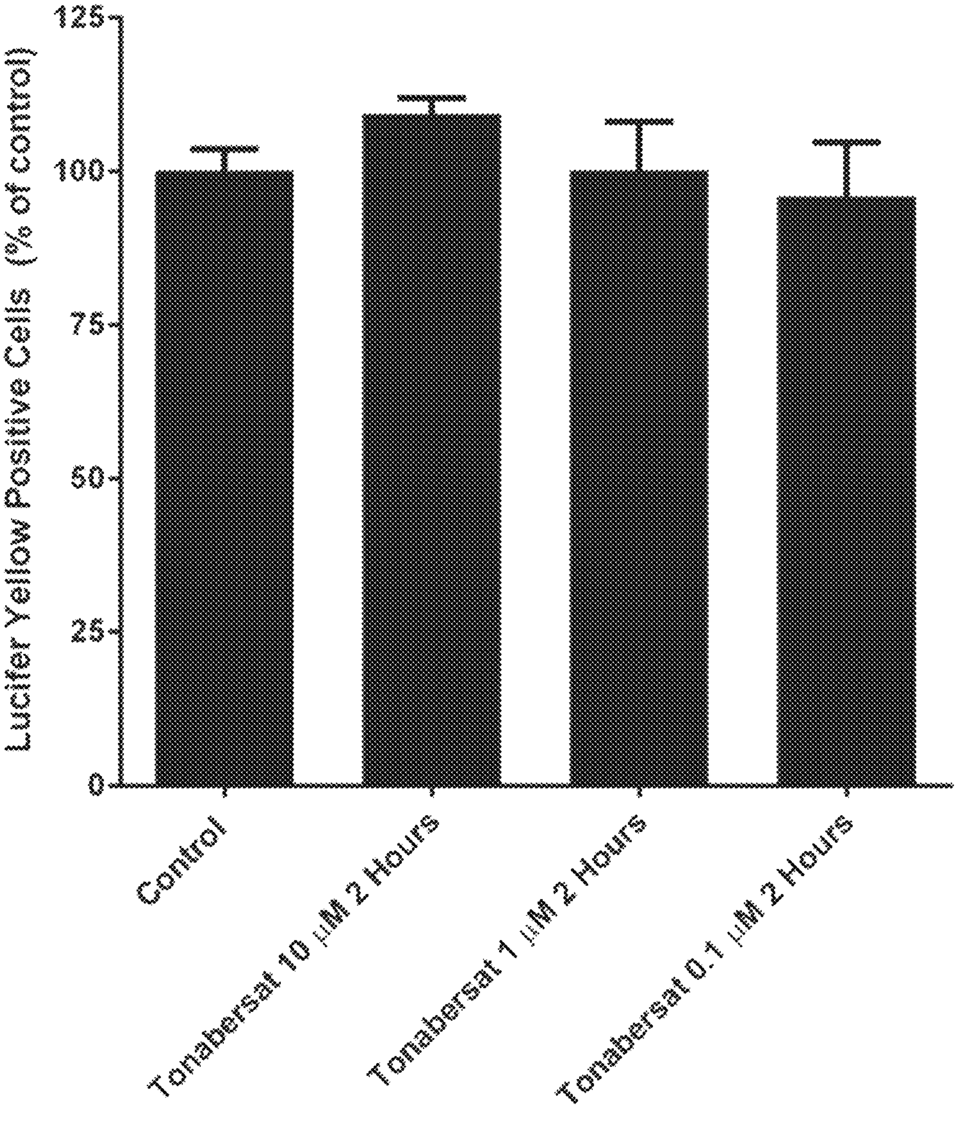
(FIG. 16C) Lower concentrations of Tonabersat (10 μM, 1 μM, 0.1 μM) did not cause GJ uncoupling after two hours in this experiment, or after (FIG. 16D) 24 hours. Bars represent mean±S.E.M (One-way ANOVA followed by Tukey's post-hoc test) n=3 wells, 3 independent experiments. *=$p<0.05$, =$p<0.001$, *=$p<0.001$.

Example 10: Tonabersat can Uncouple Gap Junctions in a Concentration and Time-Dependent Manner An in vitro scrape-loading assay with extracellular Lucifer Yellow (LY), a fluorescent dye that is transferred only through coupled GJs was performed to test whether Tonabersat inhibits GJ communication (M. H. el-Fouly, et al., Experimental cell research 168, 422 (February, 1987)). A single scrape wound was made to a confluent monolayer of hCMVEC cells to enable LY dye to gain access to the cytoplasm of cells at the edge of the wounded region and allow the dye to transfer to adjacent cells through GJs. As expected, we observed LY transfer in vehicle control (FIG. 16A), which is indicative of functional cell-to-cell communication via coupled GJs (el-Fouly, 1987). Carbenoxolone, a broad spectrum gap-junction blocker, significantly reduced GJ communication down to 77.8±7.4% compared to control ($p<0.0001$) (FIG. 16B). In Tonabersat the extent of GJ uncoupling increased over time (FIG. 16B). LY positive cells were significantly down to 72.5±7.4% at 2 hours ($p=0.0132$), and was reduced to 62.8±7.4% by 6 hours ($p=0.0003$) compared to control. LY positive cells was maximally reduced to 50.5±8.4% ($p<0.0001$) compared to control by 24 hours in 50 μM Tonabersat (FIG. 12B). At a higher concentration of 100 μM Tonabersat, LY positive cells were further significantly reduced to 46.7±7.8% ($p<0.0001$). However, 50 μM Tonabersat immediately ($p=0.986$) or 1 hour prior to the assay ($p=0.054$) did not significantly reduce GJ coupling when compared to control (FIG. 16B). At lower Tonabersat concentrations (0.1, 1 and 10 μM), there was no significant reduction in LY positive cells at both 2 hours ($p>0.7$), and 24 hours ($p>0.3$) compared to control (FIG. 16C,D). Taken together, these results indicate that Tonabersat mediated uncoupling GJs is concentration-dependent (≥50 μM), and the extent of this uncoupling effect is dependent on the time period of Tonabersat treatment (at the higher uncoupling doses).

Discussion

These examples show the discovery of novel mechanism of actions of tonabersat that involves of direct and immediate block of Cx43 hemichannels, and a concentration- and time-dependent reduction in GJ coupling. Short-term exposure to certain, lower concentrations of Tonabersat (10 μM) effectively inhibited Cx43 hemichannel mediated ATP release during injury and reperfusion in vitro, and this was consistent with reduced RGC loss in an established in vivo retinal ischaemia-reperfusionmodel. However, exposure to higher concentrations of Tonabersat (<100 μM) not only uncoupled GJs, but a more sustained, longer-term treatment can elicit the targeted internalization and degradation of Cx43 plaques via the lysosomal pathway.

It has been surprisingly discovered that tonabersat exhibits a concentration-dependent inhibition of connexin hemichannels. A lower, 10 μM concentration was the more effective tonabersat concentration for hemichannel inhibition, which exceeded the efficacy of peptide5 used in this study. Furthermore, the inhibition was selective to hemichannel-mediated ATP release as a combined probenecid treatment was required to observe the inhibitory effects of tonabersat (FIG. 8B). These data suggest that while tonabersat effectively blocks hemichannels, it and its analogues and other compounds of Formula I are unlikely to inhibit ATP released from pannexin channels in ischemic injury. If tonabersat effectively inhibited both connexin hemichannels and pannexin channels, the level of the inhibition would have been comparable to the combined peptide5 and probenecid treatments or CBX (55% vs. 65%, respectively). Conversely, tonabersat treatment alone induced a slight increase in ATP compared to injury alone, albeit not significant. It is also of note that 100 μM Tonabersat was not as effective in lowering ATP as 10 μM Tonabersat in these experiments. As higher tonabersat concentrations was not linked to cell toxicity (FIG. 14), tonabersat may have dual effects during injury whereby hemichannels are targeted for inhibition, but pannexin channels may be triggered to open in an off-target effect. These data indicate that a modest dose/concentration of tonabersat combined with a pannexin channel blocker such as probenecid will be effective as a treatment for ischemia, and diseases, conditions and disorders that are characterized at least in part by ischemia.

It has also been demonstrated herein that post-ischemic (reperfusion) conditions in vitro of treated models return to normal physiological conditions post 2 hours in HAIR solution. The in vitro model enabled the inventors to test a) the contribution of connexin and pannexin channels not only in ischaemic injury but also post-ischaemia b) the effect of Tonabersat treatment in ischaemia and post-ischaemia. During post-ischaemia, connexin hemichannel accounted for almost all ATP release as shown by 100 μM peptide5 and 1 mM probenecid (FIG. 9). Importantly tonabersat at 10 μM concentration showed efficacy that was comparable to 100 μM peptide5. These data suggest that a lower concentration of tonabersat inhibits connexin hemichannel-mediated ATP release post-ischemia.

Furthermore, it has also surprisingly been discovered that both connexin hemichannel opening and pannexin channels contribute to ischemic injury (FIG. 8) by mediating ATP release, but following reperfusion pannexin channels may close and connexin hemichannels alone appear to account for almost all of the ATP release through these two channel types (FIG. 9). Pannexin channels may open in an ischemia-dependent mechanism (i.e. NMDAR), but may close shortly after reperfusion when these stimuli also subside. In contrast, Cx43 expression was shown to peak at 4 hours with peptide5 reducing vascular damage 4 and 24 hours post retina ischaemia (H. V. Danesh-Meyer et al., Brain: a journal of neurology 135, 506 (February, 2012).) This is supported by reports that peptide5 delivered 1 hour before and during ischaemia in near-term fetal sheep had minimal therapeutic benefit (J. O. Davidson, et al., Experimental neurology 248, 301 (October, 2013)), whereas peptide5 post-ischemia significantly improved the recovery of EEG activity and sleep cycling, and significantly reduced seizures.

In a previous study, a model of retinal ischemia-reperfusion injury was investigated wherein a breach in the blood-brain barrier and edema of the vascular endothelium indicated the inflammatory response and cause RGC death (H. V. Danesh-Meyer (2012)). The cause of the injury was attributed to open Cx43 HCs, given a dose of Cx43 mimetic peptide5 that targeted Cx43 HCs but not GJs (S. J. O'Carroll, et al., Cell communication & adhesion 15, 27 (May, 2008)) significantly reduced vascular leak and RGCs cell death.

The Examples herein include the in vivo retinal ischemia-reperfusion injury model, as carried out in Danesh-Meyer et al. (2012), and showed that tonabersat is protective against RGC loss following retinal ischemia-reperfusion injury. This was achieved at a low final circulating dose of 32 μM, comparable to 10 μM used for inhibiting connexin hemichannels mediated ATP release in vitro.

Tonabersat has been administered in most Phase 2 clinical trials at 20-80 mg once daily for migraine (A. W. Hauge, et al., The Lancet. Neurology 8, 718 (August, 2009)) and epilepsy (A. A. Parsons et al., British journal of pharmacology 132, 1549 (April, 2001), N. Upton et al., British journal of pharmacology 121, 1679 (August, 1997)). However, those clinical results are inconclusive (Hauge, 2009). In contrast, it has been surprisingly demonstrated herein that that the therapeutic benefits can be achieved by targeting hemichannels during and after injury, especially after ischemia or in combination with a pannexin channel blocker.

The clinical failure may be attributed to use of tonabersat where pannexin channels were also affected.

Cx43 isoform specific antisense oligodeoxynucleotide (Cx43 AsODN) transient down-regulation significantly provides vascular protection and improves functional outcomes in non-healing ocular wounds (Ormonde et al., J. Membr. Biol. (2012) 245(7):381-88). In this context, transiently counteracting the rise in Cx43 and hence de novo formation of GJ hemichannels was beneficial without permanently compromising the spatial buffering effect. It has been surprisingly discovered herein that time-dependent action of tonabersat may be utilized for controlled transient modulation of Cx following injury whilst minimizing the complete removal of the 'spatial-buffering' effect.

Figure 16D:
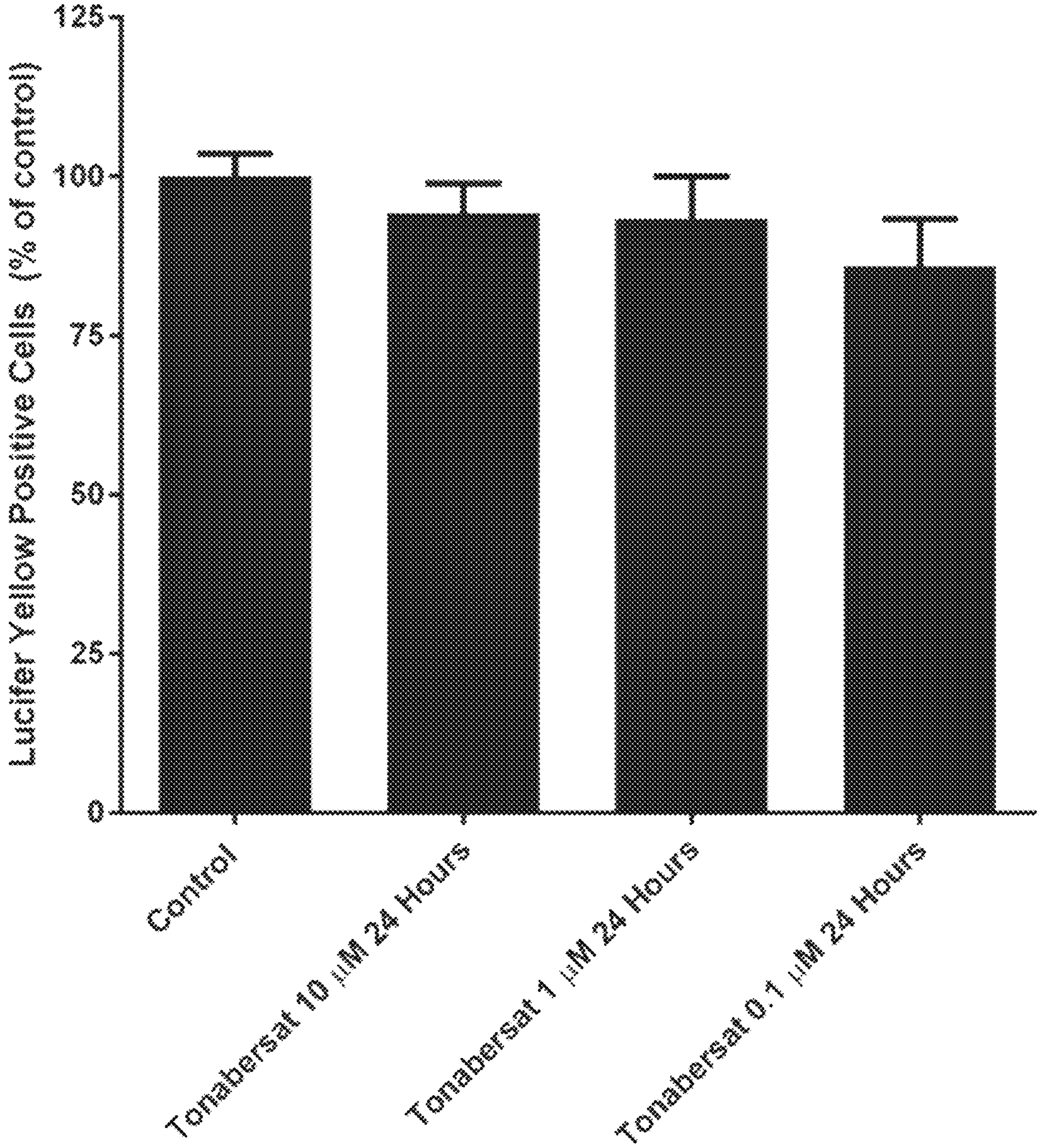

This present disclosure also demonstrates that tonabersat removes Cx43 from the plasma membrane (FIG. 16). The inventors have surprisingly discovered a reduction in the total expression of Cx43 plaques (FIG. 16), which indicates that tonabersat is likely to alter the balance between Cx43 synthesis and degradation. Therefore, internalized Cx43 channels targeted by tonabersat are sent for degradation via the lysosomal pathway.

There are two major routes for degradation of connexin channels, the lysosomal and proteasomal pathways. The rationale for examining the lysosomal pathway is based on the idea that plasma membrane connexins are solely degraded by the lysosomes whereas cytosolic and nuclear connexins are degraded by proteasomes. The accumulation of cytoplasmic Cx43 in the presence of lysosome inhibitor indicates that Tonabersat targets Cx43 for degradation. The perinuclear localization of Cx43 is indicative of accumulation of new protein in the Golgi, which further supports the idea that while tonabersat enhances the degradation of cell surface Cx43 channels, it has no effect on Cx43 transcription or translation of new protein. The PCR data also suggest that tonabersat does not regulate Cx43 mRNA transcription; rather, the observed reduction in Cx43 occurs at the level of protein turnover by internalization and degradation.

In conclusion, the inventors have surprisingly discovered, amongst other things, novel mechanism of actions of tonabersat that include direct and immediate block of connexin hemichannels, and, at higher concentrations, a concentration- and time-dependent inhibition of Cx43 GJ coupling. Exposure to high concentrations of tonabersat not only uncoupled GJs, but the sustained long-term treatment caused Cx43 plaques to be targeted for internalization and degradation via the lysosomal pathway. In the present disclosure, it has been demonstrated that both connexin hemichannels and pannexin channels can mediate ATP release during ischemic injury, with connexin hemichannels being the primary contributor to ATP leak post-injury. Short-term exposure to lower concentrations of tonabersat effectively inhibited Cx43 hemichannel mediated ATP release during injury but especially during reperfusion in vitro, and this was consistent with reduced RGC loss in an in vivo retinal ischemia-reperfusion model, Tonabersat is thus not CNS specific as previously assumed, is not restricted to Cx26 modulation, and does not affect Cx43 protein synthesis, but rather acts directly on connexin hemichannels or through junction internalization.

Example 11: Transfection In Vitro Assay of Unmodified and Chemically Modified Oligonucleotide Structures of Connexin 43 Antisense Compounds HUVEC cells (C-003-5C, Invitrogen, primary Human endothelial cells) were used to test the transfection of chemically modified backbones of the Connexin 43 antisense compounds. Cells were transfected with Oligofectamine® using the manufacturer's recommended protocol for 4 hr and 12 hr in serum-free media. The antisense concentration was 200 nM in buffer. The antisense compounds used had unmodified (O) or fully modified (PTO) backbones, where the modified backbone had all thiophosphoriate linkages between the nucleotides. The unmodified sequence SEQ1-O would have the sequence GTAATTGCGGCAAGAAGAATTGTTTCTGT (SEQ ID NO: 23). The modified sequence SEQ1-PTO would have the sequence of: GsTsAsAsTsTsGsCsGsGsCsAsAsGsAsAsGsAsAsTsTsGsTsTsTsCsTsGsT (SEQ ID NO: 23), wherein the subscript "s" indicates the thiophosphoriate linkage between the two nucleotides. Likewise, the unmodified and modified sequences for SEQ4-O and SEQ4-2PTO would be ACCCATGTTGCCTGGGCACC (SEQ ID NO: 5), and AsCsCsCsAsTsGsTsTsGsCsCsTsGsGsGsCsAsCsC (SEQ ID NO: 5), respectively. All sequences for the transfection study were labelled with FAM for fluorescence labelling. The transfected cells were analyzed by FACS (fluorescent-activated cell sorting), and confocal microscopy.

Results:

Over 95% transfection efficiency was observed with all oligonucleotide types. Cells accumulate more PTO-oligonucleotides compared to nonmodified oligonucleotides. Most uptake of the antisense oligonucleotides takes place within 4 hours, as summarized in Table 40.

TABLE 66

| 4 hr post-transfection | | | | |
|---|---|---|---|---|
| % Transfected | SEQ4-Q | SEQ4-PTO | SEQ1-O | SEQ1-PTO |
| Total | 99 | 100 | 99 | 100 |
| M2 | 64 | 9 | 56 | 26 |
| M3 | 34 | 44 | 42 | 63 |
| M4 | 1 | 48 | 2 | 11 |

TABLE 67

| 4 hr post-transfection | | | | |
|---|---|---|---|---|
| % transfected | SEQ4-Q | SEQ4-PTO | SEQ1-O | SEQ1-PTO |
| Total | 99 | 99 | 98 | 100 |
| M2 | 55 | 9 | 56 | 15 |
| M3 | 41 | 44 | 40 | 49 |
| M4 | 2 | 47 | 2 | 35 |

Figures 17A, 17B, 17C:
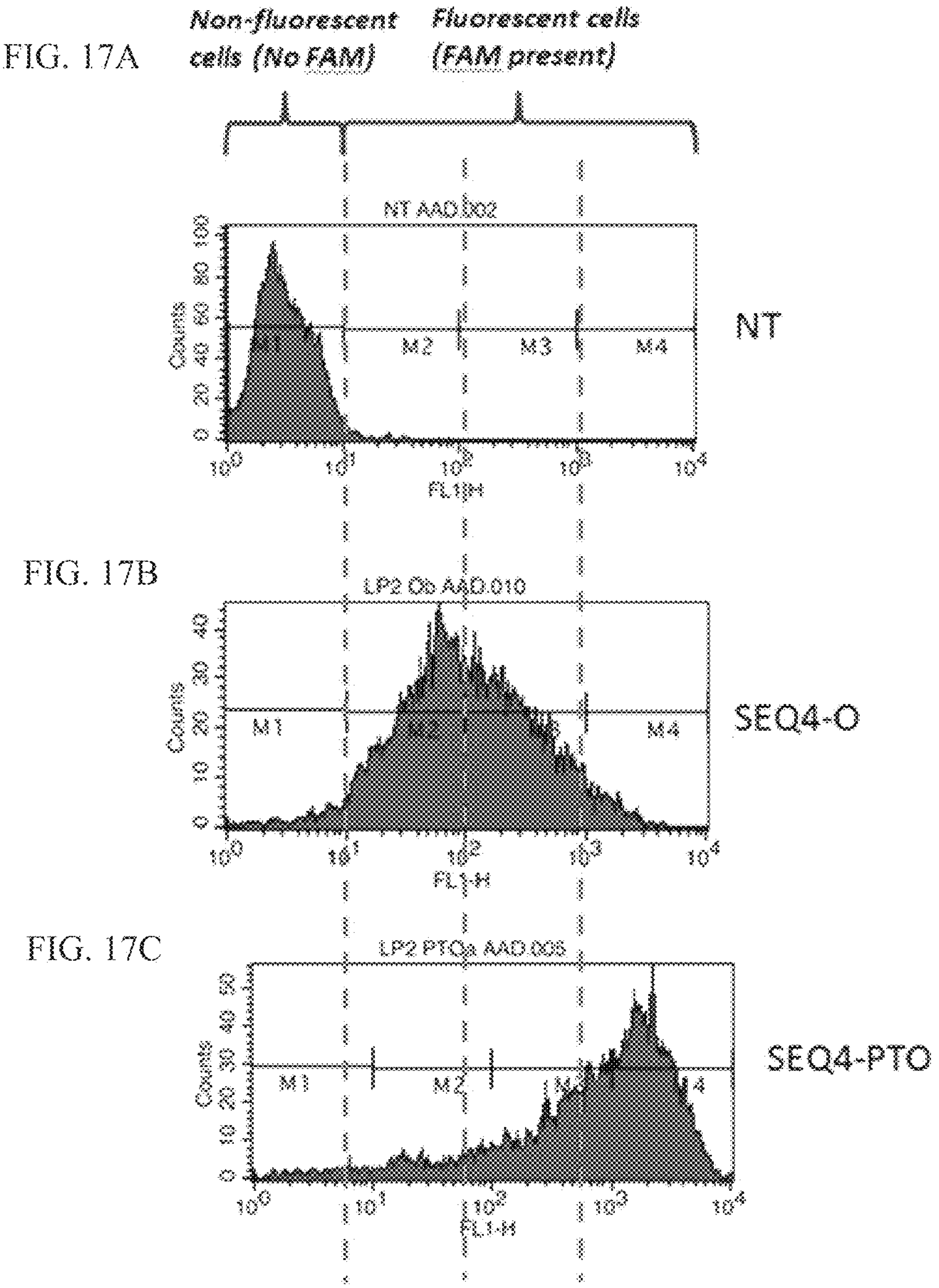
FIG. 17A-FIG. 17C. FACS data for the transfection uptake of several selected antisense oligonucleotides.

FIG. 17 shows the FACS data for the transfection uptake of several selected antisense oligonucleotides.

Figure 18:
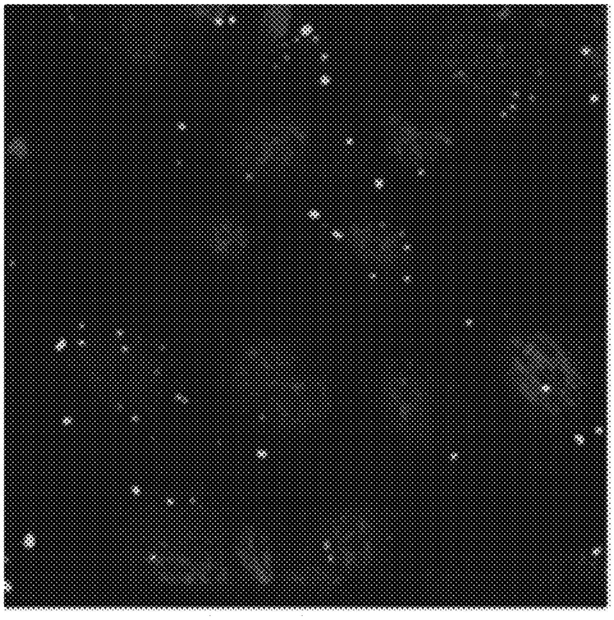
FIG. 18. Image of live cells via confocal microscopy shows uptake of FAM-labelled SEQ4-PTO (modified) in HUVEC cells (4 hr post-transfection). Green represents the oligo SEQ1-O (FAM labelled), Blue represents cell nucleus stained by DAPI.
Figure 19:
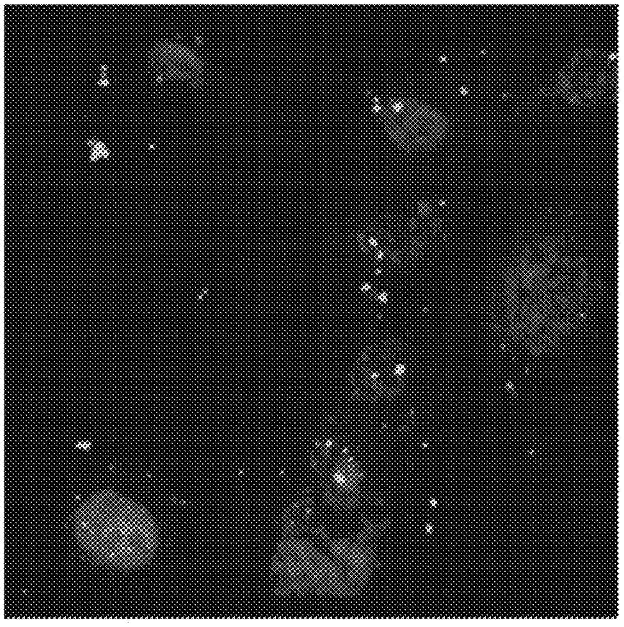
FIG. 19. Green represents the oligo SEQ1-O (FAM labelled), Blue represents cell nucleus stained by DAPI.

The image of live cells via confocal microscopy shows uptake of FAM-labelled SEQ1-O (unmodified) in HUVEC cells (4 hr post-transfection), as shown in FIGS. 18 and 19. FIG. 18 shows the image of live cells via confocal microscopy shows uptake of FAM-labelled SEQ4-PTO (modified) in HUVEC cells (4 hr post-transfection). Green represents the oligo SEQ1-O (FAM labelled), Blue represents cell nucleus stained by DAPI. As can be seen in FIG. 18, the labelled connexin 43 modulator is in close proximity to the nucleus and occasionally in the nucleus as shown in FIG. 18.

The oligonucleotide (green) is observed to accumulate in the nucleus (blue), as shown in FIGS. 18 and 19. In FIG. 19, green represents the oligo SEQ1-O (FAM labelled), and blue represents cell nucleus stained by DAPI.

Next, the knockdown efficiency of Connexin 43 in HUVEC cells was measured by qPCR for an oligonucleotide series with the same sequence but with a different number of PTO-modifications on the oligonucleotide backbone. The sequences tested were SEQ1 and SEQ4, with none, 2, or all phosphorthioate linkages in the backbone. For the sequences with two phosphorthioate linkages in the backbone, the phosphorthioate linkages were between the last nucleotide linkages at the terminus of each side of the sequence. The sequences are GsTAATTGCGGCAAGAAGAATTGTTTCTGsT (SEQ ID NO: 23) and AsCCCATGTTGCCTGGGCACsC (SEQ ID NO: 5) for SEQ1-2PTO and SEQ4-2PTO, respectively. The concentration of all oligo solutions was 200 nM.

Figure 20:
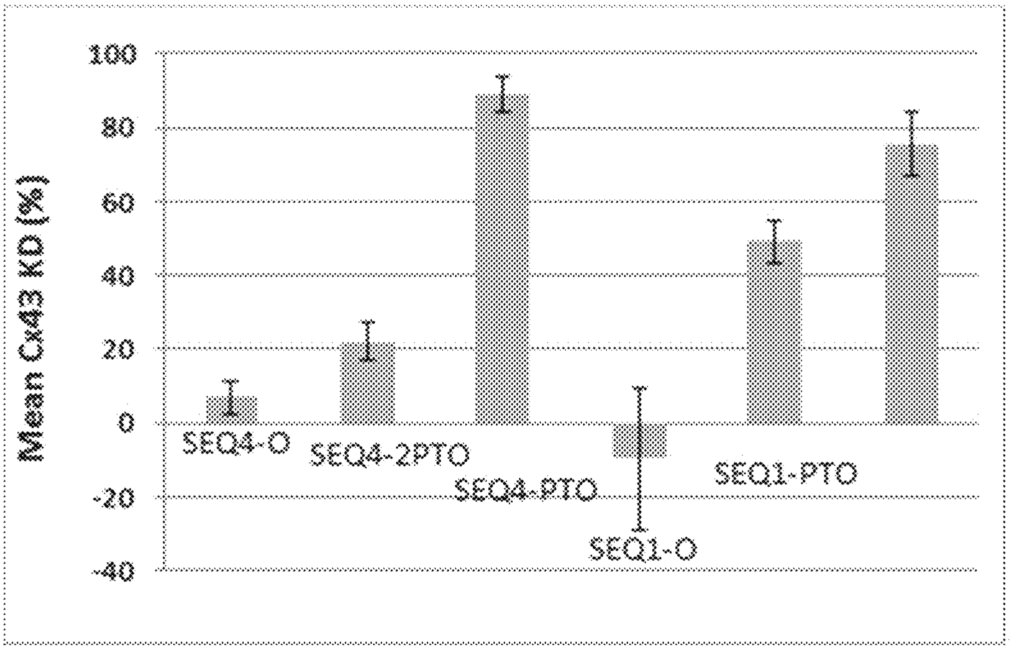
FIG. 20. Shows the knockdown efficiency of Connexin 43 as measured by qPCR. The data shows the standard deviation for 3 replicates.
Figure 21:
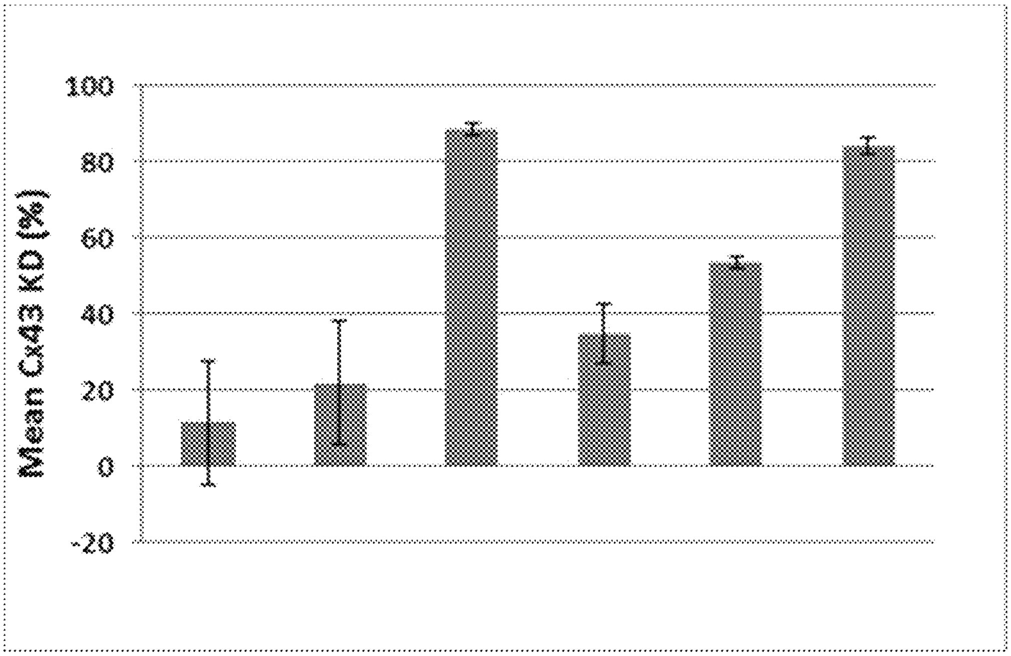
FIG. 21. Knockdown efficiency of Connexin 43 as measured by Western Blot (n=3). The data show standard deviation for 3 replicates.

FIG. 20 shows the knockdown efficiency of Connexin 43 as measured by qPCR (n=3). The data shows the standard deviation for 3 replicates. FIG. 21 shows the knockdown efficiency of Connexin 43 as measured by Western Blot. The data show standard deviation for 3 replicates.

The results show that the full PTO backbone exhibited the most Cxn43 knockdown by both qPCR and Western blot analyses. Furthermore, protecting the antisense with one PTO link on both ends (2-PTO) resulted in some degree of Cxn43 knockdown. Unmodified (0) backbone oligonucleotides resulted in much lower levels of Cxn43 knockdown efficiency than all PTO-backbone oligonucleotides.

Figure 22A:
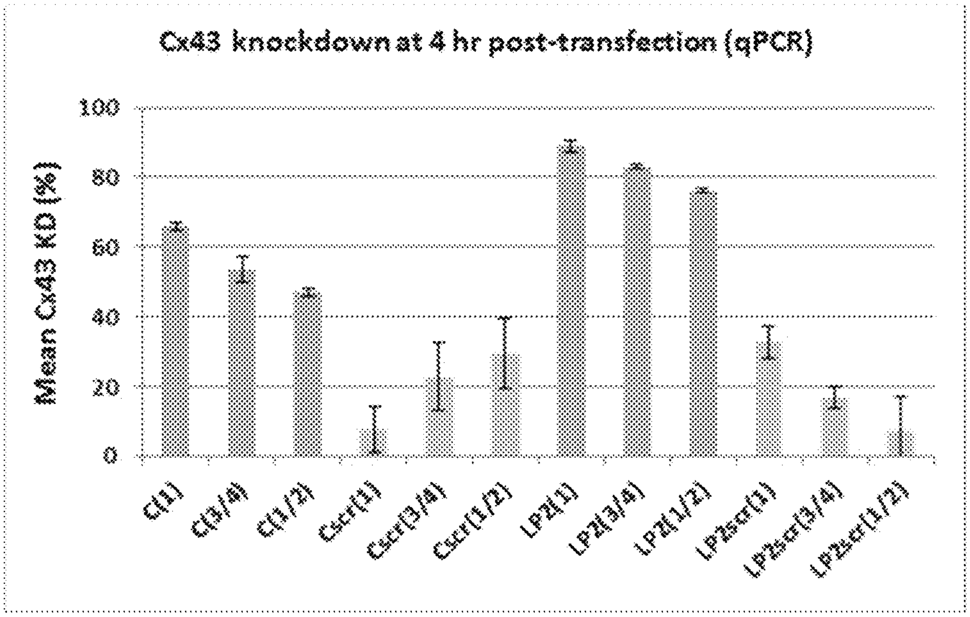
FIG. 22A-FIG. 22B Knockdown efficiency of modified (PTO) and unmodified sequences measured by qPCR at 4 hours (FIG. 22A) and 8 hours (FIG. 22B) after transfection, respectively. Oligo concentration: (1)=200 nM; (¾)=150 nM; (½)=100 nM; C: SEQ1; SEQ4: 37501; Cscr: SEQ1 scrambled; LP2scr: SEQ4 scrambled; Orange bars: negative controls. (n=3 for each result).
Figure 22B:
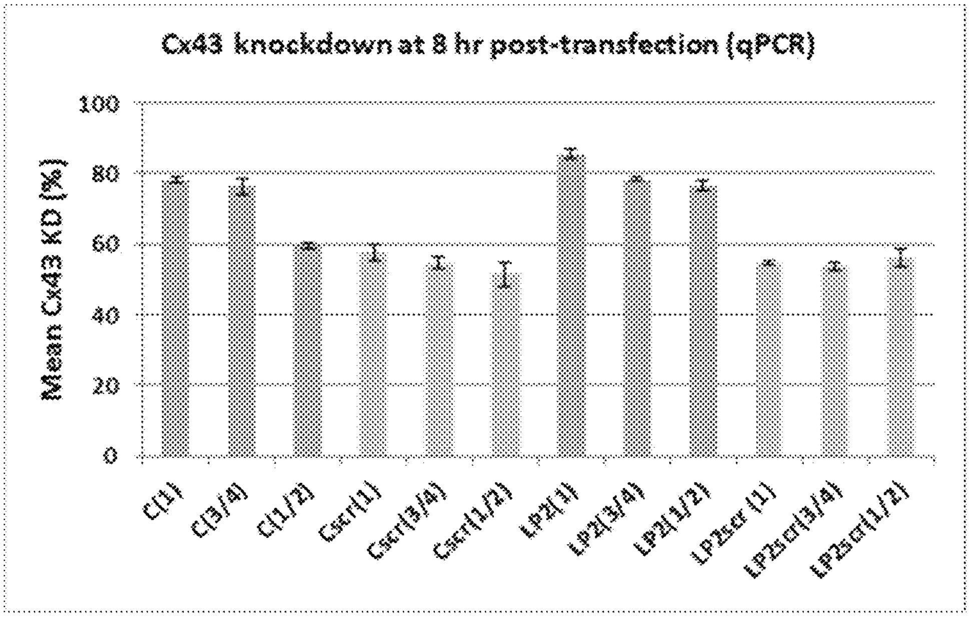

The knockdown efficiency of modified (PTO) and unmodified sequences, both the full intact sequence and for scrambled sequences, was observed over time. The knockdown efficiency was measured by qPCR, as shown in FIG. 22. The data show standard deviation for 3 replicates.

FIGS. 22 A and B shows the knockdown efficiency of modified (PTO) and unmodified sequences measured by qPCR at 4 hours and 8 hours after transfection, respectively. Oligo concentration: (1)=200 nM; (¾)=150 nM; (½)=100 nM; C: SEQ1; SEQ4: 37501; Cscr: SEQ1 scrambled; LP2scr: SEQ4 scrambled; Orange bars: negative controls. (n=3 for each result). The results show lesser non-specific negative control effects detected at 4 hr post-transfection, and the oligo at 150 nM exhibited the largest difference from its corresponding negative control.

FIG. 23 shows the knockdown efficiency as measured by Western blot. The data show standard deviation for 3 replicates. The results show 4 and 8 hr post-transfection exhibited very little knockdown, lesser non-specific negative control effects were detected at 12 hr post-transfection, and the oligo at 150 nM concentration exhibited the largest difference from its corresponding negative control.

Figure 24:
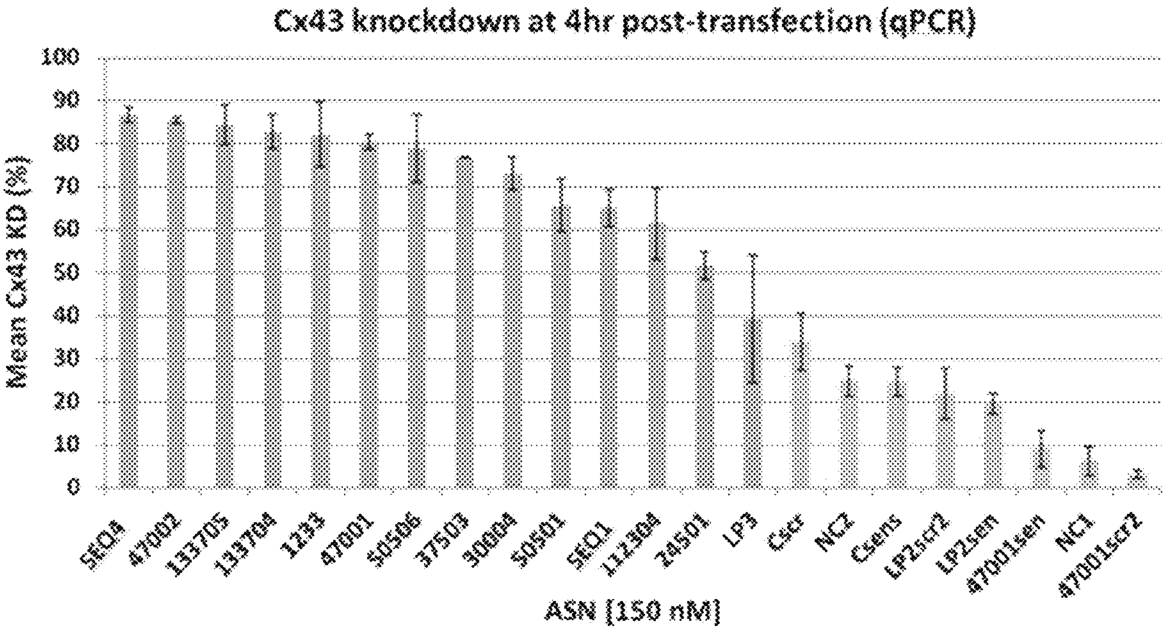

Different sequences were analyzed by qPCR for their knockdown efficiency of connexin 43 to compare sense strands and other antisense strands to Cxn43, as shown in FIG. 24.

Figure 25:
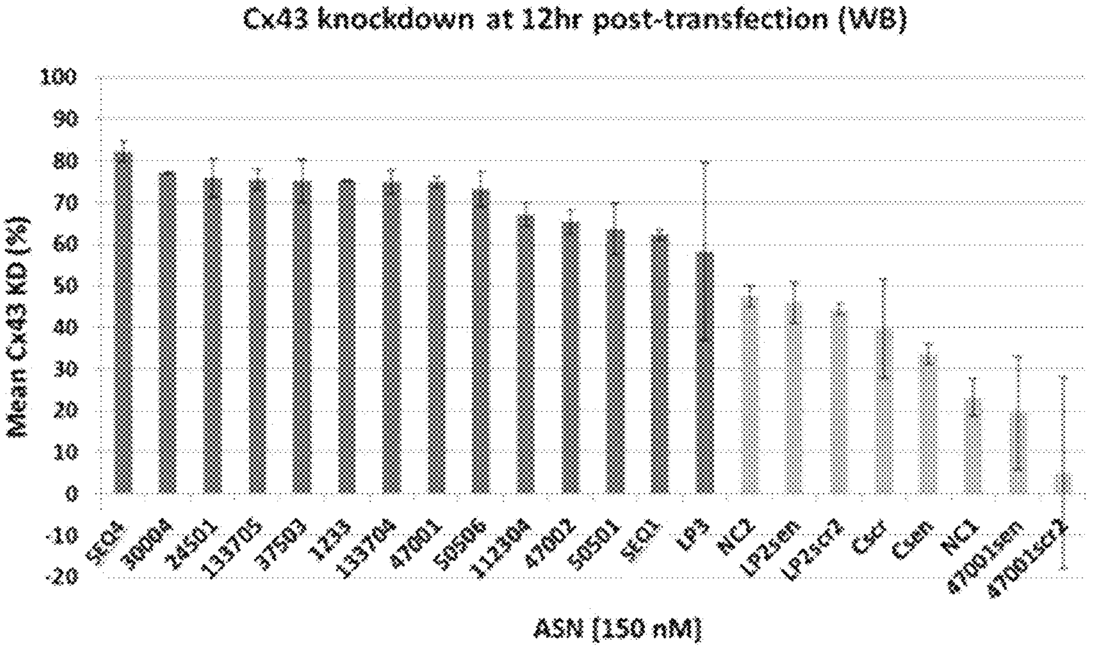
FIG. 25. Different sequences analyzed by Western Blot for their knockdown efficiency of connexin 43. Cscr: SEQ1 scrambled, Csen: SEQ1 sense strand, LP2scr2: SEQ4 scrambled, LP2sen: SEQ4 sense strand, 47001scr2: SEQ5 scrambled, 47001sen: SEQ5 sense strand, NC1: universal negative 1, NC2: universal negative 2.

The sequences were also analyzed by Western blot (WB) for knockdown efficiency, as shown in the FIG. 25. The results indicate that all the antisense oligos had higher knockdown efficiency of Connexin 43 than the negative controls. From the knockdown efficiency results, a variety of other sequences (all with all-thiophosphoriate linkages in the entire backbone) were identified that could also knockdown Connexin 43. Table 68 shows their relative knockdown difference compared to SEQ1.

TABLE 68

| SEQ # | Absolute Difference from SEQ1 |
|---|---|
| SEQ4 | 22 |
| SEQ11 | 20 |
| SEQ5 | 19 |
| SEQ6 | 18 |
| SEQ7 | 17 |
| SEQ8 | 15 |
| SEQ9 | 14 |
| SEQ10 | 12 |

Figure 26:
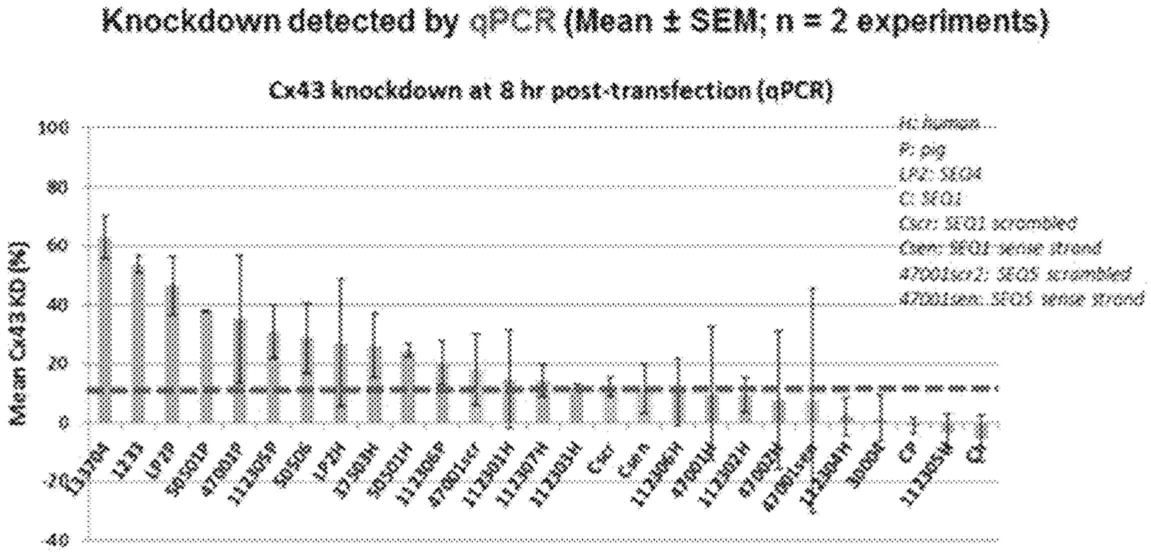
FIG. 26. Cxn43 knockdown results of oligonucleotide sequences in different cell types. H: human, P: pig, LP2: SEQ4, C: SEQ1, Cscr: SEQ1 scrambled, Csen: SEQ1 sense strand, 47001scr2: SEQ5 scrambled, 47001sen: SEQ5 sense strand, the other numbers represent other antisense sequences to Connexin 43, as described herein.

The oligonucleotide sequences were then tested for their knockdown efficiency in another cell type: PAOEC (P304-05, Cell Applications Inc.), Pig Aortic endothelial cells, as primary cells. The cells were seeded for 24 hr to reach 50-80% confluency prior to experiment. Cells were transfected by Oligofectamine® using the recommended protocol at 200 nM oligo concentration for 4 hr in serum-free media. Samples were harvested at 8 hr (for qPCR analysis) and 12 hr (for western blot analysis). FIG. 26 shows the knockdown results.

The dashed line in FIG. 26 indicates the mean negative control effect (~12%). The results show that in general, pig version antisense oligos performed better than the corresponding human versions.

Figure 27:
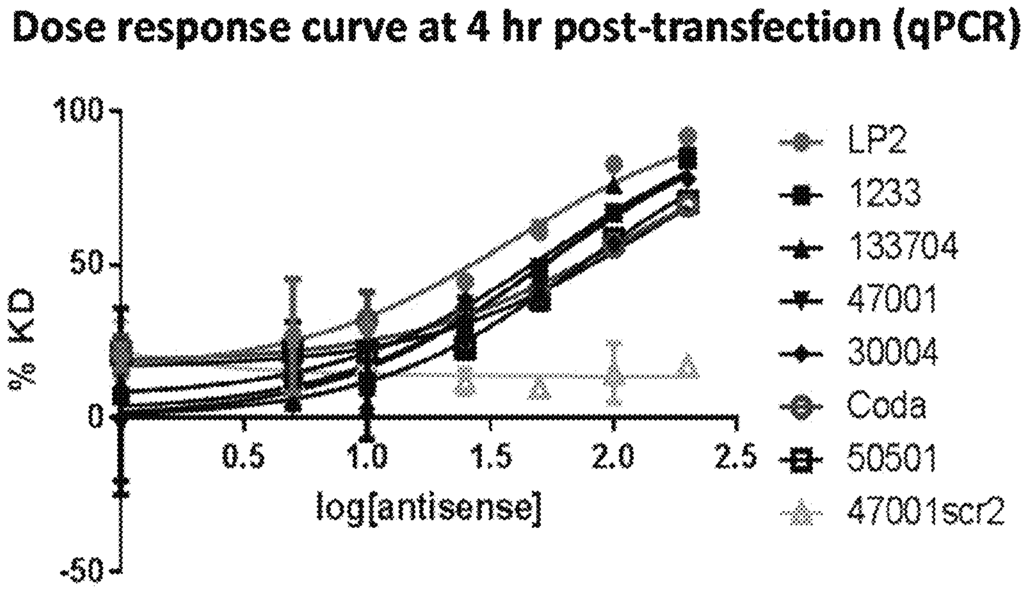
FIG. 27. Dose-response performance in HUVEC cells by qPCR for various oligonucleotide sequences. LP2: SEQ4, Coda: SEQ1, 47001scr2: SEQ5 scrambled, the other numbers represent other antisense sequences to Connexin 43, as described herein.

Selected oligos were then analyzed for their dose-response performance in HUVEC cells by qPCR. The concentrations tested were: 1, 5, 10, 25, 50, 100, and 200 nM, as shown in FIG. 27. The results show that the scrambled sequence (not antisense for Connexin 43) did not have any dose-response, whereas the selected antisense oligo sequences (all with phosphorthioate backbones) did exhibit a dose-response.

Figure 28A:
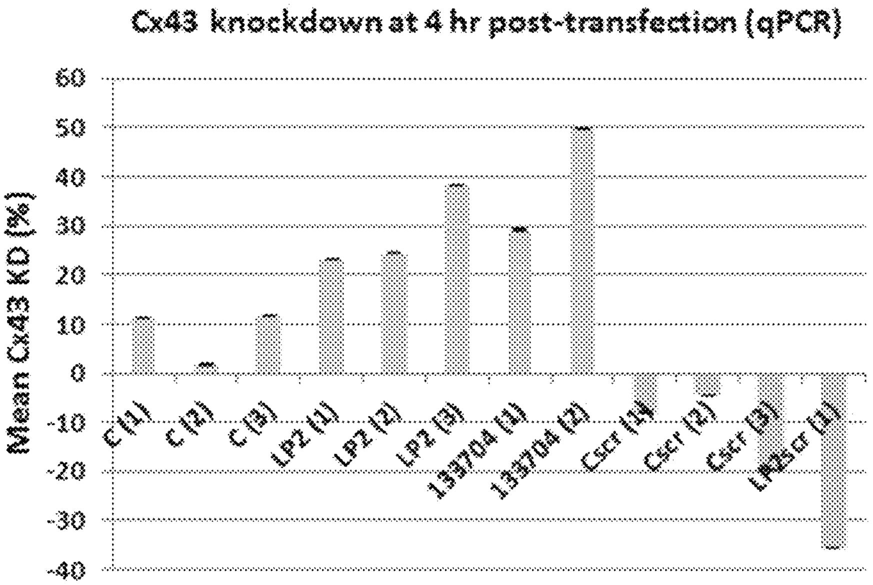
FIG. 28A and FIG. 28B Knockdown efficiency of Cxn43 by the unmodified sequences (no phosphorthioate linkages in the backbone) as measured by qPCR. Oligo concentration: (1)=200 nM; (2)=400 nM; (3)=600 nM C: SEQ1; SEQ4: 37501; Cscr: SEQ1 scrambled; LP2scr: SEQ4 scrambled.
Figure 28B:
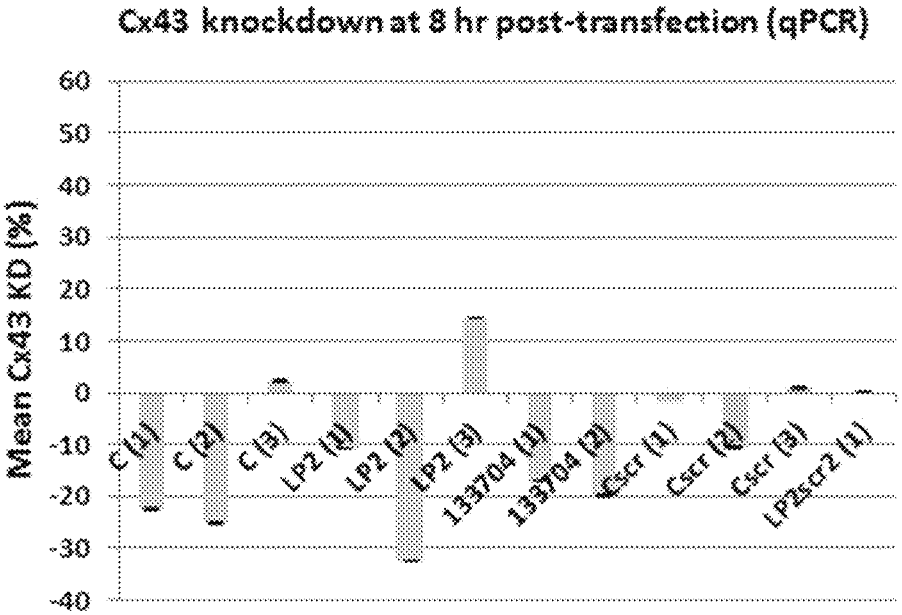

Knockdown efficiency of Cxn43 by the unmodified sequences (no phosphorthioate linkages in the backbone) was measured by qPCR for several sequences, as shown in FIGS. 28 A and B. The results indicate knockdown is detected at 4 hr but not at 8 hr post-transfection. The antisense Connexin 43 oligos exhibited a dose response for SEQ4 and 133704. SEQ1 did not exhibit a knockdown effect over ~10% at 4 hr for all concentrations. The negative controls exhibited higher Cxn43 mRNA levels compared to vehicle control.

Figure 29A:
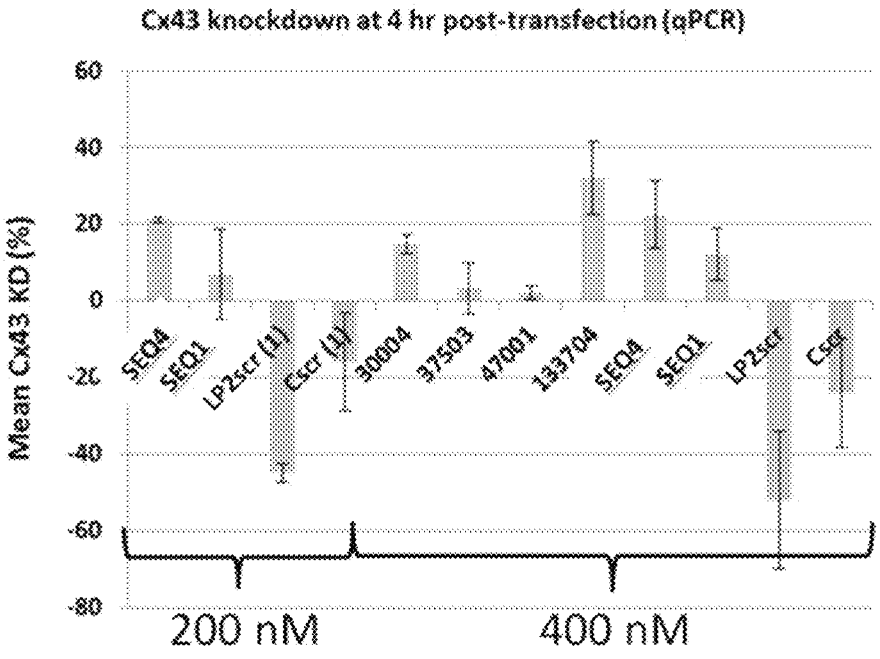
FIG. 29A and FIG. 29B Knockdown efficiency comparison of the modified (with all-thiophosphoriate backbone) sequences. Oligo concentration: (1)=200 nM; (2)=400 nM; (3)=600 nM C: SEQ1; SEQ4: 37501; Cscr: SEQ1 scrambled; LP2scr: SEQ4 scrambled FIG. 30A and FIG. 30B In vitro knockdown of unmodified oligo sequences. Cscr: SEQ1 scrambled; 133704: another antisense oligo to Connexin 43.
Figure 29B:
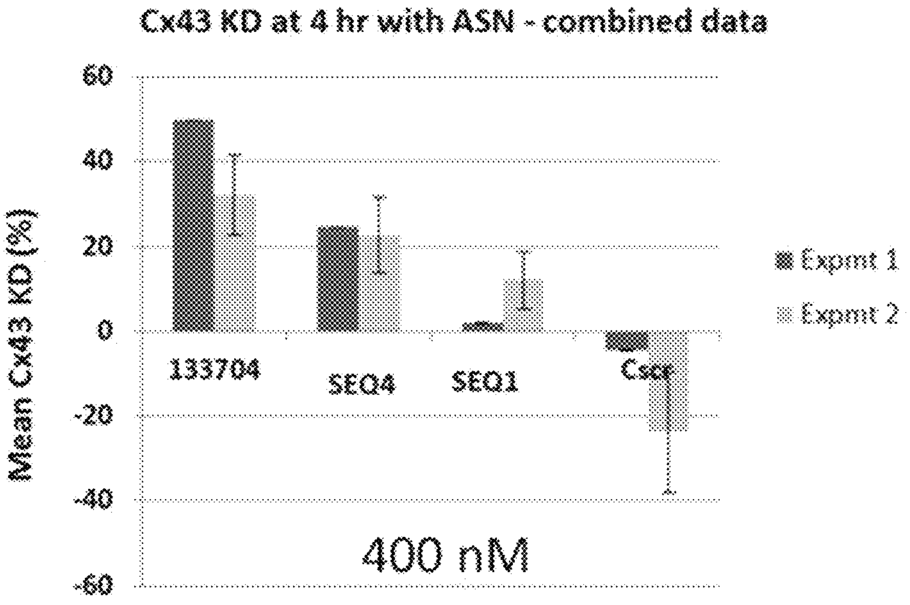

The knockdown efficiency of the modified (with all-thiophosphoriate backbone) sequence was compared to the unmodified sequence at both 400 nM and 150 nM, as shown in FIG. 29.

Figure 30A:
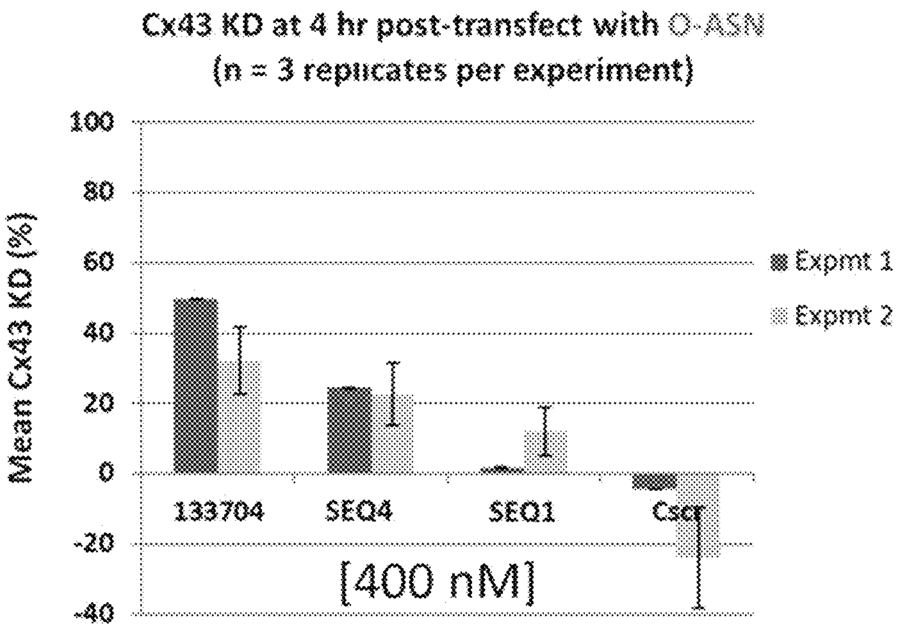
Figure 30B:
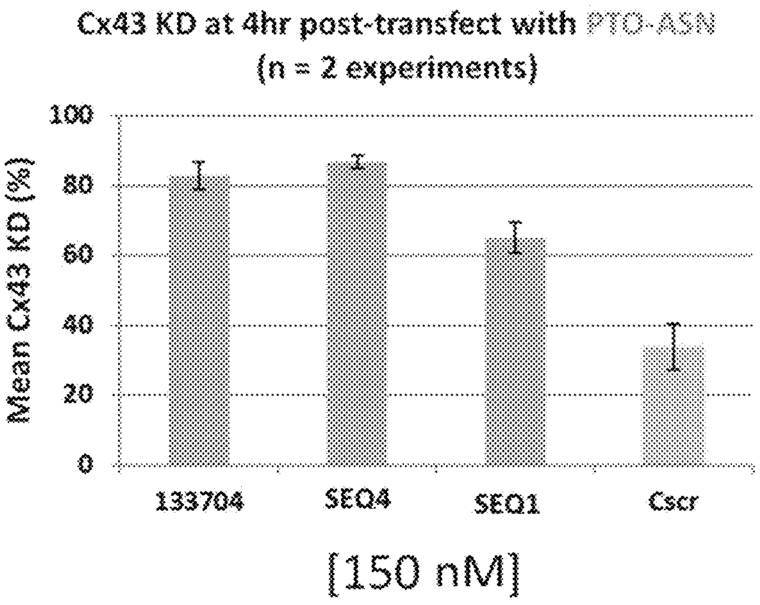

The results indicate that at 200 nM, not much knockdown (KD) is detected with ASN treatment, while at 400 nM, low levels of knockdown are detected for some ASN sequences. Overall, the unmodified oligo sequences can induce knockdown in vitro but the extent is small and variable from experiment to experiment, as shown in FIG. 30.

The results indicate the modified oligo backbone (PTO-ASN) exhibited much more knockdown efficiency than the corresponding unmodified oligo (O-ASN), even though a much higher dose of the unmodified oligo was used.

Example 12. Other Sequences Identified by a Series of Screening Events to Identify Other Effective Antisense Oligonucleotides to Connexin 43

The DNA sequence of the target-of-interest was obtained from the NCBI database (National Center for Biotechnology Information). DNA was synthesized and inserted into the pDONR221 cloning vector for amplification using *E coli* cells. Subsequently, the vector containing the target DNA was extracted from the *E coli* cells and the target DNA was isolated using restriction enzymes. The target DNA was used as the template for in vitro transcription to generate the corresponding RNA and used for performing RNAse H and DNAzyme assays.

For RNAse H assay, target RNA was labeled with $^{32}P$ at one end and probed with a 12-nucleotides randomized oligonucleotide library in the presence of RNAse H enzyme. Subsequently the partially digested sample product was analyzed by performing a denaturing polyacrylamide gel electrophoresis. The size of the fragments generated by RNAse H cleavage compared to a standard ladder indicated the distance of the corresponding accessible regions from the labeled end of the RNA. Regions that were situated on the untranslated ends of the RNA were not determined due to the resolution limit of the gel.

For DNAzyme assays, 20-nucleotide DNAzymes were designed by looking for the enzymatic targets of purine (A, G) and pyrimidine (C, T) pairs on the target RNA, in order to probe the specific accessible sites. Subsequently the samples were analyzed by performing non-denaturing agarose gel electrophoresis and RNA gel stain. The size of the fragments generated by DNAzyme cleavage confirmed the specific accessible sites. Sites that were situated on the untranslated ends of the RNA were not determined due to the resolution limit of the gel.

The sequences of the target binding arms of active DNAzymes are used to synthesize antisense oligonucleotides with phosphorothioate (PTO) backbones—which were then screened for knockdown of the protein by Western blotting and of the RNA by qPCR in cell culture assays.

Cells were grown in 6-well culture plates for 24 hr and reached 50-70% confluence prior to antisense oligonucleotide treatments using the transfection agent Oligofectamine®. Cells were harvested for qPCR and Western blotting analysis between 4 and 24 hr after transfection.

qPCR was performed to determine the efficacy of antisense oligonucleotide in knockdown of the target RNA. Briefly, total RNA was extracted from the cells after transfection. The isolated RNA was DNAse-treated and reverse-transcribed into cDNA. The cDNA subsequently underwent qPCR thermal cycling. The Ct values (the number of cycles required for the fluorescent intensity to cross the set threshold) obtained from the qPCR were converted into relative abundance of RNA. The RNA level of the target was normalised to selected reference genes and compared between antisense oligonucleotide versus vehicle treatments.

Western blotting was also performed to determine the efficacy of antisense oligonucleotide in knockdown of the target protein. Briefly, total proteins were extracted from the cells after transfection and the concentration was determined by performing bicinchoninic acid (BCA) assay. Subsequently, equal amounts of total protein were loaded for gel electrophoresis and blotted onto nitrocellulose membranes, which were then probed with a specific antibody against the target protein. Densitometry was used to quantify the band intensity of the target protein. Knockdown was quantified by comparing antisense oligonucleotide versus vehicle treatments. Table 56, set forth in the Appendix in Application Ser. Nos. 62/080,217, 62/085,226, 62/146,128, and 62/147,488, incorporated here by reference, showed all ASN tested, and the summarized test results.

Table 67 shows the sites where the RNAase enzyme activity was found and represents general regions of accessibility. These were refined by a DNAzyme walk across those regions. From this a range of ASN were designed and tested.

Table 68 lists all the ASN that were then tested on cells for knockdown activity.

Table 61 lists the current lead ASN sequences we are further developing and characterising.

Results

These ASN sequences resulted from DNAzymes designed around 8 accessible regions which were identified by the RNAse H assay, as listed in Table 57.

TABLE 57

| ASN code name | SEQ IDENTIFIER-NOT A SEQ ID NO. | SEQ ID NO: | ASN sequence | SEQ ID NO: | Sense sequence (target) | ASN target site from 5' end |
|---|---|---|---|---|---|---|
| 24501 | SEQ 122 | 24 | ACCCATGTTGCCTGGGCACC | 48 | GGTGCCCAGGCAACATGGGT | 237-256 |
| 24502 | SEQ 123 | 25 | GTTGCCTGGGCACCACTCTT | 49 | AAGAGTGGTGCCCAGGCAAC | 231-250 |
| LP1 | SEQ 13 | 26 | GCCTGGGCACCACTCTTTTG | 50 | CAAAAGAGTGGTGCCCAGGC | 228-247 |
| 24503 | SEQ 124 | 27 | TGGGCACCACTCTTTTGCTT | 51 | AGCAAAAGAGTGGTGCCCAG | 226-245 |
| 30004 | SEQ 125 | 28 | GTAGGCTTGAACCTTGTCAA | 52 | CTTGACAAGGTTCAAGCCTA | 281-300 |
| 37503 | SEQ 126 | 29 | TCTCCCCAGGCTGACTCAAC | 53 | GTTGAGTCAGCCTGGGGAGA | 372-389 |
| SEQ4/ 37501 | SEQ 127 | 30 | CCAGGCTGACTCAACCGCTG | 54 | CAGCGGTTGAGTCAGCCTGG | 368-385 |
| 37502 | SEQ 128 | 31 | CTCAACCGCTGTCCCCAGCA | 55 | TGCTGGGGACAGCGGTTGAG | 357-374 |
| 47001 | SEQ 8 | 32 | CAGAAGCGCACATGAGAGAT | 56 | ATCTCTCATGTGCGCTTCTG | 464-483 |
| 47002 | SEQ 11 | 33 | GAAGCGCACATGAGAGATTG | 57 | CAATCTCTCATGTGCGCTTC | 462-481 |
| 50501 | SEQ 129 | 34 | AGTGTGGGTACAGACACAAA | 58 | TTTGTGTCTGTACCCACACT | 500-519 |
| 50502 | SEQ 130 | 35 | TGGGTACAGACACAAATATG | 59 | CATATTTGTGTCTGTACCCA | 496-515 |

TABLE 57-continued

| ASN code name | SEQ IDENTIFIER-NOT A SEQ ID NO. | SEQ ID NO: | ASN sequence | SEQ ID NO: | Sense sequence (target) | ASN target site from 5' end |
|---|---|---|---|---|---|---|
| 50503 | SEQ 131 | 36 | GGTACAGACACAAATATGAT | 60 | ATCATATTTGTGTCTGTACC | 494-513 |
| LP3 | SEQ 12 | 37 | CAGACACAAATATGATCTGC | 61 | GCAGATCATATTTGTGTCTG | 490-509 |
| 50504 | SEQ 132 | 38 | GACACAAATATGATCTGCAG | 62 | CTGCAGATCATATTTGTGTC | 488-507 |
| 50505 | SEQ 133 | 39 | ACAAATATGATCTGCAGGAC | 63 | GTCCTGCAGATCATATTTGT | 485-504 |
| 50506 | SEQ 9 | 40 | ATATGATCTGCAGGACCCAG | 64 | CTGGGTCCTGCAGATCATAT | 481-500 |
| 87201 | SEQ 134 | 41 | ATGATGAAGATGGTTTTCTC | 65 | GAGAAAACCATCTTCATCAT | 863-882 |
| 87202 | SEQ 135 | 42 | ATGAAGATGATGAAGATGGT | 66 | ACCATCTTCATCATCTTCAT | 869-888 |
| 87203 | SEQ 136 | 43 | AGCATGAAGATGATGAAGAT | 67 | ATCTTCATCATCTTCATGCT | 872-891 |
| 87204 | SEQ 137 | 44 | ATGAAGATGGTTTTCTCCGT | 68 | ACGGAGAAAACCATCTTCAT | 860-879 |
| 1233 | SEQ 7 | 45 | AGGCTGTGCATGGGAGTTAG | 69 | CTAACTCCCATGCACAGCCT | 1233-1252 |
| 133704 | SEQ 6 | 46 | CGCTGGTCCACAATGGCTAG | 70 | CTAGCCATTGTGGACCAGCG | 1316-1335 |
| 133705 | SEQ 5 | 47 | GCTGGCTCTGCTTGAAGGTC | 71 | GACCTTCAAGCAGAGCCAGC | 1335-1354 |

A subset of ASN was then chosen to take forward for further analysis. Other ASN were excluded from this based on showing lower levels of knockdown in preliminary cell screening assays, and/or if high cross-reactivity was detected by sequence alignments with other known human genes.

TABLE 58

List of ASN subset used in further analysis due to promising profile

| ASN code name | SEQ ID NO. for ASN sequence | ASN sequence | ASN target site from 5' end |
|---|---|---|---|
| 24501 | SEQ ID NO.: 5 | ACCCATGTTGCCTGG GCACC | 237-256 |
| 30004 | SEQ ID NO.: 6 | GTAGGCTTGAACCTT GTCAA | 281-300 |
| 37503 | SEQ ID NO.: 7 | TCTCCCCAGGCTGAC TCAAC | 372-389 |
| LP2/ 37501 | SEQ ID NO.: 4 | CCAGGCTGACTCAAC CGCTG | 368-385 |
| 47001 | SEQ ID NO.: 8 | CAGAAGCGCACATGA GAGAT | 464-483 |
| 47002 | SEQ ID NO.: 9 | GAAGCGCACATGAGA GATTG | 462-481 |
| 50501 | SEQ ID NO.: 10 | AGTGTGGGTACAGAC ACAAA | 500-519 |
| LP3 | SEQ ID NO.: 11 | CAGACACAAATATGA TCTGC | 490-509 |
| 50506 | SEQ ID NO.: 12 | ATATGATCTGCAGGA CCCAG | 481-500 |
| 112304 | SEQ ID NO.: 13 | GTAATTGCGGCAAGA AGAAT | 1134-1153 |

TABLE 58-continued

List of ASN subset used in further analysis due to promising profile

| ASN code name | SEQ ID NO. for ASN sequence | ASN sequence | ASN target site from 5' end |
|---|---|---|---|
| 1233 | SEQ ID NO.: 14 | AGGCTGTGCATGGGA GTTAG | 1233-1252 |
| 133704 | SEQ ID NO.: 15 | CGCTGGTCCACAATG GCTAG | 1316-1335 |
| 133705 | SEQ ID NO.: 16 | GCTGGCTCTGCTTGA AGGTC | 1335-1354 |

Figure 31:
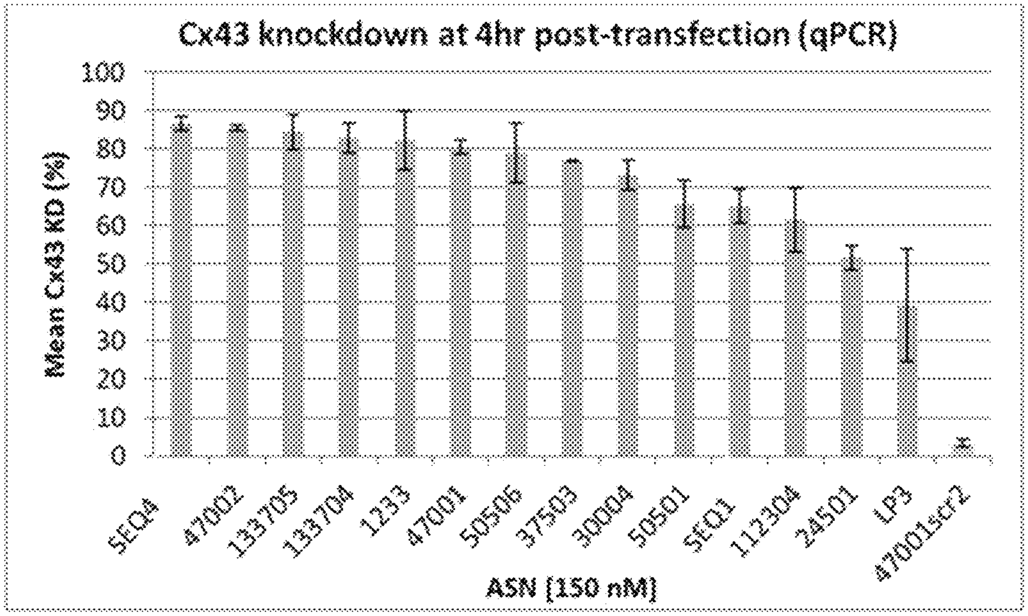
FIG. 31 Comparative Knockdown activity of the ASN from Table 4 at 4 hr post-transfection.
Figure 32:
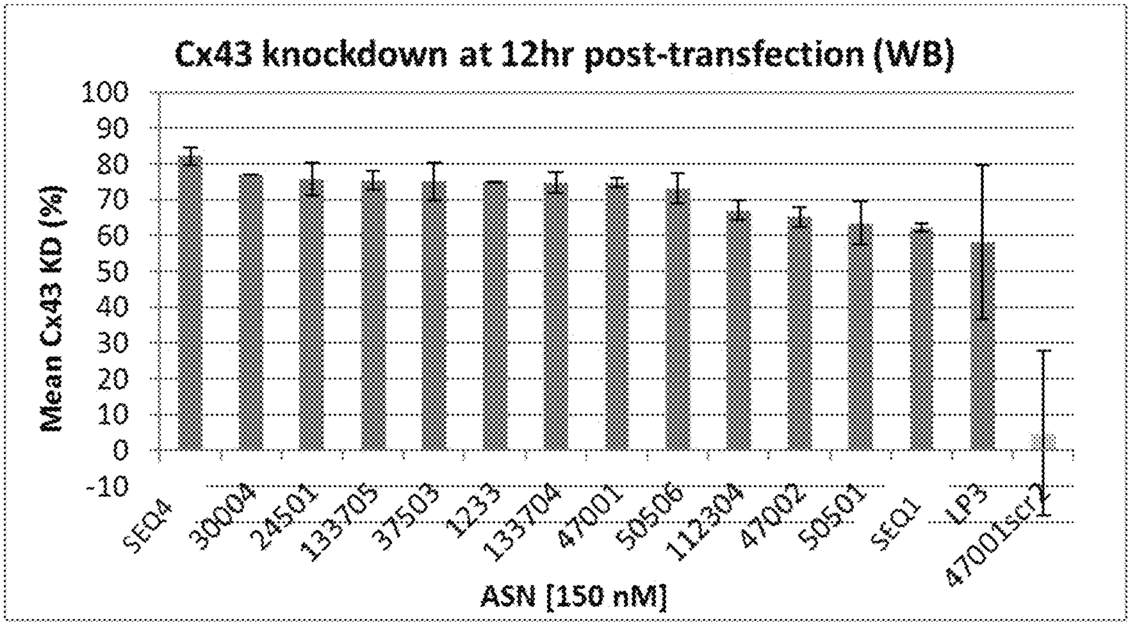
FIG. 32. Comparative Knockdown activity of the ASN from Table 4 at 12 hr post-transfection.

The relative RNA knockdown activities of the antisense oligonucleotides (ASN) are shown in FIG. 31. The relative protein knockdown activities obtained from Western Blot analysis of the antisense oligonucleotides are shown in FIG. 32. The results are from two replicate experiments in HUVEC cells. (n=2) The yellow bar ("47001scr2") indicates the activity of the negative control oligonucleotide. The results indicate that other ASNs are highly efficient at regulating Cxn43 activity.

The cell screening experiments were performed using HUVEC cells (human umbilical vein endothelial cells; Invitrogen), with two biological replicates in each experiment. The identifiers of "CODA" are SEQ1, and "LP2" are SEQ4.

The following top ASN candidates were selected from those that gave a percentage knockdown within the top 10% detected in both the qPCR and Western blot analyses, as shown in Table 61.

TABLE 61

| Current top ASN candidates for Cxn43 Knockdown in HUVEC | | |
|---|---|---|
| Sample | Avg % KD qPCR | WB |
| SEQ4/37501 | 87 | 82 |
| SEQ 5/133705 | 84 | 75 |
| SEQ6/133705 | 83 | 75 |
| SEQ7/1233 | 82 | 75 |
| SEQ8/47001 | 81 | 75 |
| SEQ9/50506 | 79 | 73 |
| SEQ10/37503 | 77 | 75 |

Figure 33:
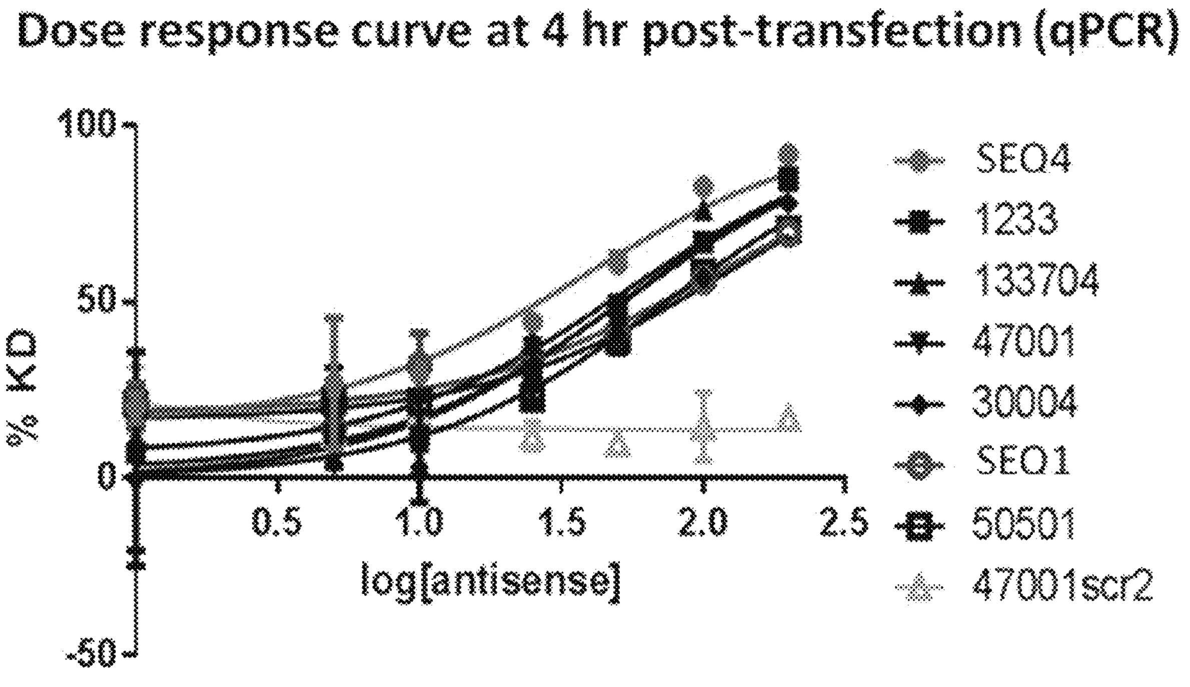
FIG. 33. Dose-response curves for candidate Connexin 43 antisense oligonucleotides.

FIG. 33 shows a dose response curve of some selected ASNs to induce the knockdown of Cxn43 RNA at 4 hrs after administration to cells. The screening results are from one experiment in HUVEC cells. (n=2 biological replicates). The grey line ("47001scr2") indicates the negative control oligonucleotide. The ASN concentrations were: 1, 5, 10, 25, 50, 100, and 200 nM. The term "% KD" is the percentage of knockdown in Cxn43 RNA levels. The indicator "Coda" is CoDa001 human connexin 43 ASN in clinical development; the indicator "scr2" is a scrambled ASN control which is not expected to have Cxn43 Knockdown activity.

Example 13. Use of Connexin 43 Modulating Peptide to Prevent Vascular Leak after Ischemia Reperfusion Injury A connexin 43 (Cxn43) modulating peptide was used to control the increase in ocular pressure of models induced with ischemia perfusion. The peptide sequence used was SEQ-pept5 (SEQ ID NO: 168), at a dosage described below. Mice were subjected to ischemia perfusion, then treated with Evans Blue Dye via intraperitoneal injection to monitor the baseline of the model. 100 mg/ml of Evans Blue in 0.9% saline solution was introduced into the mice, with 1 ml/100 g body weight dosage. The injections were performed intraperitoneally. The amount of dye leak was measured, as was the connexin 43 spot count, following ischemia-reperfusion. FIG. 34 shows the dye perfusion of Evans Blue Dye post-ischemia to map the connexin 43 following ischemia-reperfusion.

Figure 35A:
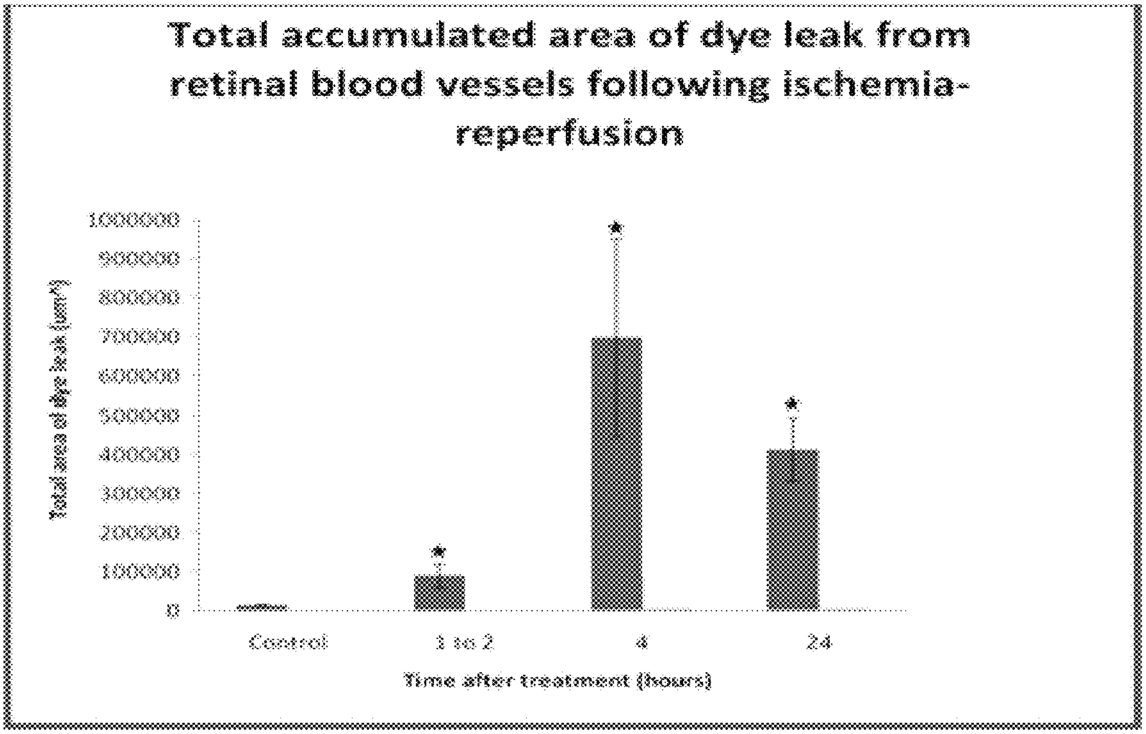
FIG. 35A-FIG. 35B. The calculated (via ImageJ, as described herein) area of dye leak (FIG. 35A) or Connexin 43 spot count (FIG. 35B) as a function of time following ischemia-reperfusion. The results show the baseline performance of dye leakage.
Figure 35B:
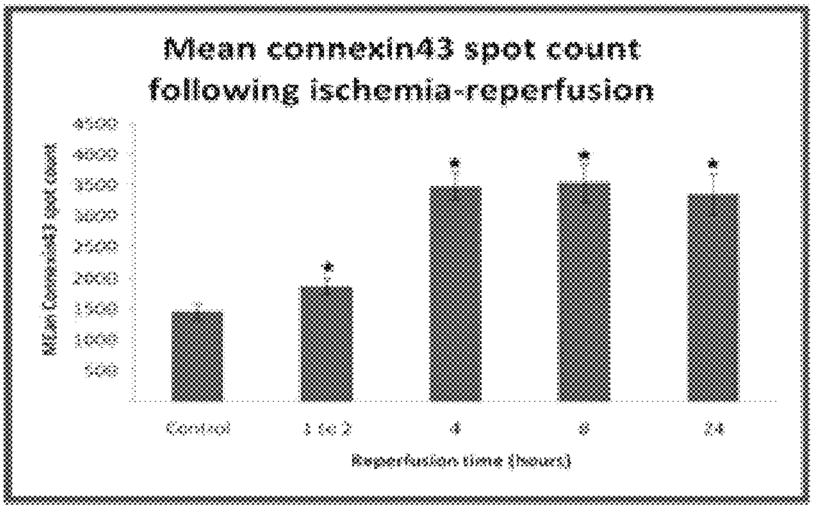

FIG. 35 shows the calculated (via ImageJ, as described herein) area of dye leak or Connexin 43 spot count as a function of time following ischemia-reperfusion. The results show the baseline performance of dye leakage.

Figure 36:
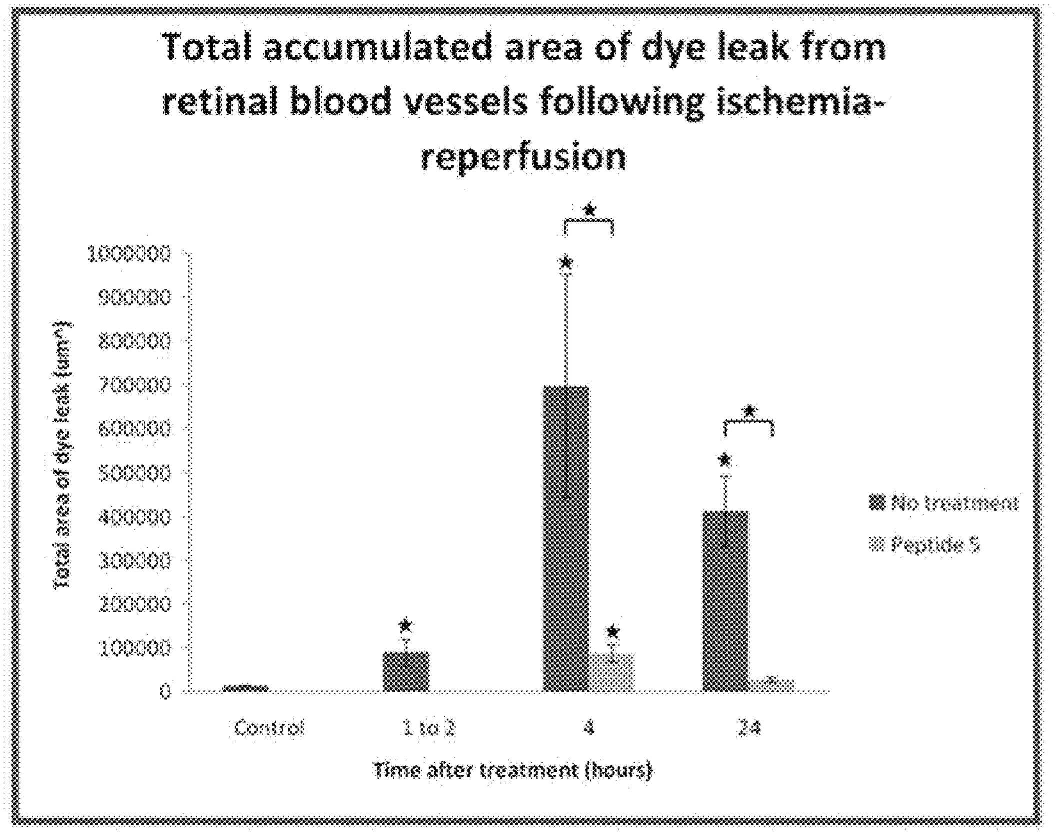
FIG. 36. The effects on the total dye leak following treatment with, and without, the Cxn43 modulating agent.

The treatment of the ischemia-reperfusion model was analyzed to determine the effect of treatment with an connexin 43 modulator. FIG. 36 shows the effects on the total dye leak following treatment with, and without, the Cxn43 modulating agent. The Cxn43 modulating agent used in this study was SEQ ID NO: 168 ("Peptide 5"). The injection was intraperitoneal injection. 1 mL of a 2 mM Cxn43 modulator peptide was used as a 0.9% saline solution. The final blood peptide concentration was 100 μM.

Figure 37:
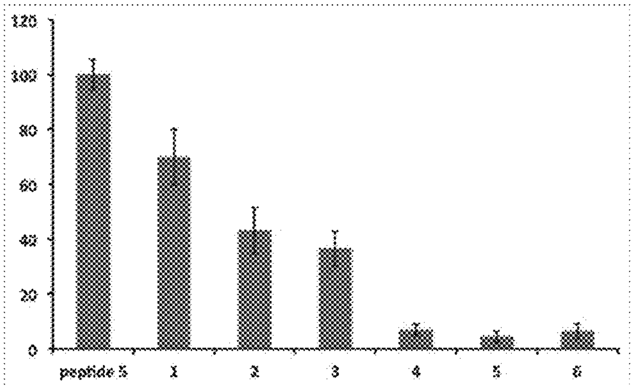
FIG. 37. The ability to retard the expression of Cxn43 (Y-axis) compared for variants of a particular core sequence. Peptide 5=SEQ ID NO: 168, Mod 1=SEQ ID NO: 171, Mod 2=SEQ ID NO: 172, Mod 3=SEQ ID NO: 173, Mod 4=SEQ ID NO: 174, Mod 5=SEQ ID NO: 175, Mod 6=SEQ ID NO: 176.

The peptide fragment efficiency was also monitored for a range of sequence variations on a common peptide sequence core. As shown in FIG. 37, the ability to retard the expression of Cxn43 (Y-axis) was compared for variants of a particular core sequence. The results indicated that the sequence must retain a KT at the carboxy terminus to retain activity in retarding Cxn43 activity. The peptides were administered at a concentration of 100 μM.

The sequences in FIG. 37 are: Peptide 5=SEQ ID NO: 168, Mod 1=SEQ ID NO: 171, Mod 2=SEQ ID NO: 172, Mod 3=SEQ ID NO: 173, Mod 4=SEQ ID NO: 174, Mod 5=SEQ ID NO: 175, Mod 6=SEQ ID NO: 176.

Example 14: Nanoparticle (Nps) and Microparticle (MPs) Preparation and Analysis Particle Preparation Water-oil-water (double) emulsion is one method by which PLGA can be used to encapsulate hydrophobic and hydrophilic drugs in micro- or nano-scale form. Briefly, PLGA (Poly(D,L-lactic-co-glycolic acid) (PLGA 50:50, MW 13,600, inherent viscosity 0.19 dl/g, Sigma-Aldrich) was dissolved into an organic phase (oil) that is emulsified with a surfactant or stabilizer (water). The hydrophobic forms of the connexin 43 modulator were added directly to the oil phase, whereas hydrophilic forms of the connexin 43 modulator may be first emulsified with the polymer solution prior to formation of particles. High intensity sonication bursts facilitated the formation of small polymer droplets. The resulting emulsion was then added to a larger aqueous phase and stirred for several hours, which allowed the solvent to evaporate. Hardened nanoparticles were collected and washed by centrifugation.

Preparation and characterisation of PLGA Nps and Mps PLGA Nps and Mps containing Cxn43 modulators were performed using the double emulsion solvent evaporation method (Y.-S. Chen, et al., Drug Deliv. 18 (2011) 493-50). Briefly, for Nps, 5 mM of Cxn43 MP (plain or FITC-labelled) aqueous solution was emulsified in DCM (dichloromethane, Sigma-Aldrich) containing 30 mg/ml of PLGA using a probe sonicator (Hielscher, Teltow, Germany) at an amplitude of 50 W and a duty cycle of 0.6 s for 1 min on an ice bath to form the primary w/o emulsion. The resulting primary w/o emulsion was further emulsified in an aqueous solution of 3% w/v PVA (polyvinyl alcohol (PVA, MW 130,000, hydrolysis degree 95-97%, Sigma-Aldrich) to form a multiple w/o/w emulsion. This was subsequently poured into 50 ml of an aqueous PVA solution (0.1% w/v) to stabilise the double emulsion during the evaporation process with the resultant Nps recovered by ultracentrifugation (ProteomeLab™ XL-A/XL-I; Type 70 Ti rotor, Beckman Coulter, Auckland, New Zealand) at 30,000 rpm at 4° C. For Mps, 10 mM of Cxn43 MP aqueous solution was emulsified in DCM containing 100 mg/ml of PLGA. The formed primary w/o emulsion was further emulsified in a PVA solution (5% w/v) and then homogenised at 8000 rpm for 5 min (IKA works, Ultra-Turrax T10, Wilmington, USA) before pouring it into 50 ml of a 0.1% w/v PVA solution and evaporating the organic phase at room temperature.

Nps and Mps were then lyophilised (VirTis, SP Scientific, Gardiner, N.Y., USA) for 24 h and the particle morphology was investigated using scanning electron microscopy (SEM) (Philips XL30S FEG, Eindhoven, Netherlands), while the particle size, zeta potential (ZP) and polydispersity index (PDI) were determined using a Zetasizer Nano and Mastersizer (Malvern Instruments, Worcestershire, UK), respectively.

Entrapment Efficiency and In Vitro Cxn43 MP Release from PLGA Nps and Mps

A 2.5 mg mass of FITC-labelled Cxn43 MP-loaded Nps and Mps was added to 0.25 ml of DMSO to allow for polymer dissolution. Subsequently, 0.5 ml of water was added and the mixture was allowed to stand for 15 min at room temperature before shaking for 30 min to facilitate extraction of FITC-labelled Cxn43 MP into the aqueous phase. Samples were centrifuged at 13,000 rpm and 4° C. for 5 min and Cxn43 MP concentrations in the supernatant were quantified using a microplate reader (Spectra Max M2 Microplate Reader, Molecular Devices, Silicon Valley, Calif., USA). For in vitro release studies, 15 mg of FITC-labelled Cxn43 MP-loaded Nps and Mps was suspended in 0.7 ml of PBS and shaken at 100 rpm and 37° C. over the period of the release experiment. A volume of 0.6 ml of supernatant was withdrawn at pre-determined time points and replaced with fresh medium to maintain sink conditions. Samples were centrifuged at 13,000 rpm and the supernatant was assayed for FITC-labelled Cxn43 MP using a fluorometer as described above. Cumulative amounts of Cxn43 MP released were calculated, with each study performed in triplicate.

In Vitro Block of Cxn43 Hemichannel Docking

ARPE-19 cells (P9-12, American Type Culture Collection (ATCC, Manassas, Va., USA) were initially assessed for the expression of Cxn43 protein. Cells were routinely cultured in DMEM/F12 (Gibco, NZ) containing 10% FCS at 37° C. with 5% CO2 and 95% relative humidity. Upon confluence, cells were harvested with TrypLE™ Express and seeded onto coverslips at a density of 1×105 cells/ml per well. After 48 h of adhesion, each well was washed with PBS three times, followed by addition of 1 ml of FITC-Cxn43 MP solution or FITC-Cxn43 MP loaded Mps and Nps suspensions, which were freshly prepared by mixing the freeze-dried particles with cell growth medium, with the final Cxn43 MP concentration kept at 5 micromolar (according to the previously confirmed entrapment efficiencies). At pre-determined time points (8 and 24 h), suspensions were removed and cells were carefully washed with PBS three times to remove any residual particles. Cells were fixed with 4% cold PFA at room temperature for 20 min before incubation with a rabbit anti-Cxn43 antibody (C6219, Sigma Aldrich, 1:2000) at 4° C. overnight. After removing the primary antibody, cells were incubated with a goat anti-rabbit secondary antibody labelled with Alexa 568 (A11011, Invitrogen, 1:500) for 2 h. Nuclei were counterstained with DAPI (4',6-diamidino-2-phenylindole, 100 nM in PBS) before mounting cells onto slides using Citifluor mounting medium (AF1, ProSciTech, Sydney, Australia).

In Vivo Retinal Ischaemia-Reperfusion Rat Model

All procedures were compliant with the ARVO Statement of the Use of Animals in Ophthalmic and Vision Research and were approved by the University of Auckland Animal Ethics Committee. Adult male Wistar rats weighing 200-300 g were housed under a 12-h light/dark cycle and received food and water ad libitum. Animals were grouped according to housing time periods after reperfusion and formulations applied (Table 109).

TABLE 109

Cxn43MP, connexin43 mimetic peptide; Nps, nanoparticles; Mps, microparticles; GFAP, glial fibrillary acidic protein; Brn3a, brain-specific homeobox/POU domain protein 3A.

| | Number of animals (one eye per animal for each time period of housing post-ischemia and intravitreal injection | |
|---|---|---|
| Study Arm | 28 d | 90 d |
| Control (no ischaemia) | — | — |
| 1 h Ischaemia + Saline injection (vehicle control) | 3 (GFAP & Cxn43) + 6 (Brn3a) | — |
| 1 h Ischaemia + Cxn43 MP solution | 3 (GFAP & Cxn43) + 6 (Brn3a) | — |
| 1 h Ischaemia + Cxn43 MP loaded PLGA Nps | 3 (GFAP & Cxn43) + 6 (Brn3a) | — |
| 1 h Ischaemia + Cxn43 MP loaded PLGA Mps | 3 (GFAP & Cxn43) + 6 (Brn3a) | 3 (GFAP & Cxn43) + 6 (Brn3a) |

Rats were anaesthetised with an intramuscular injection (0.1 ml/100 g body weight) of Ketamine (100 mg/ml; Parnell Laboratories, Auckland, New Zealand) and Domitor (metadomidine hydrochloride 1 mg/ml; Novartis Animal Health, Sydney, Australia) with a ratio of 6:4. A topical anaesthetic (Minims oxybuprocaine hydrochloride 0.4% w/v; Bausch & Lomb, Surrey, UK) was applied to the left eye to remove the corneal reflex prior to cannulation, while Refresh Tear Plus eye drops (Allergan, Auckland, New Zealand) were administered to the right eye (control) to prevent it from drying. Retinal ischaemia was achieved by cannulating the anterior chamber with a 30 G needle inserted into the anterior chamber of the left eye approximately 1 mm anterior to the limbus. The needle connected to silicone tubing was attached to an elevated infusion line of sterile 0.9% saline, with the height of the saline bag calibrated to produce 120 mmHg. This state was maintained for 1 h followed by removal of the cannula, causing normalisation of the IOP and reperfusion of the retina. If any ocular complications such as lens damage or excessive haemorrhage occurred as a result of the procedure the animal was excluded from the study.

Intravitreal Injection of Cxn43 MP Formulations

Intravitreal injection was performed immediately following ischaemia-reperfusion. A Hamilton syringe (Model 701 LT SYR, Hamilton Company, Reno, Nev., USA) with a 30 G needle was inserted posterior to the limbus in the superior retina at a 450 angle to avoid contact with the lens capsule and to direct the contents into the vitreous chamber. Each rat received 2 μl of 580 micromolar Cxn43 MP diluted in 0.9% saline. A final peptide concentration of 20 micromolar was intended, assuming a vitreous volume of 50 al. A volume of 0.1 ml/100 g body weight of Antisedan (atipamezole 5 mg/mL, Pfizer, Auckland, New Zealand) in saline (1:9) was then injected subcutaneously to allow the animal to recover.

Cxn43 and GFAP Labelling in Retinal Cross-Sections

After 28 d of reperfusion, rats were euthanized with CO2 and eyes were enucleated (n=3 for each group). Eyes were immediately fixed by submersion in 4% PFA for 30 min, followed by overnight cryoprotection with gradually increasing sucrose from 10% to 30%. Eyes were then embedded in optimal cutting temperature (OCT) compound (ProSciTech, Sydney, Australia) and snap frozen with liquid nitrogen. Sections of 20 micrometer thickness were mounted onto slides and were further fixed in 20° C. ethanol for 10 min before incubation with blocking buffer (10% normal goat serum (Gibco, NZ) and 0.1% Triton X-100 in PBS) for 1 h at room temperature. A rabbit anti-Cxn43 (C6219, Sigma Aldrich, 1:2000) and mouse anti-GFAP conjugated to Cy3

(C9205, Sigma Aldrich, 1:1000) primary antibody in 10% normal goat serum and 2% Triton X-100 were applied overnight at 4° C. Tissues were washed with PBS three times for 15 min. A goat antirabbit Alexa488 secondary antibody (A11034, Invitrogen, 1:1000) in 10% normal goat serum to visualise Cxn43 was applied for 2 h in the dark at room temperature before mounting the sections.

RGC Labelling in Retinal Wholemounts

After 28 and 90 d of reperfusion, rats were euthanised with CO2 and eyes were enucleated (n=6 per group). The posterior segment of the eye was carefully removed after cutting along the cornealscleral limbus junction and the retina, sclera and optic nerve were fixed in 4% PFA in 0.01 M PBS for 1 h. A small cut was inserted to mark the superior quadrant and four radial cuts were made around the circumference to divide the superior, inferior, temporal, and nasal retinal quadrants and allow flat mounting. The optic nerve and sclera were then gently detached and the free retina was flattened onto slides carefully. Surviving RGC were labelled by applying a goat anti-Brn3a primary antibody (SC-31984, Santa-Cruz Biotechnology, 1:100) in 2% horse serum (Gibco, Auckland, New Zealand) and 2% Triton X-100 in PBS at 4° C. overnight. Tissues were washed with PBS three times for 15 min, before a donkey anti-goat Cy3-tagged secondary antibody (705-165-147, Jackson Immuno Research, 1:500) in 2% horse serum was applied for 2 h at room temperature in the dark. After further washing with PBS, retinas were flat-mounted and stored at 4° C. until imaged.

Confocal Microscopy and Image Analysis

Immunolabelling was imaged with a confocal laser scanning microscope (FV1000, Olympus, Tokyo, Japan). For Cxn43 and GFAP labelling in retinal cross-sections eight images were taken per sample with six sections used per eye. For RGC labelling in retinal whole mounts, two fields per quadrant of each retina were imaged with six retinas used per group. This method insured that similar regions were assessed in each eye and avoided any possible area prejudice. Gain (voltage) and offset settings were adjusted to best discriminate individual labelling and to avoid oversaturation of the image. Quantification was performed using automated spot counts in ImageJ. For Cxn43 quantification in cross-sections, each image was converted to a binary image using a threshold of 45. Spots fewer than three pixels were considered as noise and not counted. For RGC quantification in wholemounts each image was converted to a binary image using a threshold of 23. To separate clusters the watershed algorithm was applied. Spots of fewer than 20 pixels were considered noise and were excluded from particle counts.

Statistical Analysis

Results were expressed as mean values with a standard deviation (SD). Analysis of variance (one-way ANOVA) with Tukey-Kramer comparison was used to test for significant differences ($p<0.05$) between groups. All data analysis was carried out using Minitab #Statistical Software Version 15 (Minitab Inc., State College, Pa., USA).

Characterisation of PLGA Nps and Mps

Using the double emulsion and solvent evaporation method, Cxn43 MP loaded PLGA Nps and Mps of desirable sizes with narrow size distribution were obtained (FIG. 110). FIG. 110 shows the morphology of the freeze-dried Nps (A) and Mps (B) immediately after preparation as well as the change in surface morphology and porosity after three days in release media (D (Nps) and C (Mps), respectively). As demonstrated, both Nps and Mps exhibited spherical structures and a relatively smooth and even surface morphology after preparation (FIGS. 110A and B). Although the formation of some agglomerates was observed, no free drug crystals were present, indicating complete loading of Cxn43 MP into the PLGA matrix. After three days in release media, Mps exhibited slight pore formation on the particle surface (FIG. 1C) while Nps were almost completely eroded with mainly particle capsules remaining (FIG. 1D).

The particle size was mainly influenced by the PLGA concentration. The higher the PLGA concentration used, the higher the mean diameter obtained as seen by the larger sized Mps. This is most likely due to the greater probability of smaller polymer aggregates coalescing in a more concentrated solution, hence leading to larger droplets. Moreover, the higher shear forces necessary during the emulsification process due to the increasing viscosity of the organic phase may have resulted in poorer dispersability of the PLGA solution into the aqueous phase.

The mean ZP (zeta potential) of Nps was −31.3±0.94 mV and since Cxn43 MP is neutral at pH 7.4 the negative charge was attributed to PLGA. The ZP is an important physicochemical characteristic as it influences both particle stability and mucoadhesion. Highly positive or negative ZP values cause repulsion between particles and therefore prevent aggregation and thus in theory tend to stabilise particle suspensions. The ocular vitreous is composed of more than 98% water, with collagen and hyaluronan molecules comprising the two main solid components. Anionic particles may diffuse freely through the vitreous via electrostatic repulsion between the particles and the negatively charged vitreous meshwork if their sizes are small enough to avoid sterical trapping. The mesh pore size of bovine vitreous has been shown to be between 1 and 2 μm (L. Cheng, et al., J. Neurosci. 22 (2002) 3977-3986). Therefore, Nps will freely diffuse through the vitreous towards the retina, while Mps may get trapped in the meshwork due to their larger size.

Entrapment Efficiency and In Vitro Cxn43 MP Release from PLGA Nps and Mps

The entrapment efficiencies (EE) of FITC-labelled Cxn43 MP loaded PLGA Nps and Mps are listed in FIG. 110. The reproducibility of the method was good, as indicated by the loading amount and entrapment efficiency calculations were carried out on three batches per group prepared under identical conditions. High yields (≥90%) were obtained for both particles, with Cxn43 MP EE being higher for the larger Mps (≥97%) compared to the much smaller Nps (≥70%), with an almost complete peptide encapsulation obtained for Mps. The relatively high concentration of PLGA used for Mps contributed to the high EE by lowering the diffusivity of the active into the external water phase during processing.

Particle Sizing Analysis

Figure 38E:
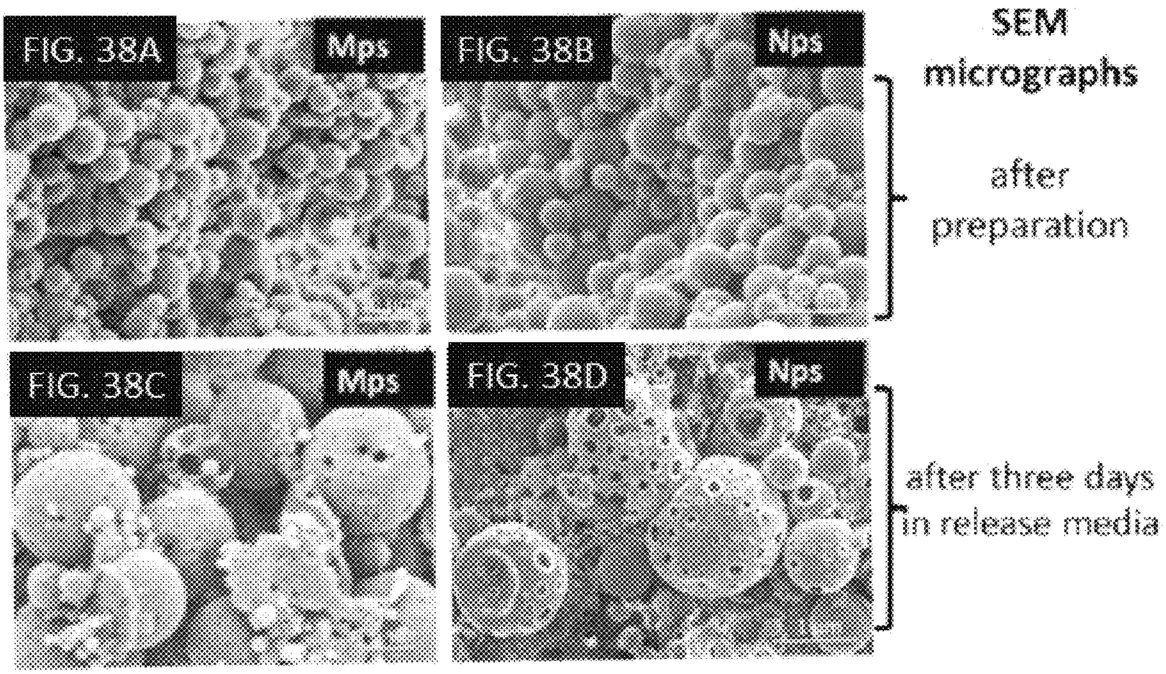

Samples for Scanning Electron Microscopy (SEM) were prepared the day of imaging. A strip of double-sided carbon tape was affixed to a SEM stub. A small quantity of lyophilized particles were applied to the surface of the tape, and the tape surface was gently subject to flowing nitrogen to remove loose particles. The sample was then sputter coated with gold or gold-paladium for 30-120 seconds. The SEM stub was then placed in the SEM for analysis. Typical parameters for visualizing particles were a working distance of 5-15 mm, beam strength of 5-12 kV, and a spot size of 1-3 microns. Microparticles were observed at 100× magnification and nanoparticles were distinguishable at 3,000× magnification. At least three images were collected per batch in order to obtain a representative sample of particle size and morphology. Measurements were taken directly from the SEM images using the "measure" function in ImageJ. A minimum of 150 measurements of the diameter of particles selected randomly from the field of view were taken to acquire a representative size distribution. Representative images of the microparticles and nanoparticles are shown in FIG. 38.

Other methods may be employed to measure the particle size, including but not limited to light scattering, zeta potential analysis, coulter counting (electrical sensing zone method), and optical microscopy.

Example 15. Use of Microparticles and Nanoparticles for Extended Release Formulations of Connexin Modulators Microparticles and nanoparticles were loaded with the chemically modified C12-C12-SEQ-Pept5 connexin 43 modulator peptide (SEQ ID NO:237) via a method similar to that described above. To obtain a representative image of the particles after release media, an aliquot of each particle type was added to 1×PBS buffer for three days. The particles were collected via a method similar to that described above, and imaged post-release. The images are shown in FIG. 110 above. The particle size analysis (as determined by the method described above, using ImageJ particle sizing of multiple SEM images) are given in the bottom of FIG. 38 for the as-made particles (which were not yet subject to the release media).

Figure 39:
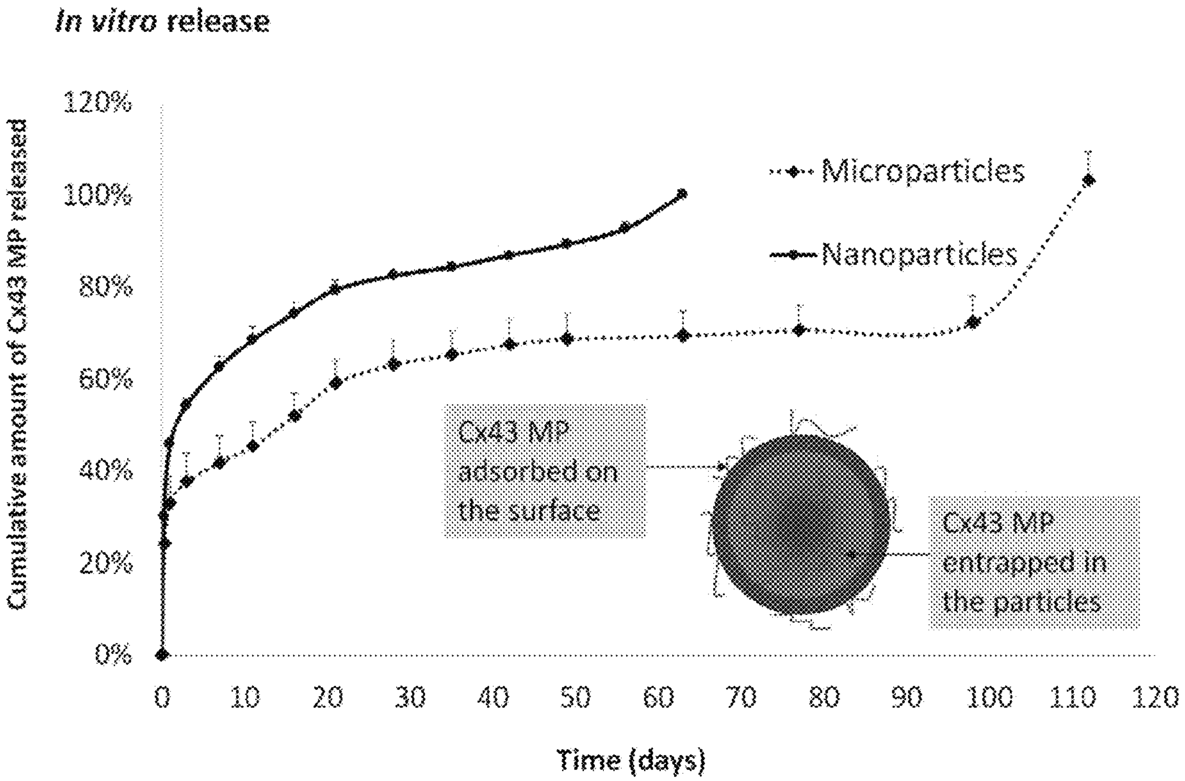
FIG. 39. In vitro release study of connexin 43 modulator from particulate formulations (data points represent mean values±SD, n=3).

In vitro release of the connexin 43 modulator from the particles was monitored by UV-Vis of the solution over the particles. Particles were added to the release media, 1×PBS buffer, and aliquots of the buffer solution were monitored by UV-Vis to determine the amount of peptide released. The results are shown in FIG. 39.

The in vitro release results indicate that the particulate formulations exhibit a sustained release of the connexin 43 modulator over time. The initial burst of modulator released is likely due to the modulator physiadsorbed to the particle surface, whereas the sustained release of the modulator is likely due to the diffusion of the modulator from the core of the particles. The particle size is hereby an important parameter, with the Mps exhibiting a relatively small initial burst compared to Nps due to the decrease in surface area to volume ratio with increased particle size. This resulted in reduced surface area available for the medium to penetrate into the particles and erode the polymer and therefore slowed down the release rate of Cxn43 MP.

Example 16. Use of Chemically Modified Peptides and Particulate Sustained Release Formulations to Treat Glaucoma-Modelled Oculae The effects of chemical modification and particulate formulation delivery were measured on rats modelled for glaucoma with a retinal ischemia reperfusion. First, a retinal ischemia reperfusion model was created. A total of 121 adult male Wistar rats weighing 200 to 300 g were used for the study. Retinal ischemia was modeled in the left eye (120 mmHg for 60 min), with the right eye as the control, and then the connexin 43 modulator peptide formulations were injected intravitreally immediately as solutions in 1×PBS delivery agent. The connexin 43 modulator peptide used was SEQ-Pept5, in both its unmodified and chemically modified (didodecyl) forms. The formulations used were neat (just diluted in 1×PBS delivery media) solutions of nanoparticles or microparticles. After reperfusion, Evan's blue dye was injected intraperitoneally 4 hr after reperfusion to visualize vessel leak using confocal microscopy. Retinal whole mounts were collected at 8 hr and 28 days for Cxn43 quantitification, and 28 and 90 days for gangliol cell (RGC) density quantification.

The results as shown in FIG. 40 indicate that the vessel leak after 4 hr post-ischemia was significantly reduced in the retina for the eyes treated with any of the connexin 43 modulators tested. The results also indicated a reduction in vessel leak for the chemically modified (didodecyl) form of SEQ-Pept5 (C12-C12 Cxn43 MP) (SEQ ID NO: 237) compared to the unmodified peptide (Cxn43 MP) (SEQ-Pept5, SEQ ID NO: 168).

Spot counts were measured for models treated with both forms of the connexin 43 modulator peptide. As shown in FIG. 41, the results indicated that spot counts were reduced moreso with the chemically modified (C12-C12 Cxn43 MP) connexin 43 modulator peptide than the unmodified peptide. The lowest spot count was observed at just 8 hr after ischemia.

After 28 days post-ischemia, cross-sections of the tissues were observed by confocal microscopy and the mean Cxn43 count was measured for Evan's Blue dye-stained samples. The results, as shown in FIG. 42, indicate that the formulations involving nanoparticles for the delivery resulted in lower Cxn43 expression than formulations without the nanoparticles, or even formulations with the microparticles. Also, over the extended duration, both of the particulate formulations yielded a reduction in Cxn43 expression compared to the initial ischemia timepoint.

Retinal ganglion cell count was also monitored for the models treated with the formulations involving nanoparticles, microparticles, or neat, and with the unmodified and chemically modified peptide. The results, as shown in FIG. 43, show that the chemically modified peptide treatment resulted in over 93% RGC survival after 28 days compare to less than 70% for untreated eyes (ischemia only).

Example 17. Connexin 43 is Upregulated in the Retina of Humans Diagnosed with AMD Impairment of choridal perfusion and/or choroidal inflammation, or choroidal overperfusion induces vascular leak in the choroid and Bruch's membrane and results in endothelial cell loss in the retinal pigment epithelium. Impairment of choridal perfusion and/or choroidal inflammation, or choroidal overperfusion and choriocapillaris dropout results from connexin 43 upregulation, and connexin 43 upregulation may be a contributing cause of AMD. Abnormal vasculature was observed in the choroid of AMD organ donor retinae associated with changes in Cxn43 expression, supporting the role of connexin 43 upregulation in AMD. This indicates that Retinal Pigment Epithelium degeneration and Drusen development are potentially downstream consequences of AMD, rather than primary causes of AMD. Alterations in choroidal blood flow and impairment of choridal perfusion and/or choroidal inflammation, or choroidal overperfusion are merely contributory factors to AMD. Vascular leak and inflammation are associated with AMD choroidal changes which are then subsequently associated with retinal neovascularisation.

Figure 44A:
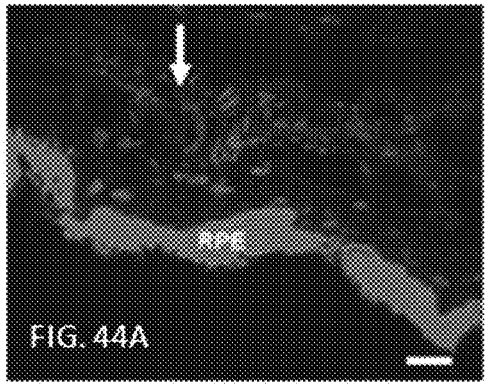
FIG. 44A-FIG. 44B. Representative images of stained tissues indicating Cxn43 distribution located within the choroid of a young (29 year old) donor without AMD (FIG. 44A), and an elderly donor diagnosed with AMD (FIG. 44B). In the young donor the Cxn43 labeling (red, under the "RPE" label) is especially dense adjacent to Bruch's membrane, and the label primarily demarcates gap junctions between endothelial cells (white arrow). The elongated nuclei stained with the nuclear marker DAPI are endothelial cell nuclei. Scale bars represent 20 μm.
Figure 44B:
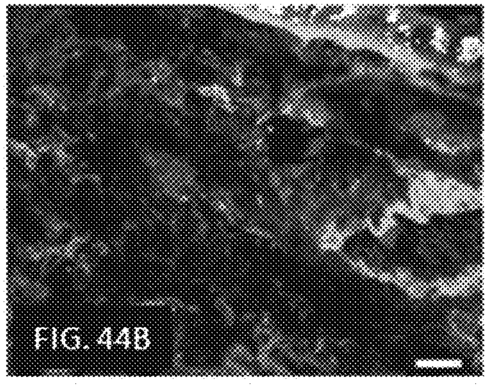

As shown in FIG. 44, connexin 43 expression as observed in stained samples of human donors with AMD was upregulated in multiple areas of the choroid, retinal pigment epithelium, and associated areas adjacent to the Bruch's membrane. As observed in FIG. 44 Panel A, a non-AMD donor had Cxn43 expression confined to the retinal pigmental epithelium. There was significant Cxn43 label in the retinal pigmental epithelium but this was masked by autofluorescence of the pigment itself. As observed in FIG. 44 Panel B, in the AMD diagnosed donor, extensive Cxn43 label was observed outside of blood vessels (within the extracellular matrix). This type of label is associated with extracellular matrix fibroblasts and inflammatory cell clusters, which was evident within areas of denser connective tissue deposition.

The inventors have made the surprising development that regulation of Cxn43 in the retina is a potential treatment for AMD.

Example 18. Treatment of Acute Macular Degeneration (AMD) with Connexin 43 Modulator Coadministered with an Anti-VEGF Compound The excessive use of anti-VEGF reagents currently used to treat AMD leads to choriocapillaris dropout, thereby increasing incidence of the disease. This was supported by the CATT 2 study showing increased incidence of new geographic atrophy in patients treated long term with Avastin or Lucentis (Martin D F, Maguire M G, Fine S L, Ying G S, Jaffe G J, Grunwald J E, et al. Ophthalmology; 119(7): 1388-98, 2012). The incidence in patients treated monthly (average 23 injections over two years) with the smaller Lucentis molecule (where greater penetration into the choroid could be expected) was greater than in Avastin treated patients (29.4% versus 19.5% respectively). Patients treated as needed (average 12 or 24 injections over two years respectively) had lower levels of new geographic atrophy (16 and 14% respectively). Accordingly, penetration of AMD treatment into the choroid resulted in choroid inflammation, and damage to the vascular bed that nurtures the retina, cycling back into uncontrolled choroid inflammation. The inventors have made the surprisingly discovery that breaking this chronic cycle is paramount to blocking disease progression. Excessive use of anti-VEGF reagents can also lead to the degeneration of capillary beds, particularly capillaries that have fenestrations like the ones found in the ciliary body (Ford, K. M., Invest. Ophthalmol. Vis. Sci. 53:7520-7527, 2012). The VEGF blockade in anti-cancer therapies has been found to damage the capillaries of the kidney and thyroid function in people treated locally for brain tumors (supra).

Current AMD therapies (Avastin and Lucentis, for example) are used primarily to treat the symptoms of AMD to reduce neovascularisation. For chronic diseases such as AMD that involve loss of RGCs, the inventors have appreciated that a twofold strategy of treatment would be better than a single therapy. First, choroid inflammatory progression and RGC loss in the inner retina itself must be ameliorated. Second, choroid inflammation in adjacent structures, such as underlying choroidal tissue ca be directly targeted.

Co-administration treatment with the combination of an anti-VEGF and an connexin 43 modulator results in improved benefits to the patient over single-agent therapy. The benefits of coadministration are less frequent dosing (resulting in increased patient compliance and tolerability), and fewer side effects (such as new geographic atrophy). While Lucentis is used herein, other anti-VEGF compounds or ocular treatments may be used in the methods of this invention, for example, Avastin, Eylea (aflibercept), Complement Factor D (lampalizumab), anti-SIP (iSONEP, sonepcizumab), and those AMD treatment agents described above.

Coadministration treatment is achieved by administering ranibizumab (Lucentis) by intravitreal injection on the same day as and prior to conexin 43 modulator administration. The vials containing bevacizumab are maintained at 4° C., and shaken well for at least one minute before using. The eye is washed and draped in usual sterile fashion. Topical anesthesia is given and a speculum is placed for adequate exposure. The injection quadrant is chosen by the treating physician and the site for injection measured at 3.0 to 4.0 mm posterior to the limbus. A 28- or 30-gauge needle is used to administer a 50 μL injection (0.5 mg) at 10 mg/ml concentration of the bevacizumab formulation. After injection, a paracentesis is performed at the treating physician's discretion and the speculum is removed. The dosings are applied once a month.

Next, the formulation comprising the connexin 43 modulator is administered via intravitreal or intraocular injection or by other methods of administration described herein. A 28- or 30-gauge needle is used to administer a 50 μL injection of the connexin 43 modulator formulation. The connexin 43 formulation is the SEQ/Pept5 ("Peptide 5") (SEQ ID NO: 168), dissolved in delivery medium at a concentration of 10 mg/ml and delivered 0.5 mg (50 ul). Reflux of material during administration can be minimized or prevented by using a slow steady rate of administration and by application of gentle pressure with a counter pressure device (CPD) during administration of material and withdrawal of the cannula. The dosings are applied once a month (on the same day as the Lucentis administration). The dose can also be 0.1 ug/ml, 0.5 ug/ml, 1 ug/ml, 5 ug/ml, 2.5 ug/ml, 10 ug/ml, 50 ug/ml, 100 ug/ml, 1 mg/ml, 2.5 mg/ml, 5 mg/ml, 10 mg/ml, 25 mg/ml, 50 mg/ml, 100 mg/ml, 250 mg/ml, or 500 mg/ml. The delivery medium can also be 1×PBS, citrate, ascorbate, or borate based buffer, with 0.3%, 0.4%, 0.5%, 0.6%, 0.7%, 0.8% NaCl concentration for isotonicity. The pH can also be 3, 3.5, 4, 5, 6, 6.5, 7, 7.4, or 8.

The patients are monitored by optical coherence tomography and visual acuity criteria to determine the effect of the coadministration treatment. The patient cohort treated with the co-administration treatments is compared to a patient group treated with Lucentis only, with the patient cohort treated with the co-administration exhibiting a greater visual acuity than the patient cohort treated with Lucentis only. The patient cohort treated with the co-administration protocol exhibits a recovery in the choiroid, as monitored by optical coherence tomography.

Example 19: Formulation of Connexin or Pannexin Modulators with Rho Kinase Inhibitors This invention provides a formulation containing one or more agents that enhance the ophthalmic properties of the rho kinase inhibitor compound and connexin or pannexin modulator for separate or common administration formulated in an aqueous medium whose pH is adjusted to enhance ocular surface residence time and the bioavailability in the aqueous humor of the anterior chamber, and to reduce systemic exposure. The invention provides an aqueous formulation of the rho kinase inhibitor compound and connexin or pannexin modulator that is suitable for therapeutic use and remains stable under normal use storage conditions for an extended period of time. The formulation is useful for lowering intraocular pressure in mammals. For topical administration, one to two drops of these formulations can be delivered to the surface of the eye one to four times per day. The aqueous ophthalmic formulations of this invention can have an increased residence time on the ocular surface and/or aqueous humor concentrations without a concomitant increase in systemic concentrations.

For the separate or common administration of the rho kinase inhibitor compound and connexin or pannexin modulator, an aqueous pharmaceutical formulation can comprise 0.001-2% rho kinase inhibitor compound, 1.0-50,000 μM connexin or pannexin modulator, 1-100 mM buffer suitable to maintain the pH about 6.3-7.8, 0.01-2% surfactant, and a tonicity agent to maintain a tonicity about 200-360 mOsm/kg; "about" as used herein, refers to ±15%. The pH is about 6.3-7.5, and preferably the pH is about 6.3-7.3. The compositions can further comprise, for example, sodium chloride, potassium chloride, calcium chloride and/or magnesium chloride.

For the separate or common administration of the rho kinase inhibitor compound and connexin or pannexin modulator, the concentration of the rho kinase inhibitor in the aqueous formulation is in general 0.001-2%, preferably 0.01-0.5%, more preferably 0.01-0.4%, more preferably 0.03-0.2%, and more preferably 0.03-0.15, or 0.03-0.1% (w/v). Buffers suitable to maintain the pH between 6.3 and 7.8 include citrate, phosphate, maleate, or combination thereof. Suitable buffer concentration is 1-100 mM, preferably 5-50 mM, more preferably 5-25 mM, and most preferably 10-20 mM.

For the separate or common administration of the rho kinase inhibitor compound and connexin modulator, wherein the connexin modulator is a connexin 43 modulator, the connexin 43 modulator may be present in the formulation at about 8 μM to about 20 μM final concentration, and alternatively the connexin 43 modulator is present at about 10 μM to about 20 μM final concentration, or at about 10 to about 15 μM final concentration. In certain other embodiments, the connexin 43 modulator is present at about 10 μM final concentration. In yet another embodiment, the connexin 43 modulator is present at about 1-15 μM final concentration. In other embodiments, the connexin 43 modulator is present at about a 20 μM, 30 μM, 40 μM, 50 μM, 60 μM, 70 μM, 80 μM, 90 μM, 100 μM, 10-200 μM, 200-300 μM, 300-400 μM, 400-500 μM, 500-600 μM, 600-700 μM, 700-800 μM, 800-900 μM, 900-1000 or 1000-1500 μM, or 1500 μM-2000 μM, 2000 μM-3000 μM, 3000 μM-4000 μM, 4000 μM-5000 μM, 5000 μM-6000 μM, 6000 μM-7000 μM, 7000 μM-8000 μM, 8000 μM-9000 μM, 9000 μM-10,000 μM, 10,000 μM-11,000 μM, 11,000 μM-12,000 μM, 12,000 μM-13,000 μM, 13,000 μM-14,000 μM, 14,000 μM-15,000 μM, 15,000 μM-20,000 μM, 20,000 μM-30,000 μM, 30,000 μM-50,000 μM, or greater, or any range or subrange between any two of the recited doses, or any dose falling within the range of from about 20 μM to about 50,000 μM.

For the separate or common administration of the rho kinase inhibitor compound and connexin modulator, wherein the connexin modulator is a connexin 43 modulator, the connexin modulator is any of the peptide or polynucleotide sequences described above. In some aspects, the connexin modulator can be the polynucleotide SEQ ID NO: 1. In some aspects, the rho kinase inhibitor compound can be the amino isoquinolyl amide Rhopressa.

Still other dosage levels between about 1 nanogram (ng)/kg and about 1 mg/kg body weight per day of each of the connexin or pannexin modulators in the separate or common coadministration with the rho kinase inhibitor are described herein. In certain embodiments, the dosage of each of the subject compounds will generally be in the range of about 1 ng to about 1 microgram per kg body weight, about 1 ng to about 0.1 microgram per kg body weight, about 1 ng to about 10 ng per kg body weight, about 10 ng to about 0.1 microgram per kg body weight, about 0.1 microgram to about 1 microgram per kg body weight, about 20 ng to about 100 ng per kg body weight, about 0.001 mg to about 0.01 mg per kg body weight, about 0.01 mg to about 0.1 mg per kg body weight, or about 0.1 mg to about 1 mg per kg body weight. In certain embodiments, the dosage of each of the subject compounds will generally be in the range of about 0.001 mg to about 0.01 mg per kg body weight, about 0.01 mg to about 0.1 mg per kg body weight, about 0.1 mg to about 1 mg per kg body weight. If more than one connexin or pannexin modulator is used, the dosage of each anti-connexin agent need not be in the same range as the other. For example, the dosage of one connexin or pannexin modulator may be between about 0.01 mg to about 10 mg per kg body weight, and the dosage of another connexin or pannexin modulator may be between about 0.1 mg to about 1 mg per kg body weight, 0.1 to about 10, 0.1 to about 20, 0.1 to about 30, 0.1 to about 40, or between about 0.1 to about 50 mg per kg body weight. The dosage may also be about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0, 25.0, 26.0, 27.0, 28.0, 29.0, 30.0, 31.0, 32.0, 33.0, 34.0, 35.0, 36.0, 37.0, 38.0, 39.0, 40.0, 41.0, 42.0, 43.0, 44.0, 45.0, 46.0, 47.0, 48.0, 49.0, 50.0, 52.5, 55.0, 57.5, 60.0, 62.5, 65.0, 67.5, 70.0, 72.5, 75.0, 77.5, 80.0, 82.5, 85.0, 87.5, 90.0, 92.5, 95.0, 97.5, or about 100.0 mg per kg body weight, or any range or subrange between any two of the recited doses, or any dose falling within the range of from about 0.1 to about 100 mg per kg body weight.

For the separate or common administration of the rho kinase inhibitor compound and connexin or pannexin modulator, in one embodiment, the combined use of the rho kinase inhibitor compound and connexin or pannexin modulator reduces the effective dose of any such agent compared to the effective dose when said agent administered alone. In certain embodiments, the effective dose of the agent when used in combination is about 1/15 to about 1/2, about 1/10 to about 1/3, about 1/8 to about 1/6, about 1/5, about 1/4, about 1/3 or about 1/2 the dose of the agent when used alone. In another preferred embodiment, the combined use of the rho kinase inhibitor compound and connexin or pannexin modulator reduces the frequency in which said agent is administered compared to the frequency when said agent is administered alone. Thus, these combinations allow the use of lower and/or fewer doses of each agent than previously required to achieve desired therapeutic goals.

In one embodiment, the dose of the rho kinase inhibitor compound and connexin or pannexin modulator when coadministered as separate or common administrations may be 10, 100 or 1000 fold lower than any of the recited doses set forth herein.

Surfactants (surface active agents) or solubilizing agents suitable for the present invention are those acceptable for use in ophthalmic preparations. The surfactants can be ionic or non-ionic. Preferably, this surfactant is non-ionic. Useful surfactants include but are not limited to polysorbate 80, polyoxyl stearates, tyloxapol, polyethoxylated castor oils, poloxamers, polaxamines, medium and long chain fatty acids and phospholipids. The concentration of the surfactant in the formulation is about 0.01-3%, preferably 0.01-2%, more preferably 0.1-1% w/v.

The tonicity agent is present in an amount to achieve a final formulation tonicity between 220-360 mOsm/kG, preferably 250-340 mOsm/kG, and most preferably between 260 and 320. The tonicity agent can be ionic or non-ionic.

Non-ionic tonicity agents include compounds comprising 1,2-diols, such as glycerol, mannitol, erythritol; and sugars such as dextrose. Other non-ionic tonicity agents which also function as cosolvents can also be used such as polyethylene glycol and propylene glycol. The non-ionic tonicity agent can be present in an amount of 0-20%, preferably 0-10%, more preferably 0-5%. The non-ionic agents can be selected from: glycerol, mannitol and dextrose, in an amount 2-6%.

The tonicity agent can also be ionic agents such as sodium chloride, potassium chloride, a balanced salt solution, sodium phosphate, or sodium citrate. The ionic tonicity agents can be present in an amount of 0.3-1.5%, preferably 0.6-0.9%.

The surfactants, the tonicity agent, the buffer and any other ingredients introduced into the formulation preferably have good solubility in water, and have compatibility with other components in the formulation. Health regulations in various countries require that multi-dose ophthalmic preparations shall include a preservative. In one embodiment, benzalkonium chloride is employed as a safe preservative; benzalkonium chloride may be used with disodium ethylenediaminetetraacetic acid (EDTA), a chelating agent, to enhance its antimicrobial activity. Other suitable preservatives include benzyl alcohol, methyl parabens, propyl parabens, borate, chlorobutanol, and benzethonium chlorides. Typically, such preservatives are employed at a level of from 0.001-1%, preferably, 0.001-0.25%, and most preferably 0.001-0.2%.

Optionally, the formulation can include a viscosity enhancer to increase the residence time of the formulation on the ocular surface. As a non-limiting example, hydroxypropyl methyl cellulose, can be used as a viscosity enhancer for the present invention.

Example 20: Method of Treating Glaucoma with the Combination of the Connexin 43 Modulator SEQ ID NO: 1 and the Rho Kinase Inhibitor The connexin 43 modulator used is the polynucleotide SEQ ID NO: 1. The rho kinase inhibitor used is Rhopressa. The connexin 43 modulator SEQ ID NO: 1 is formulated as a nanoparticle delivery formulation as described above, at a concentration of 100 μM of connexin 43 modulator total in solution. The concentration of the rho kinase inhibitor in the aqueous formulation is 0.03-0.1% (w/v), and formulated as described above.

Adult male Wistar rats are modeled for glaucoma with a retinal ischemia reperfusion. Retinal ischemia is modeled in the left eye (120 mmHg for 60 min), with the right eye as the control, and then the connexin 43 modulator formulation (neat, and infused into particles as described above) is injected intravitreally immediately as solutions in 1×PBS delivery agent. Within one hour, the rho kinase inhibitor is then added via the administration of eye drops (50 uL). After reperfusion, Evan's blue dye is injected intraperitoneally 4 hr after reperfusion to visualize vessel leak using confocal microscopy and optical coherence tomography. Retinal whole mounts are collected at 8 hr and 28 days for Cxn43 quantitification, and 28 and 90 days for gangliol cell (RGC) densities quantification. Other cohorts of rats are treated with only the connexin 43 modulator, and other cohorts of rates are treated with only the rho kinase inhibitor, at the same concentration as used in the combination coadministration.

The results will indicate the vessel leak after 4 hr post-ischemia is significantly reduced in the reinal for the eyes treated with the combination of the rho kinase inhibitor and the connexin 43 modulator compared to control. It will be surprisingly shown that the connexin 43 modulator works in the presence of the rho kinase inhibitor. The results will also show the surprising reduction in vessel leak for eyes treated with the combination of the rho kinase inhibitor and the connexin 43 modulator compared to any eye with just single treatment.

Spot counts are also measured for all cohort models. It will be shown that spot counts were reduced moreso with the combination treatment than any single treatment.

After 28 days post-ischemia, cross-sections of the tissues are observed by confocal microscopy and coherence tomography. The mean Cxn43 count is measured for Evan's Blue dye-stained samples. The results will show that the combination formulations will result in lower Cxn43 expression than any single administration formulation.

Retinal ganglion cell count is monitored for the models. The results will surprisingly show greater RGC survival for the coadministration treatment over any single administration treatment and untreated eyes (ischemia only).

Figure 45:
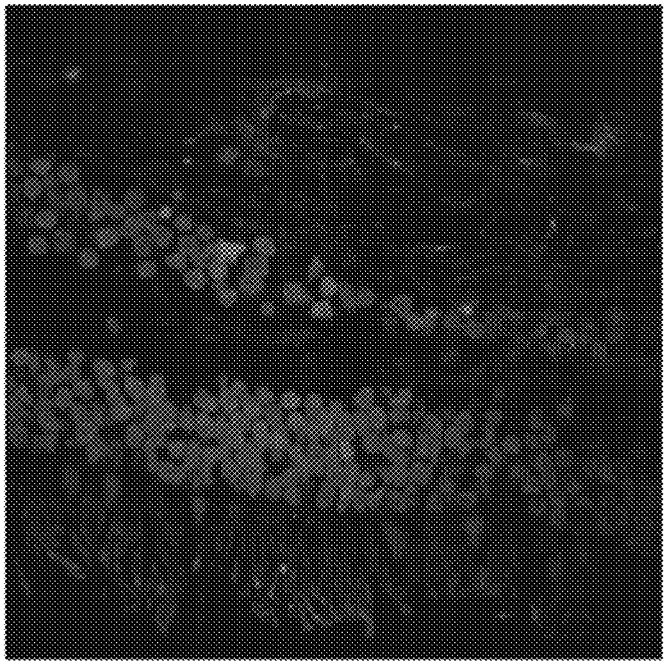
FIG. 45. Representative images of stained tissues indicating Cxn43 expression profile in retina images taken near a haemorrhage of a retina sample of a deceased human. Merged images of nuclei stained with DAPI (blue) and Cxn43 gap junction plaques (red).

Example 21: Connexin 43 is Upregulated Following Hemorrhage in Diabetic Humans Human retina samples were obtained from human donors. FIGS. 45 and 46 shows two human diabetic retinopathy retina images taken near a haemorrhage, labelled for Cxn43 (red) and DAPI (blue) with rods and cones showing up at the bottom of FIG. 45.

Upon injury, Cxn43 levels Cxn43 rise as a result of injury to an extent even greater than in normals as in the skin (as diabetic rats heal more slowly). In diabetic retinopathy this results in inflammatory regions with high Cxn43 and blood vessel leakage.

There appears to be a thickening of the RGC astrocyte layer, a piling up of small vessels and high levels of Cxn43 associated with them and astrocytes. Diabetics have reduced Cxn43 and vessel loss but not in areas of haemorrhage and neovascularisation, as there appears to be higher Cxn43 levels at inflammatory sites. The inventors have made the surprising discovery that Cxn43 regulation in diabetic retinopathy is a viable drug target.

Example 22. In Vitro Block of Cxn43 Hemichannel Docking with Particle Formulations The blocking ability of Cxn43 modulators formulated in nanoparticles or microparticles was analyzed in vitro to establish the ability of the formulations to modulate Cxn43 activity. The microparticle (MP) and nanoparticle (Np) formulations were prepared as described above.

In vitro results from blocking Cxn43 hemichannels are shown in FIG. 47. After 8 h of exposure to a Cxn43 MP solution, Cxn43 labelling in ARPE-19 cells was reduced (FIG. 47B); however, levels returned to normal after 24 h (FIG. 47C). However, cells treated with Cxn43 MP loaded Nps and Mps, exhibited reduced Cxn43 labelling at the later time point compared to the 8 h evaluation. There were no differences in Cxn43 labelling after 8 h of incubation with Nps (FIG. 47D) and Mps (FIG. 47F), while after 24 h of exposure, both Nps (FIG. 47E) and Mps (FIG. 47G) groups exhibited reduced Cxn43 labelling confirming the delayed release and thus activity of Cxn43 MP. Each group exhibited a similar cell density compared to the control, indicating that no cytotoxicity occurred due to hemichannel blocking at the concentrations used.

Microparticle (MP) formulations composed of natural amino acids might degrade upon prolonged cellular incubation, thereby losing their activity. The half-life of native Cxn43 MP in bovine vitreous is about 2 h, predicting that Cxn43 MP should be completely degraded after 14 h if unprotected. This explains why Cxn43 hemichannels were blocked within the first few hours of incubation with the simple Cxn43 MP solution while there was no difference in the level of Cxn43 labelling in the same treatment group after 24 h (FIG. 47C) compared to the control (FIG. 47A). Native Cxn43 MP in solution is likely to have been completely degraded at that time point and existing Cxn43 hemichannels would have been continuously replaced by new ones. On the contrary, there was a progressive reduction in Cxn43 plaque expression for both Cxn43 MP loaded Nps and Mps groups at 24 h (FIGS. 47E and 47), although no difference was apparent between the two groups. It seemed that both particles protected the Cxn43 MP from degradation, sustained their release and therefore prolonged their activity, although no effect was seen within 8 h possibly due to insufficient Cxn43 MP released at that time point. However, after 24 h greater concentrations of Cxn43 MP were available correlating with increased hemichannel blockage and reduced Cxn43 gap junction plaque labelling.

Example 23. Treatment of Cxn43 Upregulation with Cxn43 Particle Formulations as Observed by GFAP Labelling in Retinal Cross-Sections The microparticle (MP) and nanoparticle (Np) formulations described above were used to modulate Cxn43 upregulation in animal models, as observed by GFAP labelling in retinal cross-sections.

Qualitative changes in Cxn43 and GFAP expression in association with retinal capillaries were observed following retinal ischaemia (FIG. 48). Twenty-eight days after reperfusion, Cxn43 was significantly upregulated and mainly co-localised with GFAP (FIG. 48B). There was marked astrocytosis in the ischaemic regions with astrocytic foot processes losing their normal organised appearance. Intravitreal injection of Cxn43 MP loaded Nps resulted in significantly ($p<0.01$) reduced Cxn43 upregulation present at 28 d (FIG. 48D). Native Cxn43 MP in solution and Cxn43 MP loaded Mps at 28 d and 90 d exhibited similar results, where Cxn43 expression was reduced along with astrocytes extending their processes and proliferating into the periaxonal area (FIG. 48C-F). Cxn43 spot counts, correlating with astrocytosis, were performed (FIG. 48G) and revealed that retinal Cxn43 was also significantly above normal levels ($p<0.01$) at 28 d (80.7±7.9) after ischaemia-reperfusion compared to uninjured retinas (8.9±1.3). Treatment with native Cxn43 MP in solution resulted in a significantly reduced Cxn43 spot count to 21.7±5.2 at 28 d ($p<0.01$); but was still significantly increased compared to the control ($p<0.05$). However, Nps loaded with Cxn43 MP displayed the greatest effect with the Cxn43 spot count down to 10.4±7.5 after 28 d, with no significant difference compared to the uninjured control ($p>0.05$), confirming their protective and sustained release properties. Mps loaded with Cxn43 MP were also able to limit Cxn43 expression seen after 28 d (15.4±3.2) and 90 d (19.9±1.4) compared to the untreated ischaemic eyes ($p<0.01$), again confirming the availability of stable Cxn43 MP at this time point.

These results indicate that the microparticle (MP) and nanoparticle (Np) formulations can modulate Cxn43 upregulation in a sustained manner in ischemia-induced models in mammals.

Example 24. Treatment of Cxn43 Upregulation with Cxn43 Particle Formulations as Observed by RGC Loss in Retinal Wholemounts The microparticle (MP) and nanoparticle (Np) formulations described above were used to modulate Cxn43 upregulation as observed by RGC loss in retinal wholemounts.

The normal distribution of retinal ganlgion cells (RGC) in flatmounts of uninjured retinas is shown in FIG. 49A, where a high cell density and clearly outlined retinal vasculature were visible. An example of the RGC degeneration pattern in untreated ischaemic retinas is shown in FIG. 49B, with RGC distribution 28 d after ischaemia-reperfusion significantly reduced with almost complete loss of blood vessel delineation and large patches devoid of RGC noted in many areas. This indicates that the retina responded to the ischaemic insult with neurodegeneration following increased hemichannel mediated vascular permeability. Eyes treated with native Cxn43 MP in solution (FIG. 49C) and Nps-Cxn43 MP (FIG. 49D) exhibited fewer patches of RGC loss. FIGS. 49E and F illustrate the RGC distribution at 28 d and 90 d in eyes treated with Mps-Cxn43 MP with some RGC loss apparent. A summary of the RGC density (number/mm2) is depicted in FIG. 49G. Following ischaemia-reperfusion, the RGC density was significantly reduced ($p<0.01$) at 28 d in animals without treatment (1605±100) compared to uninjured controls (2283±139), with only 70% of cells surviving. The density in the Nps-Cxn43 MP group (1964±194) was similar to that of the Cxn43 MP in solution treatment, while RGC counts after Mps-Cxn43 MP treatment (1670±148 at 28 d and 1727±221 at 90 d) exhibited a trend towards RGC sparing but exhibited no significant change compared to untreated eyes.

Ischaemia-reperfusion injury led to a significant loss of RGC in retinas at 28 d compared to uninjured controls, with intravitreal injection of Cxn43 MP in solution ($p<0.05$) or Nps-Cxn43 MP ($p<0.01$) significantly reducing RGC death compared to no treatment, correlating with reduced Cxn43 labelling. Although slower Cxn43 MP release from Mps also decreased Cxn43 levels at 28 d and 90 d following ischaemia-reperfusion, this treatment group failed to rescue RGC. This could be attributed to insufficient initial Cxn43 MP release from Mps during the immediate acute stage after injury. In addition, Mps may get trapped in the meshwork due to their larger size compared to the Nps and released Cxn43 MP would therefore have to diffuse larger distances to the retina, increasing the risk of enzymatic degradation. Results therefore suggest that the RGC rescue effect may be more attributable to the initial burst of Cxn43 MP than the continuous slow release, suggesting that the sooner Cxn43 hemichannels are blocked after ischaemia the better. Although we do not have any Cxn43 and RGC count data from injured animals receiving no treatment at 90 d, previous studies have demonstrated that death of RGC significantly increases with time, with more than 50% loss after 56 d (S. S. L. Chew, et al., Invest. Ophthalmol. Vis. Sci. 52 (2011) 3620-3629.). Thus, although particle treatments did not show significant advantages compared to the peptide in solution in terms of RGC survival at the time points investigated, the sustained Cxn43 MP delivery effect may still be beneficial for preservation of the RGC layer in the long term.

Example 26. Alternative Method for Preparation of Nanoparticles and Microparticles An alternative route to the production of nanoparticles and microparticles is as follows: 100 mg of poly(lactic-coglycolic acid) (PLGA) is placed in a test tube, followed by the addition of 1 ml of dichloromethane solvent. Next, the tube is sealed and the polymer allowed to dissolve overnight. To a separate tube, a solution of 2 ml of 0.3% w/w D-α-Tocopherol polyethylene glycol 1000 succinate (Vitamin E-TPGS, Sigma 57668) emulsifier in water is prepared. The amount of polymer to add will determine the particle size.

For hydrophobic forms of the connexin 43 modulator: 5 μg of the connexin 43 modulator is added in dry form to the PLGA solution. The tube is vortexed unti the solution is homogeneous by visual inspection.

For hydrophilic forms of the connexin 43 modulator: 50 ul of an aqueous solution (at 10 μM concentration of the connexin 43 modulator in 1×PBS buffer) is added to the PLGA solution. The solution is precooled by placing the tube on ice for 30 seconds, then sonicated for 10 seconds to emulsify the connexin 43 modulator in the solution to achieve a homogeneous opaque solution (VWR #97043-960). The tube is placed back on ice.

For both forms of the connexin 43 modulator, the Vitamin E-TPGS tube is vortexed at high vortex speed using a benchtop vortexer (VWR Scientific #58816-121) while adding 1 ml of the PLGA-modulator solution dropwise. Vortexing is continued for 15 seconds.

Ice-water is placed in the sonicator. Next, the emulsion is sonicated for three 10 second bursts (40% amplitude for a 700 W sonicator). The tube is moved around in the solution so as to ensure even sonication. Each sonication is performed 5 seconds apart to allow the solution to cool.

Next, 1 ml of 0.3% Vitamin E-TPGS is added in water to the emulsion via glass pipette. Next, the emulsion is transferred dropwise into 45 ml of 0.3% w/v Vitamin E-TPGS magnetically stirred at 360 rpm. The solution is stirred for 3 hours.

Next, the resulting solution is transferred into centrifuge tubes and centrifuged in a fixed-angle rotor centrifuge for 15 min at 17,000×g. The supernatant is discarded. Next, 15 ml diH2O is added and the tube is vortexed to completely resuspend the particles. These steps are repeated four times. The fluid volume of the last pellet resuspension is 4-5 ml. A weight ratio of 1:2 trehalose:polymer is added (however, a small aliquot of particles are prepared without trehalose for SEM imaging).

The nanoparticles are then transferred to a preweighed 5 ml centrifuge tube and frozen at −80° C. for a minimum of 30 min. The nanoparticles are then lyophilized 72 hr for a 5 ml volume and then stored at −80° C.

The inventions described and claimed herein have many attributes and embodiments including, but not limited to, those set forth or described or referenced in this Detailed Disclosure. It is not intended to be all-inclusive and the inventions described and claimed herein are not limited to or by the features or embodiments identified in this Detailed Disclosure, which is included for purposes of illustration only and not restriction. A person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. The invention also includes all of the steps, features, compositions and compounds referred to or indicated in this specification, individually or collectively, and any and all combinations of any two or more of said steps or features.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents. Reference to any applications, patents and publications in this specification is not, and should not be taken as, an acknowledgment or any form of suggestion that they constitute valid prior art or form part of the common general knowledge in any country in the world.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants. Furthermore, titles, headings, or the like are provided to enhance the reader's comprehension of this document, and should not be read as limiting the scope of the present invention. Any examples of aspects, embodiments or components of the invention referred to herein are to be considered non-limiting.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

We claim:

1. A method for inhibiting inflammasome activity in a subject, comprising administering to said subject a connexin 43 hemichannel modulator according to Formula I or Formula II in an amount effective to modulate inflammasome activity.

2. The method according to claim 1, wherein the modulator is a compound according to Formula I.

3. The method according to claim 1, wherein the modulator is a compound according to Formula II.

4. The method according to claim 2, wherein the modulator is tonabersat.

5. A method according to claim 1, wherein said inflammasome is the NLRP3 inflammasome.

6. A method according to claim 1, wherein said inhibition of inflammasome activity comprises inhibition of inflammasome activation .

7. The method according to claim 1, wherein said inhibition of inflammasome activity comprises inhibition of activation of an inflammatory cascade by an inflammasome.

8. The method according to claim 6, wherein the inflammasome is the NLRP3 inflammasome.

9. The method according to claim 7, wherein the inflammasome is the NLRP3 inflammasome.

10. The method according to claim 1, wherein the subject has lung inflammation, an inflammatory cardiac insult, acute respiratory distress syndrome, acute lung injury, pericardial effusion, pericarditis, or systemic inflammatory response syndrome.

11. The method according to claim 10, wherein the subject is human, the connexin 43 hemichannel modulator is tonabersat or a prodrug of tonabersat, and the connexin 43 hemichannel modulator is administered during or before lung inflammation.

12. A method according to any of claim 1, 2, 4-9, 10 or 11, wherein said connexin 43 hemichannel modulator is administered by oral, systemic, intranasal, parenteral, transdermal or ocular administration, or by implantation or infusion.

13. The method according to any of claim 1, 2, 4-9, 10 or 11 , wherein the compound according to Formula I is tonabersat.

14. The method according to any of claim 1-9, 10 or 11, wherein the subject is human.

15. The method according to claim 10, wherein the prodrug of tonabersat is a compound according to Formula II.

16. The method according to any of claim 1, 2, 4-9, 10 or 11, wherein the subject is human, the compound according to Formula I is tonabersat, and the tonabersat is administered orally.

17. A method for inhibiting inflammasome activity in a human subject, comprising administering a tonabersat compound to said human subject in an amount effective to modulate inflammasome activity.

18. A method according to claim 16, wherein NLRP3 inflammasome activity is inhibited.

19. A method according to claim 17, wherein the inhibition of NLRP3 inflammasome activity comprises inhibition of NLRP3 inflammasome activation.

20. The method according to claim 17, wherein the inhibition of NLRP3 inflammasome activity comprises inhibition of the activation of an inflammatory cascade by the NLRP3 inflammasome.

21. A method according to any of claim 17-19 or 20, wherein tonabersat compound is tonabersat.

22. A method according to any of claim 17-19 or 20, wherein tonabersat compound is a tonabersat prodrug.

23. A method according to claim 21, wherein the tonabersat prodrug is a compound according to Formula II.

24. A method according to claim 21, wherein the tonabersat is administered orally.

25. A method according to claim 21, wherein the tonabersat is administered by systemic, intranasal, parenteral, transdermal or ocular administration, or by implantation or infusion.

* * * * *

UNITED STATES PATENT AND TRADEMARK OFFICE

CERTIFICATE OF CORRECTION

PATENT NO. : 11,401,516 B2
APPLICATION NO. : 16/673729
DATED : August 2, 2022
INVENTOR(S) : Colin Richard Green et al.

It is certified that error appears in the above-identified patent and that said Letters Patent is hereby corrected as shown below:

In the Specification

Column 20, Lines 42-43 “C.sub.1-6 alkyl amino, amino, amino-C.sub.1-6 alkyl,” should read --$C_{1-6}$ alkyl amino, amino, amino-$C_{1-6}$ alkyl,--

(II)

Column 21, Lines 1-17 “ 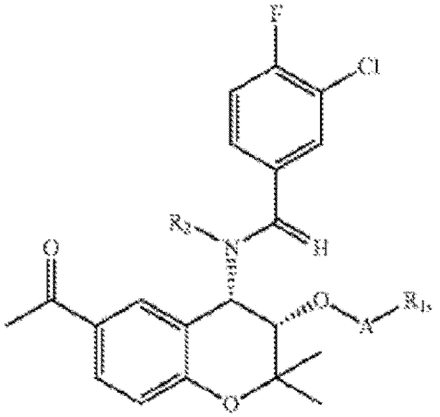 ” should read (II)

-- 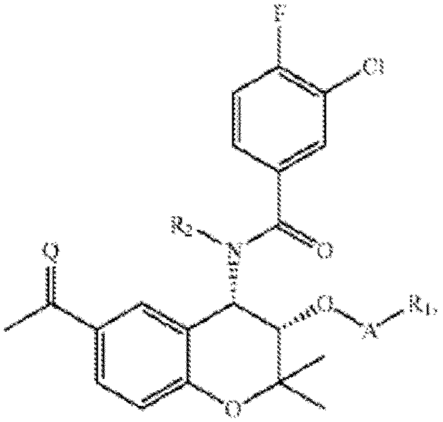 --

Signed and Sealed this
Eighteenth Day of April, 2023

Katherine Kelly Vidal

Katherine Kelly Vidal
*Director of the United States Patent and Trademark Office*

Column 21, Line 26 “or $C_{1-4}$ fluoroalkyl” should read --and $C_{1-4}$ fluoroalkyl--

Column 21, Line 28 “[5] or [6]” should read --[5] and [6]--

Column 21, Lines 45-50 “ 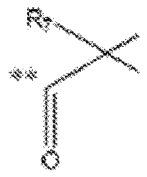 [3] ” should read -- 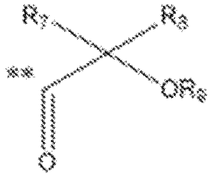 [3] --

Column 21, Line 65 “alkyl, $C_{1-4}$ fluoroalkyl, or” should read --alkyl, $C_{1-4}$ fluoroalkyl, and--

Column 21, Line 66 “$R_7$ is independently selected from H, $C_{1-4}$ alkyl, or” should read --$R_7$ is independently selected from H, $C_{1-4}$ alkyl, and--

Column 22, Line 2 “H, $C_{1-4}$ alkyl, or $C_{1-4}$ fluoroalkyl, or” should read --H, $C_{1-4}$ alkyl, or $C_{1-4}$ fluoroalkyl,--

Column 22, Line 4 “acid, or a peptide as described herein, or” should read --acid, or a peptide as described herein, and--

Column 22, Line 7 (and continuing into Line 8) “$R_9$ is selected from H, —$N(R_{11})(R_{12})$, or —$N^+(R_{11})(R_{12})(R_{13})X^-$, or —$N(R_{11})C(O)R_{14}$” should read -- $R_9$ is selected from H, —$N(R_{11})(R_{12})$, or —$N^+(R_{11})(R_{12})(R_{13})X^-$, and —$N(R_{11})C(O)R_{14}$;--

Column 22, Line 10 “from H, $C_{1-4}$ alkyl, or $C_{1-4}$ fluoroalkyl,” should read --from H, $C_{1-4}$ alkyl, and $C_{1-4}$ fluoroalkyl,--

Column 22, Line 12 “$R_{15}$ is selected from $C_{1-4}$ alkyl or $C_{1-4}$ fluoroalkyl, and” should read --$R_{15}$ is selected from $C_{1-4}$ alkyl and $C_{1-4}$ fluoroalkyl, and--

Column 22, Line 23 “$C_{1-4}$ alkyl, or $C_{1-4}$ fluoroalkyl,” should read --$C_{1-4}$ alkyl, and $C_{1-4}$ fluoroalkyl, --

Column 22, Lines 41-46 “ 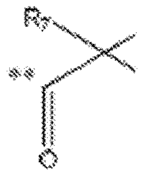 [23] ” should read -- 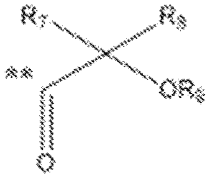 [23] --

Column 23, Line 2 “Q is an oxime of formula =$NHOR_{43}$, wherein $R_{43}$ is” should read --Q is an oxime of formula =$NOR_{43}$, wherein $R_{43}$ is--

Column 23, Line 8 “$R_{30}$” should read --$R_{300}$--

Column 23, Line 11 “or $C_{1-4}$ fluoroalkyl” should read --and $C_{1-4}$ fluoroalkyl--
Column 23, Lines 14-15 “[5] or [6]” should read --[5] and [6]--

Column 23, Lines 31-36 " 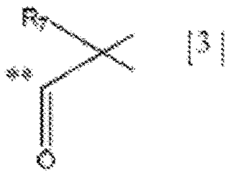 " should read -- 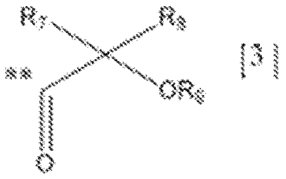 --

Column 23, Line 51 "alkyl, $C_{1-4}$ fluoroalkyl, or" should read --alkyl, $C_{1-4}$ fluoroalkyl, and--

Column 23, Line 52 "$R_7$ is independently selected from H, $C_{1-4}$ alkyl, or" should read --$R_7$ is independently selected from H, $C_{1-4}$ alkyl, and--

Column 23, Line 55 "H, $C_{1-4}$ alkyl, or $C_{1-4}$ fluoroalkyl, or" should read --H, $C_{1-4}$ alkyl, or $C_{1-4}$ fluoroalkyl,--

Column 23, Line 57 "acid, or a peptide as described herein, or" should read --acid, or a peptide as described herein, and--

Column 23, Line 62 "from H, $C_{1-4}$ alkyl, or $C_{1-4}$ fluoroalkyl," should read --from H, $C_{1-4}$ alkyl, and $C_{1-4}$ fluoroalkyl,--

Column 23, Line 63 "$R_{14}$ is H, $C_{1-4}$ alkyl, or $C_{1-4}$ fluoroalkyl" should read --$R_{14}$ is H, $C_{1-4}$ alkyl, or $C_{1-4}$ fluoroalkyl,--

Column 23, Line 64 "$R_{15}$ is selected from $C_{1-4}$ alkyl or $C_{1-4}$ fluoroalkyl, and" should read --$R_{15}$ is selected from $C_{1-4}$ alkyl and $C_{1-4}$ fluoroalkyl, and--

Column 24, Lines 20-21 "In some aspects, the pro-drug can be those described in WO 2014/006407, and herein incorporated by reference." should read --In some aspects, the pro-drug can be those described in WO 2014/006407, also published as US 2015/0322034, and herein incorporated by reference.--

Column 33, Lines 39-40 "Comparative Knockdown activity of the ASN from Table 4 at 4 hr post-transfection." should read --Comparative Knockdown activity of SEQ ID NO.:1, SEQ ID NO.:4, and the ASN from Table 58 at 4 hr post-transfection.--

Column 33, Lines 41-42 "Comparative Knockdown activity of the ASN from Table 4 at 12 hr post-transfection." should read --Comparative Knockdown activity of SEQ ID NO.:1, SEQ ID NO.:4, and the ASN from Table 58 at 12 hr post-transfection.--

Column 39, Line 24, "mono or di $C_{1-6}$ alkyl amino, amino, amino-C.sub.1-6 alkyl," should read --mono or di $C_{1-6}$ alkyl amino, amino, amino-$C_{1-6}$ alkyl,--

SEQUENCE LISTING

```
<160> NUMBER OF SEQ ID NOS: 256

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

gtaattgcgg caagaagaat tgtttctgtc                                      30


<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

gtaattgcgg caggaggaat tgtttctgtc                                      30


<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

ggcaagagac accaaagaca ctaccagcat                                      30


<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

ccaggctgac tcaaccgctg                                                 20


<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

acccatgttg cctgggcacc                                                 20
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 6
gtaggcttga accttgtcaa 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 7
tctccccagg ctgactcaac 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 8
cagaagcgca catgagagat 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 9
gaagcgcaca tgagagattg 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 10
agtgtgggta cagacacaaa 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 11
cagacacaaa tatgatctgc 20

<210> SEQ ID NO 12

<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 12
atatgatctg caggacccag 20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 13
gtaattgcgg caagaagaat 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 14
aggctgtgca tgggagttag 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15
cgctggtcca caatggctag 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16
gctggctctg cttgaaggtc 20

<210> SEQ ID NO 17
<211> LENGTH: 3088
<212> TYPE: DNA
<213> ORGANISM: Homo sapiens

<400> SEQUENCE: 17
acaaaaaagc ttttacgagg tatcagcact tttctttcat tagggggaag gcgtgaggaa 60
agtaccaaac agcagcggag ttttaaactt taaatagaca ggtctgagtg cctgaacttg 120
ccttttcatt ttacttcatc ctccaaggag ttcaatcact tggcgtgact tcactacttt 180
taagcaaaag agtggtgccc aggcaacatg ggtgactgga gcgccttagg caaactcctt 240

```
gacaaggttc aagcctactc aactgctgga gggaaggtgt ggctgtcagt acttttcatt    300
ttccgaatcc tgctgctggg gacagcggtt gagtcagcct ggggagatga gcagtctgcc    360
tttcgttgta acactcagca acctggttgt gaaaatgtct gctatgacaa gtctttccca    420
atctctcatg tgcgcttctg ggtcctgcag atcatatttg tgtctgtacc cacactcttg    480
tacctggctc atgtgttcta tgtgatgcga aaggaagaga aactgaacaa gaaagaggaa    540
gaactcaagg ttgcccaaac tgatggtgtc aatgtggaca tgcacttgaa gcagattgag    600
ataaagaagt tcaagtacgg tattgaagag catggtaagg tgaaaatgcg aggggggttg    660
ctgcgaacct acatcatcag tatcctcttc aagtctatct ttgaggtggc cttcttgctg    720
atccagtggt acatctatgg attcagcttg agtgctgttt acacttgcaa aagagatccc    780
tgcccacatc aggtggactg tttcctctct cgccccacgg agaaaaccat cttcatcatc    840
ttcatgctgg tggtgtcctt ggtgtccctg gccttgaata tcattgaact cttctatgtt    900
ttcttcaagg gcgttaagga tcgggttaag ggaaagagcg acccttacca tgcgaccagt    960
ggtgcgctga gccctgccaa agactgtggg tctcaaaaat atgcttattt caatggctgc   1020
tcctcaccaa ccgctcccct ctcgcctatg tctcctcctg ggtacaagct ggttactggc   1080
gacagaaaca attcttcttg ccgcaattac aacaagcaag caagtgagca aaactgggct   1140
aattacagtg cagaacaaaa tcgaatgggg caggcgggaa gcaccatctc taactcccat   1200
gcacagcctt ttgatttccc cgatgataac cagaattcta aaaaactagc tgctggacat   1260
gaattacagc cactagccat tgtggaccag cgaccttcaa gcagagccag cagtcgtgcc   1320
agcagcagac ctcggcctga tgacctggag atctagatac aggcttgaaa gcatcaagat   1380
tccactcaat tgtggagaag aaaaaaggtg ctgtagaaag tgcaccaggt gttaattttg   1440
atccggtgga ggtggtactc aacagcctta ttcatgaggc ttagaaaaca caaagacatt   1500
agaataccta ggttcactgg gggtgtatgg ggtagatggg tggagaggga ggggataaga   1560
gaggtgcatg ttggtattta aagtagtgga ttcaaagaac ttagattata aataagagtt   1620
ccattaggtg atacatagat aagggctttt tctccccgca aacaccccta agaatggttc   1680
tgtgtatgtg aatgagcggg tggtaattgt ggctaaatat ttttgtttta ccaagaaact   1740
gaaataattc tggccaggaa taaatacttc ctgaacatct taggtctttt caacaagaaa   1800
aagacagagg attgtcctta agtccctgct aaaacattcc attgttaaaa tttgcacttt   1860
gaaggtaagc tttctaggcc tgaccctcca ggtgtcaatg gacttgtgct actatatttt   1920
tttattcttg gtatcagttt aaaattcaga caaggcccac agaataagat tttccatgca   1980
tttgcaaata cgtatattct tttccatcc acttgcacaa tatcattacc atcacttttt    2040
catcattcct cagctactac tcacattcat ttaatggttt ctgtaaacat ttttaagaca   2100
gttgggatgt cacttaacat ttttttttt tgagctaaag tcagggaatc aagccatgct    2160
taatatttaa caatcactta tatgtgtgtc gaagagtttg ttttgtttgt catgtattgg   2220
tacaagcaga tacagtataa actcacaaac acagatttga aaataatgca catatggtgt   2280
tcaaatttga acctttctca tggatttttg tggtgtgggc caatatggtg tttacattat   2340
ataattcctg ctgtggcaag taaagcacac ttttttttc tcctaaaatg tttttccctg    2400
tgtatcctat tatggatact ggttttgtta attatgattc tttattttct ctccttttt    2460
taggatatag cagtaatgct attactgaaa tgaatttcct ttttctgaaa tgtaatcatt   2520
gatgcttgaa tgatagaatt ttagtactgt aaacaggctt tagtcattaa tgtgagagac   2580
ttagaaaaaa tgcttagagt ggactattaa atgtgcctaa atgaattttg cagtaactgg   2640
```

```
tattcttggg ttttcctact taatacacag taattcagaa cttgtattct attatgagtt   2700

tagcagtctt ttggagtgac cagcaacttt gatgtttgca ctaagatttt atttggaatg   2760

caagagaggt tgaaagagga ttcagtagta cacatacaac taatttattt gaactatatg   2820

ttgaagacat ctaccagttt ctccaaatgc ctttttaaa actcatcaca gaagattggt   2880

gaaaatgctg agtatgacac ttttcttctt gcatgcatgt cagctacata aacagttttg   2940

tacaatgaaa attactaatt tgtttgacat tccatgttaa actacggtca tgttcagctt   3000

cattgcatgt aatgtagacc tagtccatca gatcatgtgt tctggagagt gttctttatt   3060

caataaagtt ttaatttagt ataaacat                                        3088
```

```
<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser His Val Arg
1


<210> SEQ ID NO 19
<211> LENGTH: 382
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Gly Asp Trp Ser Ala Leu Gly Lys Leu Leu Asp Lys Val Gln Ala
1               5                   10                  15

Tyr Ser Thr Ala Gly Gly Lys Val Trp Leu Ser Val Leu Phe Ile Phe
            20                  25                  30

Arg Ile Leu Leu Leu Gly Thr Ala Val Glu Ser Ala Trp Gly Asp Glu
        35                  40                  45

Gln Ser Ala Phe Arg Cys Asn Thr Gln Gln Pro Gly Cys Glu Asn Val
    50                  55                  60

Cys Tyr Asp Lys Ser Phe Pro Ile Ser His Val Arg Phe Trp Val Leu
65                  70                  75                  80

Gln Ile Ile Phe Val Ser Val Pro Thr Leu Leu Tyr Leu Ala His Val
                85                  90                  95

Phe Tyr Val Met Arg Lys Glu Glu Lys Leu Asn Lys Lys Glu Glu Glu
            100                 105                 110

Leu Lys Val Ala Gln Thr Asp Gly Val Asn Val Asp Met His Leu Lys
        115                 120                 125

Gln Ile Glu Ile Lys Lys Phe Lys Tyr Gly Ile Glu Glu His Gly Lys
    130                 135                 140

Val Lys Met Arg Gly Gly Leu Leu Arg Thr Tyr Ile Ile Ser Ile Leu
145                 150                 155                 160

Phe Lys Ser Ile Phe Glu Val Ala Phe Leu Leu Ile Gln Trp Tyr Ile
                165                 170                 175

Tyr Gly Phe Ser Leu Ser Ala Val Tyr Thr Cys Lys Arg Asp Pro Cys
            180                 185                 190

Pro His Gln Val Asp Cys Phe Leu Ser Arg Pro Thr Glu Lys Thr Ile
```

-continued

```
        195                 200                 205

Phe Ile Ile Phe Met Leu Val Val Ser Leu Val Ser Leu Ala Leu Asn
    210                 215                 220

Ile Ile Glu Leu Phe Tyr Val Phe Phe Lys Gly Val Lys Asp Arg Val
225                 230                 235                 240

Lys Gly Lys Ser Asp Pro Tyr His Ala Thr Ser Gly Ala Leu Ser Pro
                245                 250                 255

Ala Lys Asp Cys Gly Ser Gln Lys Tyr Ala Tyr Phe Asn Gly Cys Ser
            260                 265                 270

Ser Pro Thr Ala Pro Leu Ser Pro Met Ser Pro Pro Gly Tyr Lys Leu
        275                 280                 285

Val Thr Gly Asp Arg Asn Asn Ser Ser Cys Arg Asn Tyr Asn Lys Gln
    290                 295                 300

Ala Ser Glu Gln Asn Trp Ala Asn Tyr Ser Ala Glu Gln Asn Arg Met
305                 310                 315                 320

Gly Gln Ala Gly Ser Thr Ile Ser Asn Ser His Ala Gln Pro Phe Asp
                325                 330                 335

Phe Pro Asp Asp Asn Gln Asn Ser Lys Lys Leu Ala Ala Gly His Glu
            340                 345                 350

Leu Gln Pro Leu Ala Ile Val Asp Gln Arg Pro Ser Ser Arg Ala Ser
        355                 360                 365

Ser Arg Ala Ser Ser Arg Pro Arg Pro Asp Asp Leu Glu Ile
    370                 375                 380


<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Arg Pro Thr Glu Lys
1               5


<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Trp Arg Gln Ala Ala Phe Val Asp Ser Tyr
1               5                   10


<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ile Cys Val Val Gln Asp Trp Gly His His Arg Cys Thr
1               5                   10


<210> SEQ ID NO 23
```

<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
gtaattgcgg caagaagaat tgtttctgt 29

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
acccatgttg cctgggcacc 20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
gttgcctggg caccactctt 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
gcctgggcac cactcttttg 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
tgggcaccac tcttttgctt 20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
gtaggcttga accttgtcaa 20

<210> SEQ ID NO 29
<211> LENGTH: 20

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 29
tctccccagg ctgactcaac 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 30
ccaggctgac tcaaccgctg 20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 31
ctcaaccgct gtccccagca 20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 32
cagaagcgca catgagagat 20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 33
gaagcgcaca tgagagattg 20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
agtgtgggta cagacacaaa 20

<210> SEQ ID NO 35
<211> LENGTH: 20
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 35
tgggtacaga cacaaatatg 20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ggtacagaca caaatatgat 20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cagacacaaa tatgatctgc 20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gacacaaata tgatctgcag 20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
acaaatatga tctgcaggac 20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
atatgatctg caggacccag 20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 41
atgatgaaga tggttttctc 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 42
atgaagatga tgaagatggt 20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 43
agcatgaaga tgatgaagat 20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 44
atgaagatgg ttttctccgt 20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 45
aggctgtgca tgggagttag 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 46
cgctggtcca caatggctag 20

<210> SEQ ID NO 47
<211> LENGTH: 20
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 47
gctggctctg cttgaaggtc                                                  20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ggtgcccagg caacatgggt                                                  20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
aagagtggtg cccaggcaac                                                  20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
caaaagagtg gtgcccaggc                                                  20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
agcaaaagag tggtgcccag                                                  20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cttgacaagg ttcaagccta                                                  20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 53
gttgagtcag cctggggaga 20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 54
cagcggttga gtcagcctgg 20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 55
tgctggggac agcggttgag 20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 56
atctctcatg tgcgcttctg 20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 57
caatctctca tgtgcgcttc 20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 58
tttgtgtctg tacccacact 20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 59
catatttgtg tctgtaccca 20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 60
atcatatttg tgtctgtacc 20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 61
gcagatcata tttgtgtctg 20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62
ctgcagatca tatttgtgtc 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 63
gtcctgcaga tcatatttgt 20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 64
ctgggtcctg cagatcatat 20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 65
gagaaaacca tcttcatcat 20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 66
accatcttca tcatcttcat 20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 67
atcttcatca tcttcatgct 20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 68
acggagaaaa ccatcttcat 20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 69
ctaactccca tgcacagcct 20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 70
ctagccattg tggaccagcg 20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 71
gaccttcaag cagagccagc 20

<210> SEQ ID NO 72
<211> LENGTH: 46
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

```
Leu Thr Ala Val Gly Gly Glu Ser Ile Tyr Tyr Asp Glu Gln Ser Lys
1               5                   10                  15

Phe Val Cys Asn Thr Glu Gln Pro Gly Cys Glu Asn Val Cys Tyr Asp
            20                  25                  30

Ala Phe Ala Pro Leu Ser His Val Arg Phe Trp Val Phe Gln
        35                  40                  45
```

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

```
Leu Thr Ala Val Gly Gly Glu Ser Ile Tyr Tyr Asp Glu Gln Ser
1               5                   10                  15
```

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

```
Asp Glu Gln Ser Lys Phe Val Cys Asn Thr Glu Gln Pro
1               5                   10
```

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

```
Thr Glu Gln Pro Gly Cys Glu Asn Val Cys Tyr Asp Ala
1               5                   10
```

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

```
Val Cys Tyr Asp Ala Phe Ala Pro Leu Ser His Val Arg
1               5                   10
```

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

```
Ala Pro Leu Ser His Val Arg Phe Trp Val Phe Gln
1               5                   10
```

<210> SEQ ID NO 78
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Phe Glu Val Gly Phe Leu Ile Gly Gln Tyr Phe Leu Tyr Gly Phe Gln
1               5                   10                  15

Val His Pro Phe Tyr Val Cys Ser Arg Leu Pro Cys His Pro Lys Ile
            20                  25                  30

Asp Cys Phe Ile Ser Arg Pro Thr Glu Lys Thr Ile Phe Leu Leu
        35                  40                  45
```

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

```
Phe Glu Val Gly Phe Leu Ile Gly Gln Tyr Phe
1               5                   10
```

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Leu Ile Gly Gln Tyr Phe Leu Tyr Gly Phe Gln Val
1               5                   10
```

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

```
Gly Phe Gln Val His Pro Phe Tyr Val Cys Ser Arg Leu Pro
1               5                   10
```

<210> SEQ ID NO 82
<211> LENGTH: 12

<212> TYPE: PRT
<213> ORGANISM: Artificial Sequence
<220> FEATURE:
<223> OTHER INFORMATION: Description of Artificial Sequence: Synthetic peptide

<400> SEQUENCE: 82

Ser Arg Leu Pro Cys His Pro Lys Ile Asp Cys Phe
1 5 10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Ile Asp Cys Phe Ile Ser Arg Pro Thr Glu Lys Thr
1 5 10

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Ser Arg Pro Thr Glu Lys Thr Ile Phe Leu Leu
1 5 10

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Ser Arg Pro Thr Glu Lys Thr Ile Phe Ile Ile
1 5 10

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Tyr Val Cys Ser Arg Leu Pro Cys His Pro
1 5 10

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Gln Val His Pro Phe Tyr Val Cys Ser Arg Leu 1               5                   10

<210> SEQ ID NO 88
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Phe Glu Val Gly Phe Leu Ile Gly Gln Tyr Phe Leu Tyr
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Gln Tyr Phe Leu Tyr Gly Phe Gln Val His Pro
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Phe Gln Val His Pro Phe Tyr Val Cys Ser Arg
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Val Gly Gly Glu Ser Ile Tyr Tyr Asp Glu Gln
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Tyr Asp Glu Gln Ser Lys Phe Val Cys Asn Thr Glu
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

Asn Thr Glu Gln Pro Gly Cys Glu Asn Val Cys Tyr
1 5 10

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 94

Cys Tyr Asp Ala Phe Ala Pro Leu Ser His Val Arg
1 5 10

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 95

Phe Ala Pro Leu Ser His Val Arg Phe Trp Val Phe
1 5 10

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 96

Leu Ile Gly Gln Tyr
1 5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 97

Gln Val His Pro Phe
1 5

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 98

Tyr Val Cys Ser Arg
1 5

<210> SEQ ID NO 99

<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 99

Ser Arg Leu Pro Cys
1               5

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 100

Leu Pro Cys His Pro
1               5

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Gly Glu Ser Ile Tyr
1               5

<210> SEQ ID NO 102
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 102

Tyr Asp Glu Gln Ser Lys
1               5

<210> SEQ ID NO 103
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 103

Ser Lys Phe Val Cys Asn
1               5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 104

Thr Glu Gln Pro Gly Cys Glu Asn
1 5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Val Cys Tyr Asp Ala Phe Ala Pro
1 5

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

Leu Ser His Val Arg Phe Trp Val Phe Gln
1 5 10

<210> SEQ ID NO 107
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Leu Ile Gln Tyr Phe Leu Tyr Gly Phe Gln Val His Pro Phe
1 5 10

<210> SEQ ID NO 108
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Val His Pro Phe Tyr Cys Ser Arg Leu Pro Cys His Pro
1 5 10

<210> SEQ ID NO 109
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

Val Gly Gly Glu Ser Ile Tyr Tyr Asp Glu Gln Ser Lys Phe Val Cys
1 5 10 15

Asn Thr Glu Gln Pro Gly
20

<210> SEQ ID NO 110
<211> LENGTH: 22

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 110

Thr Glu Gln Pro Gly Cys Glu Asn Val Cys Tyr Asp Ala Phe Ala Pro
1 5 10 15

Leu Ser His Val Arg Phe
20

<210> SEQ ID NO 111
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 111

Ala Phe Ala Pro Leu Ser His Val Arg Phe Trp Val Phe Gln
1 5 10

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 112

Ile Asp Cys Phe Ile Ser Arg Pro Thr Glu Lys Thr Ile Phe Leu Leu
1 5 10 15

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 113

Asp Cys Phe Ile Ser Arg Pro Thr Glu Lys Thr
1 5 10

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 114

Ser Arg Pro Thr Glu Lys Thr
1 5

<210> SEQ ID NO 115
<211> LENGTH: 42
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 115

Leu Leu Ile Gln Trp Tyr Ile Tyr Gly Phe Ser Leu Ser Ala Val Tyr
1 5 10 15

Thr Cys Lys Arg Asp Pro Cys Pro His Gln Val Asp Cys Phe Leu Ser
20 25 30

Arg Pro Thr Glu Lys Thr Ile Phe Ile Ile
35 40

<210> SEQ ID NO 116
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 116

Leu Ile Gly Gln Tyr Phe Leu Tyr Gly Phe Gln Val His Pro Phe Tyr
1 5 10 15

Val Cys Ser Arg Leu Pro Cys His Pro Lys Ile Asp Cys Phe Ile Ser
20 25 30

Arg Pro Thr Glu Lys Thr Ile Phe Leu Leu
35 40

<210> SEQ ID NO 117
<211> LENGTH: 2782
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 117
gggcggcgcg gaggggcagg gccagaggga agcgctttgt tccgcgcgtg gttcccgcgc 60
ctgggggtgc gcgggagagg cgcgaatccg agtgccgcgc gcggcccggg gacttgcacg 120
ggcgtgcggg gtggaaccgc aggaagcgga gctctcgggt tcccgccccg ccccgccccg 180
ccggcggcgg aggcagcgag cgcgagagcc cagcggagtc gctgggagcc tgaggcaccg 240
agacacaaag gcaggcggga tgcgggagca ggcaaaggga aagcgaaagc cgcgcgcccg 300
gccggtgact gggtgaaggc gccgcgcagc tttcccgacg ccggctgtac ccggacctcc 360
tggtcgagcc tggcgcgccg cagccatggc catcgctcaa ctggccacgg agtacgtgtt 420
ctcggatttc ttgctgaagg agcccacgga gcccaagttc aaggggctgc gactggagct 480
ggctgtggac aagatggtca cgtgcattgc ggtggggctg cccctgctgc tcatctcgct 540
ggccttcgcg caggagatct cgattggtac acagataagc tgtttctctc caagttcttt 600
ctcctggcgt caggctgcct ttgtggattc atattgctgg gcggctgttc agcagaagaa 660
ctcactgcag agcgagtctg gaaacctccc actgtggctg cataagtttt tcccctacat 720
cctgctgctc tttgcgatcc tcctgtacct gccccccgctg ttctggcgtt tcgcagctgc 780
tcctcatatt tgctcagact tgaagtttat catggaagaa cttgacaaag tttacaaccg 840
tgcaattaag gctgcaaaga gtgcgcgtga ccttgacatg agagatggag cctgctcagt 900
tccaggtgtt accgagaact tagggcaaag tttgtgggag gtatctgaaa gccacttcaa 960
gtacccaatt gtggagcagt acttgaagac aaagaaaaat tctaataatt taatcatcaa 1020
gtacattagc tgccgcctgc tgacactcat cattatactg ttagcgtgta tctacctggg 1080
ctattacttc agcctctcct cactctcaga cgagtttgtg tgcagcatca aatcagggat 1140
cctgagaaac gacagcaccg tgcccgatca gtttcagtgc aaactcattg ccgtgggcat 1200
cttccagttg ctcagtgtca ttaaccttgt ggtttatgtc ctgctggctc ccgtggttgt 1260
ctacacgctg tttgttccat tccgacagaa gacagatgtt ctcaaagtgt acgaaatcct 1320
ccccactttt gatgttctgc atttcaaatc tgaagggtac aacgatttga gcctctacaa 1380
tctcttcttg gaggaaaata taagtgaggt caagtcatac aagtgtctta aggtactgga 1440
gaatattaag agcagtggtc aggggatcga cccaatgcta ctcctgacaa accttggcat 1500
gatcaagatg gatgttgttg atggcaaaac tcccatgtct gcagagatga gagaggagca 1560
ggggaaccag acggcagagc tccaaggtat gaacatagac agtgaaacta aagcaaataa 1620
tggagagaag aatgcccgac agagacttct ggattcttct tgctgatgat tttttccctt 1680
gagctgtaaa tctgtgactt ctgcgacatg ggatttaatt tggctaaagc acccctgttg 1740
gtttcacagc tggtttgcaa taaatggttc ttggtggaga tactgagcat gtcttattga 1800
gtccctaatg gaaatggtga tcaacaaaag gttatggaag aatggtttat gaacttccca 1860
taggaagcac ctgagagata gtaaactgca gcaagtaact atgtgtaagt cctcatcaaa 1920
tgaaaagcag aaagacaaga acaattagtc aagagcagta gccctgtcag agcctcggag 1980
caataccttt ctgtacccgt ggtgagacaa gacccagagc tactggaaaa caagcacttt 2040
ggaagatttg ttttgttttc atggaataat aatatgtcag ggtataattt aacgtgagtt 2100
tcttatgtgc ccttaaagac tgttagacaa gaaaagcatt cactggctaa taatccatag 2160
gtcgacctat gtcctaagtt aggtgtaagg tccgatgcct tggcccacac tcgagctctc 2220
tttacattgt tagttgtcaa ccttggctga tggaaatccc gtaaccacta tttgttgcac 2280
tgtgccttga agggcagcag gcccaagtgc tgctctgact gaaaactgag ttaacaagat 2340
gaaatctaaa ggatattcac agtgacttca attcaggaag aatgcttcca aaagagccca 2400
gtggggaaat ctgacatcac agaagacatt aattcagtca ctttcaaaga gtttgtctac 2460
aggcggtttc tctgttatca aaggcatttg aaataggatt ttacttaaac aataatggaa 2520
cacaggagta tttaaagtga agaacacttt gcctgaatgt gatcagggca cataagtgac 2580
attggcatgc ttcatatggc gtgcttggag ccagaaaaac ttagcggttt attttgttta 2640
tatttaagca cagctttaaa aaattcatta tcgtttattc agtgtccgaa ttgaggccat 2700
ttgggaagaa aattctagca ctggtggaga attatagaat aaagattata aatggttgga 2760
taagacaaaa aaaaaaaaaa aa 2782

<210> SEQ ID NO 118
<211> LENGTH: 3069
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 118
atgcaccacc tcctggagca gtcggcggac atggcgaccg cgctgctggc gggagagaag 60
ctgcgggagc tgatcctgcc gggcgcgcag gacgacaagg cgggcgcgct ggccgcgctg 120
cttctgcagc tgaagctgga gctgccgttc gaccgggtgg tcaccatcgg caccgtgctg 180
gtgcccatcc tgctggtcac cctggtcttc accaagaact tcgcagagga acccatttac 240
tgttacaccc cgcacaactt cacgcgcgac caggcgctgt acgcccgcgg ctactgctgg 300
acggagctgc gggacgcgct gcccggcgtg gacgccagcc tgtggccgtc gctgtttgag 360

```
cacaagttcc tgccctacgc gctgctggcc ttcgccgcca tcatgtacgt gcccgcgctg    420
ggctgggagt tcctggcctc cacgcgcctc acctccgagc tcaacttcct gctgcaggag    480
atcgacaact gttaccaccg ggcggccgag ggccgcgcgc ccaagatcga gaagcagatc    540
cagtccaagg gcccgggcat cacggagcgc gagaagcgcg agatcatcga gaacgcggag    600
aaggagaaga gcccggagca gaacctgttc gagaagtacc tggagcgccg cggccgcagc    660
aacttcctgg ccaagctgta cctggcgcgg cacgtgctga tcctgctgct gagcgccgtg    720
cccatctcct acctgtgcac ctactacgcc acgcagaagc agaacgagtt cacctgcgcg    780
ctgggcgcgt ccccggacgg ggcggcaggt gcggggcccg cggtgcgcgt gagctgcaag    840
ctcccgtccg tgcaactgca gcgcatcatc gcgggcgtgg acatcgtgct gctgtgcgtc    900
atgaacctca tcatcctcgt caacctcatc cacctcttca tcttccgcaa gagcaacttc    960
atcttcgaca agctgcacaa ggtgggcatc aagacgcgcc ggcagtggcg ccgctcgcag   1020
ttctgcgaca tcaacatcct ggccatgttc tgcaacgaga accgcgacca catcaagtcg   1080
ctcaaccggc tggacttcat caccaacgag agcgacctca tgtacgacaa cgtggtccgg   1140
cagctgctgg cggcgctggc gcagtccaac cacgacgcca cccccacggt gcgcgactcg   1200
ggggtgcaga ccgtggaccc cagcgccaac cccgccgagc ccgacggcgc cgccgagccg   1260
cccgtggtca agcggccgcg caagaagatg aagtggatcc ccaccagcaa cccgcttccg   1320
cagcccttca aggagccgct ggccatcatg cgcgtggaga acagcaaggc ggagaagccg   1380
aagcccgcgc gcaggaagac ggccacggac acgctgatcg cgccgctgct ggaccgctcc   1440
gcccaccact acaagggcgg agggggcgac ccgggccccg gccccgcccc tgcccccgcc   1500
ccgccgcccg cccctgacaa gaagcacgcg cgccacttct ccctggacgt gcacccctac   1560
atcctcggca ccaagaaggc caaggccgag gcggtgcccg ccgccctgcc cgcctcccgg   1620
agccaggagg ggggcttcct gtcccaggcg gaggactgtg ggctaggcct ggccccggcg   1680
cccatcaaag atgctccgct ccccgagaag gaaatcccgt accccacaga gccagcccgg   1740
gcagggcttc cctcgggggg cccgttccac gtccgctcac ctcccgccgc ccctgctgtg   1800
gcccctctga caccagccag cctgggcaag gcggagcccc tcaccatcct gagccgaaac   1860
gccacacacc cgctgctgca catcaacacg ctgtacgagg cccgggagga ggaggacggg   1920
ggcccccgcc tgccgcagga cgtgggggac ctcatcgcca tccctgcccc acagcagatc   1980
ctcatcgcca ccttcgacga gccgagaacg gtcgtgagta ctgtggagtt ttgagggatg   2040
gcaccgtcca ggccgccgag agcccctctg cctgtgtcgt gtggcctggc cagcctcccg   2100
gtggacacca gccctgcgtg gacgtggcct gtgcttcgcc cgcactgcgc gcatccccaa   2160
cctctgtccg catgcctggg gccttcgccc ccacgtgctc gacaggggaa cccgcccgga   2220
cggcatcgcc aggcactggc tggggtgggg aaaggtggcc cagtggagcc ggtggccagg   2280
aaggctgaag cccgcttccc atgctcctgc atcaggtgcc cagccgtggg tgggggccct   2340
gaggtgaaga gtttattttt ttagtccgtt tcgtcctggc cccgggctgt ggcgagacag   2400
cccaactccc ccagcccagc tcccccagcc cagagccagg gaagaggaag gtggggccag   2460
tcccaccagt ggggtggcca cgcccatggg gtcacatgct caggggtcac cccctgcagg   2520
gacctgatgc cctcgggtgg gagggaccga ggtccaccct cgggtcaaag gtcaacgtgc   2580
actttctcct tgtcgcctga cagacatttt attttactaa gactgctgta ccgaacaagc   2640
atatttatca tcaggagaca ggatgggttt aaagcaggat ggtgtgtgtg tgaacgggca   2700
```

```
tgagcagagg tgagcgtgag cgagcgggtg tgtatgtacg agtgtgcacg tgtgtgcgtg   2760
tgcacagagg gtgtggtgcc agcttgagtg ggagtgtgtg agtgtgagca ggcgggcgag   2820
tgcgtgagtg cacgccagcg cgtggcccat gtatgaggag tgaaggggcc caacgcaata   2880
accacgtccc ccacccgggc cccccgccgc ggctgaggcc acatggcttc ctgtgggagc   2940
cccggccggc acccggctgg tcccacccca aatacctcag ccatggagac catgtcatgc   3000
agaattaaca aggtagcacc gagcatatca ataaatatta ttctgataat caaaaaaaaa   3060
aaaaaaaaa                                                           3069
```

<210> SEQ ID NO 119
<211> LENGTH: 2984
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 119

```
atgcaccacc tcctggagca gtcggcggac atggcgaccg cgctgctggc gggagagaag     60
ctgcgggagc tgatcctgcc gggcgcgcag gacgacaagg cgggcgcgct ggccgcgctg    120
cttctgcagc tgaagctgga gctgccgttc gaccgggtgg tcaccatcgg caccgtgctg    180
gtgcccatcc tgctggtcac cctggtcttc accaagaact tcgcagagga acccatttac    240
tgttacaccc cgcacaactt cacgcgcgac caggcgctgt acgcccgcgg ctactgctgg    300
acggagctgc gggacgcgct gcccggcgtg gacgccagcc tgtggccgtc gctgtttgag    360
cacaagttcc tgccctacgc gctgctggcc ttcgccgcca tcatgtacgt gcccgcgctg    420
ggctgggagt tcctggcctc cacgcgcctc acctccgagc tcaacttcct gctgcaggag    480
atcgacaact gttaccaccg ggcggccgag ggccgcgcgc ccaagatcga gaagcagatc    540
cagtccaagg gcccgggcat cacggagcgc gagaagcgcg agatcatcga gaacgcggag    600
aaggagaaga gcccggagca gaacctgttc gagaagtacc tggagcgccg cggccgcagc    660
aacttcctgg ccaagctgta cctggcgcgg cacgtgctga tcctgctgct gagcgccgtg    720
cccatctcct acctgtgcac ctactacgcc acgcagaagc agaacgagtt cacctgcgcg    780
ctgggcgcgt ccccggacgg ggcggcaggt gcggggcccg cggtgcgcgt gagctgcaag    840
ctcccgtccg tgcaactgca gcgcatcatc gcgggcgtgg acatcgtgct gctgtgcgtc    900
atgaacctca tcatcctcgt caacctcatc cacctcttca tcttccgcaa gagcaacttc    960
atcttcgaca agctgcacaa ggtgggcatc aagacgcgcc ggcagtggcg ccgctcgcag   1020
ttctgcgaca tcaacatcct ggccatgttc tgcaacgaga accgcgacca catcaagtcg   1080
ctcaaccggc tggacttcat caccaacgag agcgacctca tgtacgacaa cgtggtccgg   1140
cagctgctgg cggcgctggc gcagtccaac cacgacgcca cccccacggt gcgcgactcg   1200
ggggtgcaga ccgtggaccc cagcgccaac cccgccgagc ccgacggcgc cgccgagccg   1260
cccgtggtca agcggccgcg caagaagatg aagtggatcc ccaccagcaa cccgcttccg   1320
cagcccttca aggagccgct ggccatcatg cgcgtggaga acagcaaggc ggagaagccg   1380
aagcccgcgc gcaggaagac ggccacggac acgctgatcg cgccgctgct ggaccgctcc   1440
gcccaccact acaagggcgg agggggcgac ccgggccccg gccccgcccc tgcccccgcc   1500
ccgccgcccg cccctgacaa gaagcacgcg cgccacttct ccctggacgt gcacccctac   1560
atcctcggca ccaagaaggc caaggccgag gcggtgcccg ccgccctgcc cgcctcccgg   1620
```

agccaggagg ggggcttcct gtcccaggcg gaggactgtg ggctaggcct ggccccggcg 1680
cccatcaaag atgctccgct ccccgagaag gaaatcccgt accccacaga gccagcccgg 1740
gcagggcttc cctcgggggg cccgttccac gtccgctcac ctcccgccgc ccctgctgtg 1800
gcccctctga caccagccag cctgggcaag gcggagcccc tcaccatcct gagccgaaac 1860
gccacacacc cgctgctgca catcaacacg ctatcctcat cgccaccttc gacgagccga 1920
gaacggtcgt gagtactgtg gagttttgag ggatggcacc gtccaggccg ccgagagccc 1980
ctctgcctgt gtcgtgtggc ctggccagcc tcccggtgga caccagccct gcgtggacgt 2040
ggcctgtgct tcgcccgcac tgcgcgcatc cccaacctct gtccgcatgc ctggggcctt 2100
cgcccccacg tgctcgacag gggaacccgc ccggacggca tcgccaggca ctggctgggg 2160
tggggaaagg tggcccagtg gagccggtgg ccaggaaggc tgaagcccgc ttcccatgct 2220
cctgcatcag gtgcccagcc gtgggtgggg gccctgaggt gaagagttta tttttttagt 2280
ccgtttcgtc ctggccccgg gctgtggcga gacagcccaa ctcccccagc ccagctcccc 2340
cagcccagag ccagggaaga ggaaggtggg gccagtccca ccagtggggt ggccacgccc 2400
atggggtcac atgctcaggg gtcaccccct gcagggacct gatgccctcg ggtgggaggg 2460
accgaggtcc accctcgggt caaaggtcaa cgtgcacttt ctccttgtcg cctgacagac 2520
attttatttt actaagactg ctgtaccgaa caagcatatt tatcatcagg agacaggatg 2580
ggtttaaagc aggatggtgt gtgtgtgaac gggcatgagc agaggtgagc gtgagcgagc 2640
gggtgtgtat gtacgagtgt gcacgtgtgt gcgtgtgcac agagggtgtg gtgccagctt 2700
gagtgggagt gtgtgagtgt gagcaggcgg gcgagtgcgt gagtgcacgc cagcgcgtgg 2760
cccatgtatg aggagtgaag gggcccaacg caataaccac gtcccccacc cgggcccccc 2820
gccgcggctg aggccacatg gcttcctgtg ggagccccgg ccggcacccg gctggtccca 2880
ccccaaatac ctcagccatg gagaccatgt catgcagaat taacaaggta gcaccgagca 2940
tatcaataaa tattattctg ataatcaaaa aaaaaaaaaa aaaa 2984

<210> SEQ ID NO 120
<211> LENGTH: 3035
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 120
atgcaccacc tcctggagca gtcggcggac atggcgaccg cgctgctggc gggagagaag 60
ctgcgggagc tgatcctgcc gggcgcgcag gacgacaagg cgggcgcgct ggccgcgctg 120
cttctgcagc tgaagctgga gctgccgttc gaccgggtgg tcaccatcgg caccgtgctg 180
gtgcccatcc tgctggtcac cctggtcttc accaagaact tcgcagggtg gacgctcttc 240
tctggctcct gggattggct gtgaggacaa aacataaagg aacccattta ctgttacacc 300
ccgcacaact tcacgcgcga ccaggcgctg tacgcccgcg gctactgctg gacggagctg 360
cgggacgcgc tgcccggcgt ggacgccagc ctgtggccgt cgctgtttga gcacaagttc 420
ctgccctacg cgctgctggc cttcgccgcc atcatgtacg tgcccgcgct gggctgggag 480
ttcctggcct ccacgcgcct cacctccgag ctcaacttcc tgctgcagga gatcgacaac 540
tgttaccacc gggcggccga gggccgcgcg cccaagatcg agaagcagat ccagtccaag 600
ggcccgggca tcacggagcg cgagaagcgc gagatcatcg agaacgcgga gaaggagaag 660

```
agcccggagc agaacctgtt cgagaagtac ctggagcgcc gcggccgcag caacttcctg    720
gccaagctgt acctggcgcg gcacgtgctg atcctgctgc tgagcgccgt gcccatctcc    780
tacctgtgca cctactacgc cacgcagaag cagaacgagt tcacctgcgc gctgggcgcg    840
tccccggacg gggcggcagg tgcggggccc gcggtgcgcg tgagctgcaa gctcccgtcc    900
gtgcaactgc agcgcatcat cgcgggcgtg gacatcgtgc tgctgtgcgt catgaacctc    960
atcatcctcg tcaacctcat ccacctcttc atcttccgca agagcaactt catcttcgac   1020
aagctgcaca aggtgggcat caagacgcgc cggcagtggc gccgctcgca gttctgcgac   1080
atcaacatcc tggccatgtt ctgcaacgag aaccgcgacc acatcaagtc gctcaaccgg   1140
ctggacttca tcaccaacga gagcgacctc atgtacgaca acgtggtccg gcagctgctg   1200
gcggcgctgg cgcagtccaa ccacgacgcc acccccacgg tgcgcgactc gggggtgcag   1260
accgtggacc ccagcgccaa ccccgccgag cccgacggcg ccgccgagcc gcccgtggtc   1320
aagcggccgc gcaagaagat gaagtggatc cccaccagca acccgcttcc gcagcccttc   1380
aaggagccgc tggccatcat gcgcgtggag aacagcaagg cggagaagcc gaagcccgcg   1440
cgcaggaaga cggccacgga cacgctgatc gcgccgctgc tggaccgctc cgcccaccac   1500
tacaagggcg gagggggcga cccgggcccc ggccccgccc ctgcccccgc cccgccgccc   1560
gcccctgaca agaagcacgc gcgccacttc tccctggacg tgcaccccta catcctcggc   1620
accaagaagg ccaaggccga ggcggtgccc gccgccctgc ccgcctcccg gagccaggag   1680
gggggcttcc tgtcccaggc ggaggactgt gggctaggcc tggccccggc gcccatcaaa   1740
gatgctccgc tccccgagaa ggaaatcccg taccccacag agccagcccg ggcagggctt   1800
ccctcggggg gcccgttcca cgtccgctca cctcccgccg cccctgctgt ggcccctctg   1860
acaccagcca gcctgggcaa ggcggagccc ctcaccatcc tgagccgaaa cgccacacac   1920
ccgctgctgc acatcaacac gctatcctca tcgccacctt cgacgagccg agaacggtcg   1980
tgagtactgt ggagttttga gggatggcac cgtccaggcc gccgagagcc cctctgcctg   2040
tgtcgtgtgg cctggccagc ctcccggtgg acaccagccc tgcgtggacg tggcctgtgc   2100
ttcgcccgca ctgcgcgcat ccccaacctc tgtccgcatg cctggggcct tcgcccccac   2160
gtgctcgaca ggggaacccg cccggacggc atcgccaggc actggctggg gtggggaaag   2220
gtggcccagt ggagccggtg gccaggaagg ctgaagcccg cttcccatgc tcctgcatca   2280
ggtgcccagc cgtgggtggg ggccctgagg tgaagagttt atttttttag tccgtttcgt   2340
cctggccccg ggctgtggcg agacagccca actcccccag cccagctccc ccagcccaga   2400
gccagggaag aggaaggtgg ggccagtccc accagtgggg tggccacgcc catggggtca   2460
catgctcagg ggtcaccccc tgcagggacc tgatgccctc gggtgggagg gaccgaggtc   2520
caccctcggg tcaaaggtca acgtgcactt tctccttgtc gcctgacaga cattttattt   2580
tactaagact gctgtaccga acaagcatat ttatcatcag gagacaggat gggtttaaag   2640
caggatggtg tgtgtgtgaa cgggcatgag cagaggtgag cgtgagcgag cgggtgtgta   2700
tgtacgagtg tgcacgtgtg tgcgtgtgca cagagggtgt ggtgccagct tgagtgggag   2760
tgtgtgagtg tgagcaggcg ggcgagtgcg tgagtgcacg ccagcgcgtg gcccatgtat   2820
gaggagtgaa ggggcccaac gcaataacca cgtcccccac ccgggccccc cgccgcggct   2880
gaggccacat ggcttcctgt gggagccccg gccggcaccc ggctggtccc accccaaata   2940
cctcagccat ggagaccatg tcatgcagaa ttaacaaggt agcaccgagc atatcaataa   3000
atattattct gataatcaaa aaaaaaaaaa aaaaa                              3035
```

<210> SEQ ID NO 121
<211> LENGTH: 1609
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 121
atgtcacttg cacacacagc tgcagagtac atgctctcag atgccctgct gcctgaccgc 60
aggggacccc gcctcaaagg actgcgtctg gaactgcccc tggaccggat agtcaagttc 120
gtagctgtgg gctccccctt gttgctgatg tccctggcat tcgcccagga gttctcctct 180
gggtctccga tcagctgctt ctctcccagt aacttcagca tccggcaggc agcctacgtg 240
gacagctcct gctgggactc actgcttcac cataagcagg acgggcctgg ccaggacaaa 300
atgaaatctc tctggcccca caaggccctc ccctactccc tgctggccct ggccttgctc 360
atgtacctgc cggtgctgct gtggcagtat gcagctgtgc cagccctcag ctccgatctg 420
ctgttcatca tcagcgaact ggacaaatct tataatcgct ccatccgcct cgtgcagcac 480
atgctgaaga tccggcagaa gagttccgac ccctatgtgt tctggaatga gctggagaag 540
gctcggaaag aacgatactt tgaattccct ttgctagagc ggtacctggc atgtaagcag 600
cgttcacatt cgctagtggc tacctacctc ctgaggaact ccctcttgct catcttcacc 660
tccgccactt acctatacct tggtcatttc catctggatg tcttcttcca ggaagaattc 720
agctgctcca tcaagacagg gctgctaagt gatgagaccc atgtccccaa tctgatcaca 780
tgcaggctga catcactgtc cattttccag attgttagcc tctccagtgt agcaatatac 840
accatattgg ttccagtgat aatatacaac ctcacacggc tatgtcggtg ggacaaacga 900
cttttatctg tctatgagat gctcccagct tttgatctcc tcagcagaaa gatgctagga 960
tgtcccatca atgacctcaa tgtgatcctt cttttcctcc gagctaacat ctctgagctc 1020
atctctttta gctggctgag tgtcttatgt gtgttgaagg atacaaccac ccagaagcac 1080
aatattgaca cagtagttga ttttatgact ttattggctg gcttagaacc ctcaaaaccc 1140
aaacacctca ccaactcggc atgtgatgaa cacccatagt taagaaacca tggagcaaga 1200
aagcttgtgg aaagtctctc tccttcctca taagacatgc acactaatac acatacacac 1260
caaaaaatta cacattttaa aactgctaag cttggattta actgaatcat atatctttta 1320
tcatgttatc ctaaaagtga gaagacataa ccaagacatg gaaataaatg tgaaagctgg 1380
agccgaagag tcaaagagct aaaaaattaa gtctagaaca ttctatgagg atagtataaa 1440
taaaaagaaa tacagtctag acatgctgca aggaaagaag attctaaagt ccgtttatgg 1500
aggcaattcc atatcctttc ttgaacgcac attcagctta ccccagagag caagtgaggc 1560
aatctggcaa aagattaata aagatgtaaa cccctggaaa aaaaaaaaa 1609

<210> SEQ ID NO 122
<211> LENGTH: 425
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

Met Ala Ile Ala Gln Leu Ala Thr Glu Tyr Val Phe Ser Asp Phe Leu
1 5 10 15

```
Leu Lys Glu Pro Thr Glu Pro Lys Phe Lys Gly Leu Arg Leu Glu Leu
            20                  25                  30

Ala Val Asp Lys Met Val Thr Cys Ile Ala Val Gly Leu Pro Leu Leu
        35                  40                  45

Leu Ile Ser Leu Ala Phe Ala Gln Glu Ile Ser Ile Gly Thr Gln Ile
    50                  55                  60

Ser Cys Phe Ser Pro Ser Ser Phe Ser Trp Arg Gln Ala Ala Phe Val
65                  70                  75                  80

Asp Ser Tyr Cys Trp Ala Ala Val Gln Gln Lys Asn Ser Leu Gln Ser
                85                  90                  95

Glu Ser Gly Asn Leu Pro Leu Trp Leu His Lys Phe Phe Pro Tyr Ile
            100                 105                 110

Leu Leu Leu Phe Ala Ile Leu Leu Tyr Leu Pro Pro Leu Phe Trp Arg
        115                 120                 125

Phe Ala Ala Ala Pro His Ile Cys Ser Asp Leu Lys Phe Ile Met Glu
    130                 135                 140

Glu Leu Asp Lys Val Tyr Asn Arg Ala Ile Lys Ala Ala Lys Ser Ala
145                 150                 155                 160

Arg Asp Leu Asp Met Arg Asp Gly Ala Cys Ser Val Pro Gly Val Thr
                165                 170                 175

Glu Asn Leu Gln Ser Leu Trp Glu Val Ser Glu Ser His Phe Lys Tyr
            180                 185                 190

Pro Ile Val Glu Gln Tyr Leu Lys Thr Lys Lys Asn Ser Asn Asn Leu
        195                 200                 205

Ile Ile Lys Tyr Ile Ser Cys Arg Leu Leu Thr Leu Ile Ile Ile Leu
    210                 215                 220

Leu Ala Cys Ile Tyr Leu Gly Tyr Tyr Phe Ser Leu Ser Ser Leu Ser
225                 230                 235                 240

Asp Glu Phe Val Cys Ser Ile Lys Ser Gly Ile Leu Arg Asn Asp Ser
                245                 250                 255

Thr Val Pro Asp Gln Phe Gln Cys Lys Leu Ile Ala Val Gly Ile Phe
            260                 265                 270

Gln Leu Leu Ser Val Ile Asn Leu Val Val Tyr Val Leu Leu Ala Pro
        275                 280                 285

Val Val Val Tyr Thr Leu Phe Val Pro Phe Arg Gln Lys Thr Asp Val
    290                 295                 300

Leu Lys Val Tyr Glu Ile Leu Pro Thr Phe Asp Val Leu His Phe Lys
305                 310                 315                 320

Ser Glu Gly Tyr Asn Asp Leu Ser Leu Tyr Asn Leu Phe Leu Glu Glu
                325                 330                 335

Asn Ile Ser Glu Val Lys Ser Tyr Lys Cys Leu Lys Val Leu Glu Asn
            340                 345                 350

Ile Lys Ser Ser Gly Gln Gly Ile Asp Pro Met Leu Leu Leu Thr Asn
        355                 360                 365

Leu Gly Met Ile Lys Met Asp Val Val Asp Gly Lys Thr Pro Met Ser
    370                 375                 380

Ala Glu Met Arg Glu Glu Gln Gly Asn Gln Thr Ala Glu Leu Gln Gly
385                 390                 395                 400

Met Asn Ile Asp Ser Glu Thr Lys Ala Asn Asn Gly Glu Lys Asn Ala
                405                 410                 415

Arg Gln Arg Leu Leu Asp Ser Ser Cys
            420                 425
```

<210> SEQ ID NO 123
<211> LENGTH: 677
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 123

Met His His Leu Leu Glu Gln Ser Ala Asp Met Ala Thr Ala Leu Leu
1 5 10 15

Ala Gly Glu Lys Leu Arg Glu Leu Ile Leu Pro Gly Ala Gln Asp Asp
20 25 30

Lys Ala Gly Ala Leu Ala Ala Leu Leu Leu Gln Leu Lys Leu Glu Leu
35 40 45

Pro Phe Asp Arg Val Val Thr Ile Gly Thr Val Leu Val Pro Ile Leu
50 55 60

Leu Val Thr Leu Val Phe Thr Lys Asn Phe Ala Glu Glu Pro Ile Tyr
65 70 75 80

Cys Tyr Thr Pro His Asn Phe Thr Arg Asp Gln Ala Leu Tyr Ala Arg
85 90 95

Gly Tyr Cys Trp Thr Glu Leu Arg Asp Ala Leu Pro Gly Val Asp Ala
100 105 110

Ser Leu Trp Pro Ser Leu Phe Glu His Lys Phe Leu Pro Tyr Ala Leu
115 120 125

Leu Ala Phe Ala Ala Ile Met Tyr Val Pro Ala Leu Gly Trp Glu Phe
130 135 140

Leu Ala Ser Thr Arg Leu Thr Ser Glu Leu Asn Phe Leu Leu Gln Glu
145 150 155 160

Ile Asp Asn Cys Tyr His Arg Ala Ala Glu Gly Arg Ala Pro Lys Ile
165 170 175

Glu Lys Gln Ile Gln Ser Lys Gly Pro Gly Ile Thr Glu Arg Glu Lys
180 185 190

Arg Glu Ile Ile Glu Asn Ala Glu Lys Glu Lys Ser Pro Glu Gln Asn
195 200 205

Leu Phe Glu Lys Tyr Leu Glu Arg Arg Gly Arg Ser Asn Phe Leu Ala
210 215 220

Lys Leu Tyr Leu Ala Arg His Val Leu Ile Leu Leu Leu Ser Ala Val
225 230 235 240

Pro Ile Ser Tyr Leu Cys Thr Tyr Tyr Ala Thr Gln Lys Gln Asn Glu
245 250 255

Phe Thr Cys Ala Leu Gly Ala Ser Pro Asp Gly Ala Ala Gly Ala Gly
260 265 270

Pro Ala Val Arg Val Ser Cys Lys Leu Pro Ser Val Gln Leu Gln Arg
275 280 285

Ile Ile Ala Gly Val Asp Ile Val Leu Leu Cys Val Met Asn Leu Ile
290 295 300

Ile Leu Val Asn Leu Ile His Leu Phe Ile Phe Arg Lys Ser Asn Phe
305 310 315 320

Ile Phe Asp Lys Leu His Lys Val Gly Ile Lys Thr Arg Arg Gln Trp
325 330 335

Arg Arg Ser Gln Phe Cys Asp Ile Asn Ile Leu Ala Met Phe Cys Asn
340 345 350

Glu Asn Arg Asp His Ile Lys Ser Leu Asn Arg Leu Asp Phe Ile Thr
355 360 365

Asn Glu Ser Asp Leu Met Tyr Asp Asn Val Val Arg Gln Leu Leu Ala
370 375 380

Ala Leu Ala Gln Ser Asn His Asp Ala Thr Pro Thr Val Arg Asp Ser
385 390 395 400

Gly Val Gln Thr Val Asp Pro Ser Ala Asn Pro Ala Glu Pro Asp Gly
405 410 415

Ala Ala Glu Pro Pro Val Val Lys Arg Pro Arg Lys Lys Met Lys Trp
420 425 430

Ile Pro Thr Ser Asn Pro Leu Pro Gln Pro Phe Lys Glu Pro Leu Ala
435 440 445

Ile Met Arg Val Glu Asn Ser Lys Ala Glu Lys Pro Lys Pro Ala Arg
450 455 460

Arg Lys Thr Ala Thr Asp Thr Leu Ile Ala Pro Leu Leu Asp Arg Ser
465 470 475 480

Ala His His Tyr Lys Gly Gly Gly Gly Asp Pro Gly Pro Gly Pro Ala
485 490 495

Pro Ala Pro Ala Pro Pro Pro Ala Pro Asp Lys Lys His Ala Arg His
500 505 510

Phe Ser Leu Asp Val His Pro Tyr Ile Leu Gly Thr Lys Lys Ala Lys
515 520 525

Ala Glu Ala Val Pro Ala Ala Leu Pro Ala Ser Arg Ser Gln Glu Gly
530 535 540

Gly Phe Leu Ser Gln Ala Glu Asp Cys Gly Leu Gly Leu Ala Pro Ala
545 550 555 560

Pro Ile Lys Asp Ala Pro Leu Pro Glu Lys Glu Ile Pro Tyr Pro Thr
565 570 575

Glu Pro Ala Arg Ala Gly Leu Pro Ser Gly Gly Pro Phe His Val Arg
580 585 590

Ser Pro Pro Ala Ala Pro Ala Val Ala Pro Leu Thr Pro Ala Ser Leu
595 600 605

Gly Lys Ala Glu Pro Leu Thr Ile Leu Ser Arg Asn Ala Thr His Pro
610 615 620

Leu Leu His Ile Asn Thr Leu Tyr Glu Ala Arg Glu Glu Glu Asp Gly
625 630 635 640

Gly Pro Arg Leu Pro Gln Asp Val Gly Asp Leu Ile Ala Ile Pro Ala
645 650 655

Pro Gln Gln Ile Leu Ile Ala Thr Phe Asp Glu Pro Arg Thr Val Val
660 665 670

Ser Thr Val Glu Phe
675

<210> SEQ ID NO 124
<211> LENGTH: 392
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 124

Met Ser Leu Ala His Thr Ala Ala Glu Tyr Met Leu Ser Asp Ala Leu
1 5 10 15

Leu Pro Asp Arg Arg Gly Pro Arg Leu Lys Gly Leu Arg Leu Glu Leu
20 25 30

Pro Leu Asp Arg Ile Val Lys Phe Val Ala Val Gly Ser Pro Leu Leu

```
        35                  40                  45

Leu Met Ser Leu Ala Phe Ala Gln Glu Phe Ser Ser Gly Ser Pro Ile
    50                  55                  60

Ser Cys Phe Ser Pro Ser Asn Phe Ser Ile Arg Gln Ala Ala Tyr Val
65                  70                  75                  80

Asp Ser Ser Cys Trp Asp Ser Leu Leu His His Lys Gln Asp Gly Pro
                85                  90                  95

Gly Gln Asp Lys Met Lys Ser Leu Trp Pro His Lys Ala Leu Pro Tyr
            100                 105                 110

Ser Leu Leu Ala Leu Ala Leu Leu Met Tyr Leu Pro Val Leu Leu Trp
        115                 120                 125

Gln Tyr Ala Ala Val Pro Ala Leu Ser Ser Asp Leu Leu Phe Ile Ile
    130                 135                 140

Ser Glu Leu Asp Lys Ser Tyr Asn Arg Ser Ile Arg Leu Val Gln His
145                 150                 155                 160

Met Leu Lys Ile Arg Gln Lys Ser Ser Asp Pro Tyr Val Phe Trp Asn
                165                 170                 175

Glu Leu Glu Lys Ala Arg Lys Glu Arg Tyr Phe Glu Phe Pro Leu Leu
            180                 185                 190

Glu Arg Tyr Leu Ala Cys Lys Gln Arg Ser His Ser Leu Val Ala Thr
        195                 200                 205

Tyr Leu Leu Arg Asn Ser Leu Leu Leu Ile Phe Thr Ser Ala Thr Tyr
    210                 215                 220

Leu Tyr Leu Gly His Phe His Leu Asp Val Phe Phe Gln Glu Glu Phe
225                 230                 235                 240

Ser Cys Ser Ile Lys Thr Gly Leu Leu Ser Asp Glu Thr His Val Pro
                245                 250                 255

Asn Leu Ile Thr Cys Arg Leu Thr Ser Leu Ser Ile Phe Gln Ile Val
            260                 265                 270

Ser Leu Ser Ser Val Ala Ile Tyr Thr Ile Leu Val Pro Val Ile Ile
        275                 280                 285

Tyr Asn Leu Thr Arg Leu Cys Arg Trp Asp Lys Arg Leu Leu Ser Val
    290                 295                 300

Tyr Glu Met Leu Pro Ala Phe Asp Leu Leu Ser Arg Lys Met Leu Gly
305                 310                 315                 320

Cys Pro Ile Asn Asp Leu Asn Val Ile Leu Leu Phe Leu Arg Ala Asn
                325                 330                 335

Ile Ser Glu Leu Ile Ser Phe Ser Trp Leu Ser Val Leu Cys Val Leu
            340                 345                 350

Lys Asp Thr Thr Thr Gln Lys His Asn Ile Asp Thr Val Val Asp Phe
        355                 360                 365

Met Thr Leu Leu Ala Gly Leu Glu Pro Ser Lys Pro Lys His Leu Thr
    370                 375                 380

Asn Ser Ala Cys Asp Glu His Pro
385                 390
```

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 125

```
Ala Asp Cys Phe Leu Ser Arg Pro Thr Glu Lys Thr
1               5                   10


<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Val Ala Cys Phe Leu Ser Arg Pro Thr Glu Lys Thr
1               5                   10


<210> SEQ ID NO 127
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Val Asp Cys Phe Leu Ser Arg Pro Thr Ala Lys Thr
1               5                   10


<210> SEQ ID NO 128
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Val Asp Cys Phe Leu Ser Arg Pro Thr Glu Ala Thr
1               5                   10


<210> SEQ ID NO 129
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Ser Ala Trp Gly Asp Glu Gln Ser Ala Phe Arg Cys Asn Thr Gln
1               5                   10                  15

Gln Pro Gly Cys Glu Asn Val Cys Tyr Asp Lys Ser Phe Pro Ile Ser
            20                  25                  30

His Val Arg
        35


<210> SEQ ID NO 130
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gly Glu Ser Ile Tyr Tyr Asp Glu Gln Ser Lys Phe Val Cys Asn Thr
1               5                   10                  15
```

Glu Gln Pro Gly Cys Glu Asn Val Cys Tyr Asp Ala Phe Ala Pro Leu
            20                  25                  30

Ser His Val Arg
        35

<210> SEQ ID NO 131
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 131

Leu Leu Ile Gln Trp Tyr Ile Tyr Gly Phe Ser Leu Ser Ala Val Tyr
1               5                   10                  15

Thr Cys Lys Arg Asp Pro Cys Pro His Gln Val Asp Cys Phe Leu Ser
            20                  25                  30

Arg Pro Thr Glu Lys Thr
        35

<210> SEQ ID NO 132
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 132

Leu Ile Gly Gln Tyr Phe Leu Tyr Gly Phe Gln Val His Pro Phe Tyr
1               5                   10                  15

Val Cys Ser Arg Leu Pro Cys His Pro Lys Ile Asp Cys Phe Ile Ser
            20                  25                  30

Arg Pro Thr Glu Lys Thr
        35

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 133

Lys Gln Ile Glu Ile Lys Lys Phe Lys
1               5

<210> SEQ ID NO 134
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 134

Asp Gly Val Asn Val Glu Met His Leu Lys Gln Ile Glu Ile Lys Lys
1               5                   10                  15

Phe Lys Tyr Gly Ile Glu Glu His Gly Lys
            20                  25

<210> SEQ ID NO 135

<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Gly Val Asn Val Glu Met His Leu Lys Gln Ile Glu Ile Lys Lys
1               5                   10                  15

Phe Lys Tyr Gly Ile Glu Glu Gln Gly Lys
            20                  25

<210> SEQ ID NO 136
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Tyr Gly Arg Lys Lys Arg Arg Gln Arg Arg Arg Lys Gln Ile Glu Ile
1               5                   10                  15

Lys Lys Phe Lys
            20

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Cys Ser Ser Pro Thr Ala Pro Leu Ser Pro Met Ser Pro Pro Gly Tyr
1               5                   10                  15

Lys

<210> SEQ ID NO 138
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Pro Thr Ala Pro Leu Ser Pro Met Ser Pro Pro
1               5                   10

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Arg Pro Arg Asp Asp Glu Ile
1               5

<210> SEQ ID NO 140
<211> LENGTH: 20

<212> TYPE: PRT
<213> ORGANISM: Artificial Sequence
<220> FEATURE:
<223> OTHER INFORMATION: Description of Artificial Sequence: Synthetic peptide

<400> SEQUENCE: 140

Pro Ser Ser Arg Ala Ser Ser Arg Ala Ser Ser Arg Pro Arg Pro Asp
1 5 10 15

Asp Leu Glu Ile
20

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 141

Arg Pro Arg Pro Asp Asp Leu Glu Ile
1 5

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 142

Arg Pro Arg Pro Asp Asp Leu Glu Val
1 5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 143

Arg Pro Arg Pro Asp Asp Val Pro Val
1 5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 144

Lys Ala Arg Ser Asp Asp Leu Ser Val
1 5

<210> SEQ ID NO 145
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 145

Gln Lys Pro Glu Val Pro Asn Gly Val Ser Pro Gly His Arg Leu Pro
1               5                   10                  15

His Gly Tyr His Ser Asp Lys Arg Arg Leu Ser Lys Ala Ser Ser Lys
            20                  25                  30

Ala Arg Ser Asp Asp Leu Ser Val
        35                  40

<210> SEQ ID NO 146
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Arg Gln Pro Lys Ile Trp Phe Pro Asn Arg Arg Lys Pro Trp Lys Lys
1               5                   10                  15

Pro Ser Ser Arg Ala Ser Ser Arg Ala Ser Ser Arg Pro Arg Pro Asp
            20                  25                  30

Asp Leu Glu Ile
        35

<210> SEQ ID NO 147
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Arg Gln Pro Lys Ile Trp Phe Pro Asn Arg Arg Lys Pro Trp Lys Lys
1               5                   10                  15

Pro Ser Ser Arg Ala Ser Ser Arg Ala Ser Ser Arg Pro Arg Pro Asp
            20                  25                  30

Asp Leu Glu Ile
        35

<210> SEQ ID NO 148
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Arg Gln Pro Lys Ile Trp Phe Pro Asn Arg Arg Lys Pro Trp Lys Lys
1               5                   10                  15

Arg Pro Arg Pro Asp Asp Leu Glu Ile
            20                  25

<210> SEQ ID NO 149
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Arg Gln Pro Lys Ile Trp Phe Pro Asn Arg Arg Lys Pro Trp Lys Lys
1 5 10 15

Arg Pro Arg Pro Asp Asp Leu Glu Val
20 25

<210> SEQ ID NO 150
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 150

Arg Gln Pro Lys Ile Trp Phe Pro Asn Arg Arg Lys Pro Trp Lys Lys
1 5 10 15

Arg Pro Arg Pro Asp Asp Val Pro Val
20 25

<210> SEQ ID NO 151
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 151

Arg Gln Pro Lys Ile Trp Phe Pro Asn Arg Arg Lys Pro Trp Lys Lys
1 5 10 15

Lys Ala Arg Ser Asp Asp Leu Ser Val
20 25

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 152

Arg Pro Lys Pro Asp Asp Leu Asp Ile
1 5

<210> SEQ ID NO 153
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 153

Gly Arg Lys Lys Arg Arg Gln Arg Pro Pro Gln Arg Pro Arg Pro Asp
1 5 10 15

Asp Leu Glu Ile
20

<210> SEQ ID NO 154
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 154

Arg Gln Ile Lys Ile Trp Phe Gln Asn Arg Arg Met Lys Trp Lys Lys
1 5 10 15

Arg Pro Arg Pro Asp Asp Leu Glu Ile
20 25

<210> SEQ ID NO 155
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 155

Arg Gln Ile Ala Ile Trp Phe Gln Asn Arg Arg Met Lys Trp Ala Ala
1 5 10 15

Arg Pro Arg Pro Asp Asp Leu Glu Ile
20 25

<210> SEQ ID NO 156
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 156

Arg Lys Lys Arg Arg Gln Arg Arg Arg Arg Pro Arg Pro Asp Asp Leu
1 5 10 15

Glu Ile

<210> SEQ ID NO 157
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 157

Thr Arg Ser Ser Arg Ala Gly Leu Gln Phe Pro Val Gly Arg Val His
1 5 10 15

Arg Leu Leu Arg Lys Arg Pro Arg Pro Asp Asp Leu Glu Ile
20 25 30

<210> SEQ ID NO 158
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 158

Gly Trp Thr Leu Asn Ser Ala Gly Tyr Leu Leu Gly Lys Ile Asn Lys
1 5 10 15

Ala Leu Ala Ala Leu Ala Lys Lys Ile Leu Arg Pro Arg Pro Asp Asp
20 25 30

Leu Glu Ile
35

```
<210> SEQ ID NO 159
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Lys Leu Ala Leu Lys Leu Ala Leu Lys Ala Leu Lys Ala Ala Leu Lys
1               5                   10                  15

Leu Ala Arg Pro Arg Pro Asp Asp Leu Glu Ile
            20                  25


<210> SEQ ID NO 160
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ala Ala Val Ala Leu Leu Pro Ala Val Leu Leu Ala Leu Leu Ala Pro
1               5                   10                  15

Arg Pro Arg Pro Asp Asp Leu Glu Ile
            20                  25


<210> SEQ ID NO 161
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Val Pro Met Leu Lys Pro Met Leu Lys Glu Arg Pro Arg Pro Asp Asp
1               5                   10                  15

Leu Glu Ile


<210> SEQ ID NO 162
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Arg Pro Arg Pro
            20                  25                  30

Asp Asp Leu Glu Ile
        35


<210> SEQ ID NO 163
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 163

Leu Leu Ile Ile Leu Arg Arg Arg Ile Arg Lys Gln Ala His Ala His
1 5 10 15

Ser Lys Arg Pro Arg Pro Asp Asp Leu Glu Ile
20 25

<210> SEQ ID NO 164
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 164

Lys Glu Thr Trp Trp Glu Thr Trp Trp Thr Glu Trp Ser Gln Pro Lys
1 5 10 15

Lys Lys Arg Lys Val Arg Pro Arg Pro Asp Asp Leu Glu Ile
20 25 30

<210> SEQ ID NO 165
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 165

Arg Gly Gly Arg Leu Ser Tyr Ser Arg Arg Arg Phe Ser Thr Ser Thr
1 5 10 15

Gly Arg Arg Pro Arg Pro Asp Asp Leu Glu Ile
20 25

<210> SEQ ID NO 166
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 166

Ser Asp Leu Trp Glu Met Met Met Val Ser Leu Ala Cys Gln Tyr Arg
1 5 10 15

Pro Arg Pro Asp Asp Leu Glu Ile
20

<210> SEQ ID NO 167
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 167

Thr Ser Pro Leu Asn Ile His Asn Gly Gln Lys Leu Arg Pro Arg Pro
1 5 10 15

Asp Asp Leu Glu Ile
20

<210> SEQ ID NO 168
<211> LENGTH: 12

<212> TYPE: PRT
<213> ORGANISM: Artificial Sequence
<220> FEATURE:
<223> OTHER INFORMATION: Description of Artificial Sequence: Synthetic peptide

<400> SEQUENCE: 168

Val Asp Cys Phe Leu Ser Arg Pro Thr Glu Lys Thr
1 5 10

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 169

Ser Arg Pro Thr Glu Lys Thr Ile Phe Ile Ile
1 5 10

<210> SEQ ID NO 170
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 170

Val Cys Tyr Asp Lys Ser Phe Pro Ile Ser His Val Arg
1 5 10

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 171

Cys Phe Leu Ser Arg Pro Thr Glu Lys Thr
1 5 10

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 172

Leu Ser Arg Pro Thr Glu Lys Thr
1 5

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 173

Ser Arg Pro Thr Glu Lys Thr 1 5

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 174

Val Asp Cys Phe Leu Ser Arg Pro Thr Glu
1 5 10

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 175

Val Asp Cys Phe Leu Ser Arg Pro
1 5

<210> SEQ ID NO 176
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 176

Val Asp Cys Phe Leu Ser
1 5

<210> SEQ ID NO 177
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 177

Gly Arg Lys Lys Arg Arg Gln Arg Pro Pro Gln Val Asp Cys Phe Leu
1 5 10 15

Ser Arg Pro Thr Glu Lys Thr
20

<210> SEQ ID NO 178
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 178

Arg Gln Ile Lys Ile Trp Phe Gln Asn Arg Arg Met Lys Trp Lys Lys
1 5 10 15

Val Asp Cys Phe Leu Ser Arg Pro Thr Glu Lys Thr
20 25

<210> SEQ ID NO 179
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 179

```
Arg Gln Ile Ala Ile Trp Phe Gln Asn Arg Arg Met Lys Trp Ala Ala
1               5                   10                  15

Val Asp Cys Phe Leu Ser Arg Pro Thr Glu Lys Thr
            20                  25
```

<210> SEQ ID NO 180
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 180

```
Arg Lys Lys Arg Arg Gln Arg Arg Arg Val Asp Cys Phe Leu Ser Arg
1               5                   10                  15

Pro Thr Glu Lys Thr
            20
```

<210> SEQ ID NO 181
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 181

```
Thr Arg Ser Ser Arg Ala Gly Leu Gln Phe Pro Val Gly Arg Val His
1               5                   10                  15

Arg Leu Leu Arg Lys Val Asp Cys Phe Leu Ser Arg Pro Thr Glu Lys
            20                  25                  30

Thr
```

<210> SEQ ID NO 182
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 182

```
Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu Val Asp Cys Phe Leu Ser
            20                  25                  30

Arg Pro Thr Glu Lys Thr
        35
```

<210> SEQ ID NO 183
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 183

Lys Leu Ala Leu Lys Leu Ala Leu Lys Ala Leu Lys Ala Ala Leu Lys
1 5 10 15

Leu Ala Val Asp Cys Phe Leu Ser Arg Pro Thr Glu Lys Thr
20 25 30

<210> SEQ ID NO 184
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 184

Ala Ala Val Ala Leu Leu Pro Ala Val Leu Leu Ala Leu Leu Ala Pro
1 5 10 15

Val Asp Cys Phe Leu Ser Arg Pro Thr Glu Lys Thr
20 25

<210> SEQ ID NO 185
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 185

Val Pro Met Leu Lys Pro Met Leu Lys Glu Val Asp Cys Phe Leu Ser
1 5 10 15

Arg Pro Thr Glu Lys Thr
20

<210> SEQ ID NO 186
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 186

Met Ala Asn Leu Gly Tyr Trp Leu Leu Ala Leu Phe Val Thr Met Trp
1 5 10 15

Thr Asp Val Gly Leu Cys Lys Lys Arg Pro Lys Pro Val Asp Cys Phe
20 25 30

Leu Ser Arg Pro Thr Glu Lys Thr
35 40

<210> SEQ ID NO 187
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 187

Leu Leu Ile Ile Leu Arg Arg Arg Ile Arg Lys Gln Ala His Ala His
1 5 10 15

Ser Lys Val Asp Cys Phe Leu Ser Arg Pro Thr Glu Lys Thr 20 25 30

<210> SEQ ID NO 188
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 188

Lys Glu Thr Trp Trp Glu Thr Trp Trp Thr Glu Trp Ser Gln Pro Lys
1 5 10 15

Lys Lys Arg Lys Val Val Asp Cys Phe Leu Ser Arg Pro Thr Glu Lys
20 25 30

Thr

<210> SEQ ID NO 189
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 189

Arg Gly Gly Arg Leu Ser Tyr Ser Arg Arg Arg Phe Ser Thr Ser Thr
1 5 10 15

Gly Arg Val Asp Cys Phe Leu Ser Arg Pro Thr Glu Lys Thr
20 25 30

<210> SEQ ID NO 190
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 190

Ser Asp Leu Trp Glu Met Met Met Val Ser Leu Ala Cys Gln Tyr Val
1 5 10 15

Asp Cys Phe Leu Ser Arg Pro Thr Glu Lys Thr
20 25

<210> SEQ ID NO 191
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 191

Thr Ser Pro Leu Asn Ile His Asn Gly Gln Lys Leu Val Asp Cys Phe
1 5 10 15

Leu Ser Arg Pro Thr Glu Lys Thr
20

<210> SEQ ID NO 192
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 192

Phe Glu Val Ala Phe Leu Leu Ile Gln Trp Ile
1 5 10

<210> SEQ ID NO 193
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 193

Leu Leu Ile Gln Trp Tyr Ile Gly Phe Ser Leu
1 5 10

<210> SEQ ID NO 194
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 194

Ser Leu Ser Ala Val Tyr Thr Cys Lys Arg Asp Pro Cys Pro His Gln
1 5 10 15

<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 195

Ser Arg Pro Thr Glu Lys Thr Ile Phe Ile Ile
1 5 10

<210> SEQ ID NO 196
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 196

Leu Gly Thr Ala Val Glu Ser Ala Trp Gly Asp Glu Gln
1 5 10

<210> SEQ ID NO 197
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 197

Gln Ser Ala Phe Arg Cys Asn Thr Gln Gln Pro Gly
1 5 10

<210> SEQ ID NO 198

<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 198

Gln Gln Pro Gly Cys Glu Asn Val Cys Tyr Asp Lys
1 5 10

<210> SEQ ID NO 199
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 199

Val Cys Tyr Asp Lys Ser Phe Pro Ile Ser His Val Arg
1 5 10

<210> SEQ ID NO 200
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 200

Lys Arg Asp Pro Cys His Gln Val Asp Cys Phe Leu Ser Arg Pro Thr
1 5 10 15

Glu Lys

<210> SEQ ID NO 201
<211> LENGTH: 16
<212> TYPE: PRT
<213> ORGANISM: Unknown
<220> FEATURE:
<223> OTHER INFORMATION: Description of Unknown: ANTP peptide

<400> SEQUENCE: 201

Arg Gln Pro Lys Ile Trp Phe Pro Asn Arg Arg Lys Pro Trp Lys Lys
1 5 10 15

<210> SEQ ID NO 202
<211> LENGTH: 11
<212> TYPE: PRT
<213> ORGANISM: Human immunodeficiency virus

<400> SEQUENCE: 202

Gly Arg Lys Lys Arg Arg Gln Arg Pro Pro Gln
1 5 10

<210> SEQ ID NO 203
<211> LENGTH: 26
<212> TYPE: PRT
<213> ORGANISM: Unknown
<220> FEATURE:
<223> OTHER INFORMATION: Description of Unknown: Transportan peptide

<400> SEQUENCE: 203

Gly Trp Thr Leu Asn Ser Ala Gly Tyr Leu Leu Gly Lys Ile Asn Lys 1 5 10 15

Ala Leu Ala Ala Leu Ala Lys Lys Ile Leu
20 25

<210> SEQ ID NO 204
<211> LENGTH: 21
<212> TYPE: PRT
<213> ORGANISM: Unknown
<220> FEATURE:
<223> OTHER INFORMATION: Description of Unknown: Buforin II peptide

<400> SEQUENCE: 204

Thr Arg Ser Ser Arg Ala Gly Leu Gln Phe Pro Val Gly Arg Val His
1 5 10 15

Arg Leu Leu Arg Lys
20

<210> SEQ ID NO 205
<211> LENGTH: 9
<212> TYPE: PRT
<213> ORGANISM: Unknown
<220> FEATURE:
<223> OTHER INFORMATION: Description of Unknown: Tat peptide

<400> SEQUENCE: 205

Arg Lys Lys Arg Arg Gln Arg Arg Arg
1 5

<210> SEQ ID NO 206
<211> LENGTH: 16
<212> TYPE: PRT
<213> ORGANISM: Drosophila sp.

<400> SEQUENCE: 206

Arg Gln Ile Lys Ile Trp Phe Gln Asn Arg Arg Met Lys Trp Lys Lys
1 5 10 15

<210> SEQ ID NO 207
<211> LENGTH: 18
<212> TYPE: PRT
<213> ORGANISM: Unknown
<220> FEATURE:
<223> OTHER INFORMATION: Description of Unknown: MAP peptide

<400> SEQUENCE: 207

Lys Leu Ala Leu Lys Leu Ala Leu Lys Ala Leu Lys Ala Ala Leu Lys
1 5 10 15

Leu Ala

<210> SEQ ID NO 208
<211> LENGTH: 16
<212> TYPE: PRT
<213> ORGANISM: Unknown
<220> FEATURE:
<223> OTHER INFORMATION: Description of Unknown: K-FGF peptide

<400> SEQUENCE: 208

Ala Ala Val Ala Leu Leu Pro Ala Val Leu Leu Ala Leu Leu Ala Pro
1 5 10 15

<210> SEQ ID NO 209

<211> LENGTH: 10
<212> TYPE: PRT
<213> ORGANISM: Unknown
<220> FEATURE:
<223> OTHER INFORMATION: Description of Unknown:
Ku70 peptide

<400> SEQUENCE: 209

Val Pro Met Leu Lys Pro Met Leu Lys Glu
1 5 10

<210> SEQ ID NO 210
<211> LENGTH: 28
<212> TYPE: PRT
<213> ORGANISM: Unknown
<220> FEATURE:
<223> OTHER INFORMATION: Description of Unknown:
Prion peptide

<400> SEQUENCE: 210

Met Ala Asn Leu Gly Tyr Trp Leu Leu Ala Leu Phe Val Thr Met Trp
1 5 10 15

Thr Asp Val Gly Leu Cys Lys Lys Arg Pro Lys Pro
20 25

<210> SEQ ID NO 211
<211> LENGTH: 18
<212> TYPE: PRT
<213> ORGANISM: Unknown
<220> FEATURE:
<223> OTHER INFORMATION: Description of Unknown:
pVEC peptide

<400> SEQUENCE: 211

Leu Leu Ile Ile Leu Arg Arg Arg Ile Arg Lys Gln Ala His Ala His
1 5 10 15

Ser Lys

<210> SEQ ID NO 212
<211> LENGTH: 21
<212> TYPE: PRT
<213> ORGANISM: Unknown
<220> FEATURE:
<223> OTHER INFORMATION: Description of Unknown:
Pep-1 peptide

<400> SEQUENCE: 212

Lys Glu Thr Trp Trp Glu Thr Trp Trp Thr Glu Trp Ser Gln Pro Lys
1 5 10 15

Lys Lys Arg Arg Val
20

<210> SEQ ID NO 213
<211> LENGTH: 18
<212> TYPE: PRT
<213> ORGANISM: Unknown
<220> FEATURE:
<223> OTHER INFORMATION: Description of Unknown:
SynB1 peptide

<400> SEQUENCE: 213

Arg Gly Gly Arg Leu Ser Tyr Ser Arg Arg Arg Phe Ser Thr Ser Thr
1 5 10 15

Gly Arg

<210> SEQ ID NO 214
<211> LENGTH: 15
<212> TYPE: PRT
<213> ORGANISM: Unknown
<220> FEATURE:
<223> OTHER INFORMATION: Description of Unknown:
Pep-7 peptide

<400> SEQUENCE: 214

Ser Asp Leu Trp Glu Met Met Met Val Ser Leu Ala Cys Gln Tyr
1 5 10 15

<210> SEQ ID NO 215
<211> LENGTH: 12
<212> TYPE: PRT
<213> ORGANISM: Unknown
<220> FEATURE:
<223> OTHER INFORMATION: Description of Unknown:
HN-1 peptide

<400> SEQUENCE: 215

Thr Ser Pro Leu Asn Ile His Asn Gly Gln Lys Leu
1 5 10

<210> SEQ ID NO 216
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 216

Tyr Gly Arg Lys Lys Arg Arg Gln Arg Arg Arg Ser Arg Pro Arg Asp
1 5 10 15

Asp Glu Ile

<210> SEQ ID NO 217
<211> LENGTH: 1191
<212> TYPE: DNA
<213> ORGANISM: Homo sapiens

<400> SEQUENCE: 217
atgagttgga gctttctgac tcgcctgcta gaggagattc acaaccattc cacatttgtg 60
gggaagatct ggctcactgt tctgattgtc ttccggatcg tccttacagc tgtaggagga 120
gaatccatct attacgatga gcaaagcaaa tttgtgtgca acacagaaca gccgggctgt 180
gagaatgtct gttatgatgc gtttgcacct ctctcccatg tacgcttctg ggtgttccag 240
atcatcctgg tggcaactcc ctctgtgatg tacctgggct atgctatcca caagattgcc 300
aaaatggagc acggtgaagc agacaagaag gcagctcgga gcaagcccta tgcaatgcgc 360
tggaaacaac accgggctct ggaagaaacg gaggaggaca acgaagagga tcctatgatg 420
tatccagaga tggagttaga aagtgataag gaaaataaag agcagagcca acccaaacct 480
aagcatgatg gccgacgacg gattcgggaa gatgggctca tgaaaatcta tgtgctgcag 540
ttgctggcaa ggaccgtgtt tgaggtgggt tttctgatag ggcagtattt tctgtatggc 600
ttccaagtcc acccgtttta tgtgtgcagc agacttcctt gtcctcataa gatagactgc 660
tttatttcta gacccactga aaagaccatc ttccttctga taatgtatgg tgttacaggc 720
ctttgcctct tgcttaacat ttgggagatg cttcatttag ggtttgggac cattcgagac 780
tcactaaaca gtaaaaggag ggaacttgag gatccgggtg cttataatta tcctttcact 840

```
tggaatacac catctgctcc ccctggctat aacattgctg tcaaaccaga tcaaatccag    900

tacaccgaac tgtccaatgc taagatcgcc tacaagcaaa acaaggccaa cacagcccag    960

gaacagcagt atggcagcca tgaggagaac ctcccagctg acctggaggc tctgcagcgg   1020

gagatcagga tggctcagga acgcttggat ctggcagttc aggcctacag tcaccaaaac   1080

aaccctcatg gtccccggga gaagaaggcc aaagtggggt ccaaagctgg gtccaacaaa   1140

agcactgcca gtagcaaatc aggggatggg aagaactctg tctggattta a            1191


<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ser Arg Pro Arg Asp Asp Leu Glu Ile
1               5


<210> SEQ ID NO 219
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Tyr Gly Arg Lys Lys Arg Arg Gln Arg Arg Arg Arg Pro Arg Asp Asp
1               5                   10                  15

Glu Ile


<210> SEQ ID NO 220
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 4Hyp

<400> SEQUENCE: 220

Gly Ala Gly Xaa Pro Tyr
1               5


<210> SEQ ID NO 221
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Tyr
<220> FEATURE:
<221> NAME/KEY: MOD_RES
<222> LOCATION: (3)..(3)
<223> OTHER INFORMATION: D-4Hyp
<220> FEATURE:
<221> NAME/KEY: MOD_RES
<222> LOCATION: (5)..(5)
```

<223> OTHER INFORMATION: D-Ala

<400> SEQUENCE: 221

Tyr Pro Xaa Gly Ala Gly
1               5

<210> SEQ ID NO 222
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Arg Val Ile Arg Val Trp Phe Gln Asn Lys Arg Cys Lys Asp Lys Lys
1               5                   10                  15

Val Asp Cys Phe Leu Ser Arg Pro Thr Glu Lys Thr
            20                  25

<210> SEQ ID NO 223
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val Val Asp Cys Phe Leu
            20                  25                  30

Ser Arg Pro Thr Glu Lys Thr
        35

<210> SEQ ID NO 224
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Gly Ala Leu Phe Leu Ala Phe Leu Ala Ala Ala Leu Ser Leu Met Gly
1               5                   10                  15

Leu Trp Ser Gln Pro Lys Lys Lys Arg Arg Val Val Asp Cys Phe Leu
            20                  25                  30

Ser Arg Pro Thr Glu Lys Thr
        35

<210> SEQ ID NO 225
<211> LENGTH: 16
<212> TYPE: PRT
<213> ORGANISM: Unknown
<220> FEATURE:
<223> OTHER INFORMATION: Description of Unknown:
      plsl peptide

<400> SEQUENCE: 225

Arg Val Ile Arg Val Trp Phe Gln Asn Lys Arg Cys Lys Asp Lys Lys
1               5                   10                  15

-continued

<210> SEQ ID NO 226
<211> LENGTH: 27
<212> TYPE: PRT
<213> ORGANISM: Unknown
<220> FEATURE:
<223> OTHER INFORMATION: Description of Unknown:
MGB Peptide P-beta sequence

<400> SEQUENCE: 226

Gly Ala Leu Phe Leu Gly Phe Leu Gly Ala Ala Gly Ser Thr Met Gly
1 5 10 15

Ala Trp Ser Gln Pro Lys Lys Lys Arg Lys Val
20 25

<210> SEQ ID NO 227
<211> LENGTH: 27
<212> TYPE: PRT
<213> ORGANISM: Unknown
<220> FEATURE:
<223> OTHER INFORMATION: Description of Unknown:
MGB Peptide P-alpha sequence

<400> SEQUENCE: 227

Gly Ala Leu Phe Leu Ala Phe Leu Ala Ala Ala Leu Ser Leu Met Gly
1 5 10 15

Leu Trp Ser Gln Pro Lys Lys Lys Arg Arg Val
20 25

<210> SEQ ID NO 228
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 228
aaaacucaug uucaagacag aagggu 26

<210> SEQ ID NO 229
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 229
acccuucugu cuugaacaug aguuuu 26

<210> SEQ ID NO 230
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 230
ccaucugaug guguccuacc uaauu 25

<210> SEQ ID NO 231
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 231
aauuagguag gacaccauca gaugg 25

<210> SEQ ID NO 232
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 232
gggcucuugg cuugcuauuc gaauu 25

<210> SEQ ID NO 233
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 233

Gly Arg Gly Asp Ser Pro Lys
1 5

<210> SEQ ID NO 234
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 234
agcugcauca gguuggcac 19

<210> SEQ ID NO 235
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 235
cggaaucagu gaaugcuuau acauccgt 28

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 236
ctgctttctg ttgagaggct 20

<210> SEQ ID NO 237
<211> LENGTH: 12
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 237

Val Asp Cys Phe Leu Ser Arg Pro Thr Glu Lys Thr
1 5 10

<210> SEQ ID NO 238
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 238
aauucgaaua gcaagccaag agccc 25

<210> SEQ ID NO 239
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 239
ccuuccaccu uuagauaaag agaaa 25

<210> SEQ ID NO 240
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 240
uuucucuuua ucuaaaggug gaagg 25

<210> SEQ ID NO 241
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 241

Cys Asp Glu Gln Ser Ala Phe Arg Cys Asn Thr Gln Gln
1 5 10

<210> SEQ ID NO 242
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 242
tggtaaggtg aaaatgcgag g 21

<210> SEQ ID NO 243
<211> LENGTH: 23

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 243
gcactcaagc tgaatccata gat 23

<210> SEQ ID NO 244
<211> LENGTH: 39
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 244

```
Met Tyr Val Phe Tyr Val Met Tyr Asp Gly Phe Ser Met Gln Arg Leu
1               5                   10                  15

Val Lys Cys Asn Ala Trp Pro Cys Pro Asn Thr Val Asp Cys Phe Val
            20                  25                  30

Ser Arg Pro Thr Glu Lys Thr
        35
```

<210> SEQ ID NO 245
<211> LENGTH: 39
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 245

```
Met Tyr Val Phe Tyr Phe Leu Tyr Asn Gly Tyr His Leu Pro Trp Val
1               5                   10                  15

Leu Lys Cys Gly Ile Asp Pro Cys Pro Asn Leu Val Asp Cys Phe Ile
            20                  25                  30

Ser Arg Pro Thr Glu Lys Thr
        35
```

<210> SEQ ID NO 246
<211> LENGTH: 39
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 246

```
Leu Tyr Ile Phe His Arg Leu Tyr Lys Asp Tyr Asp Met Pro Arg Val
1               5                   10                  15

Val Ala Cys Ser Val Glu Pro Cys Pro His Thr Val Asp Cys Tyr Ile
            20                  25                  30

Ser Arg Pro Thr Glu Lys Lys
        35
```

<210> SEQ ID NO 247
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 247

Leu Tyr Leu Leu His Thr Leu Trp His Gly Phe Asn Met Pro Arg Leu
1 5 10 15

Val Gln Cys Ala Asn Val Ala Pro Cys Pro Asn Ile Val Asp Cys Tyr
20 25 30

Ile Ala Arg Pro Thr Glu Lys Lys
35 40

<210> SEQ ID NO 248
<211> LENGTH: 39
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 248

Leu Tyr Val Phe His Ser Phe Tyr Pro Lys Tyr Ile Leu Pro Pro Val
1 5 10 15

Val Lys Cys His Ala Asp Pro Cys Pro Asn Ile Val Asp Cys Phe Ile
20 25 30

Ser Lys Pro Ser Glu Lys Asn
35

<210> SEQ ID NO 249
<211> LENGTH: 39
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 249

Met Tyr Val Phe Tyr Leu Leu Tyr Pro Gly Tyr Ala Met Val Arg Leu
1 5 10 15

Val Lys Cys Asp Val Tyr Pro Cys Pro Asn Thr Val Asp Cys Phe Val
20 25 30

Ser Arg Pro Thr Glu Lys Thr
35

<210> SEQ ID NO 250
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 250

Leu Tyr Gly Trp Thr Met Glu Pro Val Phe Val Cys Gln Arg Ala Pro
1 5 10 15

Cys Pro Tyr Leu Val Asp Cys Phe Val Ser Arg Pro Thr Glu Lys Thr
20 25 30

<210> SEQ ID NO 251
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 251

Leu Tyr Gly Trp Thr Met Glu Pro Val Phe Val Cys Gln Arg Ala Pro
1 5 10 15

Cys Pro Tyr Leu Val Asp Cys Phe Val Ser Arg Pro Thr Glu Lys Thr
20 25 30

<210> SEQ ID NO 252
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 252

Gly Ala Leu His Tyr Phe Leu Phe Gly Phe Leu Ala Pro Lys Lys Phe
1 5 10 15

Pro Cys Thr Arg Pro Pro Cys Thr Gly Val Val Asp Cys Tyr Val Ser
20 25 30

Arg Pro Thr Glu Lys Ser
35

<210> SEQ ID NO 253
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 253

Leu Leu Ile Gln Trp Tyr Ile Tyr Gly Phe Ser Leu Ser Ala Val Tyr
1 5 10 15

Thr Cys Lys Arg Asp Pro Cys Pro His Gln Val Asp Cys Phe Leu Ser
20 25 30

Arg Pro Thr Glu Lys Thr
35

<210> SEQ ID NO 254
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 254

Ile Ala Gly Gln Tyr Phe Leu Tyr Gly Phe Glu Leu Lys Pro Leu Tyr
1 5 10 15

Arg Cys Asp Arg Trp Pro Cys Pro Asn Thr Val Asp Cys Phe Ile Ser
20 25 30

Arg Pro Thr Glu Lys Thr
35

<210> SEQ ID NO 255
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 255

Leu Val Gly Gln Tyr Leu Leu Tyr Gly Phe Glu Val Arg Pro Phe Phe
1 5 10 15

-continued

```
Pro Cys Ser Arg Gln Pro Cys Pro His Val Val Asp Cys Phe Val Ser
            20                  25                  30

Arg Pro Thr Glu Lys Thr
        35


<210> SEQ ID NO 256
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Ile Val Gly Gln Tyr Phe Ile Tyr Gly Ile Phe Leu Thr Thr Leu His
1               5                   10                  15

Val Cys Arg Arg Ser Pro Cys Pro His Pro Val Asn Cys Tyr Val Ser
            20                  25                  30

Arg Pro Thr Glu Lys Asn
        35
```